(12) United States Patent
Maier et al.

(10) Patent No.: US 8,440,830 B2
(45) Date of Patent: May 14, 2013

(54) TETRAHYDRO-FUSED PYRIDINES AS HISTONE DEACETYLASE INHIBITORS

(75) Inventors: Thomas Maier, Stockach (DE); Thomas Beckers, Constance (DE); Thomas Baer, Reichenau (DE); Matthias Vennemann, Constance (DE); Volker Gekeler, Constance (DE); Astrid Zimmermann, Muehltal (DE); Petra Gimmnich, Constance (DE); Kamlesh Padiya, Virar (IN); Hemant Joshi, Navi Mumbai (IN); Uday Joshi, Thane (IN); Mahindra Makhija, Ghatkopar (IN); Dipak Harel, Maharashtra (IN)

(73) Assignee: 4SC AG, Planegg-Martinsried (DE)

( * ) Notice: Subject to any disclaimer, the term of this patent is extended or adjusted under 35 U.S.C. 154(b) by 246 days.

(21) Appl. No.: 12/678,806

(22) PCT Filed: Sep. 19, 2008

(86) PCT No.: PCT/EP2008/008208
§ 371 (c)(1),
(2), (4) Date: Aug. 23, 2010

(87) PCT Pub. No.: WO2009/037001
PCT Pub. Date: Mar. 26, 2009

(65) Prior Publication Data
US 2011/0021494 A1 Jan. 27, 2011

(30) Foreign Application Priority Data

| Sep. 19, 2007 | (EP) | 07116791 |
| Sep. 19, 2007 | (IN) | 1819/MUM/2007 |
| Mar. 24, 2008 | (IN) | 616/MUM/2008 |

(51) Int. Cl.
C07D 471/04 (2006.01)
A61K 31/4355 (2006.01)
A61K 31/4365 (2006.01)
A61K 31/4353 (2006.01)
A61K 31/437 (2006.01)

(52) U.S. Cl.
USPC ........... 546/113; 546/114; 546/115; 514/300; 514/301; 514/302

(58) Field of Classification Search .................. 546/113, 546/114, 115; 514/300, 301, 302
See application file for complete search history.

(56) References Cited

FOREIGN PATENT DOCUMENTS

| EP | 0555480 A1 | 8/1993 |
| WO | 03092686 A1 | 11/2003 |
| WO | 2007118137 A1 | 10/2007 |
| WO | 2009037001 A3 | 3/2009 |

OTHER PUBLICATIONS

Simone, Oncology: Introduction, Cecil Textbook of Medicine, 20th Edition, 1996 vol. 1, pp. 1004-1010.* Trisha Gura "Cancer Models: Systems for Identifying New Drugs Are Often Faulty" Science Nov. 7, 1997: vol. 278. No. 5340, pp. 1041-1042.*
Zips et. al. "New Anticancer Agents: In Vitro and In Vivo Evaluation" on vivo 2005, 19, 1-7.*
Weinmann, H. et al., "Histone deacetylase inhibitors: a survey of recent patents." (Expert Opinion on Therapeutic Patents), 2005,1677-1690, 15:12.

* cited by examiner

Primary Examiner — David K O Dell
(74) Attorney, Agent, or Firm — Millen, White, Zelano & Branigan, P.C.

(57) ABSTRACT

The compounds of formula (I), wherein ring D and ring E together form a fused ring system selected from formula (II), (III), (IV), (V), (VI), (VII), and the salts of these compounds are novel, effective inhibitors of histone deacetylases.

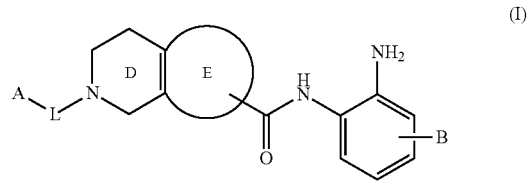

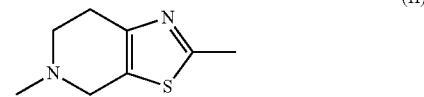

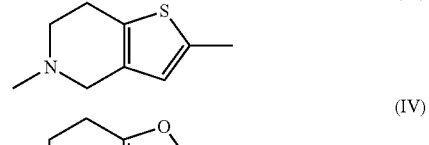

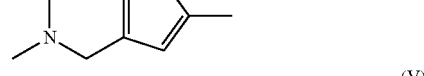

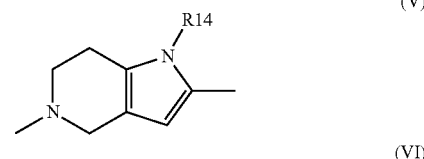

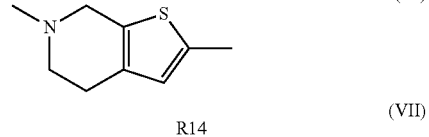

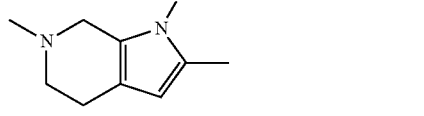

30 Claims, No Drawings

TETRAHYDRO-FUSED PYRIDINES AS HISTONE DEACETYLASE INHIBITORS

FIELD OF APPLICATION OF THE INVENTION

The invention relates to novel tetrahydrofusedpyridine derivatives, which are used in the pharmaceutical industry for the production of pharmaceutical compositions.

The invention further relates to certain salts of these tetrahydrofusedpyridine derivatives, which are used in the pharmaceutical industry for the production of pharmaceutical compositions.

KNOWN TECHNICAL BACKGROUND

Transcriptional regulation in cells is a complex biological process, regulated by multiprotein complexes including transcription factors, coactivators and repressors, receptors as well as platform/DNA binding proteins. One basic principle in transcriptional regulation is based on the posttranslational modification of histone proteins, namely histone proteins H2A/B, H3 and H4 forming the octameric histone core complex. The complex N-terminal modifications at lysine residues by acetylation or methylation and at serine residues by phosphorylation constitute part of the so called "histone code" (Strahl & Ellis, Nature 403, 41-45, 2000). In a simple model, acetylation of positively charged lysine residues decreases affinity to negatively charged DNA, which now becomes accessible for the entry of transcription factors.

Histone acetylation and deacetylation is catalysed by histone acetyltransferases (HATs) and histone deacetylases (HDACs). In many cases, HDACs are associated with transcriptional repressor complexes, switching chromatin to a transcriptionally inactive, silent structure (Marks et al. Nature Cancer Rev 1, 194-202, 2001). The opposite holds true for HATs, which are frequently associated with transcriptional activator complexes. Nevertheless, opposite functions for HATs and HDACs have been described in the literature. The cAMP response element binding protein (CBP) and p300 as HATs contain the transcriptional repressor domain CRD1 (cell cycle regulatory domain 1), allowing these proteins to act as transcriptional repressors (Snowden et al., Mol Cell Biol 20, 2676-2686, 2000). Transcriptional signatures of HDAC inhibitors show a similar proportion of induced and repressed genes. In one study, HDAC inhibition abrogates interferon-induced gene transcription presumably by antagonizing the co-activator function of HDAC1 for the interferon stimulated gene factor 3 (ISGF3; Nusinzon & Horvath, Science STKE August 2005). In melanoma cells, interaction of NfκB p65 with STAT1 is dependent on STAT1 acetylation. HDAC inhibitor or interferon α mediated STAT1 hyperacetylation causes the cytoplasmatic retention of NfκB, finally leading to repression of NFκB regulated genes (Krämer et al. Gen Develop 20, 473-485, 2006).

Three different classes of HDACs have been described so far, namely class I (HDAC 1-3, 8) with Mr=42-55 kDa primarily located in the nucleus and sensitive towards inhibition by Trichostatin A (TSA), class II (HDAC 4-7, 9, 10) with Mr=120-130 kDa and TSA sensitivity and class DI (Sir2 homologues) which are quite distinct by their $NAD^+$ dependency and TSA insensitivity (Ruijter et al. Biochem. J. 370, 737-749, 2003; Khochbin et al. Curr Opin Gen Dev 11, 162-166, 2001; Verdin et al. Trends Gen 19, 286-293, 2003). HDAC 11 with Mr=39 kDa displayed homology to class I and II family members (Gao et al. J Biol Chem 277,25748-25755, 2002) and is now defined as the sofar only class IV member (Gregoretti et al. J Mol Biol 338, 17-31, 2004). HATs and HDACs exist in large complexes together with transcription factor and platform proteins in cells (Fischle et al. Mol Cell 9, 45-47, 2002).

Substrates different to histone proteins exist. For HDACs these include transcription factors like p53 STAT proteins and TFII E, α-tubulin as a major protein of microtubles, or chaperones like heat shock protein 90 (Hsp90; Johnstone & Licht, Cancer Cell 4, 13-18, 2003). Therefore the correct name for HDACs would be lysine-specific protein deacetylases. As a consequence of these findings, inhibitors of HDACs affect not only chromatin structure and gene transcription but also protein function and stability by regulating protein acetylation in general. This function of HDACs in protein acetylation might also be important for understanding of immediate gene repression by treatment with HDIs (von Lint et al. Gene Expression 5, 245-253, 1996). In this regard, proteins involved in oncogenic transformation, apoptosis regulation and malignant cell growth are of particular importance.

Different publications highlight the pathophysiological importance of reversible histone acetylation for cancer drug development (reviewed by Kramer et al. Trends Endocrin Metabol 12, 294-300, 2001; Marks et al. Nature Cancer Rev 1, 194-202, 2001; Minucci & Pelicci, Nature Rev Canc 6, 38-51, 2006; Yoo, & Jones Nat. Rev. Drug Discov. 5, 37-50 2006):

(i) Mutations of CBP as a HAT are associated with Rubinstein-Taybi syndrome, a cancer predisposition (Murata et al. Hum Mol Genet 10, 1071-1076, 2001), (ii) Aberrant recruitment of HDAC1 activity by transcription factors in acute promyelocytic leukemia (APL) is mediated by the PML-retinoic acid receptor α fusion gene (He et al. Nat genet 18, 126-135, 1998)

(iii) Aberrant recruitment of HDAC activity by the overexpressed BCL6 protein was shown in non-Hodgkins lymphoma (Dhordain et al. Nucleic Acid Res 26, 4645-4651, 1998) and finally (iv) Aberrant recruitment of HDAC activity by the AML-ETO fusion protein was shown for acute myelogenous leukemia (AML M2 subtype; Wang et al. Proc Natl Acad Sci USA 95, 10860-10865, 1998). In this AML subtype, the recruitment of HDAC1 activity causally leads to gene silencing, a differentiation block and oncogenic transformation.

(v) HDAC1 gene knock-out in mice showed that HDAC1 has a profound function in embryonal stem cell proliferation by repressing cyclin-dependent kinase inhibitors $p21^{waf1}$ and $p27^{kip1}$ (Lagger et al. Embo J. 21, 2672-2681, 2002). Since $p21^{waf1}$ is induced by HDIs in many cancer cell lines, HDAC1 might be a crucial component in cancer cell proliferation as well. Initial siRNA based gene-knock down experiments in HeLa cells support this hypothesis (Glaser et al. 310, 529-536, 2003)

(vi) HDAC2 is overexpressed in colon carcinoma upon constitutive activation of the wnt/β-catenin/TCF signalling pathay by loss of functional adenomatosis polyposis coli (APC) protein as reported by Zhu et al. (Cancer Cell 5, 455-463, 2004)

(vii) A high expression of HDAC1, 2 and 3 in prostate adenocarcinomas was shown by immunohistochemistry, with HDAC2 as an independent prognostic factor for patient survival and HDAC1/2 correlating positively with tumor grade (Roeske et al, EORTC-NCI-AACR meeting Prague 2006, Abstract 350)

About 2%-3% of all genes are regulated by histone acetylation as estimated by differential display analysis and array based whole genome studies (von Lint et al. Gene Expression 5, 245-253, 1996, Sasakawa et al. Biochem Pharmacol 69, 603-16, 2005). Studies with the HDAC classI/II selective inhibitor suberoylanilide hydroxamic acid (SAHA) in multiple myeloma cells showed that these transcriptional changes can be grouped into distinct functional gene classes important for e.g. regulation of apoptosis or proliferation (Mitsiades et al. Proc Natl Acad Sci 101, pp 540, 2004). In a different study with the natural compound KF228 (Depsipeptide) and the cancer cell lines ACHN (renal cancer), PC3 (prostate cancer) and U937 (histiocytic leukemia), 105 up- and 100 down-regulated genes were identified (Sasakawa et al. Biochem Pharmacol 69, 603-16, 2005). Genes encoding proteins important for cell cycle/mitosis regulation (e.g. $p21^{waf1}$, CyclinA2, SAK, MKLP1), chromatin structure (e.g. histone proteins like histone H1, apoptosis/survival (e.g. caspase 9, TNF/TNFR family members), protein turnover (e.g. ubiquitin ligase E2H) or mitogenic/stress signaling (e.g. MKK3, MAPKAPK3, Ki67) were induced or repressed by treatment with FK228. Two of these genes (caspase 9 and mitogen activated protein kinase phosphatase 1/MKP1 were used as biomarkers to predict the response of human tumors xenografted onto nude mice to therapy with FK228 (Sasakawa et al. Biochem Pharmacol 69, 603-16, 2005). In a different study, the transcriptional changes in the acute human T-lymphoblastic leukemia cell line CCRF-CEM by SAHA and FK228 were studied (Peart et al. Proc Natl Acad Sci 102, 3697-3702, 2005). According to the experimental and statistical condition applied, the expression of 22.1% (SAHA) and 24.8% (FK228) of analyzed genes (about 10.000 unique accession numbers) were changed. Only a small subset of genes was identified that discriminated between both HDAC inhibitors. Finally, HDI regulated genes were functionally clustered showing alterations genes encoding protein involved, for example, in apoptosis regulation (e.g. caspases 3 and 5, APAF1, BCL XL, IKB, TNF) and proliferation (e.g. cyclins G1, G2, E1, B2, E2 and CKD2, CDC25c).

HDAC inhibitors arrest cells at G1 and G2/M within the cell cycle and deplete S-phase cells, as shown for Depsipeptide as an example (Sandor et al., British J Cancer 83, 817-825, 2000). The interaction of HDAC3 with the mitotic kinase Aurora B was shown recently (Li et al. Genes Dev. 20:2566-79, 2006). In this study, phosphorylation of histone H3 at $S^{10}$ by Aurora B was dependent on HDAC3 mediated N-terminal histone H3 deacetylation, giving a hint to the partial M-phase arrest seen by many HDIs.

HDAC inhibitory compounds induce p53 and caspase3/8 independent apoptosis and have broad anti-tumor activity. Anti-angiogenic activity was described also, which might be related to down-regulation of VEGF and HIF1α. In summary, HDAC inhibition affects tumor cells at different molecular levels and multiple cellular proteins are targeted.

Interestingly, HDAC inhibitors were found to induce cellular differentiation and this pharmacological activity might contribute to their anti-cancer activity as well. For example it was shown recently that suberoylanilide hydroxamic acid (SAHA) induces differentiation of breast cancer cell lines, exemplified by resynthesis of milk fat membrane globule protein (MFMG), milk fat globule protein and lipid (Munster et al. Cancer Res. 61, 8492, 2001). Also, induction of fetal hemoglobin synthesis in hematopoietic cells of the erythrocyte lineage has been studied in a clinical trial with the butyrate analog AN-9 (Patnaik et al. Clin Cancer Res. 8(7): 2142-8, 2002).

There is growing rational for synergism of HDAC inhibitors with chemotherapeutic as well as target specific cancer drugs. For example, synergism was shown for (i) SAHA with the kinase/cdk inhibitor flavopiridol (Alemenara et al. Leukemia 16, 1331-1343, 2002) or with the death receptor DR4/5 ligand TRAIL (Butler et al. Int J Cancer 119, 944-54, 2006; Sonnemann et al. Invest New drugs 23, 90-109, 2005), (ii) for LAQ-824 with the bcr-abl kinase inhibitor Glivec in CML cells (Nimmanapalli et al. Cancer Res. 63, 5126-5135, 2003) or the KDR/VEGFR2 kinase inhibitor PTK787/ZK222584 in angiogenesis (Qian et al. Cancer Res. 64, 6626-34, 2004), (iii) for SAHA and Trichostatin A (TSA) with etoposide (VP16), cisplatin and doxorubicin (Kim et al. Cancer Res. 63, 7291-7300, 2003), for TSA in combination with retinoid acid in acute myeloid leukemia/AML (Ferrara et al. Canc Res 61, 2-7, 2001) (iv) for LBH589 with the Hsp90 inhibitor 17-allyl-amino-demethoxy-geldanamycin (17-AAG; George et al. Blood online, Oct. 28, 2004) or the proteasome inhibitor bortezomib/Velcade (Maiso et al. Canc Res 66, 5781-5789, 2006, (iiv) PXD101 with 5-FU in colon cancer models (Tumber et al. Canc Chem Pharmacol nov. 2006) and Taxol or Carboplatin in ovarian carcinoma models (Qian et al. Mol Canc ther 5, 2086-95) Also it was shown that HDAC inhibition causes reexpression of estrogen or androgen receptors in breast and prostate cancer cells with the potential to resensitize these tumors to anti-hormone therapy (Yang et al. Cancer Res. 60, 6890-6894, 2000; Nakayama et al. Lab Invest 80, 1789-1796, 2000). Finally, histone deacetylase inhibitors sensitize towards cellular radiation responses as reviewed recently (Karagiannis & El-Osta, Oncogene 25, 3885-93, 2006).

HDAC inhibitors from various chemical classes were described in the literature with four most important classes, namely (i) hydroxamic acid analogs, (ii) benzamide analogs, (iii) cyclic peptides/peptolides and (iv) fatty acid analogs. A comprehensive summary of known HDAC inhibitors was published by various authors (Miller et al. J Med Chem 46, 5097-5116, 2003; Dokmanovic & Marks, J Cell Biochem 96, 293-304, 2005; Drummond et al. Ann Rev Pharmacol Toxicol 45, 495-528, 2005; Bolden J E, et al. Nat Rev Drug Discov 5:769-784, 2006; Sorbera, *Drugs of the Future* 31, 335-344, 2006). There is only limited data published regarding specificity of these histone deacetylase inhibitors. In general most hydroxamate based HDI are not specific regarding class I and II HDAC enzymes. For example TSA inhibits HDACs 1, 3, 4, 6 and 10 with $IC_{50}$ values around 20 nM, whereas HDAC8 was inhibited with $IC_{50}$=0.49 (Tatamiya et al, AACR Annual Meeting 2004, Abstract #2451). But there are exceptions like the experimental HDI Tubacin, selective for the class II enzyme HDAC 6 (Haggarty et al. Proc. Natl. Acad. Sci. USA 100, 4389-4394, 2003). In addition, data on class I selectivity of benzamide HDIs are emerging. MS-275 inhibited class I HDAC1 and 3 with $IC_{50}$=0.51 µM and 1.7 µM, respectively. In contrast class II HDACs 4, 6, 8 and 10 were inhibited with $IC_{50}$ values of >100 µM, >100 µM, 82.5 mM and 94.7 µM, respectively (Tatamiya et al, AACR Annual Meeting 2004, Abstract #2451). Comparable data were published by Hu et al. with inhibition of $IC_{50}$=0.3 µM, 8 µM and >100 µM for HDAC1, 3 and 8, respectively (Hu et al. J Pharmacol Exp Therap 307, 720-28, 2003). Finally, the benzamide analog MGCD0103 inhibited HDAC1, 2, 3 and 11 with $IC_{50}$ from 0.1-2 µM and HDACs 4 to 8 with $IC_{50}$ values >20 µM (Kalita et al. AACR-NCI-EORTC Conference Philadelphia 2005; Abstract C216).

Clinical studies in cancer with HDAC inhibitors are ongoing, namely with SAHA (Zolinza™ by Merck Inc.; Kelly et al. J Clin Oncol 23, 3923-31, 2005), CRA-024781 (Pharmacyclics Inc.; Buggy et al, Mol Canc Therap 5, 1309-17, 2006), ITF-2357 (Italfarmaco; J Hepatology 42, 210-17, 2005), Valproic acid (Topotarget; Göttlicher et al. EMBO J. 20, 6969-78, 2001), FK228/Depsipeptide (Gloucester Pharmaceuticals/NC; Nakajima et al. Exp Cell Res 241, 126-33, 19981), MS275 (Berlex-Schering; Ryan et al. J Clin Oncol 23, 3912-22, 2005), NVP LBH-589 (Novartis; Remiszewski et al. J Med Chem 46, 4609-24, 2003), PXD-101 (Topotarget/ Curagen; Plumb et al. Mol Canc Therap 2, 721-28, 2003), and MGCD0103 (Methylgene Inc.; Kalita et al. AACR-EORTC-NCI meeting 2005, Abstract C216). These studies showed evidence of clinical efficacy, highlighted recently by partial and complete responses with FK228/Depsipeptide in patients with peripheral T-cell lymphoma (Plekarz et al. Blood, 98, 2865-2868, 2001) and approval in this indication of SAHA (Zolinza™) by Merck & Co., Inc. (Nature Biotechn 25, 17-18, 2007).

Recent publications also showed possible medical use of HDAC inhibitors in diseases different to cancer. These diseases include systemic lupus erythematosus (Mishra et al. J Clin Invest 111, 539-552, 2003; Reilly et al. J. Immunol. 173, 4171-4178, 2004), rheumatoid arthritis (Chung et al. Mol Therapy 8, 707-717, 2003; Nishida et al. Arthritis & Rheumatology 50, 3365-3376, 2004), inflammatory diseases (Leoni et al. Proc Natl Acad Sci USA 99, 2995-3000, 2002), neurodegenerative diseases like Huntington's disease (Steffan et al. Nature 413, 739-743, 2001, Hockly et al. Proc Natl Acad Sci USA 100(4): 2041-6, 2003), cardiac hyperthrophy (Kong et al., Circulation 113, 2579-88, 2006), muscle dystrophy (Minetti et al. Nat Med 12, 1147-50, 2006), adipositas (Lagace & Nachtigal, J Biol. Chem. 279, 18851-860, 2004) and diabetes (Gray & DeMeyts, Diabetes Metab Res Rev 21, 416-33, 2005).

It is known that the loss of histone acetyltransferase (HAT) activity or increased histone deacetylase (HDAC) function leads to neuronal dysfunction and degeneration. Consistent with this fact, HDAC inhibition can restore the HAT-HDAC balance in the CNS in favour of HAT activity, which may facilitate survival, reduce inflammation, and neuronal damage. HDAC inhibitors such as SAHA, TSA, and sodium butyrate have been shown to promote neuronal survival. Thus, HDAC inhibitors have potential applications for the treatment or as adjuncts in neurodegenerative disorders such as stroke, Huntington's disease, Alzheimer's disease, and other such CNS disorders (Langley, B.; Gensert, J. M.; Beal, M. F.; Ratan, R. R. *Current Drug Targets—CNS & Neurological Disorders* 2005, 4, 41-50).

In fungi such as *Candida albicans*, HDAC enzymes HDA1 and RPD3 are known to contribute to its virulent character. Some HDAC inhibitors such as SAHA have been shown to inhibit the fluconazole induced resistance induction in *Candida* cultures (Mai, A.; Rotili, D.; Massa, S.; Brosch, G.; Simonetti, G.; Passariello, C.; Palamara, A. T. *Bioorg. Med. Chem. Lett.* 2007, 17, 1221-1225). The biological activity of HDAC inhibitors also comprises antiprotozoal, antifungal, and antiviral effects. The HDAC inhibitor TSA initially was discovered as an antifungal antibiotic. Apicidin, a different natural compound type of a HDAC inhibitor, and its derivatives have been tested and shown to be effective antimalarial agents and according to one study, an increase in their HDAC inhibitory activity correlated with their improved antimalarial activity (Meinke, P. T.; Liberator, P. *Current Medicinal Chemistry* 2001, 8, 211-235).

Cancer chemotherapy was established based on the concept that cancer cells with uncontrolled proliferation and a high proportion of cells in mitosis are killed preferentially. Standard cancer chemotherapeutic drugs finally kill cancer cells upon induction of programmed cell death ("apoptosis") by targeting basic cellular processes and molecules, namely RNA/DNA (alkylating and carbamoylating agents, platin analogs and topoisomerase inhibitors), metabolism (drugs of this class are named anti-metabolites) as well as the mitotic spindle apparatus (stabilizing and destabilizing tubulin inhibitors). Inhibitors of histone deacetylases (HDIs) constitute a new class of anti cancer drugs with differentiation and apoptosis inducing activity. By targeting histone deacetylases, HDIs effect histone (protein) acetylation and chromatin structure, inducing a complex transcriptional reprogramming, examplified by reactivation of tumor suppressor genes and repression of oncogenes. Beside affecting acetylation of N-terminal lysine residues in core histone proteins, also non-histone targets important for cancer cell biology are modified by acetylation at lysine residues. These non-histone substrates are, for example, heat-shock-protein 90 (Hsp90; Bali et al. J Biol Chem 280, 26729-734, 2005), α-tubulin (Hubbert et al. Nature 417, 455-58, 2002), STAT1 or STAT3 (Yuan et al. Science 307, 269-273, 2005; Krämer et al. Gen & Develop 20, 473-485, 2006) or the p53 tumor suppressor protein (Mol Cell 24, 807-808, 2006). The medical use of HDIs might not be restricted to cancer therapy, since efficacy in animal models for eg, rheumatoid arthritis, neurodegeneration, cardiac hyperthrophy and muscle dystrophy was shown.

STATE OF THE ART

Hydroxamic acid substituted fused heterocycles as metalloproteinase inhibitors are described in WO9906410, where as JP2004-203791 describes aromatic compounds that are potent FXa inhibitors.

Various compounds as HDAC inhibitors are reported in WO2005030705, WO03024448 and WO0138322.

There still remains a need in the art for new, well-tolerated and more efficacious inhibitors of HDAC.

DESCRIPTION OF THE INVENTION

It has now been found that the tetrahydrofusedpyridine derivatives, which are described in greater details below, differ profoundly from prior art compounds and are effective inhibitors of histone deacetylases and have surprising and particularly advantageous properties.

In addition and based on the foregoing, it has also been found, that certain salts of these tetrahydrofusedpyridine derivatives have surprising and particularly advantageous properties.

The invention thus relates to compounds of formula I:

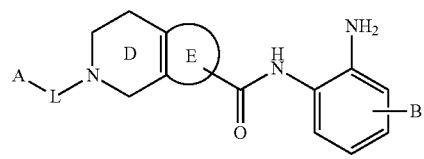

wherein ring D and ring E together form a fused ring system selected from

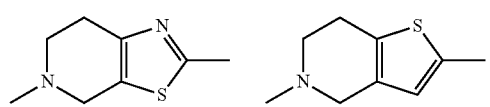

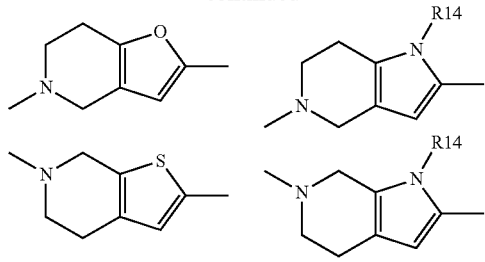

A is $(C_1-C_4)$ alkyl, $(C_1-C_4)$ alkoxy $(C_1-C_2)$ alkyl, $(C_1-C_4)$ alkylthio $(C_1-C_2)$ alkyl, mono- or -di$(C_1-C_4)$alkylamino $(C_1-C_2)$alkyl, $(C_3-C_7)$cycloalkyl optionally substituted by R1 and/or R2, $(C_3-C_7)$cycloalkyl substituted by R3, azetidinyl optionally substituted by R1 and/or R2, pyrrolidinyl optionally substituted by R1 and/or R2, piperidinyl optionally substituted by R1 and/or R2, phenyl optionally substituted by R1 and/or R2, phenyl substituted by R4, naphthyl optionally substituted by R1 and/or R2, pyridyl optionally substituted by R1 and/or R2, pyridyl substituted by R5, pyrimidinyl optionally substituted by R1 and/or R2, pyrimidinyl substituted by R8, triazinyl optionally substituted by R1 and/or R2, triazinyl substituted by R9; quinolinyl optionally substituted by R1 and/or R2, isoquinolinyl optionally substituted by R1 and/or R2, thienyl optionally substituted by R1 and/or R2, thiazolyl optionally substituted by R1 and/or R2 or indazolyl optionally substituted by R1 and/or R2;

R1 is halogen, hydroxyl, cyano, nitro, amino, carboxyl, $(C_1-C_4)$ alkyl, $(C_1-C_4)$alkoxy, $(C_1-C_4)$alkyl which is partially or completely substituted by fluorine, $(C_1-C_4)$alkoxy which is predominantly or completely substituted by fluorine, $(C_1-C_4)$alkoxy$(C_1-C_2)$alkyl, $(C_1-C_4)$alkoxycarbonyl, mono- or -di$(C_1-C_4)$alkylamino, or $(C_1-C_4)$alkylcarbonylamino;

R2 is halogen, hydroxyl, amino, $(C_1-C_4)$alkyl, or $(C_1-C_4)$ alkoxy or

R1 and R2 when ortho to each other form a methylenedioxy or ethylenedioxy group;

R3 is 3-pyridyl, or 4-pyridyl;

R4 is phenyl, phenoxy, 4-methylpiperazinyl, benzylNHC(=O)NH—, or $(C_1-C_4)$alkylphenylsulfonylamino;

R5 is $(C_1-C_4)$alkylphenylsulfonylamino or N(R6)R7, wherein R6 and R7 together and with inclusion of the nitrogen atom to which they are bonded form an azetidinyl-, pyrrolidinyl-, piperidinyl-, piperazinyl-, 4-methylpiperazinyl-, morpholinyl- or thiomorpholinyl-ring;

R8 is pyridyl or $(C_1-C_4)$alkylphenylsulfonylamino;

R9 is piperidinyl;

L is bond, —$(CH_2)_nS(O)_2$—, —C(=O)—, —C(=S)—, —$(CH_2)_nOC$(=O)—, —$(CH_2)_nN(R10)C(=O)$—, —$(CH_2)_nN(R10)C(=NR11)$-, —$(CH_2)_nN(R10)C(=S)$—, —C=C—C(=O)—, —N=C(R11)-, —$(CH_2)_nN(R10)C(=O)C(=O)$—, —$OCH_2C(=O)$—, —N(R10)C(=CR11)-, —N(R10)CH_2C(=O) or —N=C(NR11)-;

R10 is hydrogen, $(C_1-C_4)$alkyl or $(C_1-C_4)$ alkoxy$(C_1-C_2)$alkyl;

R11 is hydrogen, hydroxyl, cyano, nitro, or $(C_1-C_4)$alkyl;

B is hydrogen, halogen, $(C_1-C_4)$alkyl, $(C_1-C_4)$alkoxy, thienyl, or N(R12)R13 wherein R12 and R13 independently of one another are hydrogen, $(C_1-C_4)$alkyl, $(C_1-C_4)$alkylcarbonyl, or R12 and R13 together and with inclusion of the nitrogen atom to which they are bonded form an azetidinyl-, pyrrolidinyl-, piperidinyl-, piperazinyl-, 4-methylpiperazinyl-, morpholinyl- or thiomorpholinyl-ring;

R14 is hydrogen or $(C_1-C_4)$alkyl;

n is an integer selected from 0 to 2;

and the salts of these compounds.

Halogen means fluorine, chlorine, bromine or iodine. The preferred halogen is fluorine and chlorine.

$(C_1-C_4)$alkyl represents a straight chain or branched alkyl radical having 1 to 4 carbon atoms. Examples which may be mentioned are methyl, ethyl, propyl, isopropyl, butyl, isobutyl, secbutyl, ter-butyl.

$(C_1-C_4)$alkoxy represents straight chain or branched alkyl radicals having 1 to 4 carbon atoms and having a terminal oxygen atom. Examples, which may be mentioned, are methoxy, ethoxy, propoxy, isopropoxy, butoxy, isobutoxy, sec-butoxy, and tert-butoxy.

$(C_1-C_4)$alkoxy$(C_1-C_2)$alkyl represents $(C_1-C_2)$alkyl radicals having 1 to 2 carbon atoms, which are substituted by one of the abovementioned $(C_1-C_4)$alkoxy radicals. Examples, which may be mentioned, are the methoxymethyl, ethoxymethyl, methoxyethyl, ethoxyethyl, isopropoxymethyl and the isopropoxyethyl radicals, particularly the 2-methoxyethyl, 2-ethoxyethyl and the 2-isopropoxyethyl radicals.

$(C_1-C_4)$alkylthio represents radicals which contain one of the abovementioned $(C_1-C_4)$alkyl radicals and have a terminal sulfur atom. Examples, which may be mentioned, are the butylthio, isobutylthio, sec-butylthio, tert-butylthio, isopropylthio, propylthio and preferably the ethylthio and methylthio radicals.

$(C_1-C_4)$alkylthio$(C_1-C_2)$alkyl represents $(C_1-C_2)$alkyl radicals having 1 to 2 carbon atoms, which are substituted by one of the abovementioned $(C_1-C_4)$alkylthio radicals. Examples, which may be mentioned, are the methylthiomethyl, ethylthiomethyl, methylthioethyl, ethylthioethyl, isopropylthiomethyl, isopropylthioethyl and the butylthioethyl and butylthiomethyl radicals, particularly the 2-methylthioethyl, 2-ethylthioethyl and the 2-isopropylthioethyl radicals.

In addition to the nitrogen atom, mono- or di-$(C_1-C_4)$alkylamino radicals contain one or two of the above-mentioned $(C_1-C_4)$alkyl radicals independently. Examples which may be mentioned are methylamino, ethylamino, propylamino, isopropylamino, and butylamino. Di-$(C_1-C_4)$alkylamino is preferred and here, in particular, dimethyl-, ethylmethyl-, diethyl- or diisopropylamino.

Mono- or -di$(C_1-C_4)$alkylamino$(C_1-C_2)$alkyl represents $(C_1-C_2)$alkyl radicals having 1 to 2 carbon atoms, which are substituted by one of the above mentioned mono- or di-$(C_1-C_4)$alkylamino radicals. Examples which may be mentioned are dimethyl-, diethyl- or diisopropylaminomethyl, dimethyl-, diethyl- or diisopropylaminoethyl.

$(C_1-C_4)$alkyl which is partially or completely substituted by fluorine, represents straight chain or branched alkyl radicals having 1 to 4 carbon atoms wherein one or more hydrogen atoms are replaced by a fluorine atom. Examples which may be mentioned are the 2,2,3,3,3-pentafluoropropyl, the perfluoroethyl, the 1,2,2-trifluoroethyl, the 1,1,2,2-tetrafluoroethyl, the 2,2,2-trifluoroethyl, the trifluoromethyl, the difluoromethyl and, in particular, the 2,2-difluoroethyl radicals.

$(C_1-C_4)$alkoxy which is predominantly or completely substituted by fluorine represents straight chain or branched alkyl radicals having 1 to 4 carbon atoms and a terminal oxygen atom. Examples which may be mentioned are the 2,2,3,3,3-pentafluoropropoxy, the perfluoroethoxy, the 1,2,2-trifluoroethoxy, the 1,1,2,2-tetrafluoroethoxy, the 2,2,2-trifluoroethoxy, the trifluoromethoxy and the difluoromethoxy radical, of which the difluoromethoxy and trifluoromethoxy radical is preferred. "Predominantly" in this connection means that more than half of the hydrogen atoms of the $C_1$-$C_4$-alkoxy group are replaced by fluorine atoms.

($C_1$-$C_4$)alkoxycarbonyl represents a radical which, in addition to the carbonyl group, contains one of the above mentioned alkoxy radicals. Examples which may be mentioned are methoxycarbonyl, ethoxycarbonyl, propoxycarbonyl, isopropoxycarbonyl and butoxycarbonyl.

($C_1$-$C_4$)alkylcarbonylamino represents a radical, which contains one of the above mentioned alkyl radicals linked to a carbonyl group, which is then linked to a terminal amino group. Examples, which may be mentioned are methylcarbonylamino, ethylcarbonylamino, propylcarbonylamino, isopropylcarbonylamino.

($C_3$-$C_7$)cycloalkyl represents cyclopropyl, cyclobutyl, cyclopentyl, cyclohexyl and cycloheptyl, of which cyclohexyl and cyclopropyl is preferred.

B is selected from hydrogen, halogen, ($C_1$-$C_4$)alkyl, ($C_1$-$C_4$)alkoxy, thienyl, N(R12)R13 wherein R12 and R13 are as defined above. Examples which may be mentioned are fluorine, chlorine, methyl, ethyl, isopropyl, propyl, methoxy, 2-thienyl, 3-thienyl, pyrrolidin-1-yl, and dimethylamino.

B can be attached in the ortho, meta or para position with respect to the binding position in which the amino radical is bonded to the phenyl ring, whereby, preference is given to the attachment in the para or ortho position.

The heterocyclic groups mentioned herein refer, unless otherwise noted, in particular to all of the possible positional isomers thereof. Thus, for example, the term pyridyl or pyridinyl, alone or as part of another group, includes pyridin-2-yl, pyridin-3-yl and pyridin-4-yl with pyridin-4-yl being preferred. Thienyl includes thiophen-2-yl and thiophen-3-yl. The heterocyclic groups mentioned herein refer, unless otherwise noted, to all of the possible tautomers, e.g. the keto/enol tautomers, thereof, in pure form as well as any mixtures thereof. Thus, for example, pyridine compounds which are substituted by a hydroxyl or an oxo group in the 2- or 4-position of the pyridine ring can exist in different tautomeric forms, i.e. the enol and the keto form, which are both contemplated by the present invention in pure form as well as in any mixtures thereof.

Constituents, which are optionally substituted as stated herein, may be substituted, unless otherwise noted, at any possible position.

Compounds of the invention and salts thereof containing a double bond may exist as E isomers and Z isomers. Both said isomers as well as mixtures of said isomers are included in the invention. The Z isomer is the geometric isomer in which the carbon atoms connected by the double bond each have the two highest ranking groups on the same side of the double bond. The E isomer is the geometric isomer in which the carbon atoms connected by the double bond each have the two highest ranking groups on opposite sides of the double bond.

In a preferred embodiment the invention relates to compounds of formula I:

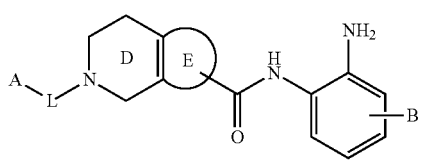

I wherein
ring D and ring E together form a fused ring system selected from

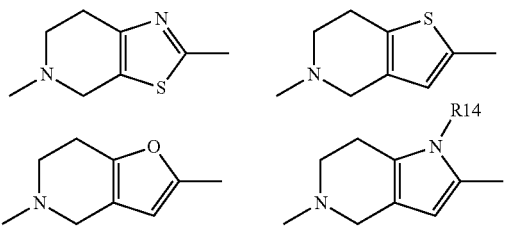

A is ($C_1$-$C_4$)alkyl, ($C_1$-$C_4$)alkoxy($C_1$-$C_2$)alkyl, ($C_1$-$C_4$)alkylthio($C_1$-$C_2$)alkyl, mono- or -di(($C_1$-$C_4$)alkylamino($C_1$-$C_2$)alkyl, ($C_3$-$C_7$)cycloalkyl optionally substituted by R1 and/or R2, ($C_3$-$C_7$)cycloalkyl substituted by R3, azetidinyl optionally substituted by R1 and/or R2, pyrrolidinyl optionally substituted by R1 and/or R2, piperidinyl optionally substituted by R1 and/or R2, phenyl optionally substituted by R1 and/or R2, phenyl substituted by R4, naphthyl optionally substituted by R1 and/or R2, pyridyl optionally substituted by R1 and/or R2, pyridyl substituted by R5, pyrimidinyl optionally substituted by R1 and/or R2, pyrimidinyl substituted by R8, triazinyl optionally substituted by R1 and/or R2, triazinyl substituted by R9; quinolinyl optionally substituted by R1 and/or R2, isoquinolinyl optionally substituted by R1 and/or R2, thienyl optionally substituted by R1 and/or R2, or thiazolyl optionally substituted by R1 and/or R2;

R1 is halogen, hydroxyl, cyano, nitro, amino, carboxyl, ($C_1$-$C_4$)alkyl, ($C_1$-$C_4$)alkoxy, ($C_1$-$C_4$)alkyl which is partially or completely substituted by fluorine, ($C_1$-$C_4$)alkoxy which is predominantly or completely substituted by fluorine, ($C_1$-$C_4$)alkoxy($C_1$-$C_2$)alkyl, ($C_1$-$C_4$)alkoxycarbonyl, mono- or -di($C_1$-$C_4$)alkylamino, or ($C_1$-$C_4$)alkylcarbonylamino;

R2 is halogen, hydroxyl, amino, ($C_1$-$C_4$)alkyl, or ($C_1$-$C_4$)alkoxy or

R1 and R2 when ortho to each other form a methylenedioxy or ethylenedioxy group;

R3 is 3-pyridyl, or 4-pyridyl;

R4 is phenyl, phenoxy, 4-methylpiperazinyl, benzylNHC(=O)NH—, or ($C_1$-$C_4$)alkylphenylsulfonylamino;

R5 is ($C_1$-$C_4$)alkylphenylsulfonylamino or N(R6)R7, wherein R6 and R7 together and with inclusion of the nitrogen atom to which they are bonded form an azetidinyl-, pyrrolidinyl-, piperidinyl-, piperazinyl-, 4-methylpiperazinyl-, morpholinyl- or thiomorpholinyl-ring;

R8 is pyridyl or ($C_1$-$C_4$)alkylphenylsulfonylamino;

R9 is piperidinyl;

L is bond, —$(CH_2)_nS(O)_2$—, —C(=O)—, —C(=S)—, —$(CH_2)_nOC(=O)$—, —$(CH_2)_nN(R10)C(=O)$—, —$(CH_2)_nN(R10)C(=NR11)$-, —$(CH_2)_nN(R10)C(=S)$—, —C=C—C(=O)—, —N=C(R11)-, —$(CH_2)_nN(R10)C(=O)C(=O)$—, —$OCH_2C(=O)$—, —N(R10)C(=CR11)-, or —N=C(NR11)-;

R10 is hydrogen, ($C_1$-$C_4$)alkyl or ($C_1$-$C_4$) alkoxy($C_1$-$C_2$)alkyl;

R11 is hydrogen, hydroxyl, cyano, nitro, or ($C_1$-$C_4$)alkyl;

B is hydrogen, halogen, ($C_1$-$C_4$)alkyl, ($C_1$-$C_4$)alkoxy, thienyl, or N(R12)R13 wherein R12 and R13 independently of one another are hydrogen, ($C_1$-$C_4$)alkyl, ($C_1$-$C_4$)alkylcarbonyl, or R12 and R13 together and with inclusion of the nitrogen atom to which they are bonded form an azetidinyl-, pyrrolidinyl-, piperidinyl-, piperazinyl-, 4-methylpiperazinyl-, morpholinyl- or thiomorpholinyl-ring;

R14 is hydrogen or ($C_1$-$C_4$)alkyl;

n is an integer selected from 0 to 2;

and the salts of these compounds.

In a preferred embodiment the invention relates to compounds of formula I as defined above, wherein
ring D and ring E together form a fused ring system selected from

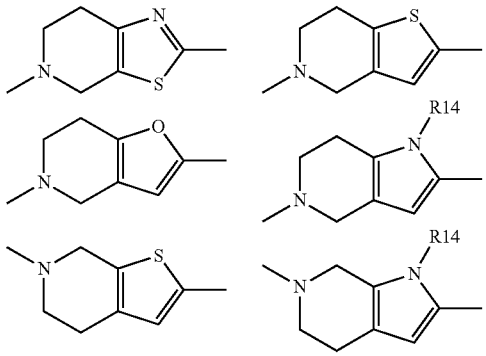

A is (C$_1$-C$_4$) alkyl, (C$_1$-C$_4$)alkoxy(C$_1$-C$_2$)alkyl, (C$_1$-C$_4$)alkylthio (C$_1$-C$_2$)alkyl, mono- or -di(C$_1$-C$_4$)alkylamino(C$_1$-C$_2$)alkyl, cyclohexyl optionally substituted by R1 and/or R2, cyclohexyl substituted by R3, azetidinyl optionally substituted by R1 and/or R2, piperidinyl optionally substituted by R1 and/or R2, phenyl optionally substituted by R1 and/or R2, phenyl substituted by R4, naphthyl optionally substituted by R1 and/or R2, pyridyl optionally substituted by R1 and/or R2, pyridyl substituted by R5, pyrimidinyl optionally substituted by R1 and/or R2, pyrimidinyl substituted by R8, triazinyl optionally substituted by R1 and/or R2, triazinyl substituted by R9, quinolinyl optionally substituted by R1 and/or R2, isoquinolinyl optionally substituted by R1 and/or R2, thienyl optionally substituted by R1 and/or R2, or thiazolyl optionally substituted by R1 and/or R2 or indazolyl optionally substituted by R1 and/or R2;

R1 is fluorine, hydroxyl, cyano, nitro, amino, carboxyl, (C$_1$-C$_4$)alkyl, (C$_1$-C$_4$)alkoxy, (C$_1$-C$_4$)alkyl which is partially or completely substituted by fluorine, (C$_1$-C$_4$)alkoxy which is predominantly or completely substituted by fluorine, (C$_1$-C$_4$)alkoxy(C$_1$-C$_2$)alkyl, (C$_1$-C$_4$)alkoxycarbonyl, mono- or -di(C$_1$-C$_4$)alkylamino, or (C$_1$-C$_4$)alkylcarbonylamino;

R2 is fluorine, hydroxyl, amino, (C$_1$-C$_4$)alkyl, or (C$_1$-C$_4$) alkoxy or

R1 and R2 when ortho to each other form a methylenedioxy or ethylenedioxy group;

R3 is 3-pyridyl or 4-pyridyl;

R4 is phenyl, phenoxy, 4-methylpiperazinyl, benzylNHC(=O)NH—, or methylphenylsulfonylamino;

R5 is methylphenylsulfonylamino, or N(R6)R7, wherein R6 and R7 together and with inclusion of the nitrogen atom to which they are bonded form an azetidinyl-, piperidinyl-, piperazinyl-, 4-methylpiperazinyl-, or morpholinyl-ring;

R8 is pyridyl or methylphenylsulfonylamino;

R9 is piperidinyl;

L is bond, —(CH$_2$)$_n$S(O)$_2$—, —C(=O)—, —C(=S)—, —(CH$_2$)$_n$OC(=O)—, —(CH$_2$)$_n$N(R10)C(=O)—, —(CH$_2$)$_n$N(R10)C(=NR11)-, —(CH$_2$)$_n$N(R10)C(=S)—, —C=C—C(=O)—, —N=C(R11)-, —(CH$_2$)$_n$N(R10)C(=O)C(=O)—, —OCH$_2$C(=O)—, —N(R10)C(=CR11)-, —N(R10)CH$_2$C(=O)— or —N=C(NR11)-;

R10 is hydrogen, (C$_1$-C$_4$)alkyl, or (C$_1$-C$_4$)alkoxy (C$_1$-C$_2$) alkyl;

R11 is hydrogen, hydroxyl, cyano, nitro, methyl, or ethyl;

B is hydrogen, halogen, (C$_1$-C$_4$)alkyl, (C$_1$-C$_4$)alkoxy, thienyl, or N(R12)R13 wherein R12 and R13 independently of one another are hydrogen, (C$_1$-C$_4$)alkyl, or R12 and R13 together and with inclusion of the nitrogen atom to which they are bonded form a pyrrolidinyl-, ring;

R14 is hydrogen or methyl;

n is an integer selected from 0 and 1;

and the salts of these compounds.

In a further preferred embodiment the invention relates to compounds of formula I as defined above,
wherein
ring D and ring E together form a fused ring system selected from

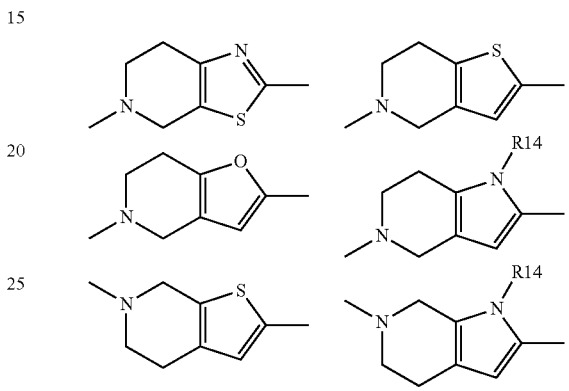

A is (C$_1$-C$_4$)alkyl, (C$_1$-C$_4$)alkoxy(C$_1$-C$_2$)alkyl, cyclohexyl optionally substituted by R1 and/or R2, cyclohexyl substituted by R3, piperidinyl optionally substituted by R1 and/or R2, phenyl optionally substituted by R1 and/or R2, phenyl substituted by R4, naphthyl optionally substituted by R1 and/or R2, pyridyl optionally substituted by R1 and/or R2, pyridyl substituted by R5, pyrimidinyl optionally substituted by R1 and/or R2, pyrimidyl substituted by R8, triazinyl optionally substituted by R1 and/or R2, triazinyl substituted by R9, quinolinyl optionally substituted by R1 and/or R2, isoquinolinyl optionally substituted by R1 and/or R2, thienyl optionally substituted by R1 and/or R2, or thiazolyl optionally substituted by R1 and/or R2 or indazolyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R3 is 3-pyridyl or 4-pyridyl

R4 is phenyl, phenoxy, 4-methylpiperazinyl, benzylNHC(=O)NH—, or methylphenylsulfonylamino, R5 is methylphenylsulfonylamino, N(R6)R7, wherein R6 and R7 together and with inclusion of the nitrogen atom to which they are bonded form an azetidinyl-, piperidinyl-, piperazinyl-, 4-methylpiperazinyl-, morpholinyl-ring;

R8 is pyridyl or methylphenylsulfonylamino;

R9 is piperidinyl;

L is bond, —(CH$_2$)$_n$S(O)$_2$—, —C(=O)—, —C(=S)—, —(CH$_2$)$_n$OC(=O)—, —(CH$_2$)$_n$N(R10)C(=O)—, —(CH$_2$)$_n$N(R10)C(=NR11)—, —(CH$_2$)$_n$N(R10)C(=S)—, —C=C—C(=O)—, —N=C(R11)—, —(CH$_2$)$_n$N(R10)C(=O)C(=O)—, —OCH$_2$C(=O)—, —N(R10)C(=CR11)—, —N(R10)CH$_2$C(=O)— or —N=C(NR11)—;

R10 is hydrogen, methyl, ethyl, propyl, methoxyethyl, ethoxyethyl, methoxymethyl, or ethoxymethyl;

R11 is hydrogen, hydroxyl, cyano, nitro, methyl, or ethyl;

B is hydrogen, fluorine, chlorine, methyl, ethyl, propyl, isopropyl, methoxy, ethoxy, thienyl, N(R12)R13 wherein R12 and R13 independently of one another are hydrogen, methyl, ethyl, or R12 and R13 together and with inclusion of the nitrogen atom to which they are bonded form a pyrrolidinyl-ring;

R14 is hydrogen or methyl;

n is an integer selected from 0 and 1;

and the salts of these compounds.

Another preferred embodiment of the invention relates to compounds of formula I
wherein
ring D and ring E together form a fused ring system selected from

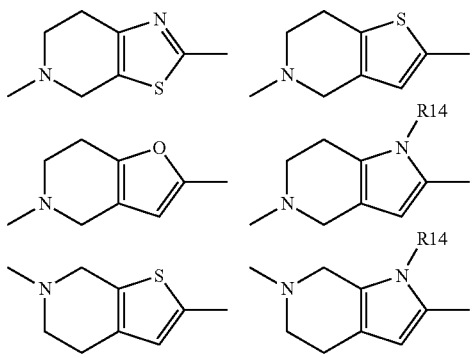

wherein L is —(CH$_2$)$_n$N(R10)C(=O)C(=O)—;

A is (C$_1$-C$_4$)alkyl, (C$_1$-C$_4$)alkoxy(C$_1$-C$_2$)alkyl, mono- or -di(C$_1$-C$_4$)alkylamino(C$_1$-C$_2$)alkyl, cyclohexyl optionally substituted by R1 and/or R2, cyclohexyl substituted by R3, phenyl optionally substituted by R1 and/or R2, phenyl substituted by R4, naphthyl optionally substituted by R1 and/or R2, pyridyl optionally substituted by R1 and/or R2, pyridyl substituted by R5, quinolinyl optionally substituted by R1 and/or R2, or isoquinolinyl optionally substituted by R1 and/or R2;

R1 is fluorine, hydroxyl, nitro, amino, carboxyl, (C$_1$-C$_4$)alkyl, (C$_1$-C$_4$)alkoxy, (C$_1$-C$_4$)alkyl which is partially or completely substituted by fluorine, (C$_1$-C$_4$)alkoxy which is predominantly or completely substituted by fluorine, (C$_1$-C$_4$)alkoxy(C$_1$-C$_2$)alkyl, (C$_1$-C$_4$)alkoxycarbonyl, mono- or -di(C$_1$-C$_4$)alkylamino or (C$_1$-C$_4$)alkylcarbonylamino;

R2 is hydroxyl, (C$_1$-C$_4$)alkyl, or (C$_1$-C$_4$)alkoxy or

R1 and R2 when ortho to each other form a methylenedioxy group;

R3 is 3-pyridyl or 4-pyridyl;

R4 is phenyl, phenoxy, or 4-methylpiperazinyl;

R5 is —N(R6)R7, wherein R6 and R7 together and with inclusion of the nitrogen atom to which they are bonded form an azetidinyl-, piperidinyl-, piperazinyl-, 4-methylpiperazinyl-, or morpholinyl-ring;

R10 is hydrogen or (C$_1$-C$_4$)alkyl;

B is hydrogen, fluorine, chlorine, (C$_1$-C$_4$)alkyl, (C$_1$-C$_4$)alkoxy, or thienyl;

R14 is hydrogen, or methyl;

n is an integer selected from 0 and 1;

and the salts of these compounds.

Another preferred embodiment of the invention relates to compounds of formula I
wherein
ring D and ring E together form a fused ring system selected from

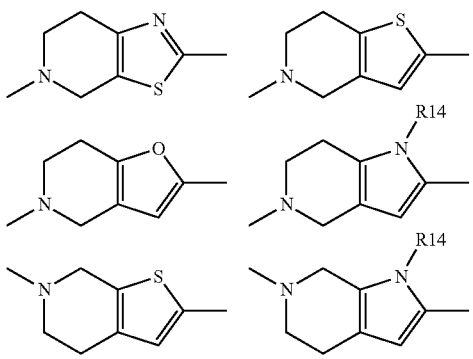

wherein L is —(CH$_2$)$_n$N(R10)C(=O)—;

A is (C$_1$-C$_4$)alkyl, (C$_1$-C$_4$)alkoxy(C$_1$-C$_2$)alkyl, (C$_1$-C$_4$)alkylthio(C$_1$-C$_2$)alkyl, mono- or -di(C$_1$-C$_4$)alkylamino(C$_1$-C$_2$)alkyl, cyclohexyl optionally substituted by R1 and/or R2, cyclohexyl substituted by R3, azetidinyl optionally substituted by R1 and/or R2, piperidinyl optionally substituted by R1 and/or R2, phenyl optionally substituted by R1 and/or R2, phenyl substituted by R4, naphthyl optionally substituted by R1 and/or R2, pyridyl optionally substituted by R1 and/or R2, pyridyl substituted by R5, quinolinyl optionally substituted by R1 and/or R2, or isoquinolinyl optionally substituted by R1 and/or R2 or indazolyl optionally substituted by R1 and/or R2;

R1 is fluorine, hydroxyl, nitro, amino, carboxyl, (C$_1$-C$_4$)alkyl, (C$_1$-C$_4$)alkoxy, (C$_1$-C$_4$)alkyl which is partially or completely substituted by fluorine, (C$_1$-C$_4$)alkoxy which is predominantly or completely substituted by fluorine, (C$_1$-C$_4$)alkoxy(C$_1$-C$_2$)alkyl, (C$_1$-C$_4$)alkoxycarbonyl, mono- or -di(C$_1$-C$_4$)alkylamino or (C$_1$-C$_4$)alkylcarbonylamino;

R2 is hydroxyl, (C$_1$-C$_4$)alkyl, or (C$_1$-C$_4$)alkoxy or

R1 and R2 when ortho to each other form a methylenedioxy group;

R3 is 3-pyridyl or 4-pyridyl;

R4 is phenyl, phenoxy, or 4-methylpiperazinyl;

R5 is —N(R6)R7, wherein R6 and R7 together and with inclusion of the nitrogen atom to which they are bonded form an azetidinyl-, piperidinyl-, piperazinyl-, 4-methylpiperazinyl-, or morpholinyl-ring;

R10 is hydrogen, (C$_1$-C$_4$)alkyl, methoxyethyl, ethoxyethyl, methoxymethyl, or ethoxymethyl;

B is hydrogen, fluorine, chlorine, (C$_1$-C$_4$)alkyl, (C$_1$-C$_4$)alkoxy, thienyl, or N(R12)R13 wherein R12 and R13 independently of one another are hydrogen, (C$_1$-C$_4$)alkyl, or R12 and R13 together and with inclusion of the nitrogen atom to which they are bonded form a pyrrolidinyl-ring;

R14 is hydrogen or methyl;

n is an integer selected from 0 and 1;

and the salts of these compounds.

Another preferred embodiment of the invention relates to compounds of formula I wherein
ring D and ring E together form a fused ring system selected from

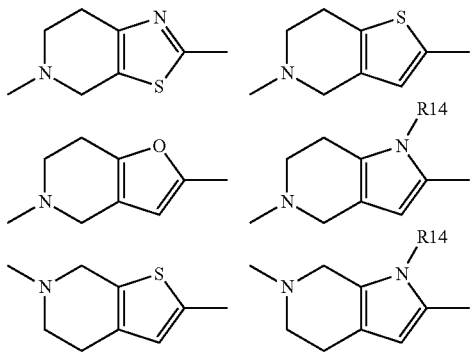

wherein L is —N(R10)CH₂C(=O)—;

A is (C₁-C₄)alkyl, (C₁-C₄)alkoxy(C₁-C₂)alkyl, (C₁-C₄)alkylthio(C₁-C₂)alkyl, mono- or -di(C₁-C₄)alkylamino(C₁-C₂)alkyl, cyclohexyl optionally substituted by R1 and/or R2, cyclohexyl substituted by R3, azetidinyl optionally substituted by R1 and/or R2, piperidinyl optionally substituted by R1 and/or R2, phenyl optionally substituted by R1 and/or R2, phenyl substituted by R4, naphthyl optionally substituted by R1 and/or R2, pyridyl optionally substituted by R1 and/or R2, pyridyl substituted by R5, quinolinyl optionally substituted by R1 and/or R2, or isoquinolinyl optionally substituted by R1 and/or R2 or indazolyl optionally substituted by R1 and/or R2;

R1 is fluorine, hydroxyl, nitro, amino, carboxyl, (C₁-C₄)alkyl, (C₁-C₄) alkoxy, (C₁-C₄)alkyl which is partially or completely substituted by fluorine, (C₁-C₄)alkoxy which is predominantly or completely substituted by fluorine, (C₁-C₄)alkoxy (C₁-C₂)alkyl, (C₁-C₄)alkoxycarbonyl, mono- or -di(C₁-C₄)alkylamino or or (C₁-C₄)alkylcarbonylamino;

R2 is hydroxyl, (C₁-C₄) alkyl, or (C₁-C₄) alkoxy or

R1 and R2 when ortho to each other form a methylenedioxy group;

R3 is 3-pyridyl or 4-pyridyl;

R4 is phenyl, phenoxy, or 4-methylpiperazinyl;

R5 is —N(R6)R7, wherein R6 and R7 together and with inclusion of the nitrogen atom to which they are bonded form an azetidinyl-, piperidinyl-, piperazinyl-, 4-methylpiperazinyl-, or morpholinyl-ring;

R10 is hydrogen, (C₁-C₄)alkyl, methoxyethyl, ethoxyethyl, methoxymethyl, or ethoxymethyl;

B is hydrogen, fluorine, chlorine, (C₁-C₄) alkyl, (C₁-C₄) alkoxy, thienyl, or N(R12)R13 wherein R12 and R13 independently of one another are hydrogen, (C₁-C₄) alkyl, or R12 and R13 together and with inclusion of the nitrogen atom to which they are bonded form a pyrrolidinyl-ring;

R14 is hydrogen or methyl;

and the salts of these compounds.

Another preferred embodiment of the invention relates to compounds of formula I
wherein
ring D and ring E together form a fused ring system selected from

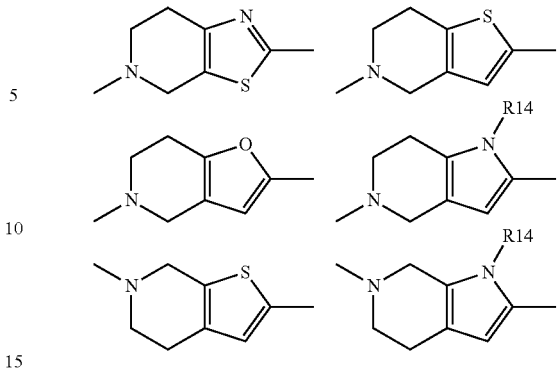

wherein L is —C(=O)—;

A is (C₁-C₄) alkyl, (C₁-C₄) alkoxy (C₁-C₂)alkyl, (C₁-C₄) alkylthio(C₁-C₂)alkyl, mono- or -di(C₁-C₄)alkylamino (C₁-C₂)alkyl, phenyl optionally substituted by R1 and/or R2, phenyl substituted by R4, naphthyl optionally substituted by R1 and/or R2, pyridyl optionally substituted by R1 and/or R2, quinolinyl optionally substituted by R1 and/or R2, or isoquinolinyl optionally substituted by R1 and/or R2;

R1 is (C₁-C₄)alkyl, (C₁-C₄)alkoxy, (C₁-C₄)alkyl which is partially or completely substituted by fluorine, (C₁-C₄) alkoxy which is predominantly or completely substituted by fluorine, (C₁-C₄)alkoxy(C₁-C₂)alkyl, (C₁-C₄)alkoxycarbonyl, or mono- or -di(C₁-C₄)alkylamino;

R2 is (C₁-C₄) alkyl or (C₁-C₄)alkoxy;

R4 is phenyl or phenoxy;

B is hydrogen, fluorine, chlorine, (C₁-C₄) alkyl, or thienyl;

R14 Is hydrogen or methyl;

and the salts of these compounds.

Another preferred embodiment of the present invention relates to compounds of formula I
wherein
ring D and ring E together form a fused ring system selected from

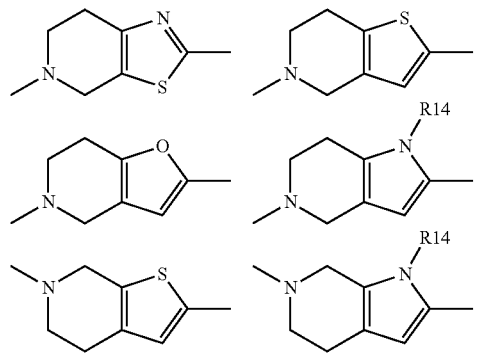

wherein L is —(CH₂)ₙN(R10)C(=N(R11))-;

A is (C₁-C₄)alkyl, (C₁-C₄)alkoxy(C₁-C₂)alkyl, (C₁-C₄)alkylthio(C₁-C₂)alkyl, mono- or -di(C₁-C₄)alkylamino(C₁-C₂) alkyl, phenyl optionally substituted by R1 and/or R2, phenyl substituted by R4, or naphthyl optionally substituted by R1 and/or R2;

R1 is (C₁-C₄)alkyl, (C₁-C₄)alkoxy, (C₁-C₄)alkyl which is partially or completely substituted by fluorine, (C₁-C₄) alkoxy which is predominantly or completely substituted by fluorine, $(C_1-C_4)$alkoxy$(C_1-C_2)$alkyl, $(C_1-C_4)$alkoxycarbonyl, or mono- or -di$(C_1-C_4)$alkylamino;

R2 is $(C_1-C_4)$alkoxy, or

R1 and R2 when ortho to each other form a methylenedioxy group;

R4 is phenyl or phenoxy;

R10 is hydrogen, or $(C_1-C_4)$alkyl;

R11 is hydrogen, cyano, or methyl;

B is hydrogen, fluorine, chlorine, $(C_1-C_4)$alkyl, $(C_1-C_4)$alkoxy, or thienyl;

R14 is hydrogen, or methyl;

n is an integer selected from 0 and 1;

and the salts of these compounds.

Another preferred embodiment of the present invention relates to compounds of formula I
wherein
ring D and ring E together form a fused ring system selected from wherein L is —N=C(R11)-;

A is $(C_1-C_4)$alkyl, phenyl optionally substituted by R1 and/or R2, phenyl substituted by R4, or naphthyl optionally substituted by R1 and/or R2;

R1 is $(C_1-C_4)$alkyl, $(C_1-C_4)$alkoxy, $(C_1-C_4)$alkyl which is partially or completely substituted by fluorine, $(C_1-C_4)$alkoxy which is predominantly or completely substituted by fluorine, $(C_1-C_4)$alkoxy$(C_1-C_2)$alkyl, $(C_1-C_4)$alkoxycarbonyl, or mono- or -di$(C_1-C_4)$alkylamino;

R2 is $(C_1-C_4)$alkoxy, or

R1 and R2 when ortho to each other form a methylenedioxy group;

R4 is phenyl;

R11 is hydrogen, or methyl;

B is hydrogen, fluorine, chlorine, $(C_1-C_4)$alkyl, $(C_1-C_4)$alkoxy, or thienyl;

R14 is hydrogen, or methyl;

and the salts of these compounds.

Another preferred embodiment of the present invention relates to compounds of formula I
wherein
ring D and ring E together form a fused ring system selected from wherein L is —N(R10)C(=C(R11))-;

A is $(C_1-C_4)$alkyl, phenyl optionally substituted by R1 and/or R2, phenyl substituted by R4, or naphthyl optionally substituted by R1 and/or R2;

R1 is fluorine, $(C_1-C_4)$alkyl, $(C_1-C_4)$alkoxy, $(C_1-C_4)$alkyl which is partially or completely substituted by fluorine, $(C_1-C_4)$alkoxy which is predominantly or completely substituted by fluorine, $(C_1-C_4)$alkoxy$(C_1-C_2)$alkyl, $(C_1-C_4)$alkoxycarbonyl, or mono- or -di$(C_1-C_4)$alkylamino;

R2 is $(C_1-C_4)$alkoxy, or

R1 and R2 when ortho to each other form a methylenedioxy group;

R4 is phenyl;

R10 is hydrogen, or $(C_1-C_4)$alkyl;

R11 is hydrogen, nitro, or methyl;

B is hydrogen, fluorine, chlorine, $(C_1-C_4)$alkyl, $(C_1-C_4)$alkoxy, or thienyl;

R14 is hydrogen, or methyl;

and the salts of these compounds.

Another preferred embodiment of the present invention relates to compounds of formula I
wherein
ring D and ring E together form a fused ring system selected from wherein L is —$(CH_2)_nS(O)_2$—;

A is $(C_1-C_4)$alkyl, phenyl optionally substituted by R1 and/or R2, phenyl substituted by R4, naphthyl optionally substituted by R1 and/or R2, thienyl optionally substituted by R1 and/or R2, thiazolyl optionally substituted by R1 and/or R2;

R1 is fluorine, $(C_1-C_4)$alkyl, $(C_1-C_4)$alkoxy, $(C_1-C_4)$alkyl which is partially or completely substituted by fluorine, $(C_1-C_4)$alkoxy which is predominantly or completely substituted by fluorine, $(C_1-C_4)$alkoxy$(C_1-C_2)$alkyl, $(C_1-C_4)$alkoxycarbonyl, mono- or -di$(C_1-C_4)$alkylamino, or $(C_1-C_4)$alkylcarbonylamino;

R2 is $(C_1-C_4)$alkyl, or $(C_1-C_4)$alkoxy, or

R1 and R2 when ortho to each other form a methylenedioxy group;
R4 is phenyl;
B is hydrogen, fluorine, chlorine, $(C_1-C_4)$alkyl, $(C_1-C_4)$alkoxy, or thienyl;
R14 is hydrogen or methyl;
n is an integer selected from 0 and 1;
and the salts of these compounds.

Another preferred embodiment of the present invention relates to compounds of formula I
wherein
ring D and ring E together form a fused ring system selected from

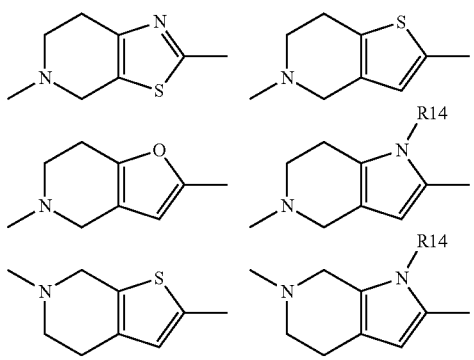

wherein L is —N(R10)C(=S)—;
A is $(C_1-C_4)$alkyl, cyclohexyl optionally substituted by R1 and/or R2, cyclohexyl substituted by R3, piperidinyl optionally substituted by R1 and/or R2, phenyl optionally substituted by R1 and/or R2, phenyl substituted by R4, naphthyl optionally substituted by R1 and/or R2, pyridyl optionally substituted by R1 and/or R2, quinolinyl optionally substituted by R1 and/or R2, or isoquinolinyl optionally substituted by R1 and/or R2;
R1 is fluorine, $(C_1-C_4)$alkyl, $(C_1-C_4)$alkoxy, $(C_1-C_4)$alkyl which is partially or completely substituted by fluorine, $(C_1-C_4)$alkoxy which is predominantly or completely substituted by fluorine, $(C_1-C_4)$alkoxy$(C_1-C_2)$alkyl, $(C_1-C_4)$alkoxycarbonyl, or mono- or -di$(C_1-C_4)$alkylamino;
R2 is $(C_1-C_4)$alkyl or $(C_1-C_4)$alkoxy, or
R1 and R2 when ortho to each other form a methylenedioxy group;
R3 is 3-pyridyl or 4-pyridyl;
R4 is phenyl;
R10 is hydrogen or $(C_1-C_4)$alkyl;
B is hydrogen, fluorine, chlorine, $(C_1-C_4)$alkyl, $(C_1-C_4)$alkoxy, or thienyl;
R14 is hydrogen or methyl;
and the salts of these compounds.

Another preferred embodiment of the present invention relates to compounds of formula I
wherein
ring D and ring E together form a fused ring system selected from

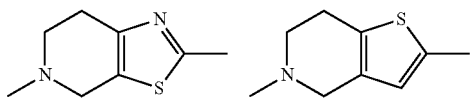

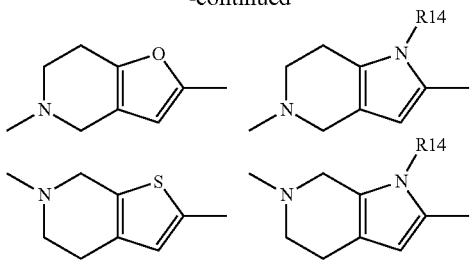

wherein L is —OCH$_2$C(=O)—;
A is $(C_1-C_4)$alkyl, phenyl optionally substituted by R1 and/or R2, phenyl substituted by R4, naphthyl optionally substituted by R1 and/or R2;
R1 is fluorine, $(C_1-C_4)$alkyl, $(C_1-C_4)$alkoxy, $(C_1-C_4)$alkyl which is partially or completely substituted by fluorine, $(C_1-C_4)$alkoxy which is predominantly or completely substituted by fluorine, $(C_1-C_4)$alkoxy$(C_1-C_2)$alkyl, $(C_1-C_4)$alkoxycarbonyl, or mono- or -di$(C_1-C_4)$alkylamino;
R2 is $(C_1-C_4)$alkyl or $(C_1-C_4)$alkoxy, or
R1 and R2 when ortho to each other form a methylenedioxy group;
R4 is phenyl;
B is hydrogen, fluorine, chlorine, $(C_1-C_4)$alkyl, $(C_1-C_4)$alkoxy, or thienyl;
R14 is hydrogen or methyl;
and the salts of these compounds.

Another preferred embodiment of the present invention relates to compounds of formula I
wherein
ring D and ring E together form a fused ring system selected from

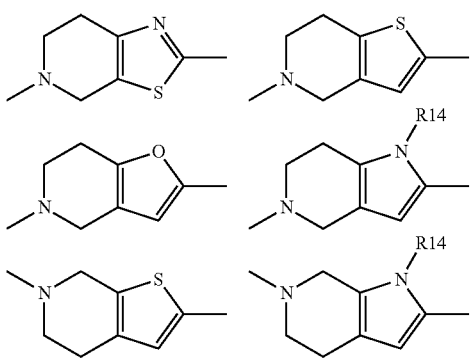

wherein L is —(CH$_2$)$_n$OC(=O)—;
A is $(C_1-C_4)$alkyl, phenyl optionally substituted by R1 and/or R2, phenyl substituted by R4, naphthyl optionally substituted by R1 and/or R2, pyridyl optionally substituted by R1 and/or R2, pyridyl substituted by R5;
R1 is fluorine, hydroxyl, nitro, amino, carboxyl, $(C_1-C_4)$alkyl, $(C_1-C_4)$alkoxy, $(C_1-C_4)$alkyl which is partially or completely substituted by fluorine, $(C_1-C_4)$alkoxy which is predominantly or completely substituted by fluorine, $(C_1-C_4)$alkoxy$(C_1-C_2)$alkyl, $(C_1-C_4)$alkoxycarbonyl, or mono- or -di$(C_1-C_4)$alkylamino;
R2 is hydroxyl, $(C_1-C_4)$alkyl, or $(C_1-C_4)$alkoxy or
R1 and R2 when ortho to each other form a methylenedioxy group;
R4 is phenyl, phenoxy, or 4-methylpiperazinyl;

R5 is —N(R6)R7, wherein R6 and R7 together and with inclusion of the nitrogen atom to which they are bonded form an azetidinyl-, piperidinyl-, piperazinyl-, 4-methylpiperazinyl-, or morpholinyl-ring;

B is hydrogen, fluorine, chlorine, $(C_1-C_4)$alkyl, $(C_1-C_4)$alkoxy, or thienyl;

R14 is hydrogen or methyl;

n is an integer selected from 0 and 1;

and the salts of these compounds.

Another preferred embodiment of the present invention relates to compounds of formula I
wherein
ring D and ring E together form a fused ring system selected from

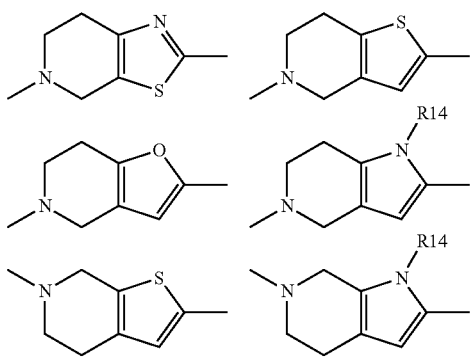

wherein L is —C═C—C(═O)—;

A is $(C_1-C_4)$alkyl, phenyl optionally substituted by R1 and/or R2, or naphthyl optionally substituted by R1 and/or R2;

R1 is fluorine, hydroxyl, $(C_1-C_4)$alkyl, $(C_1-C_4)$alkoxy, $(C_1-C_4)$alkyl which is partially or completely substituted by fluorine, $(C_1-C_4)$alkoxy which is predominantly or completely substituted by fluorine, $(C_1-C_4)$alkoxy$(C_1-C_2)$alkyl, $(C_1-C_4)$alkoxycarbonyl, or mono- or -di$(C_1-C_4)$alkylamino;

R2 is hydroxyl, $(C_1-C_4)$alkyl, or $(C_1-C_4)$alkoxy or

R1 and R2 when ortho to each other form a methylenedioxy group;

B is hydrogen, fluorine, chlorine, $(C_1-C_4)$alkyl, $(C_1-C_4)$alkoxy, or thienyl;

R14 is hydrogen or methyl;

and the salts of these compounds.

Another preferred embodiment of the present invention relates to compounds of formula I
wherein
ring D and ring E together form a fused ring system selected from

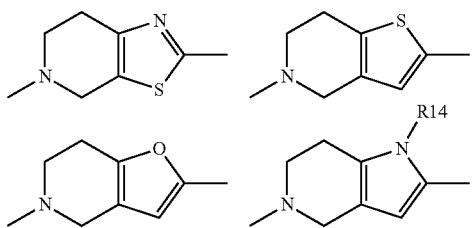

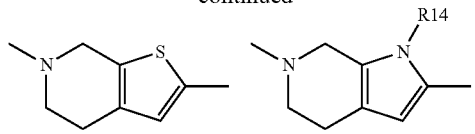

wherein L is bond;

A is $(C_1-C_4)$alkyl, phenyl optionally substituted by R1 and/or R2, phenyl substituted by R4, naphthyl optionally substituted by R1 and/or R2, pyridyl optionally substituted by R1 and/or R2, pyridyl substituted by R5, pyrimidinyl optionally substituted by R1 and/or R2, or pyrimidinyl substituted by R8;

R1 is fluorine, hydroxyl, nitro, amino, $(C_1-C_4)$alkyl, $(C_1-C_4)$alkoxy, $(C_1-C_4)$alkyl which is partially or completely substituted by fluorine, $(C_1-C_4)$alkoxy which is predominantly or completely substituted by fluorine, $(C_1-C_4)$alkoxy$(C_1-C_2)$alkyl, $(C_1-C_4)$alkoxycarbonyl, or mono- or -di$(C_1-C_4)$alkylamino;

R2 is hydroxyl, $(C_1-C_4)$alkyl, or $(C_1-C_4)$alkoxy or

R1 and R2 when ortho to each other form a methylenedioxy group;

R4 is phenyl, phenoxy, benzylNHC(═O)NH—, or methylphenylsulfonylamino;

R5 is methylphenylsulfonylamino, or N(R6)R7, wherein R6 and R7 together and with inclusion of the nitrogen atom to which they are bonded form an azetidinyl-, piperidinyl-, piperazinyl-, 4-methylpiperazinyl-, or morpholinyl-ring;

R8 is pyridyl or methylphenylsulfonylamino;

B is hydrogen, fluorine, chlorine, $(C_1-C_4)$alkyl, $(C_1-C_4)$alkoxy, or thienyl;

R14 is hydrogen or methyl;

and the salts of these compounds.

A special embodiment of the compounds of the present invention include those compounds of formula I wherein ring D and ring E together form the fused ring system

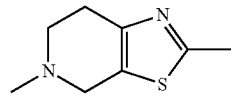

and L is bond and A, B have the meanings as defined above, and the salts of those compounds.

Another special embodiment of the compounds of the present invention include those compounds of formula I wherein
ring D and ring E together form the fused ring system

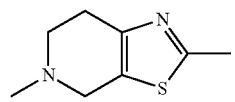

and L is —$(CH_2)_nS(O)_2$— and A, B, n have the meanings as defined above, and the salts of those compounds.

Another special embodiment of the compounds of the present invention include those compounds of formula I wherein
ring D and ring E together form the fused ring system

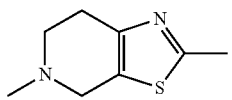

and L is —C(=O)— and A, B have the meanings as defined above, and the salts of those compounds.

Another special embodiment of the compounds of the present invention include those compounds of formula I wherein
ring D and ring E together form the fused ring system

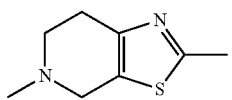

and L is —C(=S)— and A, B have the meanings as defined above, and the salts of those compounds.

Another special embodiment of the compounds of the present invention include those compounds of formula I wherein
ring D and ring E together form the fused ring system

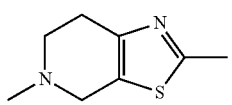

and L is —(CH$_2$)$_n$OC(=O)— and A, B, n have the meanings as defined above, and the salts of those compounds.

Another special embodiment of the compounds of the present invention include those compounds of formula I wherein
ring D and ring E together form the fused ring system

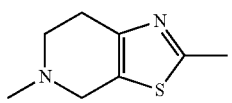

and L is —(CH$_2$)$_n$N(R10)C(=O)— and A, B, R10, n have the meanings as defined above, and the salts of those compounds.

Another special embodiment of the compounds of the present invention include those compounds of formula I wherein
ring D and ring E together form the fused ring system

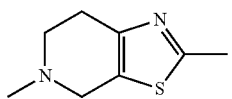

and L is —N(R10)CH$_2$C(=O)— and A, B, R10, have the meanings as defined above, and the salts of those compounds.

Another special embodiment of the compounds of the present invention include those compounds of formula I wherein
ring D and ring E together form the fused ring system

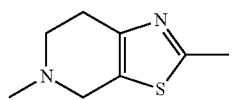

and L is —(CH$_2$)$_n$N(R10)C(=NR11)- and A, B, R10, R11, n have the meanings as defined above, and the salts of those compounds.

Another special embodiment of the compounds of the present invention include those compounds of formula I wherein
ring D and ring E together form the fused ring system

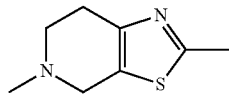

and L is —(CH$_2$)$_n$N(R10)C(=S)— and A, B, R10, n have the meanings as defined above, and the salts of those compounds.

Another special embodiment of the compounds of the present invention include those compounds of formula I wherein
ring D and ring E together form the fused ring system

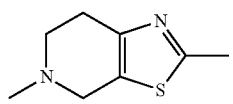

and L is —C=C—C(=O)— and A, B have the meanings as defined above, and the salts of those compounds.

Another special embodiment of the compounds of the present invention include those compounds of formula I wherein
ring D and ring E together form the fused ring system

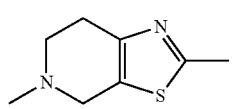

and L is —N=C(R11)- and A, B, R11 have the meanings as defined above, and the salts of those compounds.

Another special embodiment of the compounds of the present invention include those compounds of formula I wherein
ring D and ring E together form the fused ring system

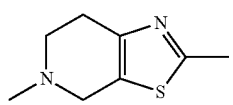

and L is —(CH$_2$)$_n$N(R10)C(=O)C(=O)— and A, B, R10, n have the meanings as defined above, and the salts of those compounds.

Another special embodiment of the compounds of the present invention include those compounds of formula I wherein
ring D and ring E together form the fused ring system

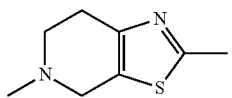

and L is —OCH$_2$C(=O)— and A, B have the meanings as defined above, and the salts of those compounds.

Another special embodiment of the compounds of the present invention include those compounds of formula I wherein
ring D and ring E together form the fused ring system

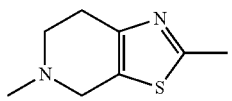

and L is —N(R10)C(=CR11)- and A, B, R10, R11 have the meanings as defined above, and the salts of those compounds.

Another special embodiment of the compounds of the present invention include those compounds of formula I wherein
ring D and ring E together form the fused ring system

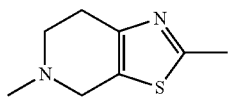

and L is —N=C(NR11)- and A, B, R11 have the meanings as defined above and the salts of those compounds.

A further special embodiment of the compounds of the present invention include those compounds of formula I wherein
ring D and ring E together form the fused ring system

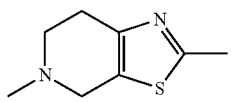

and L is bond, A is (C$_1$-C$_4$)alkyl, (C$_1$-C$_4$)alkoxy(C$_1$-C$_2$)alkyl, or (C$_1$-C$_4$)alkylthio(C$_1$-C$_2$)alkyl and B has the meaning as defined above, and the salts of those compounds.

Another special embodiment of the compounds of the present invention include those compounds of formula I wherein
ring D and ring E together form the fused ring system

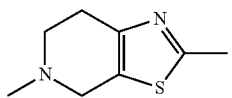

and L is —(CH$_2$)$_n$S(O)$_2$—, A is (C$_1$-C$_4$)alkyl, (C$_1$-C$_4$)alkoxy(C$_1$-C$_2$)alkyl, or (C$_1$-C$_4$)alkylthio(C$_1$-C$_2$)alkyl and B, n have the meanings as defined above, and the salts of those compounds.

Another special embodiment of the compounds of the present invention include those compounds of formula I wherein
ring D and ring E together form the fused ring system

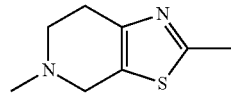

and L is —C(=O)—, A is (C$_1$-C$_4$)alkyl, (C$_1$-C$_4$)alkoxy(C$_1$-C$_2$)alkyl, or (C$_1$-C$_4$)alkylthio(C$_1$-C$_2$)alkyl and B has the meaning as defined above, and the salts of those compounds.

Another special embodiment of the compounds of the present invention include those compounds of formula I wherein
ring D and ring E together form the fused ring system

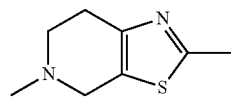

and L is —C(=S)—, A is (C$_1$-C$_4$)alkyl, (C$_1$-C$_4$)alkoxy(C$_1$-C$_2$)alkyl, or (C$_1$-C$_4$)alkylthio(C$_1$-C$_2$)alkyl and B has the meaning as defined above, and the salts of those compounds.

Another special embodiment of the compounds of the present invention include those compounds of formula I wherein
ring D and ring E together form the fused ring system

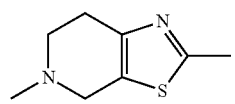

and L is —(CH$_2$)$_n$OC(=O)—, A is (C$_1$-C$_4$)alkyl, (C$_1$-C$_4$)alkoxy(C$_1$-C$_2$)alkyl, or (C$_1$-C$_4$)alkylthio(C$_1$-C$_2$)alkyl and B, n have the meanings as defined above, and the salts of those compounds.

Another special embodiment of the compounds of the present invention include those compounds of formula I wherein
ring D and ring E together form the fused ring system

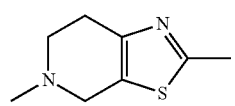

and L is —(CH$_2$)$_n$N(R10)C(=O)—, A is (C$_1$-C$_4$)alkyl, (C$_1$-C$_4$)alkoxy(C$_1$-C$_2$)alkyl, or (C$_1$-C$_4$)alkylthio(C$_1$-C$_2$)alkyl and B, R10, n have the meanings as defined above, and the salts of those compounds.

Another special embodiment of the compounds of the present invention include those compounds of formula I wherein
ring D and ring E together form the fused ring system

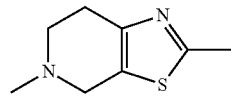

and L is —N(R10)CH$_2$C(=O)—, A is (C$_1$-C$_4$)alkyl, (C$_1$-C$_4$)alkoxy(C$_1$-C$_2$)alkyl, or (C$_1$-C$_4$)alkylthio(C$_1$-C$_2$)alkyl and B, R10, have the meanings as defined above, and the salts of those compounds.

Another special embodiment of the compounds of the present invention include those compounds of formula I wherein
ring D and ring E together form the fused ring system

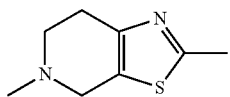

and L is —(CH$_2$)$_n$N(R10)C(=NR11)-, A is (C$_1$-C$_4$)alkyl, (C$_1$-C$_4$)alkoxy(C$_1$-C$_2$)alkyl, or (C$_1$-C$_4$)alkylthio(C$_1$-C$_2$)alkyl and B, R10, R11, n have the meanings as defined above, and the salts of those compounds.

Another special embodiment of the compounds of the present invention include those compounds of formula I wherein
ring D and ring E together form the fused ring system

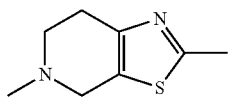

and L is —(CH$_2$)$_n$N(R10)C(=S)—, A is (C$_1$-C$_4$)alkyl, (C$_1$-C$_4$)alkoxy(C$_1$-C$_2$)alkyl, or (C$_1$-C$_4$)alkylthio(C$_1$-C$_2$)alkyl and B, R10, n have the meanings as defined above, and the salts of those compounds.

Another special embodiment of the compounds of the present invention include those compounds of formula I wherein
ring D and ring E together form the fused ring system

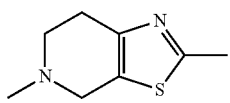

and L is —C=C—C(=O)—, A is (C$_1$-C$_4$)alkyl, (C$_1$-C$_4$)alkoxy(C$_1$-C$_2$)alkyl, or (C$_1$-C$_4$)alkylthio(C$_1$-C$_2$)alkyl and B has the meaning as defined above, and the salts of those compounds.

Another special embodiment of the compounds of the present invention include those compounds of formula I wherein
ring D and ring E together form the fused ring system

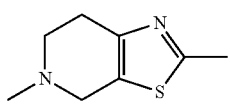

and L is —N=C(R11)-, A is (C$_1$-C$_4$)alkyl, (C$_1$-C$_4$)alkoxy(C$_1$-C$_2$)alkyl, or (C$_1$-C$_4$)alkylthio(C$_1$-C$_2$)alkyl and B, R11 have the meanings as defined above, and the salts of those compounds.

Another special embodiment of the compounds of the present invention include those compounds of formula I wherein
ring D and ring E together form the fused ring system

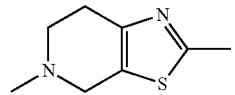

and L is —(CH$_2$)$_n$N(R10)C(=O)C(=O)—, A is (C$_1$-C$_4$)alkyl, (C$_1$-C$_4$)alkoxy(C$_1$-C$_2$)alkyl, or (C$_1$-C$_4$)alkylthio(C$_1$-C$_2$)alkyl and B, R10, n have the meanings as defined above, and the salts of those compounds.

Another special embodiment of the compounds of the present invention include those compounds of formula I wherein
ring D and ring E together form the fused ring system

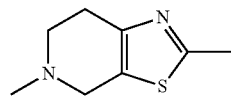

and L is —OCH$_2$C(=O)—, A is (C$_1$-C$_4$)alkyl, (C$_1$-C$_4$)alkoxy(C$_1$-C$_2$)alkyl, or (C$_1$-C$_4$)alkylthio(C$_1$-C$_2$)alkyl and, B has the meaning as defined above, and the salts of those compounds.

Another special embodiment of the compounds of the present invention include those compounds of formula I wherein
ring D and ring E together form a fused ring system selected from

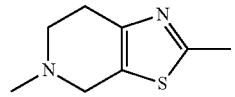

and L is —N(R10)C(=CR11)-, A is (C$_1$-C$_4$)alkyl, (C$_1$-C$_4$)alkoxy(C$_1$-C$_2$)alkyl, or (C$_1$-C$_4$)alkylthio(C$_1$-C$_2$)alkyl and B, R10, R11 have the meanings as defined above, and the salts of those compounds.

Another special embodiment of the compounds of the present invention include those compounds of formula I wherein
ring D and ring E together form a fused ring system selected from

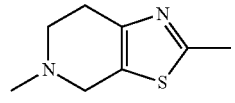

and L is —N=C(NR11)-, A is (C$_1$-C$_4$)alkyl, (C$_1$-C$_4$)alkoxy(C$_1$-C$_2$)alkyl, or (C$_1$-C$_4$)alkylthio(C$_1$-C$_2$)alkyl and B, R11 have the meanings as defined above, and the salts of those compounds.

A further special embodiment of the compounds of the present invention include those compounds of formula I wherein
ring D and ring E together form the fused ring system

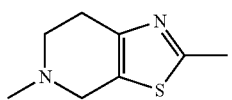

L is bond; A is phenyl optionally substituted by R1 and/or R2, phenyl substituted by R4, naphthyl optionally substituted by R1 and/or R2, pyridyl optionally substituted by R1 and/or R2, pyridyl substituted by R5, pyrimidinyl optionally substituted by R1 and/or R2, pyrimidyl substituted by R8, quinolinyl optionally substituted by R1 and/or R2, or isoquinolinyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R4 is phenyl, phenoxy, 4-methylpiperazinyl, benzylNHC(=O)NH—, or methylphenylsulfonylamino, R5 is methylphenylsulfonylamino, N(R6)R7, wherein R6 and R7 together and with inclusion of the nitrogen atom to which they are bonded form an azetidinyl-, piperidinyl-, piperazinyl-, 4-methylpiperazinyl-, or morpholinyl-ring;

R8 is pyridyl or methylphenylsulfonylamino;

and B has the meaning as defined above, and the salts of those compounds.

A further special embodiment of the compounds of the present invention include those compounds of formula I wherein
ring D and ring E together form the fused ring system

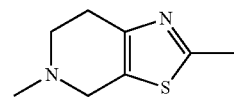

L is bond; A is phenyl optionally substituted by R1 and/or R2, phenyl substituted by R4, naphthyl optionally substituted by R1 and/or R2, pyridyl optionally substituted by R1 and/or R2, pyridyl substituted by R5, pyrimidinyl optionally substituted by R1 and/or R2, pyrimidyl substituted by R8, quinolinyl optionally substituted by R1 and/or R2, or isoquinolinyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R4 is phenyl, phenoxy, 4-methylpiperazinyl, benzylNHC(=O)NH—, or methylphenylsulfonylamino, R5 is methylphenylsulfonylamino, N(R6)R7, wherein R6 and R7 together and with inclusion of the nitrogen atom to which they are bonded form an azetidinyl-, piperidinyl-, piperazinyl-, 4-methylpiperazinyl-, or morpholinyl-ring;

R8 is pyridyl or methylphenylsulfonylamino;

and B is fluorine, chlorine, methoxy, isopropyl or thienyl, in particular thienyl; and the salts of those compounds.

Another special embodiment of the compounds of the present invention include those compounds of formula I wherein
ring D and ring E together form the fused ring system

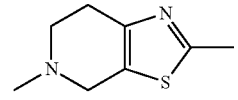

L is —(CH$_2$)$_n$S(O)$_2$—; A is phenyl optionally substituted by R1 and/or R2, phenyl substituted by R4, naphthyl optionally substituted by R1 and/or R2, thienyl optionally substituted by R1 and/or R2, or thiazolyl optionally substituted by R1 and/or R2;

R1 Is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R4 is phenyl, phenoxy, 4-methylpiperazinyl, benzylNHC(=O)NH—, or methylphenylsulfonylamino;

and B, n have the meanings as defined above, and the salts of those compounds.

A further special embodiment of the compounds of the present invention include those compounds of formula I wherein
ring D and ring E together form the fused ring system

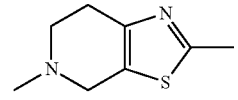

L is —(CH$_2$)$_n$S(O)$_2$—; A is phenyl optionally substituted by R1 and/or R2, phenyl substituted by R4, naphthyl optionally substituted by R1 and/or R2, thienyl optionally substituted by R1 and/or R2, or thiazolyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R4 is phenyl, phenoxy, 4-methylpiperazinyl, benzylNHC(=O)NH—, or methylphenylsulfonylamino;
and B is fluorine, chlorine, methoxy, isopropyl or thienyl, in particular thienyl, and n has the meanings as defined above, and the salts of those compounds.

Another special embodiment of the compounds of the present invention include those compounds of formula I wherein
ring D and ring E together form the fused ring system

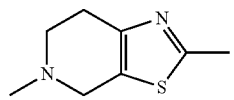

L is —C(=O)—; A is phenyl optionally substituted by R1 and/or R2, phenyl substituted by R4, naphthyl optionally substituted by R1 and/or R2, pyridyl optionally substituted by R1 and/or R2, quinolinyl optionally substituted by R1 and/or R2, or isoquinolinyl optionally substituted by R1 and/or R2;
R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, or diethylamino;
R2 is fluorine, hydroxyl, methyl, ethyl, propyl, isopropyl, methoxy, ethoxy, propoxy, or isopropoxy or
R1 and R2 when ortho to each other form a methylenedioxy group;
R4 is phenyl, phenoxy, 4-methylpiperazinyl, benzylNHC(=O)NH—, or methylphenylsulfonylamino; and B has the meaning as defined above, and the salts of those compounds.

A further special embodiment of the compounds of the present invention include those compounds of formula I wherein
ring D and ring E together form the fused ring system

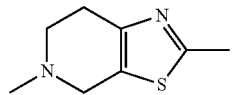

L is —C(=O)—; A is phenyl optionally substituted by R1 and/or R2, phenyl substituted by R4, naphthyl optionally substituted by R1 and/or R2, pyridyl optionally substituted by R1 and/or R2, quinolinyl optionally substituted by R1 and/or R2, or isoquinolinyl optionally substituted by R1 and/or R2;
R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, or diethylamino;
R2 is fluorine, hydroxyl, methyl, ethyl, propyl, isopropyl, methoxy, ethoxy, propoxy, or isopropoxy or
R1 and R2 when ortho to each other form a methylenedioxy group;
R4 is phenyl or phenoxy;
and B is fluorine, chlorine, methoxy, isopropyl or thienyl, in particular thienyl, and n has the meanings as defined above, and the salts of those compounds.

Another special embodiment of the compounds of the present invention include those compounds of formula I wherein
ring D and ring E together form the fused ring system

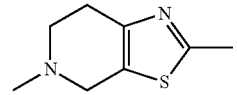

L is —(CH$_2$)$_n$OC(=O)—; A is phenyl optionally substituted by R1 and/or R2, phenyl substituted by R4, naphthyl optionally substituted by R1 and/or R2, or pyridyl optionally substituted by R1 and/or R2;
R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, or diethylamino;
R2 is fluorine, hydroxyl, methyl, ethyl, propyl, isopropyl, methoxy, ethoxy, propoxy, or isopropoxy or
R1 and R2 when ortho to each other form a methylenedioxy group;
R4 is phenyl or phenoxy;
and B, n have the meanings as defined above, and the salts of those compounds.

Another special embodiment of the compounds of the present invention include those compounds of formula I wherein
ring D and ring E together form the fused ring system

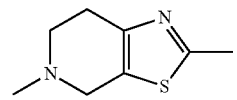

L is —(CH$_2$)$_n$OC(=O)—; A is phenyl optionally substituted by R1 and/or R2, phenyl substituted by R4, naphthyl optionally substituted by R1 and/or R2, or pyridyl optionally substituted by R1 and/or R2;
R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, or diethylamino;
R2 is fluorine, hydroxyl, methyl, ethyl, propyl, isopropyl, methoxy, ethoxy, propoxy, or isopropoxy or
R1 and R2 when ortho to each other form a methylenedioxy group;
R4 is phenyl or phenoxy;
B is fluorine, chlorine, methoxy, isopropyl or thienyl, in particular thienyl, and n has the meanings as defined above, and the salts of those compounds.

Another special embodiment of the compounds of the present invention include those compounds of formula I wherein
ring D and ring E together form the fused ring system

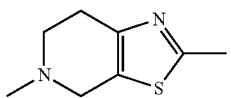

L is —(CH$_2$)$_n$N(R10)C(=O)—; A is cyclohexyl optionally substituted by R1 and/or R2, cyclohexyl substituted by R3, azetidinyl optionally substituted by R1 and/or R2, piperidinyl optionally substituted by R1 and/or R2, phenyl optionally substituted by R1 and/or R2, phenyl substituted by R4, naphthyl optionally substituted by R1 and/or R2, pyridyl optionally substituted by R1 and/or R2, pyridyl substituted by R5, quinolinyl optionally substituted by R1 and/or R2, or isoquinolinyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R3 is 3-pyridyl or 4-pyridyl;

R4 is phenyl, phenoxy, or 4-methylpiperazinyl;

R5 is —N(R6)R7, wherein R6 and R7 together and with inclusion of the nitrogen atom to which they are bonded form an azetidinyl-, piperidinyl-, piperazinyl-, 4-methylpiperazinyl-, or morpholinyl-ring;

and B, R10, n have the meanings as defined above, and the salts of those compounds.

Another special embodiment of the compounds of the present invention include those compounds of formula I wherein ring D and ring E together form the fused ring system

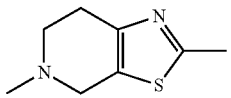

L is —(CH$_2$)$_n$N(R10)C(=O)—; A is cyclohexyl optionally substituted by R1 and/or R2, cyclohexyl substituted by R3, azetidinyl optionally substituted by R1 and/or R2, piperidinyl optionally substituted by R1 and/or R2, phenyl optionally substituted by R1 and/or R2, phenyl substituted by R4, naphthyl optionally substituted by R1 and/or R2, pyridyl optionally substituted by R1 and/or R2, pyridyl substituted by R5, quinolinyl optionally substituted by R1 and/or R2, or isoquinolinyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R3 is 3-pyridyl or 4-pyridyl;

R4 is phenyl, phenoxy, or 4-methylpiperazinyl;

R5 is —N(R6)R7, wherein R6 and R7 together and with inclusion of the nitrogen atom to which they are bonded form an azetidinyl-, piperidinyl-, piperazinyl-, 4-methylpiperazinyl-, or morpholinyl-ring;

B is fluorine, chlorine, methoxy, isopropyl or thienyl, in particular thienyl; and R10, n have the meanings as defined above, and the salts of those compounds.

Another special embodiment of the compounds of the present invention include those compounds of formula I wherein ring D and ring E together form the fused ring system

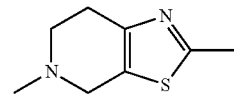

L is —N(R10)CH$_2$C(=O)—; A is cyclohexyl optionally substituted by R1 and/or R2, cyclohexyl substituted by R3, azetidinyl optionally substituted by R1 and/or R2, piperidinyl optionally substituted by R1 and/or R2, phenyl optionally substituted by R1 and/or R2, phenyl substituted by R4, naphthyl optionally substituted by R1 and/or R2, pyridyl optionally substituted by R1 and/or R2, pyridyl substituted by R5, quinolinyl optionally substituted by R1 and/or R2, or isoquinolinyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R3 is 3-pyridyl or 4-pyridyl;

R4 is phenyl, phenoxy, or 4-methylpiperazinyl;

R5 is —N(R6)R7, wherein R6 and R7 together and with inclusion of the nitrogen atom to which they are bonded form an azetidinyl-, piperidinyl-, piperazinyl-, 4-methylpiperazinyl-, or morpholinyl-ring;

and B, R10, have the meanings as defined above, and the salts of those compounds.

Another special embodiment of the compounds of the present invention include those compounds of formula I wherein ring D and ring E together form the fused ring system

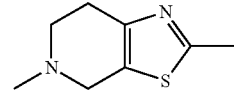

L is —N(R10)CH$_2$C(=O)—; A is cyclohexyl optionally substituted by R1 and/or R2, cyclohexyl substituted by R3, azetidinyl optionally substituted by R1 and/or R2, piperidinyl optionally substituted by R1 and/or R2, phenyl optionally substituted by R1 and/or R2, phenyl substituted by R4, naphthyl optionally substituted by R1 and/or R2, pyridyl optionally substituted by R1 and/or R2, pyridyl substituted by R5, quinolinyl optionally substituted by R1 and/or R2, or isoquinolinyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R3 is 3-pyridyl or 4-pyridyl;

R4 is phenyl, phenoxy, or 4-methylpiperazinyl;

R5 is —N(R6)R7, wherein R6 and R7 together and with inclusion of the nitrogen atom to which they are bonded form an azetidinyl-, piperidinyl-, piperazinyl-, 4-methylpiperazinyl-, or morpholinyl-ring;

B is fluorine, chlorine, methoxy, isopropyl or thienyl, in particular thienyl; and R10, n have the meanings as defined above, and the salts of those compounds.

Another special embodiment of the compounds of the present invention include those compounds of formula I wherein ring D and ring E together form the fused ring system

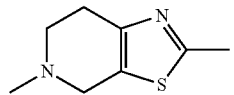

L is —(CH$_2$)$_n$N(R10)C(=NR11)- or —N=C(NR11)-; A is phenyl optionally substituted by R1 and/or R2, phenyl substituted by R4, or naphthyl optionally substituted by R1 and/or R2;

R1 is fluorine, hydroxyl; nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R4 is phenyl or phenoxy; and B, R10, R11, n have the meanings as defined above, and the salts of those compounds.

A further special embodiment of the compounds of the present invention include those compounds of formula I wherein ring D and ring E together form the fused ring system

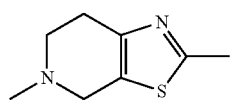

L is —(CH$_2$)$_n$N(R10)C(=NR11)- or —N=C(NR11)-; A is phenyl optionally substituted by R1 and/or R2, phenyl substituted by R4, naphthyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R4 is phenyl or phenoxy;

B is fluorine, chlorine, methoxy, isopropyl or thienyl, in particular thienyl; and R10, R11, n have the meanings as defined above, and the salts of those compounds.

Another special embodiment of the compounds of the present invention include those compounds of formula I wherein ring D and ring E together form the fused ring system

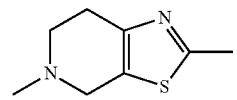

L is —(CH$_2$)$_n$N(R10)C(=S)—; A cyclohexyl optionally substituted by R1 and/or R2, cyclohexyl substituted by R3, piperidinyl optionally substituted by R1 and/or R2, phenyl optionally substituted by R1 and/or R2, phenyl substituted by R4, naphthyl optionally substituted by R1 and/or R2, pyridyl optionally substituted by R1 and/or R2, quinolinyl optionally substituted by R1 and/or R2, or isoquinolinyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R3 is 3-pyridyl or 4-pyridyl;

R4 is phenyl; and B, R10, n have the meanings as defined above, and the salts of those compounds.

A further special embodiment of the compounds of the present invention include those compounds of formula I wherein ring D and ring E together form the fused ring system

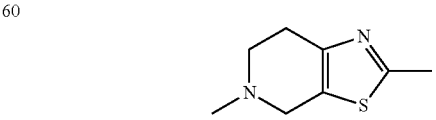

L is —(CH$_2$)$_n$N(R10)C(=S)—; A is cyclohexyl optionally substituted by R1 and/or R2, cyclohexyl substituted by R3, piperidinyl optionally substituted by R1 and/or R2, phenyl optionally substituted by R1 and/or R2, phenyl substituted by R4, naphthyl optionally substituted by R1 and/or R2, pyridyl optionally substituted by R1 and/or R2, quinolinyl optionally substituted by R1 and/or R2, or isoquinolinyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R3 is 3-pyridyl or 4-pyridyl;

R4 is phenyl; B is fluorine, chlorine, methoxy, isopropyl or thienyl, in particular thienyl; and R10, n have the meanings as defined above, and the salts of those compounds.

Another special embodiment of the compounds of the present invention include those compounds of formula I wherein ring D and ring E together form the fused ring system

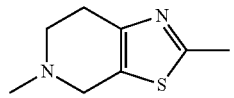

L is —C═C—C(═O)—; A is phenyl optionally substituted by R1 and/or R2, or naphthyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

and B has the meaning as defined above, and the salts of those compounds.

A further special embodiment of the compounds of the present invention include those compounds of formula I wherein ring D and ring E together form the fused ring system

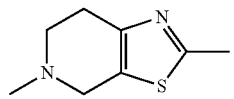

L is —C═C—C(═O)—; A phenyl optionally substituted by R1 and/or R2, or naphthyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

B is fluorine, chlorine, methoxy, isopropyl or thienyl, in particular thienyl; and the salts of those compounds.

Another special embodiment of the compounds of the present invention include those compounds of formula I wherein ring D and ring E together form the fused ring system

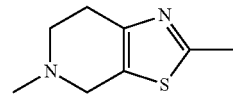

L is —N═C(R11)-; A phenyl optionally substituted by R1 and/or R2, phenyl substituted by R4 or naphthyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R4 is phenyl; and B, R11 have the meanings as defined above, and the salts of those compounds.

A further special embodiment of the compounds of the present invention include those compounds of formula I wherein ring D and ring E together form the fused ring system

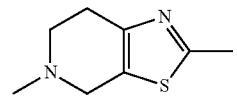

L is —N═C(R11)-; A phenyl optionally substituted by R1 and/or R2, phenyl substituted by R4 or naphthyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R4 is phenyl; B is fluorine, chlorine, methoxy, isopropyl or thienyl, in particular thienyl; R11 has the meanings as defined above, and the salts of those compounds.

Another special embodiment of the compounds of the present invention include those compounds of formula I wherein
ring D and ring E together form the fused ring system

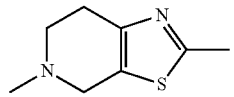

and
L is —(CH$_2$)$_n$N(R10)C(=O)C(=O)—, A is cyclohexyl optionally substituted by R1 and/or R2, cyclohexyl substituted by R3, phenyl optionally substituted by R1 and/or R2, phenyl substituted by R4, naphthyl optionally substituted by R1 and/or R2, pyridyl optionally substituted by R1 and/or R2, pyridyl substituted by R5, quinolinyl optionally substituted by R1 and/or R2, or isoquinolinyl optionally substituted by R1 and/or R2;
R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;
R2 is fluorine, hydroxyl, methyl, ethyl, propyl, isopropyl, methoxy, ethoxy, propoxy, or isopropoxy or
R1 and R2 when ortho to each other form a methylenedioxy group;
R3 is 3-pyridyl or 4-pyridyl;
R4 is phenyl, phenoxy, or 4-methylpiperazinyl;
R5 is —N(R6)R7, wherein R6 and R7 together and with inclusion of the nitrogen atom to which they are bonded form an azetidinyl-, piperidinyl-, piperazinyl-, 4-methylpiperazinyl-, morpholinyl-ring;
and B, R10, n have the meanings as defined above, and the salts of those compounds.

A further special embodiment of the compounds of the present invention include those compounds of formula I wherein
ring D and ring E together form the fused ring system

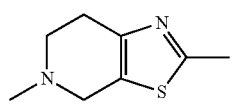

L is —(CH$_2$)$_n$N(R10)C(=O)C(=O)—; A is cyclohexyl optionally substituted by R1 and/or R2, cyclohexyl substituted by R3, phenyl optionally substituted by R1 and/or R2, phenyl substituted by R4, naphthyl optionally substituted by R1 and/or R2, pyridyl optionally substituted by R1 and/or R2, pyridyl substituted by R5, quinolinyl optionally substituted by R1 and/or R2, or isoquinolinyl optionally substituted by R1 and/or R2;
R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;
R2 is fluorine, hydroxyl, methyl, ethyl, propyl, isopropyl, methoxy, ethoxy, propoxy, or isopropoxy or
R1 and R2 when ortho to each other form a methylenedioxy group;
R3 is 3-pyridyl or 4-pyridyl;
R4 is phenyl, phenoxy, or 4-methylpiperazinyl;
R5 is —N(R6)R7, wherein R6 and R7 together and with inclusion of the nitrogen atom to which they are bonded form an azetidinyl-, piperidinyl-, piperazinyl-, 4-methylpiperazinyl-, morpholinyl-ring;
B is fluorine, chlorine, methoxy, isopropyl or thienyl, in particular thienyl; R10, n have the meanings as defined above, and the salts of those compounds.

Another special embodiment of the compounds of the present invention include those compounds of formula I wherein
ring D and ring E together form the fused ring system

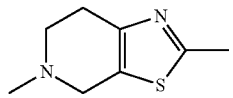

L is —OCH$_2$C(=O)—; A is phenyl optionally substituted by R1 and/or R2, phenyl substituted by R4, or naphthyl optionally substituted by R1 and/or R2;
R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;
R2 is fluorine, hydroxyl, methyl, ethyl, propyl, isopropyl, methoxy, ethoxy, propoxy, or isopropoxy or
R1 and R2 when ortho to each other form a methylenedioxy group;
R4 is phenyl; and B has the meaning as defined above, and the salts of those compounds.

A further special embodiment of the compounds of the present invention include those compounds of formula I wherein
ring D and ring E together form the fused ring system

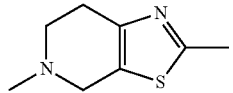

L is —OCH$_2$C(=O)—; A is phenyl optionally substituted by R1 and/or R2, phenyl substituted by R4, or naphthyl optionally substituted by R1 and/or R2;
R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R4 is phenyl; B is fluorine, chlorine, methoxy, isopropyl or thienyl, in particular thienyl; and the salts of those compounds.

Another special embodiment of the compounds of the present invention include those compounds of formula I wherein ring D and ring E together form a fused ring system selected from L is —N(R10)C(=CR11)-; A is phenyl optionally substituted by R1 and/or R2, phenyl substituted by R4, or naphthyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R4 is phenyl; and B, R10, R11 have the meanings as defined above, and the salts of those compounds.

A further special embodiment of the compounds of the present invention include those compounds of formula I wherein ring D and ring E together form a fused ring system selected from L is —N(R10)C(=CR11)-; A is phenyl optionally substituted by R1 and/or R2, phenyl substituted by R4, or naphthyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R4 is phenyl;

B is fluorine, chlorine, methoxy, isopropyl or thienyl, in particular thienyl; and R10, R11 have the meanings as defined above, and the salts of those compounds.

Another preferred embodiment of the present invention relates to compounds of formula I wherein ring D and ring E together form the fused ring system A is $(C_1-C_4)$alkyl, $(C_1-C_4)$alkoxy$(C_1-C_2)$alkyl, phenyl optionally substituted by R1 and/or R2, naphthyl optionally substituted by R1 and/or R2, or pyridyl optionally substituted by R1 and/or R2;

R1 is $(C_1-C_4)$alkyl, $(C_1-C_4)$alkoxy, $(C_1-C_4)$alkyl which is partially or completely substituted by fluorine, $(C_1-C_4)$ alkoxy which is predominantly or completely substituted by fluorine, $(C_1-C_4)$alkoxy$(C_1-C_2)$alkyl, $(C_1-C_4)$alkoxycarbonyl, or mono- or -di$(C_1-C_4)$alkylamino;

R2 is $(C_1-C_4)$alkyl, $(C_1-C_4)$alkoxy, or

R1 and R2 when ortho to each other form a methylenedioxy group;

L is —$(CH_2)_n$N(R10)C(=O)—, —$(CH_2)_n$S(O)$_2$— or —O$(CH_2)_n$C(=O)—;

R10 is hydrogen or $(C_1-C_4)$alkyl;

B is hydrogen, fluorine, chlorine, $(C_1-C_4)$alkyl, $(C_1-C_4)$ alkoxy, or thienyl;

n is an integer selected from 0 and 1;

and the salts of these compounds.

Another preferred embodiment of the present invention relates to compounds of formula I wherein ring D and ring E together form the fused ring system A is $(C_1-C_4)$alkyl, phenyl optionally substituted by R1 and/or R2, naphthyl optionally substituted by R1 and/or R2, or pyridyl optionally substituted by R1 and/or R2;

R1 is $(C_1-C_4)$alkyl, $(C_1-C_4)$alkoxy, $(C_1-C_4)$alkyl which is partially or completely substituted by fluorine, $(C_1-C_4)$ alkoxy which is predominantly or completely substituted by fluorine, $(C_1-C_4)$alkoxy$(C_1-C_2)$alkyl, $(C_1-C_4)$alkoxycarbonyl, or mono- or -di$(C_1-C_4)$alkylamino;

R2 is $(C_1-C_4)$alkyl, $(C_1-C_4)$alkoxy, or

R1 and R2 when ortho to each other form a methylenedioxy group;

L is —$(CH_2)_n$N(R10)C(=O)—, —$(CH_2)_n$S(O)$_2$— or —O$(CH_2)_n$C(=O)—;

R10 is hydrogen or $(C_1-C_4)$alkyl;

B is hydrogen, fluorine, chlorine, $(C_1-C_4)$alkyl, $(C_1-C_4)$ alkoxy, or thienyl;

n is an integer selected from 0 and 1;

and the salts of these compounds.

Another preferred embodiment of the present invention relates to compounds of formula I wherein ring D and ring E together form the fused ring system

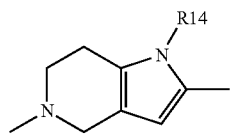

A is (C$_1$-C$_4$)alkyl, phenyl optionally substituted by R1 and/or R2, naphthyl optionally substituted by R1 and/or R2, or pyridyl optionally substituted by R1 and/or R2;

R1 is (C$_1$-C$_4$)alkyl, (C$_1$-C$_4$)alkoxy, (C$_1$-C$_4$)alkyl which is partially or completely substituted by fluorine, (C$_1$-C$_4$) alkoxy which is predominantly or completely substituted by fluorine, (C$_1$-C$_4$)alkoxy(C$_1$-C$_2$)alkyl, (C$_1$-C$_4$)alkoxycarbonyl, or mono- or -di(C$_1$-C$_4$)alkylamino;

R2 is (C$_1$-C$_4$)alkyl, (C$_1$-C$_4$)alkoxy, or

R1 and R2 when ortho to each other form a methylenedioxy group;

L is —(CH$_2$)$_n$N(R10)C(=O)—, —(CH$_2$)$_n$S(O)$_2$— or —O(CH$_2$)$_n$C(=O)—;

R10 is hydrogen or (C$_1$-C$_4$)alkyl;

R14 is hydrogen or methyl:

B is hydrogen, fluorine, chlorine, (C$_1$-C$_4$)alkyl, (C$_1$-C$_4$) alkoxy, or thienyl;

n is an integer selected from 0 and 1;

and the salts of these compounds.

Another preferred embodiment of the present invention relates to compounds of formula I wherein ring D and ring E together form the fused ring system

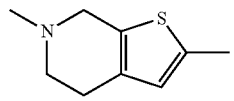

A is (C$_1$-C$_4$)alkyl, (C$_1$-C$_4$)alkoxy(C$_1$-C$_2$)alkyl, phenyl optionally substituted by R1 and/or R2, naphthyl optionally substituted by R1 and/or R2, or pyridyl optionally substituted by R1 and/or R2;

R1 is (C$_1$-C$_4$)alkyl, (C$_1$-C$_4$)alkoxy, (C$_1$-C$_4$)alkyl which is partially or completely substituted by fluorine, (C$_1$-C$_4$) alkoxy which is predominantly or completely substituted by fluorine, (C$_1$-C$_4$)alkoxy(C$_1$-C$_2$)alkyl, (C$_1$-C$_4$)alkoxycarbonyl, or mono- or -di(C$_1$-C$_4$)alkylamino;

R2 is (C$_1$-C$_4$)alkyl, (C$_1$-C$_4$)alkoxy, or

R1 and R2 when ortho to each other form a methylenedioxy group;

L is —(CH$_2$)$_n$N(R10)C(=O)—, —(CH$_2$)$_n$S(O)$_2$— or —O(CH$_2$)$_n$C(=O)—;

R10 is hydrogen or (C$_1$-C$_4$)allyl;

B is hydrogen, fluorine, chlorine, (C$_1$-C$_4$)alkyl, (C$_1$-C$_4$) alkoxy, or thienyl;

n is an integer selected from 0 and 1;

and the salts of these compounds.

Another preferred embodiment of the present invention relates to compounds of formula I wherein ring D and ring E together form the fused ring system

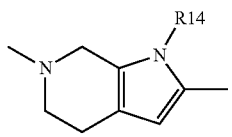

A is (C$_1$-C$_4$)alkyl, phenyl optionally substituted by R1 and/or R2, naphthyl optionally substituted by R1 and/or R2, or pyridyl optionally substituted by R1 and/or R2;

R1 is (C$_1$-C$_4$) alkyl, (C$_1$-C$_4$) alkoxy, (C$_1$-C$_4$) alkyl which is partially or completely substituted by fluorine, (C$_1$-C$_4$) alkoxy which is predominantly or completely substituted by fluorine, (C$_1$-C$_4$) alkoxy(C$_1$-C$_2$)alkyl, (C$_1$-C$_4$)alkoxycarbonyl, or mono- or -di(C$_1$-C$_4$)alkylamino;

R2 is (C$_1$-C$_4$)alkyl, (C$_1$-C$_4$)alkoxy, or

R1 and R2 when ortho to each other form a methylenedioxy group;

L is —(CH$_2$)$_n$N(R10)C(=O)—, —(CH$_2$)$_n$S(O)$_2$— or —O(CH$_2$)$_n$C(=O)—;

R10 is hydrogen or (C$_1$-C$_4$)alkyl;

R14 is hydrogen or methyl:

B is hydrogen, fluorine, chlorine, (C$_1$-C$_4$)alkyl, (C$_1$-C$_4$) alkoxy, or thienyl;

n is an integer selected from 0 and 1;

and the salts of these compounds.

In another preferred embodiment the invention relates to compounds of formula I as defined above, wherein ring D and ring E together form a fused ring system selected from

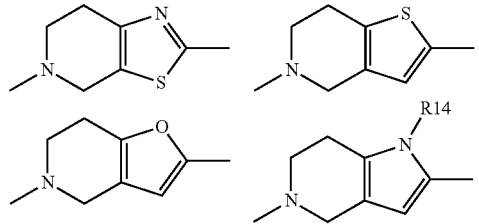

A is (C$_1$-C$_4$)alkyl, (C$_1$-C$_4$)alkoxy(C$_1$-C$_2$)alkyl, (C$_1$-C$_4$)alkylthio(C$_1$-C$_2$)alkyl, mono- or -di(C$_1$-C$_4$)alkylamino(C$_1$-C$_2$) alkyl, cyclohexyl optionally substituted by R1 and/or R2, cyclohexyl substituted by R3, azetidinyl optionally substituted by R1 and/or R2, piperidinyl optionally substituted by R1 and/or R2, phenyl optionally substituted by R1 and/or R2, phenyl substituted by R4, naphthyl optionally substituted by R1 and/or R2, pyridyl optionally substituted by R1 and/or R2, pyridyl substituted by R5, pyrimidinyl optionally substituted by R1 and/or R2, pyrimidinyl substituted by R8, triazinyl optionally substituted by R1 and/or R2, triazinyl substituted by R9, quinolinyl optionally substituted by R1 and/or R2, isoquinolinyl optionally substituted by R1 and/or R2, thienyl optionally substituted by R1 and/or R2, or thiazolyl optionally substituted by R1 and/or R2;

R1 is fluorine, hydroxyl, cyano, nitro, amino, carboxyl, (C$_1$-C$_4$)alkyl, (C$_1$-C$_4$)alkoxy, (C$_1$-C$_4$)alkyl which is partially or completely substituted by fluorine, (C$_1$-C$_4$)alkoxy which is predominantly or completely substituted by fluorine, (C$_1$-C$_4$)alkoxy(C$_1$-C$_2$)alkyl, (C$_1$-C$_4$)alkoxycarbonyl, mono- or -di(C$_1$-C$_4$)alkylamino, or (C$_1$-C$_4$)alkylcarbonylamino;

R2 is fluorine, hydroxyl, amino, $(C_1-C_4)$alkyl, or $(C_1-C_4)$alkoxy or

R1 and R2 when ortho to each other form a methylenedioxy or ethylenedioxy group;

R3 is 3-pyridyl or 4-pyridyl;

R4 is phenyl, phenoxy, 4-methylpiperazinyl, benzylNHC(=O)NH—, or methylphenylsulfonylamino;

R5 is methylphenylsulfonylamino, or N(R6)R7, wherein R6 and R7 together and with inclusion of the nitrogen atom to which they are bonded form an azetidinyl-, piperidinyl-, piperazinyl-, 4-methylpiperazinyl-, or morpholinyl-ring;

R8 is pyridyl or methylphenylsulfonylamino;

R9 is piperidinyl;

L is bond, —$(CH_2)_nS(O)_2$—, —C(=O)—, —C(=S)—, —$(CH_2)_nOC(=O)$—; —$(CH_2)_nN(R10)C(=O)$—; —$(CH_2)_nN(R10)C(=NR11)$-, —$(CH_2)_nN(R10)C(=S)$—, —C=C—C(=O)—, —N=C(R11)-; —$(CH_2)_nN(R10)C(=O)C(=O)$—, —$OCH_2C(=O)$—, —N(R10)C(=CR11)-, or —N=C(NR11)-;

R10 is hydrogen, $(C_1-C_4)$alkyl, or $(C_1-C_4)$alkoxy$(C_1-C_2)$alkyl;

R11 is hydrogen, hydroxyl, cyano, nitro, methyl, or ethyl;

B is hydrogen, halogen, $(C_1-C_4)$alkyl, $(C_1-C_4)$alkoxy, thienyl, or N(R12)R13 wherein R12 and R13 independently of one another are hydrogen, $(C_1-C_4)$alkyl, or R12 and R13 together and with inclusion of the nitrogen atom to which they are bonded form a pyrrolidinyl-, ring;

R14 is hydrogen or methyl;

n is an integer selected from 0 and 1; and the salts of these compounds.

In a further preferred embodiment the invention relates to compounds of formula I as defined above,
wherein
ring D and ring E together form a fused ring system selected from

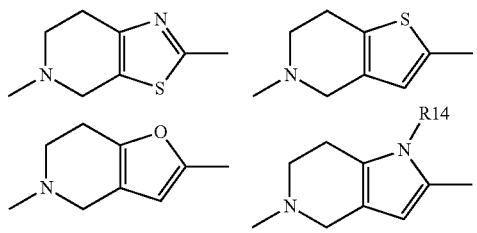

A is $(C_1-C_4)$alkyl, $(C_1-C_4)$alkoxy$(C_1-C_2)$alkyl, cyclohexyl optionally substituted by R1 and/or R2, cyclohexyl substituted by R3, piperidinyl optionally substituted by R1 and/or R2, phenyl optionally substituted by R1 and/or R2, phenyl substituted by R4, naphthyl optionally substituted by R1 and/or R2, pyridyl optionally substituted by R1 and/or R2, pyridyl substituted by R5, pyrimidinyl optionally substituted by R1 and/or R2, pyrimidyl substituted by R8, triazinyl optionally substituted by R1 and/or R2, triazinyl substituted by R9, quinolinyl optionally substituted by R1 and/or R2, isoquinolinyl optionally substituted by R1 and/or R2, thienyl optionally substituted by R1 and/or R2, or thiazolyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R3 is 3-pyridyl or 4-pyridyl

R4 is phenyl, phenoxy, 4-methylpiperazinyl, benzylNHC(=O)NH—, or methylphenylsulfonylamino, R5 is methylphenylsulfonylamino, N(R6)R7, wherein R6 and R7 together and with inclusion of the nitrogen atom to which they are bonded form an azetidinyl-, piperidinyl-, piperazinyl-, 4-methylpiperazinyl-, morpholinyl-ring;

R8 is pyridyl or methylphenylsulfonylamino;

R9 is piperidinyl;

L is bond, —$(CH_2)_nS(O)_2$—, —C(=O)—, —C(=S)—, —$(CH_2)_nOC(=O)$—, —$(CH_2)_nN(R10)C(=O)$—, —$(CH_2)_nN(R10)C(=NR11)$-, —$(CH_2)_nN(R10)C(=S)$—, —C=C—C(=O)—, —N=C(R11)-, —$(CH_2)_nN(R10)C(=O)C(=O)$—, —$OCH_2C(=O)$—, —N(R10)C(=CR11)-, or —N=C(NR11)-;

R10 is hydrogen, methyl, ethyl, propyl, methoxyethyl, ethoxyethyl, methoxymethyl, or ethoxymethyl;

R11 is hydrogen, hydroxyl, cyano, nitro, methyl, or ethyl;

B is hydrogen, fluorine, chlorine, methyl, ethyl, propyl, isopropyl, methoxy, ethoxy, thienyl, N(R12)R13 wherein R12 and R13 independently of one another are hydrogen, methyl, ethyl, or R12 and R13 together and with inclusion of the nitrogen atom to which they are bonded form a pyrrolidinyl-ring;

R14 is hydrogen or methyl;

n is an integer selected from 0 and 1;

and the salts of these compounds.

Another preferred embodiment of the invention relates to compounds of formula I
wherein
ring D and ring E together form a fused ring system selected from

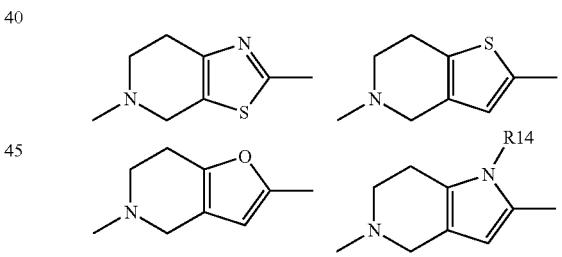

wherein L is —$(CH_2)_nN(R10)C(=O)C(=O)$—;

A is $(C_1-C_4)$alkyl, $(C_1-C_4)$alkoxy$(C_1-C_2)$alkyl, mono- or -di$(C_1-C_4)$alkylamino$(C_1-C_2)$alkyl, cyclohexyl optionally substituted by R1 and/or R2, cyclohexyl substituted by R3, phenyl optionally substituted by R1 and/or R2, phenyl substituted by R4, naphthyl optionally substituted by R1 and/or R2, pyridyl optionally substituted by R1 and/or R2, pyridyl substituted by R5, quinolinyl optionally substituted by R1 and/or R2, or isoquinolinyl optionally substituted by R1 and/or R2;

R1 is fluorine, hydroxyl, nitro, amino, carboxyl, $(C_1-C_4)$alkyl, $(C_1-C_4)$alkoxy, $(C_1-C_4)$alkyl which is partially or completely substituted by fluorine, $(C_1-C_4)$alkoxy which is predominantly or completely substituted by fluorine, $(C_1-C_4)$alkoxy$(C_1-C_2)$alkyl, $(C_1-C_4)$alkoxycarbonyl, mono- or -di$(C_1-C_4)$alkylamino or $(C_1-C_4)$alkylcarbonylamino;

R2 is hydroxyl, $(C_1-C_4)$alkyl, or $(C_1-C_4)$alkoxy or

R1 and R2 when ortho to each other form a methylenedioxy group;
R3 is 3-pyridyl or 4-pyridyl;
R4 is phenyl, phenoxy, or 4-methylpiperazinyl;
R5 is —N(R6)R7, wherein R6 and R7 together and with inclusion of the nitrogen atom to which they are bonded form an azetidinyl-, piperidinyl-, piperazinyl-, 4-methylpiperazinyl-, morpholinyl-ring;
R10 is hydrogen or $(C_1-C_4)$alkyl;
B is hydrogen, fluorine, chlorine, $(C_1-C_4)$alkyl, $(C_1-C_4)$alkoxy, or thienyl;
R14 is hydrogen, or methyl;
n is an integer selected from 0 and 1; and the salts of these compounds.

Another preferred embodiment of the invention relates to compounds of formula I wherein ring D and ring E together form a fused ring system selected from

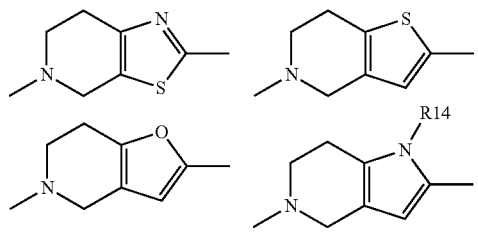

wherein L is —$(CH_2)_nN(R10)C(=O)$—;
A is $(C_1-C_4)$alkyl, $(C_1-C_4)$alkoxy$(C_1-C_2)$alkyl, $(C_1-C_4)$alkylthio$(C_1-C_2)$alkyl, mono- or -di$(C_1-C_4)$alkylamino$(C_1-C_2)$alkyl, cyclohexyl optionally substituted by R1 and/or R2, cyclohexyl substituted by R3, azetidinyl optionally substituted by R1 and/or R2, piperidinyl optionally substituted by R1 and/or R2, phenyl optionally substituted by R1 and/or R2, phenyl substituted by R4, naphthyl optionally substituted by R1 and/or R2, pyridyl optionally substituted by R1 and/or R2, pyridyl substituted by R5, quinolinyl optionally substituted by R1 and/or R2, or isoquinolinyl optionally substituted by R1 and/or R2;
R1 is fluorine, hydroxyl, nitro, amino, carboxyl, $(C_1-C_4)$alkyl, $(C_1-C_4)$alkoxy, $(C_1-C_4)$alkyl which is partially or completely substituted by fluorine, $(C_1-C_4)$alkoxy which is predominantly or completely substituted by fluorine, $(C_1-C_4)$alkoxy$(C_1-C_2)$alkyl, $(C_1-C_4)$alkoxycarbonyl, mono- or -di$(C_1-C_4)$alkylamino or or $(C_1-C_4)$alkylcarbonylamino;
R2 is hydroxyl, $(C_1-C_4)$alkyl, or $(C_1-C_4)$alkoxy or
R1 and R2 when ortho to each other form a methylenedioxy group;
R3 is 3-pyridyl or 4-pyridyl;
R4 is phenyl, phenoxy, or 4-methylpiperazinyl;
R5 is —N(R6)R7, wherein R6 and R7 together and with inclusion of the nitrogen atom to which they are bonded form an azetidinyl-, piperidinyl-, piperazinyl-, 4-methylpiperazinyl-, or morpholinyl-ring;
R10 is hydrogen, $(C_1-C_4)$alkyl, methoxyethyl, ethoxyethyl, methoxymethyl, or ethoxymethyl;
B is hydrogen, fluorine, chlorine, $(C_1-C_4)$alkyl, $(C_1-C_4)$alkoxy, thienyl, or N(R12)R13 wherein R12 and R13 independently of one another are hydrogen, $(C_1-C_4)$alkyl, or R12 and R13 together and with inclusion of the nitrogen atom to which they are bonded form a pyrrolidinyl-ring;
R14 is hydrogen or methyl;
n is an integer selected from 0 and 1;
and the salts of these compounds.

Another preferred embodiment of the invention relates to compounds of formula I
wherein
ring D and ring E together form a fused ring system selected from

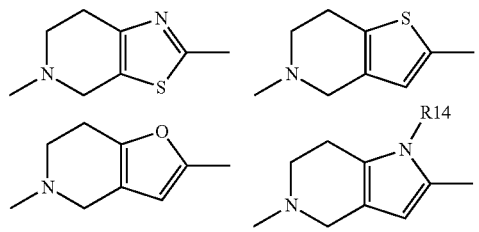

wherein L is —$C(=O)$—;
A is $(C_1-C_4)$alkyl, $(C_1-C_4)$alkoxy$(C_1-C_2)$alkyl, $(C_1-C_4)$alkylthio$(C_1-C_2)$alkyl, mono- or -di$(C_1-C_4)$alkylamino$(C_1-C_2)$alkyl, phenyl optionally substituted by R1 and/or R2, phenyl substituted by R4, naphthyl optionally substituted by R1 and/or R2,
pyridyl optionally substituted by R1 and/or R2, quinolinyl optionally substituted by R1 and/or R2, or isoquinolinyl optionally substituted by R1 and/or R2;
R1 is $(C_1-C_4)$alkyl, $(C_1-C_4)$alkoxy, $(C_1-C_4)$alkyl which is partially or completely substituted by fluorine, $(C_1-C_4)$alkoxy which is predominantly or completely substituted by fluorine, $(C_1-C_4)$alkoxy$(C_1-C_2)$alkyl, $(C_1-C_4)$alkoxycarbonyl, or mono- or -di$(C_1-C_4)$alkylamino;
R2 is $(C_1-C_4)$alkyl or $(C_1-C_4)$alkoxy;
R4 is phenyl or phenoxy;
B is hydrogen, fluorine, chlorine, $(C_1-C_4)$alkyl, or thienyl;
R14 Is hydrogen or methyl; and the salts of these compounds.

Another preferred embodiment of the present invention relates to compounds of formula I
wherein
ring D and ring E together form a fused ring system selected from

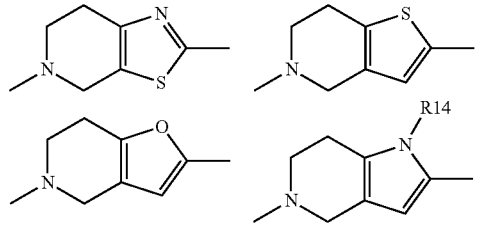

wherein L is —$(CH_2)_nN(R10)C(=N(R11))$-;
A is $(C_1-C_4)$alkyl, $(C_1-C_4)$alkoxy$(C_1-C_2)$alkyl, $(C_1-C_4)$alkylthio$(C_1-C_2)$alkyl, mono- or -di$(C_1-C_4)$alkylamino$(C_1-C_2)$alkyl, phenyl optionally substituted by R1 and/or R2, phenyl substituted by R4, or naphthyl optionally substituted by R1 and/or R2;
R1 is $(C_1-C_4)$alkyl, $(C_1-C_4)$alkoxy, $(C_1-C_4)$alkyl which is partially or completely substituted by fluorine, $(C_1-C_4)$alkoxy which is predominantly or completely substituted by fluorine, $(C_1-C_4)$alkoxy$(C_1-C_2)$alkyl, $(C_1-C_4)$alkoxycarbonyl, or mono- or -di$(C_1-C_4)$alkylamino;
R2 is $(C_1-C_4)$alkoxy, or
R1 and R2 when ortho to each other form a methylenedioxy group;
R4 is phenyl or phenoxy;

R10 is hydrogen, or $(C_1-C_4)$alkyl;
R11 is hydrogen, cyano, or methyl;
B is hydrogen, fluorine, chlorine, $(C_1-C_4)$alkyl, $(C_1-C_4)$alkoxy, or thienyl;
R14 is hydrogen, or methyl;
n is an integer selected from 0 and 1;
and the salts of these compounds.

Another preferred embodiment of the present invention relates to compounds of formula I
wherein
ring D and ring E together form a fused ring system selected from

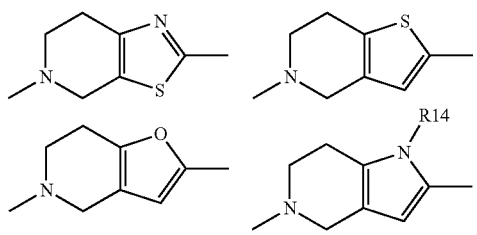

wherein L is —N=C(R11)-;
A is $(C_1-C_4)$alkyl, phenyl optionally substituted by R1 and/or R2, phenyl substituted by R4, or naphthyl optionally substituted by R1 and/or R2;
R1 is $(C_1-C_4)$alkyl, $(C_1-C_4)$alkoxy, $(C_1-C_4)$alkyl which is partially or completely substituted by fluorine, $(C_1-C_4)$alkoxy which is predominantly or completely substituted by fluorine, $(C_1-C_4)$alkoxy$(C_1-C_2)$alkyl, $(C_1-C_4)$alkoxycarbonyl, or mono- or -di$(C_1-C_4)$alkylamino;
R2 is $(C_1-C_4)$alkoxy, or
R1 and R2 when ortho to each other form a methylenedioxy group;
R4 is phenyl;
R11 is hydrogen, or methyl;
B is hydrogen, fluorine, chlorine, $(C_1-C_4)$alkyl, $(C_1-C_4)$alkoxy, or thienyl;
R14 is hydrogen, or methyl;
and the salts of these compounds.

Another preferred embodiment of the present invention relates to compounds of formula I
wherein
ring D and ring E together form a fused ring system selected from

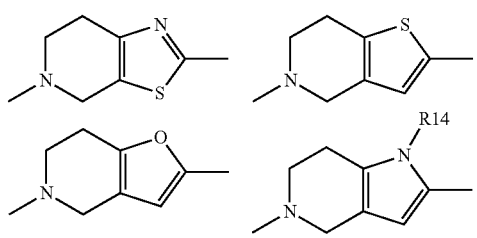

wherein L is —N(R10)C(=C(R11))-;
A is $(C_1-C_4)$alkyl, phenyl optionally substituted by R1 and/or R2, phenyl substituted by R4, or naphthyl optionally substituted by R1 and/or R2;
R1 is fluorine, $(C_1-C_4)$alkyl, $(C_1-C_4)$alkoxy, $(C_1-C_4)$alkyl which is partially or completely substituted by fluorine, $(C_1-C_4)$alkoxy which is predominantly or completely substituted by fluorine, $(C_1-C_4)$alkoxy$(C_1-C_2)$alkyl, $(C_1-C_4)$alkoxycarbonyl, or mono- or -di$(C_1-C_4)$alkylamino;
R2 is $(C_1-C_4)$alkoxy, or
R1 and R2 when ortho to each other form a methylenedioxy group;
R4 is phenyl;
R10 is hydrogen, or $(C_1-C_4)$alkyl;
R11 is hydrogen, nitro, or methyl;
B is hydrogen, fluorine, chlorine, $(C_1-C_4)$alkyl, $(C_1-C_4)$alkoxy, or thienyl;
R14 is hydrogen, or methyl;
and the salts of these compounds.

Another preferred embodiment of the present invention relates to compounds of formula I
wherein
ring D and ring E together form a fused ring system selected from

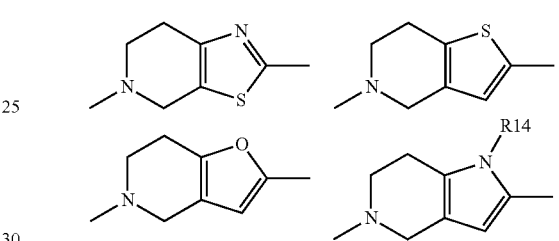

wherein L is —$(CH_2)_nS(O)_2$—;
A is $(C_1-C_4)$alkyl, phenyl optionally substituted by R1 and/or R2, phenyl substituted by R4, naphthyl optionally substituted by R1 and/or R2, thienyl optionally substituted by R1 and/or R2, thiazolyl optionally substituted by R1 and/or R2;
R1 is fluorine, $(C_1-C_4)$alkyl, $(C_1-C_4)$alkoxy, $(C_1-C_4)$alkyl which is partially or completely substituted by fluorine, $(C_1-C_4)$alkoxy which is predominantly or completely substituted by fluorine, $(C_1-C_4)$alkoxy$(C_1-C_2)$alkyl, $(C_1-C_4)$alkoxycarbonyl, mono- or -di$(C_1-C_4)$alkylamino, or $(C_1-C_4)$alkylcarbonylamino;
R2 is $(C_1-C_4)$alkyl, or $(C_1-C_4)$alkoxy, or
R1 and R2 when ortho to each other form a methylenedioxy group;
R4 is phenyl;
B is hydrogen, fluorine, chlorine, $(C_1-C_4)$alkyl, $(C_1-C_4)$alkoxy, or thienyl;
R14 is hydrogen or methyl;
n is an integer selected from 0 and 1;
and the salts of these compounds.

Another preferred embodiment of the present invention relates to compounds of formula I
wherein
ring D and ring E together form a fused ring system selected from

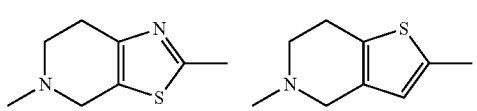

-continued wherein L is —N(R10)C(=S)—;
A is (C₁-C₄)alkyl, cyclohexyl optionally substituted by R1 and/or R2, cyclohexyl substituted by R3,
piperidinyl optionally substituted by R1 and/or R2, phenyl optionally substituted by R1 and/or R2, phenyl substituted by R4, naphthyl optionally substituted by R1 and/or R2, pyridyl optionally substituted by R1 and/or R2, quinolinyl optionally substituted by R1 and/or
R2, or isoquinolinyl optionally substituted by R1 and/or R2;
R1 is fluorine, (C₁-C₄)alkyl, (C₁-C₄)alkoxy, (C₁-C₄)alkyl which is partially or completely substituted by fluorine, (C₁-C₄)alkoxy which is predominantly or completely substituted by fluorine, (C₁-C₄)alkoxy(C₁-C₂)alkyl, (C₁-C₄)alkoxycarbonyl, or mono- or -di(C₁-C₄)alkylamino;
R2 is (C₁-C₄)alkyl or (C₁-C₄)alkoxy, or
R1 and R2 when ortho to each other form a methylenedioxy group;
R3 is 3-pyridyl or 4-pyridyl;
R4 is phenyl;
R10 is hydrogen or (C₁-C₄)alkyl;
B is hydrogen, fluorine, chlorine, (C₁-C₄)alkyl, (C₁-C₄)alkoxy, or thienyl;
R14 is hydrogen or methyl;
and the salts of these compounds.

Another preferred embodiment of the present invention relates to compounds of formula I
wherein
ring D and ring E together form a fused ring system selected from wherein L is —OCH₂C(=O)—;
A is (C₁-C₄)alkyl, phenyl optionally substituted by R1 and/or R2, phenyl substituted by R4, naphthyl optionally substituted by R1 and/or R2;
R1 is fluorine, (C₁-C₄)alkyl, (C₁-C₄)alkoxy, (C₁-C₄)alkyl which is partially or completely substituted by fluorine, (C₁-C₄)alkoxy which is predominantly or completely substituted by fluorine, (C₁-C₄)alkoxy(C₁-C₂)alkyl, (C₁-C₄)alkoxycarbonyl, or mono- or -di(C₁-C₄)alkylamino;
R2 is (C₁-C₄)alkyl or (C₁-C₄)alkoxy, or
R1 and R2 when ortho to each other form a methylenedioxy group;
R4 is phenyl;
B is hydrogen, fluorine, chlorine, (C₁-C₄)alkyl, (C₁-C₄)alkoxy, or thienyl;
R14 is hydrogen or methyl;
and the salts of these compounds.

Another preferred embodiment of the present invention relates to compounds of formula I
wherein
ring D and ring E together form a fused ring system selected from wherein L is —(CH₂)ₙOC(=O)—;
A is (C₁-C₄)alkyl, phenyl optionally substituted by R1 and/or R2, phenyl substituted by R4, naphthyl optionally substituted by R1 and/or R2, pyridyl optionally substituted by R1 and/or R2, pyridyl substituted by R5;
R1 is fluorine, hydroxyl, nitro, amino, carboxyl, (C₁-C₄)alkyl, (C₁-C₄)alkoxy, (C₁-C₄)alkyl which is partially or completely substituted by fluorine, (C₁-C₄)alkoxy which is predominantly or completely substituted by fluorine, (C₁-C₄)alkoxy(C₁-C₂)alkyl, (C₁-C₄)alkoxycarbonyl, or mono- or -di(C₁-C₄)alkylamino;
R2 is hydroxyl, (C₁-C₄)alkyl, or (C₁-C₄)alkoxy or
R1 and R2 when ortho to each other form a methylenedioxy group;
R4 is phenyl, phenoxy, or 4-methylpiperazinyl;
R5 is —N(R6)R7, wherein R6 and R7 together and with inclusion of the nitrogen atom to which they are bonded form an azetidinyl-, piperidinyl-, piperazinyl-, 4-methylpiperazinyl-, or morpholinyl-ring;
B is hydrogen, fluorine, chlorine, (C₁-C₄)alkyl, (C₁-C₄)alkoxy, or thienyl;
R14 is hydrogen or methyl;
n is an integer selected from 0 and 1;
and the salts of these compounds.

Another preferred embodiment of the present invention relates to compounds of formula I
wherein
ring D and ring E together form a fused ring system selected from wherein L is —C=C—C(=O)—;
A is (C₁-C₄)alkyl, phenyl optionally substituted by R1 and/or R2, or naphthyl optionally substituted by R1 and/or R2;
R1 is fluorine, hydroxyl, (C₁-C₄)alkyl, (C₁-C₄)alkoxy, (C₁-C₄)alkyl which is partially or completely substituted by fluorine, (C₁-C₄)alkoxy which is predominantly or completely substituted by fluorine, (C₁-C₄)alkoxy(C₁-C₂)alkyl, (C₁-C₄)alkoxycarbonyl, or mono- or -di(C₁-C₄)alkylamino;

R2 is hydroxyl, (C$_1$-C$_4$)alkyl, or (C$_1$-C$_4$)alkoxy or
R1 and R2 when ortho to each other form a methylenedioxy group;
B is hydrogen, fluorine, chlorine, (C$_1$-C$_4$)alkyl, (C$_1$-C$_4$) alkoxy, or thienyl;
R14 is hydrogen or methyl; and the salts of these compounds.

Another preferred embodiment of the present invention relates to compounds of formula I
wherein
ring D and ring E together form a fused ring system selected from

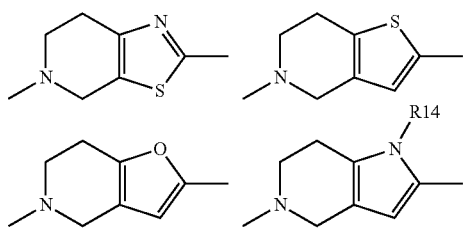

wherein L is bond;
A is (C$_1$-C$_4$)allyl, phenyl optionally substituted by R1 and/or R2, phenyl substituted by R4, naphthyl optionally substituted by R1 and/or R2, pyridyl optionally substituted by R1 and/or R2, pyridyl substituted by R5, pyrimidinyl optionally substituted by R1 and/or R2, or pyrimidinyl substituted by R8;
R1 is fluorine, hydroxyl, nitro, amino, (C$_1$-C$_4$)alkyl, (C$_1$-C$_4$) alkoxy, (C$_1$-C$_4$)alkyl which is partially or completely substituted by fluorine, (C$_1$-C$_4$)alkoxy which is predominantly or completely substituted by fluorine, (C$_1$-C$_4$)alkoxy(C$_1$-C$_2$)alkyl, (C$_1$-C$_4$)alkoxycarbonyl, or mono- or -di(C$_1$-C$_4$)alkylamino;
R2 is hydroxyl, (C$_1$-C$_4$)alkyl, or (C$_1$-C$_4$)alkoxy or
R1 and R2 when ortho to each other form a methylenedioxy group;
R4 is phenyl, phenoxy, benzylNHC(=O)NH—, or methylphenylsulfonylamino;
R5 is methylphenylsulfonylamino, or N(R6)R7, wherein R6 and R7 together and with inclusion of the nitrogen atom to which they are bonded form an azetidinyl-, piperidinyl-, piperazinyl-, 4-methylpiperazinyl-, or morpholinyl-ring;
R8 is pyridyl or methylphenylsulfonylamino;
B is hydrogen, fluorine, chlorine, (C$_1$-C$_4$)alkyl, (C$_1$-C$_4$) alkoxy, or thienyl;
R14 is hydrogen or methyl;
and the salts of these compounds.

A special embodiment of the compounds of the present invention include those compounds of formula I wherein
ring D and ring E together form the fused ring system

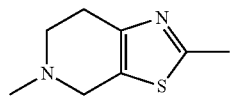

and L is bond and A, B have the meanings as defined above, and the salts of those compounds.

Another special embodiment of the compounds of the present invention include those compounds of formula I wherein
ring D and ring E together form the fused ring system

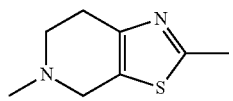

and L is —(CH$_2$)$_n$S(O)$_2$— and A, B, n have the meanings as defined above, and the salts of those compounds.

Another special embodiment of the compounds of the present invention include those compounds of formula I wherein
ring D and ring E together form the fused ring system

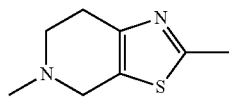

and L is —C(=O)— and A, B have the meanings as defined above, and the salts of those compounds.

Another special embodiment of the compounds of the present invention include those compounds of formula I wherein
ring D and ring E together form the fused ring system

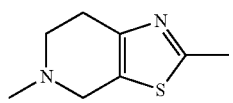

and L is —C(=S)— and A, B have the meanings as defined above, and the salts of those compounds.

Another special embodiment of the compounds of the present invention include those compounds of formula I wherein
ring D and ring E together form the fused ring system

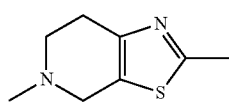

and L is —(CH$_2$)$_n$OC(=O)— and A, B, n have the meanings as defined above, and the salts of those compounds.

Another special embodiment of the compounds of the present invention include those compounds of formula I wherein
ring D and ring E together form the fused ring system

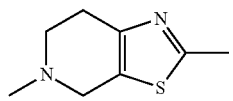

and L is —(CH$_2$)$_n$N(R10)C(=O)— and A, B, R10, n have the meanings as defined above, and the salts of those compounds.

Another special embodiment of the compounds of the present invention include those compounds of formula I wherein
ring D and ring E together form the fused ring system

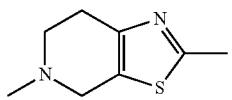

and L is —(CH$_2$)$_n$N(R10)C(=NR11)- and A, B, R10, R11, n have the meanings as defined above, and the salts of those compounds.

Another special embodiment of the compounds of the present invention include those compounds of formula I wherein
ring D and ring E together form the fused ring system

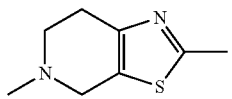

and L is —(CH$_2$)$_n$N(R10)C(=S)— and A, B, R10, n have the meanings as defined above, and the salts of those compounds.

Another special embodiment of the compounds of the present invention include those compounds of formula I wherein
ring D and ring E together form the fused ring system

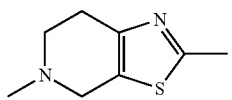

and L is —C=C—C(=O)— and A, B have the meanings as defined above, and the salts of those compounds.

Another special embodiment of the compounds of the present invention include those compounds of formula I wherein
ring D and ring E together form the fused ring system

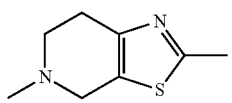

and L is —N=C(R11)- and A, B, R11 have the meanings as defined above, and the salts of those compounds.

Another special embodiment of the compounds of the present invention include those compounds of formula I wherein
ring D and ring E together form the fused ring system

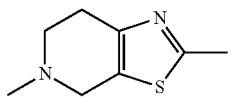

and L is —(CH$_2$)$_n$N(R10)C(=O)C(=O)— and A, B, R10, n have the meanings as defined above, and the salts of those compounds.

Another special embodiment of the compounds of the present invention include those compounds of formula I wherein
ring D and ring E together form the fused ring system

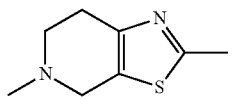

and L is —OCH$_2$C(=O)— and A, B have the meanings as defined above, and the salts of those compounds.

Another special embodiment of the compounds of the present invention include those compounds of formula I wherein
ring D and ring E together form the fused ring system

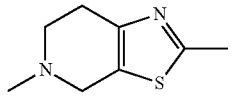

and L is —N(R10)C(=CR11)- and A, B, R10, R11 have the meanings as defined above, and the salts of those compounds.

Another special embodiment of the compounds of the present invention include those compounds of formula I wherein
ring D and ring E together form the fused ring system

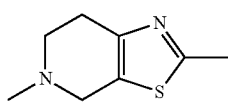

and L is —N=C(NR11)- and A, B, R11 have the meanings as defined above and the salts of those compounds.

A further special embodiment of the compounds of the present invention include those compounds of formula I wherein
ring D and ring E together form the fused ring system

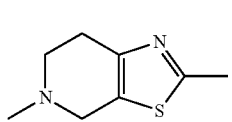

and L is bond, A is (C$_1$-C$_4$)alkyl, (C$_1$-C$_4$)alkoxy(C$_1$-C$_2$)alkyl, or (C$_1$-C$_4$)alkylthio(C$_1$-C$_2$)alkyl and B has the meaning as defined above, and the salts of those compounds.

Another special embodiment of the compounds of the present invention include those compounds of formula I wherein
ring D and ring E together form the fused ring system

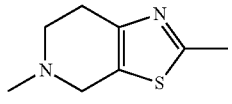

and L is —(CH$_2$)$_n$S(O)$_2$—, A is (C$_1$-C$_4$)alkyl, (C$_1$-C$_4$)alkoxy(C$_1$-C$_2$)alkyl, or (C$_1$-C$_4$)alkylthio(C$_1$-C$_2$)alkyl and B, n have the meanings as defined above, and the salts of those compounds.

Another special embodiment of the compounds of the present invention include those compounds of formula I wherein ring D and ring E together form the fused ring system

[structure: N-methyl tetrahydrothiazolopyridine]

and L is —C(=O)—, A is (C$_1$-C$_4$)alkyl, (C$_1$-C$_4$)alkoxy(C$_1$-C$_2$)alkyl, or (C$_1$-C$_4$)alkylthio(C$_1$-C$_2$)alkyl and B has the meaning as defined above, and the salts of those compounds.

Another special embodiment of the compounds of the present invention include those compounds of formula I wherein ring D and ring E together form the fused ring system

[structure: N-methyl tetrahydrothiazolopyridine]

and L is —C(=S)—, A is (C$_1$-C$_4$)alkyl, (C$_1$-C$_4$)alkoxy(C$_1$-C$_2$)alkyl, or (C$_1$-C$_4$)alkylthio(C$_1$-C$_2$)alkyl and B has the meaning as defined above, and the salts of those compounds.

Another special embodiment of the compounds of the present invention include those compounds of formula I wherein ring D and ring E together form the fused ring system

[structure: N-methyl tetrahydrothiazolopyridine]

and L is —(CH$_2$)$_n$OC(=O)—, A is (C$_1$-C$_4$)alkyl, (C$_1$-C$_4$)alkoxy(C$_1$-C$_2$)alkyl, or (C$_1$-C$_4$)alkylthio(C$_1$-C$_2$)alkyl and B, n have the meanings as defined above, and the salts of those compounds.

Another special embodiment of the compounds of the present invention include those compounds of formula I wherein ring D and ring E together form the fused ring system

[structure: N-methyl tetrahydrothiazolopyridine]

and L is —(CH$_2$)$_n$N(R10)C(=O)—, A is (C$_1$-C$_4$)alkyl, (C$_1$-C$_4$)alkoxy(C$_1$-C$_2$)alkyl, or (C$_1$-C$_4$)alkylthio(C$_1$-C$_2$)alkyl and B, R10, n have the meanings as defined above, and the salts of those compounds.

Another special embodiment of the compounds of the present invention include those compounds of formula I wherein ring D and ring E together form the fused ring system

[structure: N-methyl tetrahydrothiazolopyridine]

and L is —(CH$_2$)$_n$N(R10)C(=NR11)-, A is (C$_1$-C$_4$)alkyl, (C$_1$-C$_4$)alkoxy(C$_1$-C$_2$)alkyl, or (C$_1$-C$_4$)alkylthio(C$_1$-C$_2$)alkyl and B, R10, R11, n have the meanings as defined above, and the salts of those compounds.

Another special embodiment of the compounds of the present invention include those compounds of formula I wherein ring D and ring E together form the fused ring system

[structure: N-methyl tetrahydrothiazolopyridine]

and L is —(CH$_2$)$_n$N(R10)C(=S)—, A is (C$_1$-C$_4$)alkoxy(C$_1$-C$_2$)alkyl, or (C$_1$-C$_4$)alkylthio(C$_1$-C$_2$)alkyl and B, R10, n have the meanings as defined above, and the salts of those compounds.

Another special embodiment of the compounds of the present invention include those compounds of formula I wherein ring D and ring E together form the fused ring system

[structure: N-methyl tetrahydrothiazolopyridine]

and L is —C=C—C(=O)—, A is (C$_1$-C$_4$)alkyl, (C$_1$-C$_4$)alkoxy(C$_1$-C$_2$)alkyl, or (C$_1$-C$_4$)alkylthio(C$_1$-C$_2$)alkyl and B has the meaning as defined above, and the salts of those compounds.

Another special embodiment of the compounds of the present invention include those compounds of formula I wherein ring D and ring E together form the fused ring system

[structure: N-methyl tetrahydrothiazolopyridine]

and L is —N=C(R11)-, A is (C$_1$-C$_4$)alkyl, (C$_1$-C$_4$)alkoxy(C$_1$-C$_2$)alkyl, or (C$_1$-C$_4$)alkylthio(C$_1$-C$_2$)alkyl and B, R11 have the meanings as defined above, and the salts of those compounds.

Another special embodiment of the compounds of the present invention include those compounds of formula I wherein ring D and ring E together form the fused ring system

[structure: N-methyl tetrahydrothiazolopyridine]

and L is —(CH$_2$)$_n$N(R10)C(=O)C(=O)—, A is (C$_1$-C$_4$) alkyl, (C$_1$-C$_4$)alkoxy(C$_1$-C$_2$)alkyl, or (C$_1$-C$_4$)alkylthio(C$_1$-C$_2$)alkyl and B, R10, n have the meanings as defined above, and the salts of those compounds.

Another special embodiment of the compounds of the present invention include those compounds of formula I wherein
ring D and ring E together form the fused ring system

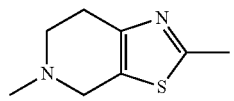

and L is —OCH$_2$C(=O)—, A is (C$_1$-C$_4$)alkyl, (C$_1$-C$_4$) alkoxy(C$_1$-C$_2$)alkyl, or (C$_1$-C$_4$)alkylthio(C$_1$-C$_2$)alkyl and, B has the meaning as defined above, and the salts of those compounds.

Another special embodiment of the compounds of the present invention include those compounds of formula I wherein
ring D and ring E together form a fused ring system selected from

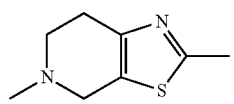

and L is —N(R10)C(=CR11)-, A is (C$_1$-C$_4$)alkyl, (C$_1$-C$_4$) alkoxy(C$_1$-C$_2$)alkyl, or (C$_1$-C$_4$)alkylthio(C$_1$-C$_2$)alkyl and B, R10, R11 have the meanings as defined above, and the salts of those compounds.

Another special embodiment of the compounds of the present invention include those compounds of formula I wherein
ring D and ring E together form a fused ring system selected from

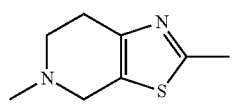

and L is —N=C(NR11)-, A is (C$_1$-C$_4$)alkyl, (C$_1$-C$_4$)alkoxy (C$_1$-C$_2$)alkyl, or (C$_1$-C$_4$)alkylthio(C$_1$-C$_2$)alkyl and B, R11 have the meanings as defined above, and the salts of those compounds.

A further special embodiment of the compounds of the present invention include those compounds of formula I wherein
ring D and ring E together form the fused ring system

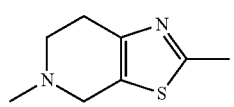

L is bond; A is phenyl optionally substituted by R1 and/or R2, phenyl substituted by R4, naphthyl optionally substituted by R1 and/or R2, pyridyl optionally substituted by R1 and/or R2, pyridyl substituted by R5, pyrimidinyl optionally substituted by R1 and/or R2, pyrimidyl substituted by R8, quinolinyl optionally substituted by R1 and/or R2, or isoquinolinyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R4 is phenyl, phenoxy, 4-methylpiperazinyl, benzylNHC (=O)NH—, or methylphenylsulfonylamino, R5 is methylphenylsulfonylamino, N(R6)R7, wherein R6 and R7 together and with inclusion of the nitrogen atom to which they are bonded form an azetidinyl-, piperidinyl-, piperazinyl-, 4-methylpiperazinyl-, or morpholinyl-ring;

R8 is pyridyl or methylphenylsulfonylamino; and B has the meaning as defined above, and the salts of those compounds.

A further special embodiment of the compounds of the present invention include those compounds of formula I wherein
ring D and ring E together form the fused ring system

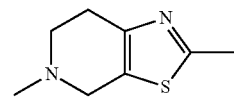

L is bond; A is phenyl optionally substituted by R1 and/or R2, phenyl substituted by R4, naphthyl optionally substituted by R1 and/or R2, pyridyl optionally substituted by R1 and/or R2, pyridyl substituted by R5, pyrimidinyl optionally substituted by R1 and/or R2, pyrimidyl substituted by R8, quinolinyl optionally substituted by R1 and/or R2, or isoquinolinyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R4 is phenyl, phenoxy, 4-methylpiperazinyl, benzylNHC (=O)NH—, or methylphenylsulfonylamino, R5 is methylphenylsulfonylamino, N(R6)R7, wherein R6 and R7 together and with inclusion of the nitrogen atom to which they are bonded form an azetidinyl-, piperidinyl-, piperazinyl-, 4-methylpiperazinyl-, or morpholinyl-ring;

R8 is pyridyl or methylphenylsulfonylamino;

and B is fluorine, chlorine, methoxy, isopropyl or thienyl, in particular thienyl; and the salts of those compounds.

Another special embodiment of the compounds of the present invention include those compounds of formula I wherein
ring D and ring E together form the fused ring system

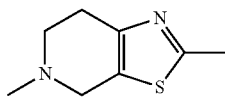

L is —(CH$_2$)$_n$S(O)$_2$—; A is phenyl optionally substituted by R1 and/or R2, phenyl substituted by R4, naphthyl optionally substituted by R1 and/or R2, thienyl optionally substituted by R1 and/or R2, or thiazolyl optionally substituted by R1 and/or R2;

R1 Is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R4 is phenyl, phenoxy, 4-methylpiperazinyl, benzylNHC(=O)NH—, or methylphenylsulfonylamino;

and B, n have the meanings as defined above, and the salts of those compounds.

A further special embodiment of the compounds of the present invention include those compounds of formula I wherein ring D and ring E together form the fused ring system

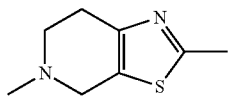

L is —(CH$_2$)$_n$S(O)$_2$—; A is phenyl optionally substituted by R1 and/or R2, phenyl substituted by R4, naphthyl optionally substituted by R1 and/or R2, thienyl optionally substituted by R1 and/or R2, or thiazolyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R4 is phenyl, phenoxy, 4-methylpiperazinyl, benzylNHC(=O)NH—, or methylphenylsulfonylamino; and B is fluorine, chlorine, methoxy, isopropyl or thienyl, in particular thienyl, and n has the meanings as defined above, and the salts of those compounds.

Another special embodiment of the compounds of the present invention include those compounds of formula I wherein ring D and ring E together form the fused ring system

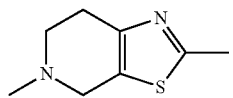

L is —C(=O)—; A is phenyl optionally substituted by R1 and/or R2, phenyl substituted by R4, naphthyl optionally substituted by R1 and/or R2, pyridyl optionally substituted by R1 and/or R2, quinolinyl optionally substituted by R1 and/or R2, or isoquinolinyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, or diethylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R4 is phenyl, phenoxy, 4-methylpiperazinyl, benzylNHC(=O)NH—, or methylphenylsulfonylamino;

and B has the meaning as defined above, and the salts of those compounds.

A further special embodiment of the compounds of the present invention include those compounds of formula I wherein ring D and ring E together form the fused ring system

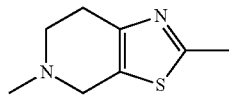

L is —C(=O)—; A is phenyl optionally substituted by R1 and/or R2, phenyl substituted by R4, naphthyl optionally substituted by R1 and/or R2, pyridyl optionally substituted by R1 and/or R2, quinolinyl optionally substituted by R1 and/or R2, or isoquinolinyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, or diethylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R4 is phenyl or phenoxy;

and B is fluorine, chlorine, methoxy, isopropyl or thienyl, in particular thienyl, and n has the meanings as defined above, and the salts of those compounds.

Another special embodiment of the compounds of the present invention include those compounds of formula I wherein ring D and ring E together form the fused ring system

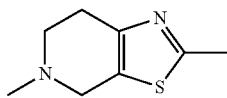

L is —(CH$_2$)$_n$OC(=O)—; A is phenyl optionally substituted by R1 and/or R2, phenyl substituted by R4, naphthyl optionally substituted by R1 and/or R2, or pyridyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, or diethylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R4 is phenyl or phenoxy;

and B, n have the meanings as defined above, and the salts of those compounds.

Another special embodiment of the compounds of the present invention include those compounds of formula I wherein ring D and ring E together form the fused ring system

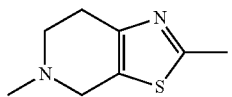

L is —(CH$_2$)$_n$OC(=O)—; A is phenyl optionally substituted by R1 and/or R2, phenyl substituted by R4, naphthyl optionally substituted by R1 and/or R2, or pyridyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, or diethylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R4 is phenyl or phenoxy;

B is fluorine, chlorine, methoxy, isopropyl or thienyl, in particular thienyl, and n has the meanings as defined above, and the salts of those compounds.

Another special embodiment of the compounds of the present invention include those compounds of formula I wherein ring D and ring E together form the fused ring system

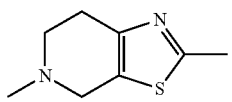

L is —(CH$_2$)$_n$N(R10)C(=O)—; A is cyclohexyl optionally substituted by R1 and/or R2, cyclohexyl substituted by R3, azetidinyl optionally substituted by R1 and/or R2, piperidinyl optionally substituted by R1 and/or R2, phenyl optionally substituted by R1 and/or R2, phenyl substituted by R4, naphthyl optionally substituted by R1 and/or R2, pyridyl optionally substituted by R1 and/or R2, pyridyl substituted by R5, quinolinyl optionally substituted by R1 and/or R2, or isoquinolinyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R3 is 3-pyridyl or 4-pyridyl;

R4 is phenyl, phenoxy, or 4-methylpiperazinyl;

R5 is —N(R6)R7, wherein R6 and R7 together and with inclusion of the nitrogen atom to which they are bonded form an azetidinyl-, piperidinyl-, piperazinyl-, 4-methylpiperazinyl-, or morpholinyl-ring;

and B, R10, n have the meanings as defined above, and the salts of those compounds.

Another special embodiment of the compounds of the present invention include those compounds of formula I wherein ring D and ring E together form the fused ring system

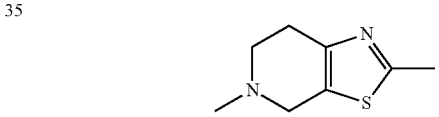

L is —(CH$_2$)$_n$N(R10)C(=O)—; A is cyclohexyl optionally substituted by R1 and/or R2, cyclohexyl substituted by R3, azetidinyl optionally substituted by R1 and/or R2, piperidinyl optionally substituted by R1 and/or R2, phenyl optionally substituted by R1 and/or R2, phenyl substituted by R4, naphthyl optionally substituted by R1 and/or R2, pyridyl optionally substituted by R1 and/or R2, pyridyl substituted by R5, quinolinyl optionally substituted by R1 and/or R2, or isoquinolinyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R3 is 3-pyridyl or 4-pyridyl;

R4 is phenyl, phenoxy, or 4-methylpiperazinyl;

R5 is —N(R6)R7, wherein R6 and R7 together and with inclusion of the nitrogen atom to which they are bonded form an azetidinyl-, piperidinyl-, piperazinyl-, 4-methylpiperazinyl-, or morpholinyl-ring;

B is fluorine, chlorine, methoxy, isopropyl or thienyl, in particular thienyl; and R10, n have the meanings as defined above, and the salts of those compounds.

Another special embodiment of the compounds of the present invention include those compounds of formula I wherein
ring D and ring E together form the fused ring system

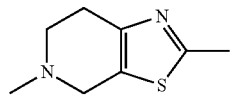

L is —(CH$_2$)$_n$N(R10)C(=NR11)- or —N=C(NR11)-; A is phenyl optionally substituted by R1 and/or R2, phenyl substituted by R4, or naphthyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R4 is phenyl or phenoxy;

and B, R10, R11, n have the meanings as defined above, and the salts of those compounds.

A further special embodiment of the compounds of the present invention include those compounds of formula I wherein
ring D and ring E together form the fused ring system

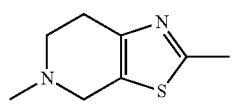

L is —(CH$_2$)$_n$N(R10)C(=NR11)- or —N=C(NR11)-; A is phenyl optionally substituted by R1 and/or R2, phenyl substituted by R4, naphthyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R4 is phenyl or phenoxy;

B is fluorine, chlorine, methoxy, isopropyl or thienyl, in particular thienyl; and R10, R11, n have the meanings as defined above, and the salts of those compounds.

Another special embodiment of the compounds of the present invention include those compounds of formula I wherein
ring D and ring E together form the fused ring system

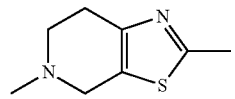

L is —(CH$_2$)$_n$N(R10)C(=S)—; A cyclohexyl optionally substituted by R1 and/or R2, cyclohexyl substituted by R3, piperidinyl optionally substituted by R1 and/or R2, phenyl optionally substituted by R1 and/or R2, phenyl substituted by R4, naphthyl optionally substituted by R1 and/or R2, pyridyl optionally substituted by R1 and/or R2, quinolinyl optionally substituted by R1 and/or R2, or isoquinolinyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R3 is 3-pyridyl or 4-pyridyl;

R4 is phenyl; and B, R10, n have the meanings as defined above, and the salts of those compounds.

A further special embodiment of the compounds of the present invention include those compounds of formula I wherein
ring D and ring E together form the fused ring system

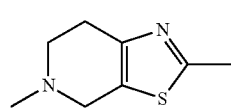

L is —(CH$_2$)$_n$N(R10)C(=S)—; A is cyclohexyl optionally substituted by R1 and/or R2, cyclohexyl substituted by R3, piperidinyl optionally substituted by R1 and/or R2, phenyl optionally substituted by R1 and/or R2, phenyl substituted by R4, naphthyl optionally substituted by R1 and/or R2, pyridyl optionally substituted by R1 and/or R2, quinolinyl optionally substituted by R1 and/or R2, or isoquinolinyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R3 is 3-pyridyl or 4-pyridyl;

R4 is phenyl; B is fluorine, chlorine, methoxy, isopropyl or thienyl, in particular thienyl;
and R10, n have the meanings as defined above, and the salts of those compounds.

Another special embodiment of the compounds of the present invention include those compounds of formula I wherein
ring D and ring E together form the fused ring system

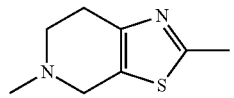

L is —C=C—C(=O)—; A is phenyl optionally substituted by R1 and/or R2, or naphthyl optionally substituted by R1 and/or R2;
R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;
R2 is fluorine, hydroxyl, methyl, ethyl, propyl, isopropyl, methoxy, ethoxy, propoxy, or isopropoxy or
R1 and R2 when ortho to each other form a methylenedioxy group;
and B has the meaning as defined above, and the salts of those compounds.

A further special embodiment of the compounds of the present invention include those compounds of formula I wherein
ring D and ring E together form the fused ring system

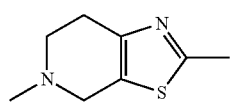

L is —C=C—C(=O)—; A phenyl optionally substituted by R1 and/or R2, or naphthyl optionally substituted by R1 and/or R2;
R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;
R2 is fluorine, hydroxyl, methyl, ethyl, propyl, isopropyl, methoxy, ethoxy, propoxy, or isopropoxy or
R1 and R2 when ortho to each other form a methylenedioxy group;
B is fluorine, chlorine, methoxy, isopropyl or thienyl, in particular thienyl; and the salts of those compounds.

Another special embodiment of the compounds of the present invention include those compounds of formula I wherein
ring D and ring E together form the fused ring system

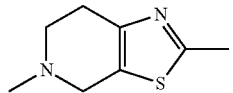

L is —N=C(R11)-; A phenyl optionally substituted by R1 and/or R2, phenyl substituted by R4 or naphthyl optionally substituted by R1 and/or R2;
R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;
R2 is fluorine, hydroxyl, methyl, ethyl, propyl, isopropyl, methoxy, ethoxy, propoxy, or isopropoxy or
R1 and R2 when ortho to each other form a methylenedioxy group;
R4 is phenyl; and B, R11 have the meanings as defined above, and the salts of those compounds.

A further special embodiment of the compounds of the present invention include those compounds of formula I wherein
ring D and ring E together form the fused ring system

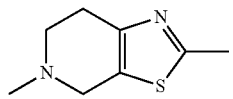

L is —N=C(R11)-; A phenyl optionally substituted by R1 and/or R2, phenyl substituted by R4 or naphthyl optionally substituted by R1 and/or R2;
R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;
R2 is fluorine, hydroxyl, methyl, ethyl, propyl, isopropyl, methoxy, ethoxy, propoxy, or isopropoxy or
R1 and R2 when ortho to each other form a methylenedioxy group;
R4 is phenyl; B is fluorine, chlorine, methoxy, isopropyl or thienyl, in particular thienyl; R11 has the meanings as defined above, and the salts of those compounds.

Another special embodiment of the compounds of the present invention include those compounds of formula I wherein
ring D and ring E together form the fused ring system

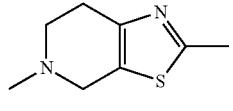

L is —(CH$_2$)$_n$N(R10)C(=O)C(=O)—, A is cyclohexyl optionally substituted by R1 and/or R2, cyclohexyl substituted by R3, phenyl optionally substituted by R1 and/or R2, phenyl substituted by R4, naphthyl optionally substituted by R1 and/or R2, pyridyl optionally substituted by R1 and/or R2, pyridyl substituted by R5, quinolinyl optionally substituted by R1 and/or R2, or isoquinolinyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R3 is 3-pyridyl or 4-pyridyl;

R4 is phenyl, phenoxy, or 4-methylpiperazinyl;

R5 is —N(R6)R7, wherein R6 and R7 together and with inclusion of the nitrogen atom to which they are bonded form an azetidinyl-, piperidinyl-, piperazinyl-, 4-methylpiperazinyl-, morpholinyl-ring; and B, R10, n have the meanings as defined above, and the salts of those compounds.

A further special embodiment of the compounds of the present invention include those compounds of formula I wherein
ring D and ring E together form the fused ring system

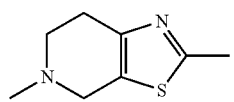

L is —(CH₂)ₙN(R10)C(=O)C(=O)—; A is cyclohexyl optionally substituted by R1 and/or R2, cyclohexyl substituted by R3, phenyl optionally substituted by R1 and/or R2, phenyl substituted by R4, naphthyl optionally substituted by R1 and/or R2, pyridyl optionally substituted by R1 and/or R2, pyridyl substituted by R5, quinolinyl optionally substituted by R1 and/or R2, or isoquinolinyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R3 is 3-pyridyl or 4-pyridyl;

R4 is phenyl, phenoxy, or 4-methylpiperazinyl;

R5 is —N(R6)R7, wherein R6 and R7 together and with inclusion of the nitrogen atom to which they are bonded form an azetidinyl-, piperidinyl-, piperazinyl-, 4-methylpiperazinyl-, morpholinyl-ring;

B is fluorine, chlorine, methoxy, isopropyl or thienyl, in particular thienyl; R10, n have the meanings as defined above, and the salts of those compounds.

Another special embodiment of the compounds of the present invention include those compounds of formula I wherein
ring D and ring E together form the fused ring system

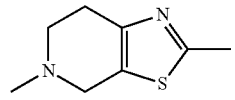

L is —OCH₂C(=O)—; A is phenyl optionally substituted by R1 and/or R2, phenyl substituted by R4, or naphthyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R4 is phenyl; and B has the meaning as defined above, and the salts of those compounds.

A further special embodiment of the compounds of the present invention include those compounds of formula I wherein
ring D and ring E together form the fused ring system

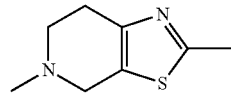

L is —OCH₂C(=O)—; A is phenyl optionally substituted by R1 and/or R2, phenyl substituted by R4, or naphthyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R4 is phenyl; B is fluorine, chlorine, methoxy, isopropyl or thienyl, in particular thienyl; and the salts of those compounds.

Another special embodiment of the compounds of the present invention include those compounds of formula I wherein
ring D and ring E together form a fused ring system selected from

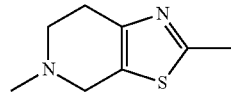

L is —N(R10)C(=CR11)—; A is phenyl optionally substituted by R1 and/or R2, phenyl substituted by R4, or naphthyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R4 is phenyl; and B, R10, R11 have the meanings as defined above, and the salts of those compounds.

A further special embodiment of the compounds of the present invention include those compounds of formula I wherein ring D and ring E together form a fused ring system selected from

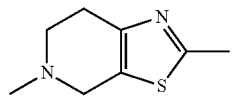

L is —N(R10)C(=CR11)—; A is phenyl optionally substituted by R1 and/or R2, phenyl substituted by R4, or naphthyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R4 is phenyl;

B is fluorine, chlorine, methoxy, isopropyl or thienyl, in particular thienyl; and R10, R11 have the meanings as defined above, and the salts of those compounds.

Another preferred embodiment of the present invention relates to compounds of formula I wherein
ring D and ring E together form the fused ring system

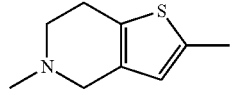

A is $(C_1$-$C_4)$alkyl, $(C_1$-$C_4)$alkoxy$(C_1$-$C_2)$alkyl, phenyl optionally substituted by R1 and/or R2, naphthyl optionally substituted by R1 and/or R2, or pyridyl optionally substituted by R1 and/or R2;

R1 is $(C_1$-$C_4)$alkyl, $(C_1$-$C_4)$alkoxy, $(C_1$-$C_4)$alkyl which is partially or completely substituted by fluorine, $(C_1$-$C_4)$ alkoxy which is predominantly or completely substituted by fluorine, $(C_1$-$C_4)$alkoxy$(C_1$-$C_2)$alkyl, $(C_1$-$C_4)$alkoxycarbonyl, or mono- or -di$(C_1$-$C_4)$alkylamino;

R2 is $(C_1$-$C_4)$alkyl, $(C_1$-$C_4)$alkoxy, or

R1 and R2 when ortho to each other form a methylenedioxy group;

L is —$(CH_2)_n$N(R10)C(=O)— or —$(CH_2)_n$S(O)$_2$—;

R10 is hydrogen or $(C_1$-$C_4)$alkyl;

B is hydrogen, fluorine, chlorine, $(C_1$-$C_4)$alkyl, $(C_1$-$C_4)$ alkoxy, or thienyl;

n is an integer selected from 0 and 1;

and the salts of these compounds.

Another preferred embodiment of the present invention relates to compounds of formula I
wherein
ring D and ring E together form the fused ring system

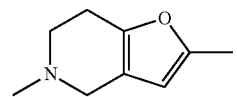

A is $(C_1$-$C_4)$alkyl, phenyl optionally substituted by R1 and/or R2, naphthyl optionally substituted by R1 and/or R2, or pyridyl optionally substituted by R1 and/or R2;

R1 is $(C_1$-$C_4)$alkyl, $(C_1$-$C_4)$alkoxy, $(C_1$-$C_4)$alkyl which is partially or completely substituted by fluorine, $(C_1$-$C_4)$ alkoxy which is predominantly or completely substituted by fluorine, $(C_1$-$C_4)$alkoxy$(C_1$-$C_2)$alkyl, $(C_1$-$C_4)$alkoxycarbonyl, or mono- or -di$(C_1$-$C_4)$alkylamino;

R2 is $(C_1$-$C_4)$alkyl, $(C_1$-$C_4)$alkoxy, or

R1 and R2 when ortho to each other form a methylenedioxy group;

L is —$(CH_2)_n$N(R10)C(=O)— or —$(CH_2)_n$S(O)$_2$—;

R10 is hydrogen or $(C_1$-$C_4)$alkyl;

B is hydrogen, fluorine, chlorine, $(C_1$-$C_4)$alkyl, $(C_1$-$C_4)$ alkoxy, or thienyl;

n is an integer selected from 0 and 1;

and the salts of these compounds.

Another preferred embodiment of the present invention relates to compounds of formula I wherein
ring D and ring E together form the fused ring system

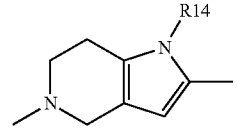

A is $(C_1$-$C_4)$alkyl, phenyl optionally substituted by R1 and/or R2, naphthyl optionally substituted by R1 and/or R2, or pyridyl optionally substituted by R1 and/or R2;

R1 is $(C_1$-$C_4)$alkyl, $(C_1$-$C_4)$alkoxy, $(C_1$-$C_4)$alkyl which is partially or completely substituted by fluorine, $(C_1$-$C_4)$ alkoxy which is predominantly or completely substituted by fluorine, $(C_1$-$C_4)$alkoxy$(C_1$-$C_2)$allyl, $(C_1$-$C_4)$alkoxycarbonyl, or mono- or -di$(C_1$-$C_4)$alkylamino;

R2 is $(C_1$-$C_4)$alkyl, $(C_1$-$C_4)$alkoxy, or

R1 and R2 when ortho to each other form a methylenedioxy group;

L is —$(CH_2)_n$N(R10)C(=O)— or —$(CH_2)_n$S(O)$_2$—;

R10 is hydrogen or $(C_1$-$C_4)$alkyl;

R14 is hydrogen or methyl:

B is hydrogen, fluorine, chlorine, $(C_1$-$C_4)$alkyl, $(C_1$-$C_4)$ alkoxy, or thienyl;

n is an integer selected from 0 and 1;

and the salts of these compounds.

Another embodiment of the compounds according to the present invention relates to compounds of formula I selected from:

$N^2$-(2-aminophenyl)-$N^5$-biphenyl-4-yl-6,7-dihydro[1,3]thiazolo[5,4-c]pyridine-2,5(4H)-dicarboxamide, $N^2$-(2-aminophenyl)-$N^5$-[4-(dimethylamino)phenyl]-6,7-dihydro[1,3]thiazolo[5,4-c]pyridine-2,5(4H)-dicarboxamide, $N^2$-(2-aminophenyl)-$N^5$-(4-methoxyphenyl)-6,7-dihydro[1,3]thiazolo[5,4-c]pyridine-2,5(4H)-dicarboxamide, $N^2$-(2-aminophenyl)-$N^5$-benzyl-6,7-dihydro[1,3]thiazolo[5,4-c]pyridine-2,5(4H)-dicarboxamide, Methyl 4-[({2-[(2-aminophenyl)carbamoyl]-6,7-dihydro[1,3]thiazolo[5,4-c]pyridin-5(4H)yl}carbonyl)amino]benzoate, $N^2$-(2-aminophenyl)-$N^5$-(4-phenoxyphenyl)-6,7-dihydro[1,3]thiazolo[5,4-c]pyridine-2,5(4H)-dicarboxamide, $N^2$-(2-aminophenyl)-$N^5$-1,3-benzodioxol-5-yl-6,7-dihydro[1,3]thiazolo[5,4-c]pyridine-2,5(4H)-dicarboxamide, $N^2$-(2-aminophenyl)-$N^5$-[2-(trifluoromethoxy)phenyl]-6,7-dihydro[1,3]thiazolo[5,4-c]pyridine-2,5(4H)-dicarboxamide, $N^2$-(2-aminophenyl)-$N^5$-[4-(trifluoromethoxy)phenyl]-6,7-dihydro[1,3]thiazolo[5,4-c]pyridine-2,5(4H)-dicarboxamide, $N^2$-(2-aminophenyl)-$N^5$-[2-(difluoromethoxy)phenyl]-6,7-dihydro[1,3]thiazolo[5,4-c]pyridine-2,5(4H)-dicarboxamide, $N^2$-(2-aminophenyl)-$N^5$-[4-(difluoromethoxy)phenyl]-6,7-dihydro[1,3]thiazolo[5,4-c]pyridine-2,5(4H)-dicarboxamide, $N^2$-(2-aminophenyl)-$N^5$-quinolin-3-yl-6,7-dihydro[1,3]thiazolo[5,4-c]pyridine-2,5(4H)-dicarboxamide, $N^2$-(2-aminophenyl)-$N^5$-(4-methylphenyl)-6,7-dihydro[1,3]thiazolo[5,4-c]pyridine-2,5(4H)-dicarboxamide, $N^2$-(2-aminophenyl)-$N^5$-(pyridin-3-ylmethyl)-6,7-dihydro[1,3]thiazolo[5,4-c]pyridine-2,5(4H)-dicarboxamide, $N^2$-(2-aminophenyl)-$N^5$-pyridin-4-yl-6,7-dihydro[1,3]thiazolo[5,4-c]pyridine-2,5(4H)-dicarboxamide, $N^2$-(2-aminophenyl)-$N^5$-(2-methoxyethyl)-6,7-dihydro[1,3]thiazolo[5,4-c]pyridine-2,5(4H)-dicarboxamide, $N^2$-(2-aminophenyl)-$N^5$-methyl-6,7-dihydro[1,3]thiazolo[5,4-c]pyridine-2,5(4H)-dicarboxamide, $N^2$-(2-aminophenyl)-$N^5$-[3-(dimethylamino)phenyl]-6,7-dihydro[1,3]thiazolo[5,4-c]pyridine-2,5(4H)-dicarboxamide, $N^2$-(2-aminophenyl)-$N^5$-(3,4-dimethoxyphenyl)-6,7-dihydro[1,3]thiazolo[5,4-c]pyridine-2,5(4H)-dicarboxamide, $N^2$-(2-aminophenyl)-$N^5$-(2-methoxyethyl)-$N^5$-methyl-6,7-dihydro[1,3]thiazolo[5,4-c]pyridine-2,5(4H)-dicarboxamide, $N^2$-(2-aminophenyl)-$N^5$-ethyl-$N^5$-isopropyl-6,7-dihydro[1,3]thiazolo[5,4-c]pyridine-2,5(4H)-dicarboxamide, $N^2$-(2-aminophenyl)-$N^5$-[4-(dimethylamino)phenyl]-$N^5$-methyl-6,7-dihydro[1,3]thiazolo[5,4-c]pyridine-2,5(4H)-dicarboxamide, $N^2$-(2-aminophenyl)-$N^5$-[3-(dimethylamino)phenyl]-$N^5$-methyl-6,7-dihydro[1,3]thiazolo[5,4-c]pyridine-2,5(4H)-dicarboxamide, $N^2$-(2-aminophenyl)-$N^5$-(3,4-dimethoxyphenyl)-$N^5$-methyl-6,7-dihydro[1,3]thiazolo[5,4-c]pyridine-2,5(4H)-dicarboxamide, $N^2$-(2-aminophenyl)-$N^5$-(3,4-dimethoxyphenyl)-$N^5$-ethyl-6,7-dihydro[1,3]thiazolo[5,4-c]pyridine-2,5(4H)-dicarboxamide, $N^2$-(2-aminophenyl)-$N^5$-(3,4-dimethoxyphenyl)-$N^5$-(2-methoxyethyl)-6,7-dihydro[1,3]thiazolo[5,4-c]pyridine-2,5(4H)-dicarboxamide, $N^2$-(2-aminophenyl)-$N^5$-methyl-$N^5$-pyridin-3-yl-6,7-dihydro[1,3]thiazolo[5,4-c]pyridine-2,5(4H)-dicarboxamide, $N^2$-(2-aminophenyl)-$N^5$-ethyl-$N^5$-pyridin-3-yl-6,7-dihydro[1,3]thiazolo[5,4-c]pyridine-2,5(4H)-dicarboxamide, $N^2$-(2-aminophenyl)-$N^5$-1,3-benzodioxol-5-yl-$N^5$-ethyl-6,7-dihydro[1,3]thiazolo[5,4-c]pyridine-2,5(4H)-dicarboxamide, $N^2$-(2-aminophenyl)-$N^5$-1,3-benzodioxol-5-yl-$N^5$-(2-methoxyethyl)-6,7-dihydro[1,3]thiazolo[5,4-c]pyridine-2,5(4H)-dicarboxamide, $N^2$-(2-aminophenyl)-$N^5$-1,3-benzodioxol-5-yl-$N^5$-methyl-6,7-dihydro[1,3]thiazolo[5,4-c]pyridine-2,5(4H)-dicarboxamide, $N^2$-(2-aminophenyl)-$N^5$-[3-(4-methylpiperazin-1-yl)phenyl]-6,7-dihydro[1,3]thiazolo[5,4-c]pyridine-2,5(4H)-dicarboxamide, $N^2$-(2-aminophenyl)-$N^5$-(2-methoxyethyl)-$N^5$-pyridin-3-yl-6,7-dihydro[1,3]thiazolo[5,4-c]pyridine-2,5(4H)-dicarboxamide, $N^2$-(2-aminophenyl)-$N^5$-(6-morpholin-4-ylpyridin-3-yl)-6,7-dihydro[1,3]thiazolo[5,4-c]pyridine-2,5(4H)-dicarboxamide, $N^2$-(2-aminophenyl)-$N^5$-(6-azetidin-1-ylpyridin-3-yl)-6,7-dihydro[1,3]thiazolo[5,4-c]pyridine-2,5(4H)-dicarboxamide, $N^2$-(2-aminophenyl)-$N^5$-[6-(dimethylamino)pyridin-3-yl]-6,7-dihydro[1,3]thiazolo[5,4-c]pyridine-2,5(4H)-dicarboxamide, $N^2$-(2-aminophenyl)-$N^5$-[6-(4-methylpiperazin-1-yl)pyridin-3-yl]-6,7-dihydro[1,3]thiazolo[5,4-c]pyridine-2,5(4H)-dicarboxamide, $N^2$-(2-aminophenyl)-$N^5$-(6-methoxypyridin-3-yl)-6,7-dihydro[1,3]thiazolo[5,4-c]pyridine-2,5(4H)-dicarboxamide, $N^2$-(2-aminophenyl)-$N^5$-pyridin-3-yl-6,7-dihydro[1,3]thiazolo[5,4-c]pyridine-2,5(4H)-dicarboxamide, $N^2$-(2-aminophenyl)-$N^5$-butyl-6,7-dihydro[1,3]thiazolo[5,4-c]pyridine-2,5(4H)-dicarboxamide, $N^2$-(2-aminophenyl)-$N^5$-(4-pyridin-3-ylcyclohexyl)-6,7-dihydro[1,3]thiazolo[5,4-c]pyridine-2,5(4H)-dicarboxamide, $N^2$-(2-aminophenyl)-$N^5$-piperidin-4-yl-6,7-dihydro[1,3]thiazolo[5,4-c]pyridine-2,5(4H)-dicarboxamide, $N^2$-(2-amino-5-methoxyphenyl)-$N^5$-(4-methoxyphenyl)-6,7-dihydro[1,3]thiazolo[5,4-c]pyridine-2,5(4H)-dicarboxamide, $N^2$-(2-aminophenyl)-$N^5$-(4-pyridin-4-ylcyclohexyl)-6,7-dihydro[1,3]thiazolo[5,4-c]pyridine-2,5(4H)-dicarboxamide, $N^2$-(2-amino-5-isopropylphenyl)-$N^5$-(4-methoxyphenyl)-6,7-dihydro[1,3]thiazolo[5,4-c]pyridine-2,5(4H)-dicarboxamide, $N^2$-(2-amino-5-methoxyphenyl)-$N^5$-isoquinolin-5-yl-6,7-dihydro[1,3]thiazolo[5,4-c]pyridine-2,5(4H)-dicarboxamide, $N^2$-(2-amino-5-methoxyphenyl)-$N^5$-[4-(dimethylamino)phenyl]-6,7-dihydro[1,3]thiazolo[5,4-c]pyridine-2,5(4H)-dicarboxamide, $N^2$-(2-amino-5-isopropylphenyl)-$N^5$-(3,4-dimethoxyphenyl)-6,7-dihydro[1,3]thiazolo[5,4-c]pyridine-2,5(4H)-dicarboxamide, $N^2$-(2-amino-5-isopropylphenyl)-$N^5$-isoquinolin-5-yl-6,7-dihydro[1,3]thiazolo[5,4-c]pyridine-2,5(4H)-dicarboxamide, N²-(2-amino-5-isopropylphenyl)-N⁵-[4-(dimethylamino) phenyl]-6,7-dihydro[1,3]thiazolo[5,4-c]pyridine-2,5 (4H)-dicarboxamide, N²-(2-amino-5-methoxyphenyl)-N⁵-(4-fluorophenyl)-6,7-dihydro[1,3]thiazolo[5,4-c]pyridine-2,5(4H)-dicarboxamide, N²-(2-amino-5-isopropylphenyl)-N⁵-(4-fluorophenyl)-6,7-dihydro[1,3]thiazolo[5,4-c]pyridine-2,5(4H)-dicarboxamide, N²-[2-amino-5-(dimethylamino)phenyl]-N⁵-(4-methoxyphenyl)-6,7-dihydro[1,3]thiazolo[5,4-c]pyridine-2,5 (4H)-dicarboxamide, N²-[2-amino-5-(2-thienyl)phenyl]-N⁵-(4-methoxyphenyl)-6,7-dihydro[1,3]thiazolo[5,4-c]pyridine-2,5(4H)-dicarboxamide, N²-[2-amino-5-(2-thienyl)phenyl]-N⁵-[4-(dimethylamino) phenyl]-6,7-dihydro[1,3]thiazolo[5,4-c]pyridine-2,5 (4H)-dicarboxamide, N²-[2-amino-5-(3-thienyl)phenyl]-N⁵-(4-methoxyphenyl)-6,7-dihydro[1,3]thiazolo[5,4-c]pyridine-2,5(4H)-dicarboxamide, N²-[2-amino-5-(dimethylamino)phenyl]-N⁵-[4-(dimethylamino)phenyl]-6,7-dihydro[1,3]thiazolo[5,4-c]pyridine-2,5(4H)-dicarboxamide, N²-(2-amino-5-pyrrolidin-1-ylphenyl)-N⁵-(4-methoxyphenyl)-6,7-dihydro[1,3]thiazolo[5,4-c]pyridine-2,5(4H)-dicarboxamide, N²-[2-amino-5-(3-thienyl)phenyl]-N⁵-[4-(dimethylamino) phenyl]-6,7-dihydro[1,3]thiazolo[5,4-c]pyridine-2,5 (4H)-dicarboxamide, N²-(2-amino-5-isopropylphenyl)-N⁵-pyridin-3-yl-6,7-dihydro[1,3]thiazolo[5,4-c]pyridine-2,5(4H)-dicarboxamide, N²-[2-amino-5-(dimethylamino)phenyl]-N⁵-(3,4-dimethoxyphenyl)-6,7-dihydro[1,3]thiazolo[5,4-c]pyridine-2,5 (4H)-dicarboxamide, N²-(2-aminophenyl)-N⁵-isoquinolin-5-yl-6,7-dihydro[1,3] thiazolo[5,4-c]pyridine-2,5(4H)-dicarboxamide, N²-(2-aminophenyl)-N⁵-[3-(dimethylamino)phenyl]-6,7-dihydro[1,3]thiazolo[5,4-c]pyridine-2,5(4H)-dicarboxamide dihydrochloride, N-(2-aminophenyl)-5-[{[4-(dimethylamino)phenyl]amino} (oxo)acetyl]-4,5,6,7-tetrahydro[1,3]thiazolo[5,4-c]pyridine-2-carboxamide, N-(2-aminophenyl)-5-{[(4-methoxyphenyl)amino](oxo) acetyl}-4,5,6,7-tetrahydro[1,3]thiazolo[5,4-c]pyridine-2-carboxamide, N-(2-aminophenyl)-5-{[(3,4-dimethoxyphenyl)amino](oxo) acetyl}-4,5,6,7-tetrahydro[1,3]thiazolo[5,4-c]pyridine-2-carboxamide, N-(2-aminophenyl)-5-{oxo[(4-pyridin-4-ylcyclohexyl) amino]acetyl}-4,5,6,7-tetrahydro[1,3]-thiazolo[5,4-c]pyridine-2-carboxamide, N-(2-aminophenyl)-5-[isoquinolin-5-ylamino)(oxo)acetyl]-4,5,6,7-tetrahydro[1,3]thiazolo[5,4-c]pyridine-2-carboxamide, N-(2-aminophenyl)-5-{oxo[(4-pyridin-3-ylcyclohexyl) amino]acetyl}-4,5,6,7-tetrahydro[1,3]thiazolo[5,4-c]pyridine-2-carboxamide, N-(2-aminophenyl)-5-{[(6-methoxypyridin-3-yl)amino] (oxo)acetyl}-4,5,6,7-tetrahydro[1,3]thiazolo[5,4-c]pyridine-2-carboxamide, N-(2-aminophenyl)-5-[{[6-(dimethylamino)pyridin-3-yl] amino}(oxo)acetyl]-4,5,6,7-tetrahydro[1,3]thiazolo[5,4-c]pyridine-2-carboxamide, N-(2-aminophenyl)-5-(oxo{[4-(trifluoromethoxy)phenyl] amino}acetyl)-4,5,6,7-tetrahydro[1,3]thiazolo[5,4-c]pyridine-2-carboxamide, N-(2-aminophenyl)-5-{[(6-morpholin-4-ylpyridin-3-yl) amino](oxo)acetyl}-4,5,6,7-tetrahydro[1,3]thiazolo[5,4-c]pyridine-2-carboxamide, N-(2-aminophenyl)-5-{[(1,3-benzodioxol-5-yl)amino](oxo) acetyl}-4,5,6,7-tetrahydro[1,3]thiazolo[5,4-c]pyridine-2-carboxamide, N-(2-aminophenyl)-5-{[(4-methylphenyl)amino](oxo) acetyl}-4,5,6,7-tetrahydro[1,3]thiazolo[5,4-c]pyridine-2-carboxamide, N-(2-aminophenyl)-5-{[(5-methylpyridin-2-yl)amino](oxo) acetyl}-4,5,6,7-tetrahydro[1,3]thiazolo[5,4-c]pyridine-2-carboxamide, N-(2-aminophenyl)-5-[oxo(quinolin-3-ylamino)acetyl]-4,5,6,7-tetrahydro[1,3]thiazolo[5,4-c]pyridine-2-carboxamide, N-(2-amino-5-methoxyphenyl)-5-{[(4-methoxyphenyl) amino](oxo)acetyl}-4,5,6,7-tetrahydro[1,3]thiazolo[5,4-c]pyridine-2-carboxamide, N-(2-aminophenyl)-5-[(butylamino)(oxo)acetyl]-4,5,6,7-tetrahydro[1,3]thiazolo[5,4-c]pyridine-2-carboxamide, N-(2-amino-5-isopropylphenyl)-5-{[(3,4-dimethoxyphenyl) amino](oxo)acetyl}-4,5,6,7-tetrahydro[1,3]thiazolo[5,4-c]pyridine-2-carboxamide, N-(2-amino-5-isopropylphenyl)-5-{[(4-methoxyphenyl) amino](oxo)acetyl}-4,5,6,7-tetrahydro[1,3]thiazolo[5,4-c]pyridine-2-carboxamide, N-(2-amino-5-methoxyphenyl)-5-{[(3,4-dimethoxyphenyl) amino](oxo)acetyl}-4,5,6,7-tetrahydro[1,3]thiazolo[5,4-c]pyridine-2-carboxamide, N-(2-amino-5-methoxyphenyl)-5-[(butylamino)(oxo) acetyl]-4,5,6,7-tetrahydro[1,3]thiazolo[5,4-c]pyridine-2-carboxamide, N-(2-amino-5-isopropylphenyl)-5-[(butylamino)(oxo) acetyl]-4,5,6,7-tetrahydro[1,3]thiazolo[5,4-c]pyridine-2-carboxamide, N-(2-aminophenyl)-5-[(benzylamino)(oxo)acetyl]-4,5,6,7-tetrahydro[1,3]thiazolo[5,4-c]pyridine-2-carboxamide, N-(2-aminophenyl)-5-[{[6-(4-methylpiperazin-1-yl)pyridin-3-yl]amino}(oxo)acetyl]-4,5,6,7-tetrahydro[1,3]thiazolo[5,4-c]pyridine-2-carboxamide, N-(2-aminophenyl)-5-{oxo[(pyridin-3-ylmethyl)amino] acetyl}-4,5,6,7-tetrahydro[1,3]thiazolo[5,4-c]pyridine-2-carboxamide, N-(2-aminophenyl)-5-(biphenyl-4-ylcarbonyl)-4,5,6,7-tetrahydro[1,3]thiazolo[5,4-c]pyridine-2-carboxamide, N-(2-aminophenyl)-5-(4-methylbenzoyl)-4,5,6,7-tetrahydro [1,3]thiazolo[5,4-c]pyridine-2-carboxamide, Methyl 4-({2-[(2-aminophenyl)carbamoyl]-6,7-dihydro[1, 3]thiazolo[5,4-c]pyridin-5(4H)yl}carbonyl)benzoate, N-(2-aminophenyl)-5-[4-(dimethylamino)benzoyl]-4,5,6,7-tetrahydro[1,3]thiazolo[5,4-c]pyridine-2-carboxamide, 5-Acetyl-N-(2-aminophenyl)-4,5,6,7-tetrahydro[1,3]thiazolo[5,4-c]pyridine-2-carboxamide, N-(2-aminophenyl)-5-(4-methoxybenzoyl)-4,5,6,7-tetrahydro[1,3]thiazolo[5,4-c]pyridine-2-carboxamide, N-(2-aminophenyl)-5-(quinolin-3-ylcarbonyl)-4,5,6,7-tetrahydro[1,3]thiazolo[5,4-c]pyridine-2-carboxamide, N-(2-aminophenyl)-5-(2-naphthoyl)-4,5,6,7-tetrahydro[1,3] thiazolo[5,4-c]pyridine-2-carboxamide, N-(2-aminophenyl)-5-[(6-methylpyridin-3-yl)carbonyl]-4,5,6,7-tetrahydro[1,3]thiazolo[5,4-c]pyridine-2-carboxamide, N-(2-aminophenyl)-5-[3-(dimethylamino)benzoyl]-4,5,6,7-tetrahydro[1,3]thiazolo[5,4-c]pyridine-2-carboxamide, N-(2-aminophenyl)-5-(anilinocarbonothioyl)-4,5,6,7-tetrahydro[1,3]thiazolo[5,4-c]pyridine-2-carboxamide, N-(2-aminophenyl)-5-({[4-(dimethylamino)phenyl]amino}carbonothioyl)-4,5,6,7-tetrahydro[1,3]thiazolo[5,4-c]pyridine-2-carboxamide, N-(2-aminophenyl)-5-[(piperidin-4-ylamino)carbonothioyl]-4,5,6,7-tetrahydro[1,3]thiazolo[5,4-c]pyridine-2-carboxamide, N-(2-aminophenyl)-5-{([(4-pyridin-3-ylcyclohexyl)amino]carbonothioyl}-4,5,6,7-tetrahydro[1,3]thiazolo[5,4-c]pyridine-2-carboxamide, N-(2-amino-5-methoxyphenyl)-5-(anilinocarbonothioyl)-4,5,6,7-tetrahydro[1,3]thiazolo[5,4-c]pyridine-2-carboxamide, N-(2-aminophenyl)-5-[(pyridin-3-ylamino)carbonothioyl]-4,5,6,7-tetrahydro[1,3]thiazolo[5,4-c]pyridine-2-carboxamide, N-(2-aminophenyl)-5-[(isoquinolin-5-ylamino)carbonothioyl]-4,5,6,7-tetrahydro[1,3]thiazolo[5,4-c]pyridine-2-carboxamide, N-(2-aminophenyl)-5-[(butylamino)carbonothioyl]-4,5,6,7-tetrahydro[1,3]thiazolo[5,4-c]pyridine-2-carboxamide, N-(2-amino-5-methoxyphenyl)-5-{[(4-methoxyphenyl)amino]carbonothioyl}-4,5,6,7-tetrahydro[1,3]thiazolo[5,4-c]pyridine-2-carboxamide, N-(2-amino-5-methoxyphenyl)-5-[(pyridin-3-ylamino)carbonothioyl]-4,5,6,7-tetrahydro[1,3]thiazolo[5,4-c]pyridine-2-carboxamide, N-(2-amino-5-isopropylphenyl)-5-[(pyridin-3-ylamino)carbonothioyl]-4,5,6,7-tetrahydro[1,3]thiazolo[5,4-c]pyridine-2-carboxamide, N-(2-amino-5-isopropylphenyl)-5-(anilinocarbonothioyl)-4,5,6,7-tetrahydro[1,3]thiazolo[5,4-c]pyridine-2-carboxamide, N-(2-amino-5-isopropylphenyl)-5-{[(4-methoxyphenyl)amino]carbonothioyl}-4,5,6,7-tetrahydro[1,3]thiazolo[5,4-c]pyridine-2-carboxamide, N-(2-aminophenyl)-5-{imino[(4-methoxyphenyl)amino]methyl}-4,5,6,7-tetrahydro[1,3]thiazolo[5,4-c]pyridine-2-carboxamide, N-(2-amino-5-isopropylphenyl)-5-{imino[(4-methoxyphenyl)amino]methyl}-4,5,6,7-tetrahydro[1,3]thiazolo[5,4-c]pyridine-2-carboxamide, N-(2-aminophenyl)-5-[(benzylamino)(imino)methyl]-4,5,6,7-tetrahydro[1,3]thiazolo[5,4-c]pyridine-2-carboxamide, N-(2-aminophenyl)-5-[anilino(methylimino)methyl]-4,5,6,7-tetrahydro[1,3]thiazolo[5,4-c]pyridine-2-carboxamide, N-(2-amino-5-methoxyphenyl)-5-[[(4-methoxyphenyl)amino](methylimino)methyl]-4,5,6,7-tetrahydro[1,3]thiazolo[5,4-c]pyridine-2-carboxamide, N-(2-aminophenyl)-5-[anilino(cyanoimino)methyl]-4,5,6,7-tetrahydro[1,3]thiazolo[5,4-c]pyridine-2-carboxamide, N-(2-aminophenyl)-5-{(cyanoimino)[(4-methoxyphenyl)amino]methyl}-4,5,6,7-tetrahydro[1,3]thiazolo[5,4-c]pyridine-2-carboxamide, N-(2-aminophenyl)-5-{(cyanoimino)[(3,4-dimethoxyphenyl)amino]methyl}-4,5,6,7-tetrahydro[1,3]thiazolo[5,4-c]pyridine-2-carboxamide, N-(2-aminophenyl)-5-{(cyanoimino)[(2-methylphenyl)amino]methyl}-4,5,6,7-tetrahydro[1,3]thiazolo[5,4-c]pyridine-2-carboxamide, N-(2-aminophenyl)-5-[(cyanoimino){[4-(dimethylamino)phenyl]amino}methyl]-4,5,6,7-tetrahydro[1,3]thiazolo[5,4-c]pyridine-2-carboxamide, N-(2-aminophenyl)-5-[(cyanoimino)(pentylamino)methyl]-4,5,6,7-tetrahydro[1,3]thiazolo[5,4-c]pyridine-2-carboxamide, N-(2-aminophenyl)-5-[(benzylamino)(cyanoimino)methyl]-4,5,6,7-tetrahydro[1,3]thiazolo[5,4-c]pyridine-2-carboxamide, N-(2-amino-5-methoxyphenyl)-5-[(cyano amino)(phenylimino)methyl]-4,5,6,7-tetrahydro[1,3]thiazolo[5,4-c]pyridine-2-carboxamide, N-(2-amino-5-methoxyphenyl)-5-{(cyanoamino)[(4-methoxyphenyl)imino]methyl}-4,5,6,7-tetrahydro[1,3]thiazolo[5,4-c]pyridine-2-carboxamide, N-(2-amino-5-isopropylphenyl)-5-{(cyanoamino)[(4-methoxyphenyl)imino]methyl}-4,5,6,7-tetrahydro[1,3]thiazolo[5,4-c]pyridine-2-carboxamide, N-(2-aminophenyl)-5-[N-phenylethanimidoyl]-4,5,6,7-tetrahydro[1,3]thiazolo[5,4-c]pyridine-2-carboxamide, N-(2-aminophenyl)-5-[N-(3,4-dimethoxyphenyl)ethanimidoyl]-4,5,6,7-tetrahydro[1,3]thiazolo[5,4-c]pyridine-2-carboxamide, N-(2-aminophenyl)-5-[N-(4-methoxyphenyl)ethanimidoyl]-4,5,6,7-tetrahydro[1,3]thiazolo[5,4-c]pyridine-2-carboxamide, N-(2-amino-5-methoxyphenyl)-5-[N-phenylethanimidoyl]-4,5,6,7-tetrahydro[1,3]thiazolo[5,4-c]pyridine-2-carboxamide, N-(2-amino-5-methoxyphenyl)-5-[N-(4-methoxyphenyl)ethanimidoyl]-4,5,6,7-tetrahydro[1,3]thiazolo[5,4-c]pyridine-2-carboxamide, N-(2-amino-5-methoxyphenyl)-5-[N-(3,4-dimethoxyphenyl)ethanimidoyl]-4,5,6,7-tetrahydro[1,3]thiazolo[5,4-c]pyridine-2-carboxamide, N-(2-amino-5-isopropylphenyl)-5-[N-(4-methoxyphenyl)ethanimidoyl]-4,5,6,7-tetrahydro[1,3]thiazolo[5,4-c]pyridine-2-carboxamide, N-(2-amino-5-isopropylphenyl)-5-[N-(3,4-dimethoxyphenyl)ethanimidoyl]-4,5,6,7-tetrahydro[1,3]thiazolo[5,4-c]pyridine-2-carboxamide, N-(2-aminophenyl)-5-{N-[4-(dimethylamino)phenyl]ethanimidoyl}-4,5,6,7-tetrahydro[1,3]thiazolo[5,4-c]pyridine-2-carboxamide, N-(2-amino-5-isopropylphenyl)-5-[N-phenylethanimidoyl]-4,5,6,7-tetrahydro[1,3]thiazolo[5,4-c]pyridine-2-carboxamide, N-(2-aminophenyl)-5-[1-anilino-2-nitrovinyl]-4,5,6,7-tetrahydro[1,3]thiazolo[5,4-c]pyridine-2-carboxamide, N-(2-aminophenyl)-5-{1-[(4-methoxyphenyl)amino]-2-nitrovinyl}-4,5,6,7-tetrahydro[1,3]thiazolo[5,4-c]pyridine-2-carboxamide, N-(2-aminophenyl)-5-[1-(butylamino)-2-nitrovinyl]-4,5,6,7-tetrahydro[1,3]thiazolo[5,4-c]pyridine-2-carboxamide, N-(2-aminophenyl)-5-{1-[(4-isopropylphenyl)amino]-2-nitrovinyl}-4,5,6,7-tetrahydro[1,3]thiazolo[5,4-c]pyridine-2-carboxamide, N-(2-aminophenyl)-5-[1-{[4-(dimethylamino)phenyl]amino}-2-nitrovinyl]-4,5,6,7-tetrahydro[1,3]thiazolo[5,4-c]pyridine-2-carboxamide, N-(2-aminophenyl)-5-{1-[(3,4-dimethoxyphenyl)amino]-2-nitrovinyl}-4,5,6,7-tetrahydro[1,3]thiazolo[5,4-c]pyridine-2-carboxamide, N-(2-amino-5-methoxyphenyl)-5-{1-[(4-methoxyphenyl)amino]-2-nitrovinyl}-4,5,6,7-tetrahydro[1,3]thiazolo[5,4-c]pyridine-2-carboxamide, N-(2-amino-5-methoxyphenyl)-5-{1-[(4-isopropylphenyl)amino]-2-nitrovinyl}-4,5,6,7-tetrahydro[1,3]thiazolo[5,4-c]pyridine-2-carboxamide, N-(2-amino-5-methoxyphenyl)-5-[1-{[4-(dimethylamino)phenyl]amino}-2-nitrovinyl]-4,5,6,7-tetrahydro[1,3]thiazolo[5,4-c]pyridine-2-carboxamide, N-(2-amino-5-isopropylphenyl)-5-[1-anilino-2-nitrovinyl]-4,5,6,7-tetrahydro[1,3]thiazolo[5,4-c]pyridine-2-carboxamide, N-[2-amino-5-(1-methylethyl)phenyl]-5-{1-[(4-methoxyphenyl)amino]-2-nitroethenyl}-4,5,6,7-tetrahydro[1,3]thiazolo[5,4-c]pyridine-2-carboxamide, N-(2-amino-5-isopropylphenyl)-5-[1-{[4-(dimethylamino)phenyl]amino}-2-nitrovinyl]-4,5,6,7-tetrahydro[1,3]thiazolo[5,4-c]pyridine-2-carboxamide, N-(2-amino-5-isopropylphenyl)-5-{1-[(4-isopropylphenyl)amino]-2-nitrovinyl}-4,5,6,7-tetrahydro[1,3]thiazolo[5,4-c]pyridine-2-carboxamide, N-(2-amino-5-methoxyphenyl)-5-{1-[(4-fluorophenyl)amino]-2-nitrovinyl}-4,5,6,7-tetrahydro[1,3]thiazolo[5,4-c]pyridine-2-carboxamide, N-(2-aminophenyl)-5-[(4-methylphenyl)sulfonyl]-4,5,6,7-tetrahydro[1,3]thiazolo[5,4-c]pyridine-2-carboxamide, N-(2-aminophenyl)-5-(benzylsulfonyl)-4,5,6,7-tetrahydro[1,3]thiazolo[5,4-c]pyridine-2-carboxamide, N-(2-aminophenyl)-5-(biphenyl-4-ylsulfonyl)-4,5,6,7-tetrahydro[1,3]thiazolo[5,4-c]pyridine-2-carboxamide, N-(2-aminophenyl)-5-[(4-methoxyphenyl)sulfonyl]-4,5,6,7-tetrahydro[1,3]thiazolo[5,4-c]pyridine-2-carboxamide, N-(2-aminophenyl)-5-(methylsulfonyl)-4,5,6,7-tetrahydro[1,3]thiazolo[5,4-c]pyridine-2-carboxamide 5-[(4-acetamidophenyl)sulfonyl]-N-(2-aminophenyl)-4,5,6,7-tetrahydro[1,3]thiazolo[5,4-c]pyridine-2-carboxamide, N-(2-aminophenyl)-5-(2-naphthylsulfonyl)-4,5,6,7-tetrahydro[1,3]thiazolo[5,4-c]pyridine-2-carboxamide, N-(2-aminophenyl)-5-(2-thienylsulfonyl)-4,5,6,7-tetrahydro[1,3]thiazolo[5,4-c]pyridine-2-carboxamide, Methyl 3-({2-[(2-aminophenyl)carbamoyl]-6,7-dihydro[1,3]thiazolo[5,4-c]pyridin-5(4H)yl}sulfonyl)thiophene-2-carboxylate, 5-[(2-acetamido-4-methyl-1,3-thiazol-5-yl)sulfonyl]-N-(2-aminophenyl)-4,5,6,7-tetrahydro[1,3]thiazolo[5,4-c]pyridine-2-carboxamide, N-(2-aminophenyl)-5-[(3-methoxyphenyl)sulfonyl]-4,5,6,7-tetrahydro[1,3]thiazolo[5,4-c]pyridine-2-carboxamide, N-(2-aminophenyl)-5-{[4-(trifluoromethyl)phenyl]sulfonyl}-4,5,6,7-tetrahydro[1,3]thiazolo[5,4-c]pyridine-2-carboxamide, N-(2-aminophenyl)-5-{[3-(trifluoromethyl)phenyl]sulfonyl}-4,5,6,7-tetrahydro[1,3]thiazolo[5,4-c]pyridine-2-carboxamide, N-(2-aminophenyl)-5-[(3-fluorophenyl)sulfonyl]-4,5,6,7-tetrahydro[1,3]thiazolo[5,4-c]pyridine-2-carboxamide, N-(2-aminophenyl)-5-(isopropylsulfonyl)-4,5,6,7-tetrahydro[1,3]thiazolo[5,4-c]pyridine-2-carboxamide, N-(2-aminophenyl)-5-{[3-(difluoromethoxy)phenyl]sulfonyl}-4,5,6,7-tetrahydro[1,3]thiazolo[5,4-c]pyridine-2-carboxamide, N-(2-aminophenyl)-5-{[4-(difluoromethoxy)phenyl]sulfonyl}-4,5,6,7-tetrahydro[1,3]thiazolo[5,4-c]pyridine-2-carboxamide, N-(2-aminophenyl)-5-{[3-(trifluoromethoxy)phenyl]sulfonyl}-4,5,6,7-tetrahydro[1,3]thiazolo[5,4-c]pyridine-2-carboxamide, N-(2-aminophenyl)-5-{[4-(trifluoromethoxy)phenyl]sulfonyl}-4,5,6,7-tetrahydro[1,3]thiazolo[5,4-c]pyridine-2-carboxamide, N-(2-amino-5-methoxyphenyl)-5-[(4-methylphenyl)sulfonyl]-4,5,6,7-tetrahydro[1,3]thiazolo[5,4-c]pyridine-2-carboxamide, N-(2-amino-5-isopropylphenyl)-5-[(4-methylphenyl)sulfonyl]-4,5,6,7-tetrahydro[1,3]thiazolo[5,4-c]pyridine-2-carboxamide, N-(2-amino-5-methoxyphenyl)-5-[(4-methoxyphenyl)sulfonyl]-4,5,6,7-tetrahydro[1,3]thiazolo[5,4-c]pyridine-2-carboxamide, N-(2-aminophenyl)-5-(phenoxyacetyl)-4,5,6,7-tetrahydro[1,3]thiazolo[5,4-c]pyridine-2-carboxamide, N-(2-aminophenyl)-5-[(4-methylphenoxy)acetyl]-4,5,6,7-tetrahydro[1,3]thiazolo[5,4-c]pyridine-2-carboxamide, N-(2-aminophenyl)-5-[(4-methoxyphenoxy)acetyl]-4,5,6,7-tetrahydro[1,3]thiazolo[5,4-c]pyridine-2-carboxamide, N-(2-aminophenyl)-5-[(2-naphthyloxy)acetyl]-4,5,6,7-tetrahydro[1,3]thiazolo[5,4-c]pyridine-2-carboxamide, N-(2-aminophenyl)-5-[(biphenyl-4-yloxy)acetyl]-4,5,6,7-tetrahydro[1,3]thiazolo[5,4-c]pyridine-2-carboxamide, N-(2-aminophenyl)-5-(methoxyacetyl)-4,5,6,7-tetrahydro[1,3]thiazolo[5,4-c]pyridine-2-carboxamide, N-(2-amino-5-isopropylphenyl)-5-[(4-methoxyphenoxy)acetyl]-4,5,6,7-tetrahydro[1,3]thiazolo[5,4-c]pyridine-2-carboxamide, N-(2-aminophenyl)-5-[(3-methoxyphenoxy)acetyl]-4,5,6,7-tetrahydro[1,3]thiazolo[5,4-c]pyridine-2-carboxamide, Methyl 2-[(2-aminophenyl)carbamoyl]-6,7-dihydro[1,3]thiazolo[5,4-c]pyridine-5(4H)carboxylate, Biphenyl-4-yl 2-[(2-aminophenyl)carbamoyl]-6,7-dihydro[1,3]thiazolo[5,4-c]pyridine-5(4H)carboxylate, 4-Methylphenyl 2-[(2-aminophenyl)carbamoyl]-6,7-dihydro[1,3]thiazolo[5,4-c]pyridine-5(4H)-carboxylate, 4-Methoxyphenyl 2-[(2-aminophenyl)carbamoyl]-6,7-dihydro[1,3]thiazolo[5,4-c]pyridine-5(4H)-carboxylate, 4-(Propoxycarbonyl)phenyl 2-[(2-aminophenyl)carbamoyl]-6,7-dihydro[1,3]thiazolo[5,4-c]pyridine-5(4H)-carboxylate, 2-Naphthyl 2-[(2-aminophenyl)carbamoyl]-6,7-dihydro[1,3]thiazolo[5,4-c]pyridine-5(4H)carboxylate, 3,4-Dimethoxyphenyl 2-[(2-aminophenyl)carbamoyl]-6,7-dihydro[1,3]thiazolo[5,4-c]pyridine-5(4H)-carboxylate, Butyl 2-[(2-aminophenyl)carbamoyl]-6,7-dihydro[1,3]thiazolo[5,4-c]pyridine-5(4H)carboxylate, Benzyl 2-[(2-aminophenyl)carbamoyl]-6,7-dihydro[1,3]thiazolo[5,4-c]pyridine-5(4H)carboxylate, Pyridin-3-ylmethyl 2-[(2-aminophenyl)carbamoyl]-6,7-dihydro[1,3]thiazolo[5,4-c]pyridine-5(4H)-carboxylate, N-(2-aminophenyl)-5-[3-(1,3-benzodioxol-5-yl)prop-2-enoyl]-4,5,6,7-tetrahydro[1,3]thiazolo[5,4-c]pyridine-2-carboxamide, N-(2-aminophenyl)-5-[3-(3,4-dihydroxyphenyl)prop-2-enoyl]-4,5,6,7-tetrahydro[1,3]thiazolo[5,4-c]pyridine-2-carboxamide, N-(2-aminophenyl)-5-pyrimidin-2-yl-4,5,6,7-tetrahydro[1,3]thiazolo[5,4-c]pyridine-2-carboxamide, N-(2-aminophenyl)-5-(4-pyridin-3-ylpyrimidin-2-yl)-4,5,6,7-tetrahydro[1,3]thiazolo[5,4-c]pyridine-2-carboxamide, N-(2-aminophenyl)-5-(5-nitropyridin-2-yl)-4,5,6,7-tetrahydro[1,3]thiazolo[5,4-c]pyridine-2-carboxamide, N-(2-aminophenyl)-5-[5-(trifluoromethyl)pyridin-2-yl]-4,5,6,7-tetrahydro[1,3]thiazolo[5,4-c]pyridine-2-carboxamide, N-(2-aminophenyl)-5-(5-{[(4-methylphenyl)sulfonyl]amino}pyrimidin-2-yl)-4,5,6,7-tetrahydro[1,3]thiazolo[5,4-c]pyridine-2-carboxamide, N-(2-aminophenyl)-5-(5-{[(4-methylphenyl)sulfonyl]amino}pyridin-2-yl)-4,5,6,7-tetrahydro[1,3]thiazolo[5,4-c]pyridine-2-carboxamide, N-(2-aminophenyl)-5-{4-[(benzylcarbamoyl)amino]phenyl}-4,5,6,7-tetrahydro[1,3]thiazolo[5,4-c]pyridine-2-carboxamide, N-(2-aminophenyl)-5-(4-{[(4-methylphenyl)sulfonyl]amino}phenyl)-4,5,6,7-tetrahydro[1,3]thiazolo[5,4-c]pyridine-2-carboxamide, N-(2-aminophenyl)-5-[(4-methylphenyl)sulfonyl]-4,5,6,7-tetrahydrothieno[3,2-c]pyridine-2-carboxamide, N-(2-aminophenyl)-5-[(4-methylphenyl)sulfonyl]-4,5,6,7-tetrahydrofuro[3,2-c]pyridine-2-carboxamide, N-(2-aminophenyl)-1-methyl-5-[(4-methylphenyl)sulfonyl]-4,5,6,7-tetrahydro-1H-pyrrolo[3,2-c]pyridine-2-carboxamide, $N^2$-(2-aminophenyl)-$N^5$-pyridin-3-yl-6,7-dihydrothieno[3,2-c]pyridine-2,5(4H)-dicarboxamide, 6,7-Dihydro-4H-thieno[3,2-c]pyridine-2,5-dicarboxylic acid 2-[(2-amino-phenyl)-amide]5-[(2-difluoromethoxy-phenyl)-amide], $N^2$-(2-aminophenyl)-$N^5$-(3,4-dimethoxyphenyl)-6,7-dihydrothieno[3,2-c]pyridine-2,5(4H)-dicarboxamide, $N^2$-[2-amino-5-(2-thienyl)phenyl]-$N^5$-butyl-6,7-dihydrothieno[3,2-c]pyridine-2,5(4H)-dicarboxamide, $N^2$-[2-amino-5-(2-thienyl)phenyl]-$N^5$-pyridin-3-yl-6,7-dihydrothieno[3,2-c]pyridine-2,5(4H)-dicarboxamide, $N^2$-(2-amino-5-thiophen-2-ylphenyl)-$N^5$-(4-methoxyphenyl)-6,7-dihydrothieno[3,2-c]-pyridine-2,5(4H)-dicarboxamide, $N^2$-(2-aminophenyl)-$N^5$-(2-methoxyethyl)-6,7-dihydrothieno[3,2-c]pyridine-2,5(4H)-dicarboxamide, $N^2$-(2-aminophenyl)-$N^5$-pyridin-3-yl-6,7-dihydrothieno[3,2-c]pyridine-2,5(4H)-dicarboxamide, 3,4-dimethoxyphenyl 2-[(2-aminophenyl)carbamoyl]-6,7-dihydrothieno[3,2-c]pyridine-5(4H)carboxylate, $N^2$-(2-aminophenyl)-1-methyl-$N^5$-pyridin-3-yl-1,4,6,7-tetrahydro-5H-pyrrolo[3,2-c]pyridine-2,5-dicarboxamide, $N^2$-(2-aminophenyl)-$N^5$-(3,4-dimethoxyphenyl)-1-methyl-1,4,6,7-tetrahydro-5H-pyrrolo[3,2-c]pyridine-2,5-dicarboxamide, 2-(difluoromethoxy)phenyl 2-[(2-aminophenyl)carbamoyl]-1-methyl-1,4,6,7-tetrahydro-5H-pyrrolo[3,2-c]pyridine-5-carboxylate, 3,4-dimethoxyphenyl 2-[(2-aminophenyl)carbamoyl]-1-methyl-1,4,6,7-tetrahydro-5H-pyrrolo[3,2-c]pyridine-5-carboxylate, $N^2$-(2-aminophenyl)-$N^6$-pyridin-3-yl-4,7-dihydrothieno[2,3-c]pyridine-2,6(5H)-dicarboxamide, $N^2$-(2-aminophenyl)-$N^6$-(3,4-dimethoxyphenyl)-4,7-dihydrothieno[2,3-c]pyridine-2,6(5H)-dicarboxamide, $N^2$-(2-aminophenyl)-$N^6$-(2-methoxyethyl)-4,7-dihydrothieno[2,3-c]pyridine-2,6(5H)-dicarboxamide, $N^2$-(2-aminophenyl)-$N^6$-[2-(difluoromethoxy)phenyl]-4,7-dihydrothieno[2,3-c]pyridine-2,6(5H)-dicarboxamide, $N^2$-(2-amino-5-isopropylphenyl)-$N^6$-pyridin-3-yl-4,7-dihydrothieno[2,3-c]pyridine-2,6(5H)-dicarboxamide, $N^2$-(2-amino-5-isopropylphenyl)-$N^6$-[3-(difluoromethoxy)phenyl]-4,7-dihydrothieno[2,3-c]pyridine-2,6(5H)-dicarboxamide, $N^2$-(2-amino-5-isopropylphenyl)-$N^6$-(4-fluorophenyl)-4,7-dihydrothieno[2,3-c]pyridine-2,6(5H)-dicarboxamide, $N^2$-(2-amino-5-isopropylphenyl)-$N^6$-(3,4-dimethoxyphenyl)-4,7-dihydrothieno[2,3-c]pyridine-2,6(5H)-dicarboxamide, 3,4-dimethoxyphenyl 2-[(2-aminophenyl)carbamoyl]-4,7-dihydrothieno[2,3-c]pyridine-6(5H)carboxylate, 3,4-dimethoxyphenyl 2-[(2-amino-5-isopropylphenyl)carbamoyl]-4,7-dihydrothieno[2,3-c]pyridine-6(5H)-carboxylate, N-(2-aminophenyl)-6-[(3-methoxyphenoxy)acetyl]-4,5,6,7-tetrahydrothieno[2,3-c]pyridine-2-carboxamide, N-(2-amino-5-isopropylphenyl)-6-[(3-methoxyphenoxy)acetyl]-4,5,6,7-tetrahydrothieno[2,3-c]pyridine-2-carboxamide, $N^2$-(aminophenyl)-1-methyl-$N^6$-pyridin-3-yl-1,4,5,7-tetrahydro-6H-pyrrolo[2,3-c]pyridine-2,6-dicarboxamide, $N^2$-(2-aminophenyl)-$N^6$-(3,4-dimethoxyphenyl)-1-methyl-1,4,5,7-tetrahydro-6H-pyrrolo[2,3-c]pyridine-2,6-dicarboxamide, $N^2$-(2-aminophenyl)-$N^6$-(2-methoxyethyl)-1-methyl-1,4,5,7-tetrahydro-6H-pyrrolo[2,3-c]pyridine-2,6-dicarboxamide, $N^2$-(2-aminophenyl)-$N^6$-pyridin-3-yl-1,4,5,7-tetrahydro-6H-pyrrolo[2,3-c]pyridine-2,6-dicarboxamide, $N^2$-(2-aminophenyl)-$N^6$-(3,4-dimethoxyphenyl)-1,4,5,7-tetrahydro-6H-pyrrolo[2,3-c]pyridine-2,6-dicarboxamide, 3,4-dimethoxyphenyl 2-[(2-aminophenyl)carbamoyl]-1-methyl-1,4,5,7-tetrahydro-6H-pyrrolo[2,3-c]pyridine-6-carboxylate, 3,4-dimethoxyphenyl 2-[(2-aminophenyl)carbamoyl]-1,4,5,7-tetrahydro-6H-pyrrolo[2,3-c]pyridine-6-carboxylate, N-(2-aminophenyl)-5-(N-1,3-benzodioxol-5-ylglycyl)-4,5,6,7-tetrahydro[1,3]thiazolo[5,4-c]pyridine-2-carboxamide, N-(2-aminophenyl)-5-[N-(3-methoxyphenyl)glycyl]-4,5,6,7-tetrahydro[1,3]thiazolo[5,4-c]pyridine-2-carboxamide, N-(2-aminophenyl)-5-[N-(6-methoxypyridin-3-yl)glycyl]-4,5,6,7-tetrahydro[1,3]thiazolo[5,4-c]pyridine-2-carboxamide, $N^2$-(2-aminophenyl)-$N^5$-[3-(trifluoromethoxy)phenyl]-6,7-dihydro[1,3]thiazolo[5,4-c]pyridine-2,5(4H)-dicarboxamide, $N^2$-(2-aminophenyl)-$N^5$-(3-morpholin-4-ylphenyl)-6,7-dihydro[1,3]thiazolo[5,4-c]pyridine-2,5(4H)-dicarboxamide, $N^2$-(2-aminophenyl)-$N^5$-[4-(methylthio)phenyl]-6,7-dihydro[1,3]thiazolo[5,4-c]pyridine-2,5(4H)-dicarboxamide, $N^2$-(2-aminophenyl)-$N^5$-[3-(methylthio)phenyl]-6,7-dihydro[1,3]thiazolo[5,4-c]pyridine-2,5(4H)-dicarboxamide, $N^2$-(2-aminophenyl)-$N^5$-(3-methoxyphenyl)-6,7-dihydro[1,3]thiazolo[5,4-c]pyridine-2,5(4H)-dicarboxamide, $N^2$-(2-aminophenyl)-$N^5$-1H-indazol-5-yl-6,7-dihydro[1,3]thiazolo[5,4-c]pyridine-2,5(4H)-dicarboxamide, $N^2$-(2-aminophenyl)-$N^5,N^5$-diethyl-6,7-dihydro[1,3]thiazolo[5,4-c]pyridine-2,5(4H)-dicarboxamide, $N^2$-(2-amino-5-chlorophenyl)-$N^5$-(4-methoxyphenyl)-6,7-dihydro[1,3]thiazolo[5,4-c]pyridine-2,5(4H)-dicarboxamide, $N^2$-(2-amino-5-chlorophenyl)-$N^5$-(3,4-dimethoxyphenyl)-6,7-dihydro[1,3]thiazolo[5,4-c]pyridine-2,5(4H)-dicarboxamide, $N^2$-(2-amino-5-chlorophenyl)-$N^5$-pyridin-3-yl-6,7-dihydro[1,3]thiazolo[5,4-c]pyridine-2,5(4H)-dicarboxamide, $N^2$-(2-aminophenyl)-$N^5$-[3-(difluoromethoxy)phenyl]-6,7-dihydro[1,3]thiazolo[5,4-c]pyridine-2,5(4H)-dicarboxamide, $N^2$-(2-aminophenyl)-$N^5$-[4-(methylsulfonyl)phenyl]-6,7-dihydro[1,3]thiazolo[5,4-c]pyridine-2,5(4H)-dicarboxamide, $N^2$-(2-aminophenyl)-$N^5$-[3-(methylsulfonyl)phenyl]-6,7-dihydro[1,3]thiazolo[5,4-c]pyridine-2,5(4H)-dicarboxamide, $N^2$-(2-amino-5-fluorophenyl)-$N^5$-1,3-benzodioxol-5-yl-6,7-dihydro[1,3]thiazolo[5,4-c]pyridine-2,5(4H)-dicarboxamide, $N^2$-(2-amino-5-fluorophenyl)-$N^5$-(3,4-dimethoxyphenyl)-6,7-dihydro[1,3]thiazolo[5,4-c]pyridine-2,5(4H)-dicarboxamide, $N^2$-[2-amino-5-(2-thienyl)phenyl]-$N^5$-pyridin-3-yl-6,7-dihydro[1,3]thiazolo[5,4-c]pyridine-2,5(4H)-dicarboxamide, $N^2$-[2-amino-5-(3-thienyl)phenyl]-$N^5$-[2-(difluoromethoxy)phenyl]-6,7-dihydro[1,3]thiazolo[5,4-c]pyridine-2,5(4H)-dicarboxamide, $N^2$-[2-amino-5-(3-thienyl)phenyl]-$N^5$-(3,4-dimethoxyphenyl)-6,7-dihydro[1,3]thiazolo[5,4-c]pyridine-2,5(4H)-dicarboxamide, $N^2$-[2-amino-5-(3-thienyl)phenyl]-$N^5$-(2-methoxyethyl)-6,7-dihydro[1,3]thiazolo[5,4-c]pyridine-2,5(4H)-dicarboxamide, $N^2$-[2-amino-5-(2-thienyl)phenyl]-$N^5$-(3,4-dimethoxyphenyl)-6,7-dihydro[1,3]thiazolo[5,4-c]pyridine-2,5(4H)-dicarboxamide, $N^2$-[2-amino-5-(2-thienyl)phenyl]-$N^5$-(2-methoxyethyl)-6,7-dihydro[1,3]thiazolo[5,4-c]pyridine-2,5(4H)-dicarboxamide, $N^2$-[2-amino-5-(2-thienyl)phenyl]-$N^5$-pyridin-3-yl-6,7-dihydro[1,3]thiazolo[5,4-c]pyridine-2,5(4H)-dicarboxamide, $N^2$-[2-amino-5-(2-thienyl)phenyl]-$N^5$-[2-(difluoromethoxy)phenyl]-6,7-dihydro[1,3]thiazolo[5,4-c]pyridine-2,5(4H)-dicarboxamide, $N^2$-(2-aminophenyl)-$N^5$-(4-cyanophenyl)-6,7-dihydro[1,3]thiazolo[5,4-c]pyridine-2,5(4H)-dicarboxamide, $N^2$-(2-aminophenyl)-$N^5$-(3-cyanophenyl)-6,7-dihydro[1,3]thiazolo[5,4-c]pyridine-2,5(4H)-dicarboxamide, $N^2$-[2-amino-5-(3-thienyl)phenyl]-$N^5$-pyridin-3-yl-6,7-dihydro[1,3]thiazolo[5,4-c]pyridine-2,5(4H)-dicarboxamide, N-(2-aminophenyl)-5-[4-(trifluoromethoxy)benzoyl]-4,5,6,7-tetrahydro[1,3]thiazolo[5,4-c]pyridine-2-carboxamide, N-(2-aminophenyl)-5-[4-(difluoromethoxy)benzoyl]-4,5,6,7-tetrahydro[1,3]thiazolo[5,4-c]pyridine-2-carboxamide, N-(2-aminophenyl)-5-[3-(trifluoromethoxy)benzoyl]-4,5,6,7-tetrahydro[1,3]thiazolo[5,4-c]pyridine-2-carboxamide, N-(2-aminophenyl)-5-[3-pyridin-3-ylprop-2-enoyl]-4,5,6,7-tetrahydro[1,3]thiazolo[5,4-c]pyridine-2-carboxamide, 3-methoxyphenyl 2-[(2-aminophenyl)carbamoyl]-6,7-dihydro[1,3]thiazolo[5,4-c]pyridine-5(4H)-carboxylate, 3,4-dimethoxyphenyl 2-{[2-amino-5-(3-thienyl)phenyl]carbamoyl}-6,7-dihydro[1,3]thiazolo[5,4-c]pyridine-5(4H)-carboxylate, 3,4-dimethoxyphenyl 2-{[2-amino-5-(2-thienyl)phenyl]carbamoyl}-6,7-dihydro[1,3]thiazolo[5,4-c]pyridine-5(4H)-carboxylate, benzyl 2-[(2-aminophenyl)carbamoyl]-6,7-dihydro[1,3]thiazolo[5,4-c]pyridine-5(4H)carboxylate, N-(2-aminophenyl)-5-[{[3-(difluoromethoxy)phenyl]amino}(oxo)acetyl]-4,5,6,7-tetrahydro[1,3]thiazolo[5,4-c]pyridine-2-carboxamide, N-(2-aminophenyl)-5-(oxo{[3-(trifluoromethoxy)phenyl]amino}acetyl)-4,5,6,7-tetrahydro[1,3]thiazolo[5,4-c]pyridine-2-carboxamide, N-(2-aminophenyl)-5-(oxo{[2-(trifluoromethoxy)phenyl]amino}acetyl)-4,5,6,7-tetrahydro[1,3]thiazolo[5,4-c]pyridine-2-carboxamide, N-(2-aminophenyl)-5-[{[2-(difluoromethoxy)phenyl]amino}(oxo)acetyl]-4,5,6,7-tetrahydro[1,3]thiazolo[5,4-c]pyridine-2-carboxamide, N-(2-aminophenyl)-5-(oxo{[2-(trifluoromethoxy)phenyl]amino}acetyl)-4,5,6,7-tetrahydro[1,3]thiazolo[5,4-c]pyridine-2-carboxamide, N-[2-amino-5-(2-thienyl)phenyl]-5-[(3-methoxyphenoxy)acetyl]-4,5,6,7-tetrahydro[1,3]thiazolo[5,4-c]pyridine-2-carboxamide, N-[2-amino-5-(3-thienyl)phenyl]-5-[(3-methoxyphenoxy)acetyl]-4,5,6,7-tetrahydro[1,3]thiazolo[5,4-c]pyridine-2-carboxamide, N-(2-amino-5-fluorophenyl)-5-[(3-methoxyphenoxy)acetyl]-4,5,6,7-tetrahydro[1,3]thiazolo[5,4-c]pyridine-2-carboxamide, N-(2-aminophenyl)-5-[(4-methoxyphenyl)sulfonyl]-4,5,6,7-tetrahydro[1,3]thiazolo[5,4-c]pyridine-2-carboxamide, $N^2$-(2-aminophenyl)-$N^5$-(6-methoxypyridin-3-yl)-6,7-dihydro[1,3]thiazolo[5,4-c]pyridine-2,5(4H)-dicarboxamide dihydrochloride, $N^2$-(2-aminophenyl)-$N^5$-pyridin-3-yl-6,7-dihydro[1,3]thiazolo[5,4-c]pyridine-2,5(4H)-dicarboxamide dihydrochloride, $N^2$-(2-aminophenyl)-$N^5$-(6-methoxypyridin-3-yl)-6,7-dihydro[1,3]thiazolo[5,4-c]pyridine-2,5(4H)-dicarboxamide-4-methylaniline (1:2), $N^2$-(2-aminophenyl)-$N^5$-pyridin-3-yl-6,7-dihydro[1,3]thiazolo[5,4-c]pyridine-2,5(4H)-dicarboxamide-4-methylaniline (1:2), N-(2-aminophenyl)-5-[(3-methoxyphenoxy)acetyl]-4,5,6,7-tetrahydro[1,3]thiazolo[5,4-c]pyridine-2-carboxamide-4-methylaniline (1:1), benzyl 2-[(2-aminophenyl)carbamoyl]-6,7-dihydro[1,3]thiazolo[5,4-c]pyridine-5(4H)carboxylate-4-methylaniline (1:1), N-(2-aminophenyl)-5-[(3-methoxyphenoxy)acetyl]-4,5,6,7-tetrahydro[1,3]thiazolo[5,4-c]pyridine-2-carboxamide methanesulfonate, benzyl 2-[(2-aminophenyl)carbamoyl]-6,7-dihydro[1,3]thiazolo[5,4-c]pyridine-5(4H)carboxylate methanesulfonate, benzyl 2-[(2-aminophenyl)carbamoyl]-6,7-dihydro[1,3]thiazolo[5,4-c]pyridine-5(4H)carboxylate sulfate, N-(2-aminophenyl)-5-[(4-methoxyphenyl)sulfonyl]-4,5,6,7-tetrahydro[1,3]thiazolo[5,4-c]pyridine-2-carboxamide sulphate, $N^2$-(2-aminophenyl)-N-5-pyridin-3-yl-1,4,6,7-tetrahydro-5H-pyrrolo[3,2-c]pyridine-2,5-dicarboxamide, $N^2$-(2-amino-5-fluorophenyl)-N6-pyridin-3-yl-4,7-dihydrothieno[2,3-c]pyridine-2,6(5H)-dicarboxamide, $N^2$-(2-amino-5-fluorophenyl)-N6-(pyridin-3-ylmethyl)-4,7-dihydrothieno[2,3-c]pyridine-2,6(5H)-dicarboxamide, $N^2$-(2-amino-5-fluorophenyl)-N6-pyridin-4-yl-4,7-dihydrothieno[2,3-c]pyridine-2,6(5H)-dicarboxamide, $N^2$-(2-amino-5-fluorophenyl)-N6-quinolin-3-yl-4,7-dihydrothieno[2,3-c]pyridine-2,6(5H)-dicarboxamide, $N^2$-(2-aminophenyl)-N6-(pyridin-3-ylmethyl)-4,7-dihydrothieno[2,3-c]pyridine-2,6(5H)-dicarboxamide, $N^2$-(2-aminophenyl)-N6-pyridin-4-yl-4,7-dihydrothieno[2,3-c]pyridine-2,6(5H)-dicarboxamide, $N^2$-(2-aminophenyl)-N6-quinolin-3-yl-4,7-dihydrothieno[2,3-c]pyridine-2,6(5H)-dicarboxamide or salts of these compounds.

Another embodiment of the compounds according to the present invention relates to compounds of formula I selected from:

$N^2$-(2-aminophenyl)-$N^5$-biphenyl-4-yl-6,7-dihydro[1,3]thiazolo[5,4-c]pyridine-2,5(4H)-dicarboxamide, $N^2$-(2-aminophenyl)-$N^5$-[4-(dimethylamino)phenyl]-6,7-dihydro[1,3]thiazolo[5,4-c]pyridine-2,5(4H)-dicarboxamide, $N^2$-(2-aminophenyl)-$N^5$-(4-methoxyphenyl)-6,7-dihydro[1,3]thiazolo[5,4-c]pyridine-2,5(4H)-dicarboxamide, $N^2$-(2-aminophenyl)-$N^5$-benzyl-6,7-dihydro[1,3]thiazolo[5,4-c]pyridine-2,5(4H)-dicarboxamide, Methyl 4-[({2-[(2-aminophenyl)carbamoyl]-6,7-dihydro[1,3]thiazolo[5,4-c]pyridin-5(4H)yl}carbonyl)amino]benzoate, $N^2$-(2-aminophenyl)-$N^5$-(4-phenoxyphenyl)-6,7-dihydro[1,3]thiazolo[5,4-c]pyridine-2,5(4H)-dicarboxamide, $N^2$-(2-aminophenyl)-$N^5$-1,3-benzodioxol-5-yl-6,7-dihydro[1,3]thiazolo[5,4-c]pyridine-2,5(4H)-dicarboxamide, $N^2$-(2-aminophenyl)-$N^5$-[2-(trifluoromethoxy)phenyl]-6,7-dihydro[1,3]thiazolo[5,4-c]pyridine-2,5(4H)-dicarboxamide, $N^2$-(2-aminophenyl)-$N^5$-[4-(trifluoromethoxy)phenyl]-6,7-dihydro[1,3]thiazolo[5,4-c]pyridine-2,5(4H)-dicarboxamide, $N^2$-(2-aminophenyl)-$N^5$-[2-(difluoromethoxy)phenyl]-6,7-dihydro[1,3]thiazolo[5,4-c]pyridine-2,5(4H)-dicarboxamide, $N^2$-(2-aminophenyl)-$N^5$-[4-(difluoromethoxy)phenyl]-6,7-dihydro[1,3]thiazolo[5,4-c]pyridine-2,5(4H)-dicarboxamide, $N^2$-(2-aminophenyl)-$N^5$-quinolin-3-yl-6,7-dihydro[1,3]thiazolo[5,4-c]pyridine-2,5(4H)-dicarboxamide, $N^2$-(2-aminophenyl)-$N^5$-(4-methylphenyl)-6,7-dihydro[1,3]thiazolo[5,4-c]pyridine-2,5(4H)-dicarboxamide, $N^2$-(2-aminophenyl)-$N^5$-(pyridin-3-ylmethyl)-6,7-dihydro[1,3]thiazolo[5,4-c]pyridine-2,5(4H)-dicarboxamide, $N^2$-(2-aminophenyl)-$N^5$-pyridin-4-yl-6,7-dihydro[1,3]thiazolo[5,4-c]pyridine-2,5(4H)-dicarboxamide, $N^2$-(2-aminophenyl)-$N^5$-(2-methoxyethyl)-6,7-dihydro[1,3]thiazolo[5,4-c]pyridine-2,5(4H)-dicarboxamide, $N^2$-(2-aminophenyl)-$N^5$-methyl-6,7-dihydro[1,3]thiazolo[5,4-c]pyridine-2,5(4H)-dicarboxamide, $N^2$-(2-aminophenyl)-$N^5$-[3-(dimethylamino)phenyl]-6,7-dihydro[1,3]thiazolo[5,4-c]pyridine-2,5(4H)-dicarboxamide, $N^2$-(2-aminophenyl)-$N^5$-(3,4-dimethoxyphenyl)-6,7-dihydro[1,3]thiazolo[5,4-c]pyridine-2,5(4H)-dicarboxamide, $N^2$-(2-aminophenyl)-$N^5$-(2-methoxyethyl)-$N^5$-methyl-6,7-dihydro[1,3]thiazolo[5,4-c]pyridine-2,5(4H)-dicarboxamide, $N^2$-(2-aminophenyl)-$N^5$-ethyl-$N^5$-isopropyl-6,7-dihydro[1,3]thiazolo[5,4-c]pyridine-2,5(4H)-dicarboxamide, $N^2$-(2-aminophenyl)-$N^5$-[4-(dimethylamino)phenyl]-$N^5$-methyl-6,7-dihydro[1,3]thiazolo[5,4-c]pyridine-2,5(4H)-dicarboxamide, $N^2$-(2-aminophenyl)-$N^5$-[3-(dimethylamino)phenyl]-$N^5$-methyl-6,7-dihydro[1,3]thiazolo[5,4-c]pyridine-2,5(4H)-dicarboxamide, $N^2$-(2-aminophenyl)-$N^5$-(3,4-dimethoxyphenyl)-$N^5$-methyl-6,7-dihydro[1,3]thiazolo[5,4-c]pyridine-2,5(4H)-dicarboxamide, $N^2$-(2-aminophenyl)-$N^5$-(3,4-dimethoxyphenyl)-$N^5$-ethyl-6,7-dihydro[1,3]thiazolo[5,4-c]pyridine-2,5(4H)-dicarboxamide, $N^2$-(2-aminophenyl)-$N^5$-(3,4-dimethoxyphenyl)-$N^5$-(2-methoxyethyl)-6,7-dihydro[1,3]thiazolo[5,4-c]pyridine-2,5(4H)-dicarboxamide, $N^2$-(2-aminophenyl)-$N^5$-methyl-$N^5$-pyridin-3-yl-6,7-dihydro[1,3]thiazolo[5,4-c]pyridine-2,5(4H)-dicarboxamide, $N^2$-(2-aminophenyl)-$N^5$-ethyl-$N^5$-pyridin-3-yl-6,7-dihydro[1,3]thiazolo[5,4-c]pyridine-2,5(4H)-dicarboxamide, $N^2$-(2-aminophenyl)-$N^5$-1,3-benzodioxol-5-yl-$N^5$-ethyl-6,7-dihydro[1,3]thiazolo[5,4-c]pyridine-2,5(4H)-dicarboxamide, $N^2$-(2-aminophenyl)-$N^5$-1,3-benzodioxol-5-yl-$N^5$-(2-methoxyethyl)-6,7-dihydro[1,3]thiazolo[5,4-c]pyridine-2,5(4H)-dicarboxamide, $N^2$-(2-aminophenyl)-$N^5$-1,3-benzodioxol-5-yl-$N^5$-methyl-6,7-dihydro[1,3]thiazolo[5,4-c]pyridine-2,5(4H)-dicarboxamide, $N^2$-(2-aminophenyl)-$N^5$-[3-(4-methylpiperazin-1-yl)phenyl]-6,7-dihydro[1,3]thiazolo[5,4-c]pyridine-2,5(4H)-dicarboxamide, $N^2$-(2-aminophenyl)-$N^5$-(2-methoxyethyl)-$N^5$-pyridin-3-yl-6,7-dihydro[1,3]thiazolo[5,4-c]pyridine-2,5(4H)-dicarboxamide, $N^2$-(2-aminophenyl)-$N^5$-(6-morpholin-4-ylpyridin-3-yl)-6,7-dihydro[1,3]thiazolo[5,4-c]pyridine-2,5(4H)-dicarboxamide, $N^2$-(2-aminophenyl)-$N^5$-(6-azetidin-1-ylpyridin-3-yl)-6,7-dihydro[1,3]thiazolo[5,4-c]pyridine-2,5(4H)-dicarboxamide, $N^2$-(2-aminophenyl)-$N^5$-[6-(dimethylamino)pyridin-3-yl]-6,7-dihydro[1,3]thiazolo[5,4-c]pyridine-2,5(4H)-dicarboxamide, $N^2$-(2-aminophenyl)-$N^5$-[6-(4-methylpiperazin-1-yl)pyridin-3-yl]-6,7-dihydro[1,3]thiazolo[5,4-c]pyridine-2,5(4H)-dicarboxamide, $N^2$-(2-aminophenyl)-$N^5$-(6-methoxypyridin-3-yl)-6,7-dihydro[1,3]thiazolo[5,4-c]pyridine-2,5(4H)-dicarboxamide, $N^2$-(2-aminophenyl)-$N^5$-pyridin-3-yl-6,7-dihydro[1,3]thiazolo[5,4-c]pyridine-2,5(4H)-dicarboxamide, $N^2$-(2-aminophenyl)-$N^5$-butyl-6,7-dihydro[1,3]thiazolo[5,4-c]pyridine-2,5(4H)-dicarboxamide, $N^2$-(2-aminophenyl)-$N^5$-(4-pyridin-3-ylcyclohexyl)-6,7-dihydro[1,3]thiazolo[5,4-c]pyridine-2,5(4H)-dicarboxamide, $N^2$-(2-aminophenyl)-$N^5$-piperidin-4-yl-6,7-dihydro[1,3]thiazolo[5,4-c]pyridine-2,5(4H)-dicarboxamide, $N^2$-(2-amino-5-methoxyphenyl)-$N^5$-(4-methoxyphenyl)-6,7-dihydro[1,3]thiazolo[5,4-c]pyridine-2,5(4H)-dicarboxamide, $N^2$-(2-aminophenyl)-$N^5$-(4-pyridin-4-ylcyclohexyl)-6,7-dihydro[1,3]thiazolo[5,4-c]pyridine-2,5(4H)-dicarboxamide, $N^2$-(2-amino-5-isopropylphenyl)-$N^5$-(4-methoxyphenyl)-6,7-dihydro[1,3]thiazolo[5,4-c]pyridine-2,5(4H)-dicarboxamide, $N^2$-(2-amino-5-methoxyphenyl)-$N^5$-isoquinolin-5-yl-6,7-dihydro[1,3]thiazolo[5,4-c]pyridine-2,5(4H)-dicarboxamide, $N^2$-(2-amino-5-methoxyphenyl)-$N^5$-[4-(dimethylamino)phenyl]-6,7-dihydro[1,3]thiazolo[5,4-c]pyridine-2,5(4H)-dicarboxamide, $N^2$-(2-amino-5-isopropylphenyl)-$N^5$-(3,4-dimethoxyphenyl)-6,7-dihydro[1,3]thiazolo[5,4-c]pyridine-2,5(4H)-dicarboxamide, $N^2$-(2-amino-5-isopropylphenyl)-$N^5$-isoquinolin-5-yl-6,7-dihydro[1,3]thiazolo[5,4-c]pyridine-2,5(4H)-dicarboxamide, $N^2$-(2-amino-5-isopropylphenyl)-$N^5$-[4-(dimethylamino)phenyl]-6,7-dihydro[1,3]thiazolo[5,4-c]pyridine-2,5(4H)-dicarboxamide, $N^2$-(2-amino-5-methoxyphenyl)-$N^5$-(4-fluorophenyl)-6,7-dihydro[1,3]thiazolo[5,4-c]pyridine-2,5(4H)-dicarboxamide, $N^2$-(2-amino-5-isopropylphenyl)-$N^5$-(4-fluorophenyl)-6,7-dihydro[1,3]thiazolo[5,4-c]pyridine-2,5(4H)-dicarboxamide, $N^2$-[2-amino-5-(dimethylamino)phenyl]-$N^5$-(4-methoxyphenyl)-6,7-dihydro[1,3]thiazolo[5,4-c]pyridine-2,5(4H)-dicarboxamide, $N^2$-[2-amino-5-(2-thienyl)phenyl]-$N^5$-(4-methoxyphenyl)-6,7-dihydro[1,3]thiazolo[5,4-c]pyridine-2,5(4H)-dicarboxamide, $N^2$-[2-amino-5-(2-thienyl)phenyl]-$N^5$-[4-(dimethylamino)phenyl]-6,7-dihydro[1,3]thiazolo[5,4-c]pyridine-2,5(4H)-dicarboxamide, $N^2$-[2-amino-5-(3-thienyl)phenyl]-$N^5$-(4-methoxyphenyl)-6,7-dihydro[1,3]thiazolo[5,4-c]pyridine-2,5(4H)-dicarboxamide, $N^2$-[2-amino-5-(dimethylamino)phenyl]-$N^5$-[4-(dimethylamino)phenyl]-6,7-dihydro[1,3]thiazolo[5,4-c]pyridine-2,5(4H)-dicarboxamide, $N^2$-(2-amino-5-pyrrolidin-1-ylphenyl)-$N^5$-(4-methoxyphenyl)-6,7-dihydro[1,3]thiazolo[5,4-c]pyridine-2,5(4H)-dicarboxamide, $N^2$-[2-amino-5-(3-thienyl)phenyl]-$N^5$-[4-(dimethylamino)phenyl]-6,7-dihydro[1,3]thiazolo[5,4-c]pyridine-2,5(4H)-dicarboxamide, $N^2$-(2-amino-5-isopropylphenyl)-$N^5$-pyridin-3-yl-6,7-dihydro[1,3]thiazolo[5,4-c]pyridine-2,5(4H)-dicarboxamide, $N^2$-[2-amino-5-(dimethylamino)phenyl]-$N^5$-(3,4-dimethoxyphenyl)-6,7-dihydro[1,3]thiazolo[5,4-c]pyridine-2,5(4H)-dicarboxamide, $N^2$-(2-aminophenyl)-$N^5$-isoquinolin-5-yl-6,7-dihydro[1,3]thiazolo[5,4-c]pyridine-2,5(4H)-dicarboxamide, $N^2$-(2-aminophenyl)-$N^5$-[3-(dimethylamino)phenyl]-6,7-dihydro[1,3]thiazolo[5,4-c]pyridine-2,5(4H)-dicarboxamide dihydrochloride, N-(2-aminophenyl)-5-[{[4-(dimethylamino)phenyl]amino}(oxo)acetyl]-4,5,6,7-tetrahydro[1,3]thiazolo[5,4-c]pyridine-2-carboxamide, N-(2-aminophenyl)-5-{[(4-methoxyphenyl)amino](oxo)acetyl}-4,5,6,7-tetrahydro[1,3]thiazolo[5,4-c]pyridine-2-carboxamide, N-(2-aminophenyl)-5-{[(3,4-dimethoxyphenyl)amino](oxo)acetyl}-4,5,6,7-tetrahydro[1,3]thiazolo[5,4-c]pyridine-2-carboxamide, N-(2-aminophenyl)-5-{oxo[(4-pyridin-4-ylcyclohexyl)amino]acetyl}-4,5,6,7-tetrahydro[1,3]-thiazolo[5,4-c]pyridine-2-carboxamide, N-(2-aminophenyl)-5-[(isoquinolin-5-ylamino)(oxo)acetyl]-4,5,6,7-tetrahydro[1,3]thiazolo[5,4-c]pyridine-2-carboxamide, N-(2-aminophenyl)-5-{oxo[(4-pyridin-3-ylcyclohexyl)amino]acetyl}-4,5,6,7-tetrahydro[1,3]thiazolo[5,4-c]pyridine-2-carboxamide, N-(2-aminophenyl)-5-{[(6-methoxypyridin-3-yl)amino](oxo)acetyl}-4,5,6,7-tetrahydro[1,3]thiazolo[5,4-c]pyridine-2-carboxamide, N-(2-aminophenyl)-5-[{[6-(dimethylamino)pyridin-3-yl]amino}(oxo)acetyl]-4,5,6,7-tetrahydro[1,3]thiazolo[5,4-c]pyridine-2-carboxamide, N-(2-aminophenyl)-5-(oxo{[4-(trifluoromethoxy)phenyl]amino}acetyl)-4,5,6,7-tetrahydro[1,3]thiazolo[5,4-c]pyridine-2-carboxamide, N-(2-aminophenyl)-5-{[(6-morpholin-4-ylpyridin-3-yl)amino](oxo)acetyl}-4,5,6,7-tetrahydro[1,3]thiazolo[5,4-c]pyridine-2-carboxamide, N-(2-aminophenyl)-5-[(1,3-benzodioxol-5-ylamino)(oxo)acetyl]-4,5,6,7-tetrahydro[1,3]thiazolo[5,4-c]pyridine-2-carboxamide, N-(2-aminophenyl)-5-{[(4-methylphenyl)amino](oxo)acetyl}-4,5,6,7-tetrahydro[1,3]thiazolo[5,4-c]pyridine-2-carboxamide, N-(2-aminophenyl)-5-{[(5-methylpyridin-2-yl)amino](oxo)acetyl}-4,5,6,7-tetrahydro[1,3]thiazolo[5,4-c]pyridine-2-carboxamide, N-(2-aminophenyl)-5-[oxo(quinolin-3-ylamino)acetyl]-4,5,6,7-tetrahydro[1,3]thiazolo[5,4-c]pyridine-2-carboxamide, N-(2-amino-5-methoxyphenyl)-5-{[(4-methoxyphenyl)amino](oxo)acetyl}-4,5,6,7-tetrahydro[1,3]thiazolo[5,4-c]pyridine-2-carboxamide, N-(2-aminophenyl)-5-[(butylamino)(oxo)acetyl]-4,5,6,7-tetrahydro[1,3]thiazolo[5,4-c]pyridine-2-carboxamide, N-(2-amino-5-isopropylphenyl)-5-{[(3,4-dimethoxyphenyl)amino](oxo)acetyl}-4,5,6,7-tetrahydro[1,3]thiazolo[5,4-c]pyridine-2-carboxamide, N-(2-amino-5-isopropylphenyl)-5-{[(4-methoxyphenyl)amino](oxo)acetyl}-4,5,6,7-tetrahydro[1,3]thiazolo[5,4-c]pyridine-2-carboxamide, N-(2-amino-5-methoxyphenyl)-5-{[(3,4-dimethoxyphenyl)amino](oxo)acetyl}-4,5,6,7-tetrahydro[1,3]thiazolo[5,4-c]pyridine-2-carboxamide, N-(2-amino-5-methoxyphenyl)-5-[(butylamino)(oxo)acetyl]-4,5,6,7-tetrahydro[1,3]thiazolo[5,4-c]pyridine-2-carboxamide, N-(2-amino-5-isopropylphenyl)-5-[(butylamino)(oxo)acetyl]-4,5,6,7-tetrahydro[1,3]thiazolo[5,4-c]pyridine-2-carboxamide, N-(2-aminophenyl)-5-[(benzylamino)(oxo)acetyl]-4,5,6,7-tetrahydro[1,3]thiazolo[5,4-c]pyridine-2-carboxamide, N-(2-aminophenyl)-5-[{[6-(4-methylpiperazin-1-yl)pyridin-3-yl]amino}(oxo)acetyl]-4,5,6,7-tetrahydro[1,3]thiazolo[5,4-c]pyridine-2-carboxamide, N-(2-aminophenyl)-5-{oxo[(pyridin-3-ylmethyl)amino]acetyl}-4,5,6,7-tetrahydro[1,3]thiazolo[5,4-c]pyridine-2-carboxamide, N-(2-aminophenyl)-5-(biphenyl-4-ylcarbonyl)-4,5,6,7-tetrahydro[1,3]thiazolo[5,4-c]pyridine-2-carboxamide, N-(2-aminophenyl)-5-(4-methylbenzoyl)-4,5,6,7-tetrahydro[1,3]thiazolo[5,4-c]pyridine-2-carboxamide, Methyl 4-({2-[(2-aminophenyl)carbamoyl]-6,7-dihydro[1,3]thiazolo[5,4-c]pyridin-5(4H)yl}carbonyl)benzoate, N-(2-aminophenyl)-5-[4-(dimethylamino)benzoyl]-4,5,6,7-tetrahydro[1,3]thiazolo[5,4-c]pyridine-2-carboxamide, 5-Acetyl-N-(2-aminophenyl)-4,5,6,7-tetrahydro[1,3]thiazolo[5,4-c]pyridine-2-carboxamide, N-(2-aminophenyl)-5-(4-methoxybenzoyl)-4,5,6,7-tetrahydro[1,3]thiazolo[5,4-c]pyridine-2-carboxamide, N-(2-aminophenyl)-5-(quinolin-3-ylcarbonyl)-4,5,6,7-tetrahydro[1,3]thiazolo[5,4-c]pyridine-2-carboxamide, N-(2-aminophenyl)-5-(2-naphthoyl)-4,5,6,7-tetrahydro[1,3]thiazolo[5,4-c]pyridine-2-carboxamide, N-(2-aminophenyl)-5-[(6-methylpyridin-3-yl)carbonyl]-4,5,6,7-tetrahydro[1,3]thiazolo[5,4-c]pyridine-2-carboxamide, N-(2-aminophenyl)-5-[3-(dimethylamino)benzoyl]-4,5,6,7-tetrahydro[1,3]thiazolo[5,4-c]pyridine-2-carboxamide, N-(2-aminophenyl)-5-(anilinocarbonothioyl)-4,5,6,7-tetrahydro[1,3]thiazolo[5,4-c]pyridine-2-carboxamide, N-(2-aminophenyl)-5-({[4-(dimethylamino)phenyl]amino}carbonothioyl)-4,5,6,7-tetrahydro[1,3]thiazolo[5,4-c]pyridine-2-carboxamide, N-(2-aminophenyl)-5-[(piperidin-4-ylamino)carbonothioyl]-4,5,6,7-tetrahydro[1,3]thiazolo[5,4-c]pyridine-2-carboxamide, N-(2-aminophenyl)-5-{[(4-pyridin-3-ylcyclohexyl)amino]carbonothioyl}-4,5,6,7-tetrahydro[1,3]thiazolo[5,4-c]pyridine-2-carboxamide, N-(2-amino-5-methoxyphenyl)-5-(anilinocarbonothioyl)-4,5,6,7-tetrahydro[1,3]thiazolo[5,4-c]pyridine-2-carboxamide, N-(2-aminophenyl)-5-[(pyridin-3-ylamino)carbonothioyl]-4,5,6,7-tetrahydro[1,3]thiazolo[5,4-c]pyridine-2-carboxamide, N-(2-aminophenyl)-5-[(isoquinolin-5-ylamino)carbonothioyl]-4,5,6,7-tetrahydro[1,3]thiazolo[5,4-c]pyridine-2-carboxamide, N-(2-aminophenyl)-5-[(butylamino)carbonothioyl]-4,5,6,7-tetrahydro[1,3]thiazolo[5,4-c]pyridine-2-carboxamide, N-(2-amino-5-methoxyphenyl)-5-{[(4-methoxyphenyl)amino]carbonothioyl}-4,5,6,7-tetrahydro[1,3]thiazolo[5,4-c]pyridine-2-carboxamide, N-(2-amino-5-methoxyphenyl)-5-[(pyridin-3-ylamino)carbonothioyl]-4,5,6,7-tetrahydro[1,3]thiazolo[5,4-c]pyridine-2-carboxamide, N-(2-amino-5-isopropylphenyl)-5-[(pyridin-3-ylamino)carbonothioyl]-4,5,6,7-tetrahydro[1,3]thiazolo[5,4-c]pyridine-2-carboxamide, N-(2-amino-5-isopropylphenyl)-5-(anilinocarbonothioyl)-4,5,6,7-tetrahydro[1,3]thiazolo[5,4-c]pyridine-2-carboxamide, N-(2-amino-5-isopropylphenyl)-5-{[(4-methoxyphenyl)amino]carbonothioyl}-4,5,6,7-tetrahydro[1,3]thiazolo[5,4-c]pyridine-2-carboxamide, N-(2-aminophenyl)-5-{imino[(4-methoxyphenyl)amino]methyl}-4,5,6,7-tetrahydro[1,3]thiazolo[5,4-c]pyridine-2-carboxamide, N-(2-amino-5-isopropylphenyl)-5-{imino[(4-methoxyphenyl)amino]methyl}-4,5,6,7-tetrahydro[1,3]thiazolo[5,4-c]pyridine-2-carboxamide, N-(2-aminophenyl)-5-[(benzylamino)(imino)methyl]-4,5,6,7-tetrahydro[1,3]thiazolo[5,4-c]pyridine-2-carboxamide, N-(2-aminophenyl)-5-[anilino(methylimino)methyl]-4,5,6,7-tetrahydro[1,3]thiazolo[5,4-c]pyridine-2-carboxamide, N-(2-amino-5-methoxyphenyl)-5-[[(4-methoxyphenyl)amino](methylimino)methyl]-4,5,6,7-tetrahydro[1,3]thiazolo[5,4-c]pyridine-2-carboxamide, N-(2-aminophenyl)-5-[anilino(cyanoimino)methyl]-4,5,6,7-tetrahydro[1,3]thiazolo[5,4-c]pyridine-2-carboxamide, N-(2-aminophenyl)-5-{(cyanoimino)[(4-methoxyphenyl)amino]methyl}-4,5,6,7-tetrahydro[1,3]thiazolo[5,4-c]pyridine-2-carboxamide, N-(2-aminophenyl)-5-{(cyanoimino)[(3,4-dimethoxyphenyl)amino]methyl}-4,5,6,7-tetrahydro[1,3]thiazolo[5,4-c]pyridine-2-carboxamide, N-(2-aminophenyl)-5-{(cyanoimino)[(2-methylphenyl)amino]methyl}-4,5,6,7-tetrahydro[1,3]thiazolo[5,4-c]pyridine-2-carboxamide, N-(2-aminophenyl)-5-[(cyanoimino){[4-(dimethylamino)phenyl]amino}methyl]-4,5,6,7-tetrahydro[1,3]thiazolo[5,4-c]pyridine-2-carboxamide, N-(2-aminophenyl)-5-[(cyanoimino)(pentylamino)methyl]-4,5,6,7-tetrahydro[1,3]thiazolo[5,4-c]pyridine-2-carboxamide, N-(2-aminophenyl)-5-[(benzylamino)(cyanoimino)methyl]-4,5,6,7-tetrahydro[1,3]thiazolo[5,4-c]pyridine-2-carboxamide, N-(2-amino-5-methoxyphenyl)-5-[(cyanoamino)(phenylimino)methyl]-4,5,6,7-tetrahydro[1,3]thiazolo[5,4-c]pyridine-2-carboxamide, N-(2-amino-5-methoxyphenyl)-5-{(cyanoamino)[(4-methoxyphenyl)imino]methyl}-4,5,6,7-tetrahydro[1,3]thiazolo[5,4-c]pyridine-2-carboxamide, N-(2-amino-5-isopropylphenyl)-5-{(cyanoamino)[(4-methoxyphenyl)imino]methyl}-4,5,6,7-tetrahydro[1,3]thiazolo[5,4-c]pyridine-2-carboxamide, N-(2-aminophenyl)-5-[N-phenylethanimidoyl]-4,5,6,7-tetrahydro[1,3]thiazolo[5,4-c]pyridine-2-carboxamide, N-(2-aminophenyl)-5-[N-(3,4-dimethoxyphenyl)ethanimidoyl]-4,5,6,7-tetrahydro[1,3]thiazolo[5,4-c]pyridine-2-carboxamide, N-(2-aminophenyl)-5-[N-(4-methoxyphenyl)ethanimidoyl]-4,5,6,7-tetrahydro[1,3]thiazolo[5,4-c]pyridine-2-carboxamide, N-(2-amino-5-methoxyphenyl)-5-[N-phenylethanimidoyl]-4,5,6,7-tetrahydro[1,3]thiazolo[5,4-c]pyridine-2-carboxamide, N-(2-amino-5-methoxyphenyl)-5-[N-(4-methoxyphenyl)ethanimidoyl]-4,5,6,7-tetrahydro[1,3]thiazolo[5,4-c]pyridine-2-carboxamide, N-(2-amino-5-methoxyphenyl)-5-[N-(3,4-dimethoxyphenyl)ethanimidoyl]-4,5,6,7-tetrahydro[1,3]thiazolo[5,4-c]pyridine-2-carboxamide, N-(2-amino-5-isopropylphenyl)-5-[N-(4-methoxyphenyl)ethanimidoyl]-4,5,6,7-tetrahydro[1,3]thiazolo[5,4-c]pyridine-2-carboxamide, N-(2-amino-5-isopropylphenyl)-5-[N-(3,4-dimethoxyphenyl)ethanimidoyl]-4,5,6,7-tetrahydro[1,3]thiazolo[5,4-c]pyridine-2-carboxamide, N-(2-aminophenyl)-5-{N-[4-(dimethylamino)phenyl]ethanimidoyl}-4,5,6,7-tetrahydro[1,3]thiazolo[5,4-c]pyridine-2-carboxamide, N-(2-amino-5-isopropylphenyl)-5-[N-phenylethanimidoyl]-4,5,6,7-tetrahydro[1,3]thiazolo[5,4-c]pyridine-2-carboxamide, N-(2-aminophenyl)-5-[1-anilino-2-nitrovinyl]-4,5,6,7-tetrahydro[1,3]thiazolo[5,4-c]pyridine-2-carboxamide, N-(2-aminophenyl)-5-{1-[(4-methoxyphenyl)amino]-2-nitrovinyl}-4,5,6,7-tetrahydro[1,3]thiazolo[5,4-c]pyridine-2-carboxamide, N-(2-aminophenyl)-5-[1-(butylamino)-2-nitrovinyl]-4,5,6,7-tetrahydro[1,3]thiazolo[5,4-c]pyridine-2-carboxamide, N-(2-aminophenyl)-5-{1-[(4-isopropylphenyl)amino]-2-nitrovinyl}-4,5,6,7-tetrahydro[1,3]thiazolo[5,4-c]pyridine-2-carboxamide, N-(2-aminophenyl)-5-[1-{[4-(dimethylamino)phenyl]amino}-2-nitrovinyl]-4,5,6,7-tetrahydro[1,3]thiazolo[5,4-c]pyridine-2-carboxamide, N-(2-aminophenyl)-5-{1-[(3,4-dimethoxyphenyl)amino]-2-nitrovinyl}-4,5,6,7-tetrahydro[1,3]thiazolo[5,4-c]pyridine-2-carboxamide, N-(2-amino-5-methoxyphenyl)-5-{1-[(4-methoxyphenyl)amino]-2-nitrovinyl}-4,5,6,7-tetrahydro[1,3]thiazolo[5,4-c]pyridine-2-carboxamide, N-(2-amino-5-methoxyphenyl)-5-{1-[(4-isopropylphenyl)amino]-2-nitrovinyl}-4,5,6,7-tetrahydro[1,3]thiazolo[5,4-c]pyridine-2-carboxamide, N-(2-amino-5-methoxyphenyl)-5-[1-{[4-(dimethylamino)phenyl]amino}-2-nitrovinyl]-4,5,6,7-tetrahydro[1,3]thiazolo[5,4-c]pyridine-2-carboxamide, N-(2-amino-5-isopropylphenyl)-5-[1-anilino-2-nitrovinyl]-4,5,6,7-tetrahydro[1,3]thiazolo[5,4-c]pyridine-2-carboxamide, N-[2-amino-5-(1-methylethyl)phenyl]-5-{1-[(4-methoxyphenyl)amino]-2-nitroethenyl}-4,5,6,7-tetrahydro[1,3]thiazolo[5,4-c]pyridine-2-carboxamide, N-(2-amino-5-isopropylphenyl)-5-[1-{[4-(dimethylamino)phenyl]amino}-2-nitrovinyl]-4,5,6,7-tetrahydro[1,3]thiazolo[5,4-c]pyridine-2-carboxamide, N-(2-amino-5-isopropylphenyl)-5-{1-[(4-isopropylphenyl)amino]-2-nitrovinyl}-4,5,6,7-tetrahydro[1,3]thiazolo[5,4-c]pyridine-2-carboxamide, N-(2-amino-5-methoxyphenyl)-5-{1-[(4-fluorophenyl)amino]-2-nitrovinyl}-4,5,6,7-tetrahydro[1,3]thiazolo[5,4-c]pyridine-2-carboxamide, N-(2-aminophenyl)-5-[(4-methylphenyl)sulfonyl]-4,5,6,7-tetrahydro[1,3]thiazolo[5,4-c]pyridine-2-carboxamide, N-(2-aminophenyl)-5-(benzylsulfonyl)-4,5,6,7-tetrahydro [1,3]thiazolo[5,4-c]pyridine-2-carboxamide,
N-(2-aminophenyl)-5-(biphenyl-4-ylsulfonyl)-4,5,6,7-tetrahydro[1,3]thiazolo[5,4-c]pyridine-2-carboxamide,
N-(2-aminophenyl)-5-[(4-methoxyphenyl)sulfonyl]-4,5,6,7-tetrahydro[1,3]thiazolo[5,4-c]pyridine-2-carboxamide,
N-(2-aminophenyl)-5-(methylsulfonyl)-4,5,6,7-tetrahydro [1,3]thiazolo[5,4-c]pyridine-2-carboxamide
5-[(4-acetamidophenyl)sulfonyl]-N-(2-aminophenyl)-4,5,6,7-tetrahydro[1,3]thiazolo[5,4-c]pyridine-2-carboxamide,
N-(2-aminophenyl)-5-(2-naphthylsulfonyl)-4,5,6,7-tetrahydro[1,3]thiazolo[5,4-c]pyridine-2-carboxamide,
N-(2-aminophenyl)-5-(2-thienylsulfonyl)-4,5,6,7-tetrahydro [1,3]thiazolo[5,4-c]pyridine-2-carboxamide,
Methyl 3-({2-[(2-aminophenyl)carbamoyl]-6,7-dihydro[1, 3]thiazolo[5,4-c]pyridin-5(4H)yl}sulfonyl)thiophene-2-carboxylate,
5-[(2-acetamido-4-methyl-1,3-thiazol-5-yl)sulfonyl]-N-(2-aminophenyl)-4,5,6,7-tetrahydro[1,3]thiazolo[5,4-c]pyridine-2-carboxamide,
N-(2-aminophenyl)-5-[(3-methoxyphenyl)sulfonyl]-4,5,6,7-tetrahydro[1,3]thiazolo[5,4-c]pyridine-2-carboxamide,
N-(2-aminophenyl)-5-{[4-(trifluoromethyl)phenyl]sulfonyl}-4,5,6,7-tetrahydro[1,3]thiazolo[5,4-c]pyridine-2-carboxamide,
N-(2-aminophenyl)-5-{[3-(trifluoromethyl)phenyl]sulfonyl}-4,5,6,7-tetrahydro[1,3]thiazolo[5,4-c]pyridine-2-carboxamide,
N-(2-aminophenyl)-5-[(3-fluorophenyl)sulfonyl]-4,5,6,7-tetrahydro[1,3]thiazolo[5,4-c]pyridine-2-carboxamide,
N-(2-aminophenyl)-5-(isopropylsulfonyl)-4,5,6,7-tetrahydro[1,3]thiazolo[5,4-c]pyridine-2-carboxamide,
N-(2-aminophenyl)-5-{[3-(difluoromethoxy)phenyl]sulfonyl}-4,5,6,7-tetrahydro[1,3]thiazolo[5,4-c]pyridine-2-carboxamide,
N-(2-aminophenyl)-5-{[4-(difluoromethoxy)phenyl]sulfonyl}-4,5,6,7-tetrahydro[1,3]thiazolo[5,4-c]pyridine-2-carboxamide,
N-(2-aminophenyl)-5-{[3-(trifluoromethoxy)phenyl]sulfonyl}-4,5,6,7-tetrahydro[1,3]thiazolo[5,4-c]pyridine-2-carboxamide,
N-(2-aminophenyl)-5-{[4-(trifluoromethoxy)phenyl]sulfonyl}-4,5,6,7-tetrahydro[1,3]thiazolo[5,4-c]pyridine-2-carboxamide,
N-(2-amino-5-methoxyphenyl)-5-[(4-methylphenyl)sulfonyl]-4,5,6,7-tetrahydro[1,3]thiazolo[5,4-c]pyridine-2-carboxamide,
N-(2-amino-5-isopropylphenyl)-5-[(4-methylphenyl)sulfonyl]-4,5,6,7
N-(2-aminophenyl)-5-(phenoxyacetyl)-4,5,6,7-tetrahydro [1,3]thiazolo[5,4-c]pyridine-2-carboxamide,
N-(2-aminophenyl)-5-[(4-methylphenoxy)acetyl]-4,5,6,7-tetrahydro[1,3]thiazolo[5,4-c]pyridine-2-carboxamide,
N-(2-aminophenyl)-5-[(4-methoxyphenoxy)acetyl]-4,5,6,7-tetrahydro[1,3]thiazolo[5,4-c]pyridine-2-carboxamide,
N-(2-aminophenyl)-5-[(2-naphthyloxy)acetyl]-4,5,6,7-tetrahydro[1,3]thiazolo[5,4-c]pyridine-2-carboxamide,
N-(2-aminophenyl)-5-[(biphenyl-4-yloxy)acetyl]-4,5,6,7-tetrahydro[1,3]thiazolo[5,4-c]pyridine-2-carboxamide,
N-(2-aminophenyl)-5-(methoxyacetyl)-4,5,6,7-tetrahydro [1,3]thiazolo[5,4-c]pyridine-2-carboxamide,
N-(2-amino-5-isopropylphenyl)-5-[(4-methoxyphenoxy) acetyl]-4,5,6,7-tetrahydro[1,3]thiazolo[5,4-c]pyridine-2-carboxamide,
N-(2-aminophenyl)-5-[(3-methoxyphenoxy)acetyl]-4,5,6,7-tetrahydro[1,3]thiazolo[5,4-c]pyridine-2-carboxamide, Methyl 2-[(2-aminophenyl)carbamoyl]-6,7-dihydro[1,3] thiazolo[5,4-c]pyridine-5(4H)carboxylate,
Biphenyl-4-yl 2-[(2-aminophenyl)carbamoyl]-6,7-dihydro [1,3]thiazolo[5,4-c]pyridine-5(4H)carboxylate,
4-Methylphenyl 2-[(2-aminophenyl)carbamoyl]-6,7-dihydro[1,3]thiazolo[5,4-c]pyridine-5(4H)-carboxylate,
4-Methoxyphenyl 2-[(2-aminophenyl)carbamoyl]-6,7-dihydro[1,3]thiazolo[5,4-c]pyridine-5(4H)-carboxylate,
4-(Propoxycarbonyl)phenyl 2-[(2-aminophenyl)carbamoyl]-6,7-dihydro[1,3]thiazolo[5,4-c]pyridine-5(4H)-carboxylate,
2-Naphthyl 2-[(2-aminophenyl)carbamoyl]-6,7-dihydro[1, 3]thiazolo[5,4-c]pyridine-5(4H)carboxylate,
3,4-Dimethoxyphenyl 2-[(2-aminophenyl)carbamoyl]-6,7-dihydro[1,3]thiazolo[5,4-c]pyridine-5(4H)-carboxylate,
Butyl 2-[(2-aminophenyl)carbamoyl]-6,7-dihydro[1,3]thiazolo[5,4-c]pyridine-5(4H)carboxylate,
Benzyl 2-[(2-aminophenyl)carbamoyl]-6,7-dihydro[1,3] thiazolo[5,4-c]pyridine-5(4H)carboxylate,
Pyridin-3-ylmethyl 2-[(2-aminophenyl)carbamoyl]-6,7-dihydro[1,3]thiazolo[5,4-c]pyridine-5(4H)-carboxylate,
N-(2-aminophenyl)-5-[3-(1,3-benzodioxol-5-yl)prop-2-enoyl]-4,5,6,7-tetrahydro[1,3]thiazolo[5,4-c]pyridine-2-carboxamide,
N-(2-aminophenyl)-5-[3-(3,4-dihydroxyphenyl)prop-2-enoyl]-4,5,6,7-tetrahydro[1,3]thiazolo[5,4-c]pyridine-2-carboxamide,
N-(2-aminophenyl)-5-pyrimidin-2-yl-4,5,6,7-tetrahydro[1, 3]thiazolo[5,4-c]pyridine-2-carboxamide,
N-(2-aminophenyl)-5-(4-pyridin-3-ylpyrimidin-2-yl)-4,5,6, 7-tetrahydro[1,3]thiazolo[5,4-c]pyridine-2-carboxamide,
N-(2-aminophenyl)-5-(5-nitropyridin-2-yl)-4,5,6,7-tetrahydro[1,3]thiazolo[5,4-c]pyridine-2-carboxamide,
N-(2-aminophenyl)-5-[5-(trifluoromethyl)pyridin-2-yl]-4,5, 6,7-tetrahydro[1,3]thiazolo[5,4-c]pyridine-2-carboxamide,
N-(2-aminophenyl)-5-(5-{[(4-methylphenyl)sulfonyl] amino}pyrimidin-2-yl)-4,5,6,7-tetrahydro[1,3]thiazolo[5, 4-c]pyridine-2-carboxamide,
N-(2-aminophenyl)-5-(5-{[(4-methylphenyl)sulfonyl] amino}pyridin-2-yl)-4,5,6,7-tetrahydro[1,3]thiazolo[5,4-c]pyridine-2-carboxamide,
N-(2-aminophenyl)-5-{4-[(benzylcarbamoyl)amino]phenyl}-4,5,6,7-tetrahydro[1,3]thiazolo[5,4-c]pyridine-2-carboxamide,
N-(2-aminophenyl)-5-(4-{[(4-methylphenyl)sulfonyl] amino}phenyl)-4,5,6,7-tetrahydro[1,3]thiazolo[5,4-c]pyridine-2-carboxamide,
N-(2-aminophenyl)-5-[(4-methylphenyl)sulfonyl]-4,5,6,7-tetrahydrothieno[3,2-c]pyridine-2-carboxamide,
N-(2-aminophenyl)-5-[(4-methylphenyl)sulfonyl]-4,5,6,7-tetrahydrofuro[3,2-c]pyridine-2-carboxamide,
N-(2-aminophenyl)-1-methyl-5-[(4-methylphenyl)sulfonyl]-4,5,6,7-tetrahydro-1H-pyrrolo[3,2-c]pyridine-2-carboxamide,
$N^2$-(2-aminophenyl)-$N^5$-pyridin-3-yl-6,7-dihydrothieno[3, 2-c]pyridine-2,5(4H)-dicarboxamide,
6,7-Dihydro-4H-thieno[3,2-c]pyridine-2,5-dicarboxylic acid 2-[(2-amino-phenyl)-amide]5-[(2-difluoromethoxy-phenyl)-amide],
$N^2$-(2-aminophenyl)-$N^5$-(3,4-dimethoxyphenyl)-6,7-dihydrothieno[3,2-c]pyridine-2,5(4H)-dicarboxamide,
$N^2$-[2-amino-5-(2-thienyl)phenyl]-$N^5$-butyl-6,7-dihydrothieno[3,2-c]pyridine-2,5(4H)-dicarboxamide,
$N^2$-[2-amino-5-(2-thienyl)phenyl]-$N^5$-pyridin-3-yl-6,7-dihydrothieno[3,2-c]pyridine-2,5(4H)-dicarboxamide, $N^2$-(2-amino-5-thiophen-2-ylphenyl)-$N^5$-(4-methoxyphenyl)-6,7-dihydrothieno[3,2-c]-pyridine-2,5(4H)-dicarboxamide, $N^2$-(2-aminophenyl)-$N^5$-(2-methoxyethyl)-6,7-dihydrothieno[3,2-c]pyridine-2,5(4H)-dicarboxamide, $N^2$-(2-aminophenyl)-$N^5$-pyridin-3-yl-6,7-dihydrothieno[3,2-c]pyridine-2,5(4H)-dicarboxamide, 3,4-dimethoxyphenyl 2-[(2-aminophenyl)carbamoyl]-6,7-dihydrothieno[3,2-c]pyridine-5(4H)carboxylate, $N^2$-(2-aminophenyl)-1-methyl-$N^5$-pyridin-3-yl-1,4,6,7-tetrahydro-5H-pyrrolo[3,2-c]pyridine-2,5-dicarboxamide, $N^2$-(2-aminophenyl)-$N^5$-(3,4-dimethoxyphenyl)-1-methyl-1,4,6,7-tetrahydro-5H-pyrrolo[3,2-c]pyridine-2,5-dicarboxamide, 2-(difluoromethoxy)phenyl 2-[(2-aminophenyl)carbamoyl]-1-methyl-1,4,6,7-tetrahydro-5H-pyrrolo[3,2-c]pyridine-5-carboxylate, 3,4-dimethoxyphenyl 2-[(2-aminophenyl)carbamoyl]-1-methyl-1,4,6,7-tetrahydro-5H-pyrrolo[3,2-c]pyridine-5-carboxylate, $N^2$-(2-aminophenyl)-$N^6$-pyridin-3-yl-4,7-dihydrothieno[2,3-c]pyridine-2,6(5H)-dicarboxamide, $N^2$-(2-aminophenyl)-$N^6$-(3,4-dimethoxyphenyl)-4,7-dihydrothieno[2,3-c]pyridine-2,6(5H)-dicarboxamide, $N^2$-(2-aminophenyl)-$N^6$-(2-methoxyethyl)-4,7-dihydrothieno[2,3-c]pyridine-2,6(5H)-dicarboxamide, $N^2$-(2-aminophenyl)-$N^6$-[2-(difluoromethoxy)phenyl]-4,7-dihydrothieno[2,3-c]pyridine-2,6(5H)-dicarboxamide, $N^2$-(2-amino-5-isopropylphenyl)-$N^6$-pyridin-3-yl-4,7-dihydrothieno[2,3-c]pyridine-2,6(5H)-dicarboxamide, $N^2$-(2-amino-5-isopropylphenyl)-$N^6$-[3-(difluoromethoxy)phenyl]-4,7-dihydrothieno[2,3-c]pyridine-2,6(5H)-dicarboxamide, $N^2$-(2-amino-5-isopropylphenyl)-$N^6$-(4-fluorophenyl)-4,7-dihydrothieno[2,3-c]pyridine-2,6(5H)-dicarboxamide, $N^2$-(2-amino-5-isopropylphenyl)-$N^6$-(3,4-dimethoxyphenyl)-4,7-dihydrothieno[2,3-c]pyridine-2,6(5H)-dicarboxamide, 3,4-dimethoxyphenyl 2-[(2-aminophenyl)carbamoyl]-4,7-dihydrothieno[2,3-c]pyridine-6(5H)carboxylate, 3,4-dimethoxyphenyl 2-[(2-amino-5-isopropylphenyl)carbamoyl]-4,7-dihydrothieno[2,3-c]pyridine-6(5H)-carboxylate, N-(2-aminophenyl)-6-[(3-methoxyphenoxy)acetyl]-4,5,6,7-tetrahydrothieno[2,3-c]pyridine-2-carboxamide, N-(2-amino-5-isopropylphenyl)-6-[(3-methoxyphenoxy)acetyl]-4,5,6,7-tetrahydrothieno[2,3-c]pyridine-2-carboxamide, $N^2$-(2-aminophenyl)-1-methyl-$N^6$-pyridin-3-yl-1,4,5,7-tetrahydro-6H-pyrrolo[2,3-c]pyridine-2,6-dicarboxamide, $N^2$-(2-aminophenyl)-$N^6$-(3,4-dimethoxyphenyl)-1-methyl-1,4,5,7-tetrahydro-6H-pyrrolo[2,3-c]pyridine-2,6-dicarboxamide, $N^2$-(2-aminophenyl)-$N^6$-(2-methoxyethyl)-1-methyl-1,4,5,7-tetrahydro-6H-pyrrolo[2,3-c]pyridine-2,6-dicarboxamide, $N^2$-(2-aminophenyl)-$N^6$-pyridin-3-yl-1,4,5,7-tetrahydro-6H-pyrrolo[2,3-c]pyridine-2,6-dicarboxamide, $N^2$-(2-aminophenyl)-$N^6$-(3,4-dimethoxyphenyl)-1,4,5,7-tetrahydro-6H-pyrrolo[2,3-c]pyridine-2,6-dicarboxamide, 3,4-dimethoxyphenyl 2-[(2-aminophenyl)carbamoyl]-1-methyl-1,4,5,7-tetrahydro-6H-pyrrolo[2,3-c]pyridine-6-carboxylate, 3,4-dimethoxyphenyl 2-[(2-aminophenyl)carbamoyl]-1,4,5,7-tetrahydro-6H-pyrrolo[2,3-c]pyridine-6-carboxylate, N-(2-aminophenyl)-5-(N-1,3-benzodioxol-5-ylglycyl)-4,5,6,7-tetrahydro[1,3]thiazolo[5,4-c]pyridine-2-carboxamide, N-(2-aminophenyl)-5-[N-(3-methoxyphenyl)glycyl]-4,5,6,7-tetrahydro[1,3]thiazolo[5,4-c]pyridine-2-carboxamide, N-(2-aminophenyl)-5-[N-(6-methoxypyridin-3-yl)glycyl]-4,5,6,7-tetrahydro[1,3]thiazolo[5,4-c]pyridine-2-carboxamide, $N^2$-(2-aminophenyl)-$N^5$-[3-(trifluoromethoxy)phenyl]-6,7-dihydro[1,3]thiazolo[5,4-c]pyridine-2,5(4H)-dicarboxamide, $N^2$-(2-aminophenyl)-$N^5$-(3-morpholin-4-ylphenyl)-6,7-dihydro[1,3]thiazolo[5,4-c]pyridine-2,5(4H)-dicarboxamide, $N^2$-(2-aminophenyl)-$N^5$-[4-(methylthio)phenyl]-6,7-dihydro[1,3]thiazolo[5,4-c]pyridine-2,5(4H)-dicarboxamide, $N^2$-(2-aminophenyl)-$N^5$-[3-(methylthio)phenyl]-6,7-dihydro[1,3]thiazolo[5,4-c]pyridine-2,5(4H)-dicarboxamide, $N^2$-(2-aminophenyl)-$N^5$-(3-methoxyphenyl)-6,7-dihydro[1,3]thiazolo[5,4-c]pyridine-2,5(4H)-dicarboxamide, $N^2$-(2-aminophenyl)-$N^5$-1H-indazol-5-yl-6,7-dihydro[1,3]thiazolo[5,4-c]pyridine-2,5(4H)dicarboxamide, $N^2$-(2-aminophenyl)-$N^5,N^5$-diethyl-6,7-dihydro[1,3]thiazolo[5,4-c]pyridine-2,5(4H)-dicarboxamide, $N^2$-(2-amino-5-chlorophenyl)-$N^5$-(4-methoxyphenyl)-6,7-dihydro[1,3]thiazolo[5,4-c]pyridine-2,5(4H)-dicarboxamide, $N^2$-(2-amino-5-chlorophenyl)-$N^5$-(3,4-dimethoxyphenyl)-6,7-dihydro[1,3]thiazolo[5,4-c]pyridine-2,5(4H)-dicarboxamide, $N^2$-(2-amino-5-chlorophenyl)-$N^5$-pyridin-3-yl-6,7-dihydro[1,3]thiazolo[5,4-c]pyridine-2,5(4H)-dicarboxamide, $N^2$-(2-aminophenyl)-$N^5$-[3-(difluoromethoxy)phenyl]-6,7-dihydro[1,3]thiazolo[5,4-c]pyridine-2,5(4H)-dicarboxamide, $N^2$-(2-aminophenyl)-$N^5$-[4-(methylsulfonyl)phenyl]-6,7-dihydro[1,3]thiazolo[5,4-c]pyridine-2,5(4H)-dicarboxamide, $N^2$-(2-aminophenyl)-$N^5$-[3-(methylsulfonyl)phenyl]-6,7-dihydro[1,3]thiazolo[5,4-c]pyridine-2,5(4H)-dicarboxamide, $N^2$-(2-amino-5-fluorophenyl)-$N^5$-1,3-benzodioxol-5-yl-6,7-dihydro[1,3]thiazolo[5,4-c]pyridine-2,5(4H)-dicarboxamide, $N^2$-(2-amino-5-fluorophenyl)-$N^5$-(3,4-dimethoxyphenyl)-6,7-dihydro[1,3]thiazolo[5,4-c]pyridine-2,5(4H)-dicarboxamide, $N^2$-[2-amino-5-(2-thienyl)phenyl]-$N^5$-pyridin-3-yl-6,7-dihydro[1,3]thiazolo[5,4-c]pyridine-2,5(4H)-dicarboxamide, $N^2$-[2-amino-5-(3-thienyl)phenyl]-$N^5$-[2-(difluoromethoxy)phenyl]-6,7-dihydro[1,3]thiazolo[5,4-c]pyridine-2,5(4H)-dicarboxamide, $N^2$-[2-amino-5-(3-thienyl)phenyl]-$N^5$-(3,4-dimethoxyphenyl)-6,7-dihydro[1,3]thiazolo[5,4-c]pyridine-2,5(4H)-dicarboxamide, $N^2$-[2-amino-5-(3-thienyl)phenyl]-$N^5$-(2-methoxyethyl)-6,7-dihydro[1,3]thiazolo[5,4-c]pyridine-2,5(4H)-dicarboxamide, $N^2$-[2-amino-5-(2-thienyl)phenyl]-$N^5$-(3,4-dimethoxyphenyl)-6,7-dihydro[1,3]thiazolo[5,4-c]pyridine-2,5(4H)-dicarboxamide, $N^2$-[2-amino-5-(2-thienyl)phenyl]-$N^5$-(2-methoxyethyl)-6,7-dihydro[1,3]thiazolo[5,4-c]pyridine-2,5(4H)-dicarboxamide, $N^2$-[2-amino-5-(2-thienyl)phenyl]-$N^5$-pyridin-3-yl-6,7-dihydro[1,3]thiazolo[5,4-c]pyridine-2,5(4H)-dicarboxamide, $N^2$-[2-amino-5-(2-thienyl)phenyl]-$N^5$-[2-(difluoromethoxy)phenyl]-6,7-dihydro[1,3]thiazolo[5,4-c]pyridine-2,5(4H)-dicarboxamide, $N^2$-(2-aminophenyl)-$N^5$-(4-cyanophenyl)-6,7-dihydro[1,3]thiazolo[5,4-c]pyridine-2,5(4H)-dicarboxamide, $N^2$-(2-aminophenyl)-$N^5$-(3-cyanophenyl)-6,7-dihydro[1,3]thiazolo[5,4-c]pyridine-2,5(4H)-dicarboxamide, $N^2$-[2-amino-5-(3-thienyl)phenyl]-$N^5$-pyridin-3-yl-6,7-dihydro[1,3]thiazolo[5,4-c]pyridine-2,5(4H)-dicarboxamide, N-(2-aminophenyl)-5-[4-(trifluoromethoxy)benzoyl]-4,5,6,7-tetrahydro[1,3]thiazolo[5,4-c]pyridine-2-carboxamide, N-(2-aminophenyl)-5-[4-(difluoromethoxy)benzoyl]-4,5,6,7-tetrahydro[1,3]thiazolo[5,4-c]pyridine-2-carboxamide, N-(2-aminophenyl)-5-[3-(trifluoromethoxy)benzoyl]-4,5,6,7-tetrahydro[1,3]thiazolo[5,4-c]pyridine-2-carboxamide, N-(2-aminophenyl)-5-[3-pyridin-3-ylprop-2-enoyl]-4,5,6,7 tetrahydro[1,3]thiazolo[5,4-c]pyridine-2-carboxamide, 3-methoxyphenyl 2-[(2-aminophenyl)carbamoyl]-6,7-dihydro[1,3]thiazolo[5,4-c]pyridine-5(4H)-carboxylate, 3,4-dimethoxyphenyl 2-{[2-amino-5-(3-thienyl)phenyl]carbamoyl}-6,7-dihydro[1,3]thiazolo[5,4-c]pyridine-5(4H)-carboxylate, 3,4-dimethoxyphenyl 2-{([2-amino-5-(2-thienyl)phenyl]carbamoyl}-6,7-dihydro[1,3]thiazolo[5,4-c]pyridine-5(4H)-carboxylate, benzyl 2-[(2-aminophenyl)carbamoyl]-6,7-dihydro[1,3]thiazolo[5,4-c]pyridine-5(4H)carboxylate, N-(2-aminophenyl)-5-[{[3-(difluoromethoxy)phenyl]amino}(oxo)acetyl]-4,5,6,7-tetrahydro[1,3]thiazolo[5,4-c]pyridine-2-carboxamide, N-(2-aminophenyl)-5-(oxo {[3-(trifluoromethoxy)phenyl]amino}acetyl)-4,5,6,7-tetrahydro[1,3]thiazolo[5,4-c]pyridine-2-carboxamide, N-(2-aminophenyl)-5-(oxo {[2-(trifluoromethoxy)phenyl]amino}acetyl)-4,5,6,7-tetrahydro[1,3]thiazolo[5,4-c]pyridine-2-carboxamide, N-(2-aminophenyl)-5-[{[2-(difluoromethoxy)phenyl]amino}(oxo)acetyl]-4,5,6,7-tetrahydro[1,3]thiazolo[5,4-c]pyridine-2-carboxamide, N-(2-aminophenyl)-5-(oxo{[2-(trifluoromethoxy)phenyl]amino}acetyl)-4,5,6,7-tetrahydro[1,3]thiazolo[5,4-c]pyridine-2-carboxamide, N-[2-amino-5-(2-thienyl)phenyl]-5-[(3-methoxyphenoxy)acetyl]-4,5,6,7-tetrahydro[1,3]thiazolo[5,4-c]pyridine-2-carboxamide, N-[2-amino-5-(3-thienyl)phenyl]-5-[(3-methoxyphenoxy)acetyl]-4,5,6,7-tetrahydro[1,3]thiazolo[5,4-c]pyridine-2-carboxamide, N-(2-amino-5-fluorophenyl)-5-[(3-methoxyphenoxy)acetyl]-4,5,6,7-tetrahydro[1,3]thiazolo[5,4-c]pyridine-2-carboxamide, N-(2-aminophenyl)-5-[(4-methoxyphenyl)sulfonyl]-4,5,6,7-tetrahydro[1,3]thiazolo[5,4-c]pyridine-2-carboxamide, $N^2$-(2-aminophenyl)-$N^5$-(6-methoxypyridin-3-yl)-6,7-dihydro[1,3]thiazolo[5,4-c]pyridine-2,5(4H)-dicarboxamide dihydrochloride, $N^2$-(2-aminophenyl)-$N^5$-pyridin-3-yl-6,7-dihydro[1,3]thiazolo[5,4-c]pyridine-2,5(4H)-dicarboxamide dihydrochloride, $N^2$-(2-aminophenyl)-$N^5$-(6-methoxypyridin-3-yl)-6,7-dihydro[1,3]thiazolo[5,4-c]pyridine-2,5(4H)-dicarboxamide-4-methylaniline (1:2), $N^2$-(2-aminophenyl)-$N^5$-pyridin-3-yl-6,7-dihydro[1,3]thiazolo[5,4-c]pyridine-2,5(4H)-dicarboxamide-4-methylaniline (1:2), N-(2-aminophenyl)-5-[(3-methoxyphenoxy)acetyl]-4,5,6,7-tetrahydro[1,3]thiazolo[5,4-c]pyridine-2-carboxamide-4-methylaniline (1:1), benzyl 2-[(2-aminophenyl)carbamoyl]-6,7-dihydro[1,3]thiazolo[5,4-c]pyridine-5(4H)carboxylate-4-methylaniline (1:1), N-(2-aminophenyl)-5-[(3-methoxyphenoxy)acetyl]-4,5,6,7-tetrahydro[1,3]thiazolo[5,4-c]pyridine-2-carboxamide methanesulfonate, benzyl 2-[(2-aminophenyl)carbamoyl]-6,7-dihydro[1,3]thiazolo[5,4-c]pyridine-5(4H)carboxylate methanesulfonate, benzyl 2-[(2-aminophenyl)carbamoyl]-6,7-dihydro[1,3]thiazolo[5,4-c]pyridine-5(4H)carboxylate sulfate, N-(2-aminophenyl)-5-[(4-methoxyphenyl)sulfonyl]-4,5,6,7-tetrahydro[1,3]thiazolo[5,4-c]pyridine-2-carboxamide sulphate or salts of these compounds.

Another embodiment of the compounds according to the present invention relates to compounds of formula I selected from:

$N^2$-(2-aminophenyl)-N5-biphenyl-4-yl-6,7-dihydro[1,3]thiazolo[5,4-c]pyridine-2,5(4H)-dicarboxamide, $N^2$-(2-aminophenyl)-N5-[4-(dimethylamino)phenyl]-6,7-dihydro[1,3]thiazolo[5,4-c]pyridine-2,5(4H)-dicarboxamide, $N^2$-(2-aminophenyl)-N5-(4-methoxyphenyl)-6,7-dihydro[1,3]thiazolo[5,4-c]pyridine-2,5(4H)-dicarboxamide, $N^2$-(2-aminophenyl)-N5-benzyl-6,7-dihydro[1,3]thiazolo[5,4-c]pyridine-2,5(4H)-dicarboxamide, Methyl 4-[({2-[(2-aminophenyl)carbamoyl]-6,7-dihydro[1,3]thiazolo[5,4-c]pyridin-5(4H)yl}carbonyl)amino]benzoate, $N^2$-(2-aminophenyl)-N5-(4-phenoxyphenyl)-6,7-dihydro[1,3]thiazolo[5,4-c]pyridine-2,5(4H)-dicarboxamide, $N^2$-(2-aminophenyl)-N5-1,3-benzodioxol-5-yl-6,7-dihydro[1,3]thiazolo[5,4-c]pyridine-2,5(4H)-dicarboxamide, $N^2$-(2-aminophenyl)-N5-[2-(trifluoromethoxy)phenyl]-6,7-dihydro[1,3]thiazolo[5,4-c]pyridine-2,5(4H)-dicarboxamide, $N^2$-(2-aminophenyl)-N5-[4-(trifluoromethoxy)phenyl]-6,7-dihydro[1,3]thiazolo[5,4-c]pyridine-2,5(4H)-dicarboxamide, $N^2$-(2-aminophenyl)-N5-[2-(difluoromethoxy)phenyl]-6,7-dihydro[1,3]thiazolo[5,4-c]pyridine-2,5(4H)-dicarboxamide, $N^2$-(2-aminophenyl)-N5-[4-(difluoromethoxy)phenyl]-6,7-dihydro[1,3]thiazolo[5,4-c]pyridine-2,5(4H)-dicarboxamide, $N^2$-(2-aminophenyl)-N5-quinolin-3-yl-6,7-dihydro[1,3]thiazolo[5,4-c]pyridine-2,5(4H)-dicarboxamide, $N^2$-(2-aminophenyl)-N5-(4-methylphenyl)-6,7-dihydro[1,3]thiazolo[5,4-c]pyridine-2,5(4H)-dicarboxamide, $N^2$-(2-aminophenyl)-N5-(pyridin-3-ylmethyl)-6,7-dihydro[1,3]thiazolo[5,4-c]pyridine-2,5(4H)-dicarboxamide, $N^2$-(2-aminophenyl)-N5-pyridin-4-yl-6,7-dihydro[1,3]thiazolo[5,4-c]pyridine-2,5(4H)-dicarboxamide, $N^2$-(2-aminophenyl)-N5-(2-methoxyethyl)-6,7-dihydro[1,3]thiazolo[5,4-c]pyridine-2,5(4H)-dicarboxamide, $N^2$-(2-aminophenyl)-N5-methyl-6,7-dihydro[1,3]thiazolo[5,4-c]pyridine-2,5(4H)-dicarboxamide, $N^2$-(2-aminophenyl)-N5-[3-(dimethylamino)phenyl]-6,7-dihydro[1,3]thiazolo[5,4-c]pyridine-2,5(4H)-dicarboxamide, $N^2$-(2-aminophenyl)-N5-(3,4-dimethoxyphenyl)-6,7-dihydro[1,3]thiazolo[5,4-c]pyridine-2,5(4H)-dicarboxamide, N²-(2-aminophenyl)-N5-(2-methoxyethyl)-N5-methyl-6,7-dihydro[1,3]thiazolo[5,4-c]pyridine-2,5(4H)-dicarboxamide,
N²-(2-aminophenyl)-N5-ethyl-N5-isopropyl-6,7-dihydro[1,3]thiazolo[5,4-c]pyridine-2,5(4H)-dicarboxamide,
N²-(2-aminophenyl)-N5-[4-(dimethylamino)phenyl]-N5-methyl-6,7-dihydro[1,3]thiazolo[5,4-c]pyridine-2,5(4H)-dicarboxamide,
N²-(2-aminophenyl)-N5-[3-(dimethylamino)phenyl]-N5-methyl-6,7-dihydro[1,3]thiazolo[5,4-c]pyridine-2,5(4H)-dicarboxamide,
N²-(2-aminophenyl)-N5-(3,4-dimethoxyphenyl)-N5-methyl-6,7-dihydro[1,3]thiazolo[5,4-c]pyridine-2,5(4H)-dicarboxamide,
N²-(2-aminophenyl)-N5-(3,4-dimethoxyphenyl)-N5-ethyl-6,7-dihydro[1,3]thiazolo[5,4-c]pyridine-2,5(4H)-dicarboxamide,
N²-(2-aminophenyl)-N5-(3,4-dimethoxyphenyl)-N5-(2-methoxyethyl)-6,7-dihydro[1,3]thiazolo[5,4-c]pyridine-2,5(4H)-dicarboxamide,
N²-(2-aminophenyl)-N5-methyl-N5-pyridin-3-yl-6,7-dihydro[1,3]thiazolo[5,4-c]pyridine-2,5(4H)-dicarboxamide,
N²-(2-aminophenyl)-N5-ethyl-N5-pyridin-3-yl-6,7-dihydro[1,3]thiazolo[5,4-c]pyridine-2,5(4H)-dicarboxamide,
N²-(2-aminophenyl)-N5-1,3-benzodioxol-5-yl-N5-ethyl-6,7-dihydro[1,3]thiazolo[5,4-c]pyridine-2,5(4H)-dicarboxamide,
N²-(2-aminophenyl)-N5-1,3-benzodioxol-5-yl-N5-(2-methoxyethyl)-6,7-dihydro[1,3]thiazolo[5,4-c]pyridine-2,5(4H)-dicarboxamide,
N²-(2-aminophenyl)-N5-1,3-benzodioxol-5-yl-N5-methyl-6,7-dihydro[1,3]thiazolo[5,4-c]pyridine-2,5(4H)-dicarboxamide,
N²-(2-aminophenyl)-N5-[3-(4-methylpiperazin-1-yl)phenyl]-6,7-dihydro[1,3]thiazolo[5,4-c]pyridine-2,5(4H)-dicarboxamide,
N²-(2-aminophenyl)-N5-(2-methoxyethyl)-N5-pyridin-3-yl-6,7-dihydro[1,3]thiazolo[5,4-c]pyridine-2,5(4H)-dicarboxamide,
N²-(2-aminophenyl)-N5-(6-morpholin-4-ylpyridin-3-yl)-6,7-dihydro[1,3]thiazolo[5,4-c]pyridine-2,5(4H)-dicarboxamide,
N²-(2-aminophenyl)-N5-(6-azetidin-1-ylpyridin-3-yl)-6,7-dihydro[1,3]thiazolo[5,4-c]pyridine-2,5(4H)-dicarboxamide,
N²-(2-aminophenyl)-N5-[6-(dimethylamino)pyridin-3-yl]-6,7-dihydro[1,3]thiazolo[5,4-c]pyridine-2,5(4H)-dicarboxamide,
N²-(2-aminophenyl)-N5-[6-(4-methylpiperazin-1-yl)pyridin-3-yl]-6,7-dihydro[1,3]thiazolo[5,4-c]pyridine-2,5(4H)-dicarboxamide,
N²-(2-aminophenyl)-N5-pyridin-3-yl-6,7-dihydro[1,3]thiazolo[5,4-c]pyridine-2,5(4H)-dicarboxamide,
N²-(2-aminophenyl)-N5-butyl-6,7-dihydro[1,3]thiazolo[5,4-c]pyridine-2,5(4H)-dicarboxamide,
N²-(2-aminophenyl)-N5-(4-pyridin-3-ylcyclohexyl)-6,7-dihydro[1,3]thiazolo[5,4-c]pyridine-2,5(4H)-dicarboxamide,
N²-(2-aminophenyl)-N5-piperidin-4-yl-6,7-dihydro[1,3]thiazolo[5,4-c]pyridine-2,5(4H)-dicarboxamide,
N²-(2-amino-5-methoxyphenyl)-N5-(4-methoxyphenyl)-6,7-dihydro[1,3]thiazolo[5,4-c]pyridine-2,5(4H)-dicarboxamide,
N²-(2-aminophenyl)-N5-(4-pyridin-4-ylcyclohexyl)-6,7-dihydro[1,3]thiazolo[5,4-c]pyridine-2,5(4H)-dicarboxamide,
N²-(2-amino-5-isopropylphenyl)-N5-(4-methoxyphenyl)-6,7-dihydro[1,3]thiazolo[5,4-c]pyridine-2,5(4H)-dicarboxamide,
N²-(2-amino-5-methoxyphenyl)-N5-isoquinolin-5-yl-6,7-dihydro[1,3]thiazolo[5,4-c]pyridine-2,5(4H)-dicarboxamide,
N²-(2-amino-5-methoxyphenyl)-N5-[4-(dimethylamino)phenyl]-6,7-dihydro[1,3]thiazolo[5,4-c]pyridine-2,5(4H)-dicarboxamide,
N²-(2-amino-5-isopropylphenyl)-N5-(3,4-dimethoxyphenyl)-6,7-dihydro[1,3]thiazolo[5,4-c]pyridine-2,5(4H)-dicarboxamide,
N²-(2-amino-5-isopropylphenyl)-N5-isoquinolin-5-yl-6,7-dihydro[1,3]thiazolo[5,4-c]pyridine-2,5(4H)-dicarboxamide,
N²-(2-amino-5-isopropylphenyl)-N5-[4-(dimethylamino)phenyl]-6,7-dihydro[1,3]thiazolo[5,4-c]pyridine-2,5(4H)-dicarboxamide,
N²-(2-amino-5-methoxyphenyl)-N5-(4-fluorophenyl)-6,7-dihydro[1,3]thiazolo[5,4-c]pyridine-2,5(4H)-dicarboxamide,
N²-(2-amino-5-isopropylphenyl)-N5-(4-fluorophenyl)-6,7-dihydro[1,3]thiazolo[5,4-c]pyridine-2,5(4H)-dicarboxamide,
N²-[2-amino-5-(dimethylamino)phenyl]-N5-(4-methoxyphenyl)-6,7-dihydro[1,3]thiazolo[5,4-c]pyridine-2,5(4H)-dicarboxamide,
N²-[2-amino-5-(2-thienyl)phenyl]-N5-(4-methoxyphenyl)-6,7-dihydro[1,3]thiazolo[5,4-c]pyridine-2,5(4H)-dicarboxamide,
N²-[2-amino-5-(2-thienyl)phenyl]-N5-[4-(dimethylamino)phenyl]-6,7-dihydro[1,3]thiazolo[5,4-c]pyridine-2,5(4H)-dicarboxamide,
N²-[2-amino-5-(3-thienyl)phenyl]-N5-(4-methoxyphenyl)-6,7-dihydro[1,3]thiazolo[5,4-c]pyridine-2,5(4H)-dicarboxamide,
N²-[2-amino-5-(dimethylamino)phenyl]-N5-[4-(dimethylamino)phenyl]-6,7-dihydro[1,3]thiazolo[5,4-c]pyridine-2,5(4H)-dicarboxamide,
N²-(2-amino-5-pyrrolidin-1-ylphenyl)-N5-(4-methoxyphenyl)-6,7-dihydro[1,3]thiazolo[5,4-c]pyridine-2,5(4H)-dicarboxamide,
N²-[2-amino-5-(3-thienyl)phenyl]-N5-[4-(dimethylamino)phenyl]-6,7-dihydro[1,3]thiazolo[5,4-c]pyridine-2,5(4H)-dicarboxamide,
N²-(2-amino-5-isopropylphenyl)-N5-pyridin-3-yl-6,7-dihydro[1,3]thiazolo[5,4-c]pyridine-2,5(4H)-dicarboxamide,
N²-[2-amino-5-(dimethylamino)phenyl]-N5-(3,4-dimethoxyphenyl)-6,7-dihydro[1,3]thiazolo[5,4-c]pyridine-2,5(4H)-dicarboxamide,
N²-(2-aminophenyl)-N5-isoquinolin-5-yl-6,7-dihydro[1,3]thiazolo[5,4-c]pyridine-2,5(4H)-dicarboxamide,
N²-(2-aminophenyl)-N5-[3-(dimethylamino)phenyl]-6,7-dihydro[1,3]thiazolo[5,4-c]pyridine-2,5(4H)-dicarboxamide dihydrochloride,
N-(2-aminophenyl)-5-[{[4-(dimethylamino)phenyl]amino}(oxo)acetyl]-4,5,6,7-tetrahydro[1,3]thiazolo[5,4-c]pyridine-2-carboxamide,
N-(2-aminophenyl)-5-{[(4-methoxyphenyl)amino](oxo)acetyl}-4,5,6,7-tetrahydro[1,3]thiazolo[5,4-c]pyridine-2-carboxamide,
N-(2-aminophenyl)-5-{[(3,4-dimethoxyphenyl)amino](oxo)acetyl}-4,5,6,7-tetrahydro[1,3]thiazolo[5,4-c]pyridine-2-carboxamide,
N-(2-aminophenyl)-5-{oxo[(4-pyridin-4-ylcyclohexyl)amino]acetyl}-4,5,6,7-tetrahydro[1,3]-thiazolo[5,4-c]pyridine-2-carboxamide, N-(2-aminophenyl)-5-[(isoquinolin-5-ylamino)(oxo) acetyl]-4,5,6,7-tetrahydro[1,3]thiazolo[5,4-c]pyridine-2-carboxamide, N-(2-aminophenyl)-5-{oxo[(4-pyridin-3-ylcyclohexyl) amino]acetyl}-4,5,6,7-tetrahydro[1,3]thiazolo[5,4-c]pyridine-2-carboxamide, N-(2-aminophenyl)-5-{[(6-methoxypyridin-3-yl)amino] (oxo)acetyl}-4,5,6,7-tetrahydro[1,3]thiazolo[5,4-c]pyridine-2-carboxamide, N-(2-aminophenyl)-5-[{[6-(dimethylamino)pyridin-3-yl] amino}(oxo)acetyl]-4,5,6,7-tetrahydro[1,3]thiazolo[5,4-c]pyridine-2-carboxamide, N-(2-aminophenyl)-5-(oxo {[4-(trifluoromethoxy)phenyl] amino}acetyl)-4,5,6,7-tetrahydro[1,3]thiazolo[5,4-c]pyridine-2-carboxamide, N-(2-aminophenyl)-5-{[(6-morpholin-4-ylpyridin-3-yl) amino](oxo)acetyl}-4,5,6,7-tetrahydro[1,3]thiazolo[5,4-c]pyridine-2-carboxamide, N-(2-aminophenyl)-5-[(1,3-benzodioxol-5-ylamino)(oxo) acetyl]-4,5,6,7-tetrahydro[1,3]thiazolo[5,4-c]pyridine-2-carboxamide, N-(2-aminophenyl)-5-{[(4-methylphenyl)amino](oxo) acetyl}-4,5,6,7-tetrahydro[1,3]thiazolo[5,4-c]pyridine-2-carboxamide, N-(2-aminophenyl)-5-{[(5-methylpyridin-2-yl)amino](oxo) acetyl}-4,5,6,7-tetrahydro[1,3]thiazolo[5,4-c]pyridine-2-carboxamide, N-(2-aminophenyl)-5-[oxo(quinolin-3-ylamino)acetyl]-4,5,6,7-tetrahydro[1,3]thiazolo[5,4-c]pyridine-2-carboxamide, N-(2-amino-5-methoxyphenyl)-5-{[(4-methoxyphenyl) amino](oxo)acetyl}-4,5,6,7-tetrahydro[1,3]thiazolo[5,4-c]pyridine-2-carboxamide, N-(2-aminophenyl)-5-[(butylamino)(oxo)acetyl]-4,5,6,7-tetrahydro[1,3]thiazolo[5,4-c]pyridine-2-carboxamide, N-(2-amino-5-isopropylphenyl)-5-{[(3,4-dimethoxyphenyl) amino](oxo)acetyl}-4,5,6,7-tetrahydro[1,3]thiazolo[5,4-c]pyridine-2-carboxamide, N-(2-amino-5-isopropylphenyl)-5-{[(4-methoxyphenyl) amino](oxo)acetyl}-4,5,6,7-tetrahydro[1,3]thiazolo[5,4-c]pyridine-2-carboxamide, N-(2-amino-5-methoxyphenyl)-5-{[(3,4-dimethoxyphenyl) amino](oxo)acetyl}-4,5,6,7-tetrahydro[1,3]thiazolo[5,4-c]pyridine-2-carboxamide, N-(2-amino-5-methoxyphenyl)-5-[(butylamino)(oxo) acetyl]-4,5,6,7-tetrahydro[1,3]thiazolo[5,4-c]pyridine-2-carboxamide, N-(2-amino-5-isopropylphenyl)-5-[(butylamino)(oxo) acetyl]-4,5,6,7-tetrahydro[1,3]thiazolo[5,4-c]pyridine-2-carboxamide, N-(2-aminophenyl)-5-[(benzylamino)(oxo)acetyl]-4,5,6,7-tetrahydro[1,3]thiazolo[5,4-c]pyridine-2-carboxamide, N-(2-aminophenyl)-5-[{[6-(4-methylpiperazin-1-yl)pyridin-3-yl]amino}(oxo)acetyl]-4,5,6,7-tetrahydro[1,3]thiazolo[5,4-c]pyridine-2-carboxamide, N-(2-aminophenyl)-5-{oxo[(pyridin-3-ylmethyl)amino] acetyl}-4,5,6,7-tetrahydro[1,3]thiazolo[5,4-c]pyridine-2-carboxamide, N-(2-aminophenyl)-5-(biphenyl-4-ylcarbonyl)-4,5,6,7-tetrahydro[1,3]thiazolo[5,4-c]pyridine-2-carboxamide, N-(2-aminophenyl)-5-(4-methylbenzoyl)-4,5,6,7-tetrahydro[1,3]thiazolo[5,4-c]pyridine-2-carboxamide, Methyl 4-({2-[(2-aminophenyl)carbamoyl]-6,7-dihydro[1,3]thiazolo[5,4-c]pyridin-5(4H)yl}carbonyl)benzoate, N-(2-aminophenyl)-5-[4-(dimethylamino)benzoyl]-4,5,6,7-tetrahydro[1,3]thiazolo[5,4-c]pyridine-2-carboxamide, 5-Acetyl-N-(2-aminophenyl)-4,5,6,7-tetrahydro[1,3]thiazolo[5,4-c]pyridine-2-carboxamide, N-(2-aminophenyl)-5-(4-methoxybenzoyl)-4,5,6,7-tetrahydro[1,3]thiazolo[5,4-c]pyridine-2-carboxamide, N-(2-aminophenyl)-5-(quinolin-3-yl carbonyl)-4,5,6,7-tetrahydro[1,3]thiazolo[5,4-c]pyridine-2-carboxamide, N-(2-aminophenyl)-5-(2-naphthoyl)-4,5,6,7-tetrahydro[1,3]thiazolo[5,4-c]pyridine-2-carboxamide, N-(2-aminophenyl)-5-[(6-methylpyridin-3-yl)carbonyl]-4,5,6,7-tetrahydro[1,3]thiazolo[5,4-c]pyridine-2-carboxamide, N-(2-aminophenyl)-5-[3-(dimethylamino)benzoyl]-4,5,6,7-tetrahydro[1,3]thiazolo[5,4-c]pyridine-2-carboxamide, N-(2-aminophenyl)-5-(anilinocarbonothioyl)-4,5,6,7-tetrahydro[1,3]thiazolo[5,4-c]pyridine-2-carboxamide, N-(2-aminophenyl)-5-({[4-(dimethylamino)phenyl] amino}carbonothioyl)-4,5,6,7-tetrahydro[1,3]thiazolo[5,4-c]pyridine-2-carboxamide, N-(2-aminophenyl)-5-[(piperidin-4-ylamino)carbonothioyl] tetrahydro[1,3]thiazolo[5,4-c]pyridine-2-carboxamide, N-(2-aminophenyl)-5-{[(4-pyridin-3-ylcyclohexyl)amino] carbonothioyl}-4,5,6,7-tetrahydro[1,3]thiazolo[5,4-c]pyridine-2-carboxamide, N-(2-amino-5-methoxyphenyl)-5-(anilinocarbonothioyl)-4,5,6,7-tetrahydro[1,3]thiazolo[5,4-c]pyridine-2-carboxamide, N-(2-aminophenyl)-5-[(pyridin-3-ylamino)carbonothioyl]-4,5,6,7-tetrahydro[1,3]thiazolo[5,4-c]pyridine-2-carboxamide, N-(2-aminophenyl)-5-[(isoquinolin-5-ylamino)carbonothioyl]-4,5,6,7-tetrahydro[1,3]thiazolo[5,4-c]pyridine-2-carboxamide, N-(2-aminophenyl)-5-[(butylamino)carbonothioyl]-4,5,6,7-tetrahydro[1,3]thiazolo[5,4-c]pyridine-2-carboxamide, N-(2-amino-5-methoxyphenyl)-5-{[(4-methoxyphenyl) amino]carbonothioyl}-4,5,6,7-tetrahydro[1,3]thiazolo[5,4-c]pyridine-2-carboxamide, N-(2-amino-5-methoxyphenyl)-5-[(pyridin-3-ylamino)carbonothioyl]-4,5,6,7-tetrahydro[1,3]thiazolo[5,4-c]pyridine-2-carboxamide, N-(2-amino-5-isopropylphenyl)-5-[(pyridin-3-ylamino)carbonothioyl]-4,5,6,7-tetrahydro[1,3]thiazolo[5,4-c]pyridine-2-carboxamide, N-(2-amino-5-isopropylphenyl)-5-(anilinocarbonothioyl)-4,5,6,7-tetrahydro[1,3]thiazolo[5,4-c]pyridine-2-carboxamide, N-(2-amino-5-isopropylphenyl)-5-{[(4-methoxyphenyl) amino]carbonothioyl}-4,5,6,7-tetrahydro[1,3]thiazolo[5,4-c]pyridine-2-carboxamide, N-(2-aminophenyl)-5-{imino[(4-methoxyphenyl)amino] methyl}-4,5,6,7-tetrahydro[1,3]thiazolo[5,4-c]pyridine-2-carboxamide, N-(2-amino-5-isopropylphenyl)-5-{imino[(4-methoxyphenyl)amino]methyl}-4,5,6,7-tetrahydro[1,3]thiazolo[5,4-c]pyridine-2-carboxamide, N-(2-aminophenyl)-5-[(benzylamino)(imino)methyl]-4,5,6,7-tetrahydro[1,3]thiazolo[5,4-c]pyridine-2-carboxamide, N-(2-aminophenyl)-5-[anilino(methylimino)methyl]-4,5,6,7-tetrahydro[1,3]thiazolo[5,4-c]pyridine-2-carboxamide, N-(2-amino-5-methoxyphenyl)-5-[[(4-methoxyphenyl) amino](methylimino)methyl]-4,5,6,7-tetrahydro[1,3]thiazolo[5,4-c]pyridine-2-carboxamide, N-(2-aminophenyl)-5-[anilino(cyanoimino)methyl]-4,5,6,7-tetrahydro[1,3]thiazolo[5,4-c]pyridine-2-carboxamide, N-(2-aminophenyl)-5-{(cyanoimino)[(4-methoxyphenyl) amino]methyl}-4,5,6,7-tetrahydro[1,3]thiazolo[5,4-c]pyridine-2-carboxamide, N-(2-aminophenyl)-5-{(cyanoimino)[(3,4-dimethoxyphenyl)amino]methyl}-4,5,6,7-tetrahydro[1,3]thiazolo[5,4-c]pyridine-2-carboxamide, N-(2-aminophenyl)-5-{(cyanoimino)[(2-methylphenyl)amino]methyl}-4,5,6,7-tetrahydro[1,3]thiazolo[5,4-c]pyridine-2-carboxamide, N-(2-aminophenyl)-5-[(cyanoimino){[4-(dimethylamino)phenyl]amino}methyl]-4,5,6,7-tetrahydro[1,3]thiazolo[5,4-c]pyridine-2-carboxamide, N-(2-aminophenyl)-5-[(cyanoimino)(pentylamino)methyl]-4,5,6,7-tetrahydro[1,3]thiazolo[5,4-c]pyridine-2-carboxamide, N-(2-aminophenyl)-5-[(benzylamino)(cyano imino)methyl]-4,5,6,7-tetrahydro[1,3]thiazolo[5,4-c]pyridine-2-carboxamide, N-(2-amino-5-methoxyphenyl)-5-[(cyano amino)(phenylimino)methyl]-4,5,6,7-tetrahydro[1,3]thiazolo[5,4-c]pyridine-2-carboxamide, N-(2-amino-5-methoxyphenyl)-5-{(cyano amino)[(4-methoxyphenyl)imino]methyl}-4,5,6,7-tetrahydro[1,3]thiazolo[5,4-c]pyridine-2-carboxamide, N-(2-amino-5-isopropylphenyl)-5-{(cyano amino)[(4-methoxyphenyl)imino]methyl}-4,5,6,7-tetrahydro[1,3]thiazolo[5,4-c]pyridine-2-carboxamide, N-(2-aminophenyl)-5-[N-phenylethanimidoyl]-4,5,6,7-tetrahydro[1,3]thiazolo[5,4-c]pyridine-2-carboxamide, N-(2-aminophenyl)-5-[N-(3,4-dimethoxyphenyl)ethanimidoyl]-4,5,6,7 tetrahydro[1,3]thiazolo[5,4-c]pyridine-2-carboxamide, N-(2-aminophenyl)-5-[N-(4-methoxyphenyl)ethanimidoyl]-4,5,6,7-tetrahydro[1,3]thiazolo[5,4-c]pyridine-2-carboxamide, N-(2-amino-5-methoxyphenyl)-5-[N-phenylethanimidoyl]-4,5,6,7-tetrahydro[1,3]thiazolo[5,4-c]pyridine-2-carboxamide, N-(2-amino-5-methoxyphenyl)-5-[N-(4-methoxyphenyl)ethanimidoyl]-4,5,6,7-tetrahydro[1,3]thiazolo[5,4-c]pyridine-2-carboxamide, N-(2-amino-5-methoxyphenyl)-5-[N-(3,4-dimethoxyphenyl)ethanimidoyl]-4,5,6,7-tetrahydro[1,3]thiazolo[5,4-c]pyridine-2-carboxamide, N-(2-amino-5-isopropylphenyl)-5-[N-(4-methoxyphenyl)ethanimidoyl]-4,5,6,7-tetrahydro[1,3]thiazolo[5,4-c]pyridine-2-carboxamide, N-(2-amino-5-isopropylphenyl)-5-[N-(3,4-dimethoxyphenyl)ethanimidoyl]-4,5,6,7-tetrahydro[1,3]thiazolo[5,4-c]pyridine-2-carboxamide, N-(2-aminophenyl)-5-{N-[4-(dimethylamino)phenyl]ethanimidoyl}-4,5,6,7-tetrahydro[1,3]thiazolo[5,4-c]pyridine-2-carboxamide, N-(2-amino-5-isopropylphenyl)-5-[N-phenylethanimidoyl]-4,5,6,7-tetrahydro[1,3]thiazolo[5,4-c]pyridine-2-carboxamide, N-(2-aminophenyl)-5-[1-anilino-2-nitrovinyl]-4,5,6,7-tetrahydro[1,3]thiazolo[5,4-c]pyridine-2-carboxamide, N-(2-aminophenyl)-5-{1-[(4-methoxyphenyl)amino]-2-nitrovinyl}-4,5,6,7-tetrahydro[1,3]thiazolo[5,4-c]pyridine-2-carboxamide, N-(2-aminophenyl)-5-[1-(butylamino)-2-nitrovinyl]-4,5,6,7-tetrahydro[1,3]thiazolo[5,4-c]pyridine-2-carboxamide, N-(2-aminophenyl)-5-{1-[(4-isopropylphenyl)amino]-2-nitrovinyl}-4,5,6,7-tetrahydro[1,3]thiazolo[5,4-c]pyridine-2-carboxamide, N-(2-aminophenyl)-5-[1-{[4-(dimethylamino)phenyl]amino}-2-nitrovinyl]-4,5,6,7-tetrahydro[1,3]thiazolo[5,4-c]pyridine-2-carboxamide, N-(2-aminophenyl)-5-{1-[(3,4-dimethoxyphenyl)amino]-2-nitrovinyl}-4,5,6,7-tetrahydro[1,3]thiazolo[5,4-c]pyridine-2-carboxamide, N-(2-amino-5-methoxyphenyl)-5-{1-[(4-methoxyphenyl)amino]-2-nitrovinyl}-4,5,6,7-tetrahydro[1,3]thiazolo[5,4-c]pyridine-2-carboxamide, N-(2-amino-5-methoxyphenyl)-5-{1-[(4-isopropylphenyl)amino]-2-nitrovinyl}-4,5,6,7-tetrahydro[1,3]thiazolo[5,4-c]pyridine-2-carboxamide, N-(2-amino-5-methoxyphenyl)-5-[1-{[4-(dimethylamino)phenyl]amino}-2-nitrovinyl]-4,5,6,7-tetrahydro[1,3]thiazolo[5,4-c]pyridine-2-carboxamide, N-(2-amino-5-isopropylphenyl)-5-[1-anilino-2-nitrovinyl]-4,5,6,7-tetrahydro[1,3]thiazolo[5,4-c]pyridine-2-carboxamide, N-[2-amino-5-(1-methylethyl)phenyl]-5-{1-[(4-methoxyphenyl)amino]-2-nitroethenyl}-4,5,6,7-tetrahydro[1,3]thiazolo[5,4-c]pyridine-2-carboxamide, N-(2-amino-5-isopropylphenyl)-5-[1-{[4-(dimethylamino)phenyl]amino}-2-nitrovinyl]-4,5,6,7-tetrahydro[1,3]thiazolo[5,4-c]pyridine-2-carboxamide, N-(2-amino-5-isopropylphenyl)-5-{1-[(4-isopropylphenyl)amino]-2-nitrovinyl}-4,5,6,7-tetrahydro[1,3]thiazolo[5,4-c]pyridine-2-carboxamide, N-(2-amino-5-methoxyphenyl)-5-{1-[(4-fluorophenyl)amino]-2-nitrovinyl}-4,5,6,7-tetrahydro[1,3]thiazolo[5,4-c]pyridine-2-carboxamide, N-(2-aminophenyl)-5-[(4-methylphenyl)sulfonyl]-4,5,6,7-tetrahydro[1,3]thiazolo[5,4-c]pyridine-2-carboxamide, N-(2-aminophenyl)-5-(benzylsulfonyl)-4,5,6,7-tetrahydro[1,3]thiazolo[5,4-c]pyridine-2-carboxamide, N-(2-aminophenyl)-5-(biphenyl-4-ylsulfonyl)-4,5,6,7-tetrahydro[1,3]thiazolo[5,4-c]pyridine-2-carboxamide, N-(2-aminophenyl)-5-[(4-methoxyphenyl)sulfonyl]-4,5,6,7-tetrahydro[1,3]thiazolo[5,4-c]pyridine-2-carboxamide, N-(2-aminophenyl)-5-(methylsulfonyl)-4,5,6,7-tetrahydro[1,3]thiazolo[5,4-c]pyridine-2-carboxamide 5-[(4-acetamidophenyl)sulfonyl]-N-(2-aminophenyl)-4,5,6,7-tetrahydro[1,3]thiazolo[5,4-c]pyridine-2-carboxamide, N-(2-aminophenyl)-5-(2-naphthylsulfonyl)-4,5,6,7-tetrahydro[1,3]thiazolo[5,4-c]pyridine-2-carboxamide, N-(2-aminophenyl)-5-(2-thienylsulfonyl)-4,5,6,7-tetrahydro[1,3]thiazolo[5,4-c]pyridine-2-carboxamide, Methyl 3-({2-[(2-aminophenyl)carbamoyl]-6,7-dihydro[1,3]thiazolo[5,4-c]pyridin-5(4H)-yl}sulfonyl)thiophene-2-carboxylate, 5-[(2-acetamido-4-methyl-1,3-thiazol-5-yl)sulfonyl]-N-(2-aminophenyl)-4,5,6,7-tetrahydro[1,3]thiazolo[5,4-c]pyridine-2-carboxamide, N-(2-aminophenyl)-5-[(3-methoxyphenyl)sulfonyl]-4,5,6,7-tetrahydro[1,3]thiazolo[5,4-c]pyridine-2-carboxamide, N-(2-aminophenyl)-5-{[4-(trifluoromethyl)phenyl]sulfonyl}-4,5,6,7-tetrahydro[1,3]thiazolo[5,4-c]pyridine-2-carboxamide, N-(2-aminophenyl)-5-{[3-(trifluoromethyl)phenyl]sulfonyl}-4,5,6,7-tetrahydro[1,3]thiazolo[5,4-c]pyridine-2-carboxamide, N-(2-aminophenyl)-5-[(3-fluorophenyl)sulfonyl]-4,5,6,7-tetrahydro[1,3]thiazolo[5,4-c]pyridine-2-carboxamide, N-(2-aminophenyl)-5-(isopropylsulfonyl)-4,5,6,7-tetrahydro[1,3]thiazolo[5,4-c]pyridine-2-carboxamide, N-(2-aminophenyl)-5-{[3-(difluoromethoxy)phenyl]sulfonyl}-4,5,6,7-tetrahydro[1,3]thiazolo[5,4-c]pyridine-2-carboxamide, N-(2-aminophenyl)-5-{[4-(difluoromethoxy)phenyl]sulfonyl}-4,5,6,7-tetrahydro[1,3]thiazolo[5,4-c]pyridine-2-carboxamide, N-(2-aminophenyl)-5-{[3-(trifluoromethoxy)phenyl]sulfonyl}-4,5,6,7-tetrahydro[1,3]thiazolo[5,4-c]pyridine-2-carboxamide, N-(2-aminophenyl)-5-{[4-(trifluoromethoxy)phenyl]sulfonyl}-4,5,6,7-tetrahydro[1,3]thiazolo[5,4-c]pyridine-2-carboxamide, N-(2-amino-5-methoxyphenyl)-5-[(4-methylphenyl)sulfonyl]-4,5,6,7-tetrahydro[1,3]thiazolo[5,4-c]pyridine-2-carboxamide, N-(2-amino-5-isopropylphenyl)-5-[(4-methylphenyl)sulfonyl]-4,5,6,7-tetrahydro[1,3]thiazolo[5,4-c]pyridine-2-carboxamide, N-(2-amino-5-methoxyphenyl)-5-[(4-methoxyphenyl)sulfonyl]-4,5,6,7-tetrahydro[1,3]thiazolo[5,4-c]pyridine-2-carboxamide, N-(2-aminophenyl)-5-(phenoxyacetyl)-4,5,6,7-tetrahydro[1,3]thiazolo[5,4-c]pyridine-2-carboxamide, N-(2-aminophenyl)-5-[(4-methylphenoxy)acetyl]-4,5,6,7-tetrahydro[1,3]thiazolo[5,4-c]pyridine-2-carboxamide, N-(2-aminophenyl)-5-[(4-methoxyphenoxy)acetyl]-4,5,6,7-tetrahydro[1,3]thiazolo[5,4-c]pyridine-2-carboxamide, N-(2-aminophenyl)-5-[(2-naphthyloxy)acetyl]-4,5,6,7-tetrahydro[1,3]thiazolo[5,4-c]pyridine-2-carboxamide, N-(2-aminophenyl)-5-[(biphenyl-4-yloxy)acetyl]-4,5,6,7-tetrahydro[1,3]thiazolo[5,4-c]pyridine-2-carboxamide, N-(2-aminophenyl)-5-(methoxyacetyl)-4,5,6,7-tetrahydro[1,3]thiazolo[5,4-c]pyridine-2-carboxamide, N-(2-amino-5-isopropylphenyl)-5-[(4-methoxyphenoxy)acetyl]-4,5,6,7-tetrahydro[1,3]thiazolo[5,4-c]pyridine-2-carboxamide, N-(2-aminophenyl)-5-[(3-methoxyphenoxy)acetyl]-4,5,6,7-tetrahydro[1,3]thiazolo[5,4-c]pyridine-2-carboxamide, Methyl 2-[(2-aminophenyl)carbamoyl]-6,7-dihydro[1,3]thiazolo[5,4-c]pyridine-5(4H)carboxylate, Biphenyl-4-yl 2-[(2-aminophenyl)carbamoyl]-6,7-dihydro[1,3]thiazolo[5,4-c]pyridine-5(4H)carboxylate, 4-Methylphenyl 2-[(2-aminophenyl)carbamoyl]-6,7-dihydro[1,3]thiazolo[5,4-c]pyridine-5(4H)-carboxylate, 4-Methoxyphenyl 2-[(2-aminophenyl)carbamoyl]-6,7-dihydro[1,3]thiazolo[5,4-c]pyridine-5(4H)-carboxylate, 4-(Propoxycarbonyl)phenyl 2-[(2-aminophenyl)carbamoyl]-6,7-dihydro[1,3]thiazolo[5,4-c]pyridine-5(4H)-carboxylate, 2-Naphthyl 2-[(2-aminophenyl)carbamoyl]-6,7-dihydro[1,3]thiazolo[5,4-c]pyridine-5(4H)carboxylate, 3,4-Dimethoxyphenyl 2-[(2-aminophenyl)carbamoyl]-6,7-dihydro[1,3]thiazolo[5,4-c]pyridine-5(4H)-carboxylate, Butyl 2-[(2-aminophenyl)carbamoyl]-6,7-dihydro[1,3]thiazolo[5,4-c]pyridine-5(4H)carboxylate, Benzyl 2-[(2-aminophenyl)carbamoyl]-6,7-dihydro[1,3]thiazolo[5,4-c]pyridine-5(4H)carboxylate, Pyridin-3-ylmethyl 2-[(2-aminophenyl)carbamoyl]-6,7-dihydro[1,3]thiazolo[5,4-c]pyridine-5(4H)-carboxylate, N-(2-aminophenyl)-5-[3-(1,3-benzodioxol-5-yl)prop-2-enoyl]-4,5,6,7-tetrahydro[1,3]thiazolo[5,4-c]pyridine-2-carboxamide, N-(2-aminophenyl)-5-[3-(3,4-dihydroxyphenyl)prop-2-enoyl]-4,5,6,7-tetrahydro[1,3]thiazolo[5,4-c]pyridine-2-carboxamide, N-(2-aminophenyl)-5-pyrimidin-2-yl-4,5,6,7-tetrahydro[1,3]thiazolo[5,4-c]pyridine-2-carboxamide, N-(2-aminophenyl)-5-(4-pyridin-3-ylpyrimidin-2-yl)-4,5,6,7-tetrahydro[1,3]thiazolo[5,4-c]pyridine-2-carboxamide, N-(2-aminophenyl)-5-(5-nitropyridin-2-yl)-4,5,6,7-tetrahydro[1,3]thiazolo[5,4-c]pyridine-2-carboxamide, N-(2-aminophenyl)-5-[5-(trifluoromethyl)pyridin-2-yl]-4,5,6,7-tetrahydro[1,3]thiazolo[5,4-c]pyridine-2-carboxamide, N-(2-aminophenyl)-5-(5-{[(4-methylphenyl)sulfonyl]amino}pyrimidin-2-yl)-4,5,6,7-tetrahydro[1,3]thiazolo[5,4-c]pyridine-2-carboxamide, N-(2-aminophenyl)-5-(5-{[(4-methylphenyl)sulfonyl]amino}pyridin-2-yl)-4,5,6,7-tetrahydro[1,3]thiazolo[5,4-c]pyridine-2-carboxamide, N-(2-aminophenyl)-5-{4-[(benzylcarbamoyl)amino]phenyl}-4,5,6,7-tetrahydro[1,3]thiazolo[5,4-c]pyridine-2-carboxamide, N-(2-aminophenyl)-5-(4-{[(4-methylphenyl)sulfonyl]amino}phenyl)-4,5,6,7-tetrahydro[1,3]thiazolo[5,4-c]pyridine-2-carboxamide, N-(2-aminophenyl)-5-[(4-methylphenyl)sulfonyl]-4,5,6,7-tetrahydrothieno[3,2-c]pyridine-2-carboxamide, N-(2-aminophenyl)-5-[(4-methylphenyl)sulfonyl]-4,5,6,7-tetrahydrofuro[3,2-c]pyridine-2-carboxamide, N-(2-aminophenyl)-1-methyl-5-[(4-methylphenyl)sulfonyl]-4,5,6,7-tetrahydro-1H-pyrrolo[3,2-c]pyridine-2-carboxamide, $N^2$-(2-aminophenyl)-N5-pyridin-3-yl-6,7-dihydrothieno[3,2-c]pyridine-2,5(4H)-dicarboxamide, $N^2$-(2-aminophenyl)-N5-pyridin-3-yl-6,7-dihydrothieno[3,2-c]pyridine-2,5(4H)-dicarboxamide, $N^2$-(2-aminophenyl)-N5-(3,4-dimethoxyphenyl)-6,7-dihydrothieno[3,2-c]pyridine-2,5(4H)-dicarboxamide, $N^2$-[2-amino-5-(2-thienyl)phenyl]-N5-butyl-6,7-dihydrothieno[3,2-c]pyridine-2,5(4H)-dicarboxamide, $N^2$-[2-amino-5-(2-thienyl)phenyl]-N5-pyridin-3-yl-6,7-dihydrothieno[3,2-c]pyridine-2,5(4H)-dicarboxamide, $N^2$-(2-amino-5-thiophen-2-ylphenyl)-N5-(4-methoxyphenyl)-6,7-dihydrothieno[3,2-c]pyridine-2,5(4H)-dicarboxamide, or salts of these compounds.

Suitable salts for compounds of formula I according to this invention are acid addition salts or salts with bases. Particular mention may be made of the pharmacologically tolerable inorganic and organic acids and bases customarily used in pharmacy. Those suitable are, on the one hand, water-insoluble and, particularly, water-soluble acid addition salts with acids such as, for example, hydrochloric acid, hydrobromic acid, phosphoric acid, nitric acid, sulphuric acid, acetic acid, citric acid, D-gluconic acid, benzoic acid, 2-(4-hydroxybenzoyl)benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid or 3-hydroxy-2-naphthoic acid, the acids being employed in salt preparation—depending on whether a mono- or polybasic acid is concerned and depending on which salt is desired—in an equimolar quantitative ratio or one differing therefrom.

On the other hand, salts with bases are—depending on substitution—also suitable. As examples of salts with bases are mentioned the lithium, sodium, potassium, calcium, aluminium, magnesium, titanium, ammonium, meglumine or guanidinium salts, here, too, the bases being employed in salt preparation in an equimolar quantitative ratio or one differing therefrom.

Pharmacologically intolerable salts, which can be obtained, for example, as process products during the preparation of the compounds of formula I according to this invention on an industrial scale, are converted into pharmacologically tolerable salts by processes known to the person skilled in the art.

According to expert's knowledge the compounds of formula I according to this invention as well as their salts may contain, e.g. when isolated in crystalline form, varying amounts of solvents. Included within the scope of the invention are therefore all solvates and in particular all hydrates of the compounds of formula I according to this invention as well as all solvates and in particular all hydrates of the salts of the compounds of formula I according to this invention.

Some of the compounds and salts according to the invention may exist in different crystalline forms (polymorphs), which are within the scope of the invention.

It is to be understood, that the present invention also includes any or all possible combinations and subsets of the embodiments defined above.

Exemplary compounds according to the present invention may include, without being restricted thereto, any compounds of formula I selected from the group consisting of those compounds of formula I disclosed in the following examples as final compounds, as well as the salts thereof.

The compounds according to the invention can be prepared, for example, as described as follows and according to the following specified reaction steps, or, particularly, in a manner as described by way of example in the following examples.

As shown in reaction scheme Ia, compounds of formula I wherein L is —(CH$_2$)$_n$N(R10)C(=O)—, R10 is H and all other symbols have the meanings as defined above can be obtained by reacting in a first step ethyl thioxamate of formula 4 with tert-butyl 3-bromo-4-oxopiperidine-1-carboxylate of formula 3 to yield 5-tert-butyl 2-ethyl 6,7-dihydro[1,3]thiazolo[5,4-c]pyridine-2,5(4H)-dicarboxylate of formula 5 which is then hydrolysed in the presence of lithium hydroxide to provide the corresponding lithium salt of formula 6. The lithium salt of formula 6 is reacted with an ortho phenylene diamine derivative of formula 7 (or alternatively a boc protected ortho phenylene diamine derivative of formula 7), wherein B has the meanings as defined above in the presence of dicyclohexyl carbodiimide and HOBt to provide the compound of formula 8 which is then deprotected to provide the corresponding compound of formula 2. The compound of formula 2 is finally reacted with an appropriate isocyanate of formula A—(CH$_2$)$_n$N=C=O wherein A and n have the meanings as defined above to provide a compound of formula I wherein L is —(CH$_2$)$_n$N(R10)C(=O)—, R10 is H and all other symbols are as defined above.

Scheme Ia

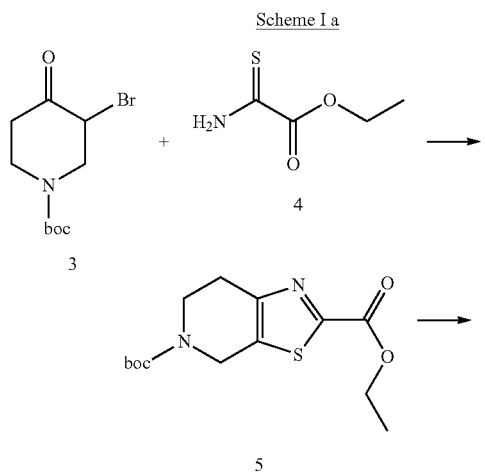

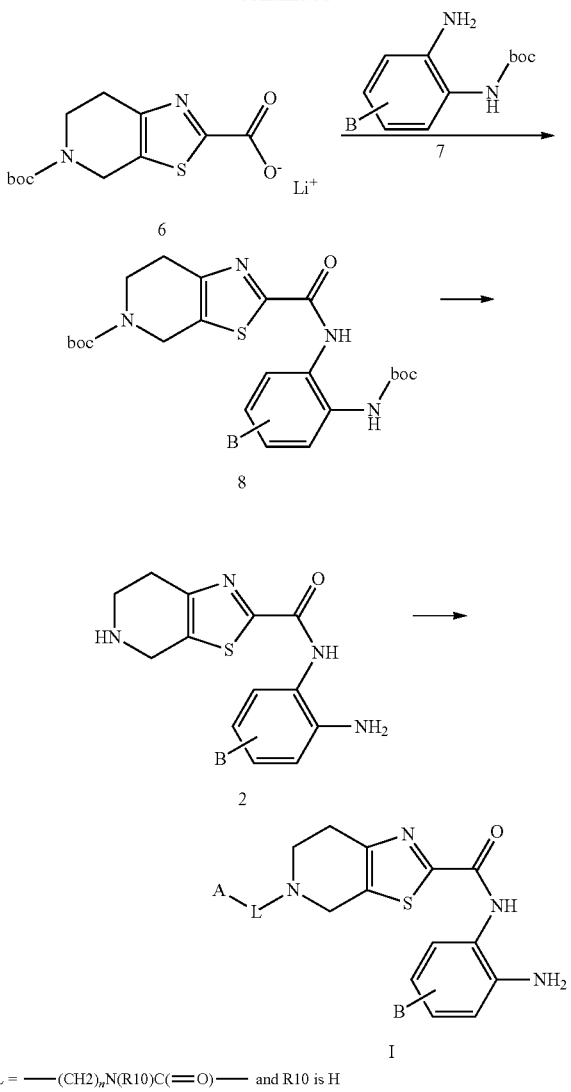

L = ——(CH2)$_n$N(R10)C(=O)—— and R10 is H

Alternatively, as shown in reaction scheme Ib, compounds of formula I wherein L is —(CH$_2$)$_n$N(R10)C(=O)— and all other symbols have the meanings as defined above can be obtained by reacting 1,1'-carbonyldiimidazole with a suitable amine of formula A—(CH$_2$)$_n$—NH(R10) wherein A, R10 and n is as defined above to obtain the corresponding imidazolylcarbonyl amide of formula 9. The compound of formula 9 is reacted with a compound of formula 2 in the presence of a catalytic amount of 4-dimethylamino pyridine to provide the compound of formula I, wherein L is —(CH$_2$)$_n$N(R10)C (=O)— and all other symbols have the meanings as defined above.

Scheme Ib

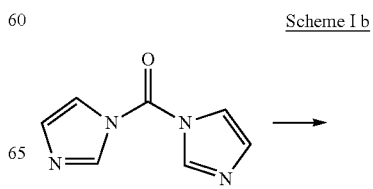

-continued

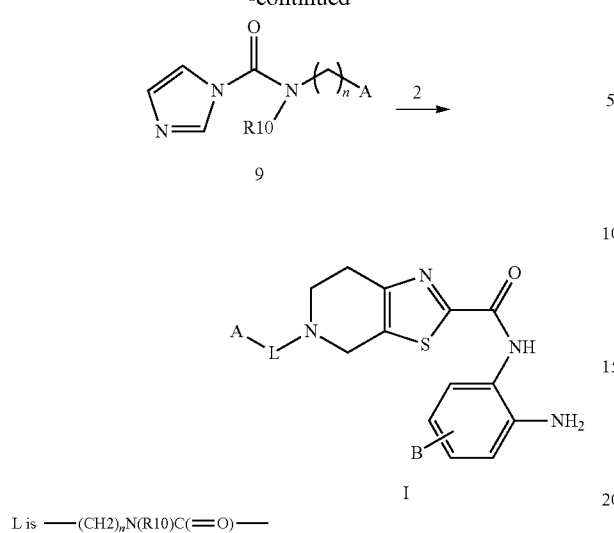

L is —(CH2)$_n$N(R10)C(=O)—

Alternatively, as shown in reaction scheme Ic, compounds of formula I wherein L is —(CH$_2$)$_n$N(R10)C(=O)—, R10 is H and all other symbols have the meanings as defined above can be obtained by reacting a suitable amine of formula A—(CH$_2$)$_n$—NH(R10) wherein A and n are as defined above and R10 is H, with triphosgene under basic conditions followed by reaction with compound of formula 2 to provide the compound of formula I.

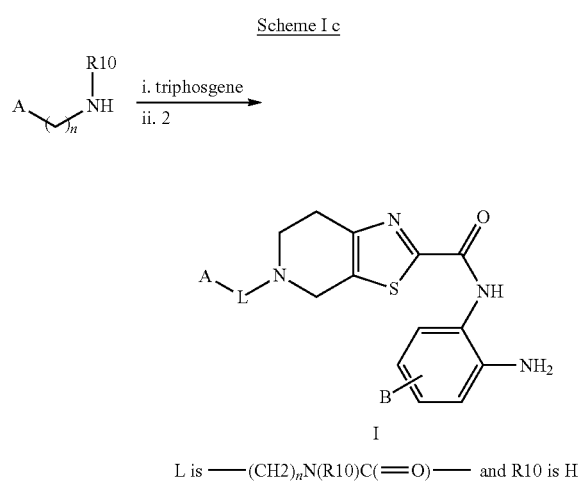

L is —(CH2)$_n$N(R10)C(=O)— and R10 is H

Alternatively, as shown in reaction scheme Id, compounds of formula I wherein L is —(CH$_2$)$_n$N(R10)C(=O)— and all other symbols have the meanings as defined above can be obtained by reacting a suitable amine of formula A—(CH$_2$)$_n$—NH(R10) wherein A, n and R10 have the meanings as defined above with phenylchloroformate or p-nitrophenyl-chloroformate (R=H or NO$_2$) to provide the corresponding phenyl or p-nitrophenyl carbonate of the amine having formula 11. The compound of formula 11 is then reacted with a compound of formula 2 under microwave conditions or alternatively at 60-100° C. in the presence of a solvent (DMF/DME/DMSO or a mixture thereof in any proportion) to provide the compound of formula I.

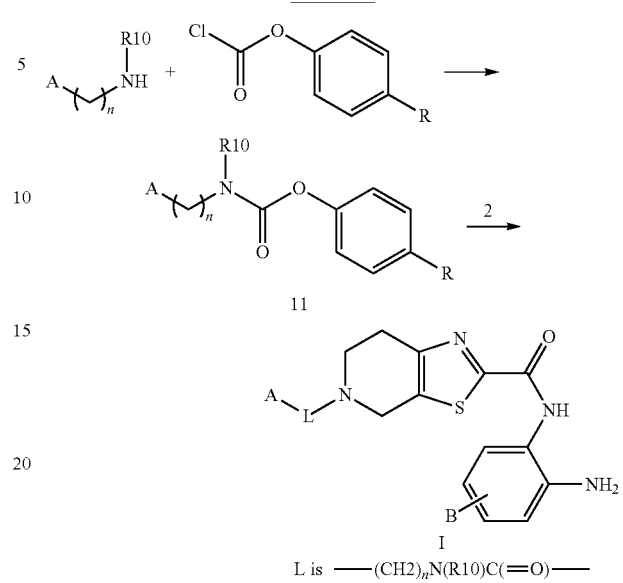

L is —(CH2)$_n$N(R10)C(=O)—

Alternatively, as shown in reaction scheme Ie, compounds of formula I wherein L is —(CH$_2$)$_n$N(R10)C(=O)— and all other symbols have the meanings as defined above can be obtained by reacting a suitable amine of formula A—(CH$_2$)$_n$—NH(R10) wherein A, n and R10 have the meanings as defined above with phenyl chloroformate to provide the compound of formula 12 which is then reacted with ethyl 4,5,6,7-tetrahydro[1,3]thiazolo[5,4-c]pyridine-2-carboxylate hydrochloride (compound of formula 13) to provide the compound of formula 14. The ester function of the compound of formula 14 is hydrolysed to afford the acid of formula 15 which is reacted with a ortho phenylene diamine derivative of formula 7 (or alternatively a mono boc protected orthophenylene derivative of formula 7), wherein B has the meanings as defined above to yield the compound of formula I.

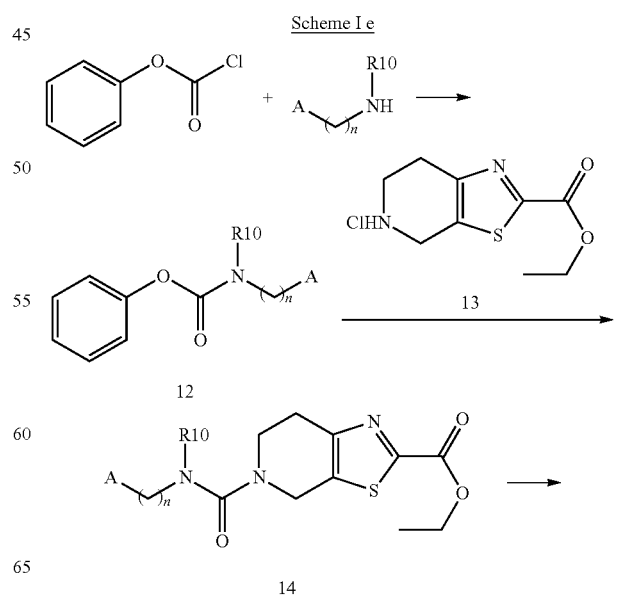

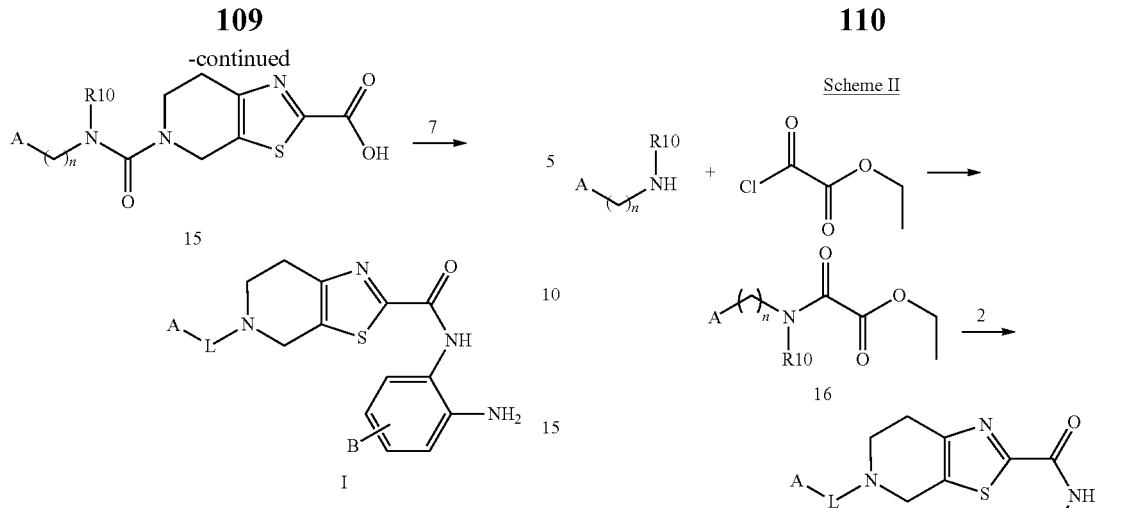

Alternatively, as shown in reaction scheme I f, compounds of formula I wherein L is —(CH$_2$)$_n$N(R10)C(=O)— and all other symbols have the meanings as defined above can be obtained by reacting compound of formula 12 as obtained in Scheme 1 e and compound of formula 2 in the presence of a base to yield the compound of formula I.

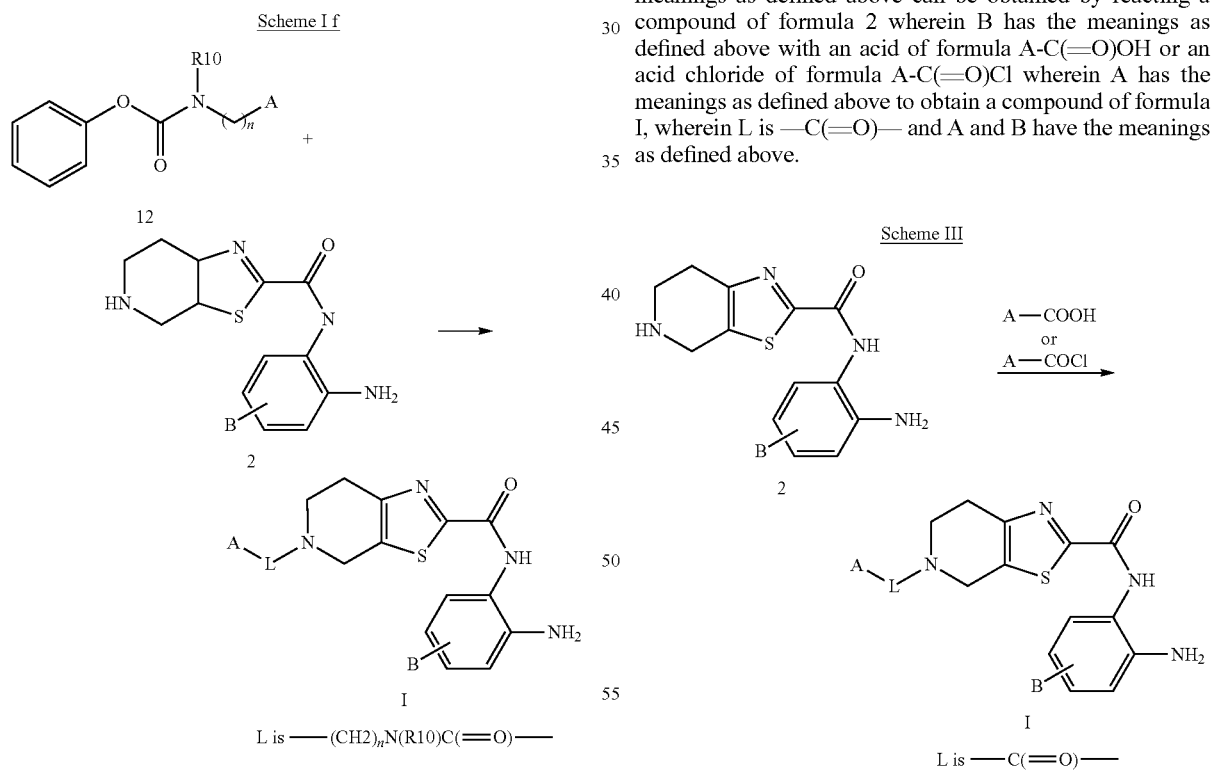

As shown in reaction scheme II, compounds of formula I wherein L is —(CH$_2$)$_n$N(R10)C(=O)C(=O)— and all other symbols have the meanings as defined above can be obtained by reacting an amine of formula A—(CH$_2$)$_n$—N(R10)H wherein n, R10 and A have the meanings as defined above with ethyl chlorooxalate to obtain the corresponding compound of formula 16 which on its part is reacted with a compound of formula 2 to obtain the compound of formula I.

As shown in reaction scheme III, compounds of formula I wherein L is —C(=O)— and all other symbols have the meanings as defined above can be obtained by reacting a compound of formula 2 wherein B has the meanings as defined above with an acid of formula A-C(=O)OH or an acid chloride of formula A-C(=O)Cl wherein A has the meanings as defined above to obtain a compound of formula I, wherein L is —C(=O)— and A and B have the meanings as defined above.

As shown in reaction scheme IV, compounds of formula I wherein L is —N(R10)C(=S)—, R10 is H and all other symbols have the meanings as defined above can be obtained by reacting a compound of formula 2 with a suitable isothiocyanate of formula A-N=C=S wherein A has the meanings as defined above to obtain the desired compound of formula I, wherein L is —N(R10)C(=S)—, R10 is H and A and B have the meanings as defined above.

Scheme IV

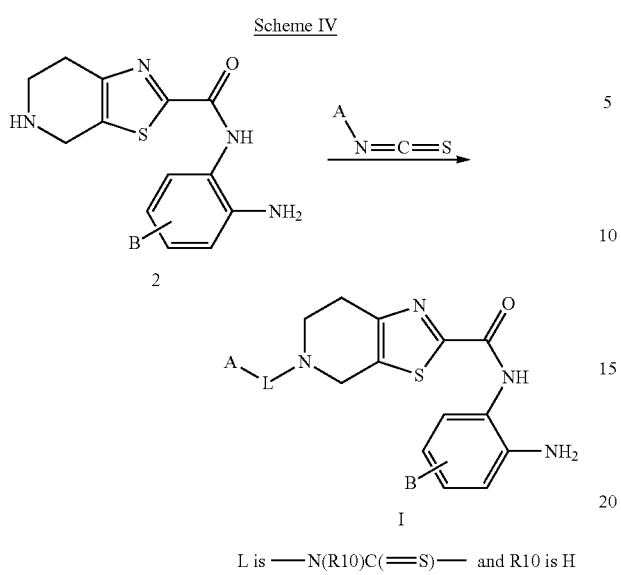

L is —N(R10)C(=S)— and R10 is H

As shown in scheme Va, compounds of formula I wherein L is —(CH₂)ₙN(R10)C(=NR11)-, R11 is hydrogen and all other symbols have the meanings as defined above can be obtained by reacting cyanobromide with an appropriate amine of formula A—(CH₂)ₙ—N(R10)H wherein n, R10 and A have the meanings as defined above to afford the cyanamide of formula 17 which on its part is then reacted with a compound of formula 2 to afford the desired compound of formula I.

Scheme Va

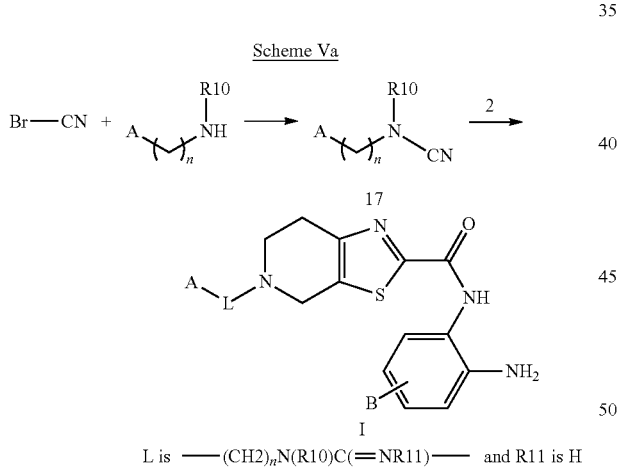

L is —(CH2)ₙN(R10)C(=NR11)— and R11 is H

As shown in scheme Vb, compounds of formula I wherein L is —(CH₂)ₙN(R10)C(=NR11)-, R10 is H, R11 is cyano and all other symbols have the meanings as defined above can be obtained by deprotecting 5-tert-butyl 2-ethyl 6,7-dihydro [1,3]thiazolo[5,4-c]pyridine-2,5(4H)-dicarboxylate (compound of formula 5) to obtain the compound of formula 18 which is reacted with an appropriate isothiocyanate of formula A—(CH₂)ₙ—N=C=S, wherein A and n have the meanings as defined above to afford the thioamide of formula 19 which is reacted with iodomethane to provide compound of formula 20. The compound of formula 20 is hydrolysed to yield the compound of formula 21. Compound of formula 21 is reacted with a mono boc protected ortho phenylene diamine of formula 7 to obtain compound of formula 22, which is reacted with cyanamide to yield the desired compound of formula I.

Scheme V b

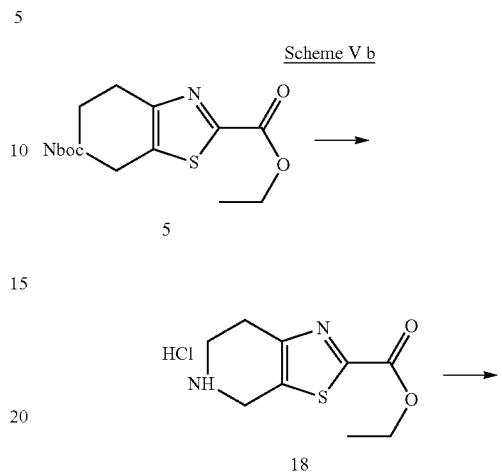

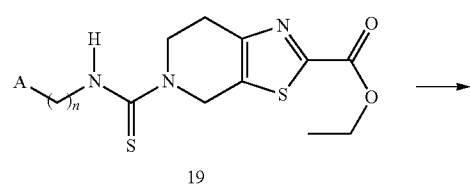

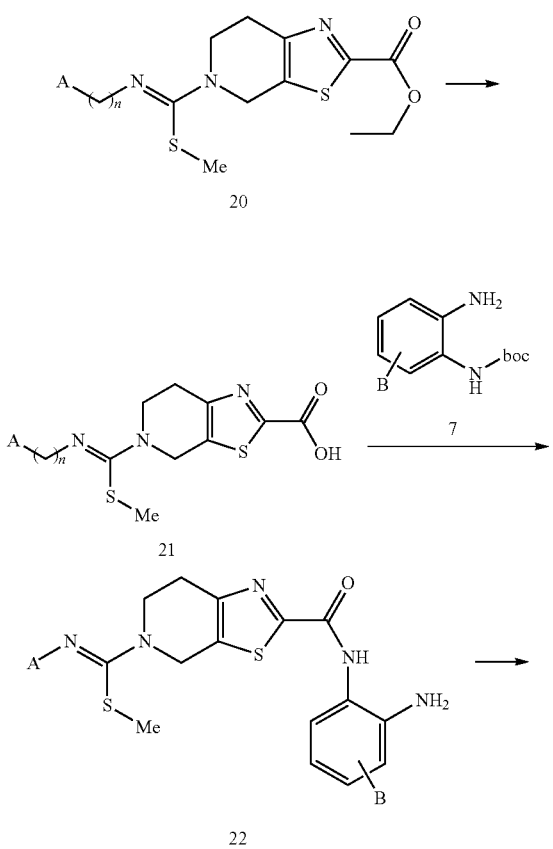

113

-continued

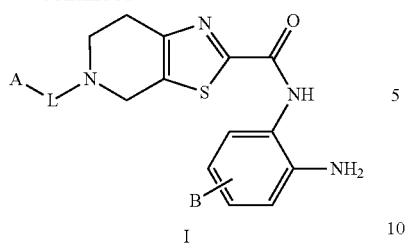

I

L is —(CH2)$_n$N(R10)C(=NR11)— and
R10=H, R11=CN

As shown in scheme Vc, compounds of formula I wherein L is —(CH$_2$)$_n$N(R10)C(=NR11)-, R10 is H, R11 is (C$_1$-C$_4$) alkyl and all other symbols have the meanings as defined above can be obtained by reacting a compound of formula 21 with mono boc protected ortho phenylene diamine of formula 7 to afford compound of formula 23. Compound of formula 23 is reacted with an alkyl amine hydrochloride to provide compound of formula 24 which is then deprotected to obtain the desired compound of formula I.

Scheme V c

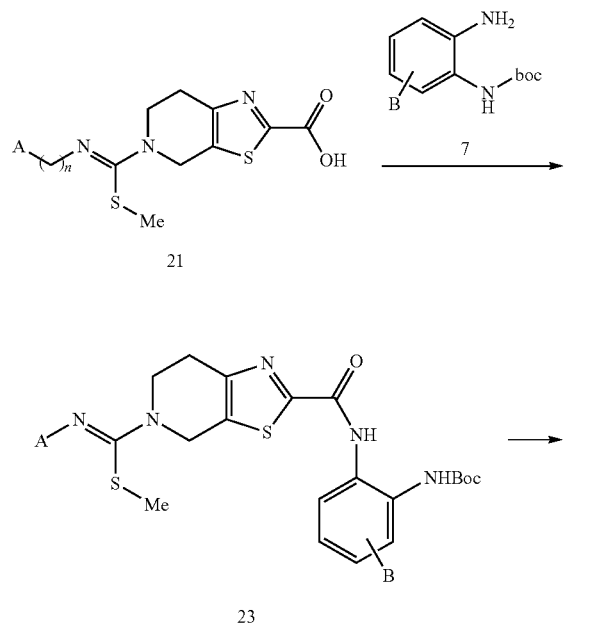

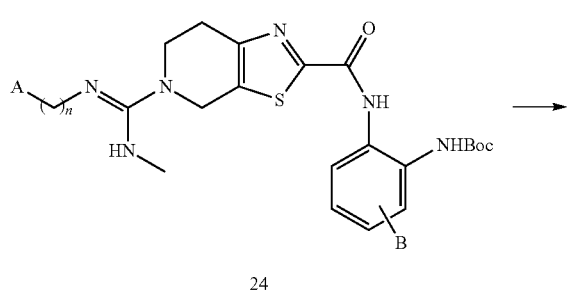

114

-continued

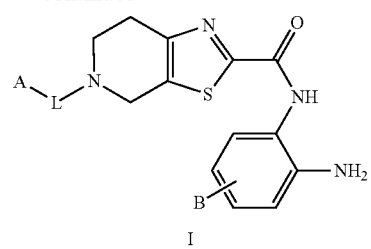

I

L is —(CH2)$_n$N(R10)C(=NR11)—
and R10=H, R11=1-4C-alkyl

As shown in scheme VIa, compounds of formula I wherein L is —(CH$_2$)$_n$N=C(R11)-, R11 is (C$_1$-C$_4$)alkyl and all other symbols have the meanings as defined above can be obtained by boc deprotection of compound of formula 5 to obtain compound of formula 25 which is acylated using acetic anhydride to obtain the acetyl compound of formula 26. Compound of formula 26 is then reacted with a suitable amine of formula A—(CH$_2$)$_n$—NH$_2$, wherein A and n have the meanings as defined above to obtain the compound of formula 27, which is then hydrolysed to obtain the compound of formula 28. The compound of formula 28 is finally reacted with mono boc protected ortho phenylene diamine of formula 7 to yield the desired compound of formula I.

Scheme VI a

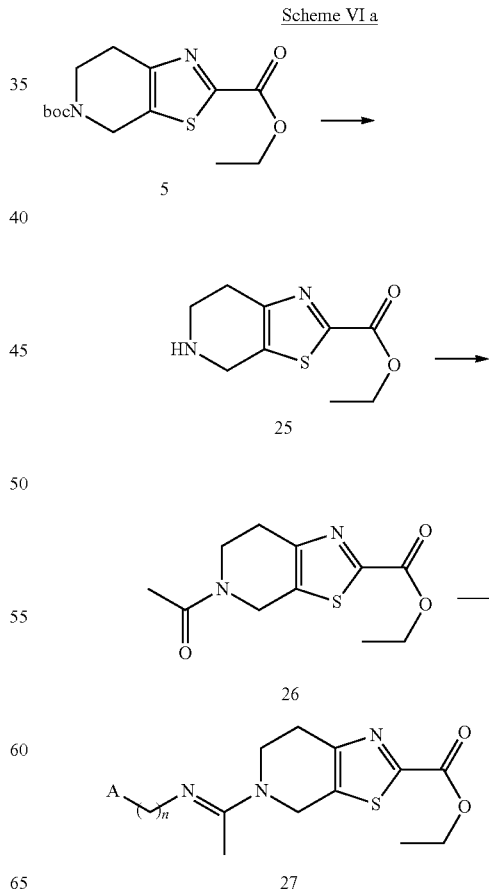

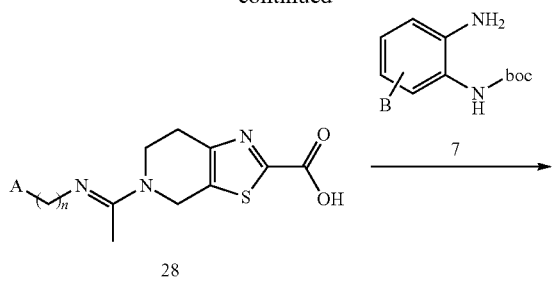

As shown in reaction scheme VII, compounds of formula I wherein L is —(CH$_2$)$_n$S(O)$_2$— and all other symbols have the meanings as defined above can be obtained by reacting a compound of formula 2 with a suitable sulfonyl chloride of formula A—(CH$_2$)$_n$—S(O)$_2$Cl, wherein A and n have the meanings as defined above to obtain the desired compound of formula I.

Scheme VII

L is —(CH2)$_n$S(O)$_2$—

As shown in reaction scheme VIII a, compounds of formula I wherein L is —OCH$_2$C(=O)— and all other symbols have the meanings as defined above can be obtained by reacting a compound of formula 2 with a suitable oxy acetic acid of formula A-O—CH$_2$—C(=O)OH wherein A has the meanings as defined above to obtain the desired compound of formula I.

Alternatively, as shown in scheme VIb, compounds of formula I wherein L is (CH$_2$)$_n$N(R10)C(=CR11), R11 is nitro and all other symbols have the meanings as defined above can be obtained by reacting a compound of formula 2 with trichloro nitro ethane to obtain a compound of formula 29 which is reacted with a suitable amine of formula A—(CH$_2$)$_n$—N(R10)H wherein A, n and R10 have the meanings as defined above to yield the desired compound of formula I.

Scheme VI b

Scheme VIII a

L is —O—CH$_2$C(=O)—

As shown in reaction scheme VIII b, compounds of formula I wherein L is —OCH$_2$C(=O)— and all other symbols have the meanings as defined above can be obtained by reacting a compound of formula 2 with a suitable oxy acetyl chloride of formula A-O—CH$_2$—C(=O)Cl, wherein A has the meanings as defined above to obtain the desired compound of formula I.

L is —(CH2)$_n$N(R10)C(=CR11)— and R11=NO$_2$

Scheme VIII b

117

-continued

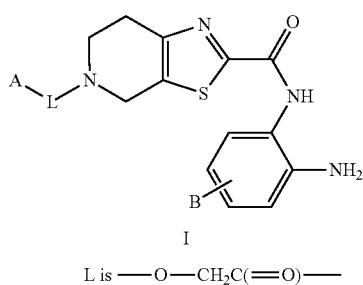

I

L is —O—CH$_2$C(=O)—

As shown in reaction scheme IX a, compounds of formula I wherein L is —(CH$_2$)$_n$OC(=O)— and all other symbols have the meanings as defined above can be obtained by reacting a compound of formula 2 with a mixture of 1,1'-carbonyldiimidazole and a suitable alcohol of formula A-(CH$_2$)$_n$—OH, wherein A and n have the meanings as defined above.

Scheme IX a

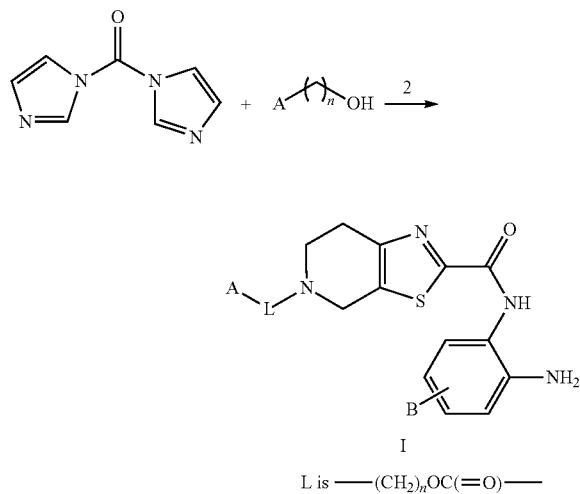

L is —(CH$_2$)$_n$OC(=O)—

Alternatively, as shown in reaction scheme IX b, compounds of formula I wherein L is —(CH$_2$)$_n$OC(=O)—, A is alkyl and all other symbols have the meanings as defined above can be obtained by reacting a compound of formula 2 with a suitable alkyl chloroformate of formula A—(CH$_2$)$_n$—OC(=O)Cl, wherein A is alkyl and n has the meanings as defined above.

Scheme IX b

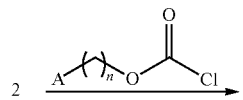

118

-continued

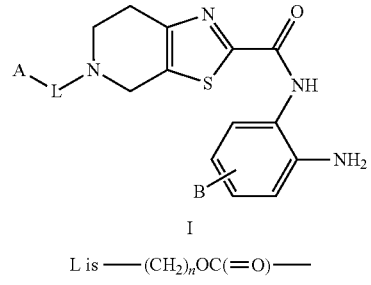

I

L is —(CH$_2$)$_n$OC(=O)— and A is alkyl

As shown in reaction scheme X, compounds of formula I wherein L is —C=C—C(=O)— and all other symbols have the meanings as defined above can be obtained by reacting a compound of formula 2 with an acrylic acid of formula A-CH=CH—C(O)OH wherein A has the meanings as defined above to yield the desired compound of formula I.

Scheme X

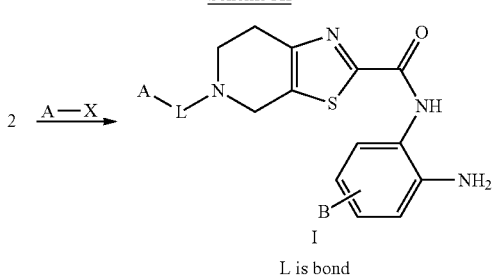

L is —C=C—C(=O)—

As shown in reaction scheme XI, compounds of formula I wherein L is a bond and all other symbols have the meanings as defined above can be obtained by reacting a compound of formula 2 with a compound of formula A-X, wherein A has the meanings as defined above and X is a suitable leaving group, such as for example a halogen atom, preferably a chlorine atom to yield the desired compound of formula I.

Scheme XI

L is bond

As shown in reaction scheme XII, compounds of formula I wherein L is —(CH$_2$)$_n$S(O)$_2$— and all other symbols have the meanings as defined above can be obtained by reacting piperidon hydrochloride with an appropriate sulfonyl chloride of formula A—(CH$_2$)$_n$—S(O)$_2$Cl wherein A and n have the meanings as defined above to obtain a compound of formula 30 which is then converted to the aldehyde of formula 31 under Vilsmeier Hack conditions. The compound of formula 31 is then reacted with ethyl thioglycolate to afford the compound of formula 32, which is then hydrolysed to obtain the compound of formula 33. The compound of formula 33 is reacted with the mono boc protected ortho phenylene diamine of formula 7 to yield the desired compound of formula I.

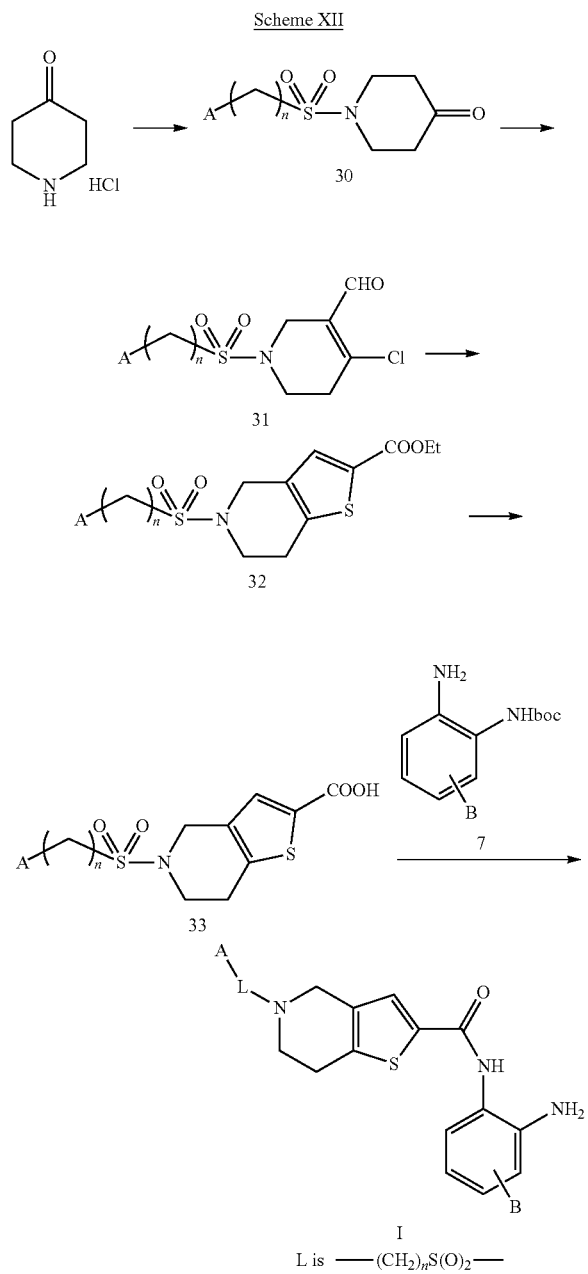

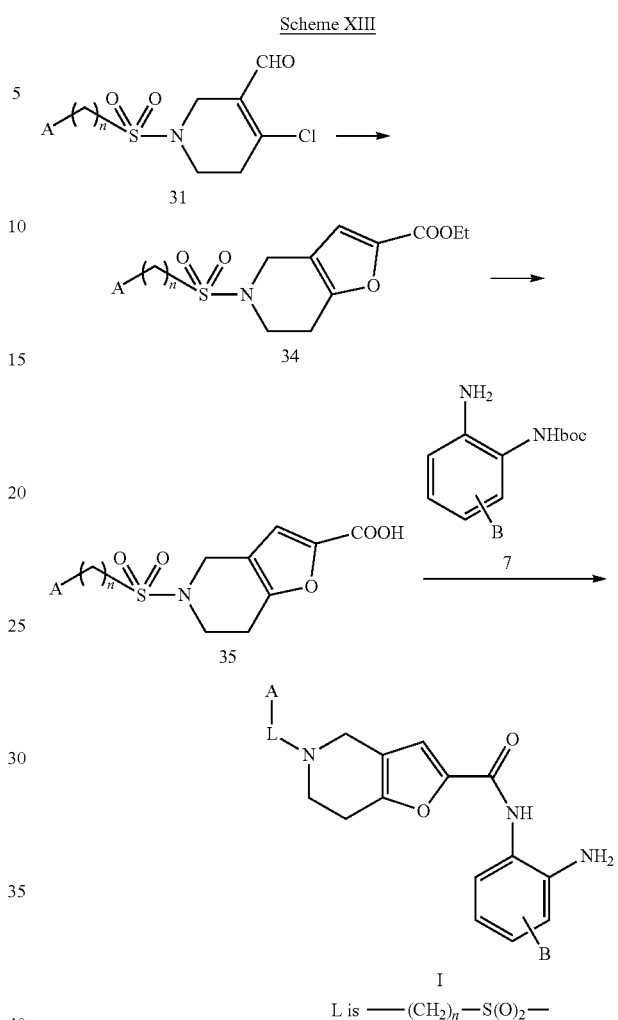

As shown in reaction scheme XIII, compounds of formula I wherein L is —(CH$_2$)$_n$S(O)$_2$— and all other symbols have the meanings as defined above can be obtained by reacting the aldehyde of formula 31 with ethyl glycolate to afford the compound of formula 34 which is hydrolysed to obtain the compound of formula 35. The compound of formula 35 is reacted with mono boc protected ortho phenylene diamine of formula 7 to yield the desired compound of formula I.

As shown in reaction scheme XIV, compounds of formula I wherein L is —(CH$_2$)$_n$S(O)$_2$— and all other symbols have the meanings as defined above can be obtained by reacting the aldehyde of formula 31 with sarcosine hydrochloride to afford the compound of formula 36 which is hydrolysed to yield the compound of formula 37. The compound of formula 37 is reacted with mono boc protected ortho phenylene diamine of formula 7 to yield the desired compound of formula I.

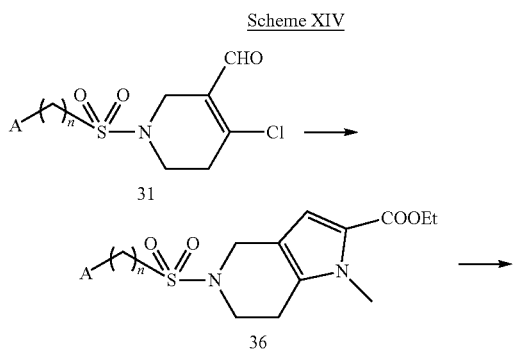

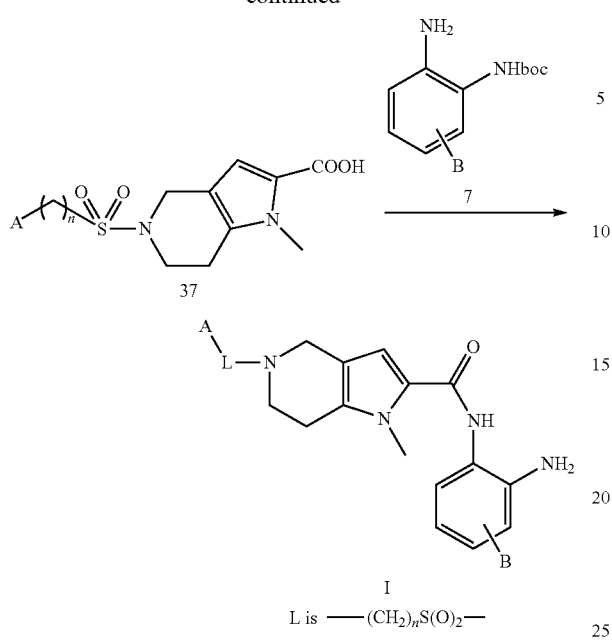
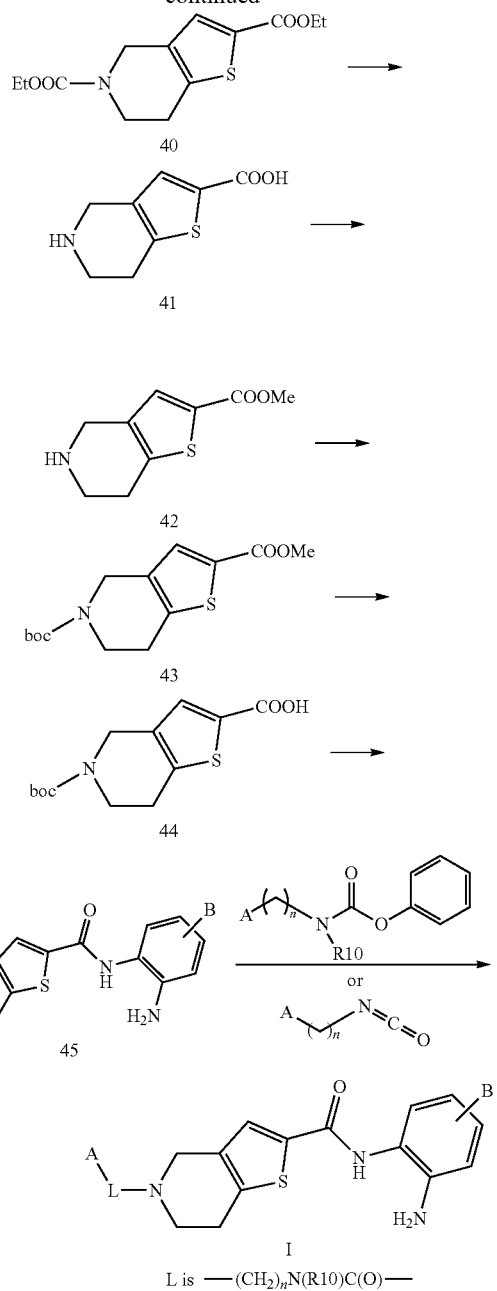

As shown in reaction scheme XV, compounds of formula I wherein L is —(CH$_2$)$_n$N(R10)C(=O)—, R10 is hydrogen and all other symbols have the meanings as defined above can be obtained by converting piperidon hydrochloride to its carbamate derivative of formula 38, which on its part is formylated under Vilsmeier Hack conditions to yield the chloro aldehyde of formula 39. The chloro aldehyde of formula 39 is reacted with ethyl thioglycolate to afford the compound of formula 40 which is hydrolysed to obtain compound of formula 41 which then is esterified to obtain the tetrahydro thieno pyridine of formula 42. The amino function of the compound of formula 42 is then boc protected to afford the compound of formula 43 and the ester function is hydrolysed to yield the compound of formula 44 The compound of formula 44 is then reacted with mono boc protected ortho phenylene diamine of formula 7 to obtain the diamine of formula 45. The compound of formula 45 is then finally reacted with a compound of formula A—(CH$_2$)$_n$N(R10)C(=O)OPh or alternatively a compound of formula A—(CH$_2$)$_n$—N=C=O to yield the desired compound of formula I.

Scheme XV

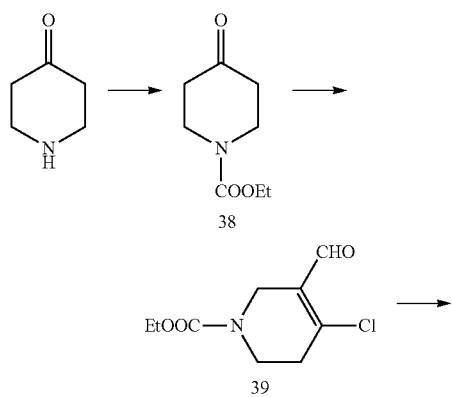

As shown in reaction scheme XVI, compounds of formula I wherein L is —(CH$_2$)$_n$NR10C(O)—, R10 is hydrogen and all other symbols are as defined above can be obtained by converting thiopene 3-carbaldehyde to its α-β unsaturated nitro derivative which is hydrogenated followed by cyclisation to yield the boc protected tetrahydro thienopyridine compound of formula 46. The cyclised compound of formula 47 is reacted with ethyl chloro formate and butyl lithium to afford the compound of formula 48 which is further hydrolysed to obtain compound of formula 49. The compound of formula 49 is then reacted with mono boc protected ortho phenylene diamine 7 to obtain the diamine of formula III. The compound of formula III is then reacted with A—(CH$_2$)$_n$NR10C(=O)OPh to yield the desired compound of formula I.

Scheme XVI

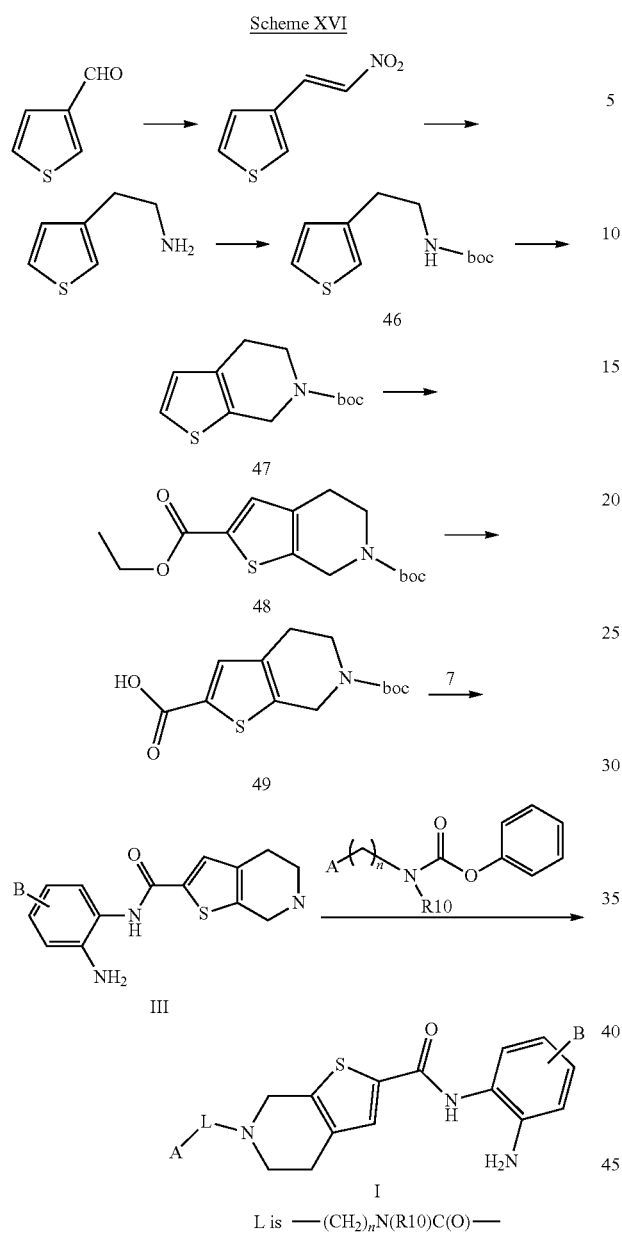

Scheme-XVII

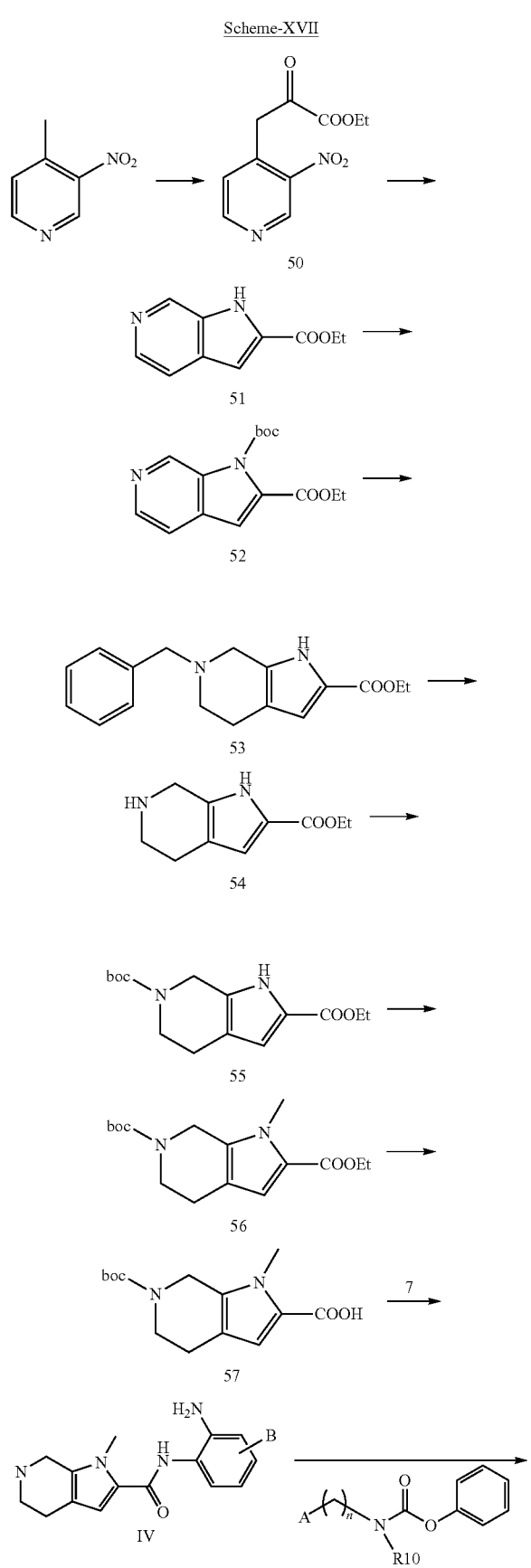

As shown in reaction scheme XVII, compounds of formula I wherein L is —(CH$_2$)$_n$NR10C(O)—, R10 is hydrogen and all other symbols are as defined above can be obtained by converting 4-methyl-3-nitro pyridine to its keto ester of formula 50 which on catalytic hydrogenation gave compound of formula 51. Compound of formula 51 is boc protected to obtain compound of formula 52 followed by reduction in the presence of benzyl bromide to yield the compound of formula 53. Compound of formula 53 is further debenzylate and again protected with boc anhydride to yield the compound of formula 55. Compound of formula 55 is treated with methyl iodide to get its N-methyl derivative 56, which on hydrolysis provided compound of formula 57. The compound of formula 57 is then reacted with mono boc protected ortho phenylene diamine 7 to obtain the diamine of formula IV. The compound of formula IV is then reacted with A—(CH$_2$)$_n$NR10C(=O)OPh to yield the desired compound of formula I.

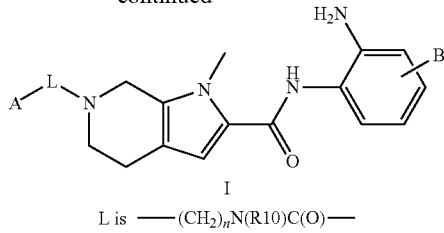

L is ——(CH₂)ₙN(R10)C(O)——

I

As shown in reaction scheme XVIII, compounds of formula I wherein L is —N(R10)CH₂C(=O)—, R10 is H and all other symbols have the meanings as defined above can be obtained by reacting A-NH₂, wherein A is as defined above with bromoacetyl bromide to afford a compound of formula 58 which is then hydrolysed to get respective acid of formula 59. Acid of formula 59 is then reacted with compound 2 to get the desired compound of formula I, wherein L is —N(R10) CH₂C(=O)—, R10 is H and A and B have the meanings as defined above.

Scheme-XVIII

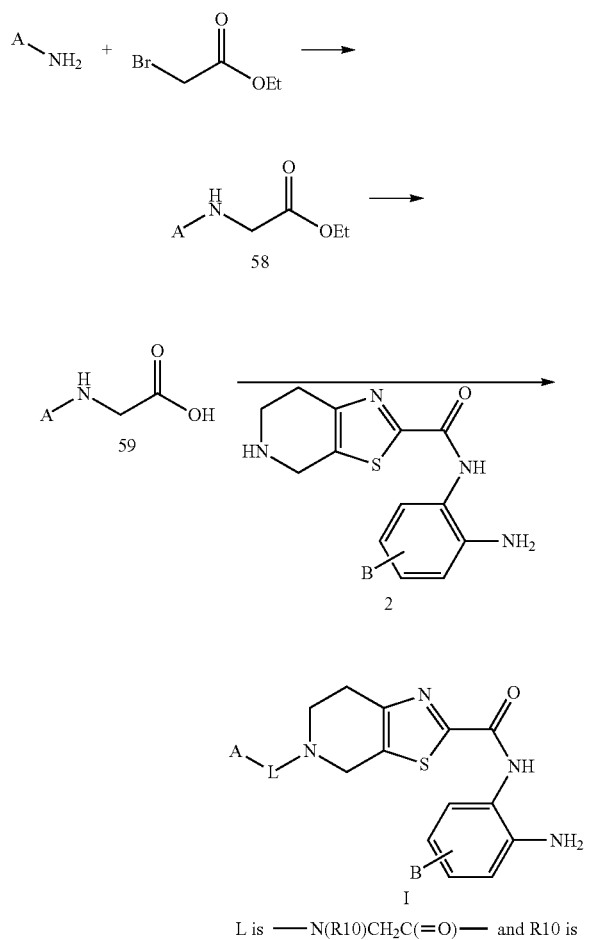

L is ——N(R10)CH₂C(=O)—— and R10 is

As shown in reaction scheme XIX, compounds of formula I wherein L is —(CH₂)ₙNR10C(O)—, R10 is hydrogen and all other symbols are as defined above can be obtained by reacting N-boc piperidone with bromo ethyl pyruvate in presence of base to affors compound of formula 60 which is then alkylated using methyl iodide to yield N-methylated compound of formula 61. Ester of formula 61 is hydrolysed to get corresponding acid 62, which is then reacted, with mono boc protected ortho phenylene diamine 7 to obtain the boc protected diamine of formula 63. Compound of formula 63 is deprotected to get free amine of formula 64. The compound of formula 64 is then reacted with A—(CH₂)ₙNR10C(=O)OPh to yield the desired compound of formula I.

Scheme-XIX

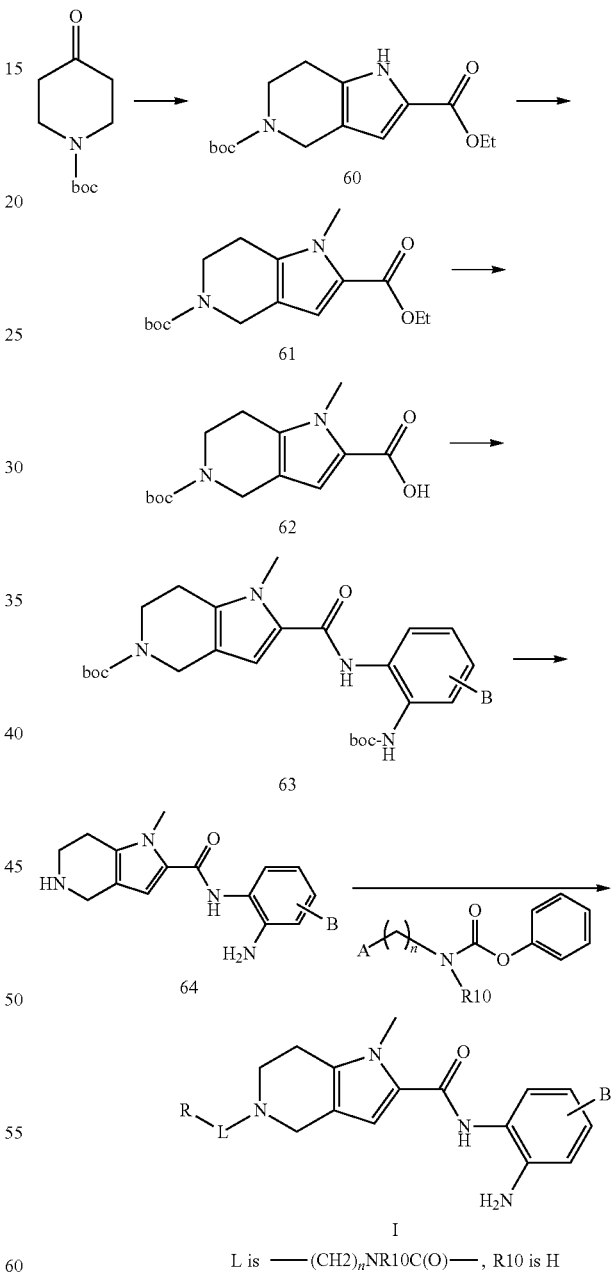

L is ——(CH2)ₙNR10C(O)——, R10 is H

As shown in reaction scheme XX, compounds of formula I wherein L is —O(CH₂)—C(O)— and all other symbols are as defined above can be obtained by reacting compound of formula 64 as shown in scheme-XIX with A—O(CH₂)—C (=O)OPh-NO2 to afford desired compound of formula I.

Scheme-XX

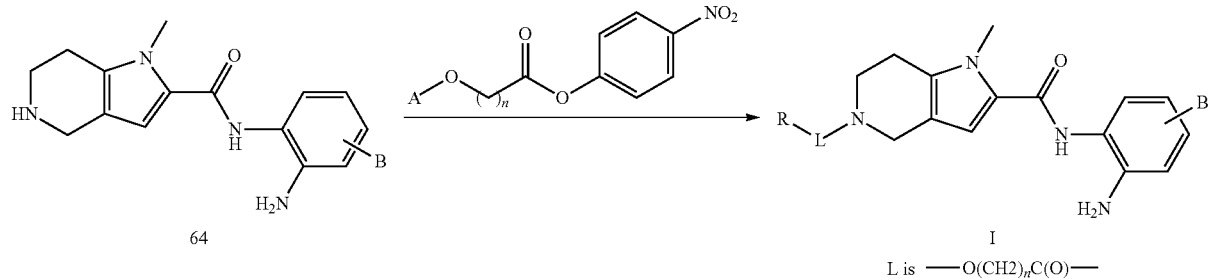

As shown in reaction scheme XXI, compounds of formula I wherein L is —O(CH₂)—C(O)— and all other symbols are as defined above can be obtained by reacting compound of formula 45 as shown in scheme-XV with A—O(CH₂)ₙC(=O)OPh-NO2 to afford desired compound of formula I.

Scheme-XXI

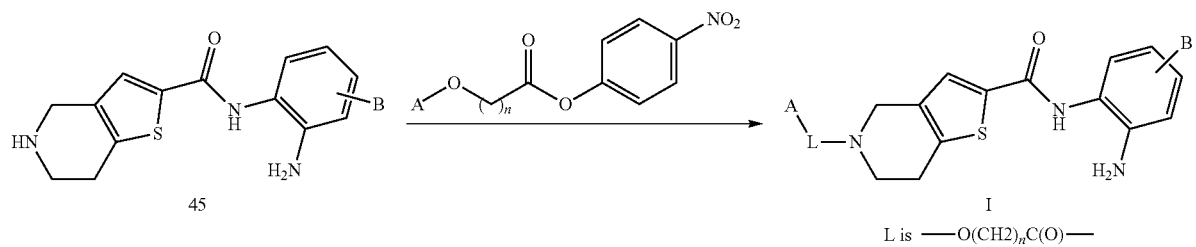

As shown in scheme XXII, compound of formula I wherein L is —O(CH₂)ₙC(O)— and all other symbols are as defined above can be obtained by reacting compound of formula IV obtained in scheme-XVII with A—O(CH₂)ₙC(=O)OPh-NO2 to afford desired compound of formula I.

Scheme-XXII

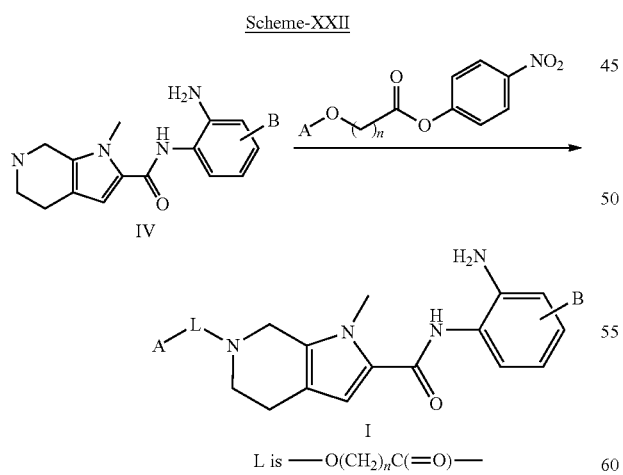

As shown in scheme XXIII, compound of formula I wherein L is —O(CH₂)ₙC(O)— and all other symbols are as defined above can be obtained by reacting compound of formula III obtained in scheme-XVI with A—O(CH₂)ₙC(=O)OPh-NO2 to afford desired compound of formula I.

Scheme-XXIII

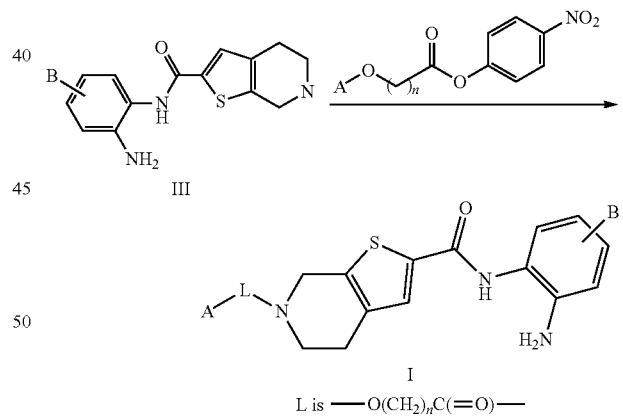

As shown in reaction scheme XXIV, compounds of formula I wherein L is —(CH₂)ₙNR10C(O)—, R10 is hydrogen and all other symbols are as defined above can be obtained by hydrolyzing compound of formula 60 obtained in reaction scheme XIX in presence of aqueous sodium hydroxide in ethanol to yield compound of formula 65. Compound of formula 65 which is then reacted, with mono boc protected ortho phenylene diamine 7 to obtain the boc protected diamine of formula 66. Compound of formula 66 is deprotected to get free amine of formula 67. The compound of formula 67 is then reacted with A-(CH₂)ₙNR10C(=O)OPh to yield the desired compound of formula I.

Scheme XXIV

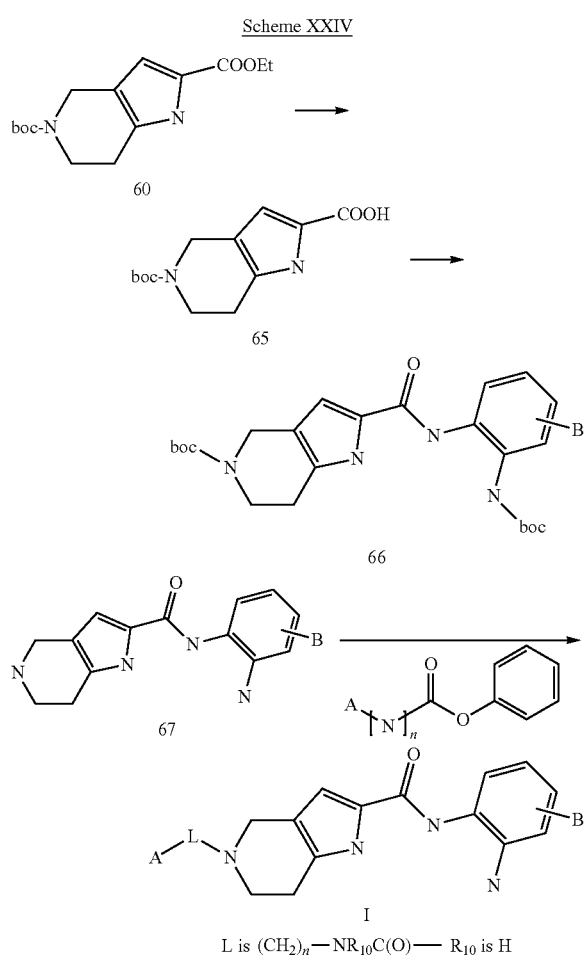

L is $(CH_2)_n$—$NR_{10}C(O)$— $R_{10}$ is H

The methods mentioned above can be expediently carried out analogously to the methods known to the person skilled in the art or as described by way of example in the following examples.

Optionally, compounds of the formula I can be converted into their salts, or, optionally, salts of the compounds of the formula I can be converted into the free compounds. Corresponding processes are habitual per se to the skilled person.

It is moreover known to the person skilled in the art that if there are a number of reactive centers on a starting or intermediate compound it may be necessary to block one or more reactive centers temporarily by protective groups in order to allow a reaction to proceed specifically at the desired reaction center. A detailed description for the use of a large number of proven protective groups is found, for example, in "Protective Groups in Organic Synthesis" by T. Greene and P. Wuts (John Wiley & Sons, Inc. 1999, 3rd Ed.) or in "Protecting Groups (Thieme Foundations Organic Chemistry Series N Group" by P. Kocienski (Thieme Medical Publishers, 2000).

The compounds according to the invention are isolated and purified in a manner known per se, for example by distilling off the solvent under reduced pressure and recrystallizing the residue obtained from a suitable solvent or subjecting it to one of the customary purification methods, such as, for example, column chromatography on a suitable support material.

Salts can be obtained by dissolving the free compound in a suitable solvent (e.g. a ketone, such as acetone, methyl ethyl ketone or methyl isobutyl ketone, an ether, such as diethyl ether, tetrahydrofuran or dioxane, a chlorinated hydrocarbon, such as methylene chloride or chloroform, or a low-molecular-weight aliphatic alcohol, such as ethanol or isopropanol) which contains the desired acid or base, or to which the desired acid or base is then added. The salts can be obtained by filtering, reprecipitating, precipitating with a nonsolvent for the addition salt or by evaporating the solvent. Salts obtained can be converted into the free compounds, which can in turn be converted into salts, by alkalization or by acidification. In this manner, pharmacologically unacceptable salts can be converted into pharmacologically acceptable salts.

Suitably, the conversions mentioned in this invention can be carried out analogously or similarly to methods which are familiar per se to the person skilled in the art.

The person skilled in the art knows on the basis of his/her knowledge and on the basis of those synthesis routes, which are shown and described within the description of this invention, how to find other possible synthesis routes for compounds according to this invention. All these other possible synthesis routes are also part of this invention.

Having described the invention in detail, the scope of the present invention is not limited only to those described characteristics or embodiments. As will be apparent to persons skilled in the art, modifications, analogies, variations, derivations, homologisations and adaptations to the described invention can be made on the base of art-known knowledge and/or, particularly, on the base of the disclosure (e.g. the explicite, implicite or inherent disclosure) of the present invention without departing from the spirit and scope of this invention as defined by the scope of the appended claims.

The following examples serve to illustrate the invention further without restricting it. Likewise, further compounds according to this invention, whose preparation is not explicitly described, can be prepared in an analogous or similar manner or in a manner familiar per se to the person skilled in the art using customary process techniques.

Any or all of the compounds of formula I according to the present invention which are specified as final compounds in the following examples, as well as the salts thereof, are a particularly interesting subject of the present invention.

In the examples, mp/M.P. stands for melting point, h for hour(s), min for minutes, conc. for concentrated, calc. for calculated, fnd.for found, EDCI for N-(3-Dimethylaminopropyl)-N'-ethylcarbodiimide hydrochloride, HOBT for 1-Hydroxybenzotriazole hydrate, DCC for N,N'-Dicyclohexylcarbodiimide, TEA for triethyl amine, DMF for N,N-Dimethylformamide, DMAP for 4-(Dimethylamino) pyridine, Boc anhydride/boc/(BOC)$_2$O for di-tert-butyl dicarbonate, DCM for dichoromethane, tBuOK for potassium tert.butoxide, DMSO for dimethyl sulfoxide, NaOH for sodium hydroxide, THF for tetrahydrofuran, PTSA for 4-methyl benzene sulfonic acid, and all other abbreviations have their meanings customary per se to the skilled person.

EXAMPLES

Preparation 1 tert-Butyl 2-amino-4-methoxyphenylcarbamate

Step I:

To a solution of NaH (2.2 eq) in tetrahydrofuran, HMDS (2.2 eq) was added at 0° C. and the reaction mixture was stirred for 15 Min. Then, 4-methoxy-2-nitroaniline (1.0 eq) in tetrahydrofuran was added at 0° C., continued the reaction at room temperature for 5 hrs. Then, (Boc)$_2$O (1.0 eq.) was added, stirred the reaction at room temp overnight. Water was added and the organic layer was separated, dried over anhydrous $Na_2SO_4$ and concentrated under reduced pressure to afford crude product, which, on purification by column chromatography afforded the desired tert-butyl 4-methoxy-2-nitrophenylcarbamate. (Yield=63%)

Step II:
tert-Butyl 4-methoxy-2-nitrophenylcarbamate as obtained in step I (1.0 eq) in MeOH was hydrogenated using Pd/C under $H_2$ atmosphere. After completion of the reaction, reaction mixture was filtered through celite and evaporated to dryness to get desired tert-butyl 2-amino-4-methoxyphenylcarbamate. (Yield=83%)

$^1$H NMR (DMSO-D6) δ (ppm) 1.38 (s, 9H), 3.64 (s, 3H), 4.82 (s, 2H), 6.11 (dd, 1H, J=6.3 & 2.7 Hz), 6.97 (d, 1H, J=2.7 Hz) 8.11 (s, 1H).

Preparation 2 tert-Butyl 2-amino-4-isopropylphenylcarbamate

Step I:
To a solution of 4-isopropylaniline (1.0 eq) in dichloromethane at 0° C., triethylamine (2.2 eq) was added and stirred for 15 min. Then, acetic anhydride (1.0 eq) in dichloromethane was added at 0° C., after addition the reaction was continued at room temperature for 5 hrs. Water was added and the organic layer was separated, dried over anhydrous $Na_2SO_4$, concentrated under reduced pressure to afford crude product, which, on purification by column chromatography afforded the desired N-(4-isopropylphenyl)acetamide. (Yield=95%)

Step II:
N-(4-Isopropylphenyl)acetamide obtained in step I above was nitrated using nitric acid (1.2 eq)+$H_2SO_4$ (1.0 eq) at 0 to 5° C. for 2 hrs. After the completion of the reaction, reaction mixture was added to ice and pH was adjusted to 8, extracted with dichloromethane, which was evaporated to dryness to obtain N-(4-isopropyl-2-nitrophenyl)acetamide.

Step III:
To a solution of N-(4-isopropyl-2-nitrophenyl)acetamide obtained in step II above (1.0 eq) in MeOH and water was added KOH (1.5 eq) at room temperature and stirred for 5 hrs. Water was added to the reaction mixture and the organic layer was separated, dried over anhydrous $Na_2SO_4$ and concentrated under reduced pressure to afford crude product, which, on purification by column chromatography afforded the desired 4-isopropyl-2-nitroaniline. (Yield=65%).

Step IV:
To a solution of NaH (2.2 eq) in tetrahydrofuran, HMDS (2.2 eq) was added at 0° C. and the reaction mixture was stirred for 15 min. Then, 4-isopropyl-2-nitroaniline (1.0 eq) in tetrahydrofuran was added at 0° C., continued the reaction at room temperature for 5 hrs. Then, $(Boc)_2O$ (1.0 eq.) was added, stirred the reaction at room temp overnight. Water was added and the organic layer was separated, dried over anhydrous $Na_2SO_4$ and concentrated under reduced pressure to afford crude product, which, on purification by column chromatography afforded the desired tert-butyl 4-isopropyl-2-nitrophenylcarbamate. (Yield=70%)

Step V:
tert-Butyl 4-isopropyl-2-nitrophenylcarbamate as obtained in step IV (1.0 eq) in MeOH was hydrogenated using Pd/C under $H_2$ atmosphere. After completion of the reaction, reaction mixture was filtered through celite and evaporated to dryness to get desired tert-butyl 2-amino-4-isopropylphenylcarbamate. (Yield=80%)

$^1$H NMR (DMSO-D6) δ (ppm) 1.15 (d, 6H, J=6.9 Hz), 1.45 (s, 9H), 2.71 (m, 1H), 4.82 (s, 2H), 6.42 (d, 1H, J=8.1 Hz), 6.65 (s, 1H), 7.05 (d, 1H, J=8.1 Hz), 8.21 (s, 1H).

Preparation 3 tert-Butyl 4-(dimethylamino)-2-nitrophenylcarbamate

Step I:
To a solution of N,N-dimethylbenzene-1,4-diamine (1.0 eq) in dichloromethane, triethylamine (2.2 eq) was added at 0° C. and stirred for 15 min. To the above mixture was then added a solution of acetic anhydride (1.0 eq) in dichloromethane at 0° C., after addition the reaction was continued at room temperature for 5 hrs. Water was added and the organic layer was separated, dried over anhydrous $Na_2SO_4$, concentrated under reduced pressure to afford crude product, which, on purification by column chromatography afforded the desired N-[4-(dimethylamino)phenyl]acetamide. (Yield=69%)

Step II:
N-[4-(dimethylamino)phenyl]acetamide obtained in step I above was nitrated using nitric acid (1.2 eq)+$H_2SO_4$ (1.0 eq) at 0 to 5° C. for 2 hrs. After the completion of the reaction, reaction mixture was added to ice and pH was adjusted to 8, extracted with dichloromethane, which was evaporated to dryness to obtain N-[4-(dimethylamino)-2-nitrophenyl]acetamide.

Step III:
To a solution of N-[4-(dimethylamino)-2-nitrophenyl]acetamide obtained in step 11 above (1.0 eq) in MeOH and water was added KOH (1.5 eq) at room temperature and stirred for 5 hrs. Water was added to the reaction mixture and the organic layer was separated, dried over anhydrous $Na_2SO_4$ and concentrated under reduced pressure to afford crude product, which, on purification by column chromatography afforded the desired N-(4-amino-3-nitrophenyl)-N,N-dimethylamine. (Yield=65%).

Step IV:
To a solution of NaH (2.2 eq) in tetrahydrofuran, HMDS (2.2 eq) was added at 0° C. and the reaction mixture was stirred for 15 min. Then, N-(4-amino-3-nitrophenyl)-N,N-dimethylamine (1.0 eq) in tetrahydrofuran was added at 0° C., continued the reaction at room temperature for 5 hrs. Then, $(Boc)_2O$ (1.0 eq.) was added, stirred the reaction at room temp overnight. Water was added and the organic layer was separated, dried over anhydrous $Na_2SO_4$ and concentrated under reduced pressure to afford crude product, which, on purification by column chromatography afforded the desired tert-butyl 4-(dimethylamino)-2-nitrophenylcarbamate. (Yield=67%)

Step V:
tert-Butyl 4-(dimethylamino)-2-nitrophenylcarbamate as obtained in step IV (1.0 eq) in MeOH was hydrogenated using Pd/C under $H_2$ atmosphere. After completion of the reaction, reaction mixture was filtered through celite and evaporated to dryness to get desired tert-butyl 2-amino-4-(dimethylamino)phenylcarbamate. (Yield=90%)

$^1$H NMR (DMSO-D6) δ (ppm) 1.40 (s, 9H), 2.78 (s, 6H), 4.60 (s, 2H), 5.96 (dd, 1H, J=6.3 & 2.7 Hz), 6.0 (d, 1H, J=2.7 Hz), 6.86 (d, 1H, J=3.0 HZ), 8.01 (s, 1H).

Preparation 4 tert-Butyl 2-amino-4-thien-2-ylphenylcarbamate

Step I:
To a solution of 4-bromoaniline (1.0 eq) in dichloromethane, triethylamine (2.2 eq) was added at 0° C. and stirred for 15 min. To this mixture was added acetic anhydride (1.0 eq) in dichloromethane at 0° C., after addition the reaction was continued at room temperature for 5 hrs. Water was added and the organic layer was separated, dried over anhydrous $Na_2SO_4$, concentrated under reduced pressure to afford crude product, which, on purification by column chromatography afforded the desired N-(4-bromophenyl)acetamide. (Yield=65%)

Step II:

N-(4-Bromophenyl)acetamide obtained in step I above was nitrated using nitric acid (1.2 eq)+$H_2SO_4$ (1.0 eq) at 0 to 5° C. for 2 hrs. After the completion of the reaction, reaction mixture was added to ice and pH was adjusted to 8, extracted with dichloromethane, which was evaporated to dryness to obtain N-(4-bromo-2-nitrophenyl)acetamide. (Yield=95%)

Step III:

To a solution of N-(4-bromo-2-nitrophenyl)acetamide obtained in step II above (1.0 eq) in MeOH and water was added KOH (1.5 eq) at room temperature and stirred for 5 hrs. Water was added to the reaction mixture and the organic layer was separated, dried over anhydrous $Na_2SO_4$ and concentrated under reduced pressure to afford crude product, which, on purification by column chromatography afforded the desired 4-bromo-2-nitroaniline. (Yield=95%)

Step IV:

To a solution of NaH (2.2 eq) in tetrahydrofuran, HMDS (2.2 eq) was added at 0° C. and the reaction mixture was stirred for 15 min. Then, 4-bromo-2-nitroaniline (1.0 eq) in tetrahydrofuran was added at 0° C., continued the reaction at room temperature for 5 hrs. Then, $(Boc)_2O$ (1.0 eq.) was added, stirred the reaction at room temp overnight. Water was added and the organic layer was separated, dried over anhydrous $Na_2SO_4$ and concentrated under reduced pressure to afford crude product, which, on purification by column chromatography afforded the desired tert-butyl 4-bromo-2-nitrophenylcarbamate. (Yield=72%)

$^1H$ NMR (DMSO-$d_6$) δ (ppm) 1.42 (s, 9H), 7.57 (d, 1H, J=8.7 Hz), 7.85 (dd, 1H, J=8.7 & 2.4 Hz), 8.11 (d, 1H, J=2.4 Hz), 9.67 (s, 1H).

Step V:

To a solution of tert-butyl 4-bromo-2-nitrophenylcarbamate obtained in step IV above (1.0 eq) in toluene, was added 10 mol % of tetrakis Pd, heated to 90° C. for 30 min, then aq $K_2CO_3$ and ethanol were added, followed by addition of 2-thienyl boronic acid portionwise and then reaction was refluxed overnight. Water was added to the reaction mixture and the organic layer was separated, dried over anhydrous $Na_2SO_4$ and concentrated under reduced pressure to afford crude product, which, on purification by column chromatography afforded the desired tert-butyl 2-nitro-4-thien-2-ylphenylcarbamate. (Yield=88%)

$^1H$ NMR (DMSO-$d_6$) δ (ppm); 1.44 (s, 9H), 7.16 (dd, 1H, J=3.6 & 1.5 Hz), 7.61 (m, 2H), 7.67 (d, 1H, J=8.7 Hz), 7.93 (dd, 1H, J=8.7 & 2.1 Hz), 8.13 (d, 1H, J=2.4 Hz), 9.64 (s, 1H).

Step VI:

To a solution of tert-butyl 2-nitro-4-thien-2-ylphenylcarbamate as obtained in step V above (1.0 eq) in MeOH was hydrogenated using Pd/C under $H_2$ atmosphere. After completion of the reaction, reaction mixture was filtered through celite and evaporated to dryness to get desired tert-butyl 2-amino-4-thien-2-ylphenylcarbamate (Yield=95%).

$^1H$ NMR (DMSO-$d_6$) δ (ppm); 1.45 (s, 9H), 5.00 (s, 2H), 6.83 (dd, 1H, J=8.1 & 1.8 Hz), 6.97 (d, 1H, J=2.1 Hz), 7.07 (dd, 1H, J=3.6 & 1.5 Hz), 7.27 (m, 2H), 7.42 (dd, 1H, J=4.2 & 0.9 Hz), 8.34 (s, 1H).

Preparation 5 tert-Butyl 2-amino-4-thien-3-ylphenylcarbamate

Step I:

To a solution of tert-butyl 4-bromo-2-nitrophenylcarbamate obtained in step IV preparation 4 above (1.0 eq) in toluene, was added 10 mol % of tetrakis Pd, heated to 90° C. for 30 min, then aq $K_2CO_3$ and ethanol were added, followed by addition of 3-thienyl boronic acid portionwise and then reaction was refluxed overnight. Water was added to the reaction mixture and the organic layer was separated, dried over anhydrous $Na_2SO_4$ and concentrated under reduced pressure to afford crude product, which, on purification by column chromatography afforded the desired tert-butyl 2-nitro-4-thien-3-ylphenylcarbamate. (Yield=88%)

$^1H$ NMR (DMSO-$d_6$) δ (ppm); 1.44 (s, 9H), 7.64 (m, 3H), 8.02 (m, 2H), 8.23 (d, 1H, J=2.1 Hz), 9.61 (s, 1H).

Step II:

To a solution of tert-butyl 2-nitro-4-thien-2-ylphenylcarbamate as obtained in step I above (1.0 eq) in MeOH was hydrogenated using Pd/C under $H_2$ atmosphere. After completion of the reaction, reaction mixture was filtered through celite and evaporated to dryness to get desired tert-butyl 2-amino-4-thien-2-ylphenylcarbamate (Yield=95%).

$^1H$ NMR (DMSO-$d_6$) δ (ppm); 1.44 (s, 9H), 4.89 (s, 2H), 6.86 (dd, 1H, J=8.1 & 2.1 Hz), 7.00 (d, 1H, J=2.1 Hz), 7.23 (d, 1H, J=8.1 Hz), 7.37 (dd, 1H, J=4.8 & 1.2 Hz), 7.57 (m, 2H), 8.30 (s, 1H).

Preparation 6 tert-Butyl 2-amino-4-pyrrolidin-1-ylphenylcarbamate

Step I:

To a solution of 4-fluoronitrobenzene (1.0 eq.) in isopropyl alcohol, pyrrolidine (2.2 eq) and triethylamine (11.0 eq) were added and reaction mixture was refluxed overnight. Reaction mixture was cooled to room temperature, product obtained was collected by filtration and dried to get the desired 1-(4-nitrophenyl)pyrrolidine. (Yield=85%)

Step II:

To a solution of 1-(4-nitrophenyl)pyrrolidine as obtained in step I above (1.0 eq) in MeOH was hydrogenated using Pd/C under $H_2$ atmosphere. After completion of the reaction, reaction mixture was filtered through celite and evaporated to dryness to get desired 4-pyrrolidin-1-ylaniline. (Yield=78%)

Step III:

To a solution of 4-pyrrolidin-1-ylaniline as obtained in step II above (1.0 eq) in dichloromethane, triethylamine (2.2 eq) was added at 0° C. and stirred for 15 min. To this mixture was added acetic anhydride (1.0 eq) in dichloromethane at 0° C., after addition the reaction was continued at room temperature for 5 hrs. Water was added and the organic layer was separated, dried over anhydrous $Na_2SO_4$, concentrated under reduced pressure to afford crude product, which, on purification by column chromatography afforded the desired N-(4-pyrrolidin-1-ylphenyl)acetamide. (Yield=90%)

Step IV:

N-(4-Pyrrolidin-1-ylphenyl)acetamide obtained in step III above was nitrated using nitric acid (1.2 eq)+$H_2SO_4$ (1.0 eq) at 0 to 5° C. for 2 hrs. After the completion of the reaction, reaction mixture was added to ice and pH was adjusted to 8, extracted with dichloromethane, which was evaporated to dryness to obtain N-(2-nitro-4-pyrrolidin-1-ylphenyl)acetamide Step V:

To a solution of N-(2-nitro-4-pyrrolidin-1-ylphenyl)acetamide obtained in step IV above (1.0 eq) in MeOH and water was added NaOH (1.5 eq) at room temperature and stirred for 5 hrs. Water was added to the reaction mixture and the organic layer was separated, dried over anhydrous $Na_2SO_4$ and concentrated under reduced pressure to afford crude product, which, on purification by column chromatography afforded the desired 2-nitro-4-pyrrolidin-1-ylaniline. (Yield=85%)

Step VI:

To a solution of NaH (2.2 eq) in tetrahydrofuran, HMDS (2.2 eq) was added at 0° C. and the reaction mixture was stirred for 15 min. Then, 2-nitro-4-pyrrolidin-1-ylaniline (1.0 eq) in tetrahydrofuran was added at 0° C., continued the reaction at room temperature for 5 hrs. Then, $(Boc)_2O$ (1.0 eq.) was added, stirred the reaction at room temp overnight. Water was added and the organic layer was separated, dried over anhydrous $Na_2SO_4$ and concentrated under reduced pressure to afford crude product, which, on purification by column chromatography afforded the desired tert-butyl 2-nitro-4-pyrrolidin-1-ylphenylcarbamate. (Yield=65%)

Step VII:

To a solution of tert-butyl 2-nitro-4-pyrrolidin-1-ylphenylcarbamate obtained in step VI above (1.0 eq) in MeOH was hydrogenated using Pd/C under $H_2$ atmosphere. After completion of the reaction, reaction mixture was filtered through celite and evaporated to dryness to get desired tert-butyl 2-amino-4-pyrrolidin-1-ylphenylcarbamate. (Yield=90%)

$^1$H NMR (DMSO-D6) δ (ppm); 1.40 (s, 9H), 1.91 (m, 4H), 3.12 (m, 4H), 4.5 (s, 2H), 5.76 (s, 1H), 5.8 (m, 1H), 5.9 (d, 1H, J=2.7 Hz), 7.9 (s, 1H).

Example 1

$N^2$-(2-aminophenyl)-N5-biphenyl-4-yl-6,7-dihydro[1,3]thiazolo[5,4-c]pyridine-2,5(4H)-dicarboxamide Step I Preparation of Ethyloxamate Solution of diethyl oxalate (1 mole, 136 ml) in absolute ethanol (100 ml) was cooled to 0° C. 68.1 ml of ammonium hydroxide was added and mixture was stirred for 4 h at 0° C. White precipitate formed was filtered, collected and recrystallised from ethanol. Yield 67.5 gm. M. P. 108-110° C.

NMR: $^1$H NMR ($CDCl_3$) δ(ppm) 8.20 (br s, 1H, NH), 7.92 (br s, 1H, NH), 4.20 (q, 2H, J=7.2 Hz), 1.23 (t, 2H, J=7.2 Hz).

Step II

Preparation of Ethyl Thioxamate

Ethyl oxamate (46.8 gm, 0.4 mole) obtained in step I was dissolved in 400 ml of toluene and heated to 100° C. Phosphorus pentasulphide (88.9 gm, 0.4 mole) was added under stirring and continued further stirring for 2 h. Reaction mixture was cooled to 50° C. and filtered by vacuum filtration. The precipitate was filtered and purified by column chromatography. Yield 20.0 gm. M. P. 58-61° C.

$^1$H NMR ($CDCl_3$) δ(ppm): −8.28 (br s, 1H, NH), 7.85 (br s, 1H, NH), 4.37 (q, 2H, J=7.2 Hz), 1.41 (t, 2H, J=7.2 Hz).

Step III

N-boc 4-piperidone 4-piperidone monohydrate hydrochloride (250 g, 1.62 mole) was dissolved in dioxane (1.5 L) and water (0.5 L). 217 g of $NaHCO_3$ was added at 0° C. followed by slow addition of $(BOC)_2O$ (459 g, 2.1 mole). Reaction mixture was stirred for overnight. Solution was concentrated; residue was taken in water and extracted with ethyl acetate, washed with water and dried over anhydrous $Na_2SO_4$. Solvent was evaporated and product obtained was washed with hexane to get N-boc 4-piperidone (280 g).

$^1$H NMR ($CDCl_3$) δ(ppm) 3.32 (t, 4H, J=6.3 Hz), 2.44 (t, 4H), J=6.3 Hz)

Step IV

N-boc-3-bromo-4-piperidone

N-boc-4-piperidone (100 gm, 0.5 mole) obtained in step H1 was dissolved in 4.0 L of dichloromethane. Bromine (96.3 gm, 0.6 mole) in 100 ml of dichloromethane was added at room temperature under stirring and nitrogen bubbling. After completion of bromine addition, the reaction mixture was stirred further at room temperature for additional 30 minutes and then filtered. Filtrate was concentrated and crystallized by dichloromethane/petroleum ether to get the product N-boc-3-bromo-4-piperidone (45.0 gm).

NMR: $^1$H NMR ($CDCl_3$) δ(ppm) 4.34 (br s, 1H), 3.98 (s, 3H), 3.70 (m, 2H), 3.03 (s, 1H), 1.50 (s, 9H).

Step V 5-tert-butyl 2-ethyl 6,7-dihydro[1,3]thiazolo[5,4-c]pyridine-2,5(4H)-dicarboxylate N-boc-3-bromo-4-piperidone (110 gm, 0.395 mole) obtained in step IV was dissolved in 500 ml of dry toluene. Ethyl thioxamate (68.4 g, 0.514 mole) obtained in step II and PPTS (10 gm, 0.039 mole) were added to toluene solution. Mixture was refluxed azeotropically for 8 h, followed by concentration. The residue obtained was taken in water and extracted with dichloromethane. The organic layer was washed with water, brine and dried over anhydrous sodium sulphate and concentrated. Residue obtained was purified by column chromatography using 1% $MeOH/CH_2Cl_2$ as eluent to get the 39.0 gm of N-boc-4,5,6,7-tetrahydrothiazolo-[5,4-c]-pyridine-2-ethylcarboxylate.

$^1$H NMR ($CDCl_3$) δ(ppm) 4.72 (s, 2H), 4.47 (q, 2H, 7.2 Hz), 3.74 (m, 2H), 2.97 (t, 2H, J=5.4 Hz), 2.40 (t, 2H, J=6.3 Hz), 1.50 (s, 9H), 1.43 (t, 3H, J=7.2 Hz).

Step VI

Lithium salt of N-boc-4,5,6,7-tetrahydrothiazolo-[5,4-c]-pyridine-2-carboxylate 5-tert-butyl 2-ethyl 6,7-dihydro[1,3]thiazolo[5,4-c]pyridine-2,5(4H)-dicarboxylate (39 gm, 0.125 mole) obtained in step V was dissolved in mixture of solvents containing 170 ml THF and 30 ml water. To this solution was added 6.3 gm of $LiOH.H_2O$ (0.15 mole) and stirred for 4 h Reaction mixture was then concentrated to dryness. Solid mass was taken in ether and stirred for 1 h Ether layer was decanted and residue was dried under vacuum to get Lithium salt of N-boc-4,5,6,7-tetrahydrothiazolo-[5,4-c]-pyridine-2-carboxylate. 36.0 gm yield.

¹H NMR (DMSO-d₆) δ(ppm) 4.54 (s, 2H), 3.63 (t, 2H, J=6.0 Hz), 2.71 (t, 2H, J=5.4 Hz), 141 (s, 9H).

Step VII tert-butyl 2-({2-[(tert-butoxycarbonyl)amino] phenyl}carbamoyl)-6,7-dihydro[1,3]thiazolo[5,4-c] pyridine-5(4H)-carboxylate 53.36 gm of DCC (0.26 mole) and 28 gm of HOBt (0.21 mole) were added to the well stirred solution of Lithium salt of N-boc-4,5,6,7-tetrahydrothiazolo-[5,4-c]pyridine-2-carboxylate (50 gm, 0.172 mole) obtained in step VI in 1.5 L of dichloromethane. Mono boc protected o-phenylene diamine (43.0 gm, 0.21 mole) was then added and mixture was stirred for overnight. The reaction mixture was washed with water, cold-dil HCl(5%), brine, dried over anhydrous Na₂SO₄ and then concentrated. Crude mass (100.0 gm) obtained was purified by column chromatography using 18% ethyl acetate/petroleum ether as eluent to yield 22.0 gm of tert-butyl 2-({2-[(tert-butoxycarbonyl)amino]phenyl}carbamoyl)-6,7-dihydro[1,3]thiazolo[5,4-c]pyridine-5(4H)-carboxylate. M.P.: 188° C.

¹H NMR (DMSO-d₆) δ(ppm) 10.07 (s, 1H), 9.16 (s, 1H), 7.80 (m, 1H), 7.33 (m, 1H), 7.27 (m, 2H), 4.71 (s, 2H), 3.70 (t, 2H, J=5.7 Hz), 2.83 (t, 2H, J=5.4 Hz), 1.49 (s, 9H), 1.43 (s, 9H).

Step VIII

N-(2-aminophenyl)-4,5,6,7-tetrahydro[1,3]thiazolo [5,4-c]pyridine-2-carboxamide

TFA (70 ml) was added dropwise under stirring to N-boc-4,5,6,7-tetrahydrothiazolo-[5,4-c]-pyridine-2-(2'-boc-aminophenyl)carboxamide (22 g gm) obtained in step VII which was dissolved in 70 ml of dichloromethane, and stirred for 2 hr at room temperature. Reaction mixture was concentrated and dried under vacuum. Residue was taken in water and dichloromethane. Solid K₂CO₃ was added slowly with continuous stirring till pH become basic (8-9). Reaction mixture was extracted with dichloromethane, washed with brine, dried over anhydrous Na₂SO₄ and concentrated to yield 9.0 gm of 4,5,6,7-tetrahydrothiazolo-[5,4-c]-pyridine-2-(2'-aminophenyl)carboxamide.

¹H NMR (DMSO-d₆) δ(ppm) 9.90 (s, 1H), 7.27 (dd, 1H, J=1.2 Hz, 7.8), 6.96 (dt, 1H, J=1.5 Hz, 7.5 Hz), 6.78 (dd, 1H, J=1.2 Hz, 7.5 Hz), 6.60 (dt, 1H, J=1.5 Hz, 7.8 Hz), 4.90 (s, 2H), 3.97 (s, 2H), 3.00 (t, 2H, J=5.7 Hz), 2.76 (t, 2H, J=5.7 Hz).

Step IX

N²-(2-aminophenyl)-N5-biphenyl-4-yl-6,7-dihydro [1,3]thiazolo[5,4-c]pyridine-2,5(4H)-dicarboxamide Biphenylisocyanate was added to a solution of 4,5,6,7-tetrahydrothiazolo-[5,4-c]-pyridine-2-(2'-aminophenyl)carboxamide obtained in step VIII in DMF. The reaction mixture was stirred for 3 h at room temperature and then concentrated under vacuum. The residue was diluted with water and extracted with dichloromethane washed with brine, dried over anhydrous Na₂SO₄ and concentrated to yield the title compound.

¹HNMR (DMSO-d₆) δ(ppm) 8.89 (s, 1H, NH), 7.57 (m, 4H), 7.44 (m, 5H), 7.38 (d, 1H, J=7.2 Hz), 7.11 (t, 1H, J=7.5 Hz), 6.86 (m, 2H), 6.54 (s, 1H), 4.87 (br s, 2H, NH2), 4.82 (s, 2H), 3.85 (t, 2H, J=5.4 Hz), 2.95 (m, 2H).

Examples 2-11 were Obtained by Following the Procedure of Example 1

Example 2

N²-(2-aminophenyl)-N5-[4-(dimethylamino)phenyl]-6,7-dihydro[1,3]thiazolo[5,4-c]pyridine-2,5(4H)-dicarboxamide ¹HNMR (DMSO-d₆) δ(ppm) 9.97 (s, 1H, NH), 8.48 (s, 1H, NH), 7.27 (dd, 2H, J=8.1 Hz, 1.2 Hz), 7.24 (d, 2H, J=8.0 Hz), 6.97 (dt, 1H, J=7.4 Hz, 1.5 Hz), 6.79 (dd, 1H, J=8.0 Hz), 6.66 (d, 2H, J=9.0 Hz), 6.61 (dt, 1H, J=7.6 Hz), 4.93 (br s, 2H, NH2), 4.81 (s, 2H), 3.85 (t, 2H, J=5.7 Hz), 2.95 (m, 2H), 2.82 (s, 6H).

Example 3

N²-(2-aminophenyl)-N5-(4-methoxyphenyl)-6,7-dihydro[1,3]thiazolo[5,4-c]pyridine-2,5(4H)-dicarboxamide ¹HNMR (DMSO-d₆) δ(ppm) 9.97 (s, 1H, NH), 8.63 (s, 1H, NH), 7.35 (d, 2H, J=9.0 Hz), 7.27 (d, 1H, J=6.9 Hz), 6.97 (dt, 1H, J=7.5 Hz, 1.2 Hz), 6.84 (d, 1H, J=9.0 Hz), 6.79 (d, 1H, J=7.5 Hz), 6.61 (dt, 1H, J=7.4 Hz, 1.2 Hz), 4.93 (br s, 2H, NH2), 4.82 (s, 2H), 3.86 (s, 3H), 2.94 (m, 2H), 2.96 (m, 2H).

Example 4

N²-(2-aminophenyl)-N5-benzyl-6,7-dihydro[1,3] thiazolo[5,4-c]pyridine-2,5(4H)-dicarboxamide ¹HNMR (DMSO-d₆) δ(ppm) 8.88 (s, 1H, NH), 7.45 (d, 2H, J=7.5 Hz), 7.32 (m, 5H), 7.09 (dt, 1H, J=7.1 Hz, 1.5 Hz), 6.85 (t, 2H, J=7.5 Hz), 4.88 (m, 2H), 4.75 (s, 2H), 4.47 (d, 2H, J=5.4 Hz), 3.89 (br s, 2H, NH2), 3.76 (t, 2H, J=5.7 Hz), 2.97 (t, 2H, J=5.7 Hz).

Example 5

Methyl 4-[({2-[(2-aminophenyl)carbamoyl]-6,7-dihydro[1,3]thiazolo[5,4-c]pyridin-5(4H)-yl}carbonyl)amino]benzoate ¹HNMR (DMSO-d₆) δ(ppm) 9.98 (s, 1H, NH), 9.18 (s, 1H, NH), 7.84 (d, 2H, J=8.7 Hz), 7.63 (d, 2H, J=9.0 Hz), 7.25 (d, 2H, J=6.9 Hz), 6.96 (t, 1H, J=6.9 Hz), 6.77 (d, 1H, J=7.2 Hz), 6.60 (t, 1H, J=7.8 Hz), 4.92 (br s, 2H, NH2), 4.85 (s, 2H), 3.88 (t, 2H, J=5.1 Hz), 3.79 (s, 3H), 2.97 (m, 2H).

Example 6

N²-(2-aminophenyl)-N5-(4-phenoxyphenyl)-6,7-dihydro[1,3]thiazolo[5,4-c]pyridine-2,5(4H)-dicarboxamide ¹HNMR (DMSO-d₆) δ(ppm) 9.97 (s, 1H, NH), 8.82 (s, 1H, NH), 7.48 (d, 2H, J=9.0 Hz), 7.36 (dt, 2H, J=8.0, 1.5 Hz), 7.27 (dd, 1H, J=7.8 Hz, 1.2 Hz), 7.08 (tt, 1H, J=6.9 Hz, 1.2 Hz, 0.9 Hz), 6.98 (m, 5H), 6.80 (dd, 1H, J=8.1 Hz, 1.2 Hz), 6.61 (dt, 1H, J=7.8 Hz, 1.2 Hz), 4.93 (br s, 2H, NH2), 4.84 (s, 2H), 3.88 (t, 2H, J=5.4 Hz), 2.97 (s, 2H).

Example 7

N²-(2-aminophenyl)-N5-1,3-benzodioxol-5-yl-6,7-dihydro[1,3]thiazolo[5,4-c]pyridine-2,5(4H)-dicarboxamide ¹HNMR (DMSO-d₆) δ (ppm) 9.97 (s, 1H, NH), 8.67 (s, 1H, NH), 7.27 (dd, 2H, J=6.6 Hz, 0.9 Hz), 7.13 (d, 1H, J=1.8 Hz), 6.97 (dt, 2H, J=7.6 Hz, 1.5 Hz), 6.81 (m, 3H), 6.61 (dt, 1H, J=7.0 Hz, 1.5 Hz), 5.95 (s, 2H), 4.93 (br s, 2H, NH2), 4.82 (s, 2H), 3.85 (t, 2H, J=5.4 Hz), 2.95 (m, 2H).

Example 8

N²-(2-aminophenyl)-N5-[2-(trifluoromethoxy)phenyl]-6,7-dihydro[1,3]thiazolo[5,4-c]pyridine-2,5(4H)-dicarboxamide ¹HNMR (DMSO-d₆) δ(ppm) 9.98 (s, 1H, NH), 8.69 (s, 1H, NH), 7.51 (dd, 2H, J=8.1 Hz, 1.5 Hz), 7.36-7.30 (m, 2H), 7.28-7.20 (m, 2H), 6.97 (m, 1H), 6.79 (dd, 1H, J=7.8 Hz, 1.2 Hz), 6.61 (m, 1H), 4.93 (br s, 2H), NH2), 4.83 (s, 2H), 3.87 (t, 2H, J=5.4 Hz), 2.96 (m, 2H).

Example 9

N²-(2-aminophenyl)-N5-[4-(trifluoromethoxy)phenyl]-6,7-dihydro[1,3]thiazolo[5,4-c]pyridine-2,5(4H)-dicarboxamide ¹HNMR (DMSO-d₆) δ(ppm) 9.95 (s, 1H, NH), 8.97 (s, 1H, NH), 7.56 (dd, 2H, J=8.1 Hz, 1.5 Hz), 7.25 (d, 2H, J=8.1 Hz), 6.96 (m, 1H), 6.77 (dd, 1H, J=8.1 Hz, 1.2 Hz), 6.59 (m, 1H), 4.91 (br s, 2H, NH2), 4.83 (s, 2H), 3.87 (t, 2H, J=5.7 Hz), 2.96 (t, 2H, J=5.1 Hz).

Example 10

N²-(2-aminophenyl)-N5-[2-(difluoromethoxy)phenyl]-6,7-dihydro[1,3]thiazolo[5,4-c]pyridine-2,5(4H)-dicarboxamide ¹HNMR (DMSO-d₆) δ(ppm) 9.98 (s, 1H, NH), 8.45 (s, 1H, NH), 7.48 (m, 1H), 7.28-7.16 (m, 4H), 7.01 (t, 1H, J=74.4 Hz, OCHF2), 7.00-6.94 (m, 1H), 6.78 (dd, 1H, J=6.9 Hz, 1.2 Hz), 6.61 (m, 1H), 4.94 (br s, 2H, NH2), 4.83 (s, 2H), 3.87 (t, 2H, J=5.7 Hz), 2.97 (t, 2H, J=5.1 Hz).

Example 11

N²-(2-aminophenyl)-N5-[4-(difluoromethoxy)phenyl]-6,7-dihydro[1,3]thiazolo[5,4-c]pyridine-2,5(4H)-dicarboxamide ¹H NMR (DMSO-d₆) δ(ppm) 10.00 (s, 1H, NH), 8.85 (s, 1H, NH), 7.50 (d, 2H, J=9.0 Hz), 7.27 (dd, 1H, J=7.8 Hz, 1.2 Hz), 7.12 (t, 1H, J=7.4 Hz), 7.09 (d, 2H, J=9.04 Hz), 6.98 (t, 1H, J=8.4 Hz), 6.79 (dd, 1H, J=8.4 Hz, 1.2 Hz), 6.61 (dt, 1H, J=7.5 Hz, 1.5 Hz), 4.93 (s, 2H), 4.84 (s, 2H), 3.89 (m, 2H), 2.97 (m, 2H).

Example 12

N²-(2-aminophenyl)-N5-quinolin-3-yl-6,7-dihydro[1,3]thiazolo[5,4-c]pyridine-2,5(4H)-dicarboxamide 1,1'-Carbonyldiimidazole was added to a solution quinoline-3yl amine in 10 mL of dry DMF. The reaction mixture was stirred at room temperature for 3 h to obtain imidazolyl-carbonyl amide. N-(2-aminophenyl)-4,5,6,7-tetrahydro[1,3]thiazolo[5,4-c]pyridine-2-carboxamide. obtained in step VIII of Example 1 was then added followed by catalytic amount of 4-dimethylamino pyridine. The reaction mixture was stirred at room temperature overnight. Reaction mixture was concentrated, diluted with water, extracted with dichloromethane, washed with brine solution, and dried over anhydrous Na2SO4. Concentrated and purified by column chromatography to yield the title compound.

¹HNMR (DMSO-d₆) δ(ppm) 9.99 (s, 1H, NH), 9.26 (s, 1H, NH), 8.97 (d, 2H, J=2.4 Hz), 8.44 (d, 1H, J=2.4 Hz), 7.93 (d, 1H, J=8.4 Hz), 7.87 (d, 1H, J=7.8 Hz), 7.57 (m, 2H), 7.27 (d, 1H, J=7.8 Hz), 6.98 (dt, 1H, J=7.8 Hz, 1.2 Hz), 6.79 (d, 1H, J=8.2), 6.61 (dt, 1H, J=7.5 Hz, 0.9 Hz), 4.93 (br s, 2H, NH2), 4.93 (s, 2H), 3.95 (t, 2H, J=5.4 Hz), 3.02 (m, 2H)

Examples 13-17 were Obtained by Following the Procedure of Example 12

Example 13

N²-(2-aminophenyl)-N⁵-(4-methylphenyl)-6,7-dihydro[1,3]thiazolo[5,4-c]-pyridine-2,5(4H)-dicarboxamide ¹HNMR (DMSO-d₆) δ(ppm) 9.97 (s, 1H, NH), 8.69 (s, 1H, NH), 7.34 (d, 2H, J=8.7 Hz), 7.27 (dd, 1H, J=7.8 Hz, 1.2 Hz), 7.05 (d, 2H, J=8.1 Hz), 6.97 (dt, 1H, J=7.04 Hz, 1.5 Hz), 6.79 (dd, 1H, J=7.8 Hz, 1.2 Hz), 6.61 (dt, 1H, J=6.9 Hz, 1.2 Hz), 4.93 (br s, 2H, NH2), 4.83 (s, 2H), 3.86 (t, 2H, J=5.4 Hz), 2.96 (m, 2H)

Example 14

N²-(2-aminophenyl)-N⁵-(pyridin-3-ylmethyl)-6,7-dihydro[1,3]thiazolo[5,4-c]pyridine-2,5(4H)-dicarboxamide ¹HNMR (DMSO-d₆) δ(ppm) 9.95 (s, 1H, NH), 8.49 (s, 1H, NH), 8.43 (d, 1H, J=3.3 Hz), 7.66 (m, 1H), 7.45 (t, 1H, J=5.7 Hz), 7.33 (m, 1H), 7.26 (dd, 1H, J=7.4 Hz), 6.97 (dt, 1H, J=7.8 Hz, 1.2 Hz), 6.78 (dd, 1H, J=8.1 Hz, 1.2 Hz), 6.62 (dt, 1H, J=7.2 Hz, 1.2 Hz), 4.92 (br s, 2H, NH2), 4.37 (s, 2H), 4.29 (d, 2H, J=5.7 Hz), 3.76 (t, 2H, J=5.4 Hz), 2.89 (m, 2H)

Example 15

N²-(2-aminophenyl)-N⁵-pyridin-4-yl-6,7-dihydro[1,3]thiazolo[5,4-c]pyridine-2,5(4H)-dicarboxamide ¹HNMR (DMSO-d₆) δ(ppm)) 9.98 (s, 1H, NH), (s, 1H, NH), 8.32 (d, 1H, J=6.3 Hz), 7.49 (dd, 2H, J=4.8, 1.5), 7.25 (dd, 1H, J=7.5 Hz, 1.2 Hz), 6.96 (dt, 1H, J=7.2 Hz, 1.2 Hz), 6.77 (dd, 1H, J=7.8 Hz, 1.2 Hz), 6.59 (dt, 1H, J=7.2 Hz, 1.2 Hz), 4.92 (br s, 2H, NH2), 4.85 (s, 2H), 3.88 (t, 2H, J=5.7 Hz), 2.97 (m, 2H).

Example 16

N²-(2-aminophenyl)-N⁵-(2-methoxyethyl)-6,7-dihydro[1,3]thiazolo[5,4-c]-pyridine-2,5(4H)-dicarboxamide ¹HNMR (DMSO-d₆) δ(ppm)) 9.91 (s, 1H, NH), 9.93 (s, 1H, NH), 7.25 (dd, 2H, J=1.2 Hz, 7.8 Hz), 6.96 (dt, 2H, J=7.4 Hz, 1.5 Hz), 6.83 (t, 1H, J=5.4 Hz), 6.77 (dd, 1H, J=8.1 Hz, 1.5 Hz), 6.59 (dt, 1H, J=7.85 Hz, 1.2 Hz), 4.91 (br s, 2H, NH2), 4.68 (s, 2H), 3.70 (t, 2H, J=5.7 Hz), 3.31 (s, 3H), 3.21 (s, 4H), 2.85 (t, 2H, J=5.4 Hz).

Example 17

$N^2$-(2-aminophenyl)-$N^5$-methyl-6,7-dihydro[1,3]thiazolo[5,4-c]pyridine-2,5(4H)-dicarboxamide $^1$HNMR (DMSO-$d_6$) δ(ppm) 9.94 (s, 1H, NH), 7.26 (dd, 1H, J=7.8 Hz, 1.2 Hz), 6.97 (m, 2H), 6.78 (dd, 1H, J=8.1 Hz, 1.2 Hz), 6.73-6.72 (m, 1H), 6.63-6.58 (m, 1H), 4.92 (br s, 2H, NH2), 4.68 (s, 2H), 3.69 (t, 2H, J=5.7 Hz), 2.86 (s, 2H, J=5.4 Hz), 2.60 (s, 3H)

Example 18

$N^2$-(2-aminophenyl)-$N^5$-[3-(dimethylantino)phenyl]-6,7-dihydro[1,3]thiazolo[5,4-c]pyridine-2,5(4H)-dicarboxamide Saturated NaHCO$_3$ solution was added to a solution of NN dimenthyl benzene 1,3 diamine (1.0 mmol) dissolved in 6 mL of dichloromethane. The biphasic mixture was cooled to 0° C. Triphosgene (0.45 mmol) was then added and mixture was stirred at room temperature for 30 minutes. Dichloromethane layer containing isocyanate product was separated washed with brine and dried over anhydrous Na$_2$SO$_4$. This isocyanate solution was added slowly to N-(2-aminophenyl)-4,5,6,7-tetrahydro[1,3]thiazolo[5,4-c]pyridine-2-carboxamide. obtained in step VIII of Example 1 (1 mmol) solution in 10 mL of dry DMF. Resultant mixture was stirred at room temperature for 3 h Reaction mixture was concentrated, diluted with water, extracted with dichloromethane, washed with brine solution, and dried over anhydrous Na$_2$SO$_4$. Concentrated and purified by column chromatography to to yield the title compound.

$^1$HNMR (DMSO-$d_6$) δ(ppm) 9.99 (s, 1H, NH), 8.59 (s, 1H, NH), 7.26 (dd, 1H, J=8.1 Hz, 1.5 Hz), 7.30 (t, 1H, J=8.1 Hz), 6.97 (dt, 1H, J=7.4 Hz, 1.5 Hz), 6.86 (m, 2H), 6.79 (dd, 1H, J=8.8 Hz, 1.2 Hz), 6.61 (dt, 1H, J=7.6 Hz, 1.2 Hz), 6.36 (dd, 1H, J=8.2 Hz), 4.94 (br s, 2H, NH2), 4.83 (s, 2H), 3.86 (t, 2H, J=5.7 Hz), 2.96 (m, 2H).

Example 19

$N^2$-(2-aminophenyl)-$N^5$-(3,4-dimethoxyphenyl)-6,7-dihydro[1,3]thiazolo[5,4-c]pyridine-2,5(4H)-dicarboxamide Obtained following the procedure of example 18.
$^1$HNMR (DMSO-$d_6$) δ(ppm) 9.99 (s, 1H, NH), 8.63 (s, 1H, NH), 7.26 (dd, 2H, J=7.4 Hz, 0.9 Hz), 7.15 (d, 1H, J=2.4 Hz), 6.97 (dt, 2H, J=8.5 Hz, 2.4 Hz), 6.81 (m, 2H), 6.61 (dt, 1H, J=7.0 Hz, 0.9 Hz), 4.93 (br s, 2H, NH2), 4.82 (s, 2H), 3.86 (t, 2H, J=5.4 Hz), 3.71 (s, 3H), 3.69 (s, 3H), 2.96 (m, 2H)

Example 20

$N^2$-(2-aminophenyl)-$N^5$-(2-methoxyethyl)-$N^5$-methyl-6,7-dihydro[1,3]thiazolo[5,4-c]pyridine-2,5 (41:1)-dicarboxamide Triphosgene (0.45 mmol) was dissolved in 18 mL of dichloromethane and cooled to 0° C. To this solution was added respective (2-methox-ethyl)methylamine (1.0 mmol) followed by triethylamine (2.0 mmol). The reaction mixture was stirred at 0° C. for 30 minutes. This solution was then transferred slowly to N-(2-aminophenyl)-4,5,6,7-tetrahydro[1,3]thiazolo[5,4-c]pyridine-2-carboxamide. obtained in step VIII of Example 1 (1 mmol) dissolved in 10 mL of dry DMF and allowed to stirred at room temperature for 2 h Reaction mixture was concentrated, diluted with water, extracted with dichloromethane, washed with brine solution, and dried over anhydrous Na$_2$SO$_4$. Concentrated and purified by column chromatography to yield the title compound.

$^1$HNMR (DMSO-$d_6$) δ(ppm) 9.95 (s, 1H, NH), 7.26 (dd, 1H, J=6.6 Hz, 1.2 Hz), 6.95 (m, 1H), 6.78 (dd, 1H, J=8.1 Hz, 1.2 Hz), 6.60 (m, 1H), 4.49 (s, 2H), 3.48 (m, 4H), 3.34 (s, 3H), 2.98 (m, 2H), 2.73 (s, 3H).

Example 21

$N^2$-(2-aminophenyl)-$N^5$-ethyl-$N^5$-isopropyl-6,7-dihydro[1,3]thiazolo[5,4-c]-pyridine-2,5(4H)-dicarboxamide Obtained following the procedure of example 20.
$^1$HNMR (DMSO-$d_6$) δ(ppm) 9.94 (s, 1H, NH), 7.24 (dd, 1H, J=7.8 Hz, 1.2 Hz), 6.95 (m, 1H), 6.77 (dd, 1H, J=7.8 Hz, 1.2 Hz), 6.59 (m, 1H), 4.91 (br s, 2H, NH2), 4.46 (s, 2H), 3.82 (m, 1H), 3.49 (t, 2H, J=5.7 Hz), 3.07 (q, 2H, 6.9 Hz), 2.94-2.92 (m, 2H), 1.12 (d, 6H, J=6.6 Hz), 0.98 (t, 3H, J=6.9 Hz).

Example 22

$N^2$-(2-aminophenyl)-$N^5$-[4-(dimethylamino)phenyl]-$N^5$-methyl-6,7-dihydro-[1,3]thiazolo[5,4-c]pyridine-2,5(4H)-dicarboxamide Triphosgene (0.45 mmol) was dissolved in 18 mL of dichloromethane and solution cooled to −78° C. To this solution was added pyridine (1.0 mmol) followed by N,N,N'-trimethyl benzene 1,4-diamine (1.0 mmol). The reaction mixture was stirred at −78° C. for 15 minutes and then brought to room temperature and was stirred at room temperature for additional 3 h To this mixture was added 1N HCl solution. Dichloromethane layer was separated, washed with saturated NaHCO$_3$ solution, brine and then dried over anhydrous Na$_2$SO$_4$. This dichloromethane solution containing corresponding isocyanate was added slowly to N-(2-aminophenyl)-4,5,6,7-tetrahydro[1,3]thiazolo[5,4-c]pyridine-2-carboxamide. obtained in step VIII of Example 1 (1 mmol) dissolved in 10 mL dry DMF at 0° C. Triethylamine (1.0 eq) was added and mixture was brought to room temperature and stirred overnight. Reaction mixture was concentrated, diluted with water, extracted with dichloromethane, washed with brine solution, and dried over anhydrous Na$_2$SO$_4$. Concentrated and purified by column chromatography to yield the title compound.

$^1$HNMR (DMSO-$d_6$) δ(ppm) 9.91 (s, 1H, NH), 7.24 (dd, 2H, J=1.5 Hz, 7.8 Hz), 7.04 (d, 2H, J=10.2 Hz), 6.96 (dt, 2H, J=7.2 Hz, 1.5 Hz), 6.78 (dd, 1H, J=1.5 Hz, 8.1 Hz), 6.72 (d, 2H, J=10.2 Hz), 6.59 (dt, 1H, J=7.5 Hz, 2.0 Hz), 4.91 (br s, 2H, NH2), 4.48 (s, 2H), 3.48 (t, 2H, J=5.4 Hz), 3.03 (s, 3H), 2.54 (t, 2H, J=5.1 Hz)

Examples 23-33 were Obtained by Following the Procedure of Example 22

Example 23

$N^2$-(2-aminophenyl)-$N^5$-[3-(dimethylamino)phenyl]-$N^5$-methyl-6,7-dihydro-[1,3]-thiazolo[5,4-c]pyridine-2,5(4H)-dicarboxamide Obtained following the procedure of example 22.
$^1$HNMR (DMSO-$d_6$) δ(ppm) 9.94 (s, 1H, NH), 7.25 (dd, 1H, J=6.6 Hz, 1.2 Hz), 7.16 (t, 1H, J=8.1 Hz), 6.94 (m, 1H), 6.78 (dd, 1H, J=6.6 Hz, 1.2 Hz), 6.60 (m, 1H), 6.52 (dd, 1H, J=7.2 Hz, 1.2 Hz), 6.48-6.46 (m, 2H), 4.91 (br s, 2H, NH2), 4.47 (s, 2H), 3.54 (t, 2H, J=5.7 Hz), 3.12 (s, 3H), 2.85 (s, 6H), 2.63 (t, 2H, J=4.2 Hz)

Example 24

$N^2$-(2-aminophenyl)-$N^5$-(3,4-dimethoxyphenyl)-$N^5$-methyl-6,7-dihydro[1,3]-thiazolo[5,4-c]pyridine-2,5(4H)-dicarboxamide $^1$HNMR (DMSO-$d_6$) δ(ppm): 9.98 (s, 1H), 7.25 (d, 1H, J=6.9 Hz), 6.99 (d, 1H, J=1.2 Hz), 6.94 (t, 1H), 6.85 (d, 1H, J=2.4 Hz), 6.77 (dd, 1H, J=8.1&1.2 Hz), 6.71 (dd, 1H, J=8.7&2.4 Hz), 6.60 (t, 1H), 4.9 (s, 2H), 4.4 (s, 2H), 3.74 (s, 3H), 3.71 (s, 3H), 3.54 (t, 2H), 3.32 (s, 3H), 2.5 (t, 2H).

Example 25

$N^2$-(2-aminophenyl)-$N^5$-(3,4-dimethoxyphenyl)-$N^5$-ethyl-6,7-dihydro[1,3]-thiazolo[5,4-c]pyridine-2,5(4H)-dicarboxamide $^1$HNMR (DMSO-$d_6$) δ(ppm): 9.92 (s, 1H), 7.26 (d, 1H, J=1.2 Hz), 6.96 (m, 2H), 6.80 (m, 2H), 6.65 (dd, 1H, J=4.5&1.2 Hz), 6.58 (t, 1H), 4.90 (s, 2H), 4.42 (s, 2H), 3.75 (s, 3H), 3.71 (s, 3H), 3.58 (q, 2H), 3.56 (t, 2H), 3.32 (t, 2H), 1.02 (t, 3H)

Example 26

$N^2$-(2-aminophenyl)-$N^5$-(3,4-dimethoxyphenyl)-$N^5$-(2-methoxyethyl)-6,7-dihydro[1,3]thiazolo[5,4-c]pyridine-2,5(4H)-dicarboxamide $^1$HNMR (DMSO-$d_6$) δ(ppm): 9.91 (s, 1H), 7.24 (d, 1H, J=1.0 Hz), 6.99-6.60 (m, 5H), 6.58 (t, 1H), 4.89 (s, 2H), 4.4 (s, 2H), 3.7 (s, 3H), 3.60 (s, 3H), 3.46 (t, 2H), 3.43 (t, 2H), 3.38 (t, 2H), 3.2 (s, 3H), 2.53 (t, 2H)

Example 27

$N^2$-(2-aminophenyl)-$N^5$-methyl-$N^5$-pyridin-3-yl-6,7-dihydro[1,3]thiazolo[5,4-c]pyridine-2,5(4H)-dicarboxamide $^1$HNMR (DMSO-$d_6$) δ(ppm): –9.92 (s, 1H), 8.47 (d, 1H, J=2.4 Hz), 8.32 (dd, 1H, J=4.8 & 1.2 Hz), 7067(dq, 1H), 7.39 (dd, 1H, J=8.4 & 4.8 Hz), 7.23 (d, 1H, J=7.8 Hz), 6.95 (t, 1H), 6.75 (d, 1H, J=8.1 Hz), 6.58 (t, 1H), 4.90 (s, 2H), 4.48 (s, 2H), 3.53 (t, 2H), 3.17 (s, 3H), 2.6 (t, 2H).

Example 28

$N^2$-(2-aminophenyl)-$N^5$-ethyl-$N^5$-pyridin-3-yl-6,7-dihydro[1,3]thiazolo[5,4-c]pyridine-2,5(4H)-dicarboxamide $^1$HNMR (DMSO-$d_6$) δ(ppm): 9.88 (s, 1H), 8.4 (d, 1H, J=2.4 Hz), 8.35 (d, 1H, J=2.6 Hz), 7.6 (d, 1H, J=2.4 Hz), 7.41 (dd, 1H, J=8.4&4.8 Hz), 7.23 (d, 1H, J=7.8 Hz), 6.97 (t, 1H), 6.75 (d, 1H, J=8.1 Hz), 6.58 (t, 1H), 4.9 (s, 2H), 4.43 (s, 2H), 3.64 (q, 2H), 3.47 (t, 2H), 2.52 (t, 2H), 1.03 (t, 3H).

Example 29

$N^2$-(2-aminophenyl)-$N^5$-1,3-benzodioxol-5-yl-$N^5$-ethyl-6,7-dihydro[1,3]thiazolo[5,4-c]pyridine-2,5(4H)-dicarboxamide $^1$HNMR (DMSO-$d_6$) δ(ppm): 9.90 (s, 1H), 7.23 (d, 1H, J=7.8 Hz), 6.92 (dd, 1H, J=7.8&2.0 Hz), 6.87 (d, 214, J=2.1 Hz), 6.63 (d, 1H, J=2.1 Hz), 6.58 (t, 2H), 6.03 (s, 2H), 4.90 (s, 2H), 4.41 (s, 2H), 3.55 (t, 2H), 3.49 (q, 2H), 2.51 (t, 2H), 0.99 (t, 3H).

Example 30

$N^2$-(2-aminophenyl)-$N^5$-1,3-benzodioxol-5-yl-$N^5$-(2-methoxyethyl)-6,7-dihydro[1,3]thiazolo[5,4-c]pyridine-2,5(4H)-dicarboxamide $^1$HNMR (DMSO-$d_6$) δ(ppm): 9.90 (s, 1H), 7.23 (d, 1H, J=7.8 Hz), 6.95 (t, 1H), 6.87 (m, 2H), 6.76 (d, 1H, J=8.1 Hz), 6.66 (dd, 1H, J=8.4&2.1 Hz), 6.58 (t, 1H), 6.03 (s, 2H), 4.8 (s, 2H), 4.40 (s, 2H), 3.63 (t, 2H), 3.46 (t, 2H), 3.44 (t, 2H), 3.25 (s, 3H), 2.5 (t, 2H).

Example 31

$N^2$-(2-aminophenyl)-$N^5$-1,3-benzodioxol-5-yl-$N^5$-methyl-6,7-dihydro[1,3]-thiazolo[5,4-c]pyridine-2,5(4H)-dicarboxamide $^1$HNMR (DMSO-$d_6$) δ(ppm): 9.92 (s, 1H), 7.27 (d, 1H, J=1.00 Hz), 6.94 (t, 1H), 6.90 (d, 2H, J=7.8 Hz), 6.79 (d, 1H, J=6.9 Hz), 6.67 (dd, 1H, J=6&2.4 Hz), 6.60 (t, 1H), 6.00 (s, 2H), 4.9 (s, 2H), 4.40 (s, 2H), 3.52 (t, 2H), 3.07 (s, 3H), 2.70 (t, 2H)

Example 32

$N^2$-(2-aminophenyl)-$N^5$-[3-(4-methylpiperazin-1-yl)phenyl]-6,7-dihydro-[1,3]thiazolo[5,4-c]pyridine-2,5(4H)-dicarboxamide $^1$HNMR (DMSO-$d_6$) δ(ppm): 9.97 (s, 1H), 8.62 (s, 1H), 7.1 (d, 1H, J=7.8 Hz), 7.03 (d, 2H, 7.9 Hz), 6.95 (d, 2H, J=7.5 Hz), 6.63 (d, 1H, J=7.8 Hz), 6.63 (d, 1H, J=7.8 Hz), 6.53 (d, 1H, J=8.1 Hz), 4.93 (s, 2H), 4.83 (s, 2H), 3.87 (t, 2H), 3.10 (t, 4H), 3.07 (t, 2H), 2.50 (t, 4H), 2.2 (s, 3H).

Example 33

$N^2$-(2-aminophenyl)-$N^5$-(2-methoxyethyl)-$N^5$-pyridin-3-yl-6,7-dihydro[1,3]thiazolo[5,4-c]pyridine-2,5(4H)-dicarboxamide $^1$HNMR (DMSO-d6) δ(ppm): 9.91 (s, 1H), 8.4 (s, 1H), 8.3 (d, 1H, J=3.6 Hz), 7.69 (d, 1H), J=7.5 Hz), 7.40 (t, 1H), 7.20 (d, 1H, J=7.5 Hz), 6.9 (t, 1H), 6.79 (d, 1H, J=7.2 Hz), 6.60 (t, 1H), 4.90 (s, 2H), 4.4 (s, 2H), 3.7 (s, 2H), 3.40 (s, 4H), 3.2 (s, 3H), 2.7 (s, 2H)

Example 34

$N^2$-(2-aminophenyl)-$N^5$-(6-morpholin-4-ylpyridin-3-yl)-6,7-dihydro[1,3]thiazolo[5,4-c]pyridine-2,5(4H)-dicarboxamide Step I:
6-Morpholin-4-yl-pyridin-3-yl-amine (1.0 mmol) was dissolved in 4 mL of dichloromethane and cooled to 0° C.

4-nitrophenylchloroformate (1.0 mmol) solution in 2 mL of dichloromethane was added followed by addition of pyridine (1.0 mmol). Mixture was stirred for 30 minutes at 0° C. brought to room temperature and stirred for additional 12 h. The precipitate formed was collected by filtration washed with dichloromethane and dried. The product 4-nitrophenyl carbonate of respective amine was used for next step without further purification.

Step II:

The intermediate obtained in step I (1.0 mmol) and N-(2-aminophenyl)-4,5,6,7-tetrahydro[1,3]thiazolo[5,4-c]pyridine-2-carboxamide. obtained in step VIII of Example 1 (1 mmol) were dissolved in dry DMF or dimethoxyethane/DMSO (7:3) solvent and exposed to microwave radiation at 100° C. for 20 minutes. The reaction mixture was concentrated, diluted with water, extracted with dichloromethane, washed with brine solution, and dried over anhydrous $Na_2SO_4$. Concentrated and purified by column chromatography to yield the title compound.

$^1$HNMR (DMSO-$d_6$) δ(ppm) 9.97 (s, 1H, NH), 8.64 (s, 1H, NH), 8.17 (d, 1H, J=2.7 Hz), 7.65 (dd, 1H, J=9.0 Hz, 2.7 Hz), 7.27 (dd, 1H, J=8.1 Hz, 1.2 Hz), 6.97 (dt, 1H, J=8.1 Hz, 1.5 Hz), 6.79 (d, 2H, J=9.3 Hz), 6.61 (dt, 1H, J=7.8 Hz, 1.2 Hz), 4.93 (br s, 2H, NH2), 4.83 (s, 2H), 3.86 (t, 2H, J=5.4 Hz), 3.67 (m, 4H), 3.34 (m, 4H), 2.96 (m, 2H)

Examples 35-39 were Obtained by Following the Procedure of Example 34

Example 35

$N^2$-(2-aminophenyl)-$N^5$-(6-azetidin-1-ylpyridin-3-yl)-6,7-dihydro[1,3]thiazolo[5,4-c]pyridine-2,5(4H)-dicarboxamide $^1$HNMR (DMSO-$d_6$) δ(ppm) 9.97 (s, 1H, NH), 8.59 (s, 1H, NH), 8.06 (d, 2H, J=2.4 Hz), 7.58 (dd, 1H, J=8.1 Hz, 2.4 Hz), 7.27 (dd, 1H, J=7.8 Hz, 1.2 Hz), 6.97 (m, 1H), 6.76 (dd, 1H, J=8.1 Hz, 1.2 Hz), 6.61 (m, 1H), 6.34 (d, 1H, J=9.0 Hz), 4.99 (br s, 2H, NH2), 4.82 (s, 2H), 3.87 (m, 6H), 2.95 (t, 2H, J+7.5 Hz), 2.28 (t, 2H, J=7.5)

Example 36

$N^2$-(2-aminophenyl)-$N^5$-[6-(dimethylamino)pyridin-3-yl]-6,7-dihydro[1,3]thiazolo[5,4-c]pyridine-2,5(4H)-dicarboxamide $^1$HNMR (DMSO-$d_6$) δ(ppm) 9.96 (s, 1H, NH), 8.53 (s, 1H, NM, 8.08 (d, 1H, J=2.7 Hz), 7.55 (dd, 1H, J=9.2 Hz, 2.7 Hz), 7.27 (dd, 1H, J=8.1 Hz, 1.5 Hz), 6.97 (dt, 1H, J=1.5 Hz, 7.1 Hz), 6.79 (dd, 2H, J=8.1 Hz, 1.2 Hz), 6.61 (dt, 1H, J=8.4 Hz, 1.2 Hz), 4.92 (br s, 2H, NH2), 4.82 (s, 2H), 3.85 (t, 2H, J=5.4 Hz), 3.39 (t, 4H, J=4.8 Hz), 2.97 (s, 6H), 2.96 (m, 2H)

Example 37

$N^2$-(2-aminophenyl)-$N^5$-[6-(4-methylpiperazin-1-yl)pyridin-3-yl]-6,7-dihydro[1,3]thiazolo[5,4-c]pyridine-2,5(4H)-dicarboxamide $^1$HNMR (DMSO-$d_6$) δ(ppm) 9.97 (s, 1H, NH), 8.66 (s, 1H, NH), 8.15 (d, 1H, J=2.7 Hz), 7.62 (dd, 1H, J=9.0 Hz, 2.7 Hz), 7.27 (dd, 1H, J=8.1 Hz, 1.6 Hz), 6.97 (dt, 1H, J=1.2 Hz, 8.1 Hz), 6.78 (dd, 2H, J=5.6 Hz, 2.7 Hz), 6.61 (dt, 1H, J=8.1 Hz, 1.2 Hz), 4.93 (br s, 2H, NH2), 4.83 (s, 2H), 3.86 (t, 2H, J=5.4 Hz), 3.39 (t, 41-1, J=4.8 Hz), 2.96 (m, 2H), 2.42 (t, 4H, J=5.1 Hz), 2.23 (s, 3H)

Example 38

$N^2$-(2-aminophenyl)-$N^5$-(6-methoxypyridin-3-yl)-6,7-dihydro[1,3]thiazolo[5,4-c]pyridine-2,5(4H)-dicarboxamide $^1$HNMR (DMSO-$d_6$) δ(ppm)) 9.97 (s, 1H, NH), 8.77 (s, 1H, NH), 8.19 (d, 1H, J=2.4 Hz), 7.77 (dd, 2H, J=8.6 Hz, 2.4 Hz), 7.27 (d, 1H, J=7.2 Hz), 7.27 (d, 1H, J=7.2 Hz), 6.97 (t, 1H, J=6.9 Hz, 8.1 Hz), 6.77 (t, 2H, J=9.0 Hz), 6.61 (t, 1H, J=7.5 Hz), 4.93 (br s, 2H, NH2), 4.84 (s, 2H), 3.87 (t, 2H, J=5.4 Hz), 3.80 (s, 3H), 2.97 (m, 2H).

Example 39

$N^2$-(2-aminophenyl)-$N^5$-pyridin-3-yl-6,7-dihydro[1,3]thiazolo[5,4-c]pyridine-2,5(4H)-dicarboxamide $^1$HNMR (DMSO-$d_6$) δ(ppm) 9.99 (s, 1H, NH), 8.99 (s, 1H, NH), 8.65 (d, 1H, J=2.1 Hz), 8.18 (dd, 1H, J=4.8 Hz, 1.5 Hz), 7.89 (dt, 1H, J=8.7 Hz 1.5 Hz), 7.28 (m, 2H), 6.97 (dt, 1H, J=7.4 Hz, 1.5 Hz), 6.79 (dd, 1H, J=8.0 Hz, 1.2 Hz), 6.61 (dt, 1H, J=7.1 Hz, 1.5 Hz), 4.93 (br s, 2H, NH2), 4.86 (s, 2H), 3.89 (t, 2H, J=5.7 Hz), 2.98 (t, 2H, J=5.1 Hz)

Examples 40 to 61 were also obtained by following the procedure of Example 34 except in step H, instead of using microwave radiation, the reaction was carried out in the presence of triethyl amine as base and DMF as solvent at 60 to 100° C.

Example 40

$N^2$-(2-aminophenyl)-$N^5$-butyl-6,7-dihydro[1,3]thiazolo[5,4-c]pyridine-2,5(4H)-dicarboxamide $^1$HNMR (DMSO-$d_6$) δ(ppm) 9.94 (s, 1H), 7.26 (dd, 1H, J=7.8, 1.2 Hz), 6.97 (t, 1H, J=8.7 Hz), 6.78 (dd, 1H, J=8.1, 1.5 Hz), 6.74 (t, 1H, J=8.4 Hz), 6.60 (d t, 1H, J=7.8, 1.2 Hz), 4.93 (s, 2H), 4.69 (s, 2H), 3.71 (t, 2H, J=5.7 Hz), 3.05 (q, 2H, J=6.9 Hz), 2.86 (t, 2H, J=5.7 Hz), 1.20-1.41 (m, 4H), 0.87 (t, 3H, J=7.2 Hz)

Example 41

$N^2$-(2-aminophenyl)-$N^5$-(4-pyridin-3-ylcyclohexyl)-6,7-dihydro[1,3]thiazolo[5,4-c]pyridine-2,5(4H)-dicarboxamide $^1$HNMR (DMSO-$d_6$) δ(ppm) 9.95 (s, 1H), 8.49-8.54 (m, 1H), 8.35-8.45 (m, 1H), 7.67-7.70 (m, 1H), 7.25-7.40 (m, 2H), 6.97 (t, 1H, J=8.7 Hz), 6.79 (dd, 1H, J=7.5, 1.2 Hz), 6.54-6.64 (m, 2H), 4.93 (s, 2H), 4.70-4.74 (m, 2H), 3.72-3.80 (m, 2H), 3.56 (m, 1H), 2.87 (m, 2H), 1.70-1.95 (m, 4H), 1.25-1.65 (m, 5H)

Example 42

$N^2$-(2-aminophenyl)-$N^5$-piperidin-4-yl-6,7-dihydro[1,3]thiazolo[5,4-c]pyridine-2,5(4H)-dicarboxamide $^1$HNMR (CD3OD) δ (ppm) 7.58-7.46 (m, 4H), 4.80 (s, 2H), 3.74-3.90 (m, 3H), 3.34-3.46 (m, 2H), 3.01-3.12 (m, 2H), 2.99 (t, 2H, J=5.7 Hz), 2.22-2.08 (m, 2H), 1.86-1.72 (m, 2H).

Example 43

N²-(2-amino-5-methoxyphenyl)-N⁵-(4-methoxyphenyl)-6,7-dihydro[1,3]thiazolo[5,4-c]pyridine-2,5(4H)-dicarboxamide ¹HNMR (DMSO-d₆) δ(ppm) 9.93 (s, 1H), 8.62 (s, 1H), 7.34 (d, 2H, J=9.0 Hz), 7.13 (d, 1H, J=3.0 Hz), 6.84 (d, 2H, J=9.0 Hz), 6.78 (d, 1H, J=8.7 Hz), 6.61 (dd, 1H, J=8.7, 3.0 Hz), 4.81 (s, 2H), 4.51 (b s, 2H), 3.85 (t, 2H, J=5.7 Hz), 3.70 (s, 3H), 3.64 (s, 3H), 2.95 (br t, 2H)

Example 44

N²-(2-aminophenyl)-N⁵-(4-pyridin-4-ylcyclohexyl)-6,7-dihydro[1,3]thiazolo[5,4-c]pyridine-2,5(4H)-dicarboxamide ¹HNMR (DMSO-d₆) δ (ppm) 9.95 (s, 1H), 8.49 (d, 2H, J=6.0 Hz), 7.32 (d, 2H, J=6.0 Hz), 7.28 (m, 1H), 6.97 (t, 1H, J=7.5 Hz), 6.79 (d, 1H, J=7.5 Hz), 6.61 (t, 1H, J=7.5 Hz), 6.32 (d, 1H, J=7.5 Hz), 4.91 (m, 2H), 4.73 (s, 2H), 3.82 (m, 1H), 3.76 (t, 214, J=5.7 Hz), 2.89 (b t, 2H), 2.64 (m, 1H), 1.50-2.00 (m, 8H).

Example 45

N²-(2-amino-5-isopropylphenyl)-N⁵-(4-methoxyphenyl)-6,7-dihydro[1,3]thiazolo[5,4-c]pyridine-2,5(4H)-dicarboxamide ¹HNMR (DMSO-d₆) δ(ppm) 9.93 (s, 1H), 8.63 (s, 1H), 7.36 (d, 2H, J=9.3 Hz), 7.22 (d, 1H, J=1.8 Hz), 6.82-6.90 (m, 3H), 6.74 (d, 1H, J=8.4 Hz), 4.83 (s, 2H), 4.74 (b s, 2H), 3.87 (t, 2H, J=5.4 Hz), 3.72 (s, 3H), 2.96 (b t, 2H), 2.75 (q, 1H, J=6.9 Hz), 1.15 (d, 6H, J=6.9 Hz).

Example 46

N²-(2-amino-5-methoxyphenyl)-N⁵-isoquinolin-5-yl-6,7-dihydro[1,3]thiazolo[5,4-c]pyridine-2,5(4H)-dicarboxamide ¹HNMR (DMSO-d₆) δ(ppm) 9.97 (s, 1H), 9.32 (s, 1H), 9.04 (s, 1H), 8.50 (d, 1H, J=6.0 Hz), 7.95 (d, 1H, J=7.8 Hz), 7.79 (d, 1H, J=6.0 Hz), 7.63-7.74 (m, 2H), 7.17 (d, 1H, J=2.7 Hz), 6.80 (d, 1H, J=8.7 Hz), 6.63 (dd, 1H, J=8.7, 3.0 Hz), 4.94 (s, 2H), 4.55 (b s, 2H), 3.99 (t, 2H, J=5.7 Hz), 3.67 (s, 3H), 3.07 (b t, 2H).

Example 47

N²-(2-amino-5-methoxyphenyl)-N⁵-[4-(dimethylamino)phenyl]-6,7-dihydro-[1,3]thiazolo[5,4-c]pyridine-2,5(4H)-dicarboxamide ¹HNMR (DMSO-d₆) δ(ppm) 9.96 (s, 1H), 8.49 (s, 1H), 7.25 (d, 2H, J=9.0 Hz), 7.15 (d, 1H, J=3.0 Hz), 6.79 (d, 1H, J=8.7 Hz), 6.67 (d, 2H, J=9.0 Hz), 6.63 (dd, 1H, J=8.7, 2.7 Hz), 4.82 (s, 2H), 4.53 (b s, 2H), 3.86 (t, 2H, J=5.7 Hz), 3.66 (s, 3H), 2.96 (br t, 2H), 2.83 (s, 6H).

Example 48

N²-(2-amino-5-isopropylphenyl)-N⁵-(3,4-dimethoxyphenyl)-6,7-dihydro[1,3]thiazolo[5,4-c]pyridine-2,5(4H)-dicarboxamide ¹HNMR (DMSO-d₆) δ(ppm) 9.93 (s, 1H), 8.63 (s, 1H), 7.22 (d, 1H, J=1.8 Hz), 7.16 (d, 1H, J=2.1 Hz), 6.99 (dd, 1H, J=8.7, 2.1 Hz), 6.83-6.90 (m, 2H), 6.74 (d, 1H, J=8.1 Hz), 4.84 (s, 2H), 4.74 (b s, 2H), 3.87 (t, 2H, J=5.4 Hz), 3.72 (s, 3H), 3.71 (s, 3H), 2.97 (br t, 2H), 2.78 (q, 1H, J=6.9 Hz), 1.15 (d, 6H, J=6.9 Hz).

Example 49

N²-(2-amino-5-isopropylphenyl)-N⁵-isoquinolin-5-yl-6,7-dihydro[1,3]thiazolo[5,4-c]pyridine-2,5(4H)-dicarboxamide ¹HNMR (DMSO-d₆) δ(ppm) 9.97 (s, 1H), 9.32 (s, 1H), 9.04 (s, 1H), 8.51 (d, 1H, J=6.0 Hz), 7.95 (d, 1H, J=7.8 Hz), 7.79 (d, 1H, J=6.0 Hz), 7.62-7.76 (m, 2H), 7.23 (d, 1H, J=1.8 Hz), 6.88 (dd, 1H, J=8.1, 1.8 Hz), 6.75 (d, 1H, J=8.1 Hz), 4.94 (s, 2H), 4.76 (b s, 2H), 3.99 (t, 2H, J=5.4 Hz), 3.06 (br t, 2H), 2.76 (q, 1H, J=6.9 Hz), 1.16 (d, 6H, J=6.9 Hz)

Example 50

N²-(2-amino-5-isopropylphenyl)-N⁵-[4-(dimethylamino)phenyl]-6,7-dihydro[1,3]thiazolo[5,4-c]pyridine-2,5(4H)-dicarboxamide ¹HNMR (DMSO-d₆) δ(ppm) 9.94 (s, 1H), 8.49 (s, 1H), 7.25 (d, 2H, J=9.3 Hz), 7.21 (d, 1H, J=2.1 Hz), 6.87 (dd, 1H, J=8.1, 2.1 Hz), 6.73 (d, 1H, J=8.4 Hz), 6.67 (d, 2H, J=9.3 Hz), 4.82 (s, 2H), 4.75 (b s, 2H), 3.86 (t, 2H, J=5.7 Hz), 2.95 (br t, 2H), 2.83 (s, 6H), 2.73 (q, 1H, J=6.9 Hz), 1.15 (d, 6H, J=6.9 Hz).

Example 51

N²-(2-amino-5-methoxyphenyl)-N⁵-(4-fluorophenyl)-6,7-dihydro[1,3]thiazolo[5,4-c]pyridine-2,5(4H)-dicarboxamide ¹HNMR (DMSO-d₆) δ(ppm) 9.96 (s, 1H), 8.83 (s, 1H), 7.48 (m, 2H), 7.06-7.17 (m, 3H), 6.78 (d, 1H, J=8.7 Hz), 6.63 (dd, 1H, J=8.7, 3.0 Hz), 4.85 (s, 2H), 4.53 (b s, 2H), 3.88 (t, 2H, J=5.7 Hz), 3.66 (s, 3H), 2.97 (b t, 2H).

Example 52

N²-(2-amino-5-isopropylphenyl)-N⁵-(4-fluorophenyl)-6,7-dihydro[1,3]thiazolo[5,4-c]pyridine-2,5(4H)-dicarboxamide ¹HNMR (DMSO-d₆) 15(ppm) 9.95 (s, 1H), 8.83 (s, 1H), 7.48 (m, 2H), 7.21 (d, 1H, J=1.8 Hz), 7.10 (m, 2H), 6.87 (dd, 1H, J=8.1, 2.1 Hz), 6.74 (d, 1H, J=8.1 Hz), 4.84 (s, 2H), 4.75 (s, 2H), 3.88 (t, 2H, J=5.7 Hz), 2.97 (b t, 2H), 2.75 (q, 1H, J=6.9 Hz), 1.15 (d, 6H, J=6.9 Hz).

Example 53

N²-[2-amino-5-(dimethylamino)phenyl]N⁵-(4-methoxyphenyl)-6,7-dihydro[1,3]thiazolo[5,4-c]pyridine-2,5(4H)-dicarboxamide ¹HNMR (DMSO-d₆) δ(ppm) 9.94 (s, 1H), 8.64 (s, 1H), 7.35 (d, 2H, J=9.0 Hz), 7.04 (d, 1H, J=2.7 Hz), 6.85 (d, 2H, J=9.0 Hz), 6.75 (d, 1H, J=8.7 Hz), 6.53 (dd, 1H, J=8.7, 2.7 Hz), 4.83 (s, 2H), 4.32 (b s, 2H), 3.86 (t, 2H, J=5.7 Hz), 3.71 (s, 3H), 2.97 (b, 2H), 2.75 (s, 6H).

Example 54

N²-[2-amino-5-(2-thienyl)phenyl]-N⁵-(4-methoxyphenyl)-6,7-dihydro[1,3]thiazolo[5,4-c]pyridine-2,5(4H)-dicarboxamide ¹HNMR (DMSO-$d_6$) δ(ppm) 10.05 (s, 1H), 8.62 (s, 1H), 7.54 (d, 1H, J=1.8 Hz), 7.20-7.37 (m, 5H), 7.04 (m, 1H), 6.78-6.87 (m, 3H), 5.17 (b s, 2H), 4.82 (s, 2H), 3.86 (t, 2H, J=5.7 Hz), 3.70 (s, 3H), 2.96 (b t, 2H).

Example 55

N²-[2-amino-5-(2-thienyl)phenyl]-N⁵-[4-(dimethylamino)phenyl]-6,7-dihydro[1,3]thiazolo[5,4-c]pyridine-2,5(4H)-dicarboxamide ¹HNMR (DMSO-$d_6$) δ (ppm) 10.09 (s, 1H), 8.50 (s, 1H), 7.57 (d, 1H, J=2.1 Hz), 7.38 (dd, 1H, J=5.1, 0.9 Hz), 7.31 (dd, 1H, J=8.4, 2.1 Hz), 7.23-7.27 (m, 3H), 7.06 (dd, 1H, J=8.1, 3.6 Hz), 6.83 (d, 1H, J=8.4 Hz), 6.68 (d, 2H, J=9.0 Hz), 5.20 (b s, 2H), 4.83 (s, 2H), 3.86 (t, 2H, J=5.7 Hz), 2.97 (b t, 2H), 2.83 (s, 6H).

Example 56

N²-[2-amino-5-(3-thienyl)phenyl]-N⁵-(4-methoxyphenyl)-6,7-dihydro[1,3]thiazolo[5,4-c]pyridine-2,5(4H)-dicarboxamide ¹HNMR (DMSO-$d_6$) δ(ppm) 10.72 (s, 1H), 8.78 (s, 1H), 7.93 (m, 1H), 7.87 (d, 1H, J=1.8 Hz), 7.73 (dd, 1H, J=7.5, 1.8 Hz), 7.67 (dd, 1H, J=8.1, 2.7 Hz), 7.53-7.58 (m, 2H), 7.37 (d, 2H, J=9.0 Hz), 6.82 (d, 2H, J=9.0 Hz), 4.85 (s, 2H), 3.89 (t, 2H, J=5.4 Hz), 3.69 (s, 3H), 2.97 (b t, 2H).

Example 57

N²-[2-amino-5-(dimethylamino)phenyl]-N⁵-[4-(dimethylamino)phenyl]-6,7-dihydro[1,3]thiazolo[5,4-c]pyridine-2,5(4H)-dicarboxamide ¹HNMR (DMSO-$d_6$) δ(ppm) 9.93 (s, 1H), 8.49 (s, 1H), 7.25 (d, 2H, J=9.0 Hz), 7.05 (d, 1H, J=2.4 Hz), 6.76 (d, 1H, J=8.7 Hz), 6.67 (d, 2H, J=9.0 Hz), 6.53 (dd, 1H, J=8.7, 3.0 Hz), 4.81 (s, 2H), 4.36 (b s, 2H), 3.86 (t, 2H, J=5.4 Hz), 2.95 (br t, 2H), 2.83 (s, 6H), 2.76 (s, 6H).

Example 58

N²-(2-amino-5-pyrrolidin-1-ylphenyl)-N⁵-(4-methoxyphenyl)-6,7-dihydro-[1,3]thiazolo[5,4-c]pyridine-2,5(4H)-dicarboxamide ¹HNMR (DMSO-$d_6$) δ(ppm) 9.92 (s, 1H), 8.63 (s, 1H), 7.36 (d, 2H, J=9.0 Hz), 6.93 (s, 1H), 6.85 (d, 2H, J=9.0 Hz), 6.76 (d, 1H, J=8.7 Hz), 6.76 (d, 1H, J=7.2 Hz), 4.83 (s, 2H), 4.20 (b s, 2H), 3.86 (t, 2H, J=5.4 Hz), 3.71 (s, 3H), 3.13 (b s, 4H), 2.96 (b t, 2H), 1.93 (b s, 4H)

Example 59

N²-[2-amino-5-(3-thienyl)phenyl]-N⁵-[4-(dimethylamino)phenyl]-6,7-dihydro[1,3]thiazolo[5,4-c]pyridine-2,5(4H)-dicarboxamide ¹HNMR (DMSO-$d_6$) δ(ppm) 10.06 (s, 1H), 8.49 (s, 1H), 7.55-7.61 (m, 3H), 7.35-7.43 (m, 2H), 7.25 (d, 2H, J=9.0 Hz), 6.83 (d, 1H, J=8.4 Hz), 7.68 (d, 2H, J=8.7 Hz), 5.07 (b s, 2H), 4.83 (s, 2H), 3.86 (t, 2H, J=5.7 Hz), 2.97 (br t, 2H), 2.84 (s, 6H)

Example 60

N²-(2-amino-5-isopropylphenyl)-N⁵-pyridin-3-yl-6,7-dihydro[1,3]thiazolo[5,4-c]pyridine-2,5(4H)-dicarboxamide ¹HNMR (DMSO-$d_6$) δ (ppm) 9.94 (s, 1H), 8.99 (s, 1H), 8.66 (d, 1H, J=2.1 Hz), 8.19 (m, 1H), 7.90 (m, 1H), 7.30 (dd, 1H, J=8.4, 4.8 Hz), 7.22 (d, 1H, J=1.8 Hz), 6.87 (dd, 1H, J=8.4, 2.1 Hz), 6.74 (d, 1H, J=8.4 Hz), 4.88 (s, 2H), 4.75 (b s, 2H), 3.91 (t, 2H, J=5.7 Hz), 2.99 (br t, 2H), 2.75 (q, 1H, J=6.9 Hz), 1.15 (d, 6H, J=6.9 Hz).

Example 61

N²-[2-amino-5-(dimethylamino)phenyl]-N⁵-(3,4-dimethoxyphenyl)-6,7-dihydro[1,3]thiazolo[5,4-c]pyridine-2,5(4H)-dicarboxamide ¹HNMR (DMSO-$d_6$) δ(ppm) 9.9 (s, 1H), 8.6 (s, 1H), 7.24 (d, 2H, J=7.2 Hz), 7.01 (d, 1H, J=3.0 Hz), 7.00 (dd, 1H, J=2.4 & 2.9 Hz), 6.8 (d, 1H, J=8.7 Hz), 6.71 (d, 1H, J=8.7 Hz), 6.53 (dd, 1H, J=2.7, 8.7 Hz), 4.8 (s, 2H), 3.86 (t, 2H, J=5.7, 11.4 Hz), 3.7 (d, 7H, J=3.9 Hz), 2.9 (t, 2H, J=5.7, 11.4 Hz), 2.7 (s, 6H).

Example 62

N²-(2-aminophenyl)-N⁵-isoquinolin-5-yl-6,7-dihydro[1,3]thiazolo[5,4-c]pyridine-2,5(4H)-dicarboxamide Step I:
To a solution of a 5-aminoisoquinoline (1 eq) in dichloromethane, phenyl chloroformate was added at 0° C. and after addition the reaction was continued at room temperature for 1 h Water was added and the organic layer was separated, dried over anhydrous Na2SO4 and concentrated under reduced pressure to afford crude product desired carbamate derivative of Isoqunoline.

NMR (CDCl3) d (ppm) 10.74 (s, 1H), 9.95 (s, 1H), 8.75 (d, 1H, J=6.6 Hz), 8.6 (q, 1H, J=6.6 & 6.9 Hz), 8.38 (q, 2H=5.4 Hz & 4.8 Hz), 8.05 (t, 2H, J=8.1 Hz), 7.72 (m, 1H), 7.44 (m, 2H), 7.30 (m, 3H).

Step II:
5-tert-butyl 2-ethyl 6,7-dihydro[1,3]thiazolo[5,4-c]pyridine-2,5(4H)-dicarboxylate obtained in step V of example 1 was deprotected to get the hydrochloride salt of 4,5,6,7-Tetrahydro-thiazolo[5,4-c]pyridine-2-carboxylic acid ethyl ester. To a solution of a HCl salt of 4,5,6,7-Tetrahydro-thiazolo[5,4-c]pyridine-2-carboxylic acid ethyl ester (1.0 eq) in DMF was added Et3N (1.0 eq.) followed by carbamate derivative of Isoquinoline (1.0 eq) obtained in step I above. The reaction mixture was refluxed for 3 h at 90° C. Water was added and the organic layer was separated, dried over anhydrous Na2SO4 and concentrated under reduced pressure to afford crude product, which, was hydrolysed by stirring in MeOH: water and K2CO3 (2.0 eq.) for 48 h Reaction mixture was concentrated under reduced pressure and neutralized to pH 7.0 to afford 5-(Quinolin-5-ylcarbamoyl)-4,5,6,7-tetrahydro-thiazolo[5,4-c]pyridine-2-carboxylic acid).

¹HNMR (DMSO-d₆) δ(ppm) 9.3 (s, 1H), 8.94 (s, 1H), 8.49 (d, 1H, J=6), 7.93 (d, 1H, J=7.8 Hz), 7.77 (d, 1H, J=7.8 Hz), 7.66 (m, 2H), 4.76 (s, 2H), 3.89 (t, 2H, J=5.6 Hz), 2.87 (t, 2H, J=5.6).

Step III:

To a solution of the acid derivative (1.0 eq) obtained in step II above in DMF was added triethyl amine (2.2 eq.), EDCI (1.2 eq) and HOBt (1.2 eq) and reaction was stirred for 1 h and then added ortho phenylene diamine and was stirred overnight. Water was added and the organic layer was separated, dried over anhydrous Na2SO4 and concentrated under reduced pressure to afford crude product, which, on purification by column chromatography afforded the title compound.

¹HNMR (DMSO-d₆) δ(ppm) 10.01 (s, 1H), 9.31 (s, 1H), 9.03 (s, 1H), 8.50 (d, 1H, J=6.0 Hz), 7.94 (d, 1H, J=7.8 Hz), 7.78 (d, 1H, J=6.0 Hz), 7.62-7.73 (m, 2H), 7.28 (d, 1H, J=7.8 Hz), 6.98 (t, 1H, J=8.7 Hz), 6.80 (d, 1H, J=6.9 Hz), 6.98 (t, 1H, J=7.5 Hz), 4.94 (s, 2H), 4.05 (s, 2H), 3.98 (t, 2H, J=5.4 Hz), 3.06 (b t, 2H)

Example 63

N²-(2-aminophenyl)-N⁵-[3-(dimethylamino)phenyl]-6,7-dihydro[1,3]thiazolo[5,4-c]pyridine-2,5(4H)-dicarboxamide dihydrochloride N²-(2-aminophenyl)-N⁵-[3-(dimethylamino)phenyl]-6,7-dihydro[1,3]thiazolo[5,4-c]pyridine-2,5(4H)-dicarboxamide obtained in example 18 was treated with etheral HCl to get its dihydrochloride salt.

¹H NMR (CD₃OD) δ(ppm) 7.90 (s, 1H, NH), 7.53 (m, 6H), 7.31 (m, 1H), 4.94 (s, 2H), 3.99 (t, 2H, J=5.7 Hz), 3.30 (s, 6H), 3.09 (t, 2H, J=5.7 Hz).

Example 64

N-(2-aminophenyl)-5-[{[4-(dimethylamino)phenyl]amino}(oxo)acetyl]-4,5,6,7-tetrahydro[1,3]thiazolo[5,4-c]pyridine-2-carboxamide Step-I N-(4-Dimethylamino-phenyl)-oxalamic acid ethyl ester N,N, dimethyl aniline (5.3 mmole) was dissolved in dichloromethane (20 ml). To this solution was added, pyridine (0.86 ml) and stirred at 0° C. Ethyl chlorooxalate (5.6 mmole) dissolved in dichloromethane (5 ml) was added slowly at 0° C. The reaction mixture was stirred at room temperature for 1 h, concentrated to dryness diluted with water, extracted with dichloromethane, washed with saturated brine and dried oven Na₂SO₄. Concentrate to gave the N-(4-Dimethylamino-phenyl)-oxalamic acid ethyl ester, which was used for the next step.

Step-II

N-(2-aminophenyl)-5-[{[4-(dimethylamino)phenyl]amino}(oxo)acetyl]-4,5,6,7-tetrahydro[1,3]thiazolo[5,4-c]pyridine-2-carboxamide N-(2-aminophenyl)-4,5,6,7-tetrahydro[1,3]thiazolo[5,4-c]pyridine-2-carboxamide. obtained in step VIII of Example 1 (7.3 mmol) was dissolved in 30 ml of dry DCM. To this solution trimethyl aluminum (0.55 ml) was added slowly, under stirring at 0° C. for 10 min. and then increased the temperature to RT stirred for 20 min. N-(4-Dimethylaminophenyl)-oxalamic acid ethyl ester (7.3 mmol) obtained in step I above in 10 ml of DCM was added slowly, and stirred overnight. The reaction mixture was quenced with sat. ammonium chloride solution and extracted with DCM, washed with aq. NaHCO3, Brine and dried over Na2SO4 and concentrated to get required product.

¹H NMR (DMSO-d₆) δ (ppm): −10.57 (s, 1H, NH), 10.07 (s, 1H, NH), 7.49 (d, 2H, J=9.0 Hz), 7.26 (d, 2H, J=8.1 Hz), 6.96 (dt, 1H, J=9.0 Hz, 1.5 Hz), 6.79 (d, 1H, J=8.1 Hz), 6.72 (m, 2H), 6.61 (dt, 1H, J=9.0 Hz, 1.2 Hz), 4.97 (br s, 2H, NH2), 4.93 (s, 2H), 3.97 (t, 2H, J=5.4 Hz), 3.88 (t, 1H, J=5.4 Hz), 3.01 (m, 2H), 2.56 (s, 6H).

Examples 65 to 87 were Also Obtained by Following the Procedure of Example 64

Example 65

N-(2-aminophenyl)-5-{[(4-methoxyphenyl)amino](oxo)acetyl}-4,5,6,7-tetrahydro[1,3]thiazolo[5,4-c]pyridine-2-carboxamide ¹H NMR (DMSO-d₆) δ (ppm):-(Rotamers) 10.69 & 10.76 (s, 1H), 10.01 & 10.05 (s, 1H), 7.60 (d, 2H, J=9.0 Hz), 7.26 (d, 1H, J=8.1, Hz), 6.91-7.00 (m, 3H), 6.79 (d, 1H, J=7.8 Hz), 6.61 (t, 1H, J=7.5 Hz), 4.95 (m, 4H), 3.88 & 3.96 (t, 2H, J=5.7 Hz), 3.74 (s, 3H), 2.95-3.08 (m, 2H).

Example 66

N-(2-aminophenyl)-5-{[(3,4-dimethoxyphenyl)amino](oxo)acetyl}-4,5,6,7-tetrahydro[1,3]thiazolo[5,4-c]pyridine-2-carboxamide ¹H NMR (DMSO-d₆) δ (ppm):-(Rotamers) 10.65 & 10.73 (s, 1H), 10.00 & 10.04 (s, 1H), 7.37 (d, 1H, J=2.4 Hz), 7.26 (m, 1H), 7.22 (dt, 1H, J=8.7 & 2.4 Hz), 6.91-7.02 (m, 2H), 6.78 (m, 1H), 6.61 (m, 1H), 4.85-5.00 (m, 4H), 3.90 & 3.97 (t, 1H, J=5.7 Hz), 3.74 (s, 6H), 2.95-3.05 (m, 2H).

Example 67

N-(2-aminophenyl)-5-{oxo[(4-pyridin-4-ylcyclohexyl)amino]acetyl}-4,5,6,7-tetrahydro[1,3]thiazolo[5,4-c]pyridine-2-carboxamide ¹HNMR (DMSO-d₆) δ(ppm) (Rotamers) 10.01 & 10.02 (s, 1H), 8.82 & 8.94 (d, 1H, J=8.1 Hz), 8.44-8.51 (m, 2H), 7.24-7.32 (m, 3H), 6.98 (t, 1H, J=8.1 Hz), 6.79 (d, 1H, J=8.1 Hz), 6.61 (t, 1H, J=7.8 Hz), 4.79-5.00 (m, 4H), 4.18 (m, 1H), 3.70-3.85 (m, 2H), 2.99 (m, 2H), 1.50-1.90 (m, 8H).

Example 68

N-(2-aminophenyl)-5-[(isoquinolin-5-ylamino)(oxo)acetyl]-4,5,6,7-tetrahydro[1,3]thiazolo[5,4-c]pyridine-2-carboxamide ¹HNMR (DMSO-d₆) δ(ppm) (Rotamers) 11.0 & 11.09 (s, 1H), 9.99-10.04 (m, 1H), 9.38 (s, 1H), 8.55-8.60 (m, 1H), 8.04-8.12 (m, 2H), 7.86 & 7.95 (d, 1H, J=6.0 Hz), 7.75 (m, 1H), 7.27 (d, 1H, J=7.8 Hz), 6.98 (t, 1H, J=8.1 Hz), 6.79 (d, 1H, J=8.1 Hz), 6.61 (t, 1H, J=7.8 Hz), 5.02 (m, 2H), 4.94 (s, 2H), 3.96 & 4.03 (t, 2H, J=5.7 Hz), 3.00-3.12 (m, 2H).

Example 69

N-(2-aminophenyl)-5-{oxo[(4-pyridin-3-ylcyclohexyl)amino]acetyl}-4,5,6,7-tetrahydro[1,3]thiazolo[5,4-c]pyridine-2-carboxamide $^1$H NMR (CDCl$_3$) δ (ppm):-(Rotamers) 8.91 (s, 1H), 8.49 (b s, 2H), 7.44-7.58 (m, 2H), 7.25 (m, 1H), 7.12 (t, 1H, J=7.8 Hz), 6.83-6.91 (m, 2H), 4.94 & 5.56 (s, 1H), 4.05 & 4.46 (m, 2H), 3.82 & 4.21 (m, 2H), 3.00-3.18 (m, 2H), 2.50-2.62 (m, 1H), 2.17 (b, 2H), 1.98 (b, 2H), 1.73-1.93 (m, 2H), 1.53-1.72 (m, 2H), 1.37-1.53 (m, 2H).

Example 70

N-(2-aminophenyl)-5-{[(6-methoxypyridin-3-yl)amino](oxo)acetyl}-4,5,6,7-tetrahydro[1,3]thiazolo[5,4-c]pyridine-2-carboxamide $^1$H NMR (DMSO-d$_6$) δ(ppm): −10.95 (s, 1H, NH), 10.04 (s, 1H, NH), 8.45 (d, 2H, J=9.0 Hz), 7.26 (d, 2H, J=8.1 Hz), 6.9 (t, 1H, J=7.51 Hz), 6.86 (dd, 1H, J=9.0 Hz, 3.3 Hz), 6.79 (d, 1H, J=7.8 Hz), 6.61 (t, 1H, J=7.5 Hz), 5.00 (br s, 2H, NH2), 4.94 (s, 2H), 3.93 (m, 2H), 3.84 (s, 3H), 3.01 (m, 2H).

Example 71

N-(2-aminophenyl)-5-[{[6-(dimethylamino)pyridin-3-yl]amino}(oxo)acetyl]-4,5,6,7-tetrahydro[1,3]thiazolo[5,4-c]pyridine-2-carboxamide $^1$H NMR (DMSO-d$_6$) δ(ppm): −10.67 (s, 1H, NH), 10.03 (s, 1H, NH), 8.34 (d, 1H, J=2.4 Hz), 7.81 (dt, 1H, J=9.0 Hz; 2.7 Hz), 7.26 (d, 1H, J=7.5 Hz), 6.97 (dt, 1H, J=7.5 Hz; 1.2 Hz), 6.79 (d, 1H, J=8.1 Hz), 6.68 (m, 2 Hz), 5.00 (s, 2H), 4.93 (s, 2H), 3.93 (m, 2H), 3.03 (m, 2H), 2.99 (s, 6H).

Example 72

N-(2-aminophenyl)-5-(oxo{[4-(trifluoromethoxy)phenyl]amino}acetyl)-4,5,6,7-tetrahydro[1,3]thiazolo[5,4-c]pyridine-2-carboxamide $^1$H NMR (DMSO-d$_6$) δ(ppm): −11.12 (s, 1H), 10.03 (s, 1H), 7.82-7.78 (m, 2H), 7.42-7.38 (m, 2H), 7.26 (m, 1H), 6.98 (m, 1H), 6.79 (m, 1H), 6.69 (m, 1H, 1 Hz), 4.98-4.93 (m, 4H), 3.90 (m, 2H), 3.04-3.02 (m, 2H).

Example 73

N-(2-aminophenyl)-5-{[(6-morpholin-4-ylpyridin-3-yl)amino](oxo)acetyl}-4,5,6,7-tetrahydro[1,3]thiazolo[5,4-c]pyridine-2-carboxamide $^1$H NMR (DMSO-d$_6$) δ(ppm): −10.79 (s, 1H), 10.04 (s, 1H), 8.42 (d, 1H, J=2.4 Hz), 7.90-7.85 (m, 1H), 7.27 (d, 1H, J=7.8 Hz), 6.98 (m, 1H), 6.89-6.85 (m, 1H), 6.79 (d, 1H, 1 Hz), 6.61 (m, 1H), 5.01-4.94 (m, 4H), 3.99-3.90 (m, 2H), 3724-3.69 (m, 4H), 3.42-3.39 (m, 4H), 3.04-2.99 (m, 2H).

Example 74

N-(2-aminophenyl)-5-[(1,3-benzodioxol-5-ylamino)(oxo)acetyl]-4,5,6,7-tetrahydro[1,3]thiazolo[5,4-c]pyridine-2-carboxamide $^1$H NMR (DMSO-d$_6$) δ(ppm): −10.81 (s, 1H), 10.04 (s, 1H), 7.34 (m, 1H), 7.27 (m, 1H), 7.10 (m, 1H), 7.00-6.89 (m, 2H), 6.79 (m, 1H), 6.61 (m, 1H), 6.02 (s, 2H), 4.94 (m, 4H), 3.98-3.87 (m, 2H), 3.04-2.99 (m, 2H).

Example 75

N-(2-aminophenyl)-5-{[(4-methylphenyl)amino](oxo)acetyl}-4,5,6,7-tetrahydro[1,3]thiazolo[5,4-c]pyridine-2-carboxamide $^1$H NMR (DMSO-d$_6$) δ(ppm): −10.04 (s, 1H), 7.56 (d, 2H, J=8.1 Hz), 7.28 (d, 1H, J=7.2 Hz), 7.17 (m, 2H), 6.98 (t, 1H, J=7.2 Hz), 6.79 (d, 1H, J=7.8 Hz), 6.61 (t, 1H, J=7.8 Hz), 4.92 (m, 4H), 3.96 (t, 1H, J=5.4 Hz), 3.87 (t, 1H, J=5.4 Hz), 3.02 (m, 2H).

Example 76

N-(2-aminophenyl)-5-{[(5-methylpyridin-2-yl)amino](oxo)acetyl}-4,5,6,7-tetrahydro[1,3]thiazolo[5,4-c]pyridine-2-carboxamide $^1$H NMR (DMSO-d$_6$) δ(ppm): −11.17 (s, 1H), 10.04 (s, 1H), 8.22 (s, 1H), 7.99 (d, 1H, J=8.4), 7.68 (d, 1H, J=8.4 Hz), 7.27 (d, 1H, J=8.1 Hz), 6.98 (dt, 1H, J=7.5 Hz; 1.2 Hz), 6.80 (d, 1H, J=7.8 Hz), 4.91 (m, 4H), 4.91 (m, 4H), 3.93 (m, 1H), 3.82 (m, 1H), 3.02 (m, 2H), 2.28 (s, 3H).

Example 77

N-(2-aminophenyl)-5-[oxo(quinolin-3-ylamino)acetyl]-4,5,6,7-tetrahydro-[1,3]thiazolo[5,4-c]pyridine-2-carboxamide $^1$H NMR (DMSO-d$_6$) δ(ppm): −11.44 (s, 1H), 10.05 (s, 1H), 9.03 (t, 1H, J=2.7 Hz), 7.99 (m, 2H), 7.67 (m, 2H), 7.28 (dd, 1H, J=7.8 Hz; 1.2 Hz), 6.98 (m, 1H), 6.80 (dd, 1H, J=7.8 Hz; 1.2 Hz), 6.62 (m, 1H), 5.05 (m, 2H), 4.94 (m, 2H), 3.97 (m, 2H), 3.07 (m, 2H).

Example 78

N-(2-amino-5-methoxyphenyl)-5-{[(4-methoxyphenyl)amino](oxo)acetyl}-4,5,6,7-tetrahydro[1,3]thiazolo[5,4-c]pyridine-2-carboxamide $^1$H NMR (DMSO-d$_6$) δ (ppm): −10.68 & 10.78 (s, 1H), 9.97 & 10.03 (s, 1H), 7.60 (d, 2H, J=9.0 Hz), 7.14 (m, 1H), 6.92-6.96 (m, 2H), 6.79 (d, 1H, J=8.7 Hz), 6.62-6.66 (m, 1H), 4.95 & 4.98 (s, 2H), 4.55 (b s, 2H), 3.89 & 3.97 (t, 2H, J=5.4 Hz), 3.74 & 3.75 (s, 3H), 3.66 (s, 3H), 3.02 (m, 2H).

Example 79

N-(2-aminophenyl)-5-[(butylamino)(oxo)acetyl]-4,5,6,7-tetrahydro[1,3]thiazolo[5,4-c]pyridine-2-carboxamide $^1$H NMR (DMSO-d$_6$) δ (ppm): −10.01 (s, 1H), 8.80 (m, 1H), 7.26 (d, 1H, J=8.1 Hz), 6.97 (t, 1H, J=8.1 Hz), 6.79 (d, 1H, J=8.1 Hz), 6.61 (t, 1H, J=8.1 Hz), 4.89 (m, 4H), 3.81 &

3.90 (t, 2H, J=5.7 Hz), 3.16 (m, 2H), 2.90-3.20 (m, 2H), 1.43 (m, 2H), 1.30 (m, 2H), 0.89 (m, 3H).

Example 80

N-(2-amino-5-isopropylphenyl)-5-{[(3,4-dimethoxyphenyl)amino](oxo)acetyl}-4,5,6,7-tetrahydro[1,3]thiazolo[5,4-c]pyridine-2-carboxamide $^1$H NMR (DMSO-d$_6$) δ (ppm): −10.67 & 10.74 (s, 1H), 9.97 & 10.01 (s, 1H), 7.38 (d, 1H, J=2.1 Hz), 7.19-7.23 (m, 2H), 6.95 (m, 1H), 6.88 (m, 1H), 6.74 (d, 1H, J=8.1 Hz), 4.95 & 4.99 (s, 2H), 4.75 (s, 2H), 3.90 (t, 2H), 3.74 (m, 6H), 3.04 (m, 2H), 2.75 (q, 1H, J=6.9 Hz), 1.15 (d, 6H, J=6.9 Hz).

Example 81

N-(2-amino-5-isopropylphenyl)-5-{[(4-methoxyphenyl)amino](oxo)acetyl}-4,5,6,7-tetrahydro[1,3]thiazolo[5,4-c]pyridine-2-carboxamide $^1$H NMR (DMSO-d$_6$) δ (ppm): −10.78 & 10.80 (s, 1H), 9.97 & 10.02 (s, 1H), 7.60 (d, 2H, J=9.0 Hz), 7.20 (d, 1H, J=1.8 Hz), 6.86 & 7.00 (m, 3H), 6.74 (d, 1H, J=8.4 Hz), 4.95 & 4.98 (s, 2H), 4.75 (s, 2H), 3.89 & 3.96 (t, 2H, J=5.4 Hz), 3.74 & 3.75 (s, 3H), 3.04 (m, 2H), 2.75 (q, 1H, J=6.9 Hz), 1.15 (d, 6H, J=6.9 Hz).

Example 82

N-(2-amino-5-methoxyphenyl)-5-{[(3,4-dimethoxyphenyl)amino](oxo)acetyl}-4,5,6,7-tetrahydro[1,3]thiazolo[5,4-c]pyridine-2-carboxamide $^1$H NMR (DMSO-d$_6$) δ (ppm): −10.66 & 10.74 (s, 1H), 9.99 & 10.03 (s, 1H), 7.38 (d, 1H, J=2.4 Hz), 7.20 (m, 1H), 7.14 (d, 1H, J=3.0 Hz), 6.93 & 6.95 (d, 1H, J=9.0 Hz), 6.80 (d, 1H, J=8.7 Hz), 6.60 (m, 1H), 4.94 & 4.99 (s, 2H), 4.59 (b s, 2H), 3.90 & 3.97 (t, 2H, J=5.7 Hz), 3.75 (m, 6H), 3.67 (s, 3H), 3.02 (b t, 2H).

Example 83

N-(2-amino-5-methoxyphenyl)-5-[(butylamino)(oxo)acetyl]-4,5,6,7-tetrahydro[1,3]thiazolo[5,4-c]pyridine-2-carboxamide $^1$H NMR (CDCl$_3$) δ (ppm): −9.23 (s, 1H), 8.11 & 8.32 (m, 1H), 7.44 (m, 1H), 6.84 & 7.03 (d, 1H, J=8.7 Hz), 6.69 (m, 1H), 4.94 & 5.53 (s, 2H), 4.04 & 4.45 (t, 2H, J=5.7 Hz), 3.80 & 3.87 (s, 3H), 3.34 (m, 2H), 3.04 & 3.137 (b t, 2H), 1.35 & 1.63 (m, 4H), 0.96 (m, 3H).

Example 84

N-(2-amino-5-isopropylphenyl)-5-[(butylamino)(oxo)acetyl]-4,5,6,7-tetrahydro[1,3]thiazolo[5,4-c]pyridine-2-carboxamide $^1$H NMR (DMSO-d$_6$) δ (ppm): −9.97 (s, 1H), 8.76 & 8.80 (t, 1H, J=5.4 Hz), 7.21 (d, 1H, J=1.8 Hz), 6.87 (dd, 1H, J=8.4, 2.1 Hz), 4.87 & 4.90 (s, 2H), 4.74 (b s, 2H), 3.82 & 3.90 (t, 1H, J=5.4 Hz), 3.17 (m, 2H), 2.97 (m, 2H), 2.87 (m, 2H), 2.75 (q, 1H, J=6.9 Hz), 1.10-1.52 (m, 10H), 0.88 (t, 3H, J=7.2 Hz).

Example 85

N-(2-aminophenyl)-5-[(benzylamino)(oxo)acetyl]-4,5,6,7-tetrahydro[1,3]thiazolo[5,4-c]pyridine-2-carboxamide $^1$H NMR (DMSO-d$_6$) δ(ppm): −10.01 (s, 1H, NH), 9.30 (m, 1H), 7.40-7.25 (m, 6H), 6.98 (m, 1H), 6.79 (dd, 1H, J=8.1 Hz; 1.2 Hz), 6.61 (m, 1 Hz), 4.93-4.88 (m, 4H), 4.40-4.38 (m, 2H), 3.94-3.80 (m, 2H), 2.97-2.96 (m, 2H).

Example 86

N-(2-aminophenyl)-5-[{[6-(4-methylpiperazin-1-yl)pyridin-3-yl]amino}(oxo)acetyl]-4,5,6,7-tetrahydro[1,3]thiazolo[5,4-c]pyridine-2-carboxamide $^1$HNMR (DMSO-d$_6$) δ (ppm): −10.74 (s, 1H), 10.66 (s, 1H), 8.37 (d, 1H, J=2.4 Hz), 7.83 (m, 1H), 7.25 (d, 1H, J=7.5 Hz), 6.96 (t, 1H, J=7.5 Hz), 6.85 (dd, 1H, J=9.0 Hz; 3.0 Hz), 6.78 (d, 1H, J=8.1 Hz), 6.59 (t, 1H, J=7.2 Hz), 4.98 (s, 2H), 4.92 (s, 2H), 3.92 (m, 2H), 3.42 (m, 4H), 2.99 (m, 2H), 2.49 (m, 4H), 2.20 (s, 3H)

Example 87

N-(2-aminophenyl)-5-{oxo[(pyridin-3-ylmethyl)amino]acetyl}-4,5,6,7-tetrahydro[1,3]thiazolo[5,4-c]pyridine-2-carboxamide 1HNMR (DMSO-d6) d (ppm): −9.41 (m, 1H, NH), 8.52 (m, 2H), 7.74 (m, 1H), 7.42 (m, 1H), 7.26 (d, 1H, J=7.8 Hz), 6.98 (dt, 1H, J=8.1 & 1.5 Hz), 6.80 (dd, 1H, J=7.8 & 1.2 Hz), 6.62 (dt, 1H, J=8.1 & 1.5 Hz), 4.93 (s, 2H), 4.88 (s, 2H), 4.41 (t, 2H, J=6.3 Hz), 3.92 (t, 1H, J=5.7 Hz), 3.82 (t, 1H, J=5.7 Hz), 2.96 (t, 2H, J=5.4 Hz).

Example 88

N-(2-aminophenyl)-5-(biphenyl-4-ylcarbonyl)-4,5,6,7-tetrahydro[1,3]thiazolo[5,4-c]pyridine-2-carboxamide To a solution of biphenyl-4-carboxylic acid (1.0 mmol) in dry 10 mL DMF, were added 1-hydroxybenzotriazole (1.2 mmol), 1-ethyl-3-(3'-dimethylaminopropyl)carbodiimide (2 mmol) and N-methylmorpholine (2.0 mmol). Solution was cooled to 0° C. N-(2-aminophenyl)-4,5,6,7-tetrahydro[1,3]thiazolo[5,4-c]pyridine-2-carboxamide obtained from step VIII of example 1 (1.1 mmole.) was then added and mixture was stirred at room temperature overnight. Reaction mixture was concentrated, diluted with water, extracted with dichloromethane, washed with brine solution, and dried over anhydrous Na$_2$SO$_4$. Concentrated and purified by column chromatography to yield the title compound.

$^1$H NMR (CDCl$_3$) δ(ppm): −8.93 (s, 1H, NH), 7.71-7.39 (m, 10H), 7.12 (t, 1H, J=7.5 Hz), 6.88 (m, 3H), 5.05 (s, 2H), 3.90 (s, 2H), 3.06 (s, 2H), 2.60 (s, 2H), 2.07 (m, 2H).

Examples 89 to 97 were Also Obtained by Following the Procedure of Example 88

Example 89

N-(2-aminophenyl)-5-(4-methylbenzoyl)-4,5,6,7-tetrahydro[1,3]thiazolo[5,4-c]pyridine-2-carboxamide $^1$H NMR (CDCl$_3$) δ(ppm): −8.90 (s, 1H, NH), 7.47 (d, 1H, J=7.2 Hz), 7.40 (d, 2H, J=8.1 Hz), 7.13 (m, 1H), 6.89 (t, 2H, J=7.8 Hz), 4.99 (s, 2H), 3.86 (s, 2H), 3.03 (s, 2H), 2.43 (s, 3H).

Example 90

Methyl 4-({2-[(2-aminophenyl)carbamoyl]-6,7-dihydro[1,3]thiazolo[5,4-c]pyridin-5(4H)-yl}carbonyl)benzoate $^1$H NMR (DMSO-d$_6$) δ (ppm): −10.05 (s, 1H, NH), 8.05 (d, 2H, J=8.7 Hz), 7.65 (m, 2H), 7.26 (d, 1H, J=7.5 Hz), 6.97 (t, 1H, J=6.9 Hz), 6.78 (d, 1H, J=7.5 Hz), 6.61 (t, 1H, J=7.5 Hz), 4.92 (m, 4H), 3.89 (s, 3H), 3.64 (m, 2H), 2.96 (m, 2H).

Example 91

N-(2-aminophenyl)-5-[4-(dimethylamino)benzoyl]-4,5,6,7-tetrahydro[1,3]thiazolo[5,4-c]pyridine-2-carboxamide $^1$H NMR (DMSO-d$_6$) δ(ppm): −10.00 (s, 1H, NH), 7.37 (d, 2H, J=8.7 Hz), 7.25 (dd, 1H, J=6.6 Hz, 1.2 Hz), 6.93 (t, 1H, J=7.2 Hz), 6.79-6.71 (m, 3H), 6.59 (t, 1H, J=6.3 Hz), 4.92 (s, 2H), 4.88 (s, 2H), 3.84 (s, 2H), 2.96 (s, 6H), 2.92 (m, 2H).

Example 92

5-acetyl-N-(2-aminophenyl)-4,5,6,7-tetrahydro[1,3]thiazolo[5,4-c]pyridine-2-carboxamide $^1$H NMR (DMSO-d$_6$) δ(ppm): −9.95 (s, 1H, NH), 7.27 (dd, 1H, J=6.6 Hz, 1.2 Hz), 6.95 (dt, 1H, J=6.9 Hz, 1.5 Hz), 6.77 (dd, 1H, J=6.9 Hz, 1.2 Hz), 6.60 (dt, 1H, J=6.3 Hz, 1.2 Hz), 4.91 (s, 2H), 4.82 (d, 2H, J=16.2 Hz), 3.80 (m, 2H), 2.99-2.85 (m, 2H), 2.08 (s, 3H).

Example 93

N-(2-aminophenyl)-5-(4-methoxybenzoyl)-4,5,6,7-tetrahydro[1,3]thiazolo[5,4-c]pyridine-2-carboxamide $^1$H NMR (DMSO-d$_6$) δ(ppm): −10.01 (s, 1H, NH), 7.48 (d, 2H, J=8.7 Hz), 7.26 (dd, 1H, J=7.8 Hz, 0.9 Hz), 7.03 (d, 2H, J=8.7 Hz), 6.98 (dt, 1H, J=7.4 Hz, 1.5 Hz), 6.79 (dd, 1H, J=7.5 Hz, 1.3 Hz), 6.61 (dt, 1H, J=7.2 Hz, 1.2 Hz), 4.93 (s, 2H), 4.89 (s, 2H), 3.81 (s, 5H), 3.00 (m, 2H).

Example 94

N-(2-aminophenyl)-5-(quinolin-3-ylcarbonyl)-4,5,6,7-tetrahydro[1,3]thiazolo[5,4-c]pyridine-2-carboxamide $^1$H NMR (DMSO-d$_6$) δ (ppm): −10.03 (s, 1H, NH), 9.00 (s, 1H), 8.58 (s, 1H), 8.18 (d, 2H, J=8.1 Hz), 7.88 (dt, 1H, J=7.0 Hz, 1.5 Hz), 7.71 (t, 1H, J=7.2 Hz), 7.27 (d, 1H, J=7.8 Hz), 6.98 (t, 1H, J=7.2 Hz), 6.79 (d, 1H, J=7.5 Hz), 6.61 (t, 1H, J=7.8 Hz), 5.06 (s, 2H), 4.93 (s, 2H), 4.20-3.90 (m, 2H), 3.06 (m, 2H).

Example 95

N-(2-aminophenyl)-5-(2-naphthoyl)-4,5,6,7-tetrahydro[1,3]thiazolo[5,4-c]-pyridine-2-carboxamide $^1$H NMR (DMSO-d$_6$) δ(ppm): −10.01 (s, 1H, NH), 8.10-7.99 (m, 4H), 7.65-7.58 (m, 3H), 7.27 (d, 2H, J=7.5 Hz), 6.98 (d, 2H, J=6.9 Hz), 6.79 (d, 1H, J=7.2 Hz), 6.61 (t, 1H, J=7.5 Hz), 5.02 (s, 2H), 4.93 (s, 2H), 4.04-3.76 (m, 2H), 3.03 (m, 2H).

Example 96

N-(2-aminophenyl)-5-[(6-methylpyridin-3-yl)carbonyl]-4,5,6,7-tetrahydro-[1,3]thiazolo[5,4-c]pyridine-2-carboxamide $^1$H NMR (DMSO-d$_6$) δ(ppm): −10.00 (s, 1H, NH), 8.57 (s, 1H), 7.81 (2, 1H), 7.37 (d, 2H, J=8.1 Hz), 7.24 (d, 2H, J=7.5 Hz), 6.95 (t, 1H, J=6.9 Hz), 6.77 (d, 1H, J=7.2 Hz), 6.59 (t, 1H, J=7.5 Hz), 4.91 (m, 4H), 3.70-3.49 (m, 2H), 2.99 (m, 2H), 2.49 (s, 3H).

Example 97

N-(2-aminophenyl)-5-[3-(dimethylamino)benzoyl]-4,5,6,7-tetrahydro[1,3]thiazolo[5,4-c]pyridine-2-carboxamide $^1$H NMR (DMSO-d$_6$) δ(ppm): −9.99 (s, 1H, NH), 7.27 (m, 1H), 6.97 (dt, 1H, J=7.2 Hz, 1.2 Hz), 6.80 (t, 2H, J=8.1 Hz), 6.80 (t, 2H, J=8.1 Hz), 6.72 (m, 2H), 6.61 (t, 1H, J=8.1 Hz), 4.92 (m, 4H), 3.70 (m, 2H), 2.93 (m, 9H).

Example 98

N-(2-aminophenyl)-5-(anilinocarbonothioyl)-4,5,6,7-tetrahydro[1,3]thiazolo[5,4-c]pyridine-2-carboxamide To a solution of N-(2-aminophenyl)-4,5,6,7-tetrahydro[1,3]thiazolo[5,4-c]pyridine-2-carboxamide. obtained in step VIII of Example 1 (1 eq) in dichloromethane, a solution of isothiocynato benzene (1 eq) in dichloromethane was added and the reaction was stirred at room temperature for 3 h. Water was added and the organic layer was separated, dried over anhydrous Na$_2$SO$_4$ and concentrated under reduced pressure to afford crude product, which, on purification by column chromatography afforded the title compound.

$^1$H NMR (DMSO-d$_6$) δ (ppm): −10.01 (s, 1H), 9.63 (s, 1H), 7.30-7.33 (m, 4H), 7.27 (dd, 2H, J=8.1, 1.5 Hz), 7.14 (m, 1H), 6.98 (dt, 1H, J=7.8, 1.5 Hz), 6.79 (dd, 2H, J=8.1, 1.2 Hz), 6.61 (dt, 1H, J=7.8, 1.2 Hz), 5.29 (s, 2H), 4.94 (s, 2H), 4.28 (t, 2H, J=5.7 Hz), 3.07 (br t, 2H).

Examples 99 to 110 were Also Obtained by Following the Procedure of Example 98

Example 99

N-(2-aminophenyl)-5-({[4-(dimethylamino)phenyl]amino}carbonothioyl)-4,5,6,7-tetrahydro[1,3]thiazolo[5,4-c]pyridine-2-carboxamide $^1$H NMR (DMSO-d$_6$) δ (ppm): −10.00 (s, 1H), 9.41 (s, 1H), 7.27 (dd, 1H, J=7.8 Hz), 7.08 (d, 2H, J=8.7 Hz), 6.98 (dt, 1H, J=7.8, 1.5 Hz), 6.79 (dd, 1H, J=8.1, 1.5 Hz), 6.68 (d, 2H, J=9.0 Hz), 6.61 (dt, 1H, J=7.8, 1.5 Hz), 5.28 (s, 2H), 4.94 (s, 2H), 4.26 (t, 2H, J=5.4 Hz), 3.02 (br t, 2H), 2.88 (s, 6H)

Example 100

N-(2-aminophenyl)-5-[(piperidin-4-ylamino)carbonothioyl]-4,5,6,7-tetrahydro[1,3]thiazolo[5,4-c]pyridine-2-carboxamide $^1$H NMR (CD$_3$OD) δ(ppm): −7.48-7.57 (m, 4H), 5.25 (s, 2H), 4.62-4.72 (m, 1H), 4.25 (t, 2H, J=5.4 Hz), 3.40-3.61 (m, 2H), 3.09-3.13 (m, 4H), 2.22-2.30 (m, 2H), 1.81-1.95 (m, 2H).

Example 101

N-(2-aminophenyl)-5-{[(4-pyridin-3-ylcyclohexyl)amino]carbonothioyl}-4,5,6,7-tetrahydro[1,3]thiazolo[5,4-c]pyridine-2-carboxamide $^1$H NMR (DMSO-d$_6$) δ(ppm): −9.97 (s, 1H), 8.50 (d, 1H, J=1.8 Hz), 8.40 (dd, 1H, J=4.5, 1.2 Hz), 7.65-7.72 (m, 2H), 7.25-7.33 (m, 2H), 6.98 (t, 1H, J=8.7 Hz), 6.79 (dd, 1H, J=7.8, 1.2 Hz), 6.61 (t, 1H, J=7.8 Hz), 5.12 (s, 2H), 4.94 (b s, 2H), 4.32 (m, 1H), 4.19 (t, 2H, J=5.4 Hz), 2.96 (b t 2H), 2.57 (b 1H), 2.06-2.02 (m, 2H), 1.83-1.86 (m, 2H), 1.45-1.63 (m, 4H)

Example 102

N-(2-amino-5-methoxyphenyl)-5-(anilinocarbonothioyl)-4,5,6,7-tetrahydro[1,3]thiazolo[5,4-c]pyridine-2-carboxamide $^1$H NMR (DMSO-d$_6$) δ(ppm): −9.99 (s, 1H), 9.64 (s, 1H), 7.32 (m, 4H), 7.14 (m, 2H), 6.80 (d, 1H, J=8.7 Hz), 6.64 (dd, 1H, J=8.7, 3.0 Hz), 5.30 (s, 2H), 4.54 (b s, 2H), 4.29 (t, 2H, J=5.7 Hz), 3.67 (s, 3H), 3.07 (b t, 2H).

Example 103

N-(2-aminophenyl)-5-[(pyridin-3-ylamino)carbonothioyl]-4,5,6,7-tetrahydro[1,3]thiazolo[5,4-c]pyridine-2-carboxamide $^1$H NMR (DMSO-d$_6$) δ (ppm): −10.01 (s, 1H), 9.74 (s, 1H), 8.51 (d, 1H, J=2.1 Hz), 8.33 (dd, 1H, J=7.8, 1.5 Hz), 7.76 (m, 1H), 7.37 (dd, 1H, J=7.8, 4.8 Hz), 7.27 (dd, 1H, J=8.1, 1.2 Hz), 6.98 (t, 1H, J=8.7 Hz), 6.79 (dd, 1H, J=7.8, 1.2 Hz), 6.62 (t, 1H, J=8.4 Hz), 5.33 (s, 2H), 4.94 (s, 2H), 4.31 (t, 2H, J=5.7 Hz), 3.09 (br t, 2H).

Example 104

N-(2-aminophenyl)-5-[(isoquinolin-5-ylamino)carbonothioyl]-4,5,6,7-tetrahydro[1,3]thiazolo[5,4-c]pyridine-2-carboxamide $^1$H NMR (DMSO-d$_6$) δ (ppm): −10.06 (s, 1H), 9.92 (s, 1H), 9.35 (s, 1H), 8.50 (d, 1H, J=5.7 Hz), 8.06 (d, 1H, J=8.1 Hz), 7.60-7.75 (m, 3H), 7.31 (dd, 1H, J=7.8, 1.2 Hz), 7.01 (t, 1H, J=7.2 Hz), 6.83 (dd, 1H, J=7.8, 1.5 Hz), 6.65 (t, 1H, J=7.2 Hz), 5.44 (m, 2H), 4.99 (s, 2H), 4.40 (t, 2H, J=5.4 Hz), 3.16 (b t, 2H).

Example 105

N-(2-aminophenyl)-5-[(butylamino)carbonothioyl]-4,5,6,7-tetrahydro[1,3]thiazolo[5,4-c]pyridine-2-carboxamide $^1$H NMR (DMSO-d$_6$) δ (ppm): −9.97 (s, 1H), 7.96 (t, 1H, J=4.8 Hz), 7.27 (m, 1H), 6.97 (t, 1H, J=7.8 Hz), 6.79 (d, 1H, J=7.8 Hz), 6.61 (t, 1H, J=7.8 Hz), 5.19 (s, 2H), 4.93 (m, 2H), 4.14 (t, 2H, J=5.7 Hz), 3.53 (m, 2H), 2.94 (b t, 2H), 1.54 (m, 2H), 1.27 (m, 2H), 0.89 (t, 3H, J=7.2 Hz).

Example 106

N-(2-amino-5-methoxyphenyl)-5-{[(4-methoxyphenyl)amino]carbonothioyl}-4,5,6,7-tetrahydro[1,3]thiazolo[5,4-c]pyridine-2-carboxamide $^1$H NMR (DMSO-d$_6$) δ (ppm): −9.98 (s, 1H), 9.51 (s, 1H), 7.14-7.21 (m, 3H), 6.89 (d, 2H, J=8.7 Hz), 6.97 (d, 1H, J=8.7 Hz), 6.63 (dd, 1H, J=8.7, 2.7 Hz), 5.03 (s, 2H), 4.54 (b s, 2H), 4.27 (t, 2H, J=6.0 Hz), 3.76 (s, 3H), 3.67 (s, 3H), 3.06 (b t, 2H).

Example 107

N-(2-amino-5-methoxyphenyl)-5-[(pyridin-3-ylamino)carbonothioyl]-4,5,6,7-tetrahydro[1,3]thiazolo[5,4-c]pyridine-2-carboxamide $^1$H NMR (DMSO-d$_6$) δ (ppm): −9.99 (s, 1H), 9.76 (s, 1H), 8.51 (d, 1H, J=6.0 Hz), 8.33 (dd, 1H, J=4.5, 1.5 Hz), 7.76 (m, 1H), 7.37 (dd, 1H, J=8.1, 4.5 Hz), 7.15 (d, 1H, J=2.7 Hz), 6.80 (d, 1H, J=8.7 Hz), 6.63 (dd, 1H, J=8.7, 3.0 Hz), 5.34 (s, 2H), 4.53 (b s, 2H), 4.30 (t, 2H, J=5.7 Hz), 3.67 (s, 3H), 3.09 (b t, 2H).

Example 108

N-(2-amino-5-isopropylphenyl)-5-[(pyridin-3-ylamino)carbonothioyl]-4,5,6,7-tetrahydro[1,3]thiazolo[5,4-c]pyridine-2-carboxamide $^1$HNMR (DMSO-d$_6$) δ (ppm): −9.97 (s, 1H), 9.74 (s, 1H), 8.51 (d, 1H, J=2.1 Hz), 8.33 (m, 1H), 7.77 (m, 1H), 7.36 (dd, 1H, J=8.1, 5.4 Hz), 7.22 (d, 1H, J=1.8 Hz), 6.85 (dd, 1H, J=8.1, 2.1 Hz), 6.75 (d, 1H, J=8.1 Hz), 5.34 (s, 2H), 4.75 (b s, 2H), 4.32 (t, 2H, J=5.4 Hz), 3.09 (br t, 2H), 2.76 (q, 1H, J=6.9 Hz), 1.16 (d, 6H, J=6.9 Hz).

Example 109

N-(2-amino-5-isopropylphenyl)-5-(anilinocarbonothioyl)-4,5,6,7-tetrahydro[1,3]thiazolo[5,4-c]pyridine-2-carboxamide $^1$H NMR (DMSO-d$_6$) δ (ppm): −9.96 (s, 1H), 9.63 (s, 1H), 7.28 (m, 4H), 7.22 (d, 1H, J=1.8 Hz), 7.14 (m, 1H), 6.87 (dd, 1H, J=8.1, 2.1 Hz), 6.75 (d, 1H, J=8.1 Hz), 5.29 (s, 2H), 4.75 (b s, 2H), 4.29 (t, 2H, J=5.7 Hz), 3.07 (br t, 2H), 2.76 (q, 1H, J=6.9 Hz), 1.16 (d, 6H, J=6.9 Hz).

Example 110

N-(2-amino-5-isopropylphenyl)-5-{[(4-methoxyphenyl)amino]carbonothioyl}-4,5,6,7-tetrahydro[1,3]thiazolo[5,4-c]pyridine-2-carboxamide $^1$H NMR (DMSO-d$_6$) δ (ppm): –10.08 (s, 1H), 9.49 (s, 1H), 7.24 (b, 2H), 7.18 (d, 2H, J=9.0 Hz), 6.80-7.00 (m, 4H), 5.29 (s, 2H), 4.26 (t, 2H, J=5.7 Hz), 3.74 (s, 3H), 3.04 (b t, 2H), 2.72 (m, 1H), 1.15 (d, 6H, J=6.9 Hz).

Example 111

N-(2-aminophenyl)-5-{imino[(4-methoxyphenyl)amino]methyl}-4,5,6,7-tetrahydro[1,3]thiazolo[5,4-c]pyridine-2-carboxamide

Step-I

4-Methoxy-phenyl-cyanamide

To a solution of cyanobromide (0.6 eq) in diethyl ether, a solution of 4-methoxy phenyl amine (1.0 eq) in diethyl ether was added and the reaction mixture was stirred at room temperature for 2 h. Salt separated out was filtered and the filtrate was concentrated to afford the desired 4-methoxy-phenyl-cyanamide in good yield.

Step-II

N-(2-aminophenyl)-5-{imino[(4-methoxyphenyl)amino]methyl}-4,5,6,7-tetrahydro[1,3]thiazolo[5,4-c]pyridine-2-carboxamide A solution of 4-methoxy-phenyl-cyanamide (2 eq) obtained in step I above and N-(2-aminophenyl)-4,5,6,7-tetrahydro[1,3]thiazolo[5,4-c]pyridine-2-carboxamide obtained in step VIII of example I (1.0 eq) in chlorobenzene was refluxed for 6 h. Solvent was evaporated and the residue was treated with ethereal HCl at room temperature for 5-15 h. Solvent was evaporated and the residue was dissolved in methanol—DCM system and neutralized. Organic layer was separated, dried on anhydrous Na2SO4 and concentrated under reduced pressure to afford crude product, which was then purified, by either column chromatography or preparative HPLC to afford the title compound.

$^1$H NMR (DMSO-d$_6$) δ (ppm): –10.20 (s, 1H), 8.30 (d, 1H, J=6.6 Hz), 8.15 (b, 1H), 7.53 (d, 2H, J=6.9 Hz), 6.81-7.03 (m, 6H), 5.51 (s, 2H), 3.96 (s, 2H), 3.70 (s, 3H), 2.96 (t, 2H, J=5.7 Hz), 2.55 (b, 2H).

Examples 112 and 113 were Obtained by Following the Procedure of Example 111

Example 112

N-(2-amino-5-isopropylphenyl)-5-{imino[(4-methoxyphenyl)amino]methyl}-4,5,6,7-tetrahydro[1,3]thiazolo[5,4-c]pyridine-2-carboxamide $^1$H NMR (DMSO-d$_6$) δ (ppm): –8.19 (s, 1H), 7.17-7.40 (m, 3H), 7.07 (d, 1H, J=8.1 Hz), 6.99 (d, 1H, J=7.2 Hz), 6.86 (d, 2H, J=8.7 Hz), 4.11 (s, 2H), 3.79 (s, 3H), 3.18 (t, 2H, J=5.4 Hz), 2.91 (q, 1H, J=6.9 Hz), 2.81 (b t, 2H), 1.25 (d, 6H, J=6.9 Hz).

Example 113

N-(2-aminophenyl)-5-[(benzylamino)(imino)methyl]-4,5,6,7-tetrahydro[1,3]thiazolo[5,4-c]pyridine-2-carboxamide $^1$H NMR (DMSO-d$_6$) δ(ppm): –10.64 (s, 1H), 8.27 (dd, 1H, J=8.1, 1.2 Hz), 7.25-7.41 (m, 6H), 6.97-7.01 (m, 2H), 6.85 (t, 1H, J=7.8 Hz), 6.28 (t, 1H, J=5.1 Hz), 5.51 (s, 2H), 4.59 (d, 2H, J=5.1 Hz), 3.96 (s, 2H), 2.96 (t, 2H, J=5.4), 2.61 (m, 2H)

Example 114

N-(2-aminophenyl)-5-[anilino(methylimino)methyl]-4,5,6,7-tetrahydro[1,3]thiazolo[5,4-c]pyridine-2-carboxamide. (Dihydrochloride)

Step I

Methyl 2-({2-[(tert-butoxycarbonyl)amino]phenyl}carbamoyl)-N-phenyl-6,7-dihydro[1,3]thiazolo[5,4-c]pyridine-5(4H)-carbimidothioate A suspension of 5-[(Z)-(methylthio)(phenylimino)methyl]-4,5,6,7-tetrahydro[1,3]thiazolo[5,4-c]pyridine-2-carboxylic acid obtained in step III of example 116 (1 eq), mono Boc-protected o-phenylene diamine (1.2 eq), EDCI (1.2 eq), HOBt (1.2 eq) and triethylamine in DMF were stirred at room temperature for 15 h. Solvent was evaporated and the title intermediate which was purified by either column chromatography or preparative HPLC.

Step-II tert-butyl {2-[({5-[(E)-(methylamino)(phenylimino)methyl]-4,5,6,7-tetrahydro[1,3]thiazolo[5,4-c]pyridin-2-yl}carbonyl)amino]phenyl}carbamate A solution of methyl 2-({2-[(tert-butoxycarbonyl)amino]phenyl}carbamoyl)-N-phenyl-6,7-dihydro[1,3]thiazolo[5,4-c]pyridine-5(4H)-carbimidothioate obtained form step I (1 eq), and methylamine HCl (60 eq) in DMF was heated at 50° C. in a sealed tube for 72 h. Solvent was evaporated and the residue was purified by either column chromatography or preparative HPLC to afford the tert-butyl {2-[({5-[(E)-(methylamino)(phenylimino)methyl]-4,5,6,7-tetrahydro[1,3]thiazolo[5,4-c]pyridin-2-yl}carbonyl)amino]phenyl}carbamate $^1$H NMR (DMSO-d$_6$) δ (ppm): –10.08 (s, 1H), 9.20 (s, 1H), 8.27 (s, 1H), 7.80 (dd, 1H, J=7.2, 2.4 Hz), 7.19-7.33 (m, 5H), 6.86-6.95 (m, 3H), 4.61 (s, 2H), 3.64 (t, 2H, J=5.7 Hz), 2.86 (br t, 2H), 2.64 (s, 3H), 1.47 (s, 9H)

Step-III

N-(2-aminophenyl)-5-[anilino(methylimino)methyl]-4,5,6,7-tetrahydro[1,3]thiazolo[5,4-c]pyridine-2-carboxamide tert-butyl {2-[({5-[(E)-(methylamino)(phenylimino)methyl]-4,5,6,7-tetrahydro[1,3]thiazolo[5,4-c]pyridin-2-yl}carbonyl)amino]phenyl}carbamate obtained in step II above was treated with ethereal HCl at room temperature for 5-15 h. Solvent was evaporated and the residue was purified by either column chromatography or preparative HPLC to give N-(2-aminophenyl)-5-[anilino(methylimino)methyl]-4, 5,6,7-tetrahydro[1,3]thiazolo[5,4-c]pyridine-2-carboxamide, which was then converted into its dihydrochloride salt.

$^1$H NMR (DMSO-$d_6$) δ (ppm): −10.43 (s, 1H), 10.21 (s, 1H), 8.81 (m, 1H), 7.39-7.44 (m, 3H), 7.20 (m, 5H), 4.77 (s, 2H), 3.85 (t, 2H, J=5.4 Hz), 3.03 (br t, 2H), 2.83 (d, 3H, J=4.5 Hz)

Example 115

N-(2-amino-5-methoxyphenyl)-5-[[(4-methoxyphenyl)amino](methylimino)methyl]-4,5,6,7-tetrahydro[1,3]thiazolo[5,4-c]pyridine-2-carboxamide Obtained following the procedure of example 114.
$^1$H NMR (DMSO-$d_6$) δ (ppm): −9.94 (s, 1H), 7.14-7.21 (m, 3H), 6.73-6.87 (m, 4H), 6.63 (dd, 1H, J=8.7, 3.0 Hz), 4.56 (s, 2H), 4.52 (b s, 2H), 3.66 (s, 3H), 3.59 (t, 2H, J=5.1 Hz), 2.91 (b t 2H), 2.58 (s, 3H).

Example 116

N-(2-aminophenyl)-5-[anilino(cyanoimino)methyl]-4,5,6,7-tetrahydro[1,3]thiazolo[5,4-c]pyridine-2-carboxamide Step-I ethyl 5-(anilinocarbonothioyl)-4,5,6,7-tetrahydro[1,3]thiazolo[5,4-c]pyridine-2-carboxylate 5-tert-butyl 2-ethyl 6,7-dihydro[1,3]thiazolo[5,4-c]pyridine-2,5(4H)-dicarboxylate obtained in step V of example 1 was deprotected to get the hydrochloride salt of 4,5,6,7-Tetrahydro-thiazolo[5,4-c]pyridine-2-carboxylic acid ethyl ester. To a solution of a HCl salt of 4,5,6,7-Tetrahydro-thiazolo[5,4-c]pyridine-2-carboxylic acid ethyl ester (1 eq) in dichloromethane, triethyl amine (1.2 eq) was added at 0° C. and the reaction mixture was stirred for 15 min. To this, a solution of phenyl isothiocyanate (1 eq) in dichloromethane was added and the reaction was continued at room temperature for 3 h. Water was added and the organic layer was separated, dried over anhydrous $Na_2SO_4$ and concentrated under reduced pressure to afford crude product, which, on purification by column chromatography afforded—ethyl 5-(anilinocarbonothioyl)-4,5,6,7-tetrahydro[1,3]thiazolo[5,4-c]pyridine-2-carboxylate.

$^1$H NMR (CDCl$_3$) δ (ppm): −7.59 (s, 1H), 7.36 (m, 2H), 7.150-7.24 (m, 3H), 5.07 (s, 2H), 4.48 (q, 2H, J=7.2 Hz), 4.12 (t, 2H, J=5.7 Hz), 3.08 (t, 2H, J=5.7 Hz), 1.44 (t, 3H, J=7.2 Hz).

Step-II

Ethyl 5-[(Z)-(methylthio)(phenylimino)methyl]-4,5,6,7-tetrahydro[1,3]thiazolo[5,4-c]pyridine-2-carboxylate To a solution of ethyl 5-(anilinocarbonothioyl)-4,5,6,7-tetrahydro[1,3]thiazolo[5,4-c]pyridine-2-carboxylate obtained in step I (1 eq) in acetone, $K_2CO_3$ (1.2 eq) was added and the reaction mixture was stirred for 15 min. To this, iodomethane (1.2 eq) was added and the reaction was continued at room temperature for 5 h. Solvent was evaporated and the residue was diluted dichloromethane. It was then washed with water and the organic layer was separated, dried over anhydrous $Na_2SO_4$ and concentrated under reduced pressure to afford crude product, which, on purification by column chromatography afforded the ethyl 5-[(Z)(methylthio)(phenylimino)methyl]-4,5,6,7-tetrahydro[1,3]thiazolo[5,4-c]pyridine-2-carboxylate.

$^1$H NMR (CDCl$_3$) δ(ppm): −7.28 (m, 2H), 7.03 (m, 1H), 6.91 (m, 2H), 4.91 (s, 2H), 4.50 (q, 2H, J=7.2 Hz), 4.04 (t, 2H, J=5.7 Hz), 3.14 (t, 2H, J=5.7 Hz), 2.08 (s, 3H), 1.46 (t, 3H, J=7.2 Hz).

Step-III

5-[(Z)-(methylthio)(phenylimino)methyl]-4,5,6,7-tetrahydro[1,3]thiazolo[5,4-c]pyridine-2-carboxylic acid To a solution of ethyl 5-[(Z)-(methylthio)(phenylimino)methyl]-4,5,6,7-tetrahydro[1,3]thiazolo[5,4-c]pyridine-2-carboxylate (1 eq) obtained in step II in methanol, $K_2CO_3$ (2 eq) and few drops of water were added and the reaction mixture was stirred at room temperature for 15 h. Solvent was evaporated and the residue was treated with etheral HCl. The solvent was then evaporated and the residue was as such used for further reaction without purification.

Step-IV

Methyl 2-[(2-aminophenyl)carbamoyl]-N-phenyl-6,7-dihydro[1,3]thiazolo[5,4-c]pyridine-5(4H)-carbimidothioate A suspension of ethyl 5-[(Z)-(methylthio)(phenylimino)methyl]-4,5,6,7-tetrahydro[1,3]thiazolo[5,4-c]pyridine-2-carboxylic acid obtained in step III (1 eq), mono Boc-protected o-phenylene diamine (1.2 eq), EDCI (1.2 eq), HOBt (1.2 eq) and triethylamine in DMF were stirred at room temperature for 15 h. Solvent was evaporated and the residue was treated with etheral HCl at room temperature for 5-15 h. Solvent was evaporated and the residue was purified by either column chromatography or preparative HPLC to afford methyl 2-[(2-aminophenyl)carbamoyl]-N-phenyl-6,7-dihydro[1,3]thiazolo[5,4-c]pyridine-5(4H)carbimidothioate.

$^1$H NMR (DMSO-$d_6$) δ (ppm): —(HCl salt) 10.72 (s, 1H), 7.30-7.60 (m, 9H), 5.22 (s, 2H), 4.27 (b t, 2H), 3.22 (b t, 2H), 2.44 (s, 3H).

Step-V

N-(2-aminophenyl)-5-[anilino(cyanoimino)methyl]-4,5,6,7-tetrahydro[1,3]thiazolo[5,4-c]pyridine-2-carboxamide A solution of methyl 2-[(2-aminophenyl)carbamoyl]-N-phenyl-6,7-dihydro[1,3]thiazolo[5,4-c]pyridine-5(4H)-carbimidothioate obtained in step IV (1 eq), cyanamide (10 eq) in very small quantity of THF was heated at reflux temperature for 15 h. Solvent was evaporated and the residue was purified by either column chromatography or preparative HPLC to afford the title compound.

$^1$H NMR (DMSO-$d_6$) δ (ppm): −10.02 (s, 1H), 9.62 (s, 1H), 7.30-7.38 (m, 2H), 7.26 (dd, 1H, J=7.8, 1.2 Hz), 7.05-7.14 (m, 3H), 6.98 (t, 1H, J=7.8 Hz), 6.79 (dd, 1H, J=8.1, 1.2 Hz), 6.79 (dt, 1H, J=8.1, 1.2 Hz), 4.94 (s, 2H), 4.85 (s, 2H), 3.89 (t, 2H, J=5.7 Hz), 3.01 (b t, 2H).

Examples 117 to 122 were Obtained by Following the Procedure of Example 116

Example 117

N-(2-aminophenyl)-5-{(cyanoimino)[(4-methoxyphenyl)amino]methyl}-4,5,6,7-tetrahydro[1,3]thiazolo[5,4-c]pyridine-2-carboxamide ¹H NMR (CDCl₃) δ(ppm): −8.85 (s, 1H), 7.45 (dd, 1H, J=8.4, 1.2 Hz), 7.02-7.13 (m, 4H), 6.83-6.95 (m, 4H), 4.54 (s, 2H), 3.87 (b s, 2H), 3.83 (s, 3H), 3.76 (t, 2H, J=5.7 Hz), 2.87 (t, 2H, J=5.7 Hz).

Example 118

N-(2-aminophenyl)-5-{(cyanoimino)[(3,4-dimethoxyphenyl)amino]methyl}-4,5,6,7-tetrahydro[1,3]thiazolo[5,4-c]pyridine-2-carboxamide ¹H NMR (CDCl₃) δ (ppm): −8.87 (s, 1H), 7.47 (d, 1H, J=8.7 Hz), 7.11 (m, 2H), 6.85-6.90 (m, 3H), 6.65-6.72 (m, 2H), 4.59 (s, 2H), 3.92 (s, 3H), 3.88 (s, 3H), 3.79 (t, 214, J=5.7 Hz), 2.91 (br t, 2H), 1.53 (b s, 2H).

Example 119

N-(2-aminophenyl)-5-{(cyanoimino)[(2-methylphenyl)amino]methyl}-4,5,6,7-tetrahydro[1,3]thiazolo[5,4-c]pyridine-2-carboxamide ¹H NMR (DMSO-d₆) δ (ppm): −9.98 (s, 1H), 9.19 (s, 1H), 7.24 (m, 2H), 7.16 (m, 2H), 7.08 (dd, 1H, J=7.2, 1.8 Hz), 6.97 (t, 1H, J=8.1 Hz), 6.78 (dd, 1H, J=8.1, 1.2 Hz), 6.60 (t, 1H, J=7.8 Hz), 4.92 (s, 2H), 4.88 (s, 2H), 3.89 (t, 2H, J=5.7 Hz), 2.94 (br t, 2H), 2.18 (s, 3H).

Example 120

N-(2-aminophenyl)-5-[(cyanoimino){[4-(dimethylamino)phenyl]amino}methyl]-4,5,6,7-tetrahydro[1,3]thiazolo[5,4-c]pyridine-2-carboxamide ¹H NMR (DMSO-d₆) δ (ppm): −10.00 (s, 1H), 9.27 (s, 1H), 7.26 (d, 1H, J=7.8 Hz), 6.98 (m, 3H), 6.79 (dd, 1H, J=8.1, 1.5 Hz), 6.70 (d, 2H, J=9.3 Hz), 6.63 (t, 1H, J=6.3 Hz), 4.93 (s, 2H), 4.81 (s, 2H), 3.85 (t, 2H, J=5.4 Hz), 2.97 (br t, 2H), 2.88 (s, 6H)

Example 121

N-(2-aminophenyl)-5-[(cyanoimino)(pentylamino)methyl]-4,5,6,7-tetrahydro[1,3]thiazolo[5,4-c]pyridine-2-carboxamide ¹H NMR (DMSO-d₆) δ (ppm): −10.00 (s, 1H), 7.51 (t, 1H, J=5.7 Hz), 7.26 (dd, 1H, J=7.8, 1.2 Hz), 6.98 (dt, 1H, J=7.8, 1.2 Hz), 6.79 (dd, 1H, J=8.1, 1.5 Hz), 6.61 (dt, 1H, J=7.8, 1.5 Hz), 4.93 (s, 2H), 4.80 (s, 2H), 3.83 (t, 2H, J=5.7 Hz), 3.01 (br t, 2H), 1.48-1.57 (m, 2H), 1.25-1.37 (m, 2H), 0.89 (t, 3H, J=7.5 Hz)

Example 122

N-(2-aminophenyl)-5-[(benzylamino)(cyanoimino)methyl]-4,5,6,7-tetrahydro[1,3]thiazolo[5,4-c]pyridine-2-carboxamide ¹H NMR (DMSO-d₆) δ (ppm) 9.99 (s, 1H), 8.09 (t, 1H, J=5.7 Hz), 7.23-7.39 (m, 6H), 6.96 (t, 1H, J=7.8 Hz), 6.78 (dd, 1H, J=8.1, 1.5 Hz), 6.60 (t, 1H, J=7.8 Hz), 4.92 (s, 2H), 4.84 (s, 2H), 4.54 (d, 2H, J=5.7 Hz), 3.87 (t, 2H, J=5.7 Hz), 3.02 (br t, 2H).

Example 123

N-(2-amino-5-methoxyphenyl)-5-[(cyanoamino)(phenylimino)methyl]-4,5,6,7-tetrahydro[1,3]thiazolo[5,4-c]pyridine-2-carboxamide

Step-I

Methyl 2-({2-[(tert-butoxycarbonyl)amino]-4-methoxyphenyl}carbamoyl)-N-phenyl-6,7-dihydro[1,3]thiazolo[5,4-c]pyridine-5(4H)-carbimidothioate A suspension of 5-[(Z)-(methylthio)(phenylimino)methyl]-4,5,6,7-tetrahydro[1,3]thiazolo[5,4-c]pyridine-2-carboxylic acid obtained from step III of example 116 (1 eq), (2-amino-4-methoxy-phenyl)-carbamic acid tert-butyl ester (1.2 eq), EDCI (1.2 eq), HOBt (1.2 eq) and triethylamine in DMF were stirred at room temperature for 15 h. Solvent was evaporated and the residue was purified by either column chromatography or preparative HPLC to afford methyl 2-({2-[(tert-butoxycarbonyl)amino]-4-methoxyphenyl}carbamoyl)-N-phenyl-6,7-dihydro[1,3]thiazolo[5,4-c]pyridine-5(4H)-carbimidothioate.

Step-II tert-butyl {2-[({5-[(E)-(cyanoamino)(phenylimino)methyl]-4,5,6,7-tetrahydro[1,3]thiazolo[5,4-c]pyridin-2-yl}carbonyl)amino]-5-methoxyphenyl}carbamate A solution of methyl 2-({2-[(tert-butoxycarbonyl)amino]-4-methoxyphenyl}carbamoyl)-N-phenyl-6,7-dihydro[1,3]thiazolo[5,4-c]pyridine-5(4H)-carbimidothioate (1 eq) obtained in step I, cyanamide (10 eq) in very small quantity of THF was heated at reflux temperature for 15 h.

Solvent was evaporated and the residue was purified by either column chromatography or preparative HPLC to afford the desired tert-butyl {2-[({5-[(E)-(cyanoamino)(phenylimino)methyl]-4,5,6,7-tetrahydro[1,3]thiazolo[5,4-c]pyridin-2-yl}carbonyl)amino]-5-methoxyphenyl}carbamate.

Step-III

N-(2-amino-5-methoxyphenyl)-5-[(cyanoamino)(phenylimino)methyl]-4,5,6,7-tetrahydro[1,3]thiazolo[5,4-c]pyridine-2-carboxamide tert-butyl {2-[({5-[(E)-(cyanoamino)(phenylimino)methyl]-4,5,6,7-tetrahydro[1,3]thiazolo[5,4-c]pyridin-2-yl}carbonyl)amino]-5-methoxyphenyl}carbamate obtained form step II was treated with etheral HCl at room temperature for 5-15 h. Solvent was evaporated and the residue was neutralized with base and purified by either column chromatography or preparative HPLC to yield the title compound.

¹H NMR (DMSO-d₆) δ(ppm): −9.99 (s, 1H), 9.62 (s, 1H), 7.34 (m, 2H), 7.06-7.16 (m, 4H), 6.79 (d, 1H, J=8.7 Hz), 6.63

(dd, 1H, J=8.7, 2.7 Hz), 4.86 (s, 2H), 4.53 (b s, 2H), 3.90 (t, 2H, J=5.7 Hz), 3.66 (s, 3H), 3.02 (b t, 2H).

Examples 124 and 125 were Obtained by Following the Procedure of Example 123

Example 124

N-(2-amino-5-methoxyphenyl)-5-{(cyanoamino)[(4-methoxyphenyl)imino]-methyl}-4,5,6,7-tetrahydro[1,3]thiazolo[5,4-c]pyridine-2-carboxamide $^1$H NMR (DMSO-d$_6$) δ(ppm): −9.98 (s, 1H), 9.43 (s, 1H), 7.13 (d, 1H, J=3.0 Hz), 7.09 (d, 2H, J=9.0 Hz), 6.91 (d, 2H, J=8.7 Hz), 6.79 (d, 1H, J=8.7 Hz), 6.63 (dd, 1H, J=8.7, 3.0 Hz), 4.84 (s, 2H), 4.54 (s, 2H), 3.88 (t, 2H, J=5.4 Hz), 3.75 (s, 3H), 3.66 (s, 3H), 3.00 ((b t, 2H).

Example 125

N-(2-amino-5-isopropylphenyl)-5-{(cyanoamino)[(4-methoxyphenyl)-imino]methyl}-4,5,6,7-tetrahydro[1,3]thiazolo[5,4-c]pyridine-2-carboxamide $^1$H NMR (DMSO-d6) δ (ppm): −9.97 (s, 1H), 9.43 (s, 1H), 7.20 (d, 1H, J=1.8 Hz), 7.09 (d, 2H, J=9.0 Hz), 6.92 (d, 2H, J=9.0 Hz), 6.87 (dd, 1H, J=8.1 Hz, 2.1 Hz), 6.73 (d, 1H, J=8.1 Hz), 4.84 (s, 2H), 4.75 (b s, 2H), 3.88 (t, 2H, J=5.7 Hz), 3.75 (s, 3H), 3.00 (br t, 2H), 2.73 (q, 1H, J=6.9 Hz), 1.15 (d, 6H, J=6.9 Hz).

Example 126

N-(2-aminophenyl)-5-[N-phenylethanimidoyl]-4,5,6,7-tetrahydro[1,3]thiazolo[5,4-c]pyridine-2-carboxamide Step-I Ethyl 5-acetyl-4,5,6,7-tetrahydro[1,3]thiazolo[5,4-c]pyridine-2-carboxylate 5-tert-butyl 2-ethyl 6,7-dihydro[1,3]thiazolo[5,4-c]pyridine-2,5(4H)-dicarboxylate obtained in step V of example 1 was deprotected to get the 4,5,6,7-Tetrahydro-thiazolo[5,4-c]pyridine-2-carboxylic acid ethyl ester. To a solution of 4,5,6,7-Tetrahydro-thiazolo[5,4-c]pyridine-2-carboxylic acid ethyl ester (1 eq) and triethyl amine (1 eq) in chloroform, acetic anhydride was added and the reaction mixture was stirred for 1 h at room temperature. Reaction mixture was then diluted with chloroform and washed with water. Organic layer was then separated, dried and concentrated under reduced pressure to afford the desired ethyl 5-acetyl-4,5,6,7-tetrahydro[1,3]thiazolo[5,4-c]pyridine-2-carboxylate.

Step-II

Ethyl 5-[(1E)-N-phenylethanimidoyl]-4,5,6,7-tetrahydro[1,3]thiazolo[5,4-c]pyridine-2-carboxylate To a solution of N-acetyl derivative obtained from step I (1 eq) in benzene a solution of phosphorous oxychloride (1 eq) was added and the reaction mixture was stirred for 30 min. Solution of aniline in benzene was added and stirring was continued at reflux temperature for 4 h. It was then cooled to room temperature and basified to pH 8. Crude product was extracted in dichloromethane. Organic layer was then separated, dried and concentrated under reduced pressure. The crude product ethyl 5-[(1E)-N-phenylethanimidoyl]-4,5,6,7-tetrahydro[1,3]thiazolo[5,4-c]pyridine-2-carboxylate thus obtained was as such used for further reaction without purification.

Step-III

5-[(1E)-N-phenylethanimidoyl]-4,5,6,7-tetrahydro[1,3]thiazolo[5,4-c]pyridine-2-carboxylic acid To a solution of ethyl 5-[(1E)-N-phenylethanimidoyl]-4,5,6,7-tetrahydro[1,3]thiazolo[5,4-c]pyridine-2-carboxylate obtained from step-II (1 eq) in methanol, K$_2$CO$_3$ (2 eq) and few drops of water were added and the reaction mixture was stirred at room temperature for 15 h. Solvent was evaporated and the residue was treated with ethral HCl. The solvent was then evaporated and the product 5-[(1E)-N-phenylethanimidoyl]-4,5,6,7-tetrahydro[1,3]thiazolo[5,4-c]pyridine-2-carboxylic acid was as such used for further reaction without purification.

Step-IV

N-(2-aminophenyl)-5-[N-phenylethanimidoyl]-4,5,6,7-tetrahydro[1,3]thiazolo-[5,4-c]pyridine-2-carboxamide A suspension of acid obtained from step-III (1 eq), mono Boc-protected o-phenylene diamine (1.2 eq), EDCI (1.2 eq), HOBt (1.2 eq) and triethylamine in DMF was stirred at room temperature for 15 h. Solvent was evaporated and the residue was treated with etharal HCl at room temperature for 5-15 h. Solvent was evaporated and the residue was purified by either column chromatography or preparative HPLC to afford the title compound.

$^1$H NMR (CDCl$_3$) δ (ppm): −8.92 (s, 1H), 7.47 (d, 1H, J=8.7 Hz), 7.28 (t, 1H, J=8.1 Hz), 7.13 (t, 1H, J=7.8 Hz), 7.00 (t, 1H, J=7.5 Hz), 6.85-6.92 (m, 3H), 6.70-6.76 (m, 2H), 4.93 (s, 2H), 3.94 (b s, 2H), 3.89 (t, 2H, J=5.7 Hz), 3.05 (t, 2H, J=5.7 Hz), 2.01 (s, 3H).

Examples 127-135 were Obtained by Following the Procedure of Example 126

Example 127

N-(2-aminophenyl)-5-[N-(3,4-dimethoxyphenyl)ethanimidoyl]-4,5,6,7 tetrahydro[1,3]thiazolo[5,4-c]pyridine-2-carboxamide $^1$H NMR (DMSO-d$_6$) δ (ppm): −9.99 (s, 1H), 7.27 (d, 1H, J=7.5 Hz), 6.98 (t, 1H, J=8.1 Hz), 6.78-6.82 (m, 2H), 6.61 (t, 1H, J=7.8 Hz), 6.27 (d, 1H, J=1.8 Hz), 6.13 (dd, 0.1H, J=8.4 Hz, 2.4 Hz), 4.94 (s, 2H), 4.88 (s, 2H), 3.84 (t, 2H, J=5.7 Hz), 3.69 (s, 6H), 2.98 (t, 2H, J=5.7 Hz), 2.54 (s, 3H).

Example 128

N-(2-aminophenyl)-5-[N-(4-methoxyphenyl)ethanimidoyl]-4,5,6,7-tetrahydro[1,3]thiazolo[5,4-c]pyridine-2-carboxamide $^1$H NMR (CDCl$_3$) δ (ppm): −8.92 (s, 1H), 7.46 (m, 1H), 7.12 (t, 1H, J=7.8 Hz), 6.82-6.93 (m, 4H), 6.66 (d, 2H, J=8.7

Hz), 4.92 (s, 2H), 3.94 (b, 2H), 3.87 (t, 2H, J=5.7 Hz), 3.80 (s, 3H), 3.04 (t, 2H, J=5.7 Hz), 2.00 (s, 3H).

Example 129

N-(2-amino-5-methoxyphenyl)-5-[N-phenylethanimidoyl]-4,5,6,7-tetrahydro[1,3]thiazolo[5,4-c]pyridine-2-carboxamide $^1$H NMR (DMSO-$d_6$) δ (ppm): −9.98 (s, 1H), 7.25 (m, 2H), 7.15 (d, 1H, J=2.1 Hz), 6.94 (m, 1H), 6.79 (d, 1H, J=8.7 Hz), 6.60-6.75 (m, 3H), 4.92 (s, 2H), 4.53 (b s, 2H), 3.88 (t, 2H, J=5.4 Hz), 3.67 (s, 3H), 3.01 (b t, 2H), 1.97 (s, 3H).

Example 130

N-(2-amino-5-methoxyphenyl)-5-[N-(4-methoxyphenyl)ethanimidoyl]-4,5,6,7-tetrahydro[1,3]thiazolo[5,4-c]pyridine-2-carboxamide $^1$H NMR (DMSO-$d_6$) δ (ppm): −9.967 (s, 1H), 7.15 (d, 1H, J=3.0 Hz), 6.82 (d, 2H, J=9.0 Hz), 6.79 (d, 1H, J=8.7 Hz), 6.63 (dd, 1H, J=8.7 Hz, 3.0 Hz), 6.58 (d, 2H, J=8.7 Hz), 4.89 (s, 2H), 4.53 (b s, 2H), 3.85 (t, 2H, J=5.4 Hz), 3.70 (s, 3H), 3.67 (s, 3H), 2.99 (b t, 2H), 1.95 (s, 3H).

Example 131

N-(2-amino-5-methoxyphenyl)-5-[N-(3,4-dimethoxyphenyl)ethanimidoyl]-4,5,6,7-tetrahydro[1,3]thiazolo[5,4-c]pyridine-2-carboxamide $^1$HNMR (DMSO-$d_6$) δ (ppm): −9.97 (s, 1H), 7.15 (d, 1H, J=3.0 Hz), 6.81 (d, 1H, J=8.7 Hz), 6.80 (d, 1H, J=8.7 Hz), 6.63 (dd, 1H, J=8.7, 3.0 Hz), 6.28 (d, 1H, J=2.4 Hz), 6.14 (dd, 1H, J=8.4, 2.4 Hz), 4.89 (s, 2H), 4.53 (b s, 2H), 3.85 (t, 2H, J=5.4 Hz), 3.70 (s, 6H), 3.67 (s, 3H), 2.90 (b t, 2H), 1.97 (s, 3H).

Example 132

N-(2-amino-5-isopropylphenyl)-5-[N-(4-methoxyphenyl)ethanimidoyl]-4,5,6,7-tetrahydro[1,3]thiazolo[5,4-c]pyridine-2-carboxamide $^1$H NMR (DMSO-$d_6$) δ (ppm): −9.93 (s, 1H), 7.23 (d, 1H, J=2.1 Hz), 6.87 (dd, 1H, J=8.41 Hz, 2.1 Hz), 6.82 (d, 2H, J=9.0 Hz), 6.75 (d, 1H, J=8.4 Hz), 6.58 (d, 2H, J=8.7 Hz), 4.89 (s, 2H), 4.74 (b s, 2H), 3.85 (t, 2H, J=5.7 Hz), 3.70 (s, 3H), 2.98 (b t, 2H), 2.76 (q, 1H, J=6.9 Hz), 1.95 (s, 3H), 1.21 (d, 6H, J=6.9 Hz).

Example 133

N-(2-amino-5-isopropylphenyl)-5-[N-(3,4-dimethoxyphenyl)ethanimidoyl]-4,5,6,7-tetrahydro[1,3]thiazolo[5,4-c]pyridine-2-carboxamide $^1$H NMR (DMSO-$d_6$) δ (ppm): −9.94 (s, 1H), 7.22 (d, 1H, J=2.1 Hz), 6.88 (dd, 1H, J=8.1, 2.1 Hz), 6.81 (d, 1H, J=8.4 Hz), 6.75 (d, 1H, J=8.1 Hz), 6.28 (d, 1H, J=2.1 Hz), 6.14 (dd, 1H, J=8.4, 2.1 Hz), 4.89 (s, 2H), 4.74 (s, 2H), 3.85 (t, 2H, J=5.7 Hz), 3.70 (s, 6H), 2.99 (br t, 2H), 2.76 (q, 1H, J=6.9 Hz), 1.97 (s, 3H), 1.16 (d, 6H, J=6.9 Hz).

Example 134

N-(2-aminophenyl)-5-{N-[4-(dimethylamino)phenyl]ethanimidoyl}-4,5,6,7-tetrahydro[1,3]thiazolo[5,4-c]pyridine-2-carboxamide $^1$H NMR (CDCl$_3$) δ(ppm): −8.92 (s, 1H), 7.48 (d, 1H, J=8.4 Hz), 7.12 (t, 1H, J=9.0 Hz), 6.88 (m, 2H), 6.75 (d, 2H, J=9.0 Hz), 6.65 (d, 2H, J=9.0 Hz), 4.92 (s, 2H), 3.93 (b s, 2H), 3.87 (t, 2H, J=5.7 Hz), 3.04 (t, 2H, J=5.7 Hz), 2.91 (s, 6H), 2.01 (s, 3H).

Example 135

N-(2-amino-5-isopropylphenyl)-5-[N-phenylethanimidoyl]-4,5,6,7-tetrahydro[1,3]thiazolo[5,4-c]pyridine-2-carboxamide $^1$H NMR (DMSO-$d_6$) δ(ppm): −9.94 (s, 1H), 7.20-7.27 (m, 3H), 6.85-6.97 (m, 2H), 6.74 (d, 1H, J=8.1 Hz), 6.65 (m, 2H), 4.90 (s, 2H), 4.74 (b s, 2H), 3.87 (t, 2H, J=5.7 Hz), 3.00 (t, 2H, J=5.4 Hz), 2.76 (q, 1H, J=6.9 Hz), 1.96 (s, 3H), 1.16 (d, 6H, J=6.9 Hz),

Example 136

N-(2-aminophenyl)-5-[1-anilino-2-nitroyinyl]-4,5,6,7-tetrahydro[1,3]thiazolo[5,4-c]pyridine-2-carboxamide To a solution of 1,1,1-trichloro-2-nitroethane (1 eq) in chloroform, aq. solution of K2CO3 (3 eq) and N-(2-aminophenyl)-4,5,6,7-tetrahydro[1,3]thiazolo[5,4-c]pyridine-2-carboxamide obtained in step VIII of example I (0.9 eq) was added at 0-2° C. and the reaction mixture was stirred for 30 min. A solution of aniline (0.9 eq) in chloroform was then added and stirring was continued at 0-2° C. for 30 min. Reaction mixture was diluted with chloroform. Organic layer was then separated, dried and concentrated under reduced pressure. The crude product thus obtained was purified by column chromatography or preparative HPLC to yield the title compound.

$^1$H NMR (DMSO-$d_6$) δ (ppm): −10.26 (s, 1H), 10.00 (s, 1H), 7.38 (m, 2H), 7.25 (m, 3H), 7.17 (m, 1H), 6.98 (m, 1H), 6.79 (m, 1H), 6.69 (s, 1H), 6.61 (m, 1H), 4.94 (s, 2H), 4.64 (s, 2H), 3.71 (t, 2H, J=5.4 Hz), 2.90 (b t, 2H).

Examples 137-149 were Also Obtained by Following the Procedure of Example 136

Example 137

N-(2-aminophenyl)-5-{1-[(4-methoxyphenyl)amino]-2-nitroyinyl}-4,5,6,7-tetrahydro[1,3]thiazolo[5,4-c]pyridine-2-carboxamide $^1$H NMR (DMSO-$d^6$) δ (ppm): −10.38 (s, 1H), 9.99 (s, 1H), 7.25 (m, 3H), 6.98 (m, 3H), 6.79 (dd, 1H, J=8.1, 1.5 Hz), 6.61 (m, 2H), 4.93 (s, 2H), 4.60 (s, 2H), 3.76 (s, 3H), 3.69 (t, 2H, J=5.4 Hz), 2.85 (b t, 2H).

Example 138

N-(2-aminophenyl)-5-[1-(butylamino)-2-nitrovinyl]-4,5,6,7-tetrahydro[1,3]thiazolo[5,4-c]pyridine-2-carboxamide $^1$H NMR (DMSO-$d_6$) δ (ppm): −9.99 (s, 1H), 9.14 (s, 1H), 7.25 (dd, 1H, J=8.1, 1.5 Hz), 6.97 (t, 1H, J=7.8 Hz), 6.78 (dd, 1H, J=8.1, 1.5 Hz), 6.60 (t, 1H, J=7.8 Hz), 6.50 (m, 1H), 4.93 (b s, 2H), 4.68 (s, 2H), 3.69 (t, 2H, J=5.7 Hz), 3.34 (m, 2H), 3.05 (b t, 2H), 1.58 (m, 2H), 1.36 (m, 2H), 0.89 (t, 3H, J=7.2 Hz).

Example 139

N-(2-aminophenyl)-5-{1-[(4-isopropylphenyl)amino]-2-nitrovinyl}-4,5,6,7-tetrahydro[1,3]thiazolo[5,4-c]pyridine-2-carboxamide $^1$H NMR (DMSO-$d_6$) δ (ppm): −10.28 (s, 1H), 10.00 (s, 1H), 7.25 (m, 3H), 7.17 (m, 2H), 6.98 (t, 1H, J=8.1 Hz), 6.79 (dd, 1H, J=8.1 Hz, 1.2 Hz), 6.67 (s, 1H), 6.61 (t, 1H, J=8.1 Hz), 4.93 (s, 2H), 4.63 (s, 2H), 3.72 (t, 2H, J=5.7 Hz), 2.89 (m, 3H), 1.20 (d, 6H, J=6.9 Hz).

Example 140

N-(2-aminophenyl)-5-[1-{[4-(dimethylamino)phenyl]amino}-2-nitrovinyl]-4,5,6,7-tetrahydro[1,3]thiazolo[5,4-c]pyridine-2-carboxamide $^1$H NMR (DMSO-$d_6$) δ (ppm): −10.48 (s, 1H), 9.96 (s, 1H), 7.23 (dd, 1H, J=7.8 Hz, 1.2 Hz), 7.11 (d, 2H, J=8.7 Hz), 6.96 (t, 1H, J=8.1 Hz), 6.77 (dd, 1H, J=8.1 Hz, 1.2 Hz), 6.73 (d, 2H, J=9.0 Hz), 6.55-6.62 (m, 2H), 4.90 (s, 2H), 4.58 (s, 2H), 3.65 (t, 2H, J=5.4 Hz), 2.88 (s, 6H), 2.82 (b t, 2H).

Example 141

N-(2-aminophenyl)-5-{1-[(3,4-dimethoxyphenyl)amino]-2-nitrovinyl}-4,5,6,7-tetrahydro[1,3]thiazolo[5,4-c]pyridine-2-carboxamide $^1$H NMR (DMSO-$d_6$) δ (ppm): −10.45 (s, 1H), 10.00 (s, 1H), 7.25 (dd, 1H, J=8.1 Hz, 1.5 Hz), 6.92-7.02 (m, 3H), 6.77-6.84 (m, 2H), 6.69 (s, 1H), 6.61 (t, 1H, J=7.5 Hz), 4.93 (s, 2H), 4.60 (s, 2H), 3.76 (s, 3H), 3.70 (m, 5H), 2.88 (b t, 2H).

Example 142

N-(2-amino-5-methoxyphenyl)-5-{1-[(4-methoxyphenyl)amino]-2-nitrovinyl}-4,5,6,7-tetrahydro[1,3]thiazolo[5,4-c]pyridine-2-carboxamide $^1$H NMR (DMSO-$d_6$) δ (ppm): −10.38 (s, 1H), 9.98 (s, 1H), 7.22 (d, 2H, J=9.0 Hz), 7.11 (d, 1H, J=3.0 Hz), 6.97 (d, 2H, J=9.0 Hz), 6.78 (d, 1H, J=8.7 Hz), 6.63 (m, 2H), 4.60 (s, 2H), 4.55 (b s, 2H), 3.76 (s, 3H), 3.65-3.72 (m, 2H), 3.66 (s, 3H), 2.85 (b t, 2H).

Example 143

N-(2-amino-5-methoxyphenyl)-5-{1-[(4-isopropylphenyl)amino]-2-nitrovinyl}-4,5,6,7-tetrahydro[1,3]thiazolo[5,4-c]pyridine-2-carboxamide $^1$H NMR (DMSO-$d^6$) δ(ppm): −10.27 (s, 1H), 9.99 (s, 1H), 7.25 (d, 2H, J=8.4 Hz), 7.17 (d, 2H, J=8.1 Hz), 7.11 (d, 1H, J=2.7 Hz), 6.79 (d, 1H, J=8.7 Hz), 6.67 (s, 1H), 6.63 (dd, 1H, J=8.7 Hz, 2.7 Hz), 4.63 (s, 2H), 4.53 (b s, 2H), 3.72 (b t, 2H), 3.66 (s, 3H), 2.90 (m, 3H), 1.20 (d, 6H, J=6.9 Hz).

Example 144

N-(2-amino-5-methoxyphenyl)-5-[1-{[4-(dimethylamino)phenyl]amino}-2-nitrovinyl]-4,5,6,7-tetrahydro[1,3]thiazolo[5,4-c]pyridine-2-carboxamide $^1$H NMR (DMSO-$d_6$) δ (ppm): −10.50 (s, 1H), 9.94 (s, 1H), 7.10-7.15 (m, 3H), 6.70-6.82 (m, 3H), 6.60-6.66 (m, 2H), 4.60 (s, 2H), 4.53 (b s, 2H), 3.65-3.70 (m, 5H), 2.90 (s, 6H), 2.84 (b t, 2H).

Example 145

N-(2-amino-5-isopropylphenyl)-5-[1-anilino-2-nitrovinyl]-4,5,6,7-tetrahydro[1,3]thiazolo[5,4-c]pyridine-2-carboxamide $^1$H NMR (DMSO-$d_6$) δ(ppm): −10.26 (s, 1H), 9.95 (s, 1H), 7.36-7.43 (m, 2H), 7.13-7.32 (m, 4H), 6.87 (dd, 1H, J=8.1 Hz, 2.1 Hz), 6.65-6.77 (m, 2H), 4.75 (b s, 2H), 4.64 (s, 2H), 3.73 (t, 2H, J=5.7 Hz), 2.90 (br t, 2H), 2.77 (q, 1H, J=6.9 Hz), 1.15 (d, 6H, J=6.9 Hz).

Example 146

N-[2-amino-5-(1-methylethyl)phenyl]-5-{1-[(4-methoxyphenyl)amino]-2-nitroethenyl}-4,5,6,7-tetrahydro[1,3]thiazolo[5,4-c]pyridine-2-carboxamide $^1$H NMR (DMSO-$d_6$) δ(ppm): −10.38 (s, 1H), 9.94 (s, 1H), 7.22 (d, 2H, J=8.7 Hz), 7.19 (d, 1H, J=1.8 Hz), 6.97 (d, 2H, J=9.0 Hz), 6.87 (dd, 1H, J=8.1 Hz, 2.1 Hz), 6.73 (d, 1H, J=8.4 Hz), 6.65 (s, 1H), 4.75 (b s, 2H), 4.60 (s, 2H), 3.76 (s, 3H), 3.69 (t, 2H, i=5.4 Hz), 2.85 (br t, 2H), 2.75 (q, 1H, J=6.9 Hz), 1.15 (d, 6H, J=6.9 Hz).

Example 147

N-(2-amino-5-isopropylphenyl)-5-[1-{[4-(dimethylamino)phenyl]amino}-2-nitrovinyl]-4,5,6,7-tetrahydro[1,3]thiazolo[5,4-c]pyridine-2-carboxamide $^1$H NMR (DMSO-$d_6$) δ (ppm): −10.50 (s, 1H), 9.93 (s, 1H), 7.19 (d, 1H, J=1.8 Hz), 7.13 (d, 2H, J=9.0 Hz), 6.87 (dd, 1H, J=8.1 Hz, 1.8 Hz), 6.70-6.76 (m, 3H), 6.64 (s, 1H), 4.74 (b s, 2H), 4.60 (s, 2H), 3.67 (t, 2H, J=5.4 Hz), 2.90 (s, 6H), 2.84 (b t, 2H), 2.75 (q, 1H, J=6.9 Hz), 1.15 (d, 6H, J=6.9 Hz).

Example 148

N-(2-amino-5-isopropylphenyl)-5-{1-[(4-isopropylphenyl)amino]-2-nitrovinyl}-4,5,6,7-tetrahydro[1,3]thiazolo[5,4-c]pyridine-2-carboxamide $^1$H NMR (DMSO-$d_6$) δ (ppm): −10.28 (s, 1H), 9.95 (s, 1H), 7.25 (d, 2H, J=8.4 Hz), 7.16 (m, 3H), 6.87 (dd, 1H, J=8.1, 1.8 Hz), 6.74 (d, 1H, J=8.1 Hz), 6.67 (s, 1H), 4.74 (s, 2H), 4.63 (s, 2H), 3.72 (t, 2H, J=5.4 Hz), 2.89 (m, 3H), 2.75 (q, 1H, J=6.9 Hz), 1.18 (d, 6H, J=6.9 Hz), 1.15 (d, 6H, J=6.9 Hz).

Example 149

N-(2-amino-5-methoxyphenyl)-5-{1-[(4-fluorophenyl)amino]-2-nitrovinyl}-4,5,6,7-tetrahydro[1,3]thiazolo[5,4-c]pyridine-2-carboxamide $^1$H NMR (DMSO-d$_6$) δ (ppm): −10.23 (s, 1H), 9.98 (s, 1H), 7.06-7.40 (m, 4H), 6.79 (d, 1H, J=8.7 Hz), 6.69 (m, 3H), 4.62 (s, 2H), 4.53 (s, 2H), 3.75 (t, 2H, J=5.7 Hz), 3.66 (s, 3H), 2.90 (b t, 2H)

Example 150

N-(2-aminophenyl)-5-[(4-methylphenyl)sulfonyl]-4,5,6,7-tetrahydro[1,3]-thiazolo[5,4-c]pyridine-2-carboxamide Triethyl amine (1.0 eq) was added to solution of N-(2-aminophenyl)-4,5,6,7-tetrahydro[1,3]thiazolo[5,4-c]pyridine-2-carboxamide obtained in step VIII of example I (1.0 mmol) in 10 mL THF. The solution was cooled to 0° C. 4-Methyl-benzenesulfonyl chloride (1.0 mmol) was added slowly with continuous stirring. Reaction mixture was brought to room temperature and stirred for 2 h Reaction mixture was concentrated, diluted with water, extracted dichloromethane, washed with brine solution, and dried over anhydrous Na$_2$SO$_4$. Concentrated and purified by column chromatography to yield the title compound.

$^1$H NMR (DMSO-d$_6$) δ (ppm): −9.92 (s, 1H, NH), 7.73 (d, 2H, J=12 Hz), 7.42 (d, 2H, J=12 Hz), 7.24 (d, 1H, J=11 Hz), 6.97 (t, 1H, J=11 Hz), 6.78 (d, 1H, J=11 Hz), 6.60 (t, 1H, J=11 Hz), 4.98 (s, 2H, NH), 4.50 (s, 2H), 3.48 (m, 2H), 3.30 (s, 2H), 2.88 (m, 2H).

Examples 151-171 were Also Obtained by Following the Procedure of Example 150

Example 151

N-(2-aminophenyl)-5-(benzylsulfonyl)-4,5,6,7-tetrahydro[1,3]thiazolo[5,4-c]pyridine-2-carboxamide $^1$H NMR (DMSO-d$_6$) δ (ppm): −10.00 (s, 1H, NH), 7.45-7.34 (m, 5H) 7.25 (dd, 1H, J=0.9 Hz, 6.9 Hz), 6.98 (dt, 1H, J=1.5 Hz, 8.7 Hz), 6.79 (dd, 1H, J=1.2 Hz, 7.8 Hz), 4.93 (br s, 2H), 4.58 (s, 2H), 4.55 (s, 2H), 3.56 (t, 2H, J=5.7 Hz), 2.89 (t, 2H, J=5.1 Hz).

Example 152

N-(2-aminophenyl)-5-(biphenyl-4-ylsulfonyl)-4,5,6,7-tetrahydro[1,3]thiazolo[5,4-c]pyridine-2-carboxamide 1H NMR (DMSO) (ppm): 9.89 (s, 1H, NH), 7.91 (m, 3H, CH), 7.73 (m, 2H, CH), 7.49 (m, 4H, CH), 7.23 (d, 1H, CH, J=6.6 Hz), 6.96 (t, 1H, CH, J=7.1 Hz), 6.77 (d, 1H, CH, J=6.7 Hz), 6.59 (t, 1H, CH, J=7.3 Hz), 4.88 (s, 2H, NH2), 3.59 (m, 2H, CH$_2$), 2.91 (m, 2H, CH$_2$), 1.03 (d, 2H, CH$_2$, J=6.1 Hz).

Example 153

N-(2-aminophenyl)-5-[(4-methoxyphenyl)sulfonyl]-4,5,6,7-tetrahydro[1,3]thiazolo[5,4-c]pyridine-2-carboxamide $^1$H NMR (DMSO-d$_6$) δ(ppm): −9.95 (s, 1H, NH), 7.76 (d, 2H, J=6.7 Hz), 7.23 (d, 1H, J=1.2 Hz), 7.13 (d, 2H, J=9 Hz), 6.93 (t, 1H, J=7.2 Hz), 6.77 (dd, 1H, J=7.8 Hz, 0.9), 6.56 (t, 1H, J=7.0 Hz), 4.90 (br s, 2H, NH2), 4.48 (s, 2H), 3.83 (s, 3H), 3.47 (t, 2H, J=5.7 Hz), 2.86 (m, 2H)

Example 154

N-(2-aminophenyl)-5-(methylsulfonyl)-4,5,6,7-tetrahydro[1,3]thiazolo[5,4-c]pyridine-2-carboxamide $^1$H NMR (DMSO-d$_6$) δ(ppm): −10.00 (s, 1H, NH), 7.24 (dd, 1H, J=1.2 Hz, 7.8 Hz), 6.99 (dt, 1H, J=1.2 Hz, 8.1 Hz), 6.79 (dd, 1H, J=1.5 Hz, 8.1 Hz), 6.59 (dt, 1H, J=1.5 Hz, 7.8 Hz), 4.93 (s, 2H), 4.62 (s, 2H), 3.60 (t, 2H, J=6.0 Hz), 2.99 (m, 5H).

Example 155

5-[(4-acetamidophenyl)sulfonyl]-N-(2-aminophenyl)-4,5,6,7-tetrahydro[1,3]thiazolo[5,4-c]pyridine-2-carboxamide $^1$H NMR (DMSO-d$_6$) δ(ppm): −10.36 (s, 1H, NH), 9.94 (s, 1H, NH) 7.76 (s, 4H), 7.24 (dd, 1H, J=1.2 Hz, 7.8 Hz), 6.93 (t, 1H, J=6.9 Hz), 6.75 (dd, 1H, J=1.2 Hz, 6.9 Hz), 4.90 (s, 2H), 4.49 (s, 2H), 3.48 (m, 2H), 2.87 (m, 2H).

Example 156

N-(2-aminophenyl)-5-(2-naphthylsulfonyl)-4,5,6,7-tetrahydro[1,3]thiazolo[5,4-c]pyridine-2-carboxamide $^1$H NMR (DMSO-d$_6$) δ(ppm): −9.89 (s, 1H, NH), 8.54 (s, 1H, NH), 8.20-8.00 (m, 3H), 7.85-7.60 (m, 3H), 7.21 (d, 1H, J=6.6 Hz), 6.94 (t, 2H, J=5.3 Hz), 6.75 (dd, 1H, J=1.2 Hz, 7.8 Hz), 6.57 (t, 1H, J=7.2 Hz), 4.87 (br s, 2H, NH2), 4.60 (s, 2H), 3.59 (t, 2H, J=5.7 Hz), 2.87 (m, 2H).

Example 157

N-(2-aminophenyl)-5-(2-thienylsulfonyl)-4,5,6,7-tetrahydro[1,3]thiazolo[5,4-c]pyridine-2-carboxamide $^1$H NMR (DMSO-d$_6$) δ (ppm): −9.98 (s, 1H, NH), 8.05 (dd, 1H, J=1.2 Hz, 6.3 Hz), 7.74 (dd, 1H, J=1.5 Hz, 3.6 Hz), 7.25 (m, 2H), 6.95 (dt, 1H, J=1.5 Hz, 7.2 Hz), 6.79 (dd, 1H, J=1.2 Hz, 8.1 Hz), 6.22 (dt, 1H, J=1.2 Hz, 6.3 Hz), 4.92 (br s, 2H, NH2), 4.57 (s, 2H), 3.56 (m, 2H), 2.94 (m, 2H).

Example 158

Methyl 3-({2-[(2-aminophenyl)carbamoyl]-6,7-dihydro[1,3]thiazolo[5,4-c]pyridin-5(4H)-yl}sulfonyl)thiophene-2-carboxylate $^1$H NMR (DMSO-d$_6$) (ppm): −9.98 (s, 1H, NH), 8.00 (d, 1H, J=5.0 Hz), 7.55 (d, 1H, J=5.1 Hz), 7.24 (dd, 1H, J=7.8 Hz, 1.3 Hz), 6.97 (dt, 1H, J=1.5 Hz, 8.1 Hz), 6.78 (dd, 1H, J=1.3

Hz, 7.8 Hz), 6.60 (dt, 1H, J=1.5 Hz, 7.8 Hz), 4.92 (s, 2H), 4.80 (s, 2H), 3.77 (t, 2H, J=5.0 Hz), 2.87 (t, 2H, J=5 Hz).

Example 159

5-[(2-acetamido-4-methyl-1,3-thiazol-5-yl)sulfonyl]-N-(2-aminophenyl)-4,5,6,7-tetrahydro[1,3]thiazolo[5,4-c]pyridine-2-carboxamide $^1$H NMR (DMSO-d$_6$) δ(ppm): −9.98 (s, 1H, NH), 8.00 (d, 1H, J=5.4 Hz), 7.55 (d, 1H, J=5.1 Hz), 7.24 (dd, 1H, J=1.3 Hz, 7.8 Hz), 6.95 (dt, 1H, J=1.5 Hz, 8.1 Hz), 6.78 (dd, 1H, J=1.3 Hz, 7.8 Hz), 6.60 (dt, 1H, J=1.5 Hz, 7.8 Hz), 4.92 (br s, 2H, NH2), 4.80 (s, 2H), 3.77 (t, 2H, J=5.4 Hz), 2.87 (t, 2H, J=5.4 Hz).

Example 160

N-(2-aminophenyl)-5-[(3-methoxyphenyl)sulfonyl]-4,5,6,7-tetrahydro[1,3]thiazolo[5,4-c]pyridine-2-carboxamide $^1$H NMR (DMSO-d$_6$) d (ppm): −9.96 (s, 1H, NH), 7.55 (t, 5H, J=7.8 Hz) 7.41 (d, 1H, J=7.8 Hz), 7.25-7.238 (m, 3H), 6.97 (t, 1H, J=7.5 Hz), 6.78 (d, 1H, J=6.9 Hz), 6.60 (t, 1H, J=7.2 Hz), 4.90 (br s, 2H), 4.56 (s, 2H), 3.84 (t, 2H, J=5.7 Hz), 2.88 (t, 2H, J=5.7 Hz).

Example 161

N-(2-aminophenyl)-5-{[4-(trifluoromethyl)phenyl}sulfonyl]-4,5,6,7-tetrahydro[1,3]thiazolo[5,4-c]pyridine-2-carboxamide $^1$H NMR (DMSO-d$_6$) δ(ppm): −9.97 (s, 1H, NH), 8.08 (d, 2H, J=8.4 Hz), 8.00 (d, 2H, J=8.4 Hz), 7.21 (d, 1H, J=6.9 Hz), 6.97 (dt, 1H, J=1.2 Hz, 8.1 Hz), 6.77 (dd, 1H, J=0.9 Hz, 6.9 Hz), 4.90 (br s, 2H), 4.61 (s, 2H), 3.61 (t, 2H, J=5.7 Hz), 2.90 (t, 2H, J=5.4 Hz).

Example 162

N-(2-aminophenyl)-5-{[3-(trifluoromethyl)phenyl]sulfonyl}-4,5,6,7-tetrahydro[1,3]thiazolo[5,4-c]pyridine-2-carboxamide $^1$H NMR (DMSO-d$_6$) δ(ppm): −9.94 (s, 1H, NH), 8.19-8.05 (m, 3H), 7.86 (t, 1H, J=7.8 Hz), 7.21 (dd, 1H, J=1.2 Hz, 7.8 Hz), 6.95 (dt, 1H, J=1.5 Hz, 8.1 Hz), 6.76 (dd, 1H, J=1.5 Hz, 8.1 Hz), 6.59 (dt, 1H, J=1.2 Hz, 7.8 Hz), 4.88 (br s, 2H), 4.66 (s, 2H), 3.64 (t, 2H, J=5.7 Hz), 2.82 (t, 2H, J=5.4 Hz).

Example 163

N-(2-aminophenyl)-5-[(3-fluorophenyl)sulfonyl]-4,5,6,7-tetrahydro[1,3]-thiazolo[5,4-c]pyridine-2-carboxamide $^1$H NMR (DMSO-d$_6$) δ(ppm): −9.51 (s, 1H, NH), 7.72-7.54 (m, 4H), 7.22 (dd, 1H, J=1.2 Hz, 7.8 Hz), 6.94 (dt, 1H, J=1.5 Hz, 7.2 Hz), 6.76 (dd, 1H, J=1.5 Hz, 7.8 Hz), 6.59 (dt, 1H, J=1.2 Hz, 7.8 Hz), 4.90 (br s, 2H), 4.58 (s, 2H), 3.57 (t, 2H, J=6.0 Hz), 2.88 (t, 2H, J=5.7 Hz).

Example 164

N-(2-aminophenyl)-5-(isopropylsulfonyl)-4,5,6,7-tetrahydro[1,3]thiazolo[5,4-c]pyridine-2-carboxamide $^1$H NMR (DMSO-d$_6$) δ(ppm): −9.98 (s, 1H, NH), 7.26 (dd, 1H, J=1.5 Hz, 6.1 Hz), 6.97 (dt, 1H, J=1.5 Hz, 8.1 Hz), 6.79 (dd, 1H, J=1.5 Hz, 8.1 Hz), 6.61 (dt, 1H, J=1.5 Hz, 7.8 Hz), 4.93 (s, 2H), 4.69 (s, 2H), 3.70 (t, 2H, J=5.7 Hz), 2.97 (t, 5H, J=5.4 Hz), 1.25 (d, 6H, J=6.9 Hz).

Example 165

N-(2-aminophenyl)-5-{[3-(difluoromethoxy)phenyl]sulfonyl}-4,5,6,7-tetrahydro[1,3]thiazolo[5,4-c]pyridine-2-carboxamide $^1$H NMR (DMSO-d$_6$) δ(ppm): −9.95 (s, 1H, NH), 7.74-7.66 (m, 2H), 7.59 (m, 1H), 7.53 (m, 1H), 7.37 (t, 1H, J=73.2 Hz, OCHF2), 7.24 (dd, 1H, 6.6 Hz), 6.96 (m, 1H), 6.77 (dd, 1H, J=8.1 Hz, 1.5 Hz), 6.59 (m, 1H), 4.90 (s, 2H), 4.59 (s, 2H), 3.58 (t, 2H, J=5.7 Hz), 2.88 (t, 2H, J=5.7 Hz).

Example 166

N-(2-aminophenyl)-5-{[4-(difluoromethoxy)phenyl]sulfonyl}-4,5,6,7-tetrahydro[1,3]thiazolo[5,4-c]pyridine-2-carboxamide $^1$H NMR (DMSO-d$_6$) δ(ppm): −9.95 (s, 1H, NH), 7.90 (d, 2H, J=9.0 Hz), 7.41 (d, 2H, J=9.0 Hz), 7.41 (t, 1H, J=72.9 Hz, OCHF2), 7.23 (dd, 1H, J=7.8 Hz, 1.2 Hz), 6.96 (m, 1H), 6.77 (dd, 1H, 8.1 Hz, 1.2 Hz), 6.59 (m, 1H), 4.90 (br s, 2H, NH2), 4.54 (s, 2H), 3.53 (t, 2H, J=5.7 Hz), 2.89 (t, 2H, J=5.7 Hz).

Example 167

N-(2-aminophenyl)-5-{[3-(trifluoromethoxy)phenyl]sulfonyl}-4,5,6,7-tetrahydro[1,3]thiazolo[5,4-c]pyridine-2-carboxamide $^1$H NMR (DMSO-d$_6$) δ(ppm): −9.95 (s, 1H, NH), 7.90 (dt, 1H, J=5.4 Hz, 1.8 Hz), 7.80-7.77 (m, 2H), 7.75 (m, 1H), 7.23 (dd, 1H, J=7.8 Hz, 1.2 Hz), 6.96 (m, 1H), 6.77 (dd, 1H, 8.1 Hz, 1.2 Hz), 6.59 (m, 1H), 4.89 (s, 2H), 4.64 (s, 2H), 3.62 (t, 2H, J=6.0 Hz), 2.85 (t, 2H, J=5.7 Hz).

Example 168

N-(2-aminophenyl)-5-{[4-(trifluoromethoxy)phenyl]sulfonyl}-4,5,6,7-tetrahydro[1,3]thiazolo[5,4-c]pyridine-2-carboxamide $^1$H NMR (DMSO-d$_6$) δ(ppm): −9.95 (s, 1H, NH), 7.99 (m, 2H), 7.60 (m, 2H), 7.22 (dd, 1H, J=8.1 Hz, 1.2 Hz), 6.96 (m, 1H), 6.77 (dd, 1H, J=8.1 Hz, 1.2 Hz), 6.59 (m, 1H), 4.89 (s, 2H), 4.59 (s, 2H), 3.59 (t, 2H, J=6.0 Hz), 2.88 (t, 2H, J=6.0 Hz).

Example 169

N-(2-amino-5-methoxyphenyl)-5-[(4-methylphenyl)sulfonyl]-4,5,6,7-tetrahydro[1,3]thiazolo[5,4-c]pyridine-2-carboxamide $^1$H NMR (DMSO-d$_6$) δ (ppm): −9.89 (s, 1H), 9.63 (s, 3H), 7.62 (d, 1H, J=3.0 Hz), 7.44 (d, 2H, J=8.1 Hz), 7.18 (d, 2H, J=8.7 Hz), 6.81 (d, 1H, J=9.0 Hz), 6.63 (dd, 1H, J=9.0, 3.0 Hz), 4.53 (s, 2H), 3.72 (s, 3H), 3.54 (t, 2H, J=5.4 Hz), 3.16 (b t, 2H), 2.27 (s, 3H).

Example 170

N-(2-amino-5-isopropylphenyl)-5-[(4-methylphenyl)sulfonyl]-4,5,6,7-tetrahydro[1,3]thiazolo[5,4-c]pyridine-2-carboxamide $^1$H NMR (DMSO-d$_6$) δ (ppm): −9.91 (s, 1H), 7.74 (d, 2H, J=8.4 Hz), 7.44 (d, 2H, J=8.4 Hz), 7.18 (d, 1H, J=1.8 Hz), 6.85 (dd, 1H, J=8.1, 2.1 Hz), 6.73 (d, 1H, J=8.1 Hz), 4.72 (b s, 2H), 4.51 (s, 2H), 3.51 (t, 2H, J=5.7 Hz), 2.89 (br t, 2H), 2.74 (q, 1H, J=6.9 Hz), 2.40 (s, 3H), 1.15 (d, 6H, J=6.9 Hz).

Example 171

N-(2-amino-5-methoxyphenyl)-5-[(4-methoxyphenyl)sulfonyl]-4,5,6,7-tetrahydro[1,3]thiazolo[5,4-c]pyridine-2-carboxamide $^1$H NMR (DMSO-d$_6$) δ (ppm): −9.94 (s, 1H), 7.78 (d, 2H, J=8.7 Hz), 7.12 (m, 3H), 6.77 (d, 1H, J=8.7 Hz), 6.62 (dd, 1H, J=8.7 Hz, 2.7 Hz), 4.50 (b s, 4H), 3.84 (s, 3H), 3.65 (s, 3H), 3.49 (t, 2H, J=6.0 Hz), 2.89 (b t, 2H).

Example 172

N-(2-aminophenyl)-5-(phenoxyacetyl)-4,5,6,7-tetrahydro[1,3]thiazolo[5,4-c]pyridine-2-carboxamide To the solution of phenoxy acetic acid (1.0 mmol) in dry DMF (10 mL), were added 1-hydroxybenzotriazole (1.2 mmol), 1-ethyl-3-(3'-dimethylaminopropyl)carbodiimide (2 mmol) and N-methylmorpholine (2.0 mmol). Solution was cooled to 0° C. N-(2-aminophenyl)-4,5,6,7-tetrahydro[1,3]thiazolo[5,4-c]pyridine-2-carboxamide obtained in step VIII of example I was then added and mixture was stirred at room temperature overnight. Reaction mixture was concentrated, diluted with water, extracted with dichloromethane, washed with brine solution, and dried over anhydrous Na$_2$SO$_4$. Concentrated and purified by column chromatograph to obtained the title compound.

$^1$H NMR (DMSO-d$^6$) δ(ppm): −9.99 (s, 1H, NH), 7.32-7.29 (m, 3H), 7.26-6.95 (m, 4H), 6.81 (dd, 1H, J=7.8 Hz, 1.2 Hz), 6.64 (t, 1H, J=7.8 Hz), 4.98 (br s, 2H, NH2), 4.91 (s, 2H), 4.85 (s, 2H), 3.86 (br s, 2H), 3.04-2.91 (m, 2H)

Examples 173-179 were Also Obtained by Following the Procedure of Example 172

Example 173

N-(2-aminophenyl)-5-[(4-methylphenoxy)acetyl]-4,5,6,7-tetrahydro[1,3]thiazolo[5,4-c]pyridine-2-carboxamide $^1$HNMR (DMSO-d$^6$) δ(ppm): −8.86 (s, 1H, NH), 7.47-7.43 (m, 1H), 7.12-7.09 (m, 3H), 6.86 (t, 4H, J=8.1 Hz), 4.91 (br s, 2H, NH2), 4.78-4.75 (m, 2H), 3.97-3.86 (m, 2H), 3.04-2.88 (m, 2H),

Example 174

N-(2-aminophenyl)-5-[(4-methoxyphenoxy)acetyl]-4,5,6,7-tetrahydro[1,3]-thiazolo[5,4-c]pyridine-2-carboxamide $^1$H NMR (DMSO-d$^6$) δ(ppm): −8.87 (s, 1H, NH), 7.45-7.43 (m, 1H), 7.09 (t, 1H), 6.93-6.83 (m, 6H), 4.90 (br s, 2H, NH2), 4.75-4.72 (m, 2H), 3.97-3.90 (m, 4H), 3.76 (s, 3H), 3.01-2.88 (m, 2H)

Example 175

N-(2-aminophenyl)-5-[(2-naphthyloxy)acetyl]-4,5,6,7-tetrahydro[1,3]thiazolo[5,4-c]pyridine-2-carboxamide $^1$H NMR (DMSO-d$^6$) δ(ppm): −10.0 (s, 1H, NH), 7.85 (d, 2H, J=8.1 Hz), 7.75 (t, 1H, J=8.5 Hz), 7.45 (t, 1H, J=8.5 Hz), 7.47-7.19 (m, 4H), 6.96 (t, 1H, J=8.1 Hz), 6.78 (d, 1H, J=7.2 Hz), 6.60 (t, 1H, J=7.8 Hz), 5.11 (br s, 2H, NH2), 4.99 (d, 2H, J=20 Hz), 4.90 (d, 2H, J=18 Hz), 3.10-2.91 (m, 2H), 3.10-2.90 (m, 2H).

Example 176

N-(2-aminophenyl)-5-[(biphenyl-4-yloxy)acetyl]-4,5,6,7-tetrahydro[1,3]thiazolo[5,4-c]pyridine-2-carboxamide $^1$H NMR (DMSO-d$^6$) δ (ppm): −96 (s, 1H, NH), 7.62-7.57 (m, 4H), 7.42 (t, 1H, J=7.8 Hz), 7.32-7.25 (m, 2H), 7.06-6.94 (m, 3H), 6.78 (dd, 1H, J=7.2 Hz, 1.1 Hz), 6.60 (t, 1H, J=7.8 Hz), 5.04 (br s, 2H, NH2), 4.97-4.85 (m, 4H), 3.87 (m, 2H), 3.10-2.91 (m, 2H).

Example 177

N-(2-aminophenyl)-5-(methoxyacetyl)-4,5,6,7-tetrahydro[1,3]thiazolo[5,4-c]pyridine-2-carboxamide $^1$H NMR (DMSO-d$^6$) δ (ppm): −9.97 (s, 1H, NH), 7.26 (dd, 1H, J=7.8 Hz, 1.2 Hz), 6.97 (dt, 1H, J=8.1 Hz, 1.5 Hz), 6.80 (dd, 1H, J=8.1 Hz, 1.2 Hz), 6.60 (dt, 1H, J=7.8 Hz, 1.2 Hz), 4.93 (s, 2H), 4.82 (s, 2H), 4.21 (m, 2H), 3.76 (m, 2H), 2.98 (m, 2H).

Example 178

N-(2-amino-5-isopropylphenyl)-5-[(4-methoxyphenoxy)acetyl]-4,5,6,7-tetrahydro[1,3]thiazolo[5,4-c]pyridine-2-carboxamide $^1$H NMR (DMSO-d$_6$) δ (ppm): −9.94 & 9.99 (s, 1H), 7.21 (m, 1H), 6.83-6.95 (m, 5H), 6.74 (d, 1H, J=8.1 Hz), 4.91 (s, 2H), 4.85 (s, 2H), 4.75 (b s, 2H), 3.86 (b t, 2H), 3.70 (s, 3H), 2.99 & 3.03 (br t, 2H), 2.77 (q, 1H, J=6.9 Hz), 1.16 (d, 6H, J=6.9 Hz).

Example 179

N-(2-aminophenyl)-5-[(3-methoxyphenoxy)acetyl]-4,5,6,7-tetrahydro[1,3]-thiazolo[5,4-c]pyridine-2-carboxamide $^1$H NMR (DMSO-d$_6$) δ(ppm): 9.96 (s, 1H), 7.27 (d, 1H, J=6.9 Hz), 7.18 (t, 1H, J=7.8 Hz), 6.95 (t, 1H, J=7.2 Hz), 6.62 (t, 1H, J=7.8 Hz), 6.54 (m, 3H), 4.96 (s, 2H), 4.93 (s, 2H), 4.88 (s, 2H), 3.86 (m, 2H), 3.73 (s, 3H), 2.97 (m, 2H).

Example 180

Methyl 2-[(2-aminophenyl)carbamoyl]-6,7-dihydro[1,3]thiazolo[5,4-c]pyridine-5(4H)-carboxylate Methyl chloroformate (1.0 mmol) was added drop wise to N-(2-aminophenyl)-4,5,6,7-tetrahydro[1,3]thiazolo[5,4-c]pyridine-2-carboxamide obtained from step VIII of example 1 (1.0 mmol) solution in 10 mL of dry DMF at 0° C. Reaction mixture was stirred for additional 3 h Reaction mixture was concentrated, diluted with water, extracted with dichloromethane, washed with brine solution, and dried over anhydrous Na$_2$SO$_4$. Concentrated and purified by column chromatography to get the title compound.

$^1$H NMR (DMSO-d$^6$) δ(ppm): –9.98 (s, 1H, NH), 7.26 (dd, 1H, J=7.8 Hz, 1.2 Hz), 6.97 (t, 1H, J=8.1 Hz), 6.80 (dd, 1H, J=7.8 Hz, 1.2 Hz), 6.60 (dd, 1H, J=7.5 Hz, 6.3 Hz, 1.2 Hz), 4.92 (br s, 2H, NH2), 4.76 (s, 2H), 3.76 (t, 2H, J=5.7 Hz), 3.66 (s, 3H), 2.91 (t, 2H, 5.7 Hz).

Example 181

Biphenyl-4-yl 2-[(2-aminophenyl)carbamoyl]-6,7-dihydro[1,3]thiazolo[5,4-c]pyridine-5(4H)-carboxylate 1,1'-Carbonyldiimidazole (1.0 mmol) was added to biphenyl-4-ol (1.0 mmol) dissolved in of dichloromethane (5.0 mL). Catalytic amount of p-toluenesulphonic acid was added and mixture was stirred at room temperature for 2 to 3 h This solution was then added to N-(2-aminophenyl)-4,5,6,7-tetrahydro[1,3]thiazolo[5,4-c]pyridine-2-carboxamide obtained from step VIII of example 1 (1.0 mmol) in 10 mL of dry DMF. Reaction mixture was stirred at room temperature overnight. Reaction mixture was concentrated, diluted with water, extracted with dichloromethane washed with brine solution, and dried over anhydrous Na$_2$SO$_4$. Concentrated and purified by column chromatography to yield the title compound.

$^1$H NMR (CDCl$_3$) δ (ppm): –8.91 (s, 1H, NH), 7.58 (m, 3H), 7.46 (m, 3H), 7.34 (m, 1H), 7.22 (m, 2H), 7.12 (m, 1H), 6.88 (m, 1H), 5.83 (s, 1H), 4.07-3.98 (m, 2H), 3.09 (br s, 1H).

Examples 182 to 189 were Also Obtained by Following the Procedure of Example 181

Example 182

4-methylphenyl 2-[(2-aminophenyl)carbamoyl]-6,7-dihydro[1,3]thiazolo[5,4-c]pyridine-5(4H)-carboxylate $^1$H NMR (CDCl$_3$) δ (ppm): –8.02 (s, 1H, NH), 7.48 (d, 2H, J=7.9 Hz), 7.28 (s, 2H), 7.20-7.01 (m, 3H), 6.88 (t, 2H, J=7.2 Hz), 5.01 (s, 1H), 4.89 (s, 1H), 4.04 (m, 2H), 3.07 (br s, 2H), 2.36 (s, 3H)

Example 183

4-methoxyphenyl 2-[(2-aminophenyl)carbamoyl]-6,7-dihydro[1,3]thiazolo[5,4-c]pyridine-5(4H)-carboxylate $^1$H NMR (DMSO-d$^6$) δ (ppm): –10.0 (s, 1H, NH), 7.26 (dd, 1H, J=8.1 Hz, 1.5 Hz), 7.08 (d, 2H, J=8.7 Hz), 6.93 (m, 3H), 6.78 (dd, 1H, J=8.1 Hz, 1.2 Hz), 6.60 (t, 1H, J=7.8 Hz), 4.99 (s, 1H), 4.92 (br s, 2H, NH2), 4.82 (s, 1H), 3.90 (m, 2H), 3.00 (s, 2H).

Example 184

4-(propoxycarbonyl)phenyl 2-[(2-aminophenyl)carbamoyl]-6,7-dihydro[1,3]thiazolo[5,4-c]pyridine-5(4H)-carboxylate $^1$HNMR (DMSO-d$^6$) δ (ppm): –9.97 (s, 1H, NH), 7.26 (dd, 1H, J=7.8 Hz, 1.2 Hz), 6.99-6.94 (m, 1H), 6.78 (dd, 1H, J=8.1 Hz, 1.2 Hz), 6.63-6.57 (m, 1H), 4.92 (br s, 2H, NH2), 4.76 (s, 2H), 3.76 (t, 2H, J=6.0 Hz), 2.91 (t, 2H, 5.4 Hz), 1.57 (m, 2H), 1.35 (m, 2H), 0.94 (t, 31-1, J=7.2 Hz).

Example 185

2-naphthyl 2-[(2-aminophenyl)carbamoyl]-6,7-dihydro[1,3]thiazolo[5,4-c]-pyridine-5(4H)-carboxylate $^1$H NMR (DMSO-d$^6$) δ (ppm): –10.1 (s, 1H, NH), 7.96-7.88 (m, 3H), 7.72 (s, 1H), 7.54-7.49 (m, 2H), 7.38 (d, 1H, J=8.1 Hz), 7.27 (dd, 1H, J=7.8 Hz, 1.2 Hz), 6.94 (t, 1H, J=7.2 Hz), 5.1 (s, 1H), 4.93 (s, 2H, NH2), 4.87 (s, 1H), 3.95 (m, 2H), 3.05 (m, 2H).

Example 186

3,4-dimethoxyphenyl 2-[(2-aminophenyl)carbamoyl]-6,7-dihydro[1,3]thiazolo[5,4-c]pyridine-5(4H)-carboxylate $^1$H NMR (DMSO-d$^6$) δ(ppm): –10.01 (s, 1H), 7.27 (d, 1H, J=7.8 Hz), 7.00-6.91 (m, 2H), 6.81 (m, 2H), 6.70-6.59 (m, 2H), 5.00-4.93 (m, 4H), 3.96-3.84 (m, 2H), 3.74 (s, 3H), 3.05-2.99 (m, 2H).

Example 187

Butyl 2-[(2-aminophenyl)carbamoyl]-6,7-dihydro[1,3]thiazolo[5,4-c]pyridine-5(4H)-carboxylate $^1$H NMR (DMSO-d$_6$) δ(ppm) 9.96 (s, 1H, NH), 7.26 (dd, 1H, J=7.8 Hz, 1.2 Hz), 6.97 (dt, 1H, J=8.1 Hz, 1.5 Hz), 6.78

(dd, 1H, J=8.1 Hz, 1.2 Hz), 6.61 (dt, 1H, J=7.8 Hz, 1.5 Hz), 4.92 (s, 2H), 4.76 (s, 2H), 4.06 (t, 2H, J=6.6 Hz), 3.77 (t, 2H, J=5.7 Hz), 2.90 (m, 2H), 1.59 (m, 2H), 1.37 (m, 2H).

Example 188

Benzyl 2-[(2-aminophenyl)carbamoyl]-6,7-dihydro[1,3]thiazolo[5,4-c]pyridine-5(4H)-carboxylate $^1$H NMR (DMSO-d$^6$) δ(ppm): −10.1 (s, 1H, NH), 9.97 (s, 1H), 7.40-7.33 (m, 5H), 7.26 (dd, 1H, J=7.8 Hz, 1.2 Hz), 6.95 (t, 1H, J=7.0 Hz), 6.79 (dd, 1H, J=7.8 Hz, 1.2 Hz), 6.60 (ddd, 1H, J=7.8 Hz, 7.2 Hz, 1.2 Hz), 5.15 (s, 2H), 4.92 (s, 2H, NH2), 4.80 (br s, 2H), 3.8 (t, 2H), 2.92 (t, 2H, J=5.7 Hz).

Example 189

Pyridin-3-ylmethyl 2-[(2-aminophenyl)carbamoyl]-6,7-dihydro[1,3]thiazolo[5,4-c]pyridine-5(4H)-carboxylate $^1$H NMR (DMSO-d$^6$) δ(ppm): −9.97 (s, 1H, NH), 8.63 (d, 1H, J=1.5 Hz), 8.54 (dd, 1H, J=4.8 Hz, 1.5 Hz), 7.82 (m, 1H), 7.41 (t, 1H, J=7.5 Hz, 5.1 Hz), 7.26 (dd, 1H, J=7.5 Hz, 1.5 Hz), 6.63 (m, 1H), 5.19 (s, 2H), 4.92 (s, 2H, NH2), 4.80 (br s, 2H), 3.80 (m, 2H), 2.92 (t, 2H, 5.7 Hz).

Example 190

N-(2-aminophenyl)-5-[3-(1,3-benzodioxol-5-yl)prop-2-enoyl]-4,5,6,7-tetrahydro[1,3]thiazolo[5,4-c]pyridine-2-carboxamide To the solution of 3-Benzo[1,3]dioxol-5-yl-acrylic acid (1.0 mmol) in dry 10 mL DMF, were added 1-hydroxybenzotriazole (1.2 mmol), 1 ethyl 3(3' dimethylaminopropyl) carbodiimide (2 mmol) and N-methylmorpholine (2.0 mmol). Solution was cooled to 0° C. N-(2-aminophenyl)-4,5,6,7-tetrahydro[1,3]thiazolo[5,4-c]pyridine-2-carboxamide obtained from step VIII of example I was then added and mixture was stirred at room temperature overnight. Reaction mixture was concentrated, diluted with water, extracted with dichloromethane washed with brine solution, and dried over anhydrous $Na_2SO_4$. Concentrated and purified by column chromatography to get the title compound.

$^1$H NMR (DMSO-d$_6$) δ (ppm): −9.97 (s, 1H, NH), 7.52 (m, 1H), 7.28-7.18 (m, 3H), 6.96 (m, 2H), 6.80 (dd, 1H, J=8.1 Hz, 1.2 Hz), 6.61 (dt, 1H, J=7.8 Hz, 1.2 Hz), 6.08 (s, 1H), 4.93 (m, 4H), 4.10-3.90 (m, 4H), 2.89-2.95 (m, 2H).

Example 191

N-(2-aminophenyl)-5-[3-(3,4-dihydroxyphenyl)prop-2-enoyl]-4,5,6,7-tetrahydro[1,3]thiazolo[5,4-c]pyridine-2-carboxamide Obtained by following procedure of example 190.

$^1$H NMR (DMSO-d$_6$) δ (ppm): −10.00 (s, 1H, NH), 9.54 (s, 1H), 9.00 (s, 1H) 7.40 (d, 1H, J=15 Hz), 7.26 (dd, 1H, J=7.8 Hz, 1.2 Hz), 7.14-6.94 (m, 4H), 6.77 (t, 2H, J=8.1 Hz), 6.61 (t, 1H, J=7.8 Hz), 5.12 (s, 1H), 4.94 (s, 3H), 4.05-3.95 (m, 2H), 2.98 (m, 2H)

Example 192

N-(2-aminophenyl)-5-pyrimidin-2-yl-4,5,6,7-tetrahydro[1,3]thiazolo[5,4-c]pyridine-2-carboxamide To a solution of 2-chloro pyrimidine (1.2 eq) in DMF, N-(2-aminophenyl)-4,5,6,7-tetrahydro[1,3]thiazolo[5,4-c]pyridine-2-carboxamide obtained from step VIII of example I (1.0 eq) was added and the reaction mixture was stirred at 100° C. for 15 h. Solvent was then evaporated under reduced pressure to afford crude product, which, on purification by column chromatography or preparative HPLC afforded the title compound.

$^1$H NMR (CDCl$_3$) δ (ppm): −8.90 (s, 1H), 8.35 (d, 2H, J=5.1 Hz), 7.44 (d, 1H, J=8.1 Hz), 7.10 (t, 1H, J=8.7 Hz), 6.85 (m, 2H), 6.58 (t, 1H, J=5.1 Hz), 5.12 (s, 2H), 4.24 (t, 2H, J=6.0 Hz), 3.93 (b s, 2H), 3.03 (t, 2H, J=5.7 Hz).

Examples 193-199 were Also Obtained by Following the Procedure of Example 192

Example 193

N-(2-aminophenyl)-5-(4-pyridin-3-ylpyrimidin-2-yl)-4,5,6,7-tetrahydro[1,3]thiazolo[5,4-c]pyridine-2-carboxamide $^1$H NMR (DMSO-d$_6$) δ(ppm): −10.00 (s, 1H), 9.39 (s, 1H), 8.73 (dd, 1H, J=7.8, 1.8 Hz), 8.54-8.59 (m, 2H), 7.58 (dd, 1H, J=8.1, 4.8 Hz), 7.41 (d, 1H, J=5.1 Hz), 7.26 (dd, 1H, J=7.8, 1.2 Hz), 6.97 (t, 1H, J=8.4 Hz), 6.78 (dd, 1H, J=8.1, 1.2 Hz), 6.61 (t, 1H, J=7.5 Hz), 5.23 (s, 2H), 4.93 (s, 2H), 4.29 (t, 2H, J=5.7), 3.03 (b t, 2H).

Example 194

N-(2-aminophenyl)-5-(5-nitropyridin-2-yl)-4,5,6,7-tetrahydro[1,3]thiazolo[5,4-c]pyridine-2-carboxamide $^1$H NMR (DMSO-d$_6$) δ(ppm): −99 (s, 1H), 9.02 (d, 1H, J=2.7 Hz), 8.32 (dd, 1H, J=9.3, 3.0 Hz), 7.26 (dd, 1H, J=7.8, 1.2 Hz), 7.15 (d, 1H, J=9.9 Hz), 6.95 (t, 1H, J=8.7 Hz), 6.78 (dd, 1H, J=7.8, 1.2 Hz), 6.61 (t, 1H, J=8.7 Hz), 5.17 (s, 2H), 4.93 (s, 2H), 4.21 (t, 2H, J=5.7 Hz), 3.05 (b t, 2H).

Example 195

N-(2-aminophenyl)-5-[5-(trifluoromethyl)pyridin-2-yl]-4,5,6,7-tetrahydro[1,3]thiazolo[5,4-c]pyridine-2-carboxamide $^1$H NMR (CDCl$_3$) δ(ppm): −0.90 (s, 1H), 8.46 (s, 1H), 7.73 (dd, 1H, J=9.0, 2.4 Hz), 7.46 (dd, 1H, J=8.1, 1.2 Hz), 7.12 (t, 1H, J=7.8 Hz), 6.90-6.80 (m, 3H), 5.03 (s, 2H), 4.10 (t, 2H, J=5.7 Hz), 3.93 (b s, 2H), 3.08 (t, 2H, J=5.7 Hz).

Example 196

N-(2-aminophenyl)-5-(5-{[(4-methylphenyl)sulfonyl]amino}pyrimidin-2-yl)-4,5,6,7-tetrahydro[1,3]thiazolo[5,4-c]pyridine-2-carboxamide $^1$H NMR (CDCl$_3$) δ (ppm): −8.91 (s, 1H), 8.06 (s, 2H), 7.63 (d, 2H, J=8.4 Hz), 7.46 (d, 1H, J=8.1 Hz), 7.35-7.26 (m, 2H), 7.12 (t, 1H, J=7.8 Hz), 6.86 (m, 2H), 5.09 (s, 2H), 4.23 (t, 2H, J=6.0 Hz), 3.03 (b t, 2H), 2.44 (s, 3H).

Example 197

N-(2-aminophenyl)-5-(5-{[(4-methylphenyl)sulfonyl]amino}pyridin-2-yl)-4,5,6,7-tetrahydro[1,3]thiazolo[5,4-c]pyridine-2-carboxamide $^1$H NMR (CDCl$_3$) δ(ppm): −0.90 (s, 1H), 7.74 (d, 2H, J=2.7 Hz), 7.61 (d, 2H, J=8.1 Hz), 7.44 (m, 2H), 7.26 (d, 2H, J=8.4 Hz), 7.12 (t, 1H, J=7.5 Hz), 6.84-6.90 (m, 2H), 6.70 (d, 1H, J=9.0 Hz), 6.37 (s, 1H), 4.88 (s, 2H), 3.97 (t, 2H, J=5.7 Hz), 3.03 (t, 2H, J=5.7 Hz), 2.42 (s, 3H).

Example 198

N-(2-aminophenyl)-5-{4-[(benzylcarbamoyl)amino]phenyl}-4,5,6,7-tetrahydro[1,3]thiazolo[5,4-c]pyridine-2-carboxamide $^1$H NMR (DMSO-d$_6$) δ(ppm): −92 (s, 1H), 8.33 (s, 1H), 7.23-7.35 (M, 8H), 6.94-6.99 (m, 3H), 6.79 (dd, 1H, J=8.1, 1.2 Hz), 6.60 (dt, 1H, J=7.8, 1.5 Hz), 6.52 (t, 1H, J=6.0 Hz), 4.92 (s, 2H), 4.52 (s, 2H), 4.27 (d, 1H, J=6.0 Hz), 3.64 (t, 2H, J=5.7 Hz), 2.93 (br t, 2H)

Example 199

N-(2-aminophenyl)-5-(4-{[(4-methylphenyl)sulfonyl]amino}phenyl)-4,5,6,7-tetrahydro[1,3]thiazolo[5,4-c]pyridine-2-carboxamide $^1$H NMR (CDCl$_3$) δ(ppm): −8.91 (s, 1H), 7.60 (d, 2H, J=8.4 Hz), 7.46 (dd, 1H, J=8.1, 1.2 Hz), 7.23 (d, 2H, J=8.1 Hz), 7.11 (t, 1H, J=7.5 Hz), 6.98 (d, 2H, J=9.0 Hz), 6.84-6.90 (m, 4H), 4.50 (s, 2H), 3.68 (t, 2H, J=5.7 Hz), 3.01 (t, 2H, J=5.7 Hz), 2.40 (s, 3H).

Example 200

N-(2-aminophenyl)-5-[(4-methylphenyl)sulfonyl]-4,5,6,7-tetrahydrothieno[3,2-c]pyridine-2-carboxamide Step:-I 1-[(4-methylphenyl)sulfonyl]piperidin-4-one To a solution of a piperidone hydrochloride (1 eq) in dichloromethane was added pyridine (2.1 eq) at 0° C. and the reaction mixture was stirred for 15 min. To this, a solution p-toluene sulfonyl chloride (1.1 eq) in dichloromethane was added at 0° C. and the reaction was continued at room temperature for overnight. Water was added and the organic layer was separated, dried over anhydrous Na$_2$SO$_4$ and concentrated under reduced pressure to afford crude product, which, on purification by column chromatography afforded the 1-[(4-methylphenyl)sulfonyl]piperidin-4-one.

$^1$H NMR (CDCl$_3$) δ (ppm): −7.69 (d, 2H, J=8.4 Hz), 7.36 (d, 2H, J=8.4 Hz), 3.40 (t, 4H, J=6.3 Hz), 2.56 (t, 4H, J=6.3 Hz), 2.46 (s, 3H)

Step-II 4-chloro-1-[(4-methylphenyl)sulfonyl]-1,2,5,6-tetrahydropyridine-3-carbaldehyde A solution of POCl$_3$ (1.5 eq.) in DMF (2.5 eq) at 0° C. was stirred for 15 min. 1-[(4-methylphenyl) sulfonyl]piperidin-4-one (1.0 eq) obtained from step I was added to the above solution and the reaction was continued at room temperature for 2 h Reaction was quenched with water and the organic layer was separated, dried over anhydrous Na$_2$SO$_4$ and concentrated under reduced pressure to afford crude product, which, on purification by column chromatography afforded the desired 4-chloro-1-[(4-methylphenyl)sulfonyl]-1,2,5,6-tetrahydropyridine-3-carbaldehyde.

$^1$H NMR (DMSO-d$_6$) δ (ppm): −9.94 (s, 1H), 7.69 (d, 2H, J=8.4 Hz), 7.47 (d, 2H, J=8.4 Hz), 3.67 (s, 2H), 3.26 (t, 2H, J=6.3 Hz), 2.75 (t, 2H, J=6.3 Hz), 2.50 (s, 3H).

Step-III ethyl 5-[(4-methylphenyl)sulfonyl]-4,5,6,7-tetrahydrothieno[3,2-c]pyridine-2-carboxylate To a solution of a 4-chloro-1-[(4-methylphenyl)sulfonyl]-1,2,5,6-tetrahydropyridine-3-carbaldehyde (1 eq) obtained from step II in pyridine was added triethyl amine (1.5 eq.), ethyl thioglycolate (1 eq.) at 0° C. and the reaction mixture was stirred for overnight. A solution of KOH (1.5 eq) in water was added at 0° C. and the reaction was continued at room temperature for 1 h Reaction was quenched with water and the organic layer was separated, dried over anhydrous Na$_2$SO$_4$ and concentrated under reduced pressure to afford crude product, which, on purification by column chromatography afforded ethyl 5-[(4-methylphenyl)sulfonyl]-4,5,6,7-tetrahydrothieno[3,2-c]pyridine-2-carboxylate.

$^1$H NMR (DMSO-d$_6$) δ (ppm): −7.69 (d, 2H, J=8.0 Hz), 7.58 (s, 1H), 7.44 (d, 2H, J=8.0 Hz), 4.25 (q, 2H, J=6.9 Hz), 4.16 (s, 2H) 4.10 (s, 1H), 3.74 (t, 2H, J=6.3 Hz), 2.88 (t, 2H, J=6.3 Hz), 2.39 (s, 3H), 1.26 (t, 3H, J=6.9 Hz).

Step-IV

5-[(4-methylphenyl)sulfonyl]-4,5,6,7-tetrahydrothieno[3,2-c]pyridine-2-carboxylic acid A solution of ethyl 5-[(4-methylphenyl)sulfonyl]-4,5,6,7-tetrahydrothieno[3,2-c]pyridine-2-carboxylate (1 eq) obtained from step B1 and NaOH (1.5 eq.) in ethanol was refluxed for 2 h. Reaction mixture was concentrated under reduced pressure and neutralized to get 5-[(4-methylphenyl)sulfonyl]-4,5,6,7-tetrahydrothieno[3,2-c]pyridine-2-carboxylic acid.

$^1$H NMR (DMSO-d$_6$) δ(ppm): −7.70 (d, 2H, J=8.0 Hz), 7.44 (d, 2H, J=8.0 Hz), 7.35 (s, 1H), 4.12 (s, 2H), 3.36 (t, 2H, J=6.3 Hz), 2.84 (t, 2H, J=6.3 Hz), 2.39 (s, 3H).

Step-V

N-(2-aminophenyl)-5-[(4-methylphenyl)sulfonyl]-4,5,6,7-tetrahydrothieno[3,2-c]-pyridine-2-carboxamide To a solution of 5-[(4-methylphenyl)sulfonyl]-4,5,6,7-tetrahydrothieno[3,2-c]pyridine-2-carboxylic acid (1.0 eq) obtained from step IV in DMF was added Et$_3$N (2.2 eq.), EDCI (1.2 eq) and HOBt ((1.2 eq) and reaction was stirred for 1 h Phenylene diamine was added and reaction was stirred for overnight. Reaction was then quenched with water and extracted with ethyl acetate. Organic layer was separated, dried over anhydrous Na$_2$SO$_4$ and concentrated under reduced pressure to afford crude product, which, on purification by column chromatography afforded the title compound.

$^1$H NMR (DMSO-d$_6$) δ (ppm): −9.61 (s, 1H), 7.73 (d, 2H, J=8.4 Hz), 7.67 (s, 1H), 7.45 (d, 2H, J=8.1 Hz), 7.11 (dd, 1H, J=8.1, 1.5 Hz), 6.97 (t, 1H, J=8.1 Hz), 6.77 (dd, 1H, J=8.1, 1.2 Hz), 6.97 (t, 1H, J=8.1 Hz), 4.89 (b s, 2H), 4.17 (s, 2H), 3.38 (t, 2H, J=5.7 Hz), 2.88 (t, 2H, J=5.4 Hz), 2.41 (s, 3H).

Example 201

N-(2-aminophenyl)-5-[(4-methylphenyl)sulfonyl]-4,5,6,7-tetrahydrofuro[3,2-c]pyridine-2-carboxamide

Step-I ethyl 5-[(4-methylphenyl)sulfonyl]-4,5,6,7-tetrahydrofuro[3,2-c]pyridine-2-carboxylate To a solution of ethyl glycolate (1 eq) in THF was added sodium hydride (2.5 eq) at 0° C. and the reaction mixture was stirred for 1 h 4-chloro-1-[(4-methylphenyl)sulfonyl]-1,2,5,6-tetrahydropyridine-3-carbaldehyde (1 eq) obtained in step II of example 200 in THF was added at 0° C. and was refluxed for 2 h. Reaction was quenched with water and extracted with ethyl acetate, organic layer was separated, dried over anhydrous $Na_2SO_4$ and concentrated under reduced pressure to afford crude product, which, on purification by column chromatography afforded the ethyl 5-[(4-methylphenyl)sulfonyl]-4,5,6,7-tetrahydrofuro[3,2-c]pyridine-2-carboxylate.

$^1$H NMR (CDCl$_3$) δ (ppm): −7.73 (d, 2H, J=8.10 Hz), 7.33 (d, 2H, J=8.10 Hz), 6.98 (s, 1H), 4.34 (q, 2H, J=7.2 Hz), 4.14 (s, 2H), 3.5 (t, 2H, J=5.6 Hz), 2.83 (t, 2H, J=5.6 Hz), 2.45 (s, 32H), 1.38 (t, 3H, J=7.2 Hz).

Step-II

5-[(4-methylphenyl)sulfonyl]-4,5,6,7-tetrahydrofuro[3,2-c]pyridine-2-carboxylic acid A solution of ethyl 5-[(4-methylphenyl)sulfonyl]-4,5,6,7-tetrahydrofuro[3,2-c]pyridine-2-carboxylate (1 eq) obtained form step I and NaOH (1.5 eq.) in ethanol was refluxed for 2 h Reaction mixture was concentrated under reduced pressure and neutralized to get 5-[(4-methylphenyl)sulfonyl]-4,5,6,7-tetrahydrofuro[3,2-c]pyridine-2-carboxylic acid.

$^1$H NMR (DMSO-d$_6$) δ (ppm): −7.68 (d, 2H, J=8.0 Hz), 7.46 (d, 2H, J=8.0 Hz), 6.82 (s, 1H), 3.95 (s, 2H), 3.45 (t, 2H, J=6.3 Hz), 2.71 (t, 2H, J=6.3 Hz), 2.39 (s, 3H).

Step-III

N-(2-aminophenyl)-5-[(4-methylphenyl)sulfonyl]-4,5,6,7-tetrahydrofuro[3,2-c]-pyridine-2-carboxamide To a solution of 5-[(4-methylphenyl)sulfonyl]-4,5,6,7-tetrahydrofuro[3,2-c]pyridine-2-carboxylic acid (1.0 eq) obtained from step II in DMF was added Et$_3$N (2.2 eq.), EDCI (1.2 eq) and HOBt ((1.2 eq) and reaction was stirred for 1 h Phenylene diamine was added to reaction mass and stirred for overnight. Reaction was quenched with water and the organic layer was separated, dried over anhydrous Na2SO4 and concentrated under reduced pressure to afford crude product, which, on purification by column chromatography afforded the title compound.

$^1$H NMR (DMSO-d$_6$) δ (ppm): −9.51 (s, 1H), 7.73 (d, 2H, J=8.4 Hz), 7.45 (d, 2H, J=8.1 Hz), 7.15 (s, 1H), 7.12 (dd, 1H, J=7.8, 1.5 Hz), 6.96 (t, 1H, J=8.1 Hz), 6.76 (dd, 1H, J=8.1, 1.2 Hz), 6.97 (t, 1H, J=8.1 Hz), 4.86 (b s, 2H), 4.09 (s, 2H), 3.45 (t, 2H, J=5.7 Hz), 2.79 (t, 2H, J=5.4 Hz), 2.41 (s, 3H).

Example 202

N-(2-aminophenyl)-1-methyl-5-[(4-methylphenyl)sulfonyl]-4,5,6,7-tetrahydro-1H-pyrrolo[3,2-c]pyridine-2-carboxamide

Step-I

Ethyl 1-methyl-5-[(4-methylphenyl)sulfonyl]-4,5,6,7-tetrahydro-1H-pyrrolo[3,2-c]pyridine-2-carboxylate To a solution of 4-chloro-1-[(4-methylphenyl)sulfonyl]-1,2,5,6-tetrahydropyridine-3-carbaldehyde (1 eq) obtained in step II of example 200 in DMSO was added Na$_2$CO$_3$ (4.0 eq) and sarcosine hydrochloride (2.0 eq) at room temp and the reaction mixture was stirred for 1.5 hr at 40° C. Reaction mass was then quenched with water and extracted with ethyl acetate. Organic layer was separated and dried over anhydrous Na$_2$SO$_4$, concentrated under reduced pressure to afford crude product, which, was dissolve in DMF and added to the mixture of tBuOK (1.0 eq) in DMF at 0° C. and stirred at room temperature for 2 h Reaction mass was quenched in water and extracted with ethyl acetate. Organic layer was separated dried over anhydrous Na2SO4 and concentrated under reduced pressure to afford crude product, which, on purification by column chromatography afforded ethyl 1-methyl-5-[(4-methylphenyl)sulfonyl]-4,5,6,7-tetrahydro-1H-pyrrolo[3,2-c]pyridine-2-carboxylate.

$^1$H NMR (DMSO-D$_6$) δ (ppm): −7.69 (d, 2H, J=8.10 Hz), 7.29 (d, 2H, J=8.10 Hz), 6.69 (s, 1H), 4.26 (q, 2H, J=7.2 Hz), 4.10 (s, 2H), 3.72 (s, 3H), 2.41 (t, 2H, J=6.0 Hz), 2.42 (s, 3H), 1.46 (t, 3H, J=6.0 Hz), 1.2 (t, 3H, J=7.2 Hz).

Step-II 1-methyl-5-[(4-methylphenyl)sulfonyl]-4,5,6,7-tetrahydro-1H-pyrrolo[3,2-c]pyridine-2-carboxylic acid A solution ethyl 1-methyl-5-[(4-methylphenyl)sulfonyl]-4,5,6,7-tetrahydro-1H-pyrrolo[3,2-c]pyridine-2-carboxylate (1 eq) obtained from step I and NaOH (1.5 eq.) in ethanol was refluxed for 2 h Reaction mixture was concentrated under reduced pressure and neutralized to get 1-methyl-5-[(4-methylphenyl)sulfonyl]-4,5,6,7-tetrahydro-1H-pyrrolo[3,2-c]pyridine-2-carboxylic acid.

$^1$H NMR (DMSO-d$_6$) δ(ppm): −7.67 (d, 2H, J=7.8 Hz), 7.45 (d, 2H, J=7.8 Hz), 6.46 (s, 1H), 4.01 (s, 2H), 3.79 (t, 2H, J=6.3 Hz), 3.28 (t, 2H, J=6.3 Hz), 1.99 (s, 3H).

Step-III

N-(2-aminophenyl)-1-methyl-5-[(4-methylphenyl)sulfonyl]-4,5,6,7-tetrahydro-1H-pyrrolo[3,2-c]pyridine-2-carboxamide To a solution of 1-methyl-5-[(4-methylphenyl)sulfonyl]-4,5,6,7-tetrahydro-1H-pyrrolo[3,2-c]pyridine-2-carboxylic acid (1.0 eq) obtained form step II in DMF was added Et$_3$N (2.2 eq.), EDCI (1.2 eq) and HOBt (1.2 eq). Reaction was stirred for 1 h Phenylene diamine was added to reaction and stirred for overnight. Reaction was then quenched with water and extracted with ethyl acetate. Organic layer was separated, dried over anhydrous Na$_2$SO$_4$ and concentrated under reduced pressure to afford crude product, which, on purification by column chromatography afforded the title compound.

¹H NMR (DMSO-d₆) δ (ppm): −9.13 (s, 1H), 7.70 (d, 2H, J=8.04 Hz), 7.42 (d, 2H, J=8.04 Hz), 7.09 (d, 1H, J=6.7 Hz), 6.9 (d, 1H, J=6.7 Hz), 6.77 (s, 1H), 6.73 (d, 1H, J=7.0 Hz), 6.56 (t, 1H, J=7.2 Hz), 4.8 (s, 2H), 3.99 (s, 2H), 3.65 (s, 3H), 2.70 (t, 2H, J=5.6 Hz), 2.42 (t, 2H, J=5.6 Hz), 2.39 (s, 3H).

Example 203

N²-(2-aminophenyl)-N⁵-pyridin-3-yl-6,7-dihydrothieno[3,2-c]pyridine-2,5(4H)-dicarboxamide Step:-I ethyl 4-oxopiperidine-1-carboxylate To a solution of a piperidone hydrochloride (1 eq) in dichloromethane was added Et₃N (2.1 eq) at 0° C. and the reaction mixture was stirred for 15 min. A solution ethyl chloroformate (1.1 eq) in chloroform was added at 0° C. and reaction was continued at room temperature for 3 h Reaction was quenched with water and extracted with ethyl acetate, organic layer was separated, dried over anhydrous Na₂SO₄ and concentrated under reduced pressure to afford crude product, which, on purification by column chromatography afforded the desired ethyl 4-oxopiperidine-1-carboxylate.

¹H NMR (CDCl₃) δ(ppm): −4.18 (q, 2H, J=7.2 Hz), 3.77 (t, 2H, J=7.2 Hz), 2.46 (t, 4H, J=6.3 Hz), 1.2 (t, 3H, J=7.2 Hz).

Step-II ethyl 4-chloro-5-formyl-3,6-dihydropyridine-1(2H)-carboxylate

A solution of DMF (2.5 eq) and POCl₃ (1.5 eq.) at 0° C. was stirred for 15 min. To that ethyl 4-oxopiperidine-1-carboxylate (1.0 eq) obtained from step I was added at 40° C. and reaction was continued at room temperature for 2 h Reaction was quenched with water and extracted with ethyl acetate, organic layer was separated, dried over anhydrous Na2SO4 and concentrated under reduced pressure to afford crude product, which, on purification by column chromatography afforded the desired ethyl 4-chloro-5-formyl-3,6-dihydropyridine-1(2H)-carboxylate.

¹H NMR (DMSO-d₆) δ (ppm): −10.123 (s, 1H), 4.18 (m, 4H), 3.65 (t, 2H, J=5.7 Hz), 2.71 (q, 2H, J=2.4 Hz), 1.28 (3H, J=6.9 Hz).

Step-III

Diethyl 6,7-dihydrothieno[3,2-c]pyridine-2,5(4H)-dicarboxylate

To a solution of ethyl 4-chloro-5-formyl-3,6-dihydropyridine-1(2H)-carboxylate (1 eq) obtained from step II in pyridine was added triethyl amine (1.5 eq.), ethyl thioglycolate (1 eq.) at 0° C. and the reaction mixture was stirred for overnight. A solution of KOH (1.5 eq) in water was added at 0° C. and further stirred at room temperature for 1 h Water was added and the organic layer was separated, dried over anhydrous Na2SO4 and concentrated under reduced pressure to afford crude product, which, on purification by column chromatography afforded the desired diethyl 6,7-dihydrothieno [3,2-c]pyridine-2,5(4H)-dicarboxylate.

¹H NMR (DMSO-d₆) δ (ppm): −7.50 (s, 1H), 4.55 (s, 2H), 4.35 (q, 2H, J=7.2 Hz), 4.19 (q, 2H, J=6.3 Hz), 3.81 (t, 2H, J=5.4 Hz), 2.89 (t, 2H, J=5.4 Hz), 1.33 (m, 6H).

Step-IV 4,5,6,7-tetrahydrothieno[3,2-c]pyridine-2-carboxylic acid

A solution of 6,7-Dihydro-4H-thieno[3,2-c]pyridine-2,5-dicarboxylic acid diethyl ester (1 eq) obtained in step III and aq. KOH (3 eq.) in ethanol was refluxed for 48 h Reaction mixture was concentrated under reduced pressure and neutralized to pH 7.0 to get 4,5,6,7-tetrahydrothieno[3,2-c]pyridine-2-carboxylic acid.

¹H NMR (DMSO-d₆) δ (ppm): −8.5 (s, 1H), 6.87 (s, 1H), 4.0 (s, 2H), 2.9 (t, 3H J=5.4 Hz), 2.7 (t, 2H, J=5.4 Hz).

Step-V

Methyl 4,5,6,7-tetrahydrothieno[3,2-c]pyridine-2-carboxylate

To a solution of 4,5,6,7-tetrahydrothieno[3,2-c]pyridine-2-carboxylic acid (1 eq) obtained in step IV in methanol was added thionyl chloride (1.5 eq) at 0° C., and the reaction was refluxed for 3.0 h Reaction mixture was concentrated and neutralized to afforded the methyl 4,5,6,7-tetrahydrothieno [3,2-c]pyridine-2-carboxylate.

¹H NMR (DMSO-d₆) δ (ppm): −10.0 (bs, 1H), 7.64 (s, 1H), 4.15 (s, 2H), 3.81 (s, 3H), 3.33 (t, 2H, J=6.3 Hz), 3.16 (t, 2H, J=6.3 Hz).

Step-VI 5-tert-butyl 2-methyl 6,7-dihydrothieno[3,2-c]pyridine-2,5(4H)-dicarboxylate To a solution of methyl 4,5,6,7-tetrahydrothieno[3,2-c]pyridine-2-carboxylate (1 eq) obtained in step V in DCM was added triethyl amine (1.5) at 0° C. followed by boc anhydride, and the reaction was continued at room temperature for 1 h Water was added and the organic layer was separated, dried over anhydrous Na2SO4 and concentrated under reduced pressure to afford crude product, which, on purification by column chromatography afforded the desired 5-tert-butyl 2-methyl 6,7-dihydrothieno[3,2-c]pyridine-2,5(4H)-dicarboxylate.

¹H NMR (DMSO-d₆) δ (ppm): −7.48 (s, 1H), 4.47 (s, 2H), 3.8 (s, 3H), 3.71 (t, 2H, J=6.3 Hz), 2.87 (t, 2H, J=6.3 Hz), 1.46 (s, 9H).

Step-VII 5-(tert-butoxycarbonyl)-4,5,6,7-tetrahydrothieno[3,2-c]pyridine-2-carboxylic acid A solution of 5-tert-butyl 2-methyl 6,7-dihydrothieno[3,2-c]pyridine-2,5(4H)-dicarboxylate (1 eq) obtained in step VII and NaOH (1.5 eq). was refluxed in ethanol for 2 h Reaction mixture was concentrated under reduced pressure and neutralized to get 5-(tert-butoxycarbonyl)-4,5,6,7-tetrahydrothieno[3,2-c]pyridine-2-carboxylic acid.

¹H NMR (DMSO-d₆) δ (ppm): −7.01 (s, 1H), 4.32 (s, 2H), 3.58 (t, 2H, J=6.3 Hz), 2.71 (t, 2H, J=6.3 Hz), 1.4 (s, 9H)

Step-VIII

N-(2-aminophenyl)-4,5,6,7-tetrahydrothieno[3,2-c]pyridine-2-carboxamide

To a solution of a 5-(tert-butoxycarbonyl)-4,5,6,7-tetrahydrothieno[3,2-c]pyridine-2-carboxylic acid (1.0 eq) obtained in step VII in DMF was added $Et_3N$ (2.2 eq.), EDCI (1.2 eq) and HOBt ((1.2 eq) and reaction was stirred for 1 h Monoboc phenylene diamine was added to reaction mass and reaction was stirred for overnight. Reaction mass was quenched with water and extracted with ethyl acetate organic layer was separated, dried over anhydrous $Na_2SO_4$ and concentrated under reduced pressure to afford crude product, which, on purification by column chromatography afforded the desired Boc protected Benzamide derivative of Thieno (3,2-c) pyridine which was deprotected in ether HCl in DCM to afford N-(2-aminophenyl)-4,5,6,7-tetrahydrothieno[3,2-c]pyridine-2-carboxamide.

$^1$H NMR (DMSO-$d_6$) δ (ppm): −9.54 (s, 1H), 7.65 (s, 1H), 6.98 (d, 1H, J=1.5 Hz), 6.94 (t, 1H, J=1.5, 7.2 Hz), 6.78 (d, 1H, 7.8 Hz), 6.59 (t, 1H, J=1.5, 7.1 Hz), 4.88 (s, 2H), 3.76 (s, 2H), 2.97 (t, 2H), 2.72 (t, 2H).

Step-IX

$N^2$-(2-aminophenyl)-$N^5$-pyridin-3-yl-6,7-dihydrothieno[3,2-c]pyridine-2,5(4H)-dicarboxamide To a solution of N-(2-aminophenyl)-4,5,6,7-tetrahydrothieno[3,2-c]pyridine-2-carboxamide (1.0 eq) obtained in step VIII in DMF was treated with Pyridin-3-yl-carbamic acid phenyl ester (1.0 eq) in presence of base like $Et_3N$ and stirred at 50° C. for 8 h Reaction was then quenched with water and extracted with ethyl acetate and the organic layer was separated, dried over anhydrous $Na_2SO_4$ and concentrated under reduced pressure to afford crude product, which, on purification by column chromatography afforded the title compound.

$^1$H NMR (DMSO-$d_6$) δ (ppm): −9.61 (s, 1H), 8.90 (s, 1H), 9.62 (s, 1H), 8.90 (s, 1H), 8.6 (s, 1H), 8.25 (s, 1H), 7.90 (dd, 1H, J=1.0 Hz, J=9.3 Hz), 7.7 (s, 1H), 7.4 (m, 1H), 7.0 (dd, 1H, J=1.5 & 7.8 Hz), 6.94 (m, 1H), 6.77 (dd, J=1.5&7.4 Hz), 6.58 (m, 1H), 4.59 (s, 2H) 3.80 (t, 2H, J=11.1 Hz), 3.15 (s, 1H) 2.9 (t, 2H, J=5.1 Hz).

Examples 204-210 were Prepared Using the Procedure of Example 203

Example 204

6,7-Dihydro-4H-thieno[3,2-c]pyridine-2,5-dicarboxylic acid 2-[(2-aminophenyl)-amide]5-[(2-difluoromethoxy-phenyl)-amide]

$^1$H NMR (DMSO-$d_6$) δ (ppm): −9.62 (s, 1H), 8.30 (s, 1H), 7.7 (s, 1H), 7.51 (d, 1H, J=7.2 Hz), 7.19 (m, 4H), 6.9 (m, 1H), 6.7 (m, 1H), 6.5 (m, 1H), 4.89 (s, 2H), 4.56 (s, 2H), 3.77 (t, 2H, J=5.4 Hz), 2.89 (t, 2H, J=5.4 Hz).

Example 205

$N^2$-(2-aminophenyl)-$N^5$-(3,4-dimethoxyphenyl)-6,7-dihydrothieno[3,2-c]pyridine-2,5(4H)-dicarboxamide $^1$H NMR (DMSO-$d_6$) δ (ppm): −9.61 (s, 1H), 8.53 (s, 1H), 7.74 (s, 1H), 7.16 (d, 1H, J=2.4 Hz), 7.10 (dd, 1H, J=1.2 Hz, J=8.1 Hz, 6.96 (m, 2H), 6.77 (m, 2H), 6.58 (t, 1H, J=7.8 Hz), 4.89 (s, 2H) 4.55 (s, 2H), 3.76 (t, 2H, J=5.3 Hz, J=11.0 Hz), 3.70 (s, 3H) 3.68 (s, 3H), 2.88 (t, 2H, J=5.4 Hz, J=11.1 Hz)

Example 206

$N^2$-[2-amino-5-(2-thienyl)phenyl]-$N^5$-butyl-6,7-dihydrothieno[3,2-c]pyridine-2,5(4H)-dicarboxamide $^1$H NMR (DMSO-$d_6$) δ (ppm): −9.67 (s, 1H), 7.7 (s, 1H), 7.41 (d, 1H, J=2.1 Hz), 7.3 (dd, 1H, J=1.2 & 4.5 Hz), 7.29 (dd, 1H, J=1.3 & 4.5 Hz), 7.24 (dd, 1H, J=1.2 & 3.6 Hz), 7.041 (m, 1H), 6.80 (d, 1H, J=8.4 Hz), 6.64 (t, 1H), 5.15 (s, 2H), 4.40 (s, 2H), 3.62 (t, 2H, J=5.4 Hz), 3.0 (q, 2H, J=6.0 Hz), 2.79 (t, 2H, J=5.3 Hz), 1.27 (m, 4H), 0.86 (t, 3H, J=7.2 Hz).

Example 207

$N^2$-[2-amino-5-(2-thienyl)phenyl]-$N^5$-pyridin-3-yl-6,7-dihydrothieno[3,2-c]-pyridine-2,5(4M-dicarboxamide $^1$H NMR (DMSO-$d_6$) δ (ppm): −9.7 (s, 1H), 8.9 (s, 1H), 8.66 (s, 1H), 8.16 (dd, 1H, J=1.2 & 4.5), 7.89 (m, 1H), 7.77 (s, 1H), 7.41 (d, 1H, J=2.1 Hz), 7.34 (dd, 1H, J=1.2 & 5.14 Hz), 7.28 (m, 2H), 7.23 (dd, 1H, J=1.2 & 4.5 Hz), 7.0 (m, 1H), 6.71 (d, 1H, J=8.4 Hz) 5.21 (bs, 2H), 4.605 (s, 2H), 3.81 (t, 2H, J=5.4 Hz), 3.15 (s, 1H), 2.92 (t, 2H, J=5.4 Hz).

Example 208

$N^2$-(2-amino-5-thiophen-2-ylphenyl)-$N^5$-(4-methoxyphenyl)-6,7-dihydrothieno[3,2-c]pyridine-2,5(4H)-dicarboxamide $^1$H NMR (DMSO-$d_6$) δ (ppm): −9.7 (s, 1H), 8.55 (s, 1H), 7.76 (s, 1H), 7.42 (d, 1H, J=2.4 Hz), 7.36 (s, 1H), 7.33 (d, 2H, J=2.4 Hz), 7.28 (dd, 1H, J=8.0 Hz), 7.23 (d, 1H, J=8.0 Hz), 7.04 (t, 1H, J=7.2 Hz), 6.83 (d, 2H, J=7.2 Hz), 6.78 (s, 1H), 5.16 (s, 2H), 4.55 (s, 2H), 3.76 (t, 2H, J=5.3 Hz), 3.69 (s, 3H), 2.89 (s, 2H, J=5.3 Hz).

Example 209

$N^2$-(2-aminophenyl)-$N^5$-(2-methoxyethyl)-6,7-dihydrothieno[3,2-c]pyridine-2,5(4H)-dicarboxamide $^1$H NMR (DMSO-$d_6$) d (ppm) 9.58 (s, 1H), 7.61 (s, 1H), 7.11 (dd, 1H, J=1.2 & 7.8 Hz), 6.93 (m, 1H), 6.78 (m, 2H), 6.5 (dd, 1H, J=1.2 & 3.6 Hz), 4.85 (s, 2H), 4.40 (s, 2H), 3.64 (t, 2H, J=5.4 Hz), 3.3 (m, 2H), 3.1 (m, 5H), 2.8 (t, 2H, J=5.4 Hz).

Example 210

$N^2$-(2-aminophenyl)-$N^5$-pyridin-3-yl-6,7-dihydrothieno[3,2-c]pyridine-2,5(4H)-dicarboxamide H NMR (DMSO-d6) δ (ppm) 9.30 (s, 1H), 8.66 (d, 1H, J=2.4 Hz), 8.17 (dd, 1H, J=4.5, 1.2 Hz), 7.92-7.88 (m, 1H), 7.73 (s, 1H), 7.28 (dd, 1H, J=8.4, 4.8 Hz), 7.14 (d, 1H, J=6.9

Hz), 6.95 (t, 1H, J=7.6 Hz), 6.76 (d, 1H, J=6.9 Hz), 6.58 (d, 1H, J=7.6 Hz), 4.90 (s, 2H), 4.76 (s, 2H), 3.79 (t, 2H, J=5.4 Hz), 2.76 (s, 2H).

Example 211

3,4-dimethoxyphenyl 2-[(2-aminophenyl)carbamoyl]-6,7-dihydrothieno[3,2-c]pyridine-5(4H)-carboxylate To a solution of N-(2-aminophenyl)-4,5,6,7-tetrahydrothieno[3,2-c]pyridine-2-carboxamide (1.0 eq) obtained in step VIII of example 203 in DMF was treated with Carbonic acid 3,4-dimethoxy-phenyl ester 4-nitro-phenyl ester (1.0 eq) in presence of base like Et₃N and stirred at 50° C. for 8 h Reaction was then quenched with water and extracted with ethyl acetate and the organic layer was separated, dried over anhydrous Na$_2$SO$_4$ and concentrated under reduced pressure to afford crude product, which, on purification by column chromatography afforded the title compound.

1H NMR (DMSO-d6) d (ppm) 9.62 (s, 1H), 7.75 (s, 1H), 7.10 (dd, 1H, J=2.1 & 6.9 Hz), 6.96 (m, 2H), 6.78 (m, 2H), 6.67 (dd, 1H, J=2.1 & 6.9 Hz), 6.5 (m, 1H), 4.90 (s, 2H), 4.71 (s, 1H), 4.54 (s, 1H), 3.86 (t, 2H, J=5.4 Hz), 3.73 (s, 6H), 2.98 (t, 2H, J=5.4 Hz).

Example 212

N$^2$-(2-aminophenyl)-1-methyl-N$^5$-pyridin-3-yl-1,4,6,7-tetrahydro-5H-pyrrolo[3,2-c]pyridine-2,5-dicarboxamide Step-I 5-tert-butyl 2-ethyl 1,4,6,7-tetrahydro-5H-pyrrolo[3,2-c]pyridine-2,5-dicarboxylate A solution of N-boc-4-piperidone (1 eq.) and lithium diisopropyl amide (1 eq.) in THF was stirred at −78° C. and for 2 hrs. A bromoethyl pyruvate (1.2 eq.) was added to above reaction mixture and stirred for 30 min. Reaction mixture was then quenched with ammonia solution and then extracted with ethyl acetate, dried over sodium sulphate and concentrated to dryness. The residue was then dissolved in dichoromethane and was added silica (100-200 mesh), stirred for overnight at room temperature. Crude was then purified by silica gel column chromatography to yield 5-tert-butyl 2-ethyl 1,4,6,7-tetrahydro-5H-pyrrolo[3,2-c]pyridine-2,5-dicarboxylate.

Step-II 5-tert-butyl 2-ethyl 1-methyl-1,4,6,7-tetrahydro-5H-pyrrolo[3,2-c]pyridine-2,5-dicarboxylate To a solution of 5-tert-butyl 2-ethyl 1,4,6,7-tetrahydro-5H-pyrrolo[3,2-c]pyridine-2,5-dicarboxylate (1.0 eq) in THF at 0° C. was added NaH (1.2 eq) and stirred for half an hour at room temperature. Methyl iodide (1.3 eq) was added and resulting reaction mixture was stirred for 3 hrs. Reaction mixture was then quenched with water and extracted with ethyl acetate, dried over sodium sulphate and concentrated to dryness. Crude mass was then purified by silica gel column chromatography to afford 5-tert-butyl 2-ethyl 1-methyl-1,4,6,7-tetrahydro-5H-pyrrolo[3,2-c]pyridine-2,5-dicarboxylate.

Step-III 5-(tert-butoxycarbonyl)-1-methyl-4,5,6,7-tetrahydro-1H-pyrrolo[3,2-c]pyridine-2-carboxylic acid To the solution 5-tert-butyl 2-ethyl 1-methyl-1,4,6,7-tetrahydro-5H-pyrrolo[3,2-c]pyridine-2,5-dicarboxylate (1.0 eq) in EtOH was added NaOH (1.05 eq.) and refluxed for 6 hrs. Reaction mixture was concentrated under reduced pressure and neutralized to get desired compound 5-(tert-butoxycarbonyl)-1-methyl-4,5,6,7-tetrahydro-1H-pyrrolo[3,2-c]pyridine-2-carboxylic acid.

Step-IV

N-(2-aminophenyl)-1-methyl-4,5,6,7-tetrahydro-1H-pyrrolo[3,2-c]pyridine-2-carboxamide To a solution of compound 5-(tert-butoxycarbonyl)-1-methyl-4,5,6,7-tetrahydro-1H-pyrrolo[3,2-c]pyridine-2-carboxylic acid (1.0 eq) in DMF was added DCC (1.3 eq.), and HOBt (1.3 eq) and stirred for 1 hr. Monoboc phenylene diamine was added and reaction was stirred for 48 hrs. Reaction mixture was then quenched with water and extracted with ethyl acetate, dried over sodium sulphate and concentrated to dryness. Crude mass was then purified by silica gel column chromatography to afford 2-(2-tert-Butoxycarbonylamino-phenylcarbamoyl)-1-methyl-1,4,6,7-tetrahydro-pyrrolo[3,2-c]pyridine-5-carboxylic acid tert-butyl ester which was then reacted with hydrochloric acid saturated diethyl ether to get N-(2-aminophenyl)-1-methyl-4,5,6,7-tetrahydro-1H-pyrrolo[3,2-c]pyridine-2-carboxamide.

Step-V

N$^2$-(2-aminophenyl)-1-methyl-N$^5$-pyridin-3-yl-1,4,6,7-tetrahydro-5H-pyrrolo[3,2-c]pyridine-2,5-dicarboxamide To a solution of compound N-(2-aminophenyl)-1-methyl-4,5,6,7-tetrahydro-1H-pyrrolo[3,2-c]pyridine-2-carboxamide (1.0 eq) in DMF was added Et₃N (3.0 eq.) followed by Pyridin-3-yl-carbamic acid phenyl ester (1.0 eq). Reaction was stirred at room temperature for overnight. Reaction mixture was then quenched with water and extracted with ethyl acetate, dried over sodium sulphate and concentrated to dryness. Crude mass was then purified by silica gel column chromatography to afford N$^2$-(2-aminophenyl)-1-methyl-N$^5$-pyridin-3-yl-1,4,6,7-tetrahydro-5H-pyrrolo[3,2-c]pyridine-2,5-dicarboxamide.

1H NMR (DMSO-d6) d (ppm) 8.97 (s, 1H), 8.88 (s, 1H), 8.62 (d, 1H, J=2.1 Hz), 8.12 (d, 1H, J=4.5 Hz), 7.86 (d, 1H, J=8.4 Hz), 7.51 (s, 1H); 7.24 (m, 1H), 7.13 (d, 1H, J=7.8 Hz), 6.92 (t, 1H, J=7.8 Hz), 6.75 (d, 1H, J=7.8 Hz), 6.53 (t, 1H, J=7.8 Hz), 4.9 (s, 2H), 4.59 (s, 2H), 3.53 (s, 3H) 3.70 (t, 2H, J=11.1 Hz), 2.5 (t, 2H, J=5.1 Hz)

Example 213 was Obtained by Following Procedure of Example 212

Example 213

N$^2$-(2-aminophenyl)-N$^5$-(3,4-dimethoxyphenyl)-1-methyl-1,4,6,7-tetrahydro-5H-pyrrolo[3,2-c]pyridine-2,5-dicarboxamide 1H NMR (DMSO-d6) δ (ppm) 8.94 (s, 1H), 8.48 (s, 1H), 7.49 (s, 1H), 7.16 (d, 1H, J=1.2 Hz), 7.14 (d, 1H, J=2.4 Hz), 6.96 (dd, 1H, J=8.7, 2.4 Hz), 6.92-6.89 (overlapped signal, 1H), 6.81 (d, 1H, J=8.7 Hz), 6.75 (dd, 1H, J=8.1, 1.5 Hz), 6.58 (dt, 1

Example 214

2-(difluoromethoxy)phenyl 2-[(2-aminophenyl)carbamoyl]-1-methyl-1,4,6,7-tetrahydro-5H-pyrrolo[3,2-c]pyridine-5-carboxylate To a solution of compound N-(2-aminophenyl)-1-methyl-4,5,6,7-tetrahydro-1H-pyrrolo[3,2-c]pyridine-2-carboxamide (1.0 eq) obtained in step-IV of example 212 in DMF was added $Et_3N$ (3.0 eq.) followed by Carbonic acid 2-difluoromethoxy-phenyl ester 4-nitro-phenyl ester (1.0 eq). Reaction was stirred at room temperature for overnight. Reaction mixture was then quenched with water and extracted with ethyl acetate, dried over sodium sulphate and concentrated to dryness. Crude mass was then purified by silica gel column chromatography to afford 2-(difluoromethoxy)phenyl 2-[(2-aminophenyl)carbamoyl]-1-methyl-1,4,6,7-tetrahydro-5H-pyrrolo[3,2-c]pyridine-5-carboxylate.

1H NMR (DMSO-d6) δ (ppm) 8.94 (s, 1H), 8.16 (s, 1H), 7.50 (d, 1H, J=1.2 Hz), 7.48 (s, 1H), 7.19-7.11 (m, 4H), 6.90 (dt, 1H, J=7.8, 1.5 Hz), 6.74 (dd, 1H, J=7.5, 1.2 Hz), 6.56 (dt, 1H, J=7.5, 1.2 Hz), 4.81 (s, 2H), 4.60 (s, 2H), 3.71 (t, 2H, J=5.4 Hz), 3.53 (s, 3H), 2.64 (s, 2H)

Example 215 was Prepared Using Procedure of Example 214

Example 215

3,4-dimethoxyphenyl 2-[(2-aminophenyl)carbamoyl]-1-methyl-1,4,6,7-tetrahydro-5H-pyrrolo[3,2-c]pyridine-5-carboxylate 1H NMR (DMSO-d6) δ (ppm) 8.98 (s, 1H), 7.52 (s, 1H), 7.26 (br, 1H), 7.11 (d, 1H, J=6.9 Hz), 6.91-6.88 (m, 2H), 6.75-6.73 (m, 2H), 6.63-6.54 (m, 2H), 4.79 (s, 1H), 4.74 (s, 1H), 4.59 (s, 2H), 3.73 (s, 3H), 3.71 (s, 3H), 3.55 (s, 3H), 2.72-2.67 (br, 2H)

Example 216

$N^2$-(2-aminophenyl)-$N^6$-pyridin-3-yl-4,7-dihydrothieno[2,3-c]pyridine-2,6(5H)-dicarboxamide

Step-I

3-[(E)-2-nitrovinyl]thiophene

To a solution of nitromethane (1.15 eq.) in ethanol (30 ml per gm of aldehyde) cooled to 0° C. was added dropwise a solution of 10N NaOH and stirred for 15 min. 3-thiopene carbaldehyde was added slowly under slitting at 0° C. and resulting reaction mixture was stirred for 1 hr. Reaction mixture was then poured on 10% icecold HCl solution and yellow solid was filtered and dried to yield the desired 3-[(E)-2-nitrovinyl]thiophene.

Step-II 2-(3-thienyl)ethanamine

To a suspension of LAH (2.5 Eq.) in diethyl ether was added a solution of 3-[(E)-2-nitrovinyl]thiophene in diethyl ether under nitrogen atmosphere and stirred for 1 hr. Reaction mass was then cooled and quenched with water and extracted with ethyl acetate dried over sodium sulphate and concentrated to obtain 2-(3-thienyl)ethanamine.

Step-III tert-butyl[2-(3-thienyl)ethyl]carbamate

To a solution of 2-(3-thienyl)ethanamine in water was added boc-anhydride at 0° C. slowly, and stirred for overnight at room temperature. Reaction mixture was extracted with ethyl acetate dried over sodium sulphate and concentrated. Crude was then purified by silica gel column chromatography to yield tert-butyl[2-(3-thienyl)ethyl]carbamate.

Step-IV tert-butyl 4,7-dihydrothieno[2,3-c]pyridine-6(5H)-carboxylate

To a solution of tert-butyl[2-(3-thienyl)ethyl]carbamate in toluene was added paraformaldehyde (2 equi.) and catalytic amount of PTSA and reaction mixture was then refluxed in dean stark apparatus for 4 hrs. Reaction mass wan then concentrated and extracted with dichloromethane dried over sodium sulphate and evaporated to yield tert-butyl 4,7-dihydrothieno[2,3-c]pyridine-6(5H)— carboxylate.

Step-V 6-tert-butyl 2-ethyl 4,7-dihydrothieno[2,3-c]pyridine-2,6(5H)-dicarboxylate A solution of tert-butyl 4,7-dihydrothieno[2,3-c]pyridine-6(5H)-carboxylate in dry THF was cooled to −78°, n-butyl lithium (1.5 eq.) was added slowly and reaction mixture stirred for 3-4 hrs. This reaction mixture was then added to the solution of ethylchloroformate (10 eq.) in dry THF at −78° C. Reaction mass wan then allowed to come at room temperature and stirred overnight. It was then cooled and quenched with ammonium chloride solution and extracted with ethyl acetate, dried over sodium sulphate and concentrated. The crude was then purified using column chromatography to yield 6-tert-butyl 2-ethyl 4,7-dihydrothieno[2,3-c]pyridine-2,6(5H)-dicarboxylate.

Step-VI 6-(tert-butoxycarbonyl)-4,5,6,7-tetrahydrothieno[2,3-c]pyridine-2-carboxylic acid 6-tert-butyl 2-ethyl 4,7-dihydrothieno[2,3-c]pyridine-2,6 (5H)-dicarboxylate was dissolved in THF: $H_2O$ (3:1) mixture. $LiOH.H_2O$ (1.5 eq) was added and the reaction mixture was heated at 75° C. overnight. Reaction mass was then concentrated to dryness to get the lithium salt which was then neutralised to yield 6-(tert-butoxycarbonyl)-4,5,6,7-tetrahydrothieno[2,3-c]pyridine-2-carboxylic acid.

Step-VII

N-(2-aminophenyl)-4,5,6,7-tetrahydrothieno[2,3-c]pyridine-2-carboxamide

To a solution of 6-(tert-butoxycarbonyl)-4,5,6,7-tetrahydrothieno[2,3-c]pyridine-2-carboxylic acid in dry dichloromethane was added DCC (1.3 eq.) and HOBT (1.3 eq.), stirred for 1 hr. A solution of boc protected phenalene diamine in diclromethane was added slowly and stirred at 40° C. for six hrs and then at room temperature overnight. Reaction mass was then concentrated and purified by column chromatography to afford the 2-(2-tert-Butoxycarbonylaminophenylcarbamoyl)-4,7-dihydro-5H-thieno[2,3-c]pyridine-6-carboxylic acid tert-butyl ester which was treated with ethereal HCL to get the hydrochloride salt of the free base, which was then neutralised to get N-(2-aminophenyl)-4,5,6,7-tetrahydrothieno[2,3-c]pyridine-2-carboxamide.

Step-VIII $N^2$-(2-aminophenyl)-$N^6$-pyridin-3-yl-4,7-dihydrothieno[2,3-c]pyridine-2,6(5H)-dicarboxamide To a solution of N-(2-aminophenyl)-4,5,6,7-tetrahydrothieno[2,3-c]pyridine-2-carboxamide (1.0 eq) in DMF was added Et$_3$N (3.0 eq.) followed by pyridin-3-yl-carbamic acid 4-nitro-phenyl ester (1.0 eq) and reaction was stirred at room temperature overnight. Reaction mixture was then quenched with water and extracted with dichloromethane. The organic layer was separated, dried over anhydrous sodium sulfate, concentrated under reduced pressure to afford crude product, which, on purification by column chromatography afforded the title compound.
$^1$H NMR (DMSO-d6) δ (ppm) 9.30 (s, 1H), 8.66 (d, 1H, J=2.4 Hz), 8.17 (dd, 1H, J=4.5, 1.2 Hz), 7.92-7.88 (m, 1H), 7.73 (s, 1H), 7.28 (dd, 1H, J=8.4, 4.8 Hz), 7.14 (d, 1H, J=6.9 Hz), 6.95 (t, 1H, J=7.6 Hz), 6.76 (d, 1H, J=6.9 Hz), 6.58 (d, 1H, J=7.6 Hz), 4.90 (s, 2H), 4.76 (s, 2H), 3.79 (t, 2H, J=5.4 Hz), 2.76 (s, 2H)

Examples 217-223 were Also Obtained by Following Procedure of Example 216

Example 217

$N^2$-(2-aminophenyl)-$N^6$-(3,4-dimethoxyphenyl)-4,7-dihydrothieno[2,3-c]pyridine-2,6(5H)-dicarboxamide $^1$H NMR (DMSO-d6) δ (ppm) 9.61 (s, 1H), 8.53 (s, 1H), 7.74 (s, 1H), 7.16 (d, 1H, J=2.4), 7.10 (dd, 1H, J=1.2 Hz, J=8.1 Hz, 6.96 (m, 2H), 6.77 (m, 2H), 6.58 (t, 1H, J=7.8), 4.89 (s, 2H) 4.55 (s, 2H), 3.76 (t, 2H, J=5.3 Hz, J=11.0 Hz), 3.70 (s, 3H) 3.68 (s, 3H), 2.88 (t, 2H, J=5.4 Hz, J=11.1)

Example 218

$N^2$-(2-aminophenyl)-$N^6$-(2-methoxyethyl)-4,7-dihydrothieno[2,3-c]pyridine-2,6(5H)-dicarboxamide $^1$H NMR (DMSO-d6) δ (ppm) 9.59 (s, 1H), 7.70 (s, 1H), 7.10 (dd, 1H, J=7.8, 1.2 Hz), 6.95 (dt, 1H, J=8.1, 1.5 Hz), 6.77 (d, 1H, J=1.2 Hz), 6.75-6.74 (m, 1H), 6.57 (dt, 1H, J=7.8, 1.5 Hz), 4.88 (s, 2H), 4.57 (s, 2H), 3.60 (t, 2H, J=5.7 Hz), 3.35-3.31 (overlapped signals, 5H), 3.25-3.16 (overlapped signals, 5H), 2.63 (t, 2H, J=5.1 Hz).

Example 219

$N^2$-(2-aminophenyl)-$N^6$-[2-(difluoromethoxy)phenyl]-4,7-dihydrothieno[2,3-c]pyridine-2,6(5H)-dicarboxamide $^1$H NMR (DMSO-d6) δ (ppm) 9.58 (s, 1H), 8.31 (s, 1H), 7.71 (s, 1H), 7.45 (d, 1H, J=6.9 Hz), 7.23-7.08 (overlapped signals, 4H), 6.98-6.91 (m, 2H), 6.75-6.72 (m, 1H), 6.55 (t, 1H, J=7.5 Hz), 4.87 (s, 2H), 4.69 (s, 2H), 3.72 (s, 2H), 2.72 (s, 2H).

Example 220

$N^2$-(2-amino-5-isopropylphenyl)-$N^6$-pyridin-3-yl-4,7-dihydrothieno[2,3-c]pyridine-2,6(5H)-dicarboxamide 1H NMR (DMSO-d6) δ (ppm) 9.65 (s, 1H), 8.88 (s, 1H), 8.66 (d, 1H, J=2.4 Hz), 8.17 (dd, 1H, J=4.8, 1.5 Hz), 7.94-7.88 (m, 1H), 7.77 (s, 1H), 7.28 (dd, 1H, J=8.4, 4.8 Hz)H, J, 7.00 (d, 1H, J=1.8 Hz), 6.87 (dd, 1H, J=8.4, 2.1 Hz), 6.71 (d, 1H, J=8.4 Hz), 4.77 (s, 2H), 4.69 (s, 2H), 3.79 (t, 2H, J=5.7 Hz), 2.80-2.68 (m, 3H), 1.15 (d, 6H, J=6.9 Hz)

Example 221

$N^2$-(2-amino-5-isopropylphenyl)-$N^6$-[3-(difluoromethoxy)phenyl]-4,7-dihydrothieno[2,3-c]pyridine-2,6(5H)-dicarboxamide 1H NMR (DMSO-d6) δ (ppm) 9.65 (s, 1H), 8.35 (s, 1H), 7.74 (s, 1H), 7.50 (d, 1H, J=6.9 Hz), 7.23-7.14 (m, 4H), 7.00 (d, 1H, J=1.8 Hz), 7.87 (dd, 1H, J=8.4, 2.1 Hz), 6.71 (d, 1H, J=8.4 Hz), 4.73 (s, 2H), 4.70 (s, 2H), 3.76 (t, 2H, J=5.4 Hz), 2.79-2.70 (m, 3H), 1.15 (d, 6H, J=6.9 Hz).

Example 222

$N^2$-(2-amino-5-isopropylphenyl)-$N^6$-(4-fluorophenyl)-4,7-dihydrothieno[2,3-c]pyridine-2,6(5H)-dicarboxamide 1H NMR (DMSO-d6) δ (ppm) 9.64 (s, 1H), 8.72 (s, 1H), 7.72 (s, 1H), 7.49-7.44 (m, 2H), 7.11-7.05 (m, 2H), 6.99 (d, 1H, J=2.1 Hz), 6.85 (dd, 1H, J=8.4, 2.1 Hz), 6.70 (d, 1H, J=8.1 Hz), 4.72 (s, 2H), 4.68 (s, 2H), 3.75 (t, 2H, J=5.7 Hz), Hz) 2.76-2.71 (m, 3H), 1.14 (d, 6H, J=6.9 Hz).

Example 223

$N^2$-(2-amino-5-isopropylphenyl)-$N^6$-(3,4-dimethoxyphenyl)-4,7-dihydrothieno[2,3-c]pyridine-2,6(5H)-dicarboxamide 1H NMR (DMSO-d6) δ (ppm) 9.65 (s, 1H), 8.53 (s, 1H), 7.73 (s, 1H), 7.17 (d, 1H, J=2.4 Hz), 7.01-6.98 (m, 2H), 6.88-6.82 (m, 2H), 6.71 (d, 1H, J=8.1 Hz), 4.73 (s, 2H), 4.69 (s, 2H), 3.76 (t, 2H, J=5.7 Hz), 3.71 (s, 3H), 3.70 (s, 3H), 2.77-2.70 (m, 3H), 1.15 (d, 6H, J=6.9 Hz).

Example 224

3,4-dimethoxyphenyl 2-[(2-aminophenyl)carbamoyl]-4,7-dihydrothieno[2,3-c]pyridine-6(5H)-carboxylate To a solution of 6-(tert-butoxycarbonyl)-4,5,6,7-tetrahydrothieno[2,3-c]pyridine-2-carboxylic acid (1.0 eq) obtained in step VI of example 216 in DMF was added Et$_3$N (3.0 eq.) followed by Carbonic acid 3,4-dimethoxy-phenyl ester 4-nitro-phenyl ester (1.0 eq) and reaction was stirred at room temperature overnight. Reaction mixture was then quenched with water and extracted with dichloromethane. The organic layer was separated, dried over anhydrous sodium sulfate, concentrated under reduced pressure to afford crude product, which, on purification by column chromatography afforded the title compound.

1H NMR (DMSO-d6) δ (ppm) 9.69 (s, 1H), 7.78 (s, 1H), 7.13 (dd, 1H, J=7.8, 1.2 Hz), 7.00-6.91 (m, 2H), 6.82 (d, 1H, J=2.7 Hz), 6.77 (dd, 1H, J=7.8, 1.2 Hz), 6.68 (dd, 1H, J=8.4, 2.4 Hz), 6.62-6.56 (m, 1H), 4.92 (s, 1H), 4.89 (s, 1H), 4.72 (s, 2H).

An Example 225 was Also Obtained by Following Procedure of Example 224

Example 225

3,4-dimethoxyphenyl 2-[(2-amino-5-isopropylphenyl)carbamoyl]-4,7-dihydrothieno[2,3-c]pyridine-6(5H)-carboxylate 1H NMR (DMSO-d6) δ (ppm) 9.68 (s, 1H), 7.76 (s, 1H), 7.00 (d, 1H, J=1.8 Hz), 6.93 (d, 1H, J=8.7 Hz), 6.87 (dd, 1H, J=8.4, 1.8 Hz), 6.82 (d, 1H, J=2.7 Hz), 6.72 (d, 1H, J=8.4 Hz), 6.68 (dd, 1H, J=8.7, 2.4 Hz), 4.89 (s, 2H), 4.70 (s, 2H), 3.75 (s, 3H), 3.73 (s, 3H), 2.83-2.73 (m, 3H), 1.15 (d, 6H, J=6.9 Hz).

Example 226

N-(2-aminophenyl)-6-[(3-methoxyphenoxy)acetyl]-4,5,6,7-tetrahydrothieno[2,3-c]pyridine-2-carboxamide To the solution of (3-Methoxy-phenoxy)-acetic acid (1.0 mmol) in dry DMF (10 mL), were added 1-hydroxybenzotriazole (1.2 mmol), 1-ethyl-3-(3'-dimethylaminopropyl)carbodiimide (2 mmol) and N-methylmorpholine (2.0 mmol). Solution was cooled to 0° C. N-(2-aminophenyl)-4,5,6,7-tetrahydrothieno[2,3-c]pyridine-2-carboxamide (1.0 eq) obtained in step VII of example 216 was then added and mixture was stirred at room temperature overnight.

Reaction mixture was concentrated, diluted with water, extracted with dichloromethane, washed with brine solution, and dried over anhydrous Na$_2$SO$_4$. Concentrated and purified by column chromatograph to obtained the title compound.

1H NMR (DMSO-d6) δ (ppm) 9.61 (s, 1H), 7.73 (s, 1H), 7.18-7.12 (m, 2H), 7.00-6.94 (m, 1H), 6.77 (d, 1H, J=6.9 Hz), 6.61-6.53 (m, 4H), 4.92-4.88 (m, 4H), 4.81 (s, 1H), 4.73 (s, 1H), 3.76-3.74 (m, 2H), 3.72 (s, 3H), 2.81-2.68 (m, 2H).

Example 227 was Obtained by Following Procedure of Example 226

Example 227

N-(2-amino-5-isopropylphenyl)-6-[(3-methoxyphenoxy)acetyl]-4,5,6,7-tetrahydrothieno[2,3-c]pyridine-2-carboxamide 1H NMR (DMSO-d6) δ (ppm) 9.65 (s, 1H), 7.73 (s, 1H), 7.21-7.15 (m, 1H), 7.00 (s, 1H), 6.87 (dd, 1H, J=8.1 Hz), 6.71 (d, 1H, J=8.1 Hz), 6.55-6.53 (m, 3H), 4.92-4.81 (m, 3H), 4.73-4.69 (m, 3H), 3.78-3.73 (m, 2H), 3.70 (s, 3H), 3.85-3.70 (m, 3H), 1.15 (d, 6H, J=6.9 Hz).

Example 228

N$^2$-(2-aminophenyl)-1-methyl-N$^6$-pyridin-3-yl-1,4,5,7-tetrahydro-6H-pyrrolo[2,3-c]pyridine-2,6-dicarboxamide Step-I Ethyl 3-(3-nitropyridin-4-yl)-2-oxopropanoate To a solution of freshly prepared sodium ethoxide was added diethyl oxalate (1.5 eq.) followed by 4-methyl-3-nitro pyridine (1 eq.) in toluene and reaction mixture was stirred overnight. It was then concentrated under reduced pressure and acidified with acetic acid to obtained red solid, which on further purification, by column chromatography provided the ethyl 3-(3-nitropyridin-4-yl)-2-oxopropanoate.

Step-II

Ethyl 1H-pyrrolo[2,3-c]pyridine-2-carboxylate

To a solution of ethyl 3-(3-nitropyridin-4-yl)-2-oxopropanoate (1.0 eq) in dichloromethane was added 10% Pd/C (1.5 eq.) under nitrogen atmosphere at 110 psi in an autoclave for 48 hrs. Reaction mixture was filtered through celite and concentrated to get brown solid, which, on purification by column chromatography afforded the desired ethyl 1H-pyrrolo[2,3-c]pyridine-2-carboxylate.

Step-III 1-tert-butyl 2-ethyl 1H-pyrrolo[2,3-c]pyridine-1,2-dicarboxylate

To a solution of ethyl 1H-pyrrolo[2,3-c]pyridine-2-carboxylate (1 eq) in dry THF was added DMAP (0.1 eq) at 0° C. followed by (Boc)$_2$O (2.0 eq.) and stirred overnight. Water was added to it and extracted with dichloromethane, dried over anhydrous sodium sulphate and concentrated under reduced pressure to afford crude product, which, on purification by column chromatography afforded the desired 1-tert-butyl 2-ethyl 1H-pyrrolo[2,3-c]pyridine-1,2-dicarboxylate.

Step-IV

Ethyl 6-benzyl-4,5,6,7-tetrahydro-1H-pyrrolo[2,3-c]pyridine-2-carboxylate

To a solution of 1-tert-butyl 2-ethyl 1H-pyrrolo[2,3-c]pyridine-1,2-dicarboxylate (1.0 eq) in DMF was added benzyl bromide (1.0 eq.) and heated to 80° C. for 4 hrs. Reaction mixture was evaporated to dryness. The product obtained was dissolved aqueous ethanol and NaBH$_4$ (1.5 eq.) was added at 0° C. and stirred for 4 hrs. Reaction was quenched with water, extracted with dichloromethane, dried over anhydrous sodium sulphate and concentrated under reduced pressure to afford crude product, which, on purification by column chromatography afforded ethyl 6-benzyl-4,5,6,7-tetrahydro-1H-pyrrolo[2,3-c]pyridine-2-carboxylate.

Step-V

Ethyl 4,5,6,7-tetrahydro-1H-pyrrolo[2,3-c]pyridine-2-carboxylate

To a solution of ethyl 6-benzyl-4,5,6,7-tetrahydro-1H-pyrrolo[2,3-c]pyridine-2-carboxylate (1.0 eq) in ethanol was added 10% Pd/C (w/w), and the reaction was carried under hydrogen atmosphere overnight. Reaction mixture was filtered through celite and concentrated to afford crude product which on purification afforded compound ethyl 4,5,6,7-tetrahydro-1H-pyrrolo[2,3-c]pyridine-2-carboxylate.

Step-VI 6-tert-butyl 2-ethyl 1,4,5,7-tetrahydro-6H-pyrrolo[2,3-c]pyridine-2,6-dicarboxylate To a solution of compound ethyl 4,5,6,7-tetrahydro-1H-pyrrolo[2,3-c]pyridine-2-carboxylate (1.0 eq) in DCM was added triethylamine (1.5 eq) at 0° C. followed by (boc)$_2$O and stirred for two hrs. Reaction mixture was then quenched with water and extracted with dichloromethane, dried over anhydrous sodium sulfate and concentrated under reduced pressure to afford crude product, which, on purification by column chromatography afforded the desired compound 6-tert-butyl 2-ethyl 1,4,5,7-tetrahydro-6H-pyrrolo[2,3-c]pyridine-2,6-dicarboxylate.

Step-VII 6-tert-butyl 2-ethyl 1-methyl-1,4,5,7-tetrahydro-6H-pyrrolo[2,3-c]pyridine-2,6-dicarboxylate To a solution of 6-tert-butyl 2-ethyl 1,4,5,7-tetrahydro-6H-pyrrolo[2,3-c]pyridine-2,6-dicarboxylate (1.0 eq) in dry THF was added NaH (1.2 eq) at 0° C. and reaction mixture was stirred at room temperature for 30 min. Methyl iodide (6.0 eq.) was added and stirred further at room temperature for 3 hrs. Reaction mixture was quenched with water and extracted with dichloromethane, over anhydrous sodium sulfate and concentrated under reduced pressure to afford crude product, which, on purification by column chromatography afforded the desired 6-tert-butyl 2-ethyl 1-methyl-1,4,5,7-tetrahydro-6H-pyrrolo[2,3-c]pyridine-2,6-dicarboxylate.

Step-VIII 6-(tert-butoxycarbonyl)-1-methyl-4,5,6,7-tetrahydro-1H-pyrrolo[2,3-c]pyridine-2-carboxylic acid To a solution of compound 6-tert-butyl 2-ethyl 1-methyl-1,4,5,7-tetrahydro-6H-pyrrolo[2,3-c]pyridine-2,6-dicarboxylate (1.0 eq) in ethanol was added NaOH (1.05 eq.) and refluxed for 6 hrs. Reaction mixture was concentrated under reduced pressure to get sodium salt of the acid, which on neutralization gave 6-(tert-butoxycarbonyl)-1-methyl-4,5,6,7-tetrahydro-1H-pyrrolo[2,3-c]pyridine-2-carboxylic acid.

Step-IX

N-(2-aminophenyl)-1-methyl-4,5,6,7-tetrahydro-1H-pyrrolo[2,3-c]pyridine-2-carboxamide To a solution of compound 6-(tert-butoxycarbonyl)-1-methyl-4,5,6,7-tetrahydro-1H-pyrrolo[2,3-c]pyridine-2-carboxylic acid (1.0 eq) in DMF was added Dicyclohexyl carbo diimide (1.3 eq.) and hydroxy benzotriazole (1.3 eq) and reaction was stirred for 1 hr. followed by addition of monoboc protected phenylene diamine. The reaction was stirred further for 48 hrs. Water was added and reaction mixture was extracted with dichloromethane, dried over anhydrous sodium sulfate, concentrated under reduced pressure to afford crude product, which, on purification by column chromatography afforded the desired compound 2-(2-tert-Butoxycarbonylamino-phenylcarbamoyl)-1-methyl-1,4,5,7-tetrahydro-pyrrolo[2,3-c]pyridine-6-carboxylic acid tert-butyl ester which was treated with ethereal HCl to afford the hydrochloride salt of the base which was then neutralized to obtained the N-(2-aminophenyl)-1-methyl-4,5,6,7-tetrahydro-1H-pyrrolo[2,3-c]pyridine-2-carboxamide.

Step-X

N$^2$-(2-aminophenyl)-1-methyl-N$^6$-pyridin-3-yl-1,4,5,7-tetrahydro-6H-pyrrolo[2,3-c]pyridine-2,6-dicarboxamide To a solution of N-(2-aminophenyl)-1-methyl-4,5,6,7-tetrahydro-1H-pyrrolo[2,3-c]pyridine-2-carboxamide (1.0 eq) in DMF was added Et$_3$N (3.0 eq.) followed by pyridin-3-yl-carbamic acid 4-nitro-phenyl ester (1.0 eq) and stirred at room temperature overnight. Reaction mixture was then quenched with water and extracted with dichloromethane, dried over anhydrous sodium sulfate, concentrated under reduced pressure to afford crude product, which, on purification by column chromatography afforded the title compound.

$^1$H NMR (DMSO-d6) δ (ppm) 9.12 (s, 1H), 8.86 (s, 1H), 8.66 (s, 1H), 8.16 (d, 1H, J=4.5 Hz), 7.89 (d, 1H, J=8.4 Hz), 7.28 (d, 1H, J=8.1, 4.5 Hz), 7.12 (d, 1H, J=7.8 Hz), 6.92 (t, 1H, J=7.5 Hz), 6.84 (s, 1H), 6.75 (d, 1H, J=7.8 Hz), 6.57 (t, 1H, J=7.8 Hz), 4.90 (s, 2H), 4.59 (s, 2H), 3.76 (s, 3H), 3.71 (s, 2H)

Examples 229-232 were Also Obtained by Following Procedure of Example 228

Example 229

N$^2$-(2-aminophenyl)-N$^6$-(3,4-dimethoxyphenyl)-1-methyl-1,4,5,7-tetrahydro-6H-pyrrolo[2,3-c]pyridine-2,6-dicarboxamide $^1$H NMR (DMSO-d6) δ (ppm) 9.11 (s, 1H), 8.48 (s, 1H), 7.15 (d, 1H, J=2.4 Hz), 7.12 (dd, 1H, J=7.8, 1.5 Hz), 6.97 (dd, 1H, J=8.7, 2.7 Hz), 6.95-6.89 (m, 1H), 6.85-6.82 (m, 2H), 6.75 (dd, 1H, J=7.8, 1.5 Hz), 6.57 (dt, 1H, J=7.8, 1.5 Hz), 4.81 (s, 2H), 4.54 (s, 2H), 3.76 (s, 3H), 3.71 (s, 3H), 3.69 (s, 3H), 3.67-3.65 (m, 2H), 2.56-2.52 (m, 2H).

Example 230

N$^2$-(2-aminophenyl)-N$^6$-(2-methoxyethyl)-1-methyl-1,4,5,7-tetrahydro-6H-pyrrolo[2,3-c]pyridine-2,6-dicarboxamide 1H NMR (DMSO-d6) δ (ppm) 9.08 (s, 1H), 7.11 (dd, 1H, J=8.1, 1.5 Hz), 6.94-6.89 (m, 1H), 6.80 (s, 1H), 6.74 (dd, 1H, J=8.1, 1.5 Hz), 6.70 (d, 1H, J=5.4 Hz), 6.56 (dt, 1H, J=7.5, 1.2 Hz), 4.80 (s, 2H), 4.40 (s, 2H), 3.71 (s, 3H), 3.53 (t, 2H, J=5.4 Hz), 3.47 (d, 2H, J=6.3 Hz), 3.23 (s, 3H), 3.19 (d, 2H, J=6.0 Hz), 2.45 (m, 2H).

Example 231

N$^2$-(2-aminophenyl)-N$^6$-pyridin-3-yl-1,4,5,7-tetrahydro-6H-pyrrolo[2,3-c]pyridine-2,6-dicarboxamide 1H NMR (DMSO-d6) δ (ppm) 11.41 (s, 1H), 9.17 (s, 1H), 8.88 (s, 1H), 8.64 (d, 1H, J=2.1 Hz), 8.15 (dd, 1H, J=4.8, 1.2 Hz), 7.89-7.85 (m, 1H), 7.27 (dd, 1H, J=8.4, 4.8 Hz), 7.14 (dd, 1H, J=7.8, 1.5 Hz), 6.94 (dt, 1H, J=7.5, 1.5 Hz), 6.82 (d, 1H, J=1.8 Hz), 6.77 (dd, 1H, J=8.1, 1.5 Hz), 6.60 (dt, 1H, J=7.5, 1.2 Hz), 4.85 (s, 2H), 4.53 (s, 2H), 3.72 (t, 2H, J=5.4 Hz), 2.60 (t, 2H, J=4.8 Hz).

Example 232

$N^2$-(2-aminophenyl)-$N^6$-(3,4-dimethoxyphenyl)-1,4,5,7-tetrahydro-6H-pyrrolo[2,3-c]pyridine-2,6-dicarboxamide 1H NMR (DMSO-d6) δ (ppm) 11.39 (s, 1H), 9.15 (s, 1H), 8.50 (s, 1H), 7.15-7.13 (m, 2H), 6.98-6.92 (m, 2H), 6.84-6.75 (m, 3H), 6.60 (dt, 1H, J=7.5, 1.2 Hz), 4.85 (s, 2H), 4.49 (s, 2H), 3.71 (s, 3H), 3.69 (s, 3H), 3.68 (s, 2H), 2.58 (s, 2H)

Example 233

3,4-dimethoxyphenyl 2-[(2-aminophenyl)carbamoyl]-1-methyl-1,4,5,7-tetrahydro-6H-pyrrolo[2,3-c]pyridine-6-carboxylate To a solution of N-(2-aminophenyl)-1-methyl-4,5,6,7-tetrahydro-1H-pyrrolo[2,3-c]pyridine-2-carboxamide (1.0 eq) obtained in step IX of example 228, in DMF was added Et$_3$N (3.0 eq.) followed by carbonic acid 3,4-dimethoxy-phenyl ester 4-nitro-phenyl ester (1.0 eq) and stirred at room temperature overnight. Reaction mixture was then quenched with water and extracted with dichloromethane, dried over anhydrous sodium sulfate, concentrated under reduced pressure to afford crude product, which, on purification by column chromatography afforded the title compound.

$^1$H NMR (DMSO-d6) δ (ppm) 9.15 (s, 1H), 7.12 (dd, 1H, J=7.8, 1.2 Hz), 6.95-6.90 (m, 2H), 6.86 (s, 1H), 6.80 (s, 1H), 6.75 (dd, 1H, J=7.8, 1.2 Hz), 6.66 (dd, 1H, J=8.7, 2.4 Hz), 6.57 (dt, 1H, J=7.5, 1.2 Hz), 4.82 (s, 2H), 4.72 (s, 1H), 4.55 (s, 1H), 3.77-3.75 (m, 4H), 3.74 (s, 3H), 3.72 (s, 2H), 3.67-3.66 (m, 1H), 2.70-2.55 (m, 2H).

Example 234 was Also Obtained by Following Procedure of Example 233

Example 234

3,4-dimethoxyphenyl 2-[(2-aminophenyl)carbamoyl]-1,4,5,7-tetrahydro-6H-pyrrolo[2,3-c]pyridine-6-carboxylate 1H NMR (DMSO-d6) δ (ppm) 11.38 (s, 1H), 9.19 (s, 1H), 7.13 (dd, 1H, J=7.8, 1.2 Hz), 6.96-6.90 (m, 2H), 6.83 (d, 1H, J=1.8 Hz), 6.78-6.74 (m, 2H), 6.64 (dd, 1H, J=8.7, 2.4 Hz), 6.59 (dt, 1H, J=7.5, 1.2 Hz), 4.84 (s, 2H), 4.64 (s, 1H), 4.49 (s, 1H), 3.78-3.74 (m, 2H), 3.73 (s, 3H), 3.72 (s, 3H), 2.64-2.58 (m, 2H).

Example 235

N-(2-aminophenyl)-5-(N-1,3-benzodioxol-5-ylglycyl)-4,5,6,7-tetrahydro[1,3]thiazolo[5,4-c]pyridine-2-carboxamide Step-I (Benzo[1,3]dioxol-5-ylamino)-acetic acid ethyl ester To a solution of Benzo[1,3]dioxol-5-ylamine (1.2 eq.) and potassium carbonate (2.2 eq.) in DMF at 0° C. was added ethyl bromo acetate and stirred at room temperature for overnight. Reaction was then quenched with water and extracted with ethyl acetate, dried over sodium sulphate and concentrated under reduced pressure to afford crude product, which, on purification by column chromatography afforded the (Benzo[1,3]dioxol-5-ylamino)-acetic acid ethyl ester.

Step-II (Benzo[1,3]dioxol-5-ylamino)-acetic acid

To a solution of compound (Benzo[1,3]dioxol-5-ylamino)-acetic acid ethyl ester in methanol was added lithium hydroxide (1.2 eq.) and stirred for overnight. Reaction mixture was then concentrated and neutralized to afford (Benzo[1,3]dioxol-5-ylamino)-acetic acid.

Step-III

N-(2-aminophenyl)-5-(N-1,3-benzodioxol-5-ylglycyl)-4,5,6,7-tetrahydro[1,3]thiazolo[5,4-c]pyridine-2-carboxamide To the solution of (Benzo[1,3]dioxol-5-ylamino)-acetic acid. (1.0 mmol) in dry DMF (10 mL), were added 1-hydroxybenzotriazole (1.2 mmol), 1-ethyl-3-(3'-dimethylaminopropyl)carbodiimide (2 mmol) and N-methylmorpholine (2.0 mmol). Solution was cooled to 0° C. N-(2-aminophenyl)-4,5,6,7-tetrahydro[1,3]thiazolo[5,4-c]pyridine-2-carboxamide. obtained in step VIII of Example 1 was then added and mixture was stirred at room temperature overnight. Reaction mixture was concentrated, diluted with water, extracted with dichloromethane, washed with brine solution, and dried over anhydrous Na$_2$SO$_4$. Concentrated and purified by column chromatograph to obtained the title compound.

1H NMR (DMSO-d6) d(ppm) 10.01 (s, 1H, NH), 7.27 (m, 1H), 6.94 (t, 1H, J=6.0 Hz), 6.77 (d, 1H, J=6.0 Hz), 6.67-6.60 (m, 2H), 6.44 (m, 1H), 6.41 (m, 1H), 5.82 (s, 2H), 5.45-5.39 (m, 1H), 4.92 (s, 2H), 4.85 (s, 2H), 4.02-3.87 (m, 4H), 3.01-2.88 (m, 2H).

Examples 236-237 were Also Obtained by Following Procedure of Example 235

Example 236

N-(2-aminophenyl)-5-[N-(3-methoxyphenyl)glycyl]-4,5,6,7-tetrahydro[1,3]thiazolo[5,4-c]pyridine-2-carboxamide 1H NMR (DMSO-d6) d(ppm) 9.95 (s, 1H, NH), 7.25 (d, 1H, J=0.9 Hz), 6.96 (t, 1H, J=0.9 Hz), 6.78 (d, 1H, J=6.0 Hz), 6.62 (t, 1H, J=6.0 Hz), 6.28-6.23 (m, 2H), 6.16-6.13 (m, 1H), 5.75-5.61 (m, 1H), 4.95 (-4.81 (m, 4H), 4.00 (m, 2H), 3.88 (m, 2H), 3.66 (s, 3H), 3.01-2.88 (m, 2H).

Example 237

N-(2-aminophenyl)-5-[N-(6-methoxypyridin-3-yl)glycyl]-4,5,6,7-tetrahydro[1,3]thiazolo[5,4-c]pyridine-2-carboxamide 1H NMR (DMSO-d6) d(ppm) 10.00 (s, 1H, NH), 7.57 (m, 1H), 7.27 (d, 1H, J=7.5 Hz), 7.19 (dt, 1H, J=2.4 Hz, 6.6 Hz), 6.98 (t, 1H, J=7.2 Hz), 6.79 (d, 1H, J=7.8 Hz), 6.64-6.53 (m, 2H), 4.95 (s, 2H), 4.87 (s, 2H), 4.08-3.97 (m, 4H), 3.39 (m, 2H), 3.73 (s, 3H), 3.04-2.81 (m, 2H).

Examples 238-243 were Obtained by Following Procedure of Example 1

Example 238

$N^2$-(2-aminophenyl)-$N^5$-[3-(trifluoromethoxy)phenyl]-6,7-dihydro[1,3]thiazolo[5,4-c]pyridine-2,5(4H)-dicarboxamide 1H NMR (DMSO-d6) d(ppm) 9.98 (s, 1H, NH), 9.06 (s, 1H), 762 (s, 1H), 7.47 (d, 1H, J=8.4 Hz), 7.36 (t, 1H, J=8.1 Hz), 7.25 (d, 1H, J=6.9 Hz), 6.99-6.91 (m, 2H), 6.77 (d, 1H, J=6.9 Hz), 6.60 (dt, 1H, J=1.2 Hz, 7.8 Hz), 4.92 (s, 2H), 4.84 (s, 2H), 3.87 (t, 2H, J=5.4 Hz).

Example 239

$N^2$-(2-aminophenyl)-$N^5$-(3-morpholin-4-ylphenyl)-6,7-dihydro[1,3]thiazolo[5,4-c]pyridine-2,5(4H)-dicarboxamide $^1$H NMR (DMSO-d6) d(ppm) 9.96 (s, 1H, NH), 8.64 (s, 1H), 7.26 (d, 1H, J=7.8 Hz), 7.08 (m, 2H), 6.95 (m, 2H), 6.77 (d, 1H, J=7.8 Hz), 6.62-6.55 (m, 2H), 4.92 (s, 2H), 4.82 (s, 2H), 3.87 (t, 2H, J=5.4 Hz), 3.72 (t, 4H, J=4.2 Hz), 3.04 (t, 4H, J=4.5 Hz), 2.95 (m, 2H).

Example 240

$N^2$-(2-aminophenyl)-$N^5$-[4-(methylthio)phenyl]-6,7-dihydro[1,3]thiazolo[5,4-c]pyridine-2,5(4H)-dicarboxamide $^1$H NMR (DMSO-d6) d (ppm) 9.97 (s, 1H), 8.78 (s, 1H), 7.44 (dd, 2H, J=6.9&1.8), 7.25 (dd, 1H, J=8.1&1.5), 7.18 (dd, 2H, J=6.9 & 1.8), 6.96 (t, 1H, J=6.9), 6.77 (dd, 1H, J=8.1 & 1.2), 6.61 (t, 1H, J=7.8), 4.92 (s, 2H), 4.82 (s, 2H), 3.85 (t, 2H, J=5.7), 2.95 (t, 2H, J=5.7), 2.41 (s, 3H).

Example 241

$N^2$-(2-aminophenyl)-$N^5$-[3-(methylthio)phenyl]-6,7-dihydro[1,3]thiazolo[5,4-c]pyridine-2,5(4H)-dicarboxamide $^1$H NMR (DMSO-d6) d (ppm) 9.96 (s, 1H), 8.79 (s, 1H), 7.42 (d, 2H, J=1.5), 7.25 (m, 2H), 7.18 (t, 1H, J=7.8), 6.96 (t, 1H, J=8.1), 6.84 (dd, 1H, J=7.8 & 1.2), 6.76 (dd, 1H, J=7.8&1.2), 6.61 (t, 1H, J=8.4), 4.92 (s, 2H), 4.83 (s, 2H), 3.86 (t, 2H, J=5.4), 2.95 (t, 2H, J=5.4), 2.43 (s, 3H).

Example 242

$N^2$-(2-aminophenyl)-$N^5$-(3-methoxyphenyl)-6,7-dihydro[1,3]thiazolo[5,4-c]pyridine-2,5(4H)-dicarboxamide $^1$H NMR (DMSO-d6) d(ppm) 9.98 (s, 1H, NH), 8.76 (s, 1H), 7.27 (dd, 1H, J=7.8 Hz, 0.9 Hz), 7.17-7.11 (m, 2H), 7.04 (d, 1H, J=7.2 Hz), 6.96 (t, 1H, J=7.2 Hz), 6.78 (dd, 1H, J=8.1 Hz, 1.2 Hz), 6.60 (t, 1H, J=7.2 Hz), 6.52 (dd, 1H, J=7.2 Hz), 4.93 (s, 2H), 4.83 (s, 2H), 3.86 (t, 1H, J=5.4 Hz), 3.70 (s, 3H), 2.96 (m, 2H).

Example 243

$N^2$-(2-aminophenyl)-$N^5$-1H-indazol-5-yl-6,7-dihydro[1,3]thiazolo[5,4-c]pyridine-2,5(4H)-dicarboxamide $^1$H NMR (DMSO-d6) d (ppm) 8.77 (s, 1H, NH), 7.98 (s, 1H), 7.82 (s, 1H), 7.40 (dd, 2H, J=1.5 Hz, 9.0 Hz), 7.27 (d, 1H, J=6.9 Hz), 6.96 (t, 1H, J=7.2 Hz), 6.97 (d, 1H, J=7.5 Hz), 4.93 (s, 2H), 4.86 (s, 2H), 3.90 (t, 2H, J=5.4 Hz), 2.98 (m, 2H).

An Example 244 was Obtained by Following Procedure of Example 20

Example 244

$N^2$-(2-aminophenyl)-$N^5,N^5$-diethyl-6,7-dihydro[1,3]thiazolo[5,4-c]pyridine-2,5(4H)-dicarboxamide 1H NMR (DMSO-d6) d(ppm) 9.94 (s, 1H, NH), 7.25 (dd, 1H, J=7.2 Hz, 1.5 Hz), 6.96 (dt, 1H, J=1.5 Hz, 7.2 Hz), 6.77 (dd, 1H, J=7.2 Hz, 1.8 Hz), 6.60 (dt, 1H, J=1.5 Hz, 6.9 Hz), 4.91 (s, 2H), 4.47 (s, 2H), 3.49 (t, 1H, J=5.7 Hz), 3.17 (q, 4H, J=7.2 Hz), 2.93 (t, 2H, J=5.4).

Examples 245-260 were Obtained by Following Procedure of Example 34

Example 245

$N^2$-(2-amino-5-chlorophenyl)-$N^5$-(4-methoxyphenyl)-6,7-dihydro[1,3]thiazolo[5,4-c]pyridine-2,5(4H)-dicarboxamide $^1$H NMR (DMSO-d6) d (ppm) 10.04 (s, 1H), 8.62 (s, 1H), 7.34 (m, 3H), 7.01 (dd, 1H, J=2.4&8.4), 6.84 (dd, 2H, J=2.4&8.4), 6.76 (d, 1H, J=8.4), 5.13 (s, 2H), 4.81 (s, 2H), 3.81 (t, 1H, J=5.4 Hz), 3.69 (s, 3H), 2.95 (t, 2H, J=5.4 Hz).

Example 246

$N^2$-(2-amino-5-chlorophenyl)-$N^5$-(3,4-dimethoxyphenyl)-6,7-dihydro[1,3]thiazolo[5,4-c]pyridine-2,5(4H)-dicarboxamide $^1$H NMR (DMSO-d6) d (ppm) 10.04 (s, 1H), 8.62 (s, 1H), 7.34 (d, 1H, J=2.4 Hz), 7.14 (d, 1H, J=2.4 Hz), 6.99 (dd, 2H, J=2.4&8.4), 6.79 (dd, 2H, J=8.4&2.4), 5.13 (s, 2H), 4.82 (s, 2H), 3.85 (t, 1H, J=5.4 Hz), 3.70 (s, 3H), 3.66 (s, 3H), 2.95 (t, 2H, J=5.4 Hz).

Example 247

$N^2$-(2-amino-5-chlorophenyl)-$N^5$-pyridin-3-yl-6,7-dihydro[1,3]thiazolo[5,4-c]pyridine-2,5(4H)-dicarboxamide $^1$H NMR (DMSO-d6) d (ppm) 10.04 (s, 1H), 8.97 (s, 1H), 8.64 (d, 1H, J=2.4), 8.17 (dd, 1H, J=2.4&8.4), 7.86 (m, 1H), 7.30 (d, 1H, J=2.4 Hz), 7.28 (m, 1H), 7.01 (dd, 2H, J=8.4&2.4), 6.79 (d, 1H, J=8.7 Hz), 5.12 (s, 2H), 4.86 (s, 2H), 3.88 (t, 1H, J=5.4 Hz), 2.99 (t, 2H, J=5.4 Hz).

Example 248

$N^2$-(2-aminophenyl)-$N^5$-[3-(difluoromethoxy)phenyl]-6,7-dihydro[1,3]thiazolo[5,4-c]pyridine-2,5(4H)-dicarboxamide $^1$H NMR (DMSO-d6) d(ppm) 9.97 (s, 1H, NH), 8.96 (s, 1H), 7.32-7.24 (m, 4H), 7.16 (t, 1H, J=74.1 Hz), 6.96 (m, 1H), 6.79-6.74 (m, 2H), 6.59 (t, 1H, J=7.2 Hz), 4.92 (s, 4H), 4.84 (s, 2H), 3.87 (t, 2H, J=5.4 Hz), 2.95 (m, 2H).

Example 249

$N^2$-(2-aminophenyl)-$N^5$-[4-(methylsulfonyl)phenyl]-6,7-dihydro[1,3]thiazolo[5,4-c]pyridine-2,5(4H)-dicarboxamide $^1$H NMR (DMSO-d6) d (ppm) 9.97 (s, 1H), 9.27 (s, 1H), 7.79 (d, 2H, J=9.0), 7.24 (d, 2H, J=9.0), 7.25 (dd, 1H, J=7.8 & 1.2), 6.95 (t, 1H, J=6.9), 6.77 (dd, 1H, J=7.8 & 1.2), 6.61 (t, 1H, J=7.8), 4.92 (s, 2H), 4.86 (s, 2H), 3.89 (t, 2H, J=5.7), 3.13 (s, 3H), 2.97 (t, 2H, J=5.7).

Example 250

$N^2$-(2-aminophenyl)-$N^5$-[3-(methylsulfonyl)phenyl]-6,7-dihydro[1,3]thiazolo[5,4-c]pyridine-2,5(4H)-dicarboxamide $^1$H NMR (DMSO-d6) d (ppm) 9.97 (s, 1H), 9.19 (s, 1H), 8.09 (d, 2H, J=1.8), 7.83 (dt, 1H, J=7.8&0.9), 7.51 (m, 2H), 7.25 (dd, 1H, J=7.8 & 1.2), 6.96 (t, 1H, J=6.9), 6.77 (dd, 1H, J=7.8 & 1.2), 6.61 (t, 1H, J=7.8), 4.92 (s, 2H), 4.86 (s, 2H), 3.89 (t, 2H, J=5.7), 3.16 (s, 3H), 2.97 (t, 2H, J=5.7).

Example 251

$N^2$-(2-amino-5-fluorophenyl)-$N^5$-1,3-benzodioxol-5-yl-6,7-dihydro[1,3]thiazolo[5,4-c]pyridine-2,5(4H)-dicarboxamide $^1$H NMR (DMSO-d6) d(ppm) 10.00 (s, 1H, NH), 8.66 (s, 1H), 7.28 (dd, 1H, J=7.8 Hz, 2.4 Hz), 7.11 (d, 1H, J=1.8 Hz), 6.85-6.78 (m, 4H), 5.94 (s, 2H), 4.82 (s, 2H), 4.81 (s, 2H), 3.84 (t, 2H, J=5.7 Hz), 2.94 (m, 2H).

Example 252

$N^2$-(2-amino-5-fluorophenyl)-$N^5$-(3,4-dimethoxyphenyl)-6,7-dihydro[1,3]thiazolo[5,4-c]pyridine-2,5(4H)-dicarboxamide $^1$H NMR (DMSO-d6) d(ppm) 10.01 (s, 1H, NH), 8.61 (s, 1H), 7.30 (d, 1H, J=0.9 Hz), 7.14 (s, 1H), 6.98 (d, 1H, J=0.9 Hz), 6.82 (m, 3H), 4.82 (s, 2H), 4.82 (s, 2H), 3.85 (m, 2H), 3.70 (s, 3H), 3.69 (s, 3H), 2.95 (m, 2H).

Example 253

$N^2$-[2-amino-5-(2-thienyl)phenyl]-$N^5$-pyridin-3-yl-6,7-dihydro[1,3]thiazolo[5,4-c]pyridine-2,5(4H)-dicarboxamide $^1$H NMR (DMSO-d6) δ (ppm) 10.04 (s, 1H), 9.02 (s, 1H), 8.68 (s, 1H), 8.19 (d, 1H, J=4.2), 7.90 (d, 1H, J=8.4 Hz), 7.59-7.53 (overlapped signals, 3H), 7.40-7.29 (overlapped signals, 3H), 6.82 (d, 1H, J=8.1 Hz), 4.87 (s, 2H) 3.90 (t, 2H, J=5.1), 2.98 (br t, 2H)

Example 254

$N^2$-[2-amino-5-(3-thienyl)phenyl]-$N^5$-[2-(difluoromethoxy)phenyl]-6,7-dihydro[1,3]thiazolo[5,4-c]pyridine-2,5(4H)-dicarboxamide $^1$H NMR (DMSO-d6) δ (ppm) 10.04 (s, 1H), 6.83 (d, 1H, J=8.4 Hz), 8.46 (s, 1H), 7.60 (d, 1H, J=2.1), 7.58-7.55 (m, 2H), 7.51-7.47 (m, 1H), 7.41 (dd, 1H, J=4.8, 1.8 Hz), 7.36 (dd, 1H, J=8.4, 2.4 Hz), 7.25-7.17 (m, 4H), 5.07 (s, 2H), 4.85 (s, 2H), 3.88 (t, 2H, J=5.7 Hz), 2.99 (t, 2H, J=5.7 Hz).

Example 255

$N^2$-[2-amino-5-(3-thienyl)phenyl]-$N^5$-(3,4-dimethoxyphenyl)-6,7-dihydro[1,3]thiazolo[5,4-c]pyridine-2,5(4H)-dicarboxamide $^1$H NMR (DMSO-$d_6$) δ (ppm) 10.04 (s, 1H), 8.61 (s, 1H), 7.59 (d, 1H, J=1.8 Hz), 7.56-7.54 (m, 2H), 7.40 (dd, 1H, J=4.5, 1.8 Hz), 7.35 (dd, 1H, J=8.4, 1.8 Hz), 7.15 (d, 1H, J=2.4 Hz), 6.98 (dd, 1H, J=8.7, 2.1 Hz), 6.85-6.80 (m, 2H), 5.05 (s, 2H), 4.83 (s, 2H), 3.86 (t, 2H, J=5.4 Hz), 3.70 (s, 3H), 3.69 (s, 3H), 2.96 (t, 2H, J=5.4 Hz)

Example 256

$N^2$-[2-amino-5-(3-thienyl)phenyl]-$N^5$-(2-methoxyethyl)-6,7-dihydro[1,3]thiazolo[5,4-c]pyridine-2,5(4H)-dicarboxamide $^1$H NMR (DMSO-$d_6$) δ (ppm) 10.02 (s, 1H), 7.59 (d, 1H, J=2.1 Hz), 7.57-7.55 (m, 2H), 7.40 (dd, 1H, J=4.2, 1.8 Hz), 7.36 (dd, 1H, J=8.4, 2.1 Hz), 6.87-6.81 (m, 2H), 5.06 (s, 2H), 4.70 (m, 2H), 3.73 (t, 2H, J=5.4 Hz), 3.35 (t, 2H, J=5.7 Hz), 3.24 (s, 31-1), 3.22 (t, 2H, J=5.7 Hz), 2.87 (t, 2H, J=5.4 Hz)

Example 257

$N^2$-[2-amino-5-(2-thienyl)phenyl]-$N^5$-(3,4-dimethoxyphenyl)-6,7-dihydro[1,3]thiazolo[5,4-c]pyridine-2,5(4H)-dicarboxamide $^1$H NMR (DMSO-d6) δ (ppm) 10.00 (br, 1H), 8.65 (s, 1H), 5.57 (d, 1H, J=2.1 Hz), 7.37 (d, 1H, J=4.5 Hz), 7.30 (dd, 1H, 8.4, 2.1 Hz), 7.24 (d, 1H, J=3.0 Hz), 7.17 (d, 1H, J=2.4 Hz), 7.05 (dd, 1H, J=5.1, 3.9 Hz), 7.00 (dd, 1H, J=8.7, 2.4 Hz), 6.85 (d, 1H, J=6.3 Hz), 6.82 (d, 1H, J=6.0 Hz), 5.19 (s, 2H), 4.84 (s, 2H), 3.88 (t, 2H, J=5.7 Hz), 3.72 (s, 3H), 3.70 (s, 3H), 2.97 (t, 2H, J=5.7 Hz)

Example 258

$N^2$-[2-amino-5-(2-thienyl)phenyl]-$N^5$-(2-methoxyethyl)-6,7-dihydro[1,3]thiazolo[5,4-c]pyridine-2,5(4H)-dicarboxamide $^1$H NMR (CDCl3) δ (ppm) 8.94 (s, 1H), 7.70 (d, 1H, J=1.8 Hz), 7.35 (dd, 1H, J=8.4, 2.1 Hz), 7.20 (d, 1H, J=1.5 Hz), 7.18 (s, 1H), 7.03 (t, 1H, J=4.2 Hz), 6.84 (d, 1H, J=8.1 Hz), 5.07 (s, 1H), 4.74 (s, 2H), 4.02 (s, 2H), 3.75 (t, 2H, J=5.7 Hz), 3.49-3.48 (s, 4H), 3.38 (s, 3H), 2.97 (t, 2H, J=5.7 Hz)

Example 259

N²-[2-amino-5-(2-thienyl)phenyl]-N⁵-pyridin-3-yl-6,7-dihydro[1,3]thiazolo[5,4-c]pyridine-2,5(4H)-dicarboxamide ¹H NMR (DMSO-d6) δ (ppm) 10.05 (s, 1H), 9.00 (s, 1H), 8.66 (s, 1H), 8.17 (d, 1H, J=3.6 Hz), 7.89 (d, 1H, J=8.4 Hz), 7.55 (d, 1H, J=1.8 Hz), 7.36-7.22 (m, 41-1), 7.04 (dd, 1H, J=5.1, 3.6 Hz), 6.81 (J=8.4 Hz), 5.18 (s, 1H), 4.87 (s, 2H), 3.89 (s, 2H), 3.01 (s, 21-1).

Example 260

N²-[2-amino-5-(2-thienyl)phenyl]-N⁵-[2-(difluoromethoxy)phenyl]-6,7-dihydro[1,3]thiazolo[5,4-c]pyridine-2,5(4H)-dicarboxamide ¹H NMR (DMSO-d₆) δ (ppm) 10.05 (s, 1H), 8.44 (s, 1H), 7.55 (s, 1H), 7.48 (d, 1H, J=6.6 Hz), 7.35 (d, 1H, J=5.1 Hz), 7.36-7.12 (m, 5H), 7.05-7.00 (m, 2H), 6.81 (d, 1H, J=8.4 Hz), 5.17 (s, 2H), 4.83 (s, 2H), 3.86 (s, 2H), 2.97 (s, 2H).

Example 261

N²-(2-aminophenyl)-N⁵-(4-cyanophenyl)-6,7-dihydro[1,3]thiazolo[5,4-c]pyridine-2,5(4H)-dicarboxamide 1H NMR (DMSO-d6) δ (ppm) 9.99 (s, 1H), 9.27 (s, 1H), 7.73-7.66 (m, 4H), 7.27 (d, 1H, J=6.9 Hz), 7.00-6.95 (m, 1H), 6.79 (dd, 1H, J=8.1, 1.2 Hz), 6.64-6.58 (m, 1H), 4.93 (s, 2H), 4.87 (s, 2H), 3.90 (t, 2H, J=5.7 Hz), 2.98 (s, 2H);

Example 262

N²-(2-aminophenyl)-N⁵-(3-cyanophenyl)-6,7-dihydro[1,3]thiazolo[5,4-c]pyridine-2,5(4H)-dicarboxamide 1H NMR (DMSO-d6) δ (ppm) 9.99 (s, 1H), 9.14 (s, 1H), 7.95 (t, 1H, J=1.8 Hz), 7.79-7.76 (m, 1H), 7.51-7.40 (m, 2H), 2.27 (dd, 1H, J=7.8, 1.2 Hz), 6.97 (dt, 1H, J=7.2, 1.5 Hz), 6.79 (dd, 1H, J=8.1, 1.2 Hz), 6.61 (dt, 1H, J=7.2, 1.2 Hz), 4.94 (s, 2H), 4.87 (s, 2H), 3.89 (t, 2H, J=5.7 Hz), 3.00 (t, 2H, J=5.1 Hz).

Example 263

N²-[2-amino-5-(3-thienyl)phenyl]N⁵-pyridin-3-yl-6,7-dihydro[1,3]thiazolo[5,4-c]pyridine-2,5(4H)-dicarboxamide 1H NMR (DMSO-d6) δ (ppm) 10.56 (s, 1H), 10.38 (s, 1H), 9.20 (d, 1H, J=2.4 Hz), 8.73 (d, 1H, J=8.7 Hz), 8.52 (d, 1H, J=5.4 Hz), 7.96 (dd, 1H, J=8.7, 5.4 Hz), 7.84 (dd, 1H, J=3.0, 1.5 Hz), 7.80 (d, 1H, J=1.8 Hz), 7.66-7.61 (m, 2H), 7.52 (dd, 1H, J=5.1, 1.2 Hz), 7.33 (d, 1H, J=8.1 Hz), 4.99 (s, 2H), 4.03 (t, 2H, J=5.4 Hz), 3.04 (s, 2H)

Examples 264-266 were Obtained by Following Procedure of Example 88

Example 264

N-(2-aminophenyl)-5-[4-(trifluoromethoxy)benzoyl]-4,5,6,7-tetrahydro[1,3]thiazolo[5,4-c]pyridine-2-carboxamide ¹H NMR (DMSO-d6) d(ppm) 10.03 (s, 1H, NH), 7.63 (m, 2H), 7.47 (d, 2H, J=8.1 Hz), 7.25 (d, 1H, J=7.5 Hz), 6.96 (t, 2H, J=6.9 Hz), 6.78 (d, 1H, J=7.2 Hz), 6.60 (t, 1H, J=8.1 Hz), 4.96 (s, 2H), 4.91 (s, 2H), 4.01-3.67 (m, 2H), 2.98 (m, 2H).

Example 265

N-(2-aminophenyl)-5-[4-(difluoromethoxy)benzoyl]-4,5,6,7-tetrahydro[1,3]thiazolo[5,4-c]pyridine-2-carboxamide ¹H NMR (DMSO-d6) d(ppm) 9.99 (s, 1H, NH), 7.58-7.56 (m, 2H), 7.34 (t, 2H, J=73.8 Hz, CHF2), 6.96 (dt, 1H, J=7.2 Hz, 1.5 Hz), 6.77 (dd, 1H, J=0.9 Hz), 6.60 (dt, 1H, J=1.2 Hz, 7.5 Hz), 6.60 (dt, 1H, J=1.2 Hz, 6.6 Hz), 4.91 (s, 414), 4.03-3.70 (m, 2H), 4.03-3.70 (m, 2H), 2.97 (m, 2H).

Example 266

N-(2-aminophenyl)-5-[3-(trifluoromethoxy)benzoyl]-4,5,6,7-tetrahydro[1,3]thiazolo[5,4-c]pyridine-2-carboxamide ¹H NMR (DMSO-d6) d(ppm) 9.95 (s, 1H, NH), 7.62 (dd, 1H, J=7.8 Hz), 7.52-7.50 (m, 3H), 7.25 (d, 1H, J=7.8 Hz), 6.96 (dt, 1H, J=7.2 Hz, 1.2 Hz), 6.77 (d, 1H, J=6.9 Hz), 6.60 (t, 1H, J=6.9 Hz), 4.97 (s, 2H), 4.91 (s, 2H), 4.00-3.64 (m, 2H), 2.97 (m, 2H).

Example 267 was Obtained by Following Procedure of Example 190

Example 267

N-(2-aminophenyl)-5-[3-pyridin-3-ylprop-2-enoyl]-4,5,6,7 tetrahydro[1,3]thiazolo[5,4-c]pyridine-2-carboxamide ¹H NMR (DMSO-d6) d(ppm) 10.00 (s, 1H, NH), 8.92 (s, 1H), 8.55 (m, 1H), 8.31-8.22 (m, 1H), 7.57-7.43 (m, 3H), 7.25 (d, 1H, J=0.9 Hz), 6.96 (dt, 1H, J=0.9 Hz), 6.77 (d, 1H, J=0.9 Hz), 4.93 (s, 4H), 4.10-3.97 (m, 2H), 3.10-2.94 (m, 2H).

Examples 268-271 were Obtained by Following Procedure of Example 181

Example 268

3-methoxyphenyl 2-[(2-aminophenyl)carbamoyl]-6,7-dihydro[1,3]thiazolo[5,4-c]pyridine-5(4H)-carboxylate ¹H NMR (DMSO-d6) d(ppm) 10.01 (s, 1H, NH), 7.31-7.25 (m, 2H), 6.97 (t, 1H, J=7.2 Hz), 6.82-6.73 (m, 4H), 6.60 (t, 1H, J=7.5 Hz), 4.92 (s, 2H), 4.83 (s, 2H), 3.95-3.74 (m, 2H), 3.66 (s, 3H), 3.01 (m, 2H).

Example 269

3,4-dimethoxyphenyl 2-{[2-amino-5-(3-thienyl)phenyl]carbamoyl}-6,7-dihydro[1,3]thiazolo[5,4-c]pyridine-5(4H)-carboxylate ¹H NMR (DMSO-d6) δ (ppm) 10.91 (s, 1H), 7.61 (d, 1H, J=2.1 Hz), 7.58-7.55 (m, 2H), 7.41 (dd, 1H, J=4.5, 1.8 Hz), 7.37 (dd, 1H, J=8.4, 2.1 Hz), 6.94 (d, 1H, J=9.0 Hz), 6.84-6.82 (m, 2H), 6.69 (dd, 1H, J=8.7, 2.7 Hz), 5.07 (s, 2H), 5.01 (s, 1H), 4.85 (s, 1H), 3.98 (s, 1H), 3.85 (s, 1H) 3.75 (s, 3H), 3.74 (s, 3H), 3.07-3.01 (br s, 2H).

Example 270

3,4-dimethoxyphenyl 2-{[2-amino-5-(2-thienyl)phenyl]carbamoyl}-6,7-dihydro[1,3]thiazolo[5,4-c]pyridine-5(4H)-carboxylate $^1$H NMR (DMSO-d6) δ (ppm) 10.11 (s, 1H), 7.57 (d, 1H, J=2.1 Hz), 7.37 (dd, 1H, J=5.1, 0.9 Hz), 3.31 (dd, 1H, J=8.4, 2.1 Hz), 7.25 (dd, 1H, J=3.6, 0.9 Hz), 7.06 (dd, 1H, J=5.1, 3.6 Hz), 6.94 (d, 1H, J=9.0 Hz), 6.84-6.81 (m, 2H), 6.69 (dd, 1H, J=8.7, 2.4 Hz), 5.19 (s, 2H), 5.01 (s, 1H), 4.85 (s, 1H), 3.98 (s, 1H), 3.85 (s, 1H), 3.75 (s, 3H), 3.74 (s, 3H), 3.07 (s, 1H), 3.00 (s, 1H).

Example 271 benzyl 2-[(2-aminophenyl)carbamoyl]-6,7-dihydro[1,3]thiazolo[5,4-c]pyridine-5(4H)-carboxylate 1H NMR (DMSO-d6) δ (ppm) 10.68 (s, 1H), 7.63-7.57 (m, 2H), 7.48-7.31 (overlapped m, 7H), 5.15 (s, 2H), 4.82 (s, 2H), 3.81 (s, 2H), 2.93 (s, 2H).

Examples 272-276 were Prepared by Following the Procedure of Example No. 64

Example 272

N-(2-aminophenyl)-5-[{[3-(difluoromethoxy)phenyl]amino}(oxo)acetyl]-4,5,6,7-tetrahydro[1,3]thiazolo[5,4-c]pyridine-2-carboxamide $^1$H NMR (DMSO-d6) d(ppm) 10.09 (s, 1H, NH), 10.03 (s, 1H), 7.16 (t, 1H, J=1.8 Hz), 7.50-7.37 (m, 2H), 7.27-7.21 (m, 2H), 6.99-6.93 (m, 1H), 6.77 (d, 1H, J=7.8 Hz), 6.60 (dt, 1H, J=1.2 Hz), 4.94 (s, 4H), 4.03-3.86 (m, 2H), 3.03-3.00 (m, 2H).

Example 273

N-(2-aminophenyl)-5-(oxo{[3-(trifluoromethoxy)phenyl]amino}acetyl)-4,5,6,7-tetrahydro[1,3]thiazolo[5,4-c]pyridine-2-carboxamide $^1$H NMR (DMSO-d6) d(ppm) 11.21 (s, 1H, NH), 10.05 (s, 1H), 7.83 (s, 1H), 7.63 (d, 1H, J=8.4 Hz), 7.55-7.49 (m, 1H), 7.27 (d, 1H, J=7.8 Hz), 7.18-7.15 (m, 1H), 6.97 (t, 1H, J=7.5 Hz), 6.79 (d, 1H, J=8.1 Hz), 6.62 (dt, 1H, J=1.2 Hz, 7.9 Hz). 5.00 (s, 2H), 4.94 (s, 2H), 3.98-3.89 (m, 2H), 3.06-3.00 (m, 2H).

Example 274

N-(2-aminophenyl)-5-(oxo{[2-(trifluoromethoxy)phenyl]amino}acetyl)-4,5,6,7-tetrahydro[1,3]thiazolo[5,4-c]pyridine-2-carboxamide $^1$H NMR (DMSO-d6) d(ppm) 10.84 (s, 1H, NH), 10.03 (s, 1H), 7.86 (dd, 1H, J=1.5 Hz, 7.2 Hz), 7.46-7.36 (m, 3H), 7.25 (dd, 1H, J=1.2 Hz, 7.2 Hz), 6.94 (t, 1H, J=6.6 Hz), 6.76 (dd, 1H, J=6.6 Hz, 1.5 Hz), 6.58 (dt, 1H, J=1.2 Hz, 8.1 Hz), 4.94 (s, 2H), 4.92 (s, 2H), 3.87 (t, 2H, J=5.7 Hz), 3.03 (t, 2H, J=5.1 Hz).

Example 275

N-(2-aminophenyl)-5-[{[2-(difluoromethoxy)phenyl]amino}(oxo)acetyl]-4,5,6,7-tetrahydro[1,3]thiazolo[5,4-c]pyridine-2-carboxamide $^1$H NMR (DMSO-d6) d(ppm) 10.57 (s, 1H, NH), 10.12 (s, 1H), 7.85-7.80 (m, 1H), 7.29-7.19 (m, 4H), 6.95 (t, 1H, J=8.7 Hz), 6.95 (d, 1H, J=7.8 Hz), 6.59 (t, 1H, J=7.5 Hz), 4.98 (s, 2H), 4.92 (s, 2H), 4.02-3.88 (m, 2H), 3.04-2.99 (m, 2H).

Example 276

N-(2-aminophenyl)-5-(oxo{[2-(trifluoromethoxy)phenyl]amino}acetyl)-4,5,6,7-tetrahydro[1,3]thiazolo[5,4-c]pyridine-2-carboxamide $^1$H NMR (DMSO-d6) d(ppm) 10.85 (s, 1H, NH), 10.01 (s, 1H), 7.85-7.80 (d, 1H), 7.35-7.19 (m, 4H), 6.82 (t, 1H, J=8.7 Hz), 6.72 (d, 1H, J=7.8 Hz), 6.59 (t, 1H, J=7.5 Hz), 4.98 (s, 2H), 4.92 (s, 2H), 4.02-3.88 (m, 2H), 3.04-2.99 (m, 2H).

Examples 277-279 were Prepared by Following the Procedure of Example No. 172

Example 277

N-[2-amino-5-(2-thienyl)phenyl]-5-[(3-methoxyphenoxy)acetyl]-4,5,6,7-tetrahydro[1,3]thiazolo[5,4-c]pyridine-2-carboxamide $^1$H NMR (DMSO-d6) d (ppm) 10.01 (s, 1H), 7.54 (s, 1H), 7.36 (s, 1H), 7.34 (dd, 1H, J=8.0 & 2.4), 7.23 (d, 1H, J=2.7), 7.17 (m, 2H), 7.04 (t, 1H, J=7.2), 6.83 (d 1H, J=8.4), 6.53 (m, 3H), 5.17 (s, 2H), 4.91 (m, 4H), 3.76 (t, 2H, J=5.3 Hz), 3.71 (s, 2H), 2.90 (m, 2H).

Example 278

N-[2-amino-5-(3-thienyl)phenyl]-5-[(3-methoxyphenoxy)acetyl]-4,5,6,7-tetrahydro[1,3]thiazolo[5,4-c]pyridine-2-carboxamide $^1$H NMR (DMSO-d6) d (ppm) 10.01 (s, 1H), 7.54 (m, 3H), 7.38 (m, 2H), 7.16 (m, 1H), 6.83 (d, 1H, J=8.4), 6.53 (m, 3H), 5.17 (s, 2H), 4.91 (m, 4H), 3.86 (t, 2H, J=4.2 Hz), 3.85 (s, 2H), 2.90 (m, 2H).

Example 279

N-(2-amino-5-fluorophenyl)-5-[(3-methoxyphenoxy)acetyl]-4,5,6,7-tetrahydro[1,3]thiazolo[5,4-c]pyridine-2-carboxamide $^1$H NMR (DMSO-d6) d(ppm) 7.30 (d, 1H, J=0.9 Hz), 7.15 (t, 1H, J=0.9 Hz), 6.86 (m, 2H), 6.52 (m, 3H), 4.95-4.84 (m, 6H), 3.84 (m, 2H), 3.71 (s, 3H), 3.00-2.89 (m, 2H).

Example 280 was Obtained by Following Procedure of Example 150

Example 280

N-(2-aminophenyl)-5-[(4-methoxyphenyl)sulfonyl]-4,5,6,7-tetrahydro[1,3]thiazolo[5,4-c]pyridine-2-carboxamide 1H NMR (DMSO-d6) δ (ppm) 10.67 (s, 1H), 7.78 (d, 2H, J=12.0 Hz), 7.55-7.53 (m, 2H), 7.44-7.35 (m, 2H), 7.15 (d, 2H, J=12.0 Hz), 4.50 (s, 2H), 3.84 (s, 3H), 3.49 (t, 2H, J=5.7 Hz), 2.90 (t, 2H, J=5.1 Hz).

Examples 281-282 were Prepared by Following the Procedure of Example 63

Example 281

$N^2$-(2-aminophenyl)-$N^5$-(6-methoxypyridin-3-yl)-6,7-dihydro[1,3]thiazolo[5,4-c]pyridine-2,5(4H)-dicarboxamide dihydrochloride $^1$H NMR (DMSO-d6) δ (ppm) 10.68 (s, 1H), 9.01 (s, 1H), 8.25 (d, 1H, J=2.4 Hz), 7.86 (dd, 1H, J=9.0, 3.0 Hz), 7.54 (dd, 1H, J=7.5, 1.8 Hz), 7.48 (dd, 1H, J=7.2, 2.1 Hz), 7.42-7.32 (m, 2H), 7.81 (d, 1H, J=9.0 Hz), 4.87 (s, 2H), 3.91 (t, 2H, J=5.7 Hz), 3.81 (s, 3H), 2.98 (t, 2H, J=5.7 Hz).

Example 282

$N^2$-(2-aminophenyl)-$N^5$-pyridin-3-yl-6,7-dihydro[1,3]thiazolo[5,4-c]pyridine-2,5(4H)-dicarboxamide dihydrochloride $^1$H NMR (DMSO-d6) δ (ppm) 10.63 (s, 1H), 10.43 (s, 1H), 9.20 (d, 1H, J=2.4 Hz), 8.74 (dd, 1H, J=7.5, 1.2 Hz), 8.51 (d, 1H, J=5.4 Hz), 7.96 (dd, 1H, J=8.4, 5.4 Hz), 7.52 (dd, 1H, J=5.7, 3.6 Hz), 7.43 (dd, 1H, J=5.7, 3.6 Hz), 7.35-7.30 (m, 2H), 4.98 (s, 2H), 4.05-3.98 (m, 2H), 3.02 (s, 2H).

Example 283

$N^2$-(2-aminophenyl)-$N^5$-(6-methoxypyridin-3-yl)-6,7-dihydro[1,3]thiazolo[5,4-c]pyridine-2,5(4H)-dicarboxamide-4-methylaniline (1:2)

To a solution of $N^2$-(2-aminophenyl)-$N^5$-(6-methoxypyridin-3-yl)-6,7-dihydro[1,3]thiazolo[5,4-c]pyridine-2,5(4H)-dicarboxamide obtained in example 38 in tetrahydrofuran at 0° C. was added toluene-4-sulfonic acid (1.2 eq.) and stirred at room temperature for 3-4 hrs. White precipitated solid was filtered out and dried to afford title compound.

1H NMR (DMSO-d6) δ (ppm) 10.76 (s, 1H), 8.84 (s, 1H), 8.32 (s, 1H), 8.22 (d, 1H, J=2.4 Hz), 7.81 (dd, 1H, J=9.0, 2.7 Hz), 7.56-7.53 (m, 1H), 7.48 (d, 4H, J=8.1 Hz), 7.40 (br, 4H), 7.12 (d, 4H, J=7.8 Hz), 6.80 (d, 1H, J=9.0 Hz), 4.87 (s, 2H), 3.89 (t, 2H, J=5.7 Hz), 3.82 (s, 3H), 3.60 (br, 1H), 3.00 (t, 2H, J=5.7 Hz), 2.29 (s, 6H).

Examples 284-286 were Obtained by Following Procedure of Example 283

Example 284

$N^2$-(2-aminophenyl)-$N^5$-pyridin-3-yl-6,7-dihydro[1,3]thiazolo[5,4-c]pyridine-2,5(4H)-dicarboxamide-4-methylaniline (1:2)

1H NMR (DMSO-d6) δ (ppm) 10.60 (s, 1H), 9.76 (s, 1H), 9.10 (d, 1H, J=2.1 Hz), 8.54-8.48 (m, 2H), 7.97 (dd, 1H, J=8.7, 5.7 Hz), 7.49-7.47 (m, 5H), 7.29-7.24 (m, 314), 7.12 (d, 4H, J=7.8 Hz), 4.93 (s, 2H), 3.95 (t, 2H, J=5.4 Hz), 3.03 (s, 2H), 2.29 (s, 6H).

Example 285

N-(2-aminophenyl)-5-[(3-methoxyphenoxy)acetyl]-4,5,6,7-tetrahydro[1,3]thiazolo[5,4-c]pyridine-2-carboxamide-4-methylaniline (1:1)

1H NMR (DMSO-d6) δ (ppm) 10.59 (s, 1H), 7.50-7.46 (m, 3H), 7.29-7.28 (m, 3H), 7.21-7.16 (m, 1H), 7.11 (d, 2H, J=7.8 Hz), 6.56-6.51 (m, 3H), 4.97-4.87 (m, 4H), 3.87 (s, 2H), 3.72 (s, 3H), 3.05 (s, 1H), 2.92 (s, 1H), 2.29 (s, 3H).

Example 286 benzyl 2-[(2-aminophenyl)carbamoyl]-6,7-dihydro[1,3]thiazolo[5,4-c]pyridine-5(4H)-carboxylate-4-methylaniline (1:1)

1H NMR (DMSO-d6) δ (ppm) 10.62 (d, 1H, J=3.0 Hz), 7.50-7.46 (m, 3H), 7.46-7.35 (m, 5H), 7.34-7.28 (m, 3H), 7.11 (d, 2H, J=8.4 Hz), 5.15 (s, 2H), 4.83 (s, 2H), 3.82 (s, 2H), 2.95 (s, 2H), 2.29 (s, 3H).

Example 287

N-(2-aminophenyl)-5-[(3-methoxyphenoxy)acetyl]-4,5,6,7-tetrahydro[1,3]thiazolo[5,4-c]pyridine-2-carboxamide methanesulfonate To a solution of N-(2-aminophenyl)-5-[(3-methoxyphenoxy)acetyl]-4,5,6,7-tetrahydro[1,3]-thiazolo[5,4-c]pyridine-2-carboxamide obtained in example 179 in tetrahydrofuran at 0° C. was added methane sulfonic acid (1.2 eq.) and stirred at room temperature for 3-4 hrs. White precipitated solid was filtered out and dried to afford title compound.

1H NMR (DMSO-d6) δ (ppm) 10.67 (s, 1H), 7.54-7.51 (m, 1H), 7.36-7.33 (m, 3H), 7.21-7.16 (m, 1H), 6.56-6.51 (m, 3H), 4.97-4.87 (m, 4H), 3.88 (s, 2H), 3.72 (s, 3H), 3.05 (s, 1H), 2.93 (s, 1H), 2.35 (s, 3H).

Example 288 was Obtained by Following Procedure of Example 287

Example 288 benzyl 2-[(2-aminophenyl)carbamoyl]-6,7-dihydro[1,3]thiazolo[5,4-c]pyridine-5(4H)-carboxylate methanesulfonate 1H NMR (DMSO-d6) δ (ppm) 10.62 (s, 1H), 7.50 (d, 1H, J=6.9 Hz), 7.40-7.26 (overlapped m, 8H), 5.15 (s, 2H), 4.83 (m, 2H), 3.82 (s, 2H), 2.95 (s, 2H), 2.33 (s, 3H).

Example 289 benzyl 2-[(2-aminophenyl)carbamoyl]-6,7-dihydro[1,3]thiazolo[5,4-c]pyridine-5(4H)-carboxylate sulfate A solution of N-(2-aminophenyl)-5-(phenoxyacetyl)-4,5,6,7-tetrahydro[1,3]thiazolo[5,4-c]-pyridine-2-carboxamide obtained in example 172 in methanol cooled to 0° C. A solution of sulphuric acid in methanol (1:1) was added slowly and stirred at room temperature for 3 hrs. White precipitated solid was filtered out and dried to afford title compound.

1H NMR (DMSO-d6) δ (ppm) 10.18 (s, 1H), 7.40-7.39 (m, 4H), 7.36-7.33 (m, 2H), 7.08 (dt, 1H, J=7.5, 1.2 Hz), 6.95 (dd, 1H, J=8.1, 1.2 Hz), 6.82 (dt, 1H, J=7.5, 0.9 Hz), 5.15 (s, 2H), 4.81 (s, 2H), 3.81 (s, 2H), 2.93 (t, 2H, J=5.4 Hz).

Example 290 was Obtained by Following Procedure of Example 289

Example 290

N-(2-aminophenyl)-5-[(4-methoxyphenyl)sulfonyl]-4,5,6,7-tetrahydro[1,3]thiazolo[5,4-c]pyridine-2-carboxamide sulfate 1H NMR (DMSO-d6) δ (ppm) 10.35 (s, 1H), 7.78 (d, 2H, J=12.0 Hz), 7.38 (d, 1H, J=7.8 Hz), 7.20-7.08 (m, 4H), 7.00 (t, 1H, J=7.5 Hz), 4.50 (s, 2H), 3.84 (s, 3H), 3.49 (t, 2H, J=5.7 Hz), 2.90 (t, 2H, J=5.1 Hz).

Example 291

$N^2$-(2-aminophenyl)-N5-pyridin-3-yl-1,4,6,7-tetrahydro-5H-pyrrolo[3,2-c]pyridine-2,5-dicarboxamide 1H NMR (DMSO-d6) d (ppm) 11.05 (s, 1H), 8.95 (s, 1H), 8.81 (s, 1H), 8.62 (d, 1H, J=2.1), 8.12 (d, 1H, J=3.6) 7.84 (d, 1H, J=8.7), 7.50 (d, 1H, J=2.7), 7.24 (m, 1H), 7.14 (d, 1H, J=6.9), 6.91 (m, 1H), 6.76 (d, 1H, J=7.2) 6.57 (m, 1H), 4.81 (s, 1H), 4.64 (s, 2H), 3.71 (t, 2H, J=5.4), 2.65 (t, 2H).

Procedure for Synthesis of Example 291

Step-I 5-(tert-butoxycarbonyl)-4,5,6,7-tetrahydro-1H-pyrrolo[3,2-c]pyridine-2-carboxylic acid To a solution of 5-tert-butyl 2-ethyl 1,4,6,7-tetrahydro-5H-pyrrolo[3,2-c]pyridine-2,5-dicarboxylate (1 eq.) obtained in step I of example 212 in ethanol was added NaOH (2.00 eq.) and refluxed for 6 hrs. Reaction mixture was concentrated under reduced pressure and neutralized to get desired compound 5-(tert-butoxycarbonyl)-4,5,6,7-tetrahydro-1H-pyrrolo[3,2-c]pyridine-2-carboxylic acid.

Step-II

N-(2-aminophenyl)-4,5,6,7-tetrahydro-1H-pyrrolo[3,2]pyridine-2-carboxamide

To a solution of compound 5-(tert-butoxycarbonyl)-4,5,6,7-tetrahydro-1H-pyrrolo[3,2-c]pyridine-2-carboxylic acid (1.0 eq) in DMF was added triethyl amine (2.2 eq), Bis (2-oxo-3-oxazolidinyl) phosphonic chloride (BOP, 1.2 eq.) and stirred for 1 hr. Monoboc phenylene diamine was added and reaction was stirred for 24 hrs. Reaction mixture was then quenched with water and extracted with ethyl acetate, dried over sodium sulphate and concentrated to dryness. Crude mass was then purified by silica gel column chromatography to afford tert-butyl 2-({2-[(tert-butoxycarbonyl)amino] phenyl}carbamoyl)-1,4,6,7-tetrahydro-5H-pyrrolo[3,2-c] pyridine-5-carboxylate, which was then reacted with hydrochloric acid saturated diethyl ether to get N-(2-aminophenyl)-4,5,6,7-tetrahydro-1H-pyrrolo[3,2]pyridine-2-carboxamide Step-III $N^2$-(2-aminophenyl)-N5-pyridin-3-yl-1,4,6,7-tetrahydro-5H-pyrrolo[3,2-c]pyridine-2,5-dicarboxamide To a solution of N-(2-aminophenyl)-4,5,6,7-tetrahydro-1H-pyrrolo[3,2]pyridine-2-carboxamide (1.0 eq) in DMF was added $Et_3N$ (3.0 eq.) followed by Pyridin-3-yl-carbamic acid phenyl ester (1.0 eq). Reaction was stirred at room temperature for overnight. Reaction mixture was then quenched with water and extracted with ethyl acetate, dried over sodium sulphate and concentrated to dryness. Crude mass was then purified by silica gel column chromatography to afford $N^2$-(2-aminophenyl)-N5-pyridin-3-yl-1,4,6,7-tetrahydro-5H-pyrrolo[3,2-c]pyridine-2,5-dicarboxamide.

Examples 292-298 were Prepared Following Reaction Scheme XVI

Example 292

$N^2$-(2-amino-5-fluorophenyl)-$N^6$-pyridin-3-yl-4,7-dihydrothieno[2,3-c]pyridine-2,6(5H)-dicarboxamide 1H NMR (DMSO-d6) d (ppm): 9.62 (s, 1H), 8.89 (s, 1H), 8.66 (d, 1H, J=2.4 Hz), 8.17 (d, 1H, J=4.5 Hz), 7.89 (d, 1H, J=9 Hz), 7.76 (s, 1H), 7.28 (m, 1H), 7.11 (dd, 1H, J=10.2 Hz, 3.0 Hz), 6.80 (m, 2H), 4.85 (s, 2H), 4.77 (s, 2H), 3.79 (t, 2H, J=5.4 Hz), 2.77 (t, 2H, J=5.4 Hz).

Example 293

$N^2$-(2-amino-5-fluorophenyl)-$N^6$-(pyridin-3-ylmethyl)-4,7-dihydrothieno[2,3-c]pyridine-2,6(5H)-dicarboxamide 1H NMR (DMSO-d6) d (ppm): 9.58 (s, 1H), 8.48 (bs, 1H), 8.43 (d, 1H, J=4.5 Hz), 7.72 (s, 1H), 7.67 (d, 1H, J=7.8 Hz), 7.35 (m, 2H), 7.10 (dd, 1H, J=10.2 Hz, 2.7 Hz), 6.84 (m, 2H), 4.85 (s, 2H), 4.63 (s, 2H), 4.28 (d, 2H, J=5.7 Hz), 3.65 (t, 2H, J=5.4 Hz), 2.72 (t, 2H, J=5.7 Hz).

Example 294

$N^2$-(2-amino-5-fluorophenyl)-$N^6$-pyridin-4-yl-4,7-dihydrothieno[2,3-c]pyridine-2,6(5H)-dicarboxamide 1H NMR (DMSO-d6) d (ppm): 9.61 (s, 1H), 9.13 (s, 1H), 8.32 (bs, 2H), 7.76 (s, 1H), 7.50 (d, 2H, J=5.4 Hz), 7.11 (dd, 1H, J=9.9 Hz, 2.4 Hz), 6.83 (m, 2H), 4.84 (bs, 2H), 4.77 (s, 2H), 3.79 (t, 2H, J=5.4 Hz), 2.76 (t, 2H, J=5.4 Hz).

Example 295

$N^2$-(2-amino-5-fluorophenyl)-$N^6$-quinolin-3-yl-4,7-dihydrothieno[2,3-c]pyridine-2,6(5H)-dicarboxamide 1H NMR (DMSO-d6) d (ppm): 9.63 (s, 1H), 9.18 (s, 1H), 8.98 (d, 1H, J=3.4 Hz), 8.45 (d, 1H, J=2.1 Hz), 7.90 (m, 2H), 7.78 (s, 1H), 7.58 (m, 2H), 7.12 (dd, 1H, J=10.2 Hz, 4.5 Hz), 6.79 (m, 2H), 4.95 (bs, 2H), 4.84 (s, 2H), 3.85 (t, 2H, J=5.4 Hz), 2.80 (t, 2H, J=5.4 Hz).

Example 296

$N^2$-(2-aminophenyl)-$N^6$-(pyridin-3-ylmethyl)-4,7-dihydrothieno[2,3-c]pyridine-2,6(5H)-dicarboxamide 1H NMR (DMSO-d6) d (ppm): 9.60 (s, 1H), 8.48 (s, 1H), 8.43 (d, 1H, J=3.9 Hz), 7.71 (s, 1H), 7.67 (d, 1H, J=7.5 Hz), 7.33 (m, 2H), 7.12 (d, 1H, J=7.5 Hz), 6.96 (t, 1H, J=7.8 & 6.9 Hz), 6.78 (d, 1H, J=7.8 Hz), 6.58 (t, 1H, J=7.5 Hz), 4.90 (s, 2H), 4.60 (s, 2H), 4.29 (d, 2H, J=5.4 Hz), 3.65 (bs, 2H), 2.67 (bs, 2H).

Example 297

$N^2$-(2-aminophenyl)-$N^6$-pyridin-4-yl-4,7-dihydrothieno[2,3-c]pyridine-2,6(5H)-dicarboxamide 1H NMR (DMSO-d6) d (ppm): 9.62 (s, 1H), 9.14 (s, 1H), 8.34 (d, 2H, J=6 Hz), 7.74 (s, 1H), 7.52 (d, 2H, J=6.3 Hz), 7.13 (d, 1H, J=7.8 Hz), 6.97 (t, 1H, J=8.1 Hz & 8.4 Hz), 6.78 (d, 1H, J=7.8 Hz), 6.59 (t, 1H, J=7.8 Hz & 8.4 Hz), 5.02 (bs, 2H), 4.76 (s, 2H), 3.79 (t, 2H, J=5.4 Hz & 5.7 Hz), 2.76 (bs, 2H).

Example 298

$N^2$-(2-aminophenyl)-$N^6$-quinolin-3-yl-4,7-dihydrothieno[2,3-c]pyridine-2,6(5H)-dicarboxamide 1H NMR (DMSO-d6) d (ppm): −9.63 (s, 1H), 9.17 (s, 1H), 8.98 (d, 1H, J=2.4 Hz), 8.44 (d, 1H, J=2.1 Hz), 7.94 (d, 1H, J=8.1 Hz), 7.88 (d, 1H, J=7.5 Hz), 7.76 (s, 1H), 7.62-7.51 (m, 2H), 7.14 (d, 1H, J=7.5 Hz), 6.97 (t, 1H, J=8.1 Hz & 7.2 Hz), 6.78 (d, 1H, J=7.4 Hz), 6.59 (t, 1H, J=7.5 Hz), 4.91 (s, 2H), 4.82 (s, 2H), 3.84 (t, 2H, J=5.4 Hz), 2.80 (bs, 2H)

Commercial Utility

The compounds according to this invention have valuable pharmacological properties by inhibiting histone deacetylase activity and function, which make them commercially utilizable.

Histone deacetylase (HDAC) means an enzyme with an activity towards the ϵ-acetyl group of lysine residues within a substrate protein. HDAC substrates are histone H2A, H2B, H3 or H4 proteins and isoforms but substrate proteins different to histones like, but not limited to, heat shock protein 90 (Hsp90), α-tubulin, STAT1 or STAT3 and the tumor suppressor protein p53 exist. In particular histone deacetylases catalyse the hydrolysis the ϵ-acetyl group of lysine residues within these substrate proteins, forming the free amino group of lysine.

Inhibition of histone deacetylase by compounds according to this invention means inhibiting the activity and function of one or more HDAC isoenzymes, in particular isoenzymes selected from the so far known histone deacetylases, namely HDAC 1, 2, 3 and 8 (class I) and HDAC 4, 5, 6, 7, 10 (class II), HDAC 11 (class IV) as well as the NAD+ dependent class III (Sir2 homologues). In some preferred embodiment this inhibition is at least about 50%, more preferable at least 75% and still more preferable above 90%. Preferably, this inhibition is specific to a specific histone deacetylase class (e.g. HDAC class I enzymes), a selection of isoenzymes of highest pathophysiological relevance (e.g. HDAC 1, 2, 3 enzymes) or a single isoenzyme (e.g. the HDAC 1, HDAC 2 or HDAC 3 enzyme). The term histone deacetylase inhibitor is used to identify a compound capable of interacting with a histone deacetylase and inhibiting its activity, in particular its enzymatic activity and biological function. In this context "head group" defines the residues within a histone deacetylase inhibitor responsible for interacting with the active site of the enzyme, e.g. the $Zn^{2+}$ ion.

The inhibition of histone deacetylases is determined in biochemical assays of various formats and sources of enzymatic activity. HDAC activity is used either derived from nuclear or cellular extracts or by heterologous expression of defined HDAC isoenzymes in E. coli, insect cells or mammalian cells. Since HDAC isoenzymes are active in multiprotein complexes and form homo- and heterodimeres, nuclear extracts derived from human cancer cells, for example the human cervical carcinoma cell line HeLa, are preferred. These nuclear extracts contain class I and class II enzymes, but are enriched in class I enzymes. For expression of recombinant HDAC isoenzymes, mammalian expression systems like HEK293 cells are preferred. Nevertheless, heterologous expression of HDAC isoenzymes in insect cells alone or coexpressed with relevant human co-factors is a suitable alternative approach. The HDAC isoenzyme is expressed as a fusion protein with an affinity tag, like the FLAG epitope. By affinity chromatography, the tagged protein is purified alone or in complex with endogenous/co-expressed proteins (e.g. other HDAC isoenzymes and coactivators/platform proteins).

The biochemical assays are well described and well known to persons skilled in the art. As substrates, histone proteins, peptides derived from histone proteins or other HDAC substrates as well as acetylated lysine mimetics are used. Preferred promiscuous HDAC substrates are, for example the tripeptide Ac-NH-GGK(Ac) or the lysine mimetic Boc-K (Ac), also known as Flour-de-Lys and commercially available by Biomol, coupled with the fluorophore 7-amino-4-methylcoumarin (AMC).

The invention further relates to the use of the compounds according to this invention for inhibiting histone deacetylase activity in cells and tissues, causing hyperacetylation of substrate proteins and as a functional consequence for example the induction or repression of gene expression, the disassembly or inactivation of protein complexes, the induction of protein degration, a cell cycle arrest, the induction of differentiation and/or the induction of apoptosis.

Cellular activity of a histone deacetylase inhibitor means any cellular effect related to histone deacetylase inhibition, like inhibition of histone deacetylase activity as measured by using a cellular permeable HDAC substrate, protein hyperacetylation, transcriptional repression and activation, induction of apoptosis, differentiation and/or cytotoxicity.

The term "induction of apoptosis" and analogous terms are used to identify a compound which executes programmed cell death in cells contacted with that compound. Apoptosis is defined by complex biochemical events within the contacted cell, such as the activation of cysteine specific proteinases ("caspases") and the fragmentation of chromatin. Induction of apoptosis in cells contacted with the compound might not necessarily couple with inhibition of cell proliferation or cell differentiation. Preferably, the inhibition of proliferation, induction of differentiation and/or induction of apoptosis is specific to cells with aberrant cell growth.

"Cytotoxicity" in general means arresting proliferation and/or inducing apoptotic cell death in vitro in mammalian cells, in particular human cancer cells.

"Induction of differentiation" is defined as a process of cellular reprogramming leading to a reversible or irreversible cell cycle arrest in G0 and re-expression of a subset of genes typical for a certain specialized normal cell type or tissue (e.g. re-expression of milk fat proteins and fat in mammary carcinoma cells).

"Cell cycle independent mode of action" means no or only weak discrimination between proliferating (cycling) and non-proliferating (arrested) cells regarding cytotoxicity/apoptosis induction. As a consequence of a cell cycle independent mode of action, histone deacetylase inhibitors kill proliferating and dormant neoplastic cells.

Assays for quantification of cell proliferation, of percentage of cells in respective cell cycle stages, apoptosis or differentiation are well known to experts and state of the art. For example, metabolic activity, which is linked to cellular proliferation is quantified using the Alamar Blue/Resazurin assay (O'Brian et al. Eur J Biochem 267, 5421-5426, 2000) and induction of apoptosis is quantified by measurement of chromatin fragmentation with the cell death detection ELISA commercialized by Roche Diagnostics. Distribution of cells in respective stages of the cell cycle (G1, G2, G2/M, sub G1) is quantified by flow cytometry after DNA staining with eg propidiumiodide.

Examples for cellular assays for the determination of hyperacetylation of HDAC substrates are given by measuring core histone acetylation using specific antibodies by Western blotting, reporter gene assays using respective responsive promoters or promoter elements (e.g. the p21 promoter or the sp1 site as responsive element) or finally by image analysis again using acetylation specific antibodies for core histone proteins. Cellular enzymatic HDAC activity can be quantified by using the cell permeable HDAC substrate Boc-K(Ac)-AMC/Flour-deLys).

Compounds according to this invention can be commercially applicable due to their HDAC inhibitory, anti-proliferative, differentiation inducing and/or apoptosis inducing activity, which may be beneficial in the therapy of diseases responsive thereto, such as e.g. any of those diseases mentioned herein.

The invention further relates to a method for inhibiting, treating, ameliorating or preventing cellular neoplasia by administration of an effective amount of a compound according to this invention to a mammal, in particular a human in need of such treatment. A "neoplasia" is defined by cells displaying aberrant cell proliferation and/or survival and/or a block in differentiation. The term neoplasia includes "benign neoplasia" which is described by hyperproliferation of cells, incapable of forming an aggressive, metastasizing tumor in-vivo, and, in contrast, "malignant neoplasia" which is described by cells with multiple cellular and biochemical abnormalities, capable of forming a systemic disease, for example forming tumor metastasis in distant organs.

The compounds according to the present invention are preferably used for the treatment of malignant neoplasia, also described as cancer, characterized by tumor cells finally metastasizing into distinct organs or tissues. Examples of malignant neoplasia treated with the compounds of the present invention include solid and hematological tumors. Solid tumors are exemplified by tumors of the breast, bladder, bone, brain, central and peripheral nervous system, colon, endocrine glands (e.g. thyroid and adrenal cortex), esophagus, endometrium, germ cells, head and neck, kidney, liver, lung, larynx and hypopharynx, mesothelioma, ovary, pancreas, prostate, rectum, renal, small intestine, soft tissue, testis, stomach, skin (e.g. actinic keratosis and squamous cell carcinoma), ureter, vagina and vulva. Malignant neoplasia includes inherited cancers exemplified by Retinoblastoma and Wilms tumor. In addition, malignant neoplasia includes primary tumors in said organs and corresponding secondary tumors in distant organs ("tumor metastases"). Hematological tumors are exemplified by aggressive and indolent forms of leukemia and lymphoma, namely non-Hodgkins disease, chronic and acute myeloid leukemia (CML/AML), acute lymphoblastic leukemia (ALL), Hodgkin's disease, multiple myeloma and T-cell lymphoma. Also included are myelodysplastic syndrome, plasma cell neoplasia, paraneoplastic syndromes, and cancers of unknown primary site as well as AIDS related malignancies.

It is to be noted that a cancer disease as well as a malignant neoplasia does not necessarily require the formation of metastases in distant organs. Certain tumors exert devastating effects on the primary organ itself through their aggressive growth properties. These can lead to the destruction of the tissue and organ structure finally resulting in failure of the assigned organ function.

Neoplastic cell proliferation might also affect normal cell behavior and organ function. For example the formation of new blood vessels, a process described as neovascularization, is induced by tumors or tumor metastases. Compounds according to the invention can be commercially applicable for treatment of pathophysiological relevant processes caused by benign or neoplastic cell proliferation, such as but not limited to neovascularization by unphysiological proliferation of vascular endothelial cells.

Drug resistance is of particular importance for the frequent failure of standard cancer therapeutics. This drug resistance is caused by various cellular and molecular mechanisms like overexpression of drug efflux pumps, mutation within the cellular target protein or fusion proteins formed by chromosomal translocations. The commercial applicability of compounds according to the present invention is not limited to $1^{st}$ line treatment of patients. Patients with resistance to cancer chemotherapeutics or target specific anti-cancer drugs can be also amenable for treatment with these compounds for e.g. $2^{nd}$ or $3^{rd}$ line treatment cycles. Examples are given by acute myeloid leukemia (AML) patients with the PML-RARα fusion protein, resistant to standard therapy with retinoids or patients with advanced breast cancer resistant towards the death receptor ligand TRAIL. These patients can be resensitized towards retinoids or recombinant TRAIL by treatment with HDAC inhibitory drugs like the compounds according to the present invention.

Non-Malignant Diseases and Hyperproliferative Diseases

The invention further provides a method for treating a mammal, in particular a human, bearing a hyperproliferative disease different to cellular neoplasia, sensitive to histone deacetylase inhibitor therapy comprising administering to said mammal a pharmacologically active and therapeutically effective and tolerable amount of a compound according to this invention. These non-malignant diseases include (i) arthropathies and osteopathological conditions or diseases such as rheumatoid arthritis, osteoarthritis, gout, polyarthritis, and psoriatic arthritis, (ii) autoimmune diseases like systemic lupus erythematosus and transplant rejection, (iii) hyperproliferative diseases such as smooth muscle cell proliferation including vascular proliferative disorders, atherosclerosis, restenosis (iv) fibro-proliferative diseases such as lung fibrosis, systemic sclerosis and scleroderma, retroperitoneal fibrosis, nephrogenic systemic fibrosis, renal fibrosis, hepatic fibrosis, cardiac fibrosis, chronic kidney disease and polycystic kidney disease (v) acute and chronic inflammatory conditions or diseases and dermal conditions such as psoriasis, ulcerative colitis, Crohn's disease, chronic pancreatitis, hepatitis, liver cirrhosis, allergic rhinitis, allergic dermatitis, cystic fibrosis, chronic obstructive bronchitis, chronic obstructive pulmonary disease (COPD) and asthma (vi) endometriosis, uterine fibroids, endometrial hyperplasia, fatty liver disease, non-alcoholic steato-hepatitis and benign prostate hyperplasia (vii) cardiac dysfunction such as diastolic heart failure (viii) inhibiting immunosuppressive conditions like HIV infections (ix) neuropathological disorders like Multiple Sclerosis, Parkinsons disease, Alzheimers disease, Huntingtons disease or polyglutamine related disorders (x) pathological conditions amenable to treatment by potentiating of endogenous gene expression as well as enhancing transgene expression in gene therapy.

(xi) muscle dystrophy with Duchenne's muscular dystrophy as one example (xii) various forms of diabetes, including insulin resistant type 2 diabetes (xiii) interstitial lung diseases like idiopathic pulmonary fibrosis, asbestosis, Bleomycin- or Busulfan-induced lung fibrosis Therefore, the invention further relates to a method for treating, preventing or ameliorating diseases different to malignant neoplasia comprising arthropathies and osteopathological conditions, autoimmune diseases including transplant rejection, acute and chronic inflammatory diseases, hyperproliferative diseases or neuropathological disorders, in a patient comprising administering to said patient a therapeutically effective and tolerable amount of a compound according to the present invention.

Compounds according to the present invention may be commercially applicable for treatment, prevention or amelioration of the diseases of benign and malignant behavior as described herein, such as, for example, (hyper) proliferative diseases and/or disorders responsive to induction of apoptosis and/or disorders responsive to cell differentiation, e.g. benign or malignant neoplasia, particularly cancer, such as e.g. any of those cancer diseases described above.

In the context of their properties, functions and usabilities mentioned herein, the compounds according to the present invention are expected to be distinguished by valuable and desirable effects related therewith, such as, e.g., by high efficacy, high selectivity, low toxicity, superior bioavailability in general (such as e.g. good enteral absorption), superior therapeutic window, absence of significant side effects, and/or further beneficial effects related with their therapeutic and pharmaceutical suitability.

Crystalline compounds according to this invention, e.g. crystalline salts according to this invention, are expected to have desirable physicochemical properties and such properties may beneficially influence the stability, as well as the chemical and pharmaceutical processing, formulating and mechanical handling on a commercial scale. Thus, these crystalline compounds may be particularly suited for the manufacture of commercially viable and pharmaceutically acceptable drug compositions or dosage forms.

The present invention provides compounds according to this invention in crystalline form.

Also, the present invention provides compounds according to this invention isolated in purified or substantially pure form, such as e.g. greater than about 50%, more precisely about 60%, more precisely about 70%, more precisely about 80%, more precisely about 90%, more precisely about 95%, more precisely about 97%, more precisely about 99% wt purity as determined by art-known methods.

Also, the present invention provides compounds according to this invention in a pharmaceutically acceptable form.

Also, the present invention provides compounds according to this invention in solid or liquid pharmaceutically acceptable dosage forms, particularly solid oral dosage forms, such as tablets and capsules, as well as suppositories and other pharmaceutical dosage forms.

The present invention further includes a method for the treatment of mammals, including humans, which are suffering from one of the abovementioned conditions, illnesses, disorders or diseases. The method is characterized in that a pharmacologically active and therapeutically effective and tolerable amount of one or more of the compounds according to this invention, which function by inhibiting histone deacetylases and—in general—by modulating protein acetylation, induce various cellular effects, in particular induction or repression of gene expression, arresting cell proliferation, inducing cell differentiation and/or inducing apoptosis, is administered to the subject in need of such treatment.

The invention further includes a method for treating diseases and/or disorders responsive or sensitive to the inhibition of histone deacetylases, particularly those diseases mentioned above, such as e.g. cellular neoplasia or diseases different to cellular neoplasia as indicated above, in mammals, including humans, suffering therefrom comprising administering to said mammals in need thereof a pharmacologically active and therapeutically effective and tolerable amount of one or more of the compounds according to the present invention.

The present invention further includes a therapeutic method useful to modulate protein acetylation, gene expression, cell proliferation, cell differentiation and/or apoptosis in vivo in diseases mentioned above, in particular cancer, comprising administering to a subject in need of such therapy a pharmacologically active and therapeutically effective and tolerable amount of one or more of the compounds according to this invention, which function by inhibiting histone deacetylases.

The present invention further provides a method for regulating endogenous or heterologous promoter activity by contacting a cell with a compound according to this invention.

The invention further includes a method for treating diseases, particularly those diseases mentioned above, in mammals, including humans, suffering therefrom comprising administering to said mammals in need thereof a therapeutically effective and tolerable amount of one or more of the compounds according to the present invention, optionally, simultaneously, sequentially or separately with one or more further therapeutic agents, such as e.g. those mentioned below.

The invention further relates to the use of the compounds according to the present invention for the manufacture of a pharmaceutical composition for treating, preventing, inhibiting, ameliorating diseases, disorders, illnesses and/or conditions as mentioned herein.

The invention further relates to the use of the compounds according to the present invention for the manufacture of a pharmaceutical composition for treating, preventing, inhibiting, ameliorating diseases and/or disorders responsive or sensitive to the inhibition of histone deacetylases, particularly those diseases mentioned above, such as e.g. cellular neoplasia or diseases different to cellular neoplasia as indicated above.

The invention further relates to the use of the compounds according to the present invention for the manufacture of a pharmaceutical composition having histone deacetylase inhibitory activity.

The invention further relates to the use of the compounds according to the present invention for the manufacture of a pharmaceutical composition for treating, preventing, inhibiting, ameliorating cellular neoplasia, such as e.g. benign or malignant neoplasia comprising cancer.

The invention further relates to the use of the compounds according to the present invention for the manufacture of a pharmaceutical composition which can be used for treating, preventing or ameliorating of diseases responsive to arresting aberrant cell growth, such as e.g. (hyper) proliferative diseases of benign or malignant behavior, such as e.g. any of those diseases mentioned herein, particularly cancer, such as e.g. any of those cancer diseases described herein above.

The invention further relates to the use of the compounds according to the present invention for the manufacture of a pharmaceutical composition which can be used for treating, preventing or ameliorating of disorders responsive to induction of apoptosis, such as e.g. any of those diseases mentioned herein, particularly cancer, such as e.g. any of those cancer diseases described herein above.

The invention further relates to the use of the compounds according to the present invention for the manufacture of a pharmaceutical composition which can be used for treating, preventing or ameliorating of disorders responsive to induction of differentiation, such as e.g. any of those diseases mentioned herein, particularly cancer, such as e.g. any of those cancer diseases described herein above.

The invention further relates to the use of the compounds according to the present invention for the manufacture of a pharmaceutical composition which can be used for treating, preventing or ameliorating of benign or malignant neoplasia, particularly cancer, such as e.g. any of those cancer diseases described herein above.

The invention further relates to the use of the compounds according to the present invention for the manufacture of a pharmaceutical composition for treating, preventing, inhibiting, ameliorating diseases different to a cellular neoplasia and sensitive to histone deacetylase inhibitor therapy, such as the non-malignant diseases mentioned before.

The invention further relates to the use of the compounds according to the present invention for the manufacture of a pharmaceutical composition for inhibiting histone deacetylase activity in the treatment of diseases responsive to said inhibition or to the functional consequences thereof.

The invention further relates to a method for treating, preventing or ameliorating the diseases, disorders, illnesses and/or conditions mentioned herein in a mammal, in particular a human patient, comprising administering a pharmacologically active and therapeutically effective and tolerable amount of one or more compounds according to the present invention to said mammal in need thereof.

The invention further relates to the compounds according to this invention for use in the treatment and/or prophylaxis of diseases, especially the diseases mentioned herein.

The present invention further relates to the compounds according to this invention, or a pharmaceutical composition according to this invention for the treatment, prevention or amelioration of diseases responsive or sensitive to inhibition of histone deacetylase activity.

The present invention further relates to the compounds according to this invention, or a pharmaceutical composition according to this invention for the treatment, prevention or amelioration of benign and/or malignant neoplasia comprising cancer.

The present invention further relates to the compounds according to this invention, or a pharmaceutical composition according to this invention for the treatment, prevention or amelioration of diseases different to malignant neoplasia comprising arthropathies and osteopathological conditions, autoimmune diseases including transplant rejection, acute and chronic inflammatory diseases, hyperproliferative diseases or neuropathological disorders.

The invention further relates to pharmaceutical compositions comprising one or more of the compounds according to this invention and a pharmaceutically acceptable carrier or diluent.

The present invention further relates to pharmaceutical compositions comprising one or more of the compounds according to this invention and pharmaceutically acceptable auxiliaries and/or excipients.

The invention further relates to a pharmaceutical composition comprising one or more of the compounds according to this invention and a pharmaceutically acceptable diluent, excipient and/or carrier, e.g. for treating, preventing or ameliorating (hyper) proliferative diseases of benign or malignant behaviour and/or disorders responsive to induction of apoptosis, such as, for example, benign or malignant neoplasia, e.g. cancer, such as e.g. any of those cancer diseases described herein above.

The invention further relates to pharmaceutical compositions according to this invention having histone deacetylases inhibitory activity.

The invention further relates to pharmaceutical compositions according to this invention having apoptosis inducing activity.

The invention further relates to pharmaceutical compositions according to this invention having anti-proliferative activity.

The invention further relates to pharmaceutical compositions according to this invention having cell differentiation inducing activity.

The invention further relates to the use of a pharmaceutical composition comprising one or more of the compounds according to this invention and a pharmaceutically acceptable carrier or diluent in the manufacture of a pharmaceutical product, such as e.g. a commercial package, for use in the treatment and/or prophylaxis of the diseases as mentioned.

Additionally, the invention relates to an article of manufacture, which comprises packaging material and a pharmaceutical agent contained within said packaging material, wherein the pharmaceutical agent is therapeutically effective for inhibiting the effects of histone deacetylases, ameliorating the symptoms of an histone deacetylase mediated disorder, and wherein the packaging material comprises a label or package insert which indicates that the pharmaceutical agent is useful for preventing or treating histone deacetylase mediated disorders, and wherein said pharmaceutical agent comprises one or more compounds according to the invention. The packaging material, label and package insert otherwise parallel or resemble what is generally regarded as standard packaging material, labels and package inserts for pharmaceuticals having related utilities.

The pharmaceutical compositions according to this invention are prepared by processes, which are known per se and familiar to the person skilled in the art. As pharmaceutical compositions, the compounds of the invention (=active compounds) are either employed as such, or preferably in combination with suitable pharmaceutical auxiliaries and/or excipients, e.g. in the form of tablets, coated tablets, capsules, caplets, suppositories, powders, patches (e.g. as ITS), emulsions, suspensions, gels or solutions, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries, vehicles, excipients, diluents, carriers or adjuvants which are suitable for the desired pharmaceutical formulations, preparations or compositions on account of his/her expert knowledge. In addition to solvents, gel formers, ointment bases and other active compound excipients, for example antioxidants, dispersants, emulsifiers, preservatives, solubilizers, colorants, complexing agents or permeation promoters, can be used.

Depending upon the particular disease, to be treated or prevented, additional therapeutic active agents, which are normally administered to treat or prevent that disease, may optionally be coadministered with the compounds according to the present invention. As used herein, additional therapeutic agents that are normally administered to treat or prevent a particular disease are known as appropriate for the disease being treated.

For example, the compounds according to this invention may be combined with standard therapeutic agents or radiation used for treatment of the diseases as mentioned before.

In one particular embodiment the compounds according to this invention may be combined with one or more art-known anti-cancer agents, such as e.g. with one or more art-known chemotherapeutic and/or target specific anti-cancer agents, e.g. with one or more of those described below, and/or radiation.

Examples of known chemotherapeutic anti-cancer agents frequently used in combination therapy include, but not are limited to (i) alkylating/carbamoylating agents such as Cyclophosphamid (Endoxan®), Ifosfamid (Holoxan®), Temozolomide (Temodar®), Thiotepa (Thiotepa Lederle®), Melphalan (Alkeran®), or chloroethylnitrosourea (BCNU); (ii) platinum derivatives like cis-platin (Platinex® BMS), oxaliplatin (Eloxatin®), carboplatin (Cabroplat®BMS); (iii) antimitotic agents/tubulin inhibitors such as vinca alkaloids (vincristine, vinblastine, vinorelbine), taxanes such as Paclitaxel (Taxol®), Docetaxel (Taxotere®) and analogs as well as new formulations and conjugates thereof like the nanoparticle formulation Abraxane™ with paclitaxel bound to albumin, epothilones such as Epothilone B (Patupilone®), Aza-epothilone (Ixabepilone®) or ZK-EPO, a fully synthetic epothilone B analog; (iv) topoisomerase inhibitors such as anthracyclines (exemplified by Doxorubicin/Adriblastin®), epipodophyllotoxins (exemplified by Etoposide/Etopophos®) and camptothecin and camp-tothecin analogs (exemplified by Irinotecan/Camptosar® or Topotecan/Hycamtin®); (v) pyrimidine antagonists such as 5-fluorouracil (5-FU), Capecitabine (Xeloda®), Arabinosylcytosine/Cytarabin (Alexan®) or Gemcitabine (Gemzar®); (vi) purin antagonists such as 6-mercaptopurine (Puri-Nethol®), 6-thioguanine or fludarabine (Fludara®) and finally (vii) folic acid antagonists such as methotrexate (Farmitrexat®) or premetrexed (Alimta®).

Examples of target specific anti-cancer drug classes used in experimental or standard cancer therapy include but are not limited to (i) kinase inhibitors such as e.g. Imatinib (Glivec®), ZD-1839/Gefitinib (Iressa®), Bay43-9006 (Sorafenib, Nexavar®), SU11248/Sunitinib (Sutent®) or OSI-774/Erlotinib (Tarceva®), Dasatinib (Sprycel®), Lapatinib (Tykerb®), or, see also below, Vatalanib, Vandetanib (Zactima®) or Pazopanib; (ii) proteasome inhibitors such as PS-341/Bortezumib (Velcade®); (iii) heat shock protein 90 inhibitors like 17-allylaminogeldanamycin (17-AAG) or 17-dimethylaminogeldanamycin (17-DMAG); (iv) vascular targeting agents (VTAs) like combretastatin A4 phosphate or AVE8062/AC7700 and anti-angiogenic drugs like the VEGF antibodies, such as Bevacizumab (Avastin®), or KDR tyrosine kinase inhibitors such as Vandetanib (Zactima®) or Pazopanib; (v) monoclonal antibodies such as Trastuzumab (Herceptin®) or Rituximab (MabThera/Rituxan®) or Alemtuzumab (Campath®) or Tositumomab (Bexxar®) or C225/Cetuximab (Erbitux®) or Avastin (see above) or Panitumumab (Vectibix®) as well as mutants and conjugates of monoclonal antibodies, e.g. Gemtuzumab ozogamicin (Mylotarg®) or Ibritumomab tiuxetan (Zevalin®), and antibody fragments; (vi) oligonucleotide based therapeutics like G-3139/Oblimersen (Genasense®) or the DNMT1 inhibitor MG98; (vii) Toll-like receptor/TLR 9 agonists like Promune®, TLR 7 agonists like Imiquimod (Aldara®) or Isatoribine and analogues thereof, or TLR 7/8 agonists like Resiquimod as well as immunostimulatory RNA as TLR 7/8 agonists; (viii) protease inhibitors (ix) hormonal therapeutics such as anti-estrogens (e.g. Tamoxifen or Raloxifen), anti-androgens (e.g. Flutamide or Casodex), LHRH analogs (e.g. Leuprolide, Goserelin or Triptorelin) and aromatase inhibitors like Anastozol/Arimidex® or Letrozole/Femara®.

Other known target specific anti-cancer agents which can be used for combination therapy include bleomycin, retinoids such as all-trans retinoic acid (ATRA), DNA methyltransferase inhibitors such as 5-Aza-2'-deoxycytidine (Decitabine, (Dacogen®) and 5-Azacytidine (Vidaza®), alanosine, cytokines such as interleukin-2, interferons such as interferon α2 or interferon-γ, death receptor agonists, such as TRAIL, DR4/5 agonistic antibodies, FasL and TNF-R agonists (e.g. TRAIL receptor agonists like mapatumumab or lexatumumab), and finally histone deacetylase inhibitors different to the compounds according to this invention such as SAHA (Zolinza®), PXD101, MS275, MGCD0103, Depsipeptide/FK228, NVP-LBH589, CRA/PCI-24781, ITF2357, SB939, Valproic acid (VPA) and butyrates.

As exemplary anti-cancer agents for use in combination with the compounds according to this invention in the therapies mentioned herein any of the following drugs may be mentioned, without being restricted thereto, 5 FU, actinomycin D, ABARELIX, ABCIXIMAB, ACLARUBICIN, ADAPALENE, ALEMTUZUMAB, ALTRETAMINE, AMINOGLUTETHIMIDE, AMIPRILOSE, AMRUBICIN, ANASTROZOLE, ANCITABINE, ARTEMISININ, AZATHIOPRINE, BASILDOMAB, BENDAMUSTINE, BEVACIZUMAB, BEXXAR, BICALUTAMIDE, BLEOMYCIN, BORTEZOMIB, BROXURIDINE, BUSULFAN, CAMPATH, CAPECITABINE, CARBOPLATIN, CARBOQUONE, CARMUSTINE, CETRORELIX, CHLORAMBUCIL, CHLORMETHINE, CISPLATIN, CLADRIBINE, CLOMIFENE, CYCLOPHOSPHAMIDE, DACARBAZINE, DACLIZUMAB, DACTINOMYCIN, DASATINIB, DAUNORUBICIN, DECITABINE, DESLORELIN, DEXRAZOXANE, DOCETAXEL, DOXIFLURIDINE, DOXORUBICIN, DROLOXIFENE, DROSTANOLONE, EDELFOSINE, EFLORNITHINE, EMITEFUR, EPIRUBICIN, EPITIOSTANOL, EPTAPLATIN, ERBITUX, ERLOTINIB, ESTRAMUSTINE, ETOPOSIDE, EXEMESTANE, FADROZOLE, FINASTERIDE, FLOXURIDINE, FLUCYTOSINE, FLUDARABINE, FLUOROURACIL, FLUTAMIDE, FORMESTANE, FOSCARNET, FOSFESTROL, FOTEMUSTINE, FULVESTRANT, GEFITINIB, GENASENSE, GEMCITABINE, GLIVEC, GOSERELIN, GUSPERIMUS, HERCEPTIN, IDARUBICIN, IDOXURIDINE, IFOSFAMIDE, IMATINIB, IMPROSULFAN, INFLIXIMAB, IRINOTECAN, IXABEPILONE, LANREOTIDE, LAPATINIB, LETROZOLE, LEUPRORELIN, LOBAPL- ATIN, LOMUSTINE, LUPROLIDE, MELPHALAN, MERCAPTOPURINE, METHOTREXATE, METUREDEPA, MIBOPLATIN, MIFEPRISTONE, MILTEFOSINE, MIRIMOSTIM, MITOGUAZONE, MITOLACTOL, MITOMYCIN, MITOXANTRONE, MIZOMINE, MOTEXAFIN, MYLOTARG, NARTOGRASTIM, NEBAZUMAB, NEDAPLATIN, NILUTAMIDE, NIMUSTINE, OCTREOTIDE, ORMELOXIFENE, OXALIPLATIN, PACLITAXEL, PALIVIZUMAB, PANITUMUMAB, PATUPILONE, PAZOPANIB, PEGASPARGASE, PEGFILGRASTIM, PEMETREXED, PENTETREOTIDE, PENTOSTATIN, PERFOSFAMIDE, PIPOSULFAN, PIRARUBICIN, PLICAMYCIN, PREDNIMUSTINE, PROCARBAZINE, PROPAGERMANIUM, PROSPIDIUM CHLORIDE, RALOXIFEN, RALTITREXED, RANIMUSTINE, RANPIRNASE, RASBURICASE, RAZOXANE, RITUXIMAB, RIFAMPICIN, RITROSULFAN, ROMURTIDE, RUBOXISTAURN, SARGRAMOSTIM, SATRAPLATIN, SIROLIMUS, SOBUZOXANE, SORAFENIB, SPIROMUSTINE, STREPTOZOCIN, SUNITINIB, TAMOXIFEN, TASONERMIN, TEGAFUR, TEMOPORFIN, TEMOZOLOMIDE, TENIPOSIDE, TESTOLACTONE, THIOTEPA, THYMALFASIN, TIAMIPRINE, TOPOTECAN, TOREMIFENE, TRAIL, TRASTUZUMAB, TREOSULFAN, TRIAZIQUONE, TRIMETREXATE, TRIPTORELIN, TROFOSFAMIDE, UREDEPA, VALRUBICIN, VATALANIB, VANDETANIB, VERTEPORFIN, VINBLASTINE, VINCRISTINE, VINDESINE, VINORELBINE, VOROZOLE and ZEVALIN.

The anti-cancer agents mentioned herein above as combination partners of the compounds according to this invention are meant to include pharmaceutically acceptable derivatives thereof, such as e.g. their pharmaceutically acceptable salts.

The person skilled in the art is aware on the base of his/her expert knowledge of the kind, total daily dosage(s) and administration form(s) of the additional therapeutic agent(s) coadministered. Said total daily dosage(s) can vary within a wide range.

In practicing the present invention and depending on the details, characteristics or purposes of their uses mentioned above, the compounds according to the present invention may be administered in combination therapy separately, sequentially, simultaneously, concurrently or chronologically staggered (e.g. as combined unit dosage forms, as separate unit dosage forms or a adjacent discrete unit dosage forms, as fixed or non-fixed combinations, as kit-of-parts or as admixtures) with one or more standard therapeutics, in particular art-known chemotherapeutic and/or target specific anti-cancer agents, such as e.g. any of those mentioned above.

Thus, a further aspect of the present invention is a combination or pharmaceutical composition comprising a first active ingredient, which is a compound according to this invention, a second active ingredient, which is an art-known standard therapeutic, in particular art-known chemotherapeutic or target specific anti-cancer agent, such as one of those mentioned above, and optionally a pharmacologically acceptable carrier, diluent and/or excipient for sequential, separate, simultaneous or chronologically staggered use in therapy in any order, e.g. to treat, prevent or ameliorate in a patient diseases responsive to HDAC inhibitor treatment, such as the diseases, disorders or illnesses mentioned, in particular cancer.

In this context, the present invention further relates to a combination comprising a first active ingredient, which is at least one compound according to this invention, and a second active ingredient, which is at least one art-known standard therapeutic, for example an art-known anti-cancer agent, such as e.g. one or more of those mentioned herein above, for separate, sequential, simultaneous, concurrent or chronologically staggered use in therapy, such as e.g. in therapy of any of those diseases mentioned herein.

The term "combination" according to this invention may be present as a fixed combination, a non-fixed combination or a kit-of-parts.

A "fixed combination" is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A "kit-of-parts" is defined as a combination wherein the said first active ingredient and the said second active ingredient are present in more than one unit. One example of a "kit-of-parts" is a combination wherein the said first active ingredient and the said second active ingredient are present separately. The components of the kit-of-parts may be administered separately, sequentially, simultaneously, concurrently or chronologically staggered.

The first and second active ingredient of a combination or kit-of-parts according to this invention may be provided as separate formulations (i.e. independently of one another), which are subsequently brought together for simultaneous, sequential, separate or chronologically staggered use in combination therapy; or packaged and presented together as separate components of a combination pack for simultaneous, concurrent, sequential, separate or chronologically staggered use in combination therapy.

The type of pharmaceutical formulation of the first and second active ingredient of a combination or kit-of-parts according to this invention can be similar, i.e. both ingredients are formulated in separate tablets or capsules, or can be different, i.e. suited for different administration forms, such as e.g. one active ingredient is formulated as tablet or capsule and the other is formulated for e.g. intravenous administration.

The amounts of the first and second active ingredients of the combinations, compositions or kits according to this invention may together comprise a therapeutically effective amount for the treatment, prophylaxis or amelioration of a disease responsive or sensitive the inhibition of histone deacetylases, particularly one of those diseases mentioned herein, e.g. benign or malignant neoplasia, particularly cancer, like any one of those cancer diseases mentioned herein.

A further aspect of the present invention is a combination comprising, in non-fixed form, one or more compounds according to this invention or the salts thereof, and one or more art-known standard therapeutic, in particular art-known chemotherapeutic or target specific anti-cancer agents, such as those mentioned above, for sequential, separate, simultaneous or chronologically staggered use in therapy in any order, e.g. to treat, prevent or ameliorate in a patient diseases responsive to HDAC inhibitor treatment, such as the diseases, disorders or illnesses mentioned, in particular cancer. Optionally said combination comprises instructions for its use in therapy.

A further aspect of the present invention is a combined preparation, such as e.g. a kit of parts, comprising a preparation of a first active ingredient, which is a compound according to this invention and a pharmaceutically acceptable carrier or diluent; a preparation of a second active ingredient, which is an art-known therapeutic agent, in particular an anti-cancer agent, such as e.g. one of those mentioned above, and a pharmaceutically acceptable carrier or diluent; and optionally instructions for simultaneous, sequential, separate or chronologically staggered use in therapy, e.g. to treat benign and malignant neoplasia or diseases different to cellular neoplasia responsive or sensitive to the inhibition of histone deacetylases.

A further aspect of the present invention is a kit of parts comprising a dosage unit of a first active ingredient, which is a compound according to this invention or a salt thereof, a dosage unit of a second active ingredient, which is an art-known standard therapeutic, in particular an anti-cancer agent such as e.g. one of those mentioned above, and optionally instructions for simultaneous, sequential or separate use in therapy, e.g. to treat disorders responsive or sensitive to the inhibition of histone deacetylases, such as, for example, benign or malignant neoplasia, e.g. cancer.

A further aspect of the present invention is a pharmaceutical product comprising one or more compounds according to this invention, or one or more pharmaceutical compositions comprising said compounds; and one or more art-known therapeutic agents, in particular art-known anti-cancer agents, or one or more pharmaceutical compositions comprising said therapeutic agents, such as e.g. those mentioned above, for simultaneous, sequential or separate use in therapy, e.g. to treat diseases as mentioned before, in particular cancer. Optionally this pharmaceutical product comprises instructions for use in said therapy.

In this connection, the present invention further relates to combinations, compositions, formulations, preparations or kits according to the present invention having histone deacetylases inhibitory activity.

A further aspect of the present invention is a pharmaceutical composition as unitary dosage form comprising, in admixture, a first active ingredient, which is a N-sulphonylpyrrole derivative according to this invention or a salt thereof, a second active ingredient, which is an art-known standard therapeutic, in particular art-known chemotherapeutic or target specific anti-cancer agent, such as one of those mentioned above, and optionally a pharmacologically acceptable carrier, diluent or excipient.

The present invention further relates to a pharmaceutical composition comprising a first active ingredient, which is at least one compound according to this invention, and a second active ingredient, which is at least one art-known anti-cancer agent, such as e.g. one or more of those mentioned herein above, and, optionally, a pharmaceutically acceptable carrier or diluent, for separate, sequential, simultaneous, concurrent or chronologically staggered use in therapy, such as e.g. in therapy of diseases responsive or sensitive to the inhibition of histone deacetylases, particularly (hyper)proliferative diseases and/or disorders responsive to induction of apoptosis, such as e.g. any of those diseases mentioned herein, like benign or malignant neoplasia, especially cancer, particularly any of those cancer diseases described above.

The present invention further relates to a combination product comprising
a.) at least one compound according to this invention formulated with a pharmaceutically acceptable carrier or diluent, and
b.) at least one art-known anti-cancer agent, such as e.g. one or more of those mentioned herein above, formulated with a pharmaceutically acceptable carrier or diluent.

The present invention further relates to a kit-of-parts comprising a preparation of a first active ingredient, which is a compound according to this invention, and a pharmaceutically acceptable carrier or diluent; a preparation of a second active ingredient, which is an art-known anti-cancer agent, such as one of those mentioned above, and a pharmaceutically acceptable carrier or diluent; for simultaneous, concurrent, sequential, separate or chronologically staggered use in therapy. Optionally, said kit comprises instructions for its use in therapy, e.g. to treat diseases responsive or sensitive to the inhibition of histone deacetylases, such as e.g. cellular neoplasia or diseases different to cellular neoplasia as indicated above, particularly cancer, such as e.g. any of those cancer diseases described above.

The present invention further relates to a combined preparation comprising at least one compound according to this invention and at least one art-known anti-cancer agent for simultaneous, concurrent, sequential or separate administration.

In this connection, the present invention further relates to combinations, compositions, formulations, preparations or kits according to the present invention having histone deacetylases inhibitory activity.

Also in this connection, the present invention further relates to combinations, compositions, formulations, preparation or kits according to the present invention having anti (hyper)proliferative and/or apoptosis inducing activity.

In addition, the present invention further relates to the use of a composition, combination, formulation, preparation or kit according to this invention in the manufacture of a pharmaceutical product, such as e.g. a commercial package or a medicament, for treating, preventing, or ameliorating diseases responsive or sensitive to the inhibition of histone deacetylases, particularly those diseases mentioned herein, such as e.g. benign or malignant neoplasia, particularly cancer.

The present invention further relates to a commercial package comprising one or more compounds of the present invention together with instructions for simultaneous, sequential or separate use with one or more chemotherapeutic and/or target specific anti-cancer agents, such as e.g. any of those mentioned herein.

The present invention further relates to a commercial package consisting essentially of one or more compounds of the present invention as sole active ingredient together with instructions for simultaneous, sequential or separate use with one or more chemotherapeutic and/or target specific anti-cancer agents, such as e.g. any of those mentioned herein.

The present invention further relates to a commercial package comprising one or more chemotherapeutic and/or target specific anti-cancer agents, such as e.g. any of those mentioned herein, together with instructions for simultaneous, sequential or separate use with one or more compounds according to the present invention.

Furthermore, also an aspect of the present invention is a method for treating diseases and/or disorders responsive or sensitive to the inhibition of histone deacetylases, e.g. (hyper)proliferative diseases and/or disorders responsive to induction of apoptosis, such as e.g. cancer, in combination therapy in a patient comprising administering a pharmacologically active and therapeutically effective and tolerable amount of a pharmaceutical combination, composition, formulation, preparation or kit as described above to said patient in need thereof.

A further aspect of the present invention is a method for treating cotherapeutically diseases responsive or sensitive to inhibiting histone deacetylases, such as e.g. those diseases as mentioned before, particularly cancer, in a patient in need of such treatment comprising administering separately, sequentially, simultaneously, concurrently, fixed or non-fixed a pharmacologically active and therapeutically effective and tolerable amount of one or more of the compounds according to the present invention and a pharmacologically active and therapeutically effective and tolerable amount of one or more art-known therapeutic agents, in particular anti-cancer agents, such as those mentioned above, to said patient.

In further addition, the present invention relates to a method for treating, preventing or ameliorating (hyper) proliferative diseases and/or disorders responsive to induction of apoptosis, such as e.g. benign or malignant neoplasia, e.g. cancer, particularly any of those cancer diseases mentioned herein, in a patient comprising administering separately, simultaneously, concurrently, sequentially or chronologically staggered to said patient in need thereof an amount of a first active compound, which is a compound according to the present invention, and an amount of at least one second active compound, said at least one second active compound being a standard therapeutic agent, particularly at least one art-known anti-cancer agent, such as e.g. one or more of those chemotherapeutic and target-specific anti-cancer agents mentioned herein, wherein the amounts of the first active compound and said second active compound result in a therapeutic effect.

In yet further addition, the present invention relates to a method for treating, preventing or ameliorating (hyper) proliferative diseases and/or disorders responsive to induction of apoptosis, such as e.g. benign or malignant neoplasia, e.g. cancer, particularly any of those cancer diseases mentioned herein, in a patient comprising administering a combination according to the present invention.

The pharmaceutical compositions, combinations, preparations, formulations, kits, products or packages mentioned above may also include more than one of the compounds according to this invention and/or more than one of the art-known standard therapeutics, in particular anti-cancer agents as mentioned.

In addition, compounds according to the present invention can be used in the pre- or postsurgical treatment of cancer.

In further addition, compounds according to the present invention can be used in combination with radiation therapy, in particular in sensitization of cancer patients towards standard radiation therapy.

The administration of the compounds according to this invention, the combinations and pharmaceutical compositions according to the invention may be performed in any of the generally accepted modes of administration available in the art. Illustrative examples of suitable modes of administration include intravenous, oral, nasal, inhalativ, parenteral, topical, transdermal and rectal delivery. Oral and intravenous deliveries are preferred.

For the treatment of dermatoses, the compounds according to the invention are in particular administered in the form of those pharmaceutical compositions, which are suitable for topical application. For the production of the pharmaceutical compositions, the compounds of the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions.

The pharmaceutical compositions according to the invention are prepared by processes known per se. The dosage of the compounds according to the invention (=active compounds) is carried out in the order of magnitude customary for histone deacetylases inhibitors. Topical application forms (such as ointments) for the treatment of dermatoses thus contain the active compounds in a concentration of, for example, 0.1-99%. The customary dose in the case of systemic therapy (p.o.) may be between 0.03 and 60 mg/kg per day, (i. v.) may be between 0.03 and 60 mg/kg/h. In another embodiment, the customary dose in the case of systemic therapy (p.o.) is between 0.3 and 30 mg/kg per day, (i. v.) is between 0.3 and 30 mg/kg/h.

The choice of the optimal dosage regime and duration of medication, particularly the optimal dose and manner of administration of the active compounds necessary in each case can be determined by a person skilled in the art on the basis of his/her expert knowledge.

Biological Investigations

Isolation of HDAC Activity from HeLa Cell Nuclei:

HDAC activity is isolated from nuclear HeLa extracts according to a method originally described by Dignam et al. (Nucl. Acids Res. 11, pp 1475, 1983). Briefly, nuclei isolated from HeLa cells (CIL SA, Seneffe, Belgium) are resuspended in buffer C (20 mM Hepes pH 7.9, 25% v:v glycerol, 0.42M NaCl, 1.5 mM $MgCl_2$, 0.2 mM EDTA, 0.5 mM PefaBloc and 0.5 mM DTT) and stirred for 30 min on ice. After centrifugation, the supernatant is dialysed against buffer D (40 mM Tris HCl pH 7.4, 100 mM KCl, 0.2 mM EDTA, 0.5 mM DTT and 25% v:v glycerol) for 5 h at 4° C. After dialysis and centrifugation, the supernatant is stored in aliquots at −80° C. and used for Western blot analysis as well as the enzymatic assay as described in the following.

Isolation of rHDAC1

Human HDAC1 (Taunton et al., Science 272 (5260), p 408-11, 1996) fused with the flag epitope is stably expressed in Hek293 cells. After mass cultivation in DMEM with supplements and 2% fetal calf serum, cells are lysed and flag-HDAC1 purified by M2-agarose affinity chromatography as described (Sigma Art. No. A-2220). Fractions from the purification are analyzed by Western blot as well as for enzymatic activity as described below.

Fluorimetric HDAC Activity Assay:

The HDAC enzyme activity assay is done as described by Wegener et al. (Chem. & Biol. 10, 61-68, 2003). Briefly 40 μl of a 1:100 dilution (=0.4 μl) nuclear HeLa extract (mixture of class I and II HDACs), 29 μl enzyme buffer (15 mM Tris HCl pH 8.1, 0.25 mM EDTA, 250 mM NaCl, 10% v: v glycerol) and 1 μl test compound are added to a well of a 96 well microtiter plate and reaction started by addition of 30 μl substrate (Ac-NH-GGK (Ac)-AMC; final concentration 25 μM and final volume 100 μl alternative substrate Boc-K (Ac)-AMC/Flour-deLys by Biomol). After incubation for 90 min at 30° C., reaction is terminated by the addition of 25 μl stop solution (50 mM Tris HCl pH 8, 100 mM NaCl, 0.5 mg/ml trypsine and 2 μM TSA). After incubation at room temperature for further 40 min, fluorescence is measured using a Wallac Victor 1420 multilabel counter (excitation λ=355 nm, emission λ=460 nm) for quantification of AMC (7-amino-4-methylcoumarin) generated by trypsine cleavage of the deacetylated peptide. For the calculation of $IC_{50}$ values the fluorescence in wells without test compound (1% DMSO, negative control was set as 100% enzymatic activity and the fluorescence in wells with 2 μM TSA (positive control) are set at 0% enzymatic activity. The corresponding $IC_{50}$ values of the compounds for HDAC inhibitory activity are determined from the concentration-effect curves by means of non-linear regression analysis.

The HDAC inhibitory activity expressed by $IC_{50}$ values for selected compounds according to the present invention is shown in the following tables 1 and 2, in which the numbers of the compounds correspond to the numbers of the examples.

TABLE 1

HDAC inhibitory activity (HDAC activity isolated
from HeLa nuclear extract)

| Compound | $IC_{50}$ (M) |
| --- | --- |
| 1-24, 34-56, 62, 64-85, 88-111, 114-199. | The $IC_{50}$ values of these listed compounds are in the range from $\geq$100E−6 to 0.01E−6 |

The HDAC1 enzymatic assay is done with slight modifications with recombinant flag-HDAC1 protein isolated from HEK293 cell lysates. About 14 ng/well flag-HDAC1 is incubated with 6 μM Ac-NH-GGK(Ac)-AMC substrate for 3 h at 30° C. Termination of the reaction and all further steps are done as described for HeLa cell nuclear extracts as a source for HDAC enzymatic activity.

TABLE 2

HDAC1 inhibitory activity (recombinant HDAC1 isolated from
HEK293 cells with heterologous HDAC1 expression)

| Compound | $IC_{50}$ (M) |
| --- | --- |
| 1-24, 34-56, 62, 64-85, 88-111, 114-199. | The $IC_{50}$ values of these listed compounds are in the range from $\leq$50E−6 to 11E−9 |

Cellular Histone H3 Hyperacetylation Assay:

To assess the cellular efficacy of a histone deacetylase inhibitor in vitro, an assay is set up in black clear-bottom 96-well plates and optimized for use on the Cellomics "ArrayScan II" platform for a quantitative calculation of histone acetylation. The protocol uses a polyclonal rabbit antibody, specifically binding to acetylated lysine 1-20 (including K 9 and K14) of human histone H3 on fixed cells with an Alexa Fluor 488 labeled goat anti rabbit-IgG used for counterstaining $5 \times 10^3$ HeLa cervical carcinoma cells/well (ATCC CCL-2) in 200 μl Dulbecco's modified Eagle's medium (DMEM) containing 10% fetal calf serum are seeded at day 1 in Packard view plates and incubated for 24 h under standard cell culture conditions. On day 2, 1 μl test compound (200× final concentration) is added and incubation continued for further 24 h. On day 3, the culture medium is discarded and attached cells fixed for 15 min at room temperature by addition of 100 μl fixation buffer (3.7% v:v formaldehyde in phosphate buffered saline/PBS). After discarding the fixation buffer and one wash with blocking solution (1% BSA, 0.3% Tween 20 in PBS), cells are permeabilized at room temperature by addition of 100 μl /well permeabilization buffer (30.8 mM NaCl, 0.54 mM $Na_2HPO_4$, 0.31 mM $KH_2PO_4$, 0.1% v:v Triton X-100) for 15 min at room temperature. After discarding the permeabilization buffer and washing twice with 100 μl/well blocking solution at room temperature, the $1^{st}$ antibody (anti-K1-20 histone H3 antibody, Calbiochem No. 382158) in blocking solution (50 μl/well) is added. After incubation for 1 h at room temperature, the wells are washed twice at room temperature with 100 μl/well blocking solution before addition of the $2^{nd}$ antibody (goat-anti-rabbit Alexa Fluor 488; MoBiTec No. A -11008) in blocking solution (50 μl well). After further incubation for 1 h at room temperature, wells are washed twice with 100 μl/well blocking solution at room temperature. Finally, 100 μl/well PBS are added and image analysis performed on the Cellomics "ArrayScan II" platform. For $EC_{50}$ determination, the percentage of positive cells showing nuclear fluorescence is determined and $EC_{50}$ calculation done from concentration-effect curves by means of non-linear regression. For calibration, a positive (reference HDAC inhibitors like SAHA or NVP LBH-589) and a negative control were included.

The histone hyperacetylating cellular potency expressed by $EC_{50}$ values for selected compounds according to the present invention is shown in the following table 3, in which the numbers of the compounds correspond to the numbers of the examples.

TABLE 3

Induction of histone H3 hyperacetylation in HeLa cervical carcinoma cells

| Compound | $-\lg EC_{50}$ |
| --- | --- |
| 1 to 4, 7, 12-16, 18, 19, 36, 37, 39, 92, 96, 116-118, 122, 150, 152-154, 160, 173, 174, 176, 180, 182, 183, 186, 189, 190-194, 196, 197 | The $-\lg EC_{50}$ values of these listed compounds are in the range from 4.8 (15 μM) to 6.6 (0.15 μM) |

Cellular Cytotoxicity Assay:

The anti-proliferative activity of the histone deacetylase inhibitory compounds as described herein, is evaluated using the following cell lines: HeLa and HeLa-KB (cervical carcinoma), H460 (non small cell lung cancer), A549 (non-small cell lung cancer), MCF7 (breast carcinoma), MCF10A (normal, non tumorigenic breast epithelial), MDA-MB468 (breast carcinoma), MDA-MB435 (breast carcinoma), MDA-MB231 (breast carcinoma), SKBR-3 (breast carcinoma), SKOV-3 (ovarial carcinoma), A-2780 (ovarial carcinoma), RKO (colon carcinoma), HCT-15 (colon carcinoma), HCT-116 (colon carcinoma), PC3 (prostate carcinoma), BPH1 (benign prostate hyperplasia), AsPC1 (pancreatic carcinoma), Ca127 (tongue carcinoma), A-431 (vulva carcinoma), Hec1A (endometrial carcinoma), Saos-2 (osteosarcoma), U87MG (glioblastoma), WM266-4 (melanoma), K562 (chronic myeloid leukemia), EOL1 (acute hypereosinophilic myeloid leukemia), CCRF-CEM and CCRF-CEM VCR1000 (acute lymphoblastic leukemia sensitive and resistant towards Vincristine). For quantification of cellular proliferation/living cells the Alamar Blue (Resazurin) cell viability assay is applied (O'Brien et al. Eur J Biochem 267, 5421-5426, 2000). In this assay Resazurin is reduced to the fluorescent resorufine by cellular dehydrogenase activity, correlating with viable, proliferating cells. The examples are dissolved as 20 mM solutions in dimethylsulfoxide (DMSO) and subsequently diluted in semi-logarithmic steps. Cell lines are seeded at respective density into 96 well flat bottom plates in a volume of 200 μl per well. 24 h after seeding 1 μl each of the compound dilutions are added into each well of the 96 well plate. Each compound dilution is tested as quadruplicates. Wells containing untreated control cells are filled with 200 μl DMEM medium containing 0.5% v:v DMSO. The cells are then incubated with the compounds for 72 h at 37° C. in a humidified atmosphere containing 5% carbon dioxide. To determine the viability of the cells, 20 μl of a Resazurin solution (Sigma; 90 mg/l) are added. After 4 h incubation at 37° C. the fluorescence is measured at an extinction of $\lambda$=544 nm and an emission of $\lambda$=590 nm. For the calculation of the cell viability the emission value from untreated cells is set as 100% viability and the emission rates of treated cells are set in relation to the values of untreated cells. Viabilities are expressed as % values. The corresponding $IC_{50}$ values of the compounds for cytotoxic activity are determined from the concentration-effect curves by means of non-linear regression.

For determination of cell-cycle dependent cytotoxicity, the RKO exop21 cell system is applied (Schmidt et al. Oncogene 19: 2423-2429, 2000). Briefly, RKO cells with/without $p21^{waf1}$ expression ($2\times10^4$ cells/well induced, $6\times10^3$ cells/well not induced) are treated with the compounds for 72 h and metabolic activity quantified as described before. The expression of $p21^{waf1}$ was induced by treatment with Pronasterone A, causing a complete proliferation arrest of RKO cells in the G1 and G2 phases of the cell division cycle.

The anti-proliferative/cytotoxic potency expressed by $IC_{50}$ values for selected compounds according to the present invention is shown in the following table 4, in which the numbers of the compounds correspond to the numbers of the examples.

TABLE 4

Cytotoxicity towards A549 NSCLC cells

| Compound | $IC_{50}$ (µM) |
| --- | --- |
| 1-24, 34-56, 62, 64-85, 88-111, 114-199 | The $IC_{50}$ values of these listed compounds are in the range from $\geq 100$ to 0.2 |

The anti-proliferative activity of compounds from examples 1, 2, 3, 12 and 150 is evaluated by using a broad selection of non-malignant cell lines and fully transformed malignant cancer cell lines. Mean $IC_{50}$ values as calculated for fully malignant cancer cell lines are in the range from 2.4 to 5.4 µM.

By using proliferating and arrested RKO colon carcinoma cells with conditional $p21^{waf1}$ expression as described above the proliferation independent mode of action of the compounds of the invention is shown (see table 5). Dormant, non-proliferating as well as proliferating RKO colon carcinoma cells are hit by the compounds as described herein.

TABLE 5

Cell cycle independent cytotoxicity

| Compound | RKO proliferating $IC_{50}$ (µM) | RKO arrested ($p21^{waf1}$ expressed) $IC_{50}$ (µM) |
| --- | --- | --- |
| 1 | The $IC_{50}$ values of these listed compounds are in the range from 1.1 to 4.0 | The $IC_{50}$ values of these listed compounds are in the range from 1.1 to 4.9 |
| 2 | | |
| 3 | | |
| 12 | | |
| 150 | | |

Apoptosis Induction

The induction of apoptosis is measured by using the cell death detection ELISA (Art. No. 1774425, Roche Biochemicals, Mannheim, Germany). A549 NSCLC cells are seeded into 96 well flat bottom plates at a density of $3\times10$ E3 cells/well in a total volume of 200 µl/well. 24 h after seeding, 1 µl each of the compound dilutions in DMEM are added in a total volume of 200 µl into each well. Each compound dilution is tested at least as triplicates. Wells containing untreated control cells are filled with 200 µl DMEM containing 0.5 vol % DMSO. The cells are incubated with test compound for 48 h at 37° C. in a humidified atmosphere containing 5% carbon dioxide. As a positive control for the induction of apoptosis, cells are treated with 50 µM Cisplatin (Gry Pharmaceuticals, Kirchzarten, Germany). Medium is then removed and the cells lysed in 200 µl lysis buffer. After centrifugation as described by the manufacturer, 10 µl of cell lysate is processed as described in the protocol. The degree of apoptosis is calculated as follows: The absorbance at $\lambda=405$ nm obtained with lysates from cells treated with 50 µM cisplatin is set as 100 cpu (cisplatin units), while an absorbance at $\lambda=405$ nm of 0.0 is set as 0.0 cpu. The degree of apoptosis is expressed as cpu in relation to the value of 100 cpu reached with the lysates obtained from cells treated with 50 µM cisplatin.

Representative apoptosis inducing potency values (expressed by cpu values) for compounds according to the present invention at 10 µM follows from the following table 6, in which the numbers of the compounds correspond to the numbers of the examples.

TABLE 6

Apoptosis induction

| Compound | cpu @ 10 µM |
| --- | --- |
| 1 | The cpu values of these listed compounds are in the range from 40.0 to 130.0 |
| 2 | |
| 3 | |
| 12 | |
| 150 | |

Cell Cycle Analysis by Flow Cytometry

A549 NSCLC cells (ATTC CCL-185) are cultivated in DMEM with high glucose (supplemented with 10% FBS) at 5% CO2 and 37° C. in a humidified atmosphere under standard cell culture conditions. 24 h before compound treatment, cells are seeded at $5\times10^4$ cells/ml (=$5\times10^5$ cells/10 cm cell culture dish) to allow logarithmic proliferation during the experiment. After 24 h, cells were treated with test compound or 0.5 vol % DMSO as a control. After 24 h and 48 h treatment, the culture medium is collected and detached, floating cells are collected by short centrifugation (5 min at 1200 rpm). Attached cells are washed once with 5 ml PBS, detached by treatment with 3 ml trypsin/EDTA solution (short incubation for 3-5 min) and—together with detached, floating cells—transferred into 15 ml Falcon tubes. The cell culture dish is washed with 10 ml DMEM to collect all remaining cells. After centrifugation for 5 min at 1200 rpm at room temperature, the supernatant is discarded and the cell pellet washed twice with 10 ml PBS. The supernatant is discarded, the cells resuspended in 4 ml ice-cold fixation solution (70 vol % ethanol, 30 vol % $H_2O$; stored at −20° C.) and stored at −20° C. overnight. Next, 10 ml PBS (4° C.) is added to the cells, before centrifugation for 5 min at 1200 rpm (4° C.). The supernatant is discarded, the cell pellet washed once with 10 ml PBS (4° C.) and the cell pellet finally resuspended in about 1 ml staining solution (10 µg/ml RNAse A, 10 µg/ml propidiumiodide in PBS, final volume dependent on cell number). After incubation for 30 min at room temperature in the dark, cells are stored on ice and analyzed using the Becton Dickinson FACS Canto device. Analysis is done at an excitation of $\lambda=488$ nm with emission set as $\lambda=600$ nm.

Data analysis: Cells are analyzed according to size, granularity and propidiumiodide intensity. Size and granularity of cells are determined by measurement of forward scatter (FSC) and side scatter (SSC) of the $\lambda=488$ nm excitation light, respectively. To discriminate cells with 4N DNA content from cell doublets (two attached cells with 2N DNA content each), the ratio between the area under the propidiumiodide peak (PE-A) and the height of the propidiumiodide peak (PE-H) for each cell is determined. Cell doublets need more time to pass through the laser beam, which causes a broadening of the propidiumiodide peak and an increase of the ratio PE-A/PE-H. Using this analysis, cells in 4N and cell doublets appear as distinct clouds in a scatter plot and are excluded from the analysis. Thus, the area under the propidiumiodide peak at λ=600 nm (PE-A) is a measure for the DNA content of the cells. PE-A is blotted against the measured cell number in a histogram in order to determine the percentage of analyzed cells in an individual stage of the cell cycle.

The compounds of examples 1, 2, 3, 12, 153, 182 and 189, were tested at defined concentrations between 0.1 µM and 31.6 µM for effects on the cell division cycle of A549 NSCLC cells in-vitro. All examples induced an arrest in G1 (2N DNA content) and depletion of cells in the S-phase (>2N and <4N DNA content) and a reduction of cells in the G2/M-phase (4N DNA content) after 24 h treatment duration at concentrations around 3 µM. All compounds induced potent apoptosis after 48 h treatment at concentrations of ≧3 µM (compounds of examples 3, 12, and 189) or ≧10 µM (compounds of examples 1, 153, 182) evident by cells with less than 2N chromosomal DNA.

The invention claimed is:

1. A compound of formula I

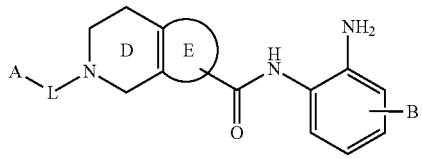

wherein
ring D and ring E together form a fused ring system, which is one of the following groups

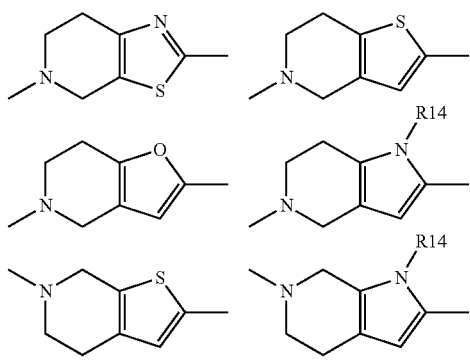

A is $(C_1-C_4)$alkyl, $(C_1-C_4)$alkoxy$(C_1-C_2)$alkyl, $(C_1-C_4)$alkylthio$(C_1-C_2)$alkyl, mono- or -di$(C_1-C_4)$alkylamino $(C_1-C_2)$alkyl, $(C_3-C_7)$cycloalkyl optionally substituted by R1 and/or R2, $(C_3-C_7)$cycloalkyl substituted by R3, azetidinyl optionally substituted by R1 and/or R2, pyrrolidinyl optionally substituted by R1 and/or R2, piperidinyl optionally substituted by R1 and/or R2, phenyl optionally substituted by R1 and/or R2, phenyl substituted by R4, naphthyl optionally substituted by R1 and/or R2, pyridyl optionally substituted by R1 and/or R2, pyridyl substituted by R5, pyrimidinyl optionally substituted by R1 and/or R2, pyrimidinyl substituted by R8, triazinyl optionally substituted by R1 and/or R2, triazinyl substituted by R9; quinolinyl optionally substituted by R1 and/or R2, isoquinolinyl optionally substituted by R1 and/or R2, thienyl optionally substituted by R1 and/or R2, thiazolyl optionally substituted by R1 and/or R2 or indazolyl optionally substituted by R1 and/or R2;

R1 is halogen, hydroxyl, cyano, nitro, amino, carboxyl, $(C_1-C_4)$alkyl, $(C_1-C_4)$alkoxy, $(C_1-C_4)$alkyl which is partially or completely substituted by fluorine, $(C_1-C_4)$alkoxy which is predominantly or completely substituted by fluorine, $(C_1-C_4)$alkoxy$(C_1-C_2)$alkyl, $(C_1-C_4)$alkoxycarbonyl, mono- or -di$(C_1-C_4)$alkylamino, or $(C_1-C_4)$alkylcarbonylamino;

R2 is halogen, hydroxyl, amino, $(C_1-C_4)$alkyl, or $(C_1-C_4)$alkoxy or

R1 and R2 when ortho to each other form a methylenedioxy or ethylenedioxy group;

R3 is 3-pyridyl, or 4-pyridyl;

R4 is phenyl, phenoxy, 4-methylpiperazinyl, benzylNHC(=O)NH—, or $(C_1-C_4)$alkylphenyl-sulfonylamino;

R5 is $(C_1-C_4)$alkylphenylsulfonylamino or N(R6)R7, wherein R6 and R7 together and with inclusion of the nitrogen atom to which they are bonded form an azetidinyl-, pyrrolidinyl-, piperidinyl-, piperazinyl-, 4-methylpiperazinyl-, morpholinyl- or thiomorpholinyl-ring;

R8 is pyridyl or $(C_1-C_4)$alkylphenylsulfonylamino;

R9 is piperidinyl;

L is bond, —$(CH_2)_nS(O)_2$—, —C(=O)—, —C(=S)—, —$(CH_2)_nOC(=O)$—, —$(CH_2)_nN(R10)C(=O)$—, —$(CH_2)_nN(R10)C(=NR11)$-, —$(CH_2)_nN(R10)C(=S)$—, —C=C—C(=O)—, —N=C(R11)-, —$(CH_2)_nN(R10)C(=O)C(=O)$—, —$OCH_2C(=O)$—, —N(R10)C(=CR11)-, —N(R10)$CH_2$C(=O)— or —N=C(NR11)-;

R10 is hydrogen, $(C_1-C_4)$alkyl or $(C_1-C_4)$alkoxy$(C_1-C_2)$alkyl;

R11 is hydrogen, hydroxyl, cyano, nitro, or $(C_1-C_4)$alkyl;

B is hydrogen, halogen, $(C_1-C_4)$alkyl, $(C_1-C_4)$alkoxy, thienyl, or N(R12)R13 wherein R12 and R13 independently of one another are hydrogen, $(C_1-C_4)$alkyl, $(C_1-C_4)$alkylcarbonyl, or R12 and R13 together and with inclusion of the nitrogen atom to which they are bonded form an azetidinyl-, pyrrolidinyl-, piperidinyl-, piperazinyl-, 4-methylpiperazinyl-, morpholinyl- or thiomorpholinyl-ring;

R14 is hydrogen or $(C_1-C_4)$alkyl; and n is an integer selected from 0 to 2;

or a salt thereof.

2. A compound of formula I according to claim 1 wherein

A is $(C_1-C_4)$alkyl, $(C_1-C_4)$alkoxy$(C_1-C_2)$alkyl, $(C_1-C_4)$alkylthio$(C_1-C_2)$alkyl, mono- or -di$(C_1-C_4)$alkylamino $(C_1-C_2)$alkyl, cyclohexyl optionally substituted by R1 and/or R2, cyclohexyl substituted by R3, azetidinyl optionally substituted by R1 and/or R2, piperidinyl optionally substituted by R1 and/or R2, phenyl optionally substituted by R1 and/or R2, phenyl substituted by R4, naphthyl optionally substituted by R1 and/or R2, pyridyl optionally substituted by R1 and/or R2, pyridyl substituted by R5, pyrimidinyl optionally substituted by R1 and/or R2, pyrimidinyl substituted by R8, triazinyl optionally substituted by R1 and/or R2, triazinyl substituted by R9, quinolinyl optionally substituted by R1 and/or R2, isoquinolinyl optionally substituted by R1 and/or R2, thienyl optionally substituted by R1 and/or R2, thiazolyl optionally substituted by R1 and/or R2 or indazolyl optionally substituted by R1 and/or R2;

R1 is fluorine, hydroxyl, cyano, nitro, amino, carboxyl, $(C_1-C_4)$alkyl, $(C_1-C_4)$alkoxy, $(C_1-C_4)$alkyl which is partially or completely substituted by fluorine, $(C_1-C_4)$alkoxy which is predominantly or completely substituted by fluorine, $(C_1-C_4)$alkoxy$(C_1-C_2)$alkyl, $(C_1-C_4)$alkoxycarbonyl, mono- or -di$(C_1-C_4)$alkylamino, or $(C_1-C_4)$alkylcarbonylamino;

R2 is fluorine, hydroxyl, amino, $(C_1-C_4)$alkyl, or $(C_1-C_4)$alkoxy or

R1 and R2 when ortho to each other form a methylenedioxy or ethylenedioxy group;

R4 is phenyl, phenoxy, 4-methylpiperazinyl, benzylNHC(=O)NH—, or methylphenylsulfonylamino;

R5 is methylphenylsulfonylamino, or N(R6)R7, wherein R6 and R7 together and with inclusion of the nitrogen atom to which they are bonded form an azetidinyl-, piperidinyl-, piperazinyl-, 4-methylpiperazinyl-, or morpholinyl-ring;

R8 is pyridyl or methylphenylsulfonylamino;

L is bond, —$(CH_2)_nS(O)_2$—, —C(=O)—, —C(=S)—, —$(CH_2)_nOC(=O)$—, —$(CH_2)_nN(R10)C(=O)$—, —$(CH_2)_nN(R10)C(=NR11)$-, —$(CH_2)_nN(R10)C(=S)$—, —C=C—C(=O)—, —N=C(R11)-, —$(CH_2)_nN(R10)C(=O)C(=O)$—, —OCH$_2$C(=O)—, —N(R10)C(=CR11)-, —N(R10)CH$_2$C(=O)— or —N=C(NR11)-;

R11 is hydrogen, hydroxyl, cyano, nitro, methyl, or ethyl;

B is hydrogen, halogen, $(C_1-C_4)$alkyl, $(C_1-C_4)$alkoxy, thienyl, or N(R12)R13 wherein R12 and R13 independently of one another are hydrogen, $(C_1-C_4)$alkyl, or R12 and R13 together and with inclusion of the nitrogen atom to which they are bonded form a pyrrolidinyl-ring;

R14 is hydrogen or methyl;

n is an integer selected from 0 and 1;

or a salt thereof.

3. A compound of formula I according to claim 1 wherein

A is $(C_1-C_4)$alkyl, $(C_1-C_4)$alkoxy$(C_1-C_2)$alkyl, cyclohexyl optionally substituted by R1 and/or R2, cyclohexyl substituted by R3, piperidinyl optionally substituted by R1 and/or R2, phenyl optionally substituted by R1 and/or R2, phenyl substituted by R4, naphthyl optionally substituted by R1 and/or R2, pyridyl optionally substituted by R1 and/or R2, pyridyl substituted by R5, pyrimidinyl optionally substituted by R1 and/or R2, pyrimidyl substituted by R8, triazinyl optionally substituted by R1 and/or R2, triazinyl substituted by R9, quinolinyl optionally substituted by R1 and/or R2, isoquinolinyl optionally substituted by R1 and/or R2, thienyl optionally substituted by R1 and/or R2, thiazolyl optionally substituted by R1 and/or R2 or indazolyl optionally substituted by R1 and/or R2;

R1 is fluorine, hydroxyl, nitro, cyano, amino, carboxyl, methyl, ethyl, propyl, isopropyl, butyl, isobutyl, methoxy, ethoxy, propoxy, isopropoxy, trifluoromethyl, difluoromethyl, difluoromethoxy, trifluoromethoxy, methoxyethyl, ethoxyethyl, methoxymethyl, ethoxymethyl, Methoxycarbonyl, ethoxycarbonyl, propoxycarbonyl, methylamino, dimethylamino, ethylamino, diethylamino, methylcarbonylamino, or ethylcarbonylamino;

R2 is fluorine, hydroxyl, methyl, ethyl, propyl, isopropyl, methoxy, ethoxy, propoxy, or isopropoxy or R1 and R2 when ortho to each other form a methylenedioxy group;

R4 is phenyl, phenoxy, 4-methylpiperazinyl, benzylNHC(=O)NH—, or methylphenylsulfonylamino, R5 is methylphenylsulfonylamino, N(R6)R7, wherein R6 and R7 together and with inclusion of the nitrogen atom to which they are bonded form an azetidinyl-, piperidinyl-, piperazinyl-, 4-methylpiperazinyl-, morpholinyl-ring;

R8 is pyridyl or methylphenylsulfonylamino;

L is bond, —$(CH_2)_nS(O)_2$—, —C(=O)—, —C(=S)—, —$(CH_2)_nOC(=O)$—, —$(CH_2)_nN(R10)C(=O)$—, —$(CH_2)_nN(R10)C(=NR11)$-, —$(CH_2)_nN(R10)C(=S)$—, —C=C—C(=O)—, —N=C(R11)-, —$(CH_2)_nN(R10)C(=O)C(=O)$—, —OCH$_2$C(=O)—, —N(R10)C(=CR11)-, —N(R10)CH$_2$C(=O)— or —N=C(NR11)-;

R10 is hydrogen, methyl, ethyl, propyl, methoxyethyl, ethoxyethyl, methoxymethyl, or ethoxymethyl;

R11 is hydrogen, hydroxyl, cyano, nitro, methyl, or ethyl;

B is hydrogen, fluorine, chlorine, methyl, ethyl, propyl, isopropyl, methoxy, ethoxy, thienyl, N(R12)R13 wherein R12 and R13 independently of one another are hydrogen, methyl, ethyl, or R12 and R13 together and with inclusion of the nitrogen atom to which they are bonded form a pyrrolidinyl-ring;

R14 is hydrogen or methyl;

n is an integer selected from 0 and 1;

or a salt thereof.

4. A compound of formula I according to claim 1 wherein

L is —$(CH_2)_nN(R10)C(=O)C(=O)$;

A is $(C_1-C_4)$alkyl, $(C_1-C_4)$alkoxy$(C_1-C_2)$alkyl, mono- or -di$(C_1-C_4)$alkylamino$(C_1-C_2)$alkyl, cyclohexyl optionally substituted by R1 and/or R2, cyclohexyl substituted by R3, phenyl optionally substituted by R1 and/or R2, phenyl substituted by R4, naphthyl optionally substituted by R1 and/or R2, pyridyl optionally substituted by R1 and/or R2, pyridyl substituted by R5, quinolinyl optionally substituted by R1 and/or R2, or isoquinolinyl optionally substituted by R1 and/or R2;

R1 is fluorine, hydroxyl, nitro, amino, carboxyl, $(C_1-C_4)$alkyl, $(C_1-C_4)$alkoxy, $(C_1-C_4)$alkyl which is partially or completely substituted by fluorine, $(C_1-C_4)$alkoxy which is predominantly or completely substituted by fluorine, $(C_1-C_4)$alkoxy$(C_1-C_2)$alkyl, $(C_1-C_4)$alkoxycarbonyl, mono- or -di$(C_1-C_4)$alkylamino or $(C_1-C_4)$alkylcarbonylamino;

R2 is hydroxyl, $(C_1-C_4)$alkyl or $(C_1-C_4)$alkoxy or

R1 and R2 when ortho to each other form a methylenedioxy group;

R4 is phenyl, phenoxy, or 4-methylpiperazinyl;

R5 is N(R6)R7, wherein R6 and R7 together and with inclusion of the nitrogen atom to which they are bonded form an azetidinyl-, piperidinyl-, piperazinyl-, 4-methylpiperazinyl-, morpholinyl-ring;

R10 is hydrogen or $(C_1-C_4)$alkyl;

B is hydrogen, fluorine, chlorine, $(C_1-C_4)$alkyl, $(C_1-C_4)$alkoxy, or thienyl;

R14 is hydrogen, or methyl;

n is an integer selected from 0 and 1;

or a salt thereof.

5. A compound of formula I according to claim 1 wherein

L is —$(CH_2)_nN(R10)C(=O)$—;

A is $(C_1-C_4)$alkyl, $(C_1-C_4)$alkoxy$(C_1-C_2)$alkyl, $(C_1-C_4)$alkylthio$(C_1-C_2)$alkyl, mono- or -di$(C_1-C_4)$alkylamino$(C_1-C_2)$alkyl, cyclohexyl optionally substituted by R1 and/or R2, cyclohexyl substituted by R3, azetidinyl optionally substituted by R1 and/or R2, piperidinyl optionally substituted by R1 and/or R2, phenyl optionally substituted by R1 and/or R2, phenyl substituted by R4, naphthyl optionally substituted by R1 and/or R2, pyridyl optionally substituted by R1 and/or R2, pyridyl substituted by R5, quinolinyl optionally substituted by R1 and/or R2, isoquinolinyl optionally substituted by R1 and/or R2, or indazolyl optionally substituted by R1 and/or R2;

R1 is fluorine, hydroxyl, nitro, amino, carboxyl, $(C_1-C_4)$alkyl, $(C_1-C_4)$alkoxy, $(C_1-C_4)$alkyl which is partially or completely substituted by fluorine, $(C_1-C_4)$alkoxy which is predominantly or completely substituted by fluorine, $(C_1-C_4)$alkoxy$(C_1-C_2)$alkyl, $(C_1-C_4)$alkoxycarbonyl, mono- or -di$(C_1-C_4)$alkylamino or $(C_1-C_4)$alkylcarbonylamino;

R2 is hydroxyl, $(C_1-C_4)$alkyl, or $(C_1-C_4)$alkoxy or

R1 and R2 when ortho to each other form a methylenedioxy group;

R3 is 3-pyridyl or 4-pyridyl;

R4 is phenyl, phenoxy, or 4-methylpiperazinyl;

R5 is N(R6)R7, wherein R6 and R7 together and with inclusion of the nitrogen atom to which they are bonded form an azetidinyl-, piperidinyl-, piperazinyl-, 4-methylpiperazinyl-, or morpholinyl-ring;

R10 is hydrogen, $(C_1-C_4)$alkyl, methoxyethyl, ethoxyethyl, methoxymethyl, or ethoxymethyl;

B is hydrogen, fluorine, chlorine, $(C_1-C_4)$alkyl, $(C_1-C_4)$alkoxy, thienyl, or N(R12)R13 wherein R12 and R13 independently of one another are hydrogen, $(C_1-C_4)$alkyl, or R12 and R13 together and with inclusion of the nitrogen atom to which they are bonded form a pyrrolidinyl-ring;

R14 is hydrogen or methyl;

n is an integer selected from 0 and 1;

or a salt thereof.

6. A compound of formula I according to claim 1 wherein L is —C(=O)—;

A is $(C_1-C_4)$alkyl, $(C_1-C_4)$alkoxy$(C_1-C_2)$alkyl, $(C_1-C_4)$alkylthio$(C_1-C_2)$alkyl, mono- or -di$(C_1-C_4)$alkylamino$(C_1-C_2)$alkyl, phenyl optionally substituted by R1 and/or R2, phenyl substituted by R4, naphthyl optionally substituted by R1 and/or R2, pyridyl optionally substituted by R1 and/or R2, quinolinyl optionally substituted by R1 and/or R2, or isoquinolinyl optionally substituted by R1 and/or R2;

R1 is $(C_1-C_4)$alkyl, $(C_1-C_4)$alkoxy, $(C_1-C_4)$alkyl which is partially or completely substituted by fluorine, $(C_1-C_4)$alkoxy which is predominantly or completely substituted by fluorine, $(C_1-C_4)$alkoxy$(C_1-C_2)$alkyl, $(C_1-C_4)$alkoxycarbonyl, or mono- or -di$(C_1-C_4)$alkylamino;

R2 is $(C_1-C_4)$alkyl or $(C_1-C_4)$alkoxy;

R4 is phenyl or phenoxy;

B is hydrogen, fluorine, chlorine, $(C_1-C_4)$alkyl, or thienyl;

R14 is hydrogen or methyl;

or a salt thereof.

7. A compound of formula I according to claim 1 wherein L is —(CH$_2$)$_n$N(R10)C(=N(R11)-;

A is $(C_1-C_4)$alkyl, $(C_1-C_4)$alkoxy$(C_1-C_2)$alkyl, $(C_1-C_4)$alkylthio$(C_1-C_2)$alkyl, mono- or -di$(C_1-C_4)$alkylamino$(C_1-C_2)$alkyl, phenyl optionally substituted by R1 and/or R2, phenyl substituted by R4, or naphthyl optionally substituted by R1 and/or R2;

R1 is $(C_1-C_4)$alkyl, $(C_1-C_4)$alkoxy, $(C_1-C_4)$alkyl which is partially or completely substituted by fluorine, $(C_1-C_4)$alkoxy which is predominantly or completely substituted by fluorine, $(C_1-C_4)$alkoxy$(C_1-C_2)$alkyl, $(C_1-C_4)$alkoxycarbonyl, or mono- or -di$(C_1-C_4)$alkylamino;

R2 is $(C_1-C_4)$alkoxy, or R1 and R2 when ortho to each other form a methylenedioxy group;

R4 is phenyl, or phenoxy;

R10 is hydrogen, or $(C_1-C_4)$alkyl;

R11 is hydrogen, cyano, or methyl;

B is hydrogen, fluorine, chlorine, $(C_1-C_4)$alkyl, $(C_1-C_4)$alkoxy, or thienyl;

R14 is hydrogen, or methyl;

n is an integer selected from 0 and 1;

or a salt thereof.

8. A compound of formula I according to claim 1 wherein L is —N=C(R11)-;

A is $(C_1-C_4)$alkyl, phenyl optionally substituted by R1 and/or R2, phenyl substituted by R4, or naphthyl optionally substituted by R1 and/or R2;

R1 is $(C_1-C_4)$alkyl, $(C_1-C_4)$alkoxy, $(C_1-C_4)$alkyl which is partially or completely substituted by fluorine, $(C_1-C_4)$alkoxy which is predominantly or completely substituted by fluorine, $(C_1-C_4)$alkoxy$(C_1-C_2)$alkyl, $(C_1-C_4)$alkoxycarbonyl, or mono- or -di$(C_1-C_4)$alkylamino;

R2 is $(C_1-C_4)$alkoxy, or R1 and R2 when ortho to each other form a methylenedioxy group;

R4 is phenyl;

R11 is hydrogen, or methyl;

B is hydrogen, fluorine, chlorine, $(C_1-C_4)$alkyl, $(C_1-C_4)$alkoxy, or thienyl;

R14 is hydrogen, or methyl;

or a salt thereof.

9. A compound of formula I according to claim 1 wherein L is —N(R10)C(=C(R11))-;

A is $(C_1-C_4)$alkyl, phenyl optionally substituted by R1 and/or R2, phenyl substituted by R4, or naphthyl optionally substituted by R1 and/or R2;

R1 is fluorine, $(C_1-C_4)$alkyl, $(C_1-C_4)$alkoxy, $(C_1-C_4)$alkyl which is partially or completely substituted by fluorine, $(C_1-C_4)$alkoxy which is predominantly or completely substituted by fluorine, $(C_1-C_4)$alkoxy$(C_1-C_2)$alkyl, $(C_1-C_4)$alkoxycarbonyl, or mono- or -di$(C_1-C_4)$alkylamino;

R2 is $(C_1-C_4)$alkoxy, or R1 and R2 when ortho to each other form a methylenedioxy group;

R4 is phenyl;

R10 is hydrogen, or $(C_1-C_4)$alkyl;

R11 is hydrogen, nitro, or methyl;

B is hydrogen, fluorine, chlorine, $(C_1-C_4)$alkyl, $(C_1-C_4)$alkoxy, or thienyl;

R14 is hydrogen, or methyl;

or a salt thereof.

10. A compound of formula I according to claim 1 wherein L is —(CH$_2$)$_n$S(O)$_2$—;

A is $(C_1-C_4)$alkyl, phenyl optionally substituted by R1 and/or R2, phenyl substituted by R4, naphthyl optionally substituted by R1 and/or R2, thienyl optionally substituted by R1 and/or R2, thiazolyl optionally substituted by R1 and/or R2;

R1 is fluorine, $(C_1-C_4)$alkyl, $(C_1-C_4)$alkoxy, $(C_1-C_4)$alkyl which is partially or completely substituted by fluorine, $(C_1-C_4)$alkoxy which is predominantly or completely substituted by fluorine, $(C_1-C_4)$alkoxy$(C_1-C_2)$alkyl, $(C_1-C_4)$alkoxycarbonyl, mono- or -di$(C_1-C_4)$alkylamino, or $(C_1-C_4)$alkylcarbonylamino;

R2 is $(C_1-C_4)$alkyl, or $(C_1-C_4)$alkoxy, or R1 and R2 when ortho to each other form a methylenedioxy group;

R4 is phenyl;

B is hydrogen, fluorine, chlorine, $(C_1-C_4)$alkyl, $(C_1-C_4)$alkoxy, or thienyl;

R14 is hydrogen or methyl;

or a salt thereof.

11. A compound of formula I according to claim 1 wherein
L is —N(R10)C(=S)—;
A is ($C_1$-$C_4$)alkyl, cyclohexyl optionally substituted by R1 and/or R2, cyclohexyl substituted by R3, piperidinyl optionally substituted by R1 and/or R2, phenyl optionally substituted by R1 and/or R2, phenyl substituted by R4, naphthyl optionally substituted by R1 and/or R2, pyridyl optionally substituted by R1 and/or R2, quinolinyl optionally substituted by R1 and/or R2, or isoquinolinyl optionally substituted by R1 and/or R2;
R1 is fluorine, ($C_1$-$C_4$)alkyl, ($C_1$-$C_4$)alkoxy, ($C_1$-$C_4$)alkyl which is partially or completely substituted by fluorine, ($C_1$-$C_4$)alkoxy which is predominantly or completely substituted by fluorine, ($C_1$-$C_4$)alkoxy($C_1$-$C_2$)alkyl, ($C_1$-$C_4$)alkoxycarbonyl, or mono- or -di($C_1$-$C_4$)alkylamino;
R2 is ($C_1$-$C_4$)alkyl or ($C_1$-$C_4$)alkoxy, or R1 and R2 when ortho to each other form a methylenedioxy group;
R4 is phenyl;
R10 is hydrogen or ($C_1$-$C_4$)alkyl;
B is hydrogen, fluorine, chlorine, ($C_1$-$C_4$)alkyl, ($C_1$-$C_4$)alkoxy, or thienyl;
R14 is hydrogen or methyl;
or a salt thereof.

12. A compound of formula I according to claim 1 wherein
L is —OCH$_2$C(=O)—;
A is ($C_1$-$C_4$)alkyl, phenyl optionally substituted by R1 and/or R2, phenyl substituted by R4, naphthyl optionally substituted by R1 and/or R2;
R1 is fluorine, ($C_1$-$C_4$)alkyl, ($C_1$-$C_4$)alkoxy, ($C_1$-$C_4$)alkyl which is partially or completely substituted by fluorine, ($C_1$-$C_4$)alkoxy which is predominantly or completely substituted by fluorine, ($C_1$-$C_4$)alkoxy($C_1$-$C_2$)alkyl, ($C_1$-$C_4$)alkoxycarbonyl, or mono- or -di($C_1$-$C_4$)alkylamino;
R2 is ($C_1$-$C_4$)alkyl or ($C_1$-$C_4$)alkoxy, or R1 and R2 when ortho to each other form a methylenedioxy group;
R4 is phenyl;
B is hydrogen, fluorine, chlorine, ($C_1$-$C_4$)alkyl, ($C_1$-$C_4$)alkoxy, or thienyl;
R14 is hydrogen or methyl;
or a salt thereof.

13. A compound of formula I according to claim 1 wherein
L is —(CH$_2$)$_n$OC(=O);
A is ($C_1$-$C_4$)alkyl, phenyl optionally substituted by R1 and/or R2, phenyl substituted by R4, naphthyl optionally substituted by R1 and/or R2, pyridyl optionally substituted by R1 and/or R2, pyridyl substituted by R5;
R1 is fluorine, hydroxyl, nitro, amino, carboxyl, ($C_1$-$C_4$)alkyl, ($C_1$-$C_4$)alkoxy, ($C_1$-$C_4$)alkyl which is partially or completely substituted by fluorine, ($C_1$-$C_4$)alkoxy which is predominantly or completely substituted by fluorine, ($C_1$-$C_4$)alkoxy($C_1$-$C_2$)alkyl, ($C_1$-$C_4$)alkoxycarbonyl, or mono- or -di($C_1$-$C_4$)alkylamino;
R2 is hydroxyl, ($C_1$-$C_4$)alkyl, or ($C_1$-$C_4$)alkoxy or R1 and R2 when ortho to each other form a methylenedioxy group;
R4 is phenyl, phenoxy, or 4-methylpiperazinyl;
R5 is N(R6)R7, wherein R6 and R7 together and with inclusion of the nitrogen atom to which they are bonded form an azetidinyl-, piperidinyl-, piperazinyl-, 4-methylpiperazinyl-, or morpholinyl-ring;
B is hydrogen, fluorine, chlorine, ($C_1$-$C_4$)alkyl, ($C_1$-$C_4$)alkoxy, or thienyl;
R14 is hydrogen or methyl;
n is an integer selected from 0 and 1;
or a salt thereof.

14. A compound of formula I according to claim 1 wherein
L is —C=C—C(=O)—;
A is ($C_1$-$C_4$)alkyl, phenyl optionally substituted by R1 and/or R2, or naphthyl optionally substituted by R1 and/or R2;
R1 is fluorine, hydroxyl, ($C_1$-$C_4$)alkyl, ($C_1$-$C_4$)alkoxy, ($C_1$-$C_4$)alkyl which is partially or completely substituted by fluorine, ($C_1$-$C_4$)alkoxy which is predominantly or completely substituted by fluorine, ($C_1$-$C_4$)alkoxy($C_1$-$C_2$)alkyl, ($C_1$-$C_4$)alkoxycarbonyl, or mono- or -di($C_1$-$C_4$)alkylamino;
R2 is hydroxyl, ($C_1$-$C_4$)alkyl, or ($C_1$-$C_4$)alkoxy or R1 and R2 when ortho to each other form a methylenedioxy group;
B is hydrogen, fluorine, chlorine, ($C_1$-$C_4$)alkyl, ($C_1$-$C_4$)alkoxy, or thienyl;
R14 is hydrogen or methyl;
or a salt thereof.

15. A compound of formula I according to claim 1 wherein
L is —N(R10)CH$_2$C(=O)—;
A is ($C_1$-$C_4$)alkyl, ($C_1$-$C_4$)alkoxy($C_1$-$C_2$)alkyl, ($C_1$-$C_4$)alkylthio($C_1$-$C_2$)alkyl, mono- or di($C_1$-$C_4$)alkylamino($C_1$-$C_2$)alkyl, cyclohexyl optionally substituted by R1 and/or R2, cyclohexyl substituted by R3, azetidinyl optionally substituted by R1 and/or R2, piperidinyl optionally substituted by R1 and/or R2, phenyl optionally substituted by R1 and/or R2, phenyl substituted by R4, naphthyl optionally substituted by R1 and/or R2, pyridyl optionally substituted by R1 and/or R2, pyridyl substituted by R5, quinolinyl optionally substituted by R1 and/or R2, isoquinolinyl optionally substituted by R1 and/or R2, or indazolyl quinolinyl optionally substituted by R1 and/or R2;
R1 is fluorine, hydroxyl, nitro, amino, carboxyl, ($C_1$-$C_4$)alkyl, ($C_1$-$C_4$)alkoxy, ($C_1$-$C_4$)alkyl which is partially or completely substituted by fluorine, ($C_1$-$C_4$)alkoxy which is predominantly or completely substituted by fluorine, ($C_1$-$C_4$)alkoxy($C_1$-$C_2$)alkyl, ($C_1$-$C_4$)alkoxycarbonyl, or mono- or -di($C_1$-$C_4$)alkylamino or ($C_1$-$C_4$)alkylcarbonylamino;
R2 is hydroxyl, ($C_1$-$C_4$)alkyl, or ($C_1$-$C_4$)alkoxy or
R1 and R2 when ortho to each other form a methylenedioxy group;
R4 is phenyl, phenoxy, or 4-methylpiperazinyl;
R5 is N(R6)R7, wherein R6 and R7 together and with inclusion of the nitrogen atom to which they are bonded form an azetidinyl-, piperidinyl-, piperazinyl-, 4-methylpiperazinyl-, or morpholinyl-ring;
R10 is hydrogen, ($C_1$-$C_4$)alkyl, methoxyethyl, ethoxyethyl, methoxymethyl or ethoxymethyl;
B is hydrogen, fluorine, chlorine, ($C_1$-$C_4$)alkyl, ($C_1$-$C_4$)alkoxy, thienyl or N(R12)R13 wherein R12 and R13 independently of one another are hydrogen, ($C_1$-$C_4$)alkyl, or R12 and R13 together and with inclusion of the nitrogen atom to which they are bonded form a pyrrolidinyl-ring;
R14 is hydrogen or methyl;
or a salt thereof.

16. A compound of formula I according to claim 1 wherein
L is bond;
A is ($C_1$-$C_4$)alkyl, phenyl optionally substituted by R1 and/or R2, phenyl substituted by R4, naphthyl optionally substituted by R1 and/or R2, pyridyl optionally substituted by R1 and/or R2, pyridyl substituted by R5, pyrimidinyl optionally substituted by R1 and/or R2, pyrimidinyl substituted by R8;

R1 is fluorine, hydroxyl, nitro, amino, ($C_1$-$C_4$)alkyl, ($C_1$-$C_4$)alkoxy, ($C_1$-$C_4$)alkyl which is partially or completely substituted by fluorine, ($C_1$-$C_4$)alkoxy which is predominantly or completely substituted by fluorine, ($C_1$-$C_4$)alkoxy($C_1$-$C_2$)alkyl, ($C_1$-$C_4$)alkoxycarbonyl, or mono- or -di($C_1$-$C_4$)alkylamino;

R2 is hydroxyl, ($C_1$-$C_4$)alkyl, or ($C_1$-$C_4$)alkoxy or R1 and R2 when ortho to each other form a methylenedioxy group;

R4 is phenyl, phenoxy, benzylNHC(=O)NH—, or methylphenylsulfonylamino;

R5 is methylphenylsulfonylamino, or N(R6)R7, wherein R6 and R7 together and with inclusion of the nitrogen atom to which they are bonded form an azetidinyl-, piperidinyl-, piperazinyl-, 4-methylpiperazinyl-, or morpholinyl-ring;

R8 is hydrogen, fluorine, chlorine, ($C_1$-$C_4$)alkyl, ($C_1$-$C_4$)alkoxy, or thienyl;

R14 is hydrogen or methyl;

or a salt thereof.

17. A compound of formula I, which is one of the following compounds

- $N^2$-(2-aminophenyl)-$N^5$-biphenyl-4-yl-6,7-dihydro[1,3]thiazolo[5,4-c]pyridine-2,5(4H)-dicarboxamide,
- $N^2$-(2-aminophenyl)-$N^5$-[4-(dimethylamino)phenyl]-6,7-dihydro[1,3]thiazolo[5,4-c]pyridine-2,5(4H)-dicarboxamide,
- $N^2$-(2-aminophenyl)-$N^5$-(4-methoxyphenyl)-6,7-dihydro[1,3]thiazolo[5,4-c]pyridine-2,5(4H)-dicarboxamide,
- $N^2$-(2-aminophenyl)-$N^5$-benzyl-6,7-dihydro[1,3]thiazolo[5,4-c]pyridine-2,5(4H)-dicarboxamide,
- Methyl 4-[({2-[(2-aminophenyl)carbamoyl]-6,7-dihydro[1,3]thiazolo[5,4-c]pyridine-5(4H)-yl}carbonyl)amino]benzoate,
- $N^2$-(2-aminophenyl)-$N^5$-(4-phenoxyphenyl)-6,7-dihydro[1,3]thiazolo[5,4-c]pyridine-2,5(4H)-dicarboxamide,
- $N^2$-(2-aminophenyl)-$N^5$-1,3-benzodioxol-5-yl-6,7-dihydro[1,3]thiazolo[5,4-c]pyridine-2,5(4H)-dicarboxamide,
- $N^2$-(2-aminophenyl)-$N^5$-[2-(trifluoromethoxy)phenyl]-6,7-dihydro[1,3]thiazolo[5,4-c]pyridine-2,5(4H)-dicarboxamide,
- $N^2$-(2-aminophenyl)-$N^5$-[4-(trifluoromethoxy)phenyl]-6,7-dihydro[1,3]thiazolo[5,4-c]pyridine-2,5(4H)-dicarboxamide,
- $N^2$-(2-aminophenyl)-$N^5$-[2-(difluoromethoxy)phenyl]-6,7-dihydro[1,3]thiazolo[5,4-c]pyridine-2,5(4H)-dicarboxamide,
- $N^2$-(2-aminophenyl)-$N^5$-[4-(difluoromethoxy)phenyl]-6,7-dihydro[1,3]thiazolo[5,4-c]pyridine-2,5(4H)-dicarboxamide,
- $N^2$-(2-aminophenyl)-$N^5$-quinolin-3-yl-6,7-dihydro[1,3]thiazolo[5,4-c]pyridine-2,5(4H)-dicarboxamide,
- $N^2$-(2-aminophenyl)-$N^5$-(4-methylphenyl)-6,7-dihydro[1,3]thiazolo[5,4-c]pyridine-2,5(4H)-dicarboxamide,
- $N^2$-(2-aminophenyl)-$N^5$-(pyridin-3-ylmethyl)-6,7-dihydro[1,3]thiazolo[5,4-c]pyridine-2,5(4H)-dicarboxamide,
- $N^2$-(2-aminophenyl)-$N^5$-pyridin-4-yl-6,7-dihydro[1,3]thiazolo[5,4-c]pyridine-2,5(4H)-dicarboxamide,
- $N^2$-(2-aminophenyl)-$N^5$-(2-methoxyethyl)-6,7-dihydro[1,3]thiazolo[5,4-c]pyridine-2,5(4H)-dicarboxamide,
- $N^2$-(2-aminophenyl)-$N^5$-methyl-6,7-dihydro[1,3]thiazolo[5,4-c]pyridine-2,5(4H)-dicarboxamide
- $N^2$-(2-aminophenyl)-$N^5$-[3-(dimethylamino)phenyl]-6,7-dihydro[1,3]thiazolo[5,4-c]pyridine-2,5(4H)-dicarboxamide,
- $N^2$-(2-aminophenyl)-$N^5$-(3,4-dimethoxyphenyl)-6,7-dihydro[1,3]thiazolo[5,4-c]pyridine-2,5(4H)-dicarboxamide,
- $N^2$-(2-aminophenyl)-$N^5$-(2-methoxyethyl)-$N^5$-methyl-6,7-dihydro[1,3]thiazolo[5,4-c]pyridine-2,5(4H)-dicarboxamide,
- $N^2$-(2-aminophenyl)-$N^5$-ethyl-$N^5$-isopropyl-6,7-dihydro[1,3]thiazolo[5,4-c]pyridine-2,5(4H)-dicarboxamide,
- $N^2$-(2-aminophenyl)-$N^5$-[4-(dimethylamino)phenyl]-$N^5$-methyl-6,7-dihydro[1,3]thiazolo[5,4-c]pyridine-2,5(4H)-dicarboxamide,
- $N^2$-(2-aminophenyl)-$N^5$-[3-(dimethylamino)phenyl]-$N^5$-methyl-6,7-dihydro[1,3]thiazolo[5,4-c]pyridine-2,5(4H)-dicarboxamide,
- $N^2$-(2-aminophenyl)-$N^5$-(3,4-dimethoxyphenyl)-$N^5$-methyl-6,7-dihydro[1,3]thiazolo[5,4-c]pyridine-2,5(4H)-dicarboxamide,
- $N^2$-(2-aminophenyl)-$N^5$-(3,4-dimethoxyphenyl)-N-5-ethyl-6,7-dihydro[1,3]thiazolo[5,4-c]pyridine-2,5(4H)-dicarboxamide,
- $N^2$-(2-aminophenyl)-$N^5$-(3,4-dimethoxyphenyl)-$N^5$-(2-methoxyethyl)-6,7-dihydro[1,3]thiazolo[5,4-c]pyridine-2,5(4H)-dicarboxamide,
- $N^2$-(2-aminophenyl)-$N^5$-methyl-$N^5$-pyridin-3-yl-6,7-dihydro[1,3]thiazolo[5,4-c]pyridine-2,5(4H)-dicarboxamide,
- $N^2$-(2-aminophenyl)-$N^5$-ethyl-$N^5$-pyridin-3-yl-6,7-dihydro[1,3]thiazolo[5,4-c]pyridine-2,5(4H)-dicarboxamide,
- $N^2$-(2-aminophenyl)-$N^5$-1,3-benzodioxol-5-yl-$N^5$-ethyl-6,7-dihydro[1,3]thiazolo[5,4-c]pyridine-2,5(4H)-dicarboxamide,
- $N^2$-(2-aminophenyl)-$N^5$-1,3-benzodioxol-5-yl-$N^5$-(2-methoxyethyl)-6,7-dihydro[1,3]thiazolo[5,4-c]pyridine-2,5(4H)-dicarboxamide,
- $N^2$-(2-aminophenyl)-$N^5$-1,3-benzodioxol-5-yl-$N^5$-methyl-6,7-dihydro[1,3]thiazolo[5,4-c]pyridine-2,5(4H)-dicarboxamide,
- $N^2$-(2-aminophenyl)-$N^5$-[3-(4-methylpiperazin-1-yl)phenyl]-6,7-dihydro[1,3]thiazolo[5,4-c]pyridine-2,5(4H)-dicarboxamide,
- $N^2$-(2-aminophenyl)-$N^5$-(2-methoxyethyl)-$N^5$-pyridin-3-yl-6,7-dihydro[1,3]thiazolo[5,4-c]pyridine-2,5(4H)-dicarboxamide,
- $N^2$-(2-aminophenyl)-$N^5$-(6-morpholin-4-ylpyridin-3-yl)-6,7-dihydro[1,3]thiazolo[5,4-c]pyridine-2,5(4H)-dicarboxamide,
- $N^2$-(2-aminophenyl)-$N^5$-(6-azetidin-1-ylpyridin-3-yl)-6,7-dihydro[1,3]thiazolo[5,4-c]pyridine-2,5(4H)-dicarboxamide,
- $N^2$-(2-aminophenyl)-$N^5$-[6-(dimethylamino)pyridin-3-yl]-6,7-dihydro[1,3]thiazolo[5,4-c]pyridine-2,5(4H)-dicarboxamide,
- $N^2$-(2-aminophenyl)-$N^5$-[6-(4-methylpiperazin-1-yl)pyridin-3-yl]-6,7-dihydro[1,3]thiazolo[5,4-c]pyridine-2,5(4H)-dicarboxamide,
- $N^2$-(2-aminophenyl)-$N^5$-(6-methoxypyridin-3-yl)-6,7-dihydro[1,3]thiazolo[5,4-c]pyridine-2,5(4H)-dicarboxamide,
- $N^2$-(2-aminophenyl)-$N^5$-pyridin-3-yl-6,7-dihydro[1,3]thiazolo[5,4-c]pyridine-2,5(4H)-dicarboxamide,
- $N^2$-(2-aminophenyl)-$N^5$-butyl-6,7-dihydro[1,3]thiazolo[5,4-c]pyridine-2,5(4H)-dicarboxamide,
- $N^2$-(2-aminophenyl)-$N^5$-(4-pyridin-3-ylcyclohexyl)-6,7-dihydro[1,3]thiazolo[5,4-c]pyridine-2,5(4H)-dicarboxamide, N²-(2-aminophenyl)-N⁵-piperidin-4-yl-6,7-dihydro[1,3]thiazolo[5,4-c]pyridine-2,5(4H)-dicarboxamide, N²-(2-amino-5-methoxyphenyl)-N⁵-(4-methoxyphenyl)-6,7-dihydro[1,3]thiazolo[5,4-c]pyridine-2,5(4H)-dicarboxamide, N²-(2-aminophenyl)-N⁵-(4-pyridin-4-ylcyclohexyl)-6,7-dihydro[1,3]thiazolo[5,4-c]pyridine-2,5(4H)-dicarboxamide, N²-(2-amino-5-isopropylphenyl)-N⁵-(4-methoxyphenyl)-6,7-dihydro[1,3]thiazolo[5,4-c]pyridine-2,5(4H)-dicarboxamide, N²-(2-amino-5-methoxyphenyl)-N⁵-isoquinolin-5-yl-6,7-dihydro[1,3]thiazolo[5,4-c]pyridine-2,5(4H)-dicarboxamide, N²-(2-amino-5-methoxyphenyl)-N⁵-[4-(dimethylamino)phenyl]-6,7-dihydro[1,3]thiazolo[5,4-c]pyridine-2,5(4H)-dicarboxamide, N²-(2-amino-5-isopropylphenyl)-N⁵-(3,4-dimethoxyphenyl)-6,7-dihydro[1,3]thiazolo[5,4-c]pyridine-2,5(4H)-dicarboxamide, N²-(2-amino-5-isopropylphenyl)-N⁵-isoquinolin-5-yl-6,7-dihydro[1,3]thiazolo[5,4-c]pyridine-2,5(4H)-dicarboxamide, N²-(2-amino-5-isopropylphenyl)-N⁵-[4-(dimethylamino)phenyl]-6,7-dihydro[1,3]thiazolo[5,4-c]pyridine-2,5(4H)-dicarboxamide, N²-(2-amino-5-methoxyphenyl)-N⁵-(4-fluorophenyl)-6,7-dihydro[1,3]thiazolo[5,4-c]pyridine-2,5(4H)-dicarboxamide, N²-(2-amino-5-isopropylphenyl)-N⁵-(4-fluorophenyl)-6,7-dihydro[1,3]thiazolo[5,4-c]pyridine-2,5(4H)-dicarboxamide, N²-[2-amino-5-(dimethylamino)phenyl]-N⁵-(4-methoxyphenyl)-6,7-dihydro[1,3]thiazolo[5,4-c]pyridine-2,5(4H)-dicarboxamide, N²-[2-amino-5-(2-thienyl)phenyl]-N⁵-(4-methoxyphenyl)-6,7-dihydro[1,3]thiazolo[5,4-c]pyridine-2,5(4H)-dicarboxamide, N²-[2-amino-5-(2-thienyl)phenyl]-N⁵-[4-(dimethylamino)phenyl]-6,7-dihydro[1,3]thiazolo[5,4-c]pyridine-2,5(4H)-dicarboxamide, N²-[2-amino-5-(3-thienyl)phenyl]-N⁵-(4-methoxyphenyl)-6,7-dihydro[1,3]thiazolo[5,4-c]pyridine-2,5(4H)-dicarboxamide, N²-[2-amino-5-(dimethylamino)phenyl]-N⁵-[4-(dimethylamino)phenyl]-6,7-dihydro[1,3]thiazolo[5,4-c]pyridine-2,5(4H)-dicarboxamide, N²-(2-amino-5-pyrrolidin-1-ylphenyl)-N⁵-(4-methoxyphenyl)-6,7-dihydro[1,3]thiazolo[5,4-c]pyridine-2,5(4H)-dicarboxamide, N²-[2-amino-5-(3-thienyl)phenyl]-N⁵-[4-(dimethylamino)phenyl]-6,7-dihydro[1,3]thiazolo[5,4-c]pyridine-2,5(4H)-dicarboxamide, N²-(2-amino-5-isopropylphenyl)-N⁵-pyridin-3-yl-6,7-dihydro[1,3]thiazolo[5,4-c]pyridine-2,5(4H)-dicarboxamide, N²-[2-amino-5-(dimethylamino)phenyl]-N⁵-(3,4-dimethoxyphenyl)-6,7-dihydro[1,3]thiazolo[5,4-c]pyridine-2,5(4H)-dicarboxamide, N²-(2-aminophenyl)-N⁵-isoquinolin-5-yl-6,7-dihydro[1,3]thiazolo[5,4-c]pyridine-2,5(4H)-dicarboxamide, N²-(2-aminophenyl)-N⁵-[3-(dimethylamino)phenyl]-6,7-dihydro[1,3]thiazolo[5,4-c]pyridine-2,5(4H)-dicarboxamide dihydrochloride, N-(2-aminophenyl)-5-[{[4-(dimethylamino)phenyl]amino}(oxo)acetyl]-4,5,6,7-tetrahydro[1,3]thiazolo[5,4-c]pyridine-2-carboxamide, N-(2-aminophenyl)-5-{[(4-methoxyphenyl)amino](oxo)acetyl}-4,5,6,7-tetrahydro[1,3]thiazolo[5,4-c]pyridine-2-carboxamide, N-(2-aminophenyl)-5-{[(3,4-dimethoxyphenyl)amino](oxo)acetyl}-4,5,6,7-tetrahydro[1,3]thiazolo[5,4-c]pyridine-2-carboxamide, N-(2-aminophenyl)-5-{oxo[(4-pyridin-4-ylcyclohexyl)amino]acetyl}-4,5,6,7-tetrahydro[1,3]thiazolo[5,4-c]pyridine-2-carboxamide, N-(2-aminophenyl)-5-[(isoquinolin-5-ylamino)(oxo)acetyl]-4,5,6,7-tetrahydro[1,3]thiazolo[5,4-c]pyridine-2-carboxamide, N-(2-aminophenyl)-5-{oxo[(4-pyridin-3-ylcyclohexyl)amino]acetyl}-4,5,6,7-tetrahydro[1,3]thiazolo[5,4-c]pyridine-2-carboxamide, N-(2-aminophenyl)-5-{[(6-methoxypyridin-3-yl)amino](oxo)acetyl}-4,5,6,7-tetrahydro[1,3]thiazolo[5,4-c]pyridine-2-carboxamide, N-(2-aminophenyl)-5-[{[(6-(dimethylamino)pyridin-3-yl]amino}(oxo)acetyl]-4,5,6,7-tetrahydro[1,3]thiazolo[5,4-c]pyridine-2-carboxamide, N-(2-aminophenyl)-5-(oxo{[4-(trifluoromethoxy)phenyl]amino}acetyl)-4,5,6,7-tetrahydro[1,3]thiazolo[5,4-c]pyridine-2-carboxamide, N-(2-aminophenyl)-5-{[(6-morpholin-4-ylpyridin-3-yl)amino](oxo)acetyl}-4,5,6,7-tetrahydro[1,3]thiazolo[5,4-c]pyridine-2-carboxamide, N-(2-aminophenyl)-5-[(1,3-benzodioxol-5-ylamino)(oxo)acetyl]-4,5,6,7-tetrahydro[1,3]thiazolo[5,4-c]pyridine-2-carboxamide, N-(2-aminophenyl)-5-{[(4-methylphenyl)amino](oxo)acetyl}-4,5,6,7-tetrahydro[1,3]thiazolo[5,4-c]pyridine-2-carboxamide, N-(2-aminophenyl)-5-{[(5-methylpyridin-2-yl)amino](oxo)acetyl}-4,5,6,7-tetrahydro[1,3]thiazolo[5,4-c]pyridine-2-carboxamide, N-(2-aminophenyl)-5-[oxo(quinolin-3-ylamino)acetyl]-4,5,6,7-tetrahydro[1,3]thiazolo[5,4-c]pyridine-2-carboxamide, N-(2-amino-5-methoxyphenyl)-5-{[(4-methoxyphenyl)amino](oxo)acetyl}-4,5,6,7-tetrahydro[1,3]thiazolo[5,4-c]pyridine-2-carboxamide, N-(2-aminophenyl)-5-[(butylamino)(oxo)acetyl]-4,5,6,7-tetrahydro[1,3]thiazolo[5,4-c]pyridine-2-carboxamide, N-(2-amino-5-isopropylphenyl)-5-{[(3,4-dimethoxyphenyl)amino](oxo)acetyl}-4,5,6,7-tetrahydro[1,3]thiazolo[5,4-c]pyridine-2-carboxamide, N-(2-amino-5-isopropylphenyl)-5-{[(4-methoxyphenyl)amino](oxo)acetyl}-4,5,6,7-tetrahydro[1,3]thiazolo[5,4-c]pyridine-2-carboxamide, N-(2-amino-5-methoxyphenyl)-5-{[(3,4-dimethoxyphenyl)amino](oxo)acetyl}-4,5,6,7-tetrahydro[1,3]thiazolo[5,4-c]pyridine-2-carboxamide, N-(2-amino-5-methoxyphenyl)-5-[(butylamino)(oxo)acetyl]-4,5,6,7-tetrahydro[1,3]thiazolo[5,4-c]pyridine-2-carboxamide, N-(2-amino-5-isopropylphenyl)-5-[(butylamino)(oxo)acetyl]-4,5,6,7-tetrahydro[1,3]thiazolo[5,4-c]pyridine-2-carboxamide, N-(2-aminophenyl)-5-[(benzylamino)(oxo)acetyl]-4,5,6,7-tetrahydro[1,3]thiazolo[5,4-c]pyridine-2-carboxamide, N-(2-aminophenyl)-5-[{[6-(4-methylpiperazin-1-yl)pyridin-3-yl]amino}(oxo)acetyl]-4,5,6,7-tetrahydro[1,3]thiazolo[5,4-c]pyridine-2-carboxamide, N-(2-aminophenyl)-5-{oxo[(pyridin-3-ylmethyl)amino]
acetyl}-4,5,6,7-tetrahydro[1,3]thiazolo[5,4-c]pyridine-
2-carboxamide, N-(2-aminophenyl)-5-(biphenyl-4-ylcarbonyl)-4,5,6,7-
tetrahydro[1,3]thiazolo[5,4-c]pyridine-2-carboxamide, N-(2-aminophenyl)-5-(4-methylbenzoyl)-4,5,6,7-tetrahy-
dro[1,3]thiazolo[5,4-c]pyridine-2-carboxamide, Methyl 4-({2-[(2-aminophenyl)carbamoyl]-6,7-dihydro
[1,3]thiazolo[5,4-c]pyridin-5(4H)-yl}carbonyl)ben-
zoate, N-(2-aminophenyl)-5-[4-(dimethylamino)benzoyl]-4,5,6,
7-tetrahydro[1,3]thiazolo[5,4-c]pyridine-2-carboxam-
ide, 5-Acetyl-N-(2-aminophenyl)-4,5,6,7-tetrahydro[1,3]thia-
zolo[5,4-c]pyridine-2-carboxamide, N-(2-aminophenyl)-5-(4-methoxybenzoyl)-4,5,6,7-tet-
rahydro[1,3]thiazolo[5,4-c]pyridine-2-carboxamide, N-(2-aminophenyl)-5-(quinolin-3-ylcarbonyl)-4,5,6,7-
tetrahydro[1,3]thiazolo[5,4-c]pyridine-2-carboxamide, N-(2-aminophenyl)-5-(2-naphthoyl)-4,5,6,7-tetrahydro
[1,3]thiazolo[5,4-c]pyridine-2-carboxamide, N-(2-aminophenyl)-5-[(6-methylpyridin-3-yl)carbonyl]-
4,5,6,7-tetrahydro[1,3]thiazolo[5,4-c]pyridine-2-car-
boxamide, N-(2-aminophenyl)-5-[3-(dimethylamino)benzoyl]-4,5,6,
7-tetrahydro[1,3]thiazolo[5,4-c]pyridine-2-carboxam-
ide, N-(2-aminophenyl)-5-(anilinocarbonothioyl)-4,5,6,7-tet-
rahydro[1,3]thiazolo[5,4-c]pyridine-2-carboxamide, N-(2-aminophenyl)-5-({[4-(dimethylamino)phenyl]
amino}carbonothioyl)-4,5,6,7-tetrahydro[1,3]thiazolo
[5,4-c]pyridine-2-carboxamide, N-(2-aminophenyl)-5-[(piperidin-4-ylamino)carbono-
thioyl]-4,5,6,7-tetrahydro[1,3]thiazolo[5,4-c]pyridine-
2-carboxamide, N-(2-aminophenyl)-5-{[(4-pyridin-3-ylcyclohexyl)
amino]carbonothioyl}-4,5,6,7-tetrahydro[1,3]thiazolo
[5,4-c]pyridine-2-carboxamide, N-(2-amino-5-methoxyphenyl)-5-(anilinocarbonothioyl)-
4,5,6,7-tetrahydro[1,3]thiazolo[5,4-c]pyridine-2-car-
boxamide, N-(2-aminophenyl)-5-[(pyridin-3-ylamino)carbono-
thioyl]-4,5,6,7-tetrahydro[1,3]thiazolo[5,4-c]pyridine-
2-carboxamide, N-(2-aminophenyl)-5-[(isoquinolin-5-ylamino)carbono-
thioyl]-4,5,6,7-tetrahydro[1,3]thiazolo[5,4-c]pyridine-
2-carboxamide, N-(2-aminophenyl)-5-[(butylamino)carbonothioyl]-4,5,6,
7-tetrahydro[1,3]thiazolo[5,4-c]pyridine-2-carboxam-
ide, N-(2-amino-5-methoxyphenyl)-5-{[(4-methoxyphenyl)
amino]carbonothioyl}-4,5,6,7-tetrahydro[1,3]thiazolo
[5,4-c]pyridine-2-carboxamide, N-(2-amino-5-methoxyphenyl)-5-[(pyridin-3-ylamino)
carbonothioyl]-4,5,6,7-tetrahydro[1,3]thiazolo[5,4-c]
pyridine-2-carboxamide, N-(2-amino-5-isopropylphenyl)-5-[(pyridin-3-ylamino)
carbonothioyl]-4,5,6,7-tetrahydro[1,3]thiazolo[5,4-c]
pyridine-2-carboxamide, N-(2-amino-5-isopropylphenyl)-5-(anilinocarbono-
thioyl)-4,5,6,7-tetrahydro[1,3]thiazolo[5,4-c]pyridine-
2-carboxamide, N-(2-amino-5-isopropylphenyl)-5-{[(4-methoxyphenyl)
amino]carbonothioyl}-4,5,6,7-tetrahydro[1,3]thiazolo
[5,4-c]pyridine-2-carboxamide, N-(2-aminophenyl)-5-isopropylphenyl)-5-{imino[(4-
methoxyphenyl)amino]methyl}-4,5,6,7-tetrahydro[1,
3]thiazolo[5,4-c]pyridine-2-carboxamide, N-(2-amino-5-isopropylphenyl)-5-{imino[(4-methox-
yphenyl)amino]methyl}-4,5,6,7-tetrahydro[1,3]thia-
zolo[5,4-c]pyridine-2-carboxamide, N-(2-aminophenyl)-5-[(benzylamino)(imino)methyl]-4,
5,6,7-tetrahydro[1,3]thiazolo[5,4-c]pyridine-2-car-
boxamide, N-(2-aminophenyl)-5-[anilino(methylimino)methyl]-4,5,
6,7-tetrahydro[1,3]thiazolo[5,4-c]pyridine-2-carboxa-
mide, N-(2-amino-5-methoxyphenyl)-5-[[(4-methoxyphenyl)
amino](methylimino)methyl]-4,5,6,7-tetrahydro[1,3]
thiazolo[5,4-c]pyridine-2-carboxamide, N-(2-aminophenyl)-5-[anilino(cyanoimino)methyl]-4,5,
6,7-tetrahydro[1,3]thiazolo[5,4-c]pyridine-2-carboxa-
mide, N-(2-aminophenyl)-5-{(cyanoimino)[(4-methoxyphenyl)
amino]methyl}-4,5,6,7-tetrahydro[1,3]thiazolo[5,4-c]
pyridine-2-carboxamide, N-(2-aminophenyl)-5-{(cyanoimino)[(3,4-dimethox-
yphenyl)amino]methyl}-4,5,6,7-tetrahydro[1,3]thia-
zolo[5,4-c]pyridine-2-carboxamide, N-(2-aminophenyl)-5-{(cyanoimino)[(2-methylphenyl)
amino]methyl}-4,5,6,7-tetrahydro[1,3]thiazolo[5,4-c]
pyridine-2-carboxamide, N-(2-aminophenyl)-5-[(cyanoimino){[4-(dimethylamino)
phenyl]amino}methyl]-4,5,6,7-tetrahydro[1,3]thiazolo
[5,4-c]pyridine-2-carboxamide, N-(2-aminophenyl)-5-[(cyanoimino)(pentylamino)me-
thyl]-4,5,6,7-tetrahydro[1,3]thiazolo[5,4-c]pyridine-2-
carboxamide, N-(2-aminophenyl)-5-[(benzylamino)(cyanoimino)me-
thyl]-4,5,6,7-tetrahydro[1,3]thiazolo[5,4-c]pyridine-2-
carboxamide, N-(2-amino-5-methoxyphenyl)-5-[(cyanoamino)(phe-
nylimino)methyl]-4,5,6,7-tetrahydro[1,3]thiazolo[5,4-
c]pyridine-2-carboxamide, N-(2-amino-5-methoxyphenyl)-5-{(cyanoamino)[(4-
methoxyphenyl)imino]methyl}-4,5,6,7-tetrahydro[1,3]
thiazolo[5,4-c]pyridine-2-carboxamide, N-(2-amino-5-isopropylphenyl)-5-{(cyanoamino)[(4-
methoxyphenyl)imino]methyl}-4,5,6,7-tetrahydro[1,3]
thiazolo[5,4-c]pyridine-2-carboxamide, N-(2-aminophenyl)-5-[N-phenylethanimidoyl]-4,5,6,7-
tetrahydro[1,3]thiazolo[5,4-c]pyridine-2-carboxamide, N-(2-aminophenyl)-5-[N-(3,4-dimethoxyphenyl)etha-
nimidoyl]-4,5,6,7 tetrahydro[1,3]thiazolo[5,4-c]pyri-
dine-2-carboxamide, N-(2-aminophenyl)-5-[N-(4-methoxyphenyl)ethanimi-
doyl]-4,5,6,7-tetrahydro[1,3]thiazolo[5,4-c]pyridine-2-
carboxamide, N-(2-amino-5-methoxyphenyl)-5-[N-phenylethanimi-
doyl]-4,5,6,7-tetrahydro[1,3]thiazolo[5,4-c]pyridine-2-
carboxamide, N-(2-amino-5-methoxyphenyl)-5-[N-(4-methoxyphenyl)
ethanimidoyl]-4,5,6,7-tetrahydro[1,3]thiazolo[5,4-c]
pyridine-2-carboxamide, N-(2-amino-5-methoxyphenyl)-5-[N-(3,4-dimethoxyphe-
nyl)ethanimidoyl]-4,5,6,7-tetrahydro[1,3]thiazolo[5,4-
c]pyridine-2-carboxamide, N-(2-amino-5-isopropylphenyl)-5-[N-(4-methoxyphenyl)
ethanimidoyl]-4,5,6,7-tetrahydro[1,3]thiazolo[5,4-c]
pyridine-2-carboxamide, N-(2-amino-5-isopropylphenyl)-5-[N-(3,4-dimethoxyphenyl)ethanimidoyl]-4,5,6,7-tetrahydro[1,3]thiazolo[5,4-c]pyridine-2-carboxamide, N-(2-aminophenyl)-5-{N-[4-(dimethylamino)phenyl]ethanimidoyl}-4,5,6,7-tetrahydro[1,3]thiazolo[5,4-c]pyridine-2-carboxamide, N-(2-amino-5-isopropylphenyl)-5-[N-phenylethanimidoyl]-4,5,6,7-tetrahydro[1,3]thiazolo[5,4-c]pyridine-2-carboxamide, N-(2-aminophenyl)-5-[1-anilino-2-nitrovinyl]-4,5,6,7-tetrahydro[1,3]thiazolo[5,4-c]pyridine-2-carboxamide, N-(2-aminophenyl)-5-{1-[(4-methoxyphenyl)amino]-2-nitrovinyl}-4,5,6,7-tetrahydro[1,3]thiazolo[5,4-c]pyridine-2-carboxamide, N-(2-aminophenyl)-5-[1-(butylamino)-2-nitrovinyl]-4,5,6,7-tetrahydro[1,3]thiazolo[5,4-c]pyridine-2-carboxamide, N-(2-aminophenyl)-5-{1-[(4-isopropylphenyl)amino]-2-nitrovinyl}-4,5,6,7-tetrahydro[1,3]thiazolo[5,4-c]pyridine-2-carboxamide, N-(2-aminophenyl)-5-[1-{[4-(dimethylamino)phenyl]amino}-2-nitrovinyl]-4,5,6,7-tetrahydro[1,3]thiazolo[5,4-c]pyridine-2-carboxamide, N-(2-aminophenyl)-5-{1-[(3,4-dimethoxyphenyl)amino]-2-nitrovinyl}-4,5,6,7-tetrahydro[1,3]thiazolo[5,4-c]pyridine-2-carboxamide, N-(2-amino-5-methoxyphenyl)-5-{1-[(4-methoxyphenyl)amino]-2-nitrovinyl}-4,5,6,7-tetrahydro[1,3]thiazolo[5,4-c]pyridine-2-carboxamide, N-(2-amino-5-methoxyphenyl)-5-{1-[(4-isopropylphenyl)amino]-2-nitrovinyl}-4,5,6,7-tetrahydro[1,3]thiazolo[5,4-c]pyridine-2-carboxamide, N-(2-amino-5-methoxyphenyl)-5-[1-{[4-(dimethylamino)phenyl]amino}-2-nitrovinyl]-4,5,6,7-tetrahydro[1,3]thiazolo[5,4-c]pyridine-2-carboxamide, N-(2-amino-5-isopropylphenyl)-5-[1-anilino-2-nitrovinyl]-4,5,6,7-tetrahydro[1,3]thiazolo[5,4-c]pyridine-2-carboxamide, N-[2-amino-5-(1-methylethyl)phenyl]-5-{1-[(4-methoxyphenyl)amino]-2-nitroethenyl}-4,5,6,7-tetrahydro[1,3]thiazolo[5,4-c]pyridine-2-carboxamide, N-(2-amino-5-isopropylphenyl)-5-[1-{[4-(dimethylamino)phenyl]amino}-2-nitrovinyl]-4,5,6,7-tetrahydro[1,3]thiazolo[5,4-c]pyridine-2-carboxamide, N-(2-amino-5-isopropylphenyl)-5-{1-[(4-isopropylphenyl)amino]-2-nitrovinyl}-4,5,6,7-tetrahydro[1,3]thiazolo[5,4-c]pyridine-2-carboxamide, N-(2-amino-5-methoxyphenyl)-5-{1-[(4-fluorophenyl)amino]-2-nitrovinyl}-4,5,6,7-tetrahydro[1,3]thiazolo[5,4-c]pyridine-2-carboxamide, N-(2-aminophenyl)-5-[(4-methylphenyl)sulfonyl]-4,5,6,7-tetrahydro[1,3]thiazolo[5,4-c]pyridine-2-carboxamide, N-(2-aminophenyl)-5-(benzylsulfonyl)-4,5,6,7-tetrahydro[1,3]thiazolo[5,4-c]pyridine-2-carboxamide, N-(2-aminophenyl)-5-(biphenyl-4-ylsulfonyl)-4,5,6,7-tetrahydro[1,3]thiazolo[5,4-c]pyridine-2-carboxamide, N-(2-aminophenyl)-5-[(4-methoxyphenyl)sulfonyl]-4,5,6,7-tetrahydro[1,3]thiazolo[5,4-c]pyridine-2-carboxamide, N-(2-aminophenyl)-5-(methylsulfonyl)-4,5,6,7-tetrahydro[1,3]thiazolo[5,4-c]pyridine-2-carboxamide, 5-[(4-acetamidophenyl)sulfonyl]-N-(2-aminophenyl)-4,5,6,7-tetrahydro[1,3]thiazolo[5,4-c]pyridine-2-carboxamide, N-(2-aminophenyl)-5-(2-naphthylsulfonyl)-4,5,6,7-tetrahydro[1,3]thiazolo[5,4-c]pyridine-2-carboxamide, N-(2-aminophenyl)-5-(2-thienylsulfonyl)-4,5,6,7-tetrahydro[1,3]thiazolo[5,4-c]pyridine-2-carboxamide, Methyl 3-({2-[(2-aminophenyl)carbamoyl]-6,7-dihydro[1,3]thiazolo[5,4-c]pyridine-5(4H)-yl}sulfonyl)thiophene-2-carboxylate, 5-[(2-acetamido-4-methyl-1,3-thiazol-5-yl)sulfonyl]-N-(2-aminophenyl)-4,5,6,7-tetrahydro[1,3]thiazolo[5,4-c]pyridine-2-carboxamide, N-(2-aminophenyl)-5-[(3-methoxyphenyl)sulfonyl]-4,5,6,7-tetrahydro[1,3]thiazolo[5,4-c]pyridine-2-carboxamide, N-(2-aminophenyl)-5-{[4-(trifluoromethyl)phenyl]sulfonyl}-4,5,6,7-tetrahydro[1,3]thiazolo[5,4-c]pyridine-2-carboxamide, N-(2-aminophenyl)-5-{[3-(trifluoromethyl)phenyl]sulfonyl}-4,5,6,7-tetrahydro[1,3]thiazolo[5,4-c]pyridine-2-carboxamide, N-(2-aminophenyl)-5-[(3-fluorophenyl)sulfonyl]-4,5,6,7-tetrahydro[1,3]thiazolo[5,4-c]pyridine-2-carboxamide, N-(2-aminophenyl)-5-(isopropylsulfonyl)-4,5,6,7-tetrahydro[1,3]thiazolo[5,4-c]pyridine-2-carboxamide, N-(2-aminophenyl)-5-{[3-(difluoromethoxy)phenyl]sulfonyl}-4,5,6,7-tetrahydro[1,3]thiazolo[5,4-c]pyridine-2-carboxamide, N-(2-aminophenyl)-5-{[4-(difluoromethoxy)phenyl]sulfonyl}-4,5,6,7-tetrahydro[1,3]thiazolo[5,4-c]pyridine-2-carboxamide, N-(2-aminophenyl)-5-{[3-(trifluoromethoxy)phenyl]sulfonyl}-4,5,6,7-tetrahydro[1,3]thiazolo[5,4-c]pyridine-2-carboxamide, N-(2-aminophenyl)-5-{[4-(trifluoromethoxy)phenyl]sulfonyl}-4,5,6,7-tetrahydro[1,3]thiazolo[5,4-c]pyridine-2-carboxamide, N-(2-amino-5-methoxyphenyl)-5-[(4-methylphenyl)sulfonyl]-4,5,6,7-tetrahydro[1,3]thiazolo[5,4-c]pyridine-2-carboxamide N-(2-amino-5-isopropylphenyl)-5-[(4-methylphenyl)sulfonyl]-4,5,6,7-tetrahydro[1,3]thiazolo[5,4-c]pyridine-2-carboxamide, N-(2-amino-5-methoxyphenyl)-5-[(4-methoxyphenyl)sulfonyl]-4,5,6,7-tetrahydro[1,3]thiazolo[5,4-c]pyridine-2-carboxamide, N-(2-aminophenyl)-5-(phenoxyacetyl)-4,5,6,7-tetrahydro[1,3]thiazolo[5,4-c]pyridine-2-carboxamide N-(2-aminophenyl)-5-[(4-methylphenoxy)acetyl]-4,5,6,7-tetrahydro[1,3]thiazolo[5,4-c]pyridine-2-carboxamide, N-(2-aminophenyl)-5-[(4-methoxyphenoxy)acetyl]-4,5,6,7-tetrahydro[1,3]thiazolo[5,4-c]pyridine-2-carboxamide, N-(2-aminophenyl)-5-[(2-naphthyloxy)acetyl]-4,5,6,7-tetrahydro[1,3]thiazolo[5,4-c]pyridine-2-carboxamide, N-(2-aminophenyl)-5-[(biphenyl-4-yloxy)acetyl]-4,5,6,7-tetrahydro[1,3]thiazolo[5,4-c]pyridine-2-carboxamide, N-(2-aminophenyl)-5-(methoxyacetyl)-4,5,6,7-tetrahydro[1,3]thiazolo[5,4-c]pyridine-2-carboxamide, N-(2-amino-5-isopropylphenyl)-5-[(4-methoxyphenoxy)acetyl]-4,5,6,7-tetrahydro[1,3]thiazolo[5,4-c]pyridine-2-carboxamide, N-(2-aminophenyl)-5-[(3-methoxyphenoxy)acetyl]-4,5,6,7-tetrahydro[1,3]thiazolo[5,4-c]pyridine-2-carboxamide, Methyl 2-[(2-aminophenyl)carbamoyl]-6,7-dihydro[1,3]thiazolo[5,4-c]pyridine-5(4H)-carboxylate, Biphenyl-4-yl 2-[(2-aminophenyl)carbamoyl]-6,7-dihydro[1,3]thiazolo[5,4-c]pyridine-5(4H)-carboxylate, 4-Methylphenyl 2-[(2-aminophenyl)carbamoyl]-6,7-dihydro[1,3]thiazolo[5,4-c]pyridine-5(4H)-carboxylate,
4-Methoxyphenyl 2-[(2-aminophenyl)carbamoyl]-6,7-dihydro[1,3]thiazolo[5,4-c]pyridine-5(4H)-carboxylate,
4-(Propoxycarbonyl)phenyl 2-[(2-aminophenyl)carbamoyl]-6,7-dihydro[1,3]thiazolo[5,4-c]pyridine-5(4H)-carboxylate,
2-Naphthyl 2-[(2-aminophenyl)carbamoyl]-6,7-dihydro[1,3]thiazolo[5,4-c]pyridine-5(4H)-carboxylate,
3,4-Dimethoxyphenyl 2-[(2-aminophenyl)carbamoyl]-6,7-dihydro[1,3]thiazolo[5,4-c]pyridine-5(4H)-carboxylate,
Butyl 2-[(2-aminophenyl)carbamoyl]-6,7-dihydro[1,3]thiazolo[5,4-c]pyridine-5(4H)-carboxylate,
Benzyl 2-[(2-aminophenyl)carbamoyl]-6,7-dihydro[1,3]thiazolo[5,4-c]pyridine-5(4H)-carboxylate,
Pyridin-3-ylmethyl 2-[(2-aminophenyl)carbamoyl]-6,7-dihydro[1,3]thiazolo[5,4-c]pyridine-5(4H)-carboxylate,
N-(2-aminophenyl)-5-[3-(1,3-benzodioxol-5-yl)prop-2-enoyl]-4,5,6,7-tetrahydro[1,3]thiazolo[5,4-c]pyridine-2-carboxamide,
N-(2-aminophenyl)-5-[3-(3,4-dihydroxyphenyl)prop-2-enoyl]-4,5,6,7-tetrahydro[1,3]thiazolo[5,4-c]pyridine-2-carboxamide,
N-(2-aminophenyl)-5-pyrimidin-2-yl-4,5,6,7-tetrahydro[1,3]thiazolo[5,4-c]pyridine-2-carboxamide,
N-(2-aminophenyl)-5-(4-pyridin-3-ylpyrimidin-2-yl)-4,5,6,7-tetrahydro[1,3]thiazolo[5,4-c]pyridine-2-carboxamide,
N-(2-aminophenyl)-5-(5-nitropyridin-2-yl)-4,5,6,7-tetrahydro[1,3]thiazolo[5,4-c]pyridine-2-carboxamide,
N-(2-aminophenyl)-5-[5-(trifluoromethyl)pyridin-2-yl]-4,5,6,7-tetrahydro[1,3]thiazolo[5,4-c]pyridine-2-carboxamide,
N-(2-aminophenyl)-5-(5-{[(4-methylphenyl)sulfonyl]amino}pyrimidin-2-yl)-4,5,6,7-tetrahydro[1,3]thiazolo[5,4-c]pyridine-2-carboxamide,
N-(2-aminophenyl)-5-(5-{[(4-methylphenyl)sulfonyl]amino}pyridine-2-yl)-4,5,6,7-tetrahydro[1,3]thiazolo[5,4-c]pyridine-2-carboxamide,
N-(2-aminophenyl)-5-{4-[(benzylcarbamoyl)amino]phenyl}-4,5,6,7-tetrahydro[1,3]thiazolo[5,4-c]pyridine-2-carboxamide,
N-(2-aminophenyl)-5-(4-{[(4-methylphenyl)sulfonyl]amino}phenyl)-4,5,6,7-tetrahydro[1,3]thiazolo[5,4-c]pyridine-2-carboxamide,
N-(2-aminophenyl)-5-[(4-methylphenyl)sulfonyl]-4,5,6,7-tetrahydrothieno[3,2-c]pyridine-2-carboxamide,
N-(2-aminophenyl)-5-[(4-methylphenyl)sulfonyl]-4,5,6,7-tetrahydrofuro[3,2-c]pyridine-2-carboxamide,
N-(2-aminophenyl)-1-methyl-5-[(4-methylphenyl)sulfonyl]-4,5,6,7-tetrahydro-1H-pyrrolo[3,2-c]pyridine-2-carboxamide,
$N^2$-(2-aminophenyl)-$N^5$-pyridine-3-yl-6,7-dihydrothieno[3,2-c]pyridine-2,5(4H)-dicarboxamide,
6,7-Dihydro-4H-thieno[3,2-c]pyridine-2,5-dicarboxylic acid 2-[(2-amino-phenyl)-amide]5-[(2-difluoromethoxy-phenyl)-amide], $N^2$-(2-aminophenyl)-$N^5$-(3,4-dimethoxyphenyl)-6,7-dihydrothieno[3,2-c]pyridine-2,5(4H)-dicarboxamide,
$N^2$-[2-amino-5-(2-thienyl)phenyl]-$N^5$-butyl-6,7-dihydrothieno[3,2-c]pyridine-2,5(4H)-dicarboxamide,
$N^2$-[2-amino-5-(2-thienyl)phenyl]-$N^5$-pyridine-3-yl-6,7-dihydrothieno[3,2-c]pyridine-2,5(4H)-dicarboxamide,
$N^2$-(2-amino-5-thiophene-2-ylphenyl)-$N^5$-(4-methoxyphenyl)-6,7-dihydrothieno[3,2-c]pyridine-2,5(4H)-dicarboxamide,
$N^2$-(2-aminophenyl)-$N^5$-(2-methoxyethyl)-6,7-dihydrothieno[3,2-c]pyridine-2,5(4H)-dicarboxamide,
$N^2$-(2-aminophenyl)-$N^5$-pyridine-3-yl-6,7-dihydrothieno[3,2-c]pyridine-2,5-(4H)dicarboxamide,
3,4-dimethoxyphenyl 2-[(2-aminophenyl)carbamoyl]-6,7-dihydrothieno[3,2-c]pyridine-5(4H)-carboxylate,
$N^2$-(2-aminophenyl)-1-methyl-$N^5$-pyridine-3-yl-1,4,6,7-tetrahydro-5H-pyrrolo[3,2-c]pyridine-2,5-dicarboxamide,
$N^2$-(2-aminophenyl)-$N^5$-(3,4-dimethoxyphenyl)-1-methyl-1,4,6,7-tetrahydro-5H-pyrrolo[3,2-c]pyridine-2,5-dicarboxamide,
2-(difluoromethoxy)phenyl 2-[(2-aminophenyl)carbamoyl]-1-methyl-1,4,6,7-tetrahydro-5H-pyrrolo[3,2-c]pyridine-5-carboxylate,
3,4-dimethoxyphenyl 2-[(2-aminophenyl)carbamoyl]-1-methyl-1,4,6,7-tetrahydro-5H-pyrrolo[3,2-c]pyridine-5-carboxylate,
$N^2$-(2-aminophenyl)-$N^6$-pyridine-3-yl-4,7-dihydrothieno[2,3-c]pyridine-2,6(5H)-dicarboxamide,
$N^2$-(2-aminophenyl)-$N^6$-(3,4-dimethoxyphenyl)-4,7-dihydrothieno[2,3-c]pyridine-2,6(5H)-dicarboxamide,
$N^2$-(2-aminophenyl)-$N^6$-(2-methoxyethyl)-4,7-dihydrothieno[2,3-c]pyridine-2,6(5H)-dicarboxamide,
$N^2$-(2-aminophenyl)-$N^6$-[2-(difluoromethoxy)phenyl]-4,7-dihydrothieno[2,3-c]pyridine-2,6(5H)-dicarboxamide,
$N^2$-(2-amino-5-isopropylphenyl)-$N^6$-pyridine-3-yl-4,7-dihydrothieno[2,3-c]pyridine-2,6(5H)-dicarboxamide,
$N^2$-(2-amino-5-isopropylphenyl)-$N^6$-[3,4 difluoromethoxy)phenyl]-4,7-dihydrothieno[2,3-c]pyridine-2,6(5H)-dicarboxamide,
$N^2$-(2-amino-5-isopropylphenyl)-$N^6$-(4-fluorophenyl)-4,7-dihydrothieno[2,3-c]pyridine-2,6(5H)-dicarboxamide,
$N^2$-(2-amino-5-isopropylphenyl)-$N^6$-(3,4-dimethoxyphenyl)-4,7-dihydrothieno[2,3-c]pyridine-2,6(5H)-dicarboxamide,
3,4-dimethoxyphenyl 2-[(2-aminophenyl)carbamoyl]-4,7-dihydrothieno[2,3-c]pyridine-6(5H)-carboxylate,
3,4-dimethoxyphenyl 2-[(2-amino-5-isopropylphenyl)carbamoyl]-4,7-dihydrothieno[2,3-c]pyridine-6(5H)-carboxylate,
N-(2-aminophenyl)-6-[(3-methoxyphenoxy)acetyl]-4,5,6,7-tetrahydrothieno[2,3-c]pyridine-2-carboxamide,
N-(2-amino-5-isopropylphenyl)-6-[(3-methoxyphenoxy)acetyl]-4,5,6,7-tetrahydrothieno[2,3-c]pyridine-2-carboxamide,
$N^2$-(2-aminophenyl)-1-methyl-$N^6$-pyridine-3-yl-1,4,5,7-tetrahydro-6H-pyrrolo[2,3-c]pyridine-2,6-dicarboxamide,
$N^2$-(2-aminophenyl)-$N^6$-(3,4-dimethoxyphenyl)-1-methyl-1,4,5,7-tetrahydro-6H-pyrrolo[2,3-c]pyridine-2,6-dicarboxamide,
$N^2$-(2-aminophenyl)-$N^6$-(2-methoxyethyl)-1-methyl-1,4,5,7-tetrahydro-6H-pyrrolo[2,3-c]pyridine-2,6-dicarboxamide,
$N^2$-(2-aminophenyl)-$N^6$-pyridine-3-yl-1,4,5,7-tetrahydro-6H-pyrrolo[2,3-c]pyridine-2,6-dicarboxamide,
$N^2$-(2-aminophenyl)-$N^6$-(3,4-dimethoxyphenyl)-1,4,5,7-tetrahydro-6H-pyrrolo[2,3-c]pyridine-2,6-dicarboxamide, 3,4-dimethoxyphenyl 2-[(2-aminophenyl)carbamoyl]-1-methyl-1,4,5,7-tetrahydro-6H-pyrrolo[2,3-c]pyridine-6-carboxylate, 3,4-dimethoxyphenyl 2-[(2-aminophenyl)carbamoyl]-1,4,5,7-tetrahydro-6H-pyrrolo[2,3-c]pyridine-6-carboxylate, N-(2-aminophenyl)-5-(N-1,3-benzodioxol-5-ylglycyl)-4,5,6,7-tetrahydro[1,3]hiazolo[5,4-c]pyridine-2-carboxamide, N-(2-aminophenyl)-5-[N-(3-methoxyphenyl)glycyl]-4,5,6,7-tetrahydro[1,3]thiazolo[5,4-c]pyridine-2-carboxamide, N-(2-aminophenyl)-5-[N-(6-methoxypyridine-3-yl)glycyl]-4,5,6,7-tetrahydro[1,3]thiazolo[5,4-c]pyridine-2-carboxamide, $N^2$-(2-aminophenyl)-$N^5$-[3-(trifluoromethoxy)phenyl]-6,7-dihydro[1,3]thiazolo[5,4-c]pyridine-2,5(4H)-dicarboxamide, $N^2$-(2-aminophenyl)-$N^5$-(3-morpholin-4-ylphenyl)-6,7-dihydro[1,3]thiazolo[5,4-c]pyridine-2,5(4H)-dicarboxamide, $N^2$-(2-aminophenyl)-$N^5$-[4-(methylthio)phenyl]-6,7-dihydro[1,3]thiazolo[5,4-c]pyridine-2,5(4H)-dicarboxamide, $N^2$-(2-aminophenyl)-$N^5$-[3-(methylthio)phenyl]-6,7-dihydro[1,3]thiazolo[5,4-c]pyridine-2,5(4H)-dicarboxamide, $N^2$-(2-aminophenyl)-$N^5$-(3-methoxyphenyl)-6,7-dihydro[1,3]thiazolo[5,4-c]pyridine-2,5(4H)-dicarboxamide, $N^2$-(2-aminophenyl)-$N^5$-1H-indazol-5-yl-6,7-dihydro[1,3]thiazolo[5,4-c]pyridine-2,5(4H)-dicarboxamide, $N^2$-(2-aminophenyl)-$N^5$,$N^5$-diethyl-6,7-dihydro[1,3]thiazolo[5,4-c]pyridine-2,5(4H)-dicarboxamide, $N^2$-(2-amino-5-chlorophenyl)-$N^5$-(4-methoxyphenyl)-6,7-dihydro[1,3]thiazolo[5,4-c]pyridine-2,5(4H)-dicarboxamide, $N^2$-(2-amino-5-chlorophenyl)-$N^5$-(3,4-dimethoxyphenyl)-6,7-dihydro[1,3]thiazolo[5,4-c]pyridine-2,5(4H)-dicarboxamide, $N^2$-(2-amino-5-chlorophenyl)-$N^5$-pyridine-3-yl-6,7-dihydro[1,3]thiazolo[5,4-c]pyridine-2,5(4H)-dicarboxamide, $N^2$-(2-aminophenyl)-$N^5$-[3-(difluoromethoxy)phenyl]-6,7-dihydro[1,3]thiazolo[5,4-c]pyridine-2,5(4H)-dicarboxamide, $N^2$-(2-aminophenyl)-$N^5$-[4-(methylsulfonyl)phenyl]-6,7-dihydro[1,3]thiazolo[5,4-c]pyridine-2,5(4H)-dicarboxamide, $N^2$-(2-aminophenyl)-$N^5$-[3-(methylsulfonyl)phenyl]-6,7-dihydro[1,3]thiazolo[5,4-c]pyridine-2,5(4H)-dicarboxamide, $N^2$-(2-amino-5-fluorophenyl)-$N^5$-1,3-benzodioxol-5-yl-6,7-dihydro[1,3]thiazolo[5,4-c]pyridine-2,5(4H)-dicarboxamide, $N^2$-(2-amino-5-fluorophenyl)-$N^5$-(3,4-dimethoxyphenyl)-6,7-dihydro[1,3]thiazolo[5,4-c]pyridine-2,5(4H)-dicarboxamide, $N^2$-[2-amino-5-(2-thienyl)phenyl]-$N^5$-pyridine-3-yl-6,7-dihydro[1,3]thiazolo[5,4-c]pyridine-2,5(4H)-dicarboxamide, $N^2$-[2-amino-5-(3-thienyl)phenyl]-$N^5$-[2-(difluoromethoxy)phenyl]-6,7-dihydro[1,3]thiazolo[5,4-c]pyridine-2,5(4H)-dicarboxamide, $N^2$-[2-amino-5-(3-thienyl)phenyl]-$N^5$-(3,4-dimethoxyphenyl)-6,7-dihydro[1,3]thiazolo[5,4-c]pyridine-2,5(4H)-dicarboxamide, $N^2$-[2-amino-5-(3-thienyl)phenyl]-$N^5$-(2-methoxyethyl)-6,7-dihydro[1,3]thiazolo[5,4-c]pyridine-2,5(4H)-dicarboxamide, $N^2$-[2-amino-5-(2-thienyl)phenyl]-$N^5$-(3,4-dimethoxyphenyl)-6,7-dihydro[1,3]thiazolo[5,4-c]pyridine-2,5(4H)-dicarboxamide, $N^2$-[2-amino-5-(2-thienyl)phenyl]-$N^5$-(2-methoxyethyl)-6,7-dihydro[1,3]thiazolo[5,4-c]pyridine-2,5(4H)-dicarboxamide, $N^2$-[2-amino-5-(2-thienyl)phenyl]-$N^5$-pyridine-3-yl-6,7-dihydro[1,3]thiazolo[5,4-c]pyridine-2,5(4H)-dicarboxamide, $N^2$-[2-amino-5-(2-thienyl)phenyl]-$N^5$-[2-(difluoromethoxy)phenyl]-6,7-dihydro[1,3]thiazolo[5,4-c]pyridine-2,5(4H)-dicarboxamide, $N^2$-(2-aminophenyl)-$N^5$-(4-cyanophenyl)-6,7-dihydro[1,3]thiazolo[5,4-c]pyridine-2,5(4H)-dicarboxamide, $N^2$-(2-aminophenyl)-N-5-(3-cyanophenyl)-6,7-dihydro[1,3]thiazolo[5,4-c]pyridine-2,5(4H)-dicarboxamide, $N^2$-[2-amino-5-(3-thienyl)phenyl]-$N^5$-pyridine-3-yl-6,7-dihydro[1,3]thiazolo[5,4-c]pyridine-2,5(4H)-dicarboxamide, N-(2-aminophenyl)-5-[4-(trifluoromethoxy)benzoyl]-4,5,6,7-tetrahydro[1,3]thiazolo[5,4-c]pyridine-2-carboxamide, N-(2-aminophenyl)-5-[4-(difluoromethoxy)benzoyl]-4,5,6,7-tetrahydro[1,3]thiazolo[5,4-c]pyridine-2-carboxamide, N-(2-aminophenyl)-5-[3-(trifluoromethoxy)benzoyl]-4,5,6,7-tetrahydro[1,3]thiazolo[5,4-c]pyridine-2-carboxamide, N-(2-aminophenyl)-5-[3-pyridine-3-ylprop-2-enoyl]-4,5,6,7 tetrahydro[1,3]thiazolo[5,4-c]pyridine-2-carboxamide, 3-methoxyphenyl 2-[(2-aminophenyl)carbamoyl]-6,7-dihydro[1,3]thiazolo[5,4-c]pyridine-5(4H)-carboxylate, 3,4-dimethoxypheny 2-{[2-amino-5-(3-thienyl)phenyl]carbamoyl}-6,7-dihydro[1,3]thiazolo[5,4-c]pyridine-5(4H)-carboxylate, 3,4-dimethoxyphenyl 2-{[2-amino-5-(2-thienyl)phenyl]carbamoyl}-6,7-dihydro[1,3]thiazolo[5,4-c]pyridine-5(4H)-carboxylate, benzyl 2-[(2-aminophenyl)carbamoyl]-6,7-dihydro[1,3]thiazolo[5,4-c]pyridine-5(4H)-carboxylate, N-(2-aminophenyl)-5-[{[3-(difluoromethoxy)phenyl]amino}(oxo)acetyl]-4,5,6,7-tetrahydro[1,3]thiazolo[5,4-c]pyridine-2-carboxamide, N-(2-aminophenyl)-5-(oxo{[3-(trifluoromethoxy)phenyl]amino}acetyl)-4,5,6,7-tetrahydro[1,3]thiazolo[5,4-c]pyridine-2-carboxamide, N-(2-aminophenyl)-5-(oxo{[2-(trifluoromethoxy)phenyl]amino}acetyl)-4,5,6,7-tetrahydro[1,3]thiazolo[5,4-c]pyridine-2-carboxamide, N-(2-aminophenyl)-5-[{[2-(difluoromethoxy)phenyl]amino}(oxo)acetyl]-4,5,6,7-tetrahydro[1,3]thiazolo[5,4-c]pyridine-2-carboxamide, N-(2-aminophenyl)-5-(oxo{[2-(trifluoromethoxy)phenyl]amino}acetyl)-4,5,6,7-tetrahydro[1,3]thiazolo[5,4-c]pyridine-2-carboxamide, N-[2-amino-5-(2-thienyl)phenyl]-5-[(3-methoxyphenoxy)acetyl]-4,5,6,7-tetrahydro[1,3]thiazolo[5,4-c]pyridine-2-carboxamide, N-[2-amino-5-(3-thienyl)phenyl]-5-[(3-methoxyphenoxy)acetyl]-4,5,6,7-tetrahydro[1,3]thiazolo[5,4-c]pyridine-2-carboxamide, N-(2-amino-5-fluorophenyl)-5-[(3-methoxyphenoxy)acetyl]-4,5,6,7-tetrahydro[1,3]thiazolo[5,4-c]pyridine-2-carboxamide, N-(2-aminophenyl)-5-[(4-methoxyphenyl)sulfonyl]-4,5,6,7-tetrahydro[1,3]thiazolo[5,4-c]pyridine-2-carboxamide, $N^2$-(2-aminophenyl)-$N^5$-(6-methoxypyridine-3-yl)-6,7-dihydro[1,3]thiazolo[5,4-c]pyridine-2,5(4H)-dicarboxamide dihydrochloride, $N^2$-(2-aminophenyl)-$N^5$-pyridine-3-yl-6,7-dihydro[1,3]thiazolo[5,4-c]pyridine-2,5(4H)-dicarboxamide dihydrochloride, $N^2$-(2-aminophenyl)-$N^5$-(6-methoxypyridine-3-yl)-6,7-dihydro[1,3]thiazolo[5,4-c]pyridine-2,5(4H)-dicarboxamide-4-methylaniline (1:2), $N^2$-(2-aminophenyl)-$N^5$-pyridine-3-yl-6,7-dihydro[1,3]thiazolo[5,4-c]pyridine-2,5(4H)-dicarboxamide-4-methylaniline (1:2), N-(2-aminophenyl)-5-[(3-methoxyphenoxy)acetyl]-4,5,6,7-tetrahydro[1,3]thiazolo[5,4-c]pyridine-2-carboxamide-4-methylaniline (1:1), benzyl 2-[(2-aminophenyl)carbamoyl]-6,7-dihydro[1,3]thiazolo[5,4-c]pyridine-5(4H)-carboxylate-4-methylaniline (1:1), N-(2-aminophenyl)-5-[(3-methoxyphenoxy)acetyl]-4,5,6,7-tetrahydro[1,3]thiazolo[5,4-c]pyridine-2-carboxamide methanesulfonate, benzyl 2-[(2-aminophenyl)carbamoyl]-6,7-dihydro[1,3]thiazolo[5,4-c]pyridine-5(4H)-carboxylate methanesulfonate, benzyl 2-[(2-aminophenyl)carbamoyl]-6,7-dihydro[1,3]thiazolo[5,4-c]pyridine-5(4H) carboxylate sulfate, N-(2-aminophenyl)-5-[(4-methoxyphenyl)sulfonyl]-4,5,6,7-tetrahydro[1,3]thiazolo[5,4-c]pyridine-2-carboxamide sulphate, $N^2$-(2-aminophenyl)-$N^5$-pyridine-3-yl-1,4,6,7-tetrahydro-5H-pyrrolo[3,2-c]pyridine-2,5-dicarboxamide, $N^2$-(2-amino-5-fluorophenyl)-$N^6$-pyridine-3-yl-4,7-dihydrothieno[2,3-c]pyridine-2,6(5H)-dicarboxamide, $N^2$-(2-amino-5-fluorophenyl)-$N^6$-(pyridine-3-ylmethyl)-4,7-dihydrothieno[2,3-c]pyridine-2,6(5H)-dicarboxamide, $N^2$-(2-amino-5-fluorophenyl)-$N^6$-pyridine-4-yl-4,7-dihydrothieno[2,3-c]pyridine-2,6(5H)-dicarboxamide, $N^2$-(2-amino-5-fluorophenyl)-$N^6$-quinoline-3-yl-4,7-dihydrothieno[2,3-c]pyridine-2,6(5H)-dicarboxamide, $N^2$-(2-aminophenyl)-$N^6$-(pyridine-3-ylmethyl)-4,7-dihydrothieno[2,3-c]pyridine-2,6(5H)-dicarboxamide, $N^2$-(2-aminophenyl)-$N^6$-pyridine-4-yl-4,7-dihydrothieno[2,3-c]pyridine-2,6(5H)-dicarboxamide, or $N^2$-(2-aminophenyl)-$N^6$-quinoline-3-yl -4,7-dihydrothieno[2,3-c]pyridine-2,6(5H)-dicarboxamide or a salt thereof.

18. A pharmaceutical composition comprising one or more compounds of formula I as claimed in claim 1 and one or more pharmaceutically acceptable excipients, diluents and/or carriers.

19. A pharmaceutical combination comprising a compound of claim 1 and a chemotherapeutic anticancer agent, which is one of the following compounds Cyclophosphamid, Ifosfamid, Temozolomide, Thiotepa, Melphalan, chloroethylnitrosourea, cisplatin, oxaliplatin, carboplatin, vincristine, vinblastine, vinorelbine, Paclitaxel, Docetaxel, paclitaxel bound to albumin, Epothilone B, Azaepothilone, ZK-EPO, Doxorubicin, Etoposide camptothecin, Irinotecan, Topotecan, 5-fluorouracil, Capecitabine, Arabinosylcytosine, Gemcitabine, 6-mercaptopurine, 6-thioguanine, fludarabine, methotrexate or premetrexed.

20. A pharmaceutical combination comprising a compound of claim 1 and a target-specific anticancer agent, which is one of the following compounds Imatinib, Gefitinib, Sorafenib, Sunitinib, Erlotinib, Dasatinib, Lapatinib, Vatalanib, Vandetanib, Pazopanib, Bortezumib, 17-allylaminogeldanamycin, 17-dimethylaminogeldanamycin, combretastatin A4 phosphate, AVE8062, Bevacizumab, Vandetanib, Pazopanib, Trastuzumab, Rituximab, Alemtuzumab, Tositumomab, Cetuximab, Avastin, Panitumumab, Gemtuzumab ozogamicin, Ibritumomab tiuxetan, Oblimersen, MG98, CPG-7909, Imiquimod, Isatoribine, Resiquimod, Tamoxifen, Raloxifen, Flutamide, Casodex, Leuprolide, Goserelin, Triptorelin, Anastozol, or Letrozole.

21. A pharmaceutical combination comprising a compound of claim 1 and an anti-cancer agent, which is one of the following compounds 5 FU, actinomycin D, ABARELIX, ABCIXIMAB, ACLARUBICIN, ADAPALENE, ALEMTUZUMAB, ALTRETAMINE, AMINOGLUTETHIMIDE, AMIPRILOSE, AMRUBICIN, ANASTROZOLE, ANCITABINE, ARTEMISININ, AZATHIOPRINE, BASILIXIMAB, BENDAMUSTINE, BEVACIZUMAB, BEXXAR, BICALUTAMIDE, BLEOMYCIN, BORTEZOMIB, BROXURIDINE, BUSULFAN, CAMPATH, CAPECITABINE, CARBOPLATIN, CARBOQUONE, CARMUSTINE, CETRORELIX, CHLORAMBUCIL, CHLORMETHINE, CISPLATIN, CLADRIBINE, CLOMIFENE, CYCLOPHOSPHAMIDE, DACARBAZINE, DACLIZUMAB, DACTINOMYCIN, DASATINIB, DAUNORUBICIN, DECITABINE, DESLORELIN, DEXRAZOXANE, DOCETAXEL, DOXIFLURIDINE, DOXORUBICIN, DROLOXIFENE, DROSTANOLONE, EDELFOSINE, EFLORNITHINE, EMITEFUR, EPIRUBICIN, EPITIOSTANOL, EPTAPLATIN, ERBITUX, ERLOTINIB, ESTRAMUSTINE, ETOPOSIDE, EXEMESTANE, FADROZOLE, FINASTERIDE, FLOXURIDINE, FLUCYTOSINE, FLUDARABINE, FLUOROURACIL, FLUTAMIDE, FORMESTANE, FOSCARNET, FOSFESTROL, FOTEMUSTINE, FULVESTRANT, GEFITINIB, GENASENSE, GEMCITABINE, GLIVEC, GOSERELIN, GUSPERIMUS, HERCEPTIN, IDARUBICIN, IDOXURIDINE, IFOSFAMIDE, IMATINIB, IMPROSULFAN, INFLIXIMAB, IRINOTECAN, IXABEPILONE, LANREOTIDE, LAPATINIB, LETROZOLE, LEUPRORELIN, LOBAPLATIN, LOMUSTINE, LUPROLIDE, MELPHALAN, MERCAPTOPURINE, METHOTREXATE, METUREDEPA, MIBOPLATIN, MIFEPRISTONE, MILTEFOSINE, MIRIMOSTIM, MITOGUAZONE, MITOLACTOL, MITOMYCIN, MITOXANTRONE, MIZORIBINE, MOTEXAFIN, MYLOTARG, NARTOGRASTIM, NEBAZUMAB, NEDAPLATIN, NILUTAMIDE, NIMUSTINE, OCTREOTIDE, ORMELOXIFENE, OXALIPLATIN, PACLITAXEL, PALIVIZUMAB, PANITUMUMAB, PATUPILONE, PAZOPANIB, PEGASPARGASE, PEGFILGRASTIM, PEMETREXED, PENTETREOTIDE, PENTOSTATIN, PERFOSFAMIDE, PIPOSULFAN, PIRARUBICIN, PLICAMYCIN, PREDNIMUSTINE, PROCARBAZINE, PROPAGERMANIUM, PROSPIDIUM CHLORIDE, RALOXIFEN, RALTITREXED, RANIMUSTINE, RANPIRNASE, RASBURICASE, RAZOXANE, RITUXIMAB, RIFAMPICIN, RITROSULFAN, ROMURTIDE, RUBOXISTAURIN, SARGRAMOSTIM, SATRAPLATIN, SIROLIMUS, SOBUZOXANE, SORAFENIB, SPIROMUSTINE, STREPTOZOCIN, SUNITINIB, TAMOXIFEN, TASONERMIN, TEGAFUR, TEMOPORFIN, TEMOZOLOMIDE, TENIPOSIDE, TESTOLACTONE, THIOTEPA, THYMALFASIN, TIAMIPRINE, TOPOTECAN, TOREMIFENE, TRAIL, TRASTUZUMAB, TREOSULFAN, TRIAZIQUONE, TRIMETREXATE, TRIPTORELIN, TROFOSFAMIDE, UREDEPA, VALRUBICIN, VATALANIB, VANDETANIB, VERTEPORFIN, VINBLASTINE, VINCRISTINE, VINDESINE, VINORELBINE, VOROZOLE or ZEVALIN.

22. A pharmaceutical composition comprising one or more compounds of claim 17 and one or more pharmaceutically acceptable excipients, diluents and/or carriers.

23. A compound of formula I according to claim 1 which is $N^2$-(2-aminophenyl)-$N^5$-pyridin-3-yl-6,7-dihydro[1,3]thiazolo[5,4-c]pyridine-2,5(4H)-dicarboxamide or a pharmaceutically acceptable salt thereof.

24. A pharmaceutical composition comprising the compound of claim 23 or a pharmaceutically acceptable salt thereof and one or more pharmaceutically acceptable excipients, diluents and/or carriers.

25. A compound of formula I according to claim 1 which is $N^2$-(2-aminophenyl)-$N^5$-biphenyl-4-yl-6,7-dihydro[1,3]thiazolo[5,4-c]pyridine-2,5(4H)-dicarboxamide, or a pharmaceutically acceptable salt thereof.

26. A compound of formula I according to claim 1 which is $N^2$-(2-aminophenyl)-$N^5$-[4-(dimethylamino)phenyl]-6,7-dihydro[1,3]thiazolo[5,4-c]pyridine-2,5(4H)-dicarboxamide, or a pharmaceutically acceptable salt thereof.

27. A compound of formula I according to claim 1 which is $N^2$-(2-aminophenyl)-$N^5$-(4-methoxyphenyl)-6,7-dihydro[1,3]thiazolo[5,4-c]pyridine-2,5(4H)-dicarboxamide, or a pharmaceutically acceptable salt thereof.

28. A compound of formula I according to claim 1 which is $N^2$-(2-aminophenyl)-$N^5$-quinolin-3-yl-6,7-dihydro[1,3]thiazolo[5,4-c]py-ridine-2,5(4H)-dicarboxamide, or a pharmaceutically acceptable salt thereof.

29. A compound of formula I according to claim 1 which is N-(2-aminophenyl)-5-[(4-methylphenyl)sulfonyl]-4,5,6,7-tetrahydro[1,3]-thi-azolo[5,4-c]pyridine-2-carboxamide, or a pharmaceutically acceptable salt thereof.

30. A compound of formula I according to claim 1 which is
N-(2-aminophenyl)-5-[(4-methoxyphenyl)sulfonyl]-4,5,6,7-tetrahydro[1,3]thi-azolo[5,4-c]pyridine-2-carboxamide,
4-methylphenyl-2-[(2-aminophenyl)carbamoyl]-6,7-dihydro[1,3]thiazolo[5,4-c]pyridine-5(4H-)-carboxylate, or
Pyridin-3-ylmethyl-2-[(2-aminophenyl)carbamoyl]-6,7-dihydro[1,3]thiazolo[5,4-c]pyridine-5(4H-)-carboxylate,
or a pharmaceutically acceptable salt thereof.

* * * * *

UNITED STATES PATENT AND TRADEMARK OFFICE
CERTIFICATE OF CORRECTION

PATENT NO. : 8,440,830 B2
APPLICATION NO. : 12/678806
DATED : May 14, 2013
INVENTOR(S) : Maier et al.

It is certified that error appears in the above-identified patent and that said Letters Patent is hereby corrected as shown below:

In the Claims

Claim 17,

Column 244, line 19 reads "$N^2$-(2-aminophenyl)-$N^5$-(3,4-dimethoxyphenyl)-N-5-" should read -- $N^2$-(2-aminophenyl)-$N^5$-(3,4-dimethoxyphenyl)-$N^5$- --

Claim 17,

Column 246, line 20 reads "N-(2-aminophenyl)-5-[{[(6-(dimethylamino)pyridine-3-" should read -- N-(2-aminophenyl)-5-[{[6-(dimethylamino)pyridine-3- --

Claim 17,

Column 248, line 1 reads "N-(2-aminophenyl)-5-isopropylphenyl)-5-{imino[(4-" should read -- N-(2-aminophenyl)-5-{imino[(4- --

Claim 17,

Column 254, line 19 reads "$N^2$-(2-aminophenyl)-N-5-(3-cyanophenyl)-6,7-dihydro" should read -- $N^2$-(2-aminophenyl)-$N^5$-(3-cyanophenyl)-6,7-dihydro--

Signed and Sealed this
First Day of October, 2013

Teresa Stanek Rea
*Deputy Director of the United States Patent and Trademark Office*